United States Patent
Lavoie et al.

(10) Patent No.: US 9,102,617 B2
(45) Date of Patent: Aug. 11, 2015

(54) ANTIMICROBIAL AGENTS

(75) Inventors: Edmond J. Lavoie, New Brunswick, NJ (US); Ajit Parhi, New Brunswick, NJ (US); Daniel S. Pilch, Somerset, NJ (US)

(73) Assignees: Rutgers, The State University of New Jersey, New Brunswick, NJ (US); University of Medicine and Dentistry of New Jersey, Somerset, NJ (US)

( * ) Notice: Subject to any disclaimer, the term of this patent is extended or adjusted under 35 U.S.C. 154(b) by 25 days.

(21) Appl. No.: 13/806,033

(22) PCT Filed: Jun. 24, 2011

(86) PCT No.: PCT/US2011/041862
§ 371 (c)(1),
(2), (4) Date: Dec. 20, 2012

(87) PCT Pub. No.: WO2011/163610
PCT Pub. Date: Dec. 29, 2011

(65) Prior Publication Data
US 2013/0109713 A1    May 2, 2013

Related U.S. Application Data

(60) Provisional application No. 61/376,993, filed on Aug. 25, 2010, provisional application No. 61/428,791, filed on Dec. 30, 2010, provisional application No. 61/358,759, filed on Jun. 25, 2010, provisional application No. 61/430,058, filed on Jan. 5, 2011.

(51) Int. Cl.
| | |
|---|---|
| *C07D 215/14* | (2006.01) |
| *A61K 9/00* | (2006.01) |
| *A61K 9/12* | (2006.01) |
| *A61K 9/16* | (2006.01) |
| *A61K 9/20* | (2006.01) |
| *A61K 9/48* | (2006.01) |
| *C07C 211/27* | (2006.01) |
| *C07C 211/29* | (2006.01) |
| *C07C 211/45* | (2006.01) |
| *C07C 211/52* | (2006.01) |
| *C07C 211/63* | (2006.01) |
| *C07C 211/64* | (2006.01) |
| *C07C 217/70* | (2006.01) |
| *C07C 217/78* | (2006.01) |
| *C07C 217/94* | (2006.01) |

(Continued)

(52) U.S. Cl.
CPC ............ *C07D 215/14* (2013.01); *A61K 9/0019* (2013.01); *A61K 9/12* (2013.01); *A61K 9/1623* (2013.01); *A61K 9/2054* (2013.01); *A61K 9/4858* (2013.01); *C07C 211/27* (2013.01); *C07C 211/29* (2013.01); *C07C 211/45* (2013.01); *C07C 211/52* (2013.01); *C07C 211/63* (2013.01); *C07C 211/64* (2013.01); *C07C 217/70* (2013.01); *C07C 217/78* (2013.01); *C07C 217/80* (2013.01); *C07C 217/94* (2013.01); *C07C 229/38* (2013.01); *C07C 257/14* (2013.01); *C07C 279/04* (2013.01); *C07C 279/06* (2013.01); *C07C 279/08* (2013.01); *C07C 279/14* (2013.01); *C07D 213/20* (2013.01); *C07D 213/30* (2013.01); *C07D 215/10* (2013.01); *C07D 215/20* (2013.01); *C07D 217/10* (2013.01); *C07D 221/18* (2013.01); *C07D 239/26* (2013.01); *C07D 307/52* (2013.01); *C07D 405/10* (2013.01); *C07D 407/10* (2013.01); *C07D 471/04* (2013.01); *C07D 491/056* (2013.01); *C07C 2101/02* (2013.01)

(58) Field of Classification Search
CPC ..................................................... C07D 215/14
See application file for complete search history.

(56) References Cited

U.S. PATENT DOCUMENTS

| | | | |
|---|---|---|---|
| 4,309,539 A | 1/1982 | Boller et al. | |
| 4,782,058 A | 11/1988 | Griffith | |

(Continued)

FOREIGN PATENT DOCUMENTS

| | | |
|---|---|---|
| DE | 4327748 A1 | 2/1995 |
| EP | 0719764 A1 | 7/1996 |

(Continued)

OTHER PUBLICATIONS

Ito N, Tamano S, Shirai T. A medium-term rat liver bioassay for rapid in vivo detection of carcinogenic potential of chemicals. Cancer Sci. Jan. 2003;94(1):3-8.*

(Continued)

*Primary Examiner* — Paul Zarek
(74) *Attorney, Agent, or Firm* — Viksnins Harris & Padys PLLP

(57) ABSTRACT

The invention provides a compound of formula I: or a salt thereof, wherein $R^3$-$R^8$ and X and Y have any of the values described in the specification, as well as compositions comprising a compound of formula I. The compounds are useful as antibacterial agents.

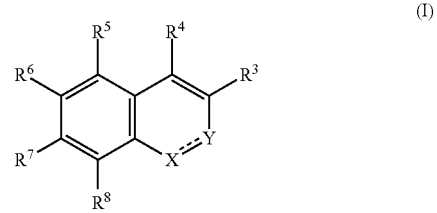

(I)

13 Claims, No Drawings

(51) Int. Cl.

| | |
|---|---|
| C07C 229/38 | (2006.01) |
| C07C 257/14 | (2006.01) |
| C07C 279/04 | (2006.01) |
| C07C 279/06 | (2006.01) |
| C07C 279/08 | (2006.01) |
| C07C 279/14 | (2006.01) |
| C07D 213/30 | (2006.01) |
| C07D 215/10 | (2006.01) |
| C07D 215/20 | (2006.01) |
| C07D 217/10 | (2006.01) |
| C07D 221/18 | (2006.01) |
| C07D 239/26 | (2006.01) |
| C07D 307/52 | (2006.01) |
| C07D 405/10 | (2006.01) |
| C07D 407/10 | (2006.01) |
| C07D 471/04 | (2006.01) |
| C07C 217/80 | (2006.01) |
| C07D 213/20 | (2006.01) |
| C07D 491/056 | (2006.01) |

(56) References Cited

U.S. PATENT DOCUMENTS

| | | | |
|---|---|---|---|
| 5,077,142 A * | 12/1991 | Sakon et al. | 428/690 |
| 5,177,067 A | 1/1993 | Guerry et al. | |
| 5,177,075 A | 1/1993 | Suto et al. | |
| 2002/0035090 A1 | 3/2002 | Zeldis et al. | |
| 2002/0077333 A1 | 6/2002 | Dey et al. | |
| 2003/0181519 A1* | 9/2003 | Mewshaw et al. | 514/520 |
| 2006/0183943 A1 | 8/2006 | Hu | |
| 2008/0027028 A1 | 1/2008 | Chichak | |
| 2008/0300239 A1 | 12/2008 | Adams et al. | |
| 2009/0076074 A1 | 3/2009 | Jung et al. | |
| 2009/0312319 A1 | 12/2009 | Ren et al. | |
| 2010/0120810 A1 | 5/2010 | Leblond et al. | |
| 2012/0022061 A1 | 1/2012 | LaVoie | |
| 2012/0059026 A1 | 3/2012 | LaVoie | |
| 2013/0116278 A1 | 5/2013 | LaVoie | |

FOREIGN PATENT DOCUMENTS

| | | |
|---|---|---|
| EP | 1078920 A1 | 2/2001 |
| EP | 1724262 A1 | 11/2006 |
| WO | WO 92/19242 A1 | 11/1992 |
| WO | WO 03/018017 A1 | 3/2003 |
| WO | WO 03/078397 A1 | 9/2003 |
| WO | WO 03/099274 A1 | 12/2003 |
| WO | WO 04/000814 A1 | 12/2003 |
| WO | WO 2004/005472 A2 | 1/2004 |
| WO | WO 2004/041210 A2 | 5/2004 |
| WO | WO 2004/087145 A2 | 10/2004 |
| WO | WO 2005/075428 A1 | 8/2005 |
| WO | WO 2006/067048 A1 | 6/2006 |
| WO | WO 2006/105289 A1 | 10/2006 |
| WO | WO 2008/016596 A2 | 2/2008 |
| WO | WO 2010/127307 A1 | 11/2010 |
| WO | WO 2011/156626 A1 | 12/2011 |

OTHER PUBLICATIONS

Bayer H, Hartmann RW. [Pyridyl-substituted tetralone derivatives: a new class of nonsteroidal aromatase inhibitors]. Arch Pharm (Weinheim). Oct. 1991;324(10):815-20.*

Roesch et al., "Synthesis of isoquinolines and pyridines by the palladium-catalyzed iminoannulation of internal alkynes", *J. Org. Chem.* 66, 8042-8051 (2001).

Wu et al., "Regulatory perspectives of Type II prodrug development and time-dependent toxicity management: Nonclinical Pharm/Tox analysis and the role of comparative toxicology", *Toxicology* 236, 1-6 (2007).

Akiba et al., "Preparation of 13-Substituted 8H-Dibenzo[a,g]quinolizin-8-onces by Intramolecular Wittig-Horner Reaction of Dialkyl 2-(o-Acyl-benzoyl)-1,2-dihydro-1-isoquinolylphosphonates", *Bull. Chem. Soc. Japan*, 57 (8), 2188-2192 (1984).

Augstein et al., "Synthesis of 11-Hydroxy-2,3,9,10-tetramethoxy-5,6,13,13a-tetrahydro-8H-dibenzo[a,g]quinolizine. A Contribution to the Structure of Stepharotine", *Stepharotine*, vol. 34, No. 5, 1349-1352 (1969).

Bedi et al., "Synthesis and biological activity of novel antibacterial quinazolines", *Bioorganic & Medicinal Chemistry Letters*, vol. 14 (20), 5211-5213 (2004).

Beilstein, Database Beilstein Institute for Organic Chemistry, XP002591901, Database Accession No. 3834367 (BRN) abstract (1918).

Beilstein, Database Beilstein Institute for Organic Chemistry, XP002591900, Database Accession No. 3837583(BNR) abstract (1930).

Beuria, T.K. et al., "Sanguinarine Blocks Cytokinesis in Bacteria by Inhibiting FtsZ Assembly and Bundling", *Biochemistry*, 44, 16584-16593 (2005).

Bild et al., "Discovery of Inhibitors of MCF-7 Tumor Cell Adhesion to Endothelial Cells and Investigation on their Mode of Action", *Archiv Der Pharmazie*, vol. 337 (12), 687-694 (2004).

Chen et al., "Synthesis and Antibacterial Evaluation of Certain Quinolone Derivatives", *J. Med. Chem.*, 44, 2374-2377 (2001).

Cole et al., "Potential Tumor-Selective Nitroimidazolylmethyluracil Prodrug Derivatives: Inhibitors of the Angiogenic Enzyme Thymidine Phosphorylase", J. Med. Chem., 46, 207-209 (2003).

Database Registry [Online], Chemical Abstracts Service, XP002570845, Database accession No. 1043562-34-0/RN, abstract (2008).

Denes et al., "The chemistry of sanguinarine", XP002570844, Chemical Abstracts Service, Database accession No. 1960:91836, abstract, *Magyar Kemiai Folyoirat*, 64, 125-130 (1958).

Dyke et al., "The Chemistry of Cryptopine—I The Epicryptopines", *Tetrahedr0n*, vol. 24, No. 3, 1455-1465 (1968).

Dyke et al., "The Chemistry of Cryptopine—II Pseudocryptopine Chloride", *Tetrahedron*, vol. 25, 5375-5381 (1969).

Dykhuizen, "Santa Rosalia revisited: Why are there so many species of bacteria?", *Antonie van Leeuwenhock*, 73, 25-33 (1998).

Foroumadi et al., "Synthesis and in vitro antibacterial evaluation of N-[5-(5-nitro-2-thienyl)-1,3,4-thiadiazole-2-yl] piperazinyl quinolones", *European Journal of Medicinal Chemistry*, 38, 851-854 (2003).

Gopinath et al., "Dehydrogenation cyclization of 2-aryl-1-tetralone oxime acetates", XP002570843, Chemical Abstracts Service, Database accession No. 1960:23123, abstract, *Current Science*, 28, 241-242 (1959).

Huecas et al., "Protein Structure and Folding: The Interactions of Cell Division Protein FtsZ with Guanine Nucleotides", *J. Biol. Chem.*, 282, 37515-37528 (2007).

Ishii et al., "Studies on the Chemical Constituents of Rutaceous Plants. LV.1 The Development of a Versatile Mehtod for the Synthesis of Antitumor-Active Benzo[c]phenanthridine Alkaloids. (5).1 A New Method for Quaternization of the Benzo[c]phenanthridine Nucleus", *Chem. Pharm. Bull.*, 32(8), 2984-2994 (1984).

Ito et al., "A medium-term rat liver bioassay for rapid in vivo detection of carcinogenic potential of chemicals", *Cancer Sci*, vol. 94 (1), 3-8 (2003).

Jackson et al., "Non-Steroidal Aromatase Inhibitors Based on a Biphenyl Scaffold: Synthesis, in vitro SAR, and Molecular Modelling", *Chem. Med. Chem.*, vol. 3, (4), 603-618 (2008).

Kaul et al., "A Bactericidal Guanidinomethyl Biaryl That Alters the Dynamics of Bacterial FtsZ Polymerization", *Journal of Medicinal Chemistry*, 55(22), 10160-10176 (2012).

Leroux et al., "N-(4-Biphenylmethyl)imidazoles as Potential Therapeutics for the Treatment of Prostate Cancer: Metabolic Robustness Due to Fluorine Substituion?", *Helvetica Chimica Acta, Verlag Helvetica*, vol. 86, 2671-2686 (2003).

Okudaira et al., "A Study of the Intestinal Absorption of an Ester-Type Prodrug, ME3229, in Rats: Active Efflux Transport as a Cause

(56) References Cited

OTHER PUBLICATIONS of Poor Bioavailability of the Active Drug", *Journal of Pharmacology and Experimental Therapeutics*, vol. 294 (2), 580-587 (2000).

Patent Cooperation Treaty, International Searching Authority, Search Report and Written Opinion for PCT/US2011/041862, 24 pages, dated Dec. 14, 2011.

Sanders et al., "Selective Cytotoxicity of Topoisomerase-Directed Protoberberines against Glioblastoma Cells", *Biochemical Pharmacology*, vol. 56, 1157-1166 (1998).

Sethi, "Enzyme Inhibition VIII: Mode of Inhibition of Reverse Transcriptase Activity by Analogues, Isomers, and Related Alkaloids of Coralyne", *Journal of Pharmaceutical Science*, vol. 74 (8), 889-891 (1985).

Wachall et al., "Imidazole Substitued Biphenyls: A new Class o Highly Potent and in Vivo Active Inhibitors of P450 17 as Potential Therapeutics for Treatment of Prostate Cancer", *Bioorganic & Medicinal Chemistry*, vol. 7 (9), 1913-1924 (1999).

Yaeko et al., "Studies on the constituents of *Bocconia cordata*. IV. Transformation of sanguinarine into bocconine", XP002570841, Chemical Abstracts Service; Database accession No. 1992:129332, abstract, *Journal of Heterocyclic Chemistry*, 28(8), 1841-1843 (1991).

Yamaguchi et al., "Utilization of Protopine and Related Alkaloids. XIV. Oxidation of the Photo-adduct of 1-Oxoanhydromethylberberine with Nitrosobenzene, and Synthesis of Ring C-Substituted Benzo[*c*]phenanthridines", *Chem. Pharm. Bull.*, 31(5), 1601-1611 (1983).

* cited by examiner

ANTIMICROBIAL AGENTS

PRIORITY OF INVENTION

This application claims priority to U.S. Provisional Application Nos. 61/358,759, filed 25 Jun. 2010; 61/376,993, filed 25 Aug. 2010; 61/428,791, filed 30 Dec. 2010; and 61/430,058, filed 5 Jan. 2011.

BACKGROUND OF THE INVENTION

The emergence of Multidrug Resistant (MDR) bacterial pathogens (e.g. methicillin-resistant *Staphylococcus aureus* (MRSA), *Acinetobacter baumannii-calcoaceticus* complex (ABC), etc.) has increased concerns as to the adequacy of current antimicrobials and pathogen treatment methods. The lethality of such pathogens, particularly MRSA, has often led to treatment methods that are experimental or would otherwise normally be avoided in standard clinical practice. For example, the antibiotic colistin was traditionally considered too nephrotoxic and neurotoxic for clinical use, but is nevertheless used to treat many MDR bacterial infections due to a paucity of available active drugs. The growing threat from MDR pathogens highlights a critical need for additional antimicrobials. In this connection, there is a pressing need for new antibiotics that exhibit novel mechanisms of action or that are able to circumvent known resistance pathways.

Elements of the bacterial cell division machinery present appealing targets for antimicrobial compounds because (i) they are essential for bacterial viability, (ii) they are widely conserved among bacterial pathogens, and (iii) they often have markedly different structures than their eukaryotic homologs. One such protein that has been identified as a potential target is the FtsZ protein. During the division process, FtsZ, along with approximately 15 other proteins, assemble at mid-cell into a large cell division complex (termed the divisome), ultimately facilitating cell cytokinesis. More importantly, FtsZ is widely conserved among many bacterial strains.

SUMMARY OF THE INVENTION

In one embodiment the invention provides compounds that display antimicrobial activity. Accordingly, the invention provides a compound of formula I:

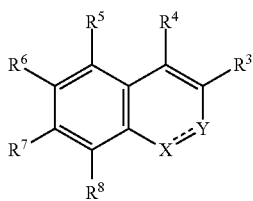

(I)

wherein $R^3$-$R^8$, X, and Y have the values defined in a), b), or c) below:

a) X is N; Y is $C(R^2)$; and $R^3$ is $R^e$; or
X is N; Y is $C(R^{15})$; and $R^3$ is $R^c$; or
X is $C(R^1)$; Y is N; and $R^3$ is $R^c$ or
X is $C(R^{16})$; Y is $C(R^{11})$; and $R^3$ is $R^e$; or
X is $C(R^1)$; Y is $C(R^{12})$; and $R^3$ is $R^e$; or
X is $C(R^{30})$; Y is $C(R^{31})$; and $R^3$ is $R^e$; or
X is $N^+$—$R^{13}$ ($Z^-$); Y is $C(R^{12})$; and $R^3$ is $R^c$; or
X is N; Y is $C(R^{12})$; and $R^3$ is $R^e$ or X is $C(R^{10})$ or $C(R^{31})$; Y is $N^+$—$R^{14}(Z^-)$; and $R^3$ is $R^c$; or
X is $C(R^{10})$ or $C(R^{31})$; Y is N; and $R^3$ is $R^c$;
$R^1$ is $R^y$ or $(C_1$-$C_6)$alkyl that is substituted with one or more $R^y$;
$R^2$ is $R^z$ or $(C_1$-$C_6)$alkyl that is substituted with one or more $R^x$;
at least one of $R^4$, $R^5$, $R^6$, $R^7$, $R^8$, and $R^{31}$ is aryl or heteroaryl wherein each aryl or heteroaryl is optionally substituted with one or more (e.g. 1, 2, 3, or 4) $R^d$; and the remainder of $R^4$, $R^5$, $R^6$, $R^7$, and $R^8$ are each independently H, halo, cyano, nitro, hydroxy, carboxy, trifluoromethyl, trifluoromethoxy, $(C_1$-$C_6)$alkyl, $(C_3$-$C_6)$cycloalkyl, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, $(C_1$-$C_6)$alkylthio, —S(O)$R^p$, —S(O)$_2R^p$, —S(O)$_3R^p$, —S(O)$_2NR^gR^h$, and —$NR^gR^h$; wherein any alkyl is optionally substituted with one or more (e.g. 1, 2, 3, or 4) $R^a$; and any remaining $R^{31}$ is —C(=$NR^{hb}$)—$NR^{hc}R^{hd}$, —$NR^{he}$—C(=$NR^{hb}$)—$NR^{hc}R^{hd}$, —$NR^{ke}$—C(=$NR^{kb}$)$R^{ke}$, or $(C_1$-$C_6)$alkyl which is substituted with one or more groups selected from —C(=$NR^{hb}$)—$NR^{hc}R^{hd}$, —$NR^{he}$—C(=$NR^{hb}$)—$NR^{hc}R^{hd}$, and —$NR^{ke}$—C(=$NR^{kb}$)$R^{ke}$; wherein any aryl, or heteroaryl of $R^4$, $R^5$, $R^6$, $R^7$, $R^8$, and $R^{31}$ is optionally substituted with one or more (e.g. 1, 2, 3, or 4) $R^b$;

each $R^{10}$ is H, halo, cyano, nitro, hydroxy, carboxy, trifluoromethyl, trifluoromethoxy, $(C_1$-$C_6)$alkyl, $(C_3$-$C_6)$cycloalkyl, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^gR^h$; wherein any alkyl of $R^{10}$ is optionally substituted with one or more (e.g. 1, 2, 3, or 4) $R^a$; and wherein any aryl, heteroaryl, or any aryl or heteroaryl portion of any aryl($C_1$-$C_6$)alkyl, heteroaryl($C_1$-$C_6$)alkyl, aryloxy, or heteroaryloxy of $R^{10}$ is optionally substituted with one or more (e.g. 1, 2, 3, or 4) $R^b$;

each $R^{11}$ is H, halo, cyano, nitro, hydroxy, carboxy, trifluoromethyl, trifluoromethoxy, $(C_1$-$C_6)$alkyl, $(C_3$-$C_6)$cycloalkyl, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^gR^h$; wherein any alkyl and any alkyl or alkanoyl portion of any aryl($C_1$-$C_6$)alkyl, heteroaryl($C_1$-$C_6$)alkyl, aryl($C_1$-$C_6$)alkanoyl or heteroaryl($C_1$-$C_6$)alkanoyl of $R^{11}$ is optionally substituted with one or more (e.g. 1, 2, 3, or 4) $R^a$; and wherein any aryl, heteroaryl, or any aryl or heteroaryl portion of any aryl($C_1$-$C_6$)alkyl, heteroaryl($C_1$-$C_6$)alkyl, aryl($C_1$-$C_6$)alkanoyl or heteroaryl($C_1$-$C_6$)alkanoyl of $R^{11}$ is optionally substituted with one or more (e.g. 1, 2, 3, or 4) $R^b$;

each $R^{12}$ is H, halo, cyano, nitro, hydroxy, carboxy, trifluoromethyl, trifluoromethoxy, $(C_1$-$C_6)$alkyl, $(C_3$-$C_6)$cycloalkyl, $(C_1$-$C_6)$alkoxy, $(C_1$-$C_6)$alkoxycarbonyl, $(C_1$-$C_6)$alkanoyloxy, aryloxy, heteroaryloxy, and —$NR^gR^h$; wherein any alkyl and any alkyl or alkanoyl portion of any aryl($C_1$-$C_6$)alkyl, heteroaryl($C_1$-$C_6$)alkyl, aryl($C_1$-$C_6$)alkanoyl or heteroaryl($C_1$-$C_6$)alkanoyl of $R^{12}$ is optionally substituted with one or more (e.g. 1, 2, 3, or 4) $R^a$; and wherein any aryl, heteroaryl, or any aryl or heteroaryl portion of any aryl($C_1$-$C_6$)alkyl, heteroaryl($C_1$-$C_6$)alkyl, aryl($C_1$-$C_6$)alkanoyl or heteroaryl($C_1$-$C_6$)alkanoyl of $R^{12}$ is optionally substituted with one or more (e.g. 1, 2, 3, or 4) $R^b$;

each $R^{13}$ is $(C_1$-$C_6)$alkyl, aryl, or aryl($C_1$-$C_6$)alkyl;
each $R^{14}$ is $(C_1$-$C_6)$alkyl, aryl, or aryl($C_1$-$C_6$)alkyl;
$R^{15}$ is $R^x$ or $(C_1$-$C_6)$alkyl that is substituted with one or more $R^x$;
$R^{16}$ is $R^z$ or $(C_1$-$C_6)$alkyl that is substituted with one or more $R^y$;
each $R^{30}$ is H or $(C_1$-$C_6)$alkyl,
each $R^a$ is independently selected from halo, cyano, nitro, hydroxy, carboxy, oxo, $(C_1$-$C_6)$alkyl, $(C_3$-$C_6)$cycloalkyl, $(C_1$-

$C_6$)alkoxy, ($C_1$-$C_6$)alkoxycarbonyl, ($C_1$-$C_6$)alkanoyloxy, aryl, heteroaryl, aryloxy, heteroaryloxy, ($C_1$-$C_6$)alkylthio, —S(O)$R^p$, —S(O)$_2R^p$, —S(O)$_3R^p$, —S(O)$_2NR^gR^h$, and —NR$^g$R$^h$; wherein each aryl, heteroaryl, aryloxy, and heteroaryloxy is optionally substituted with one or more (e.g. 1, 2, 3, or 4) groups independently selected from halo, cyano, nitro, hydroxy, carboxy, trifluoromethyl, trifluoromethoxy, ($C_1$-$C_6$)alkyl, ($C_3$-$C_6$)cycloalkyl, ($C_1$-$C_6$)alkoxy, ($C_1$-$C_6$)alkoxycarbonyl, ($C_1$-$C_6$)alkanoyloxy, ($C_1$-$C_6$)alkylthio, —S(O)$R^p$, —S(O)$_2R^p$, —S(O)$_3R^p$, —S(O)$_2NR^gR^h$, and —NR$^g$R$^h$;

each $R^b$ is independently selected from halo, cyano, nitro, hydroxy, carboxy, trifluoromethyl, trifluoromethoxy, ($C_1$-$C_6$)alkyl, ($C_3$-$C_6$)cycloalkyl, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, ($C_1$-$C_6$)alkylthio, —S(O)$R^p$, —S(O)$_2R^p$, —S(O)$_3R^p$, —S(O)$_2NR^gR^h$, and —NR$^g$R$^h$; wherein each aryl, heteroaryl, aryloxy, and heteroaryloxy is optionally substituted with one or more (e.g. 1, 2, 3, or 4) groups independently selected from halo, cyano, nitro, hydroxy, carboxy, trifluoromethyl, trifluoromethoxy, ($C_1$-$C_6$)alkyl, ($C_3$-$C_6$)cycloalkyl, ($C_1$-$C_6$)alkoxy, ($C_1$-$C_6$)alkoxycarbonyl, ($C_1$-$C_6$)alkanoyloxy, ($C_1$-$C_6$)alkylthio, —S(O)$R^p$, —S(O)$_2R^p$, —S(O)$_3R^p$, —S(O)$_2NR^gR^h$, and —NR$^g$R$^h$;

each $R^c$ is H, halo, cyano, nitro, hydroxy, carboxy, trifluoromethyl, trifluoromethoxy, ($C_1$-$C_6$)alkyl, ($C_3$-$C_6$)cycloalkyl, ($C_1$-$C_6$)alkoxy, ($C_1$-$C_6$)alkoxycarbonyl, ($C_1$-$C_6$)alkanoyloxy, aryl other than phenyl, heteroaryl other than pyrid-4-yl, aryloxy, heteroaryloxy, and —NR$^g$R$^h$; wherein any alkyl and any alkyl or alkanoyl portion of any aryl($C_1$-$C_6$)alkyl, heteroaryl($C_1$-$C_6$)alkyl, aryl($C_1$-$C_6$)alkanoyl or heteroaryl($C_1$-$C_6$)alkanoyl of $R^c$ is optionally substituted with one or more (e.g. 1, 2, 3, or 4) $R^a$; and wherein any aryl, heteroaryl, or any aryl or heteroaryl portion of any aryl($C_1$-$C_6$)alkyl, heteroaryl($C_1$-$C_6$)alkyl, aryl($C_1$-$C_6$)alkanoyl or heteroaryl($C_1$-$C_6$)alkanoyl of $R^c$ is optionally substituted with one or more (e.g. 1, 2, 3, or 4) $R^b$;

each $R^d$ is independently selected from halo, cyano, nitro, hydroxy, carboxy, trifluoromethyl, trifluoromethoxy, ($C_1$-$C_6$)alkyl, ($C_3$-$C_6$)cycloalkyl, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^g$R$^h$; wherein each aryl, heteroaryl, aryloxy, and heteroaryloxy is optionally substituted with one or more (e.g. 1, 2, 3, or 4) groups independently selected from halo, cyano, nitro, hydroxy, carboxy, trifluoromethyl, trifluoromethoxy, ($C_1$-$C_6$)alkyl, ($C_3$-$C_6$)cycloalkyl, ($C_1$-$C_6$)alkoxy, ($C_1$-$C_6$)alkoxycarbonyl, ($C_1$-$C_6$)alkanoyloxy, and —NR$^g$R$^h$;

each $R^e$ is H, halo, cyano, nitro, hydroxy, carboxy, trifluoromethyl, trifluoromethoxy, ($C_1$-$C_6$)alkyl, ($C_3$-$C_6$)cycloalkyl, ($C_1$-$C_6$)alkoxy, ($C_1$-$C_6$)alkoxycarbonyl, ($C_1$-$C_6$)alkanoyloxy, aryl, heteroaryl, aryloxy, heteroaryloxy, and —NR$^g$R$^h$; wherein any alkyl and any alkyl or alkanoyl portion of any aryl($C_1$-$C_6$)alkyl, heteroaryl($C_1$-$C_6$)alkyl, aryl($C_1$-$C_6$)alkanoyl or heteroaryl($C_1$-$C_6$)alkanoyl of $R^e$ is optionally substituted with one or more (e.g. 1, 2, 3, or 4) $R^a$; and wherein any aryl, heteroaryl, or any aryl or heteroaryl portion of any aryl($C_1$-$C_6$)alkyl, heteroaryl($C_1$-$C_6$)alkyl, aryl($C_1$-$C_6$)alkanoyl or heteroaryl($C_1$-$C_6$)alkanoyl of $R^e$ is optionally substituted with one or more (e.g. 1, 2, 3, or 4) $R^b$;

each $R^g$ and $R^h$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$) alkyl; or $R^g$ and $R^h$ together with the nitrogen to which they are attached form a aziridino, azetidino, morpholino, piperazino, pyrrolidino or piperidino; wherein any ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl or heteroaryl($C_1$-$C_6$)alkyl of $R^g$ and $R^h$ is optionally substituted with one or more groups independently selected from hydroxy, carboxy, and NR$^r$R$^u$;

each $R^j$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^m$ and $R^n$ is independently selected from H, ($C_1$-$C_6$) alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$) alkyl; or $R^m$ and $R^n$ together with the nitrogen to which they are attached form a aziridino, azetidino, morpholino, piperazino, pyrrolidino or piperidino; wherein any ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl or heteroaryl($C_1$-$C_6$) alkyl of $R^m$ and $R^n$ is optionally substituted with one or more groups independently selected from hydroxy, carboxy, and NR$^r$R$^u$;

each $R^p$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$) alkyl;

each $R^q$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^s$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^t$ and $R^u$ is independently selected from H, ($C_1$-$C_6$) alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$) alkyl; or $R^t$ and $R^u$ together with the nitrogen to which they are attached form a aziridino, azetidino, morpholino, piperazino, pyrrolidino or piperidino;

each $R^x$ is independently —NR$^m$R$^n$, —N$^+$(R$^s$)$_3$Z$^-$, —C(=NR$^j$)—NR$^m$R$^n$, or —NR$^q$—C(=NR$^j$)—NR$^m$R$^n$;

each $R^y$ is independently —NR$^m$R$^n$, —N$^+$(R$^s$)$_3$Z$^-$, —C(=NR$^j$)—NR$^m$R$^n$, or —NR$^q$—C(=NR$^j$)—NR$^m$R$^n$;

each $R^z$ is independently —C(=NR$^j$)—NR$^m$R$^n$, or —NR$^q$—C(=NR$^j$)—NR$^m$R$^n$;

each $R^{hb}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{hc}$ and $R^{hd}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-$C_6$) alkyl; or $R^{hc}$ and $R^{hd}$ together with the nitrogen to which they are attached form a aziridino, azetidino, morpholino, piperazino, pyrrolidino or piperidino; wherein any ($C_1$-$C_6$) alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl or heteroaryl($C_1$-$C_6$)alkyl of $R^{hc}$ and $R^{hd}$ is optionally substituted with one or more groups independently selected from hydroxy, carboxy, and NR$^{hm}$R$^{hn}$;

each $R^{he}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{hm}$ and $R^{hn}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-$C_6$) alkyl; or $R^{hm}$ and $R^{hn}$ together with the nitrogen to which they are attached form a aziridino, azetidino, morpholino, piperazino, pyrrolidino or piperidino;

each $R^{kb}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{ke}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

the bond represented by ---- is present; and each Z$^-$ is independently an acceptable counterion;

b) wherein:
 X is W—R$^{51}$;
 Y is C(R$^{52}$);
 W is N; R$^{51}$ is absent; or
 W is N$^+$D$^-$; R$^{51}$ is (C$_1$-C$_6$)alkyl, aryl, or aryl(C$_1$-C$_6$)alkyl; or
 W is C; R$^{51}$ is hydrogen, —N$^+$(R$^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$, —NR$^{5g}$R$^{5h}$, —NR$^{5ce}$—C(=NR$^{5cb}$)R$^{5ce}$, —NR$^{5ce}$—C(=O)—NR$^{5cc}$R$^{5cd}$, or (C$_1$-C$_6$)alkyl that is substituted with one or more R$^{5f}$;
 R$^{52}$ is a ring selected from phenyl, pyridyl, and [D$^-$N$^+$—(C$_1$-C$_6$)alkylpyridyl], which ring is optionally substituted with one or more groups selected from methylenedioxy, Z—R$^{5x}$, R$^{5f}$, R$^{5da}$, and (C$_1$-C$_6$)alkyl that is substituted with one or more R$^{5f}$; and which ring is also optionally substituted with a group R$^{6'}$, at a position ortho to the position where R$^{52}$ connects with the remainder of formula I;
 R$^6$ and R$^7$ taken together can be methylenedioxy or each R$^6$ and R$^7$ is independently selected from H, Z—R$^{5x}$, R$^{5f}$, and (C$_1$-C$_6$)alkyl that is substituted with one or more R$^{5f}$;
 R$^8$ is hydrogen, (C$_1$-C$_6$)alkyl, aryl, or aryl(C$_1$-C$_6$)alkyl wherein each (C$_1$-C$_6$)alkyl of R$^8$ is optionally substituted with one or more groups independently selected from halo, hydroxy, cyano, nitro, (C$_1$-C$_6$)alkoxy, (C$_3$-C$_6$)cycloalkyl, oxo, carboxy, aryloxy, sulfo, and —NR$^{5g}$R$^{5h}$, and wherein each aryl of R$^8$ is optionally substituted with one or more groups independently selected from (C$_1$-C$_6$)alkyl, halo, hydroxy, cyano, nitro, (C$_1$-C$_6$)alkoxy, (C$_3$-C$_6$)cycloalkyl, carboxy, aryloxy, nitro, R$^{5s}$, and —NR$^{5g}$R$^{5h}$;
 each Z is independently selected from —O—, —S—, and —N(R$^{5y}$)—;
 at least one of R$^3$, R$^4$, R$^5$, and R$^{6'}$ is selected from hydroxy, carboxy, cyano, CF$_3$SO$_3$—, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, aryl(C$_1$-C$_6$)alkyl, aryl, heteroaryl, heteroaryl(C$_1$-C$_6$)alkyl, aryl(C$_1$-C$_6$)alkanoyl, and heteroaryl(C$_1$-C$_6$)alkanoyl; and the remainder of R$^3$, R$^4$, R$^5$, and R$^{6'}$ are independently selected from H, hydroxy, carboxy, cyano, CF$_3$SO$_3$—, (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, aryl(C$_1$-C$_6$)alkyl, aryl, heteroaryl, heteroaryl(C$_1$-C$_6$)alkyl, aryl(C$_1$-C$_6$)alkanoyl, and heteroaryl(C$_1$-C$_6$)alkanoyl; wherein each (C$_1$-C$_6$)alkyl, (C$_2$-C$_6$)alkenyl, (C$_2$-C$_6$)alkynyl, (C$_1$-C$_6$)alkoxy, (C$_3$-C$_6$)cycloalkyl, and (C$_1$-C$_6$)alkanoyl of R$^3$, R$^4$, R$^5$, and R$^{6'}$ is optionally substituted with one or more groups independently selected from halo, hydroxy, cyano, nitro, (C$_1$-C$_6$)alkoxy, (C$_3$-C$_6$)cycloalkyl, oxo, carboxy, aryloxy, sulfo, —S(O)$_2$NR$^{5g}$R$^{5h}$, —N(R$^{5j}$)S(O)$_2$R$^{5k}$, —N$^+$(R$^{5a}$)$_3$D$^-$, —C(=NR$^{5b}$)—NR$^{5c}$R$^{5d}$, or —NR$^{5e}$—C(=NR$^{5b}$)—NR$^{5c}$R$^{5d}$ and —NR$^{5g}$R$^{5h}$; and wherein each aryl and heteroaryl of R$^3$, R$^4$, R$^5$, and R$^{6'}$ is optionally substituted with one or more groups independently selected from (C$_1$-C$_6$)alkyl, halo, hydroxy, cyano, nitro, (C$_1$-C$_6$)alkoxy, (C$_3$-C$_6$)cycloalkyl, carboxy, aryloxy, nitro, sulfo, —S(O)$_2$NR$^{5g}$R$^{5h}$, —N(R$^{5j}$)S(O)$_2$R$^{5k}$, R$^{5s}$, —N$^+$(R$^{5a}$)$_3$D$^-$, —C(=NR$^{5b}$)—NR$^{5c}$R$^{5d}$, or —NR$^{5e}$—C(=NR$^{5b}$)—NR$^{5c}$R$^{5d}$, —NR$^{5g}$R$^{5h}$, and (C$_1$-C$_6$)alkyl substituted with one or more groups independently selected from —N$^+$(R$^{5a}$)$_3$D$^-$, —C(=NR$^{5b}$)—NR$^{5c}$R$^{5d}$, or —NR$^{5e}$—C(=NR$^{5b}$)—NR$^{5c}$R$^{5d}$ and —NR$^{5g}$R$^{5h}$;
 each R$^{5a}$ is independently selected from H, (C$_1$-C$_6$)alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl and heteroaryl(C$_1$-C$_6$)alkyl;
 each R$^{5b}$ is independently selected from H, (C$_1$-C$_6$)alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl and heteroaryl(C$_1$-C$_6$)alkyl;
 each R$^{5c}$ and R$^{5d}$ is independently selected from H, (C$_1$-C$_6$)alkyl, (C$_3$-C$_6$)cycloalkyl, (C$_3$-C$_6$)cycloalkyl(C$_1$-C$_6$) alkyl, aryl, heteroaryl, aryl(C$_1$-C$_6$) alkyl and heteroaryl(C$_1$-C$_6$) alkyl; or R$^{5c}$ and R$^{5d}$ together with the nitrogen to which they are attached form a aziridino, azetidino, morpholino, piperazino, pyrrolidino or piperidino; wherein any (C$_1$-C$_6$) alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl or heteroaryl(C$_1$-C$_6$)alkyl of R$^{5c}$ and R$^{5d}$ is optionally substituted with one or more groups independently selected from hydroxy, carboxy, and NR$^{5m}$R$^{5n}$;
 each R$^{5e}$ is independently selected from H, (C$_1$-C$_6$)alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl and heteroaryl(C$_1$-C$_6$)alkyl;
 each R$^{5f}$ is independently selected from —N$^+$(R$^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$, —NR$^{5ce}$—C(=NR$^{5cb}$)R$^{5ce}$, —NR$^{5ce}$—C(=O)—NR$^{5cc}$R$^{5cd}$, and —NR$^{5g}$R$^{5h}$;
 each R$^{5g}$ and R$^{5h}$ is independently selected from H, (C$_1$-C$_6$)alkyl, (C$_3$-C$_6$)cycloalkyl, (C$_3$-C$_6$)cycloalkyl(C$_1$-C$_6$) alkyl, aryl, heteroaryl, aryl(C$_1$-C$_6$) alkyl and heteroaryl(C$_1$-C$_6$) alkyl; or R$^{5g}$ and R$^{5h}$ together with the nitrogen to which they are attached form a aziridino, azetidino, morpholino, piperazino, pyrrolidino or piperidino; wherein any (C$_1$-C$_6$) alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl or heteroaryl(C$_1$-C$_6$)alkyl of R$^{5g}$ and R$^{5h}$ is optionally substituted with one or more groups independently selected from hydroxy, carboxy, and NR$^{5m}$R$^{5n}$;
 each R$^{5j}$ is independently selected from H, (C$_1$-C$_6$)alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl and heteroaryl(C$_1$-C$_6$)alkyl;
 each R$^{5k}$ is independently selected from (C$_1$-C$_6$)alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl and heteroaryl(C$_1$-C$_6$)alkyl;
 each R$^{5m}$ and R$^{5n}$ is independently selected from H, (C$_1$-C$_6$)alkyl, (C$_3$-C$_6$)cycloalkyl, (C$_3$-C$_6$)cycloalkyl(C$_1$-C$_6$) alkyl, aryl, heteroaryl, aryl(C$_1$-C$_6$) alkyl and heteroaryl(C$_1$-C$_6$) alkyl; or R$^{5m}$ and R$^{5n}$ together with the nitrogen to which they are attached form a aziridino, azetidino, morpholino, piperazino, pyrrolidino or piperidino;
 each R$^{5s}$ is independently trifluoromethyl, trifluoromethoxy, aryl, or heteroaryl, wherein each aryl and heteroaryl is optionally substituted with one or more (C$_1$-C$_6$) alkyl, halo, hydroxy, cyano, nitro, (C$_1$-C$_6$)alkoxy, (C$_3$-C$_6$) cycloalkyl, carboxy, aryloxy, nitro, sulfo, —S(O)$_2$NR$^{5g}$R$^{5h}$, —N(R$^{5j}$)S(O)$_2$R$^{5k}$, trifluoromethyl, trifluoromethoxy, —N$^+$(R$^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$ and —NR$^{5g}$R$^{5h}$;
 each R$^{5u}$ and R$^{5v}$ is independently selected from H and (C$_1$-C$_6$)alkyl;
 each R$^{5x}$ is independently selected from (C$_1$-C$_6$)alkyl, (C$_1$-C$_6$)alkanoyl, and —C(=O)NR$^{5u}$R$^{5v}$;
 each R$^{5y}$ is independently selected from H and (C$_1$-C$_6$) alkyl;
 each D$^-$ is independently a counter anion;
 each R$^{5cb}$ is independently selected from H, (C$_1$-C$_6$)alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl and heteroaryl(C$_1$-C$_6$)alkyl;
 each R$^{5cc}$ and R$^{5cd}$ is independently selected from H, (C$_1$-C$_6$)alkyl, (C$_3$-C$_6$)cycloalkyl, (C$_3$-C$_6$)cycloalkyl(C$_1$-C$_6$) alkyl, aryl, heteroaryl, aryl(C$_1$-C$_6$) alkyl and heteroaryl(C$_1$-C$_6$) alkyl; or R$^{5cc}$ and R$^{5cd}$ together with the nitrogen to which they are attached form a aziridino, azetidino, morpholino, piperazino, pyrrolidino or piperidino; wherein any (C$_1$-C$_6$) alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl or heteroaryl(C$_1$-C$_6$)alkyl of $R^{5cc}$ and $R^{5cd}$ is optionally substituted with one or more groups independently selected from hydroxy, carboxy, and $NR^{5cm}R^{5cn}$;

each $R^{5ce}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5cm}$ and $R^{5cn}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^{5cm}$ and $R^{5cn}$ together with the nitrogen to which they are attached form a aziridino, azetidino, morpholino, piperazino, pyrrolidino or piperidino;

each $R^{5da}$ is carboxy or $(C_1-C_6)$alkoxycarbonyl; and the bond represented by ---- is present;

c) wherein:

X is $^+N(R^{81})(R^{82})B^-$;
Y is $C(R^{83})$;
$R^3$ is:

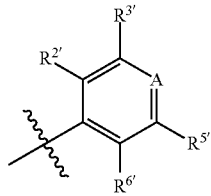

A is N or C—$R^{4'}$;

any adjacent $R^6$, $R^7$, $R^8$, $R^{4'}$ and $R^{5'}$ taken together can optionally be methylenedioxy and each remaining $R^6$, $R^7$, $R^8$, $R^{4'}$ and $R^{5'}$ is independently selected from H, fluoro, $R^{8bb}$, and Z—$R^{8x}$;

each Z is independently selected from —O—, —S—, and —N($R^{8y}$)—;

at least one of $R^4$, $R^5$, $R^{2'}$, $R^{3'}$, and $R^{6'}$ is selected from hydroxy, carboxy, cyano, $CF_3SO_3$—, $(C_1-C_6)$alkyl, $(C_2-C_6)$alkenyl, $(C_2-C_6)$alkynyl, $(C_1-C_6)$alkoxy, cycloalkyl, aryl$(C_1-C_6)$alkyl, aryl, heteroaryl, heteroaryl$(C_1-C_6)$alkyl, arylalkanoyl, and heteroarylalkanoyl; and the remainder of $R^4$, $R^5$, $R^{2'}$, $R^{3'}$, and $R^{6'}$ are independently selected from hydrogen, halo, hydroxy, carboxy, cyano, $CF_3SO_3$—, $(C_1-C_6)$alkyl, $(C_2-C_6)$alkenyl, $(C_2-C_6)$alkynyl, $(C_1-C_6)$alkoxy, cycloalkyl, aryl$(C_1-C_6)$alkyl, aryl, heteroaryl, heteroaryl$(C_1-C_6)$alkyl, aryl$(C_1-C_6)$alkanoyl, and heteroaryl$(C_1-C_6)$alkanoyl; or $R^{6'}$ and $R^{81}$ taken together are —$(CR^{13}_2)_2$— or —$CR^{14}$=$CR^{14}$—; wherein each $(C_1-C_6)$alkyl, $(C_2-C_6)$alkenyl, $(C_2-C_6)$alkynyl, $(C_1-C_6)$alkoxy, cycloalkyl, and $(C_1-C_6)$alkanoyl of $R^4$, $R^5$, $R^{2'}$, $R^{3'}$, and $R^{6'}$ is optionally substituted with one or more groups independently selected from halo, hydroxy, cyano, nitro, $(C_1-C_6)$alkoxy, cycloalkyl, oxo, carboxy, aryloxy, sulfo, —$S(O)_2NR^{8g}R^{8h}$, —$N(R^{8j})S(O)_2R^{8k}$, and —$NR^{8g}R^{8h}$; and wherein each aryl, and heteroaryl of $R^4$, $R^5$, $R^{2'}$, $R^{3'}$, and $R^{6'}$ is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{8aa}$, —$S(O)_2NR^{8g}R^{8h}$, —$N(R^{8j})S(O)_2R^{8k}$, and —$NR^{8g}R^{8h}$;

the bond represented by ---- is present and $R^{82}$ is absent except as defined below when $R^{81}$ and $R^{8a}$ taken together with the atoms to which they are attached form a 5- or 6-membered heterocyclic ring or a 5- or 6-membered heteroaryl ring;

$R^{81}$ is absent and $B^-$ is absent; or $R^{81}$ is H or $(C_1-C_6)$alkyl and $B^-$ is counterion;

or $R^{81}$ and $R^{8a}$ taken together with the atoms to which they are attached form a 5- or 6-membered heterocyclic ring or a 5- or 6-membered heteroaryl ring, wherein a) when the bond represented by ---- is present in the 5- or 6-membered heterocyclic ring or the 5- or 6-membered heteroaryl ring, $R^{82}$ is absent and $B^-$ is a counterion, b) when the bond represented by ---- is absent in the 5- or 6-membered heterocyclic ring or the 5- or 6-membered heteroaryl ring, $R^{82}$ is $(C_1-C_6)$alkyl and $B^-$ is a counterion, or c) when the bond represented by ---- is absent in the 5- or 6-membered heterocyclic ring or the 5- or 6-membered heteroaryl ring, $R^{82}$ is absent and $B^-$ is absent;

$R^{83}$ is H, $(C_1-C_6)$alkyl, $(C_1-C_6)$alkoxy, $(C_1-C_6)$alkylthio, aryloxy, arylthio, —$NR^{8a}R^{8b}$, $R^{8cc}$, or cyano; or $R^{6'}$ and $R^{83}$ taken together are —$(CR^{13}_2)_2$— or —$CR^{14}$=$CR^{14}$—;

each $R^{13}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{13}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^{8e}R^{8f}$, and wherein any aryloxy, or arylthio of $R^{13}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^{8e}R^{8f}$;

each $R^{14}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{14}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^{8e}R^{8f}$, and wherein any aryloxy, or arylthio of $R^{14}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^{8e}R^{8f}$;

$R^{8a}$ is hydrogen, $(C_1-C_6)$alkyl, aryl, aryl$(C_1-C_6)$alkyl, heteroaryl, or heteroaryl$(C_1-C_6)$alkyl; wherein each $(C_1-C_6)$alkyl of $R^{8a}$ is optionally substituted with one or more groups selected from halo, hydroxy, cyano, nitro, $(C_1-C_6)$alkoxy, cycloalkyl, oxo, carboxy, —$NR^{8g}R^{8h}$, and aryloxy, and wherein each aryl and heteroaryl of $R^{8a}$ is optionally substituted with one or more groups selected from $(C_1-C_6)$alkyl, halo, hydroxy, cyano, nitro, $(C_1-C_6)$alkoxy, cycloalkyl, carboxy, —$NR^{8g}R^{8h}$, and aryloxy;

$R^{8b}$ is hydrogen, $(C_1-C_6)$alkyl, aryl, aryl$(C_1-C_6)$alkyl, heteroaryl, heteroaryl$(C_1-C_6)$alkyl, —$C(=O)$—$R^{8m}$, —$C(=O)$—$OR^{8n}$, —$C(=O)$—$SR^{8p}$, —$C(=O)$—$NR^{8q}R^{8r}$, —$C(=S)$—$R^{8m}$, —$C(=S)$—$OR^{8n}$, —$C(=S)$—$SR^{8p}$, —$C(=S)$—$NR^{8q}R^{8r}$, or —$C(=NR^{8c})$—$R^{8d}$; wherein each $(C_1-C_6)$alkyl of $R^{8b}$ is optionally substituted with one or more groups independently selected from halo, hydroxy, cyano, nitro, $(C_1-C_6)$alkoxy, cycloalkyl, oxo, carboxy, and aryloxy; and wherein each aryl, and heteroaryl of $R^{8b}$ is optionally substituted with one or more groups independently selected from $(C_1-C_6)$alkoxy, cycloalkyl, carboxy, and aryloxy; or $R^{8a}$ and $R^{8b}$ taken together with the nitrogen to which they are attached form aziridino, azetidino, morpholino, piperazino, pyrrolidino, pyrrole, indole, or piperidino, which aziridino, azetidino, morpholino, piperazino, pyrrolidino pyrrole, indole, or piperidino can optionally be substituted with one or more $(C_1-C_6)$alkyl;

$R^{8c}$ is hydrogen, $(C_1-C_6)$alkyl, aryl, or heteroaryl;

$R^{8d}$ is hydrogen, $(C_1-C_6)$alkyl, $(C_1-C_6)$alkoxy, $(C_1-C_6)$alkylthio, $(C_1-C_6)$alkanoyl, or $-NR^{8e}R^{8f}$;

$R^{8e}$ and $R^{8f}$ are each independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; or $R^{8e}$ and $R^{8f}$ together with the nitrogen to which they are attached form a aziridino, azetidino, morpholino, piperazino, pyrrolidino or piperidino;

each $R^{8g}$ and $R^{8h}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; or $R^g$ and $R^h$ together with the nitrogen to which they are attached form a aziridino, azetidino, morpholino, piperazino, pyrrolidino or piperidino;

each $R^{8j}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl;

each $R^{8k}$ is independently selected from $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl;

each $R^{8m}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl;

each $R^{8n}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl, wherein each aryl, and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $-S(O)_2NR^{8g}R^{8h}$, $-N(R^{8j})S(O)_2R^{8k}$, and $-NR^{8g}R^{8h}$;

each $R^{8p}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl, wherein each aryl, and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $-S(O)_2NR^{8g}R^{8h}$, $-N(R^{8j})S(O)_2R^{8k}$, and $-NR^{8g}R^{8h}$;

each $R^{8q}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; and each $R^{8r}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; or $R^{8q}$ and $R^{8r}$ together with the nitrogen to which they are attached form a aziridino, azetidino, morpholino, piperazino, pyrrolidino or piperidino;

each $R^{8u}$ and $R^{8v}$ is independently selected from H and $(C_1-C_6)$alkyl;

each $R^{8x}$ is independently selected from $(C_1-C_6)$alkyl, $(C_1-C_6)$alkanoyl, and $-C(=O)NR^uR^v$;

each $R^{8y}$ is independently selected from H and $(C_1-C_6)$alkyl;

each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $-S(O)_2NR^{8g}R^{8h}$, $-N(R^j)S(O)_2R^{8k}$, and $-NR^{8g}R^{8h}$;

each $R^{8bb}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $-S(O)_2NR^{8g}R^{8h}$, $-N(R^{8j})S(O)_2R^{8k}$, and $-NR^{8g}R^{8h}$;

$R^{8cc}$ is $(C_1-C_6)$alkyl which is substituted with one or more $-N^+(R^{8ha})_3B^-$, $-C(=NR^{8hb})-NR^{8hc}R^{8hd}$, $-NR^{8he}-C(=NR^{8hb})-NR^{8hc}R^{8hd}$, $-NR^{8ke}-C(=NR^{8kb})R^{8ke}$, or $-NR^{8ke}-C(=O)-NR^{8kc}R^{8kd}$;

each $R^{8ha}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{8hb}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{8hc}$ and $R^{8hd}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{8hc}$ and $R^{8hd}$ together with the nitrogen to which they are attached form a aziridino, azetidino, morpholino, piperazino, pyrrolidino or piperidino; wherein any $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{hc}$ and $R^{hd}$ is optionally substituted with one or more groups independently selected from hydroxy, carboxy, and $NR^{hm}R^{hn}$;

each $R^{8he}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{8hm}$ and $R^{8hn}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{8hm}$ and $R^{8hn}$ together with the nitrogen to which they are attached form a aziridino, azetidino, morpholino, piperazino, pyrrolidino or piperidino;

each $R^{8kb}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{8kc}$ and $R^{kd}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{8kc}$ and $R^{8kd}$ together with the nitrogen to which they are attached form a aziridino, azetidino, morpholino, piperazino, pyrrolidino or piperidino; wherein any $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{8kc}$ and $R^{8kd}$ is optionally substituted with one or more groups independently selected from hydroxy, carboxy, and $NR^{8km}R^{8kn}$;

each $R^{8ke}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; and each $R^{8km}$ and $R^{8kn}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{8km}$ and $R^{8kn}$ together with the nitrogen to which they are attached form a aziridino, azetidino, morpholino, piperazino, pyrrolidino or piperidino; and each $B^-$ is a counterion;

or a salt or prodrug thereof.

The invention also provides a composition comprising a compound of formula I, or a pharmaceutically acceptable salt or prodrug thereof, and a pharmaceutically acceptable vehicle.

The invention also provides a method for treating a bacterial infection in a mammal comprising administering to the mammal an effective amount of a compound of formula I, or a pharmaceutically acceptable salt or prodrug thereof.

The invention also provides a compound of formula I, or a pharmaceutically acceptable salt or prodrug thereof for the prophylactic or therapeutic treatment of a bacterial infection.

The invention also provides a compound of formula I, or a pharmaceutically acceptable salt or prodrug thereof for use in medical treatment.

The invention also provides the use of a compound of formula I, or a pharmaceutically acceptable salt or prodrug thereof for the preparation of a medicament for treating a bacterial infection in a mammal.

The invention also provides processes and intermediates disclosed herein that are useful for preparing compounds of formula I or salts or prodrugs thereof.

DETAILED DESCRIPTION

The following definitions are used, unless otherwise described: halo is fluoro, chloro, bromo, or iodo. Alkyl, alkenyl, alkynyl and alkoxy, etc. denote both straight and branched groups but reference to an individual radical such as propyl embraces only the straight chain radical (a branched chain isomer such as isopropyl being specifically referred to). In one embodiment alkyl is a $(C_1$-$C_6)$alkyl, alkenyl is a $(C_2$-$C_6)$alkenyl, alkynyl is a $(C_2$-$C_6)$alkynyl and alkoxy is a $(C_1$-$C_6)$alkoxy. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(Q) wherein Q is absent or is H, O, $(C_1$-$C_4)$alkyl, phenyl or benzyl; as well as a radical of an ortho-fused bicyclic heterocycle of about eight to ten ring atoms comprising one to four heteroatoms each selected from the group consisting of non-peroxide oxygen, sulfur, and N(Q).

As used herein "cycloalkyl" refers to a saturated or partially unsaturated cyclic hydrocarbon ring system. In one embodiment "cycloalkyl" includes $(C_3$-$C_6)$cycloalkyl which can be cyclopropyl, cyclobutyl, cyclopentyl, or cyclohexyl.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, stereoisomeric, or polymorphic form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

It will also be appreciated by those skilled in the art that certain compounds of the invention can exist in more than one tautomeric form. For example, a substituent of formula —NH—C(=NH)—NH$_2$ in a compound of formula (I) could exist in tautomeric form as —N=C(NH$_2$)—NH$_2$, or a substituent of formula —NH—C(=NH)—CH$_3$ in a compound of formula (I) could exist in tautomeric form as —N=C (NH$_2$)—CH$_3$. The present invention encompasses all tautomeric forms of a compound of formula I as well as mixtures thereof that can exist in equilibrium with non-charged entities depending upon pH, which possess the useful properties described herein.

Specific values listed below for radicals, substituents, and ranges, are for illustration only; they do not exclude other defined values or other values within defined ranges for the radicals and substituents.

Specifically, $(C_1$-$C_6)$alkyl can be methyl, ethyl, propyl, isopropyl, butyl, iso-butyl, sec-butyl, pentyl, 3-pentyl, or hexyl; $(C_3$-$C_6)$cycloalkyl can be cyclopropyl, cyclobutyl, cyclopentyl, or cyclohexyl; $(C_1$-$C_6)$alkoxy can be methoxy, ethoxy, propoxy, isopropoxy, butoxy, iso-butoxy, sec-butoxy, pentoxy, 3-pentoxy, or hexyloxy; $(C_1$-$C_6)$alkanoyl can be formyl, acetyl, propanoyl, butanoyl, pentanoyl, or hexanoyl; $(C_1$-$C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; aryl can be phenyl, indenyl, or naphthoyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, benzimidazole, isoquinolyl (or its N-oxide) or quinolyl (or its N-oxide).

As used herein the term "aryl$(C_1$-$C_6)$alkyl" refers to a $(C_1$-$C_6)$alkyl radical in which one or more of the hydrogen atoms of the $(C_1$-$C_6)$alkyl radical is replaced with an aryl radical. As used herein the term "heteroaryl$(C_1$-$C_6)$ alkyl" refers to a $(C_1$-$C_6)$alkyl radical in which one or more of the hydrogen atoms of the $(C_1$-$C_6)$alkyl radical is replaced with a heteroaryl radical.

As used herein, "an aryl$(C_1$-$C_6)$alkanoyl group" refers to a group of the formula aryl-$(C_1$-$C_6)$alkanoyl-, where aryl and $(C_1$-$C_6)$alkanoyl are defined herein. Such aryl$(C_1$-$C_6)$alkanoyl groups may include, but are not limited to, benzoyl, 4-phenylbenzoyl, and naphthoyl, and the like. As used herein, "a heteroaryl$(C_1$-$C_6)$alkanoyl group" refers to a group of the formula heteroaryl-$(C_1$-$C_6)$alkanoyl-, where heteroaryl and $(C_1$-$C_6)$alkanoyl are defined herein.

As used herein, "an aryloxy group" refers to a group of the formula aryl-O—, where aryl is as defined herein. Such aryloxy groups may include, but are not limited to, phenoxy, 4-phenylphenoxy, and naphthyloxy, and the like. As used herein, "an arylthio group" refers to a group of the formula aryl-S—, where aryl is as defined herein. Such arylthio groups may include, but are not limited to, phenylthio, 4-phenylphenylthio, and naphthylthio, and the like. As used herein, "a heteroaryloxy group" refers to a group of the formula heteroaryl-O—, where hetereoaryl is as defined herein.

A specific compound of the invention is a compound of formula (I) wherein $R^3$-$R^8$, X, and Y have the values defined in a), b), and c) below:

a) X is N; Y is $C(R^2)$; and $R^3$ is $R^e$; or
   X is N; Y is $C(R^{15})$; and $R^3$ is $R^c$; or
   X is $C(R^1)$; Y is N; and $R^3$ is $R^c$ or
   X is $C(R^{16})$; Y is $C(R^{11})$; and $R^3$ is $R^e$; or
   X is $C(R^1)$; Y is $C(R^{12})$; and $R^3$ is $R^e$; or
   X is $C(R^{30})$; Y is $C(R^{31})$; and $R^3$ is $R^e$; or
   X is $N^+$—$R^{13}(Z^-)$; Y is $C(R^{12})$; and $R^3$ is $R^c$; or
   X is $C(R^{10})$; Y is $N^+$—$R^{14}(Z^-)$; and $R^3$ is $R^c$;

$R^1$ is $R^y$ or $(C_1$-$C_6)$alkyl that is substituted with one or more $R^y$;

$R^2$ is $R^z$ or $(C_1$-$C_6)$alkyl that is substituted with one or more $R^x$;

at least one of $R^4$, $R^5R^6$ and $R^7$ is aryl or heteroaryl wherein each aryl or heteroaryl is optionally substituted with one or more (e.g. 1, 2, 3, or 4) $R^d$; and the remainder of $R^4R^5R^6$ and $R^7$ are each independently H, halo, cyano, nitro, hydroxy, carboxy, trifluoromethyl, trifluoromethoxy, $(C_1$-$C_6)$alkyl, $(C_3$-$C_6)$cycloalkyl, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, $(C_1$-$C_6)$alkylthio, —S(O)$R^p$, —S(O)$_2R^p$, —S(O)$_3R^p$, —S(O)$_2$NR$^g$R$^h$, and —NR$^g$R$^h$; wherein any alkyl and any alkyl or alkanoyl portion of any aryl$(C_1$-$C_6)$alkyl, heteroaryl $(C_1$-$C_6)$alkyl, aryl$(C_1$-$C_6)$alkanoyl or heteroaryl$(C_1$-$C_6)$alkanoyl is optionally substituted with one or more (e.g. 1, 2, 3, or 4) $R^a$; and wherein any aryl, heteroaryl, or any aryl or heteroaryl portion of any aryl$(C_1$-$C_6)$alkyl, heteroaryl$(C_1$-

C$_6$)alkyl, aryl(C$_1$-C$_6$)alkanoyl or heteroaryl(C$_1$-C$_6$)alkanoyl of R$^4$, R$^5$, R$^6$ and R$^7$ is optionally substituted with one or more (e.g. 1, 2, 3, or 4) R$^b$;

R$^8$ is H, halo, cyano, nitro, hydroxy, carboxy, trifluoromethyl, trifluoromethoxy, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, (C$_1$-C$_6$)alkylthio, —S(O)R$^p$, —S(O)$_2$R$^p$, —S(O)$_3$R$^p$, —S(O)$_2$NR$^g$R$^h$, and —NR$^g$R$^h$; wherein any alkyl of R$^8$ is optionally substituted with one or more (e.g. 1, 2, 3, or 4) R$^a$; and wherein any aryl, or heteroaryl of R$^8$ is optionally substituted with one or more (e.g. 1, 2, 3, or 4) R$^b$;

each R$^{10}$ is H, halo, cyano, nitro, hydroxy, carboxy, trifluoromethyl, trifluoromethoxy, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^g$R$^h$; wherein any alkyl of R$^{10}$ is optionally substituted with one or more (e.g. 1, 2, 3, or 4) R$^a$; and wherein any aryl, heteroaryl, or any aryl or heteroaryl portion of any aryl(C$_1$-C$_6$)alkyl, heteroaryl(C$_1$-C$_6$)alkyl, aryloxy, or heteroaryloxy of R$^{10}$ is optionally substituted with one or more (e.g. 1, 2, 3, or 4) R$^b$;

each R$^{11}$ is H, halo, cyano, nitro, hydroxy, carboxy, trifluoromethyl, trifluoromethoxy, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^g$R$^h$; wherein any alkyl and any alkyl or alkanoyl portion of any aryl(C$_1$-C$_6$)alkyl, heteroaryl(C$_1$-C$_6$)alkyl, aryl(C$_1$-C$_6$)alkanoyl or heteroaryl(C$_1$-C$_6$)alkanoyl of R$^{11}$ is optionally substituted with one or more (e.g. 1, 2, 3, or 4) R$^a$; and wherein any aryl, heteroaryl, or any aryl or heteroaryl portion of any aryl(C$_1$-C$_6$)alkyl, heteroaryl(C$_1$-C$_6$)alkyl, aryl(C$_1$-C$_6$)alkanoyl or heteroaryl(C$_1$-C$_6$)alkanoyl of R$^{11}$ is optionally substituted with one or more (e.g. 1, 2, 3, or 4) R$^b$;

each R$^{12}$ is H, halo, cyano, nitro, hydroxy, carboxy, trifluoromethyl, trifluoromethoxy, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, aryloxy, heteroaryloxy, and —NR$^g$R$^h$; wherein any alkyl and any alkyl or alkanoyl portion of any aryl(C$_1$-C$_6$)alkyl, heteroaryl(C$_1$-C$_6$)alkyl, aryl(C$_1$-C$_6$)alkanoyl or heteroaryl(C$_1$-C$_6$)alkanoyl of R$^{12}$ is optionally substituted with one or more (e.g. 1, 2, 3, or 4) R$^a$; and wherein any aryl, heteroaryl, or any aryl or heteroaryl portion of any aryl(C$_1$-C$_6$)alkyl, heteroaryl(C$_1$-C$_6$)alkyl, aryl(C$_1$-C$_6$)alkanoyl or heteroaryl(C$_1$-C$_6$)alkanoyl of R$^{12}$ is optionally substituted with one or more (e.g. 1, 2, 3, or 4) R$^b$;

each R$^{13}$ is (C$_1$-C$_6$)alkyl, aryl, or aryl(C$_1$-C$_6$)alkyl;
each R$^{14}$ is (C$_1$-C$_6$)alkyl, aryl, or aryl(C$_1$-C$_6$)alkyl;
R$^{15}$ is R$^x$ or (C$_1$-C$_6$)alkyl that is substituted with one or more R$^x$;
R$^{16}$ is R$^z$ or (C$_1$-C$_6$)alkyl that is substituted with one or more R$^y$;
each R$^{30}$ is H or (C$_1$-C$_6$)alkyl,
each R$^{31}$ is —C(=NR$^{hb}$)—NR$^{hc}$R$^{hd}$, —NR$^{he}$—C(=NR$^{hb}$)—NR$^{hc}$R$^{hd}$, —NR$^{ke}$—C(=NR$^{kb}$)R$^{ke}$, or (C$_1$-C$_6$)alkyl which is substituted with one or more groups selected from —C(=NR$^{hb}$)—NR$^{hc}$R$^{hd}$, —NR$^{he}$—C(=NR$^{hb}$)—NR$^{hc}$R$^{hd}$, and —NR$^{ke}$—C(=NR$^{kb}$)R$^{ke}$;

each R$^a$ is independently selected from halo, cyano, nitro, hydroxy, carboxy, oxo, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, (C$_1$-C$_6$)alkylthio, —S(O)R$^p$, —S(O)$_2$R$^p$, —S(O)$_3$R$^p$, —S(O)$_2$NR$^g$R$^h$, and —NR$^g$R$^h$; wherein each aryl, heteroaryl, aryloxy, and heteroaryloxy is optionally substituted with one or more (e.g. 1, 2, 3, or 4) groups independently selected from halo, cyano, nitro, hydroxy, carboxy, trifluoromethyl, trifluoromethoxy, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, (C$_1$-C$_6$)alkylthio, —S(O)R$^p$, —S(O)$_2$R$^p$, —S(O)$_3$R$^p$, —S(O)$_2$NR$^g$R$^h$, and —NR$^g$R$^h$;

each R$^b$ is independently selected from halo, cyano, nitro, hydroxy, carboxy, trifluoromethyl, trifluoromethoxy, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, (C$_1$-C$_6$)alkylthio, —S(O)R$^p$, —S(O)$_2$R$^p$, —S(O)$_3$R$^p$, —S(O)$_2$NR$^g$R$^h$, and —NR$^g$R$^h$; wherein each aryl, heteroaryl, aryloxy, and heteroaryloxy is optionally substituted with one or more (e.g. 1, 2, 3, or 4) groups independently selected from halo, cyano, nitro, hydroxy, carboxy, trifluoromethyl, trifluoromethoxy, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, (C$_1$-C$_6$)alkylthio, —S(O)R$^p$, —S(O)$_2$R$^p$, —S(O)$_3$R$^p$, —S(O)$_2$NR$^g$R$^h$, and —NR$^g$R$^h$;

each R$^c$ is H, halo, cyano, nitro, hydroxy, carboxy, trifluoromethyl, trifluoromethoxy, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, aryl other than phenyl, heteroaryl other than pyrid-4-yl, aryloxy, heteroaryloxy, and —NR$^g$R$^h$; wherein any alkyl and any alkyl or alkanoyl portion of any aryl(C$_1$-C$_6$)alkyl, heteroaryl(C$_1$-C$_6$)alkyl, aryl(C$_1$-C$_6$)alkanoyl or heteroaryl(C$_1$-C$_6$)alkanoyl of R$^c$ is optionally substituted with one or more (e.g. 1, 2, 3, or 4) R$^a$; and wherein any aryl, heteroaryl, or any aryl or heteroaryl portion of any aryl(C$_1$-C$_6$)alkyl, heteroaryl(C$_1$-C$_6$)alkyl, aryl(C$_1$-C$_6$)alkanoyl or heteroaryl(C$_1$-C$_6$)alkanoyl of R$^c$ is optionally substituted with one or more (e.g. 1, 2, 3, or 4) R$^b$;

each R$^d$ is independently selected from halo, cyano, nitro, hydroxy, carboxy, trifluoromethyl, trifluoromethoxy, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^g$R$^h$; wherein each aryl, heteroaryl, aryloxy, and heteroaryloxy is optionally substituted with one or more (e.g. 1, 2, 3, or 4) groups independently selected from halo, cyano, nitro, hydroxy, carboxy, trifluoromethyl, trifluoromethoxy, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, and —NR$^g$R$^h$;

each R$^e$ is H, halo, cyano, nitro, hydroxy, carboxy, trifluoromethyl, trifluoromethoxy, (C$_1$-C$_6$)alkyl, (C$_3$-C$_6$)cycloalkyl, (C$_1$-C$_6$)alkoxy, (C$_1$-C$_6$)alkoxycarbonyl, (C$_1$-C$_6$)alkanoyloxy, aryl, heteroaryl, aryloxy, heteroaryloxy, and —NR$^g$R$^h$; wherein any alkyl and any alkyl or alkanoyl portion of any aryl(C$_1$-C$_6$)alkyl, heteroaryl(C$_1$-C$_6$)alkyl, aryl(C$_1$-C$_6$)alkanoyl or heteroaryl(C$_1$-C$_6$)alkanoyl of R$^e$ is optionally substituted with one or more (e.g. 1, 2, 3, or 4) R$^a$; and wherein any aryl, heteroaryl, or any aryl or heteroaryl portion of any aryl(C$_1$-C$_6$)alkyl, heteroaryl(C$_1$-C$_6$)alkyl, aryl(C$_1$-C$_6$)alkanoyl or heteroaryl(C$_1$-C$_6$)alkanoyl of R$^e$ is optionally substituted with one or more (e.g. 1, 2, 3, or 4) R$^b$;

each R$^g$ and R$^h$ is independently selected from H, (C$_1$-C$_6$)alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl and heteroaryl(C$_1$-C$_6$)alkyl; or R$^g$ and R$^h$ together with the nitrogen to which they are attached form a aziridino, azetidino, morpholino, piperazino, pyrrolidino or piperidino; wherein any (C$_1$-C$_6$)alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl or heteroaryl(C$_1$-C$_6$)alkyl of R$^g$ and R$^h$ is optionally substituted with one or more groups independently selected from hydroxy, carboxy, and NR$^t$R$^u$;

each R$^j$ is independently selected from H, (C$_1$-C$_6$)alkyl, (C$_3$-C$_6$)cycloalkyl, (C$_3$-C$_6$)cycloalkyl(C$_1$-C$_6$)alkyl, aryl, heteroaryl, aryl(C$_1$-C$_6$) alkyl and heteroaryl(C$_1$-C$_6$)alkyl;

each R$^m$ and R$^n$ is independently selected from H, (C$_1$-C$_6$) alkyl, (C$_3$-C$_6$)cycloalkyl, (C$_3$-C$_6$)cycloalkyl(C$_1$-C$_6$)alkyl, aryl, heteroaryl, aryl($C_1$-$C_6$) alkyl and heteroaryl($C_1$-$C_6$) alkyl; or $R^m$ and $R^n$ together with the nitrogen to which they are attached form a aziridino, azetidino, morpholino, piperazino, pyrrolidino or piperidino; wherein any ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl or heteroaryl($C_1$-$C_6$) alkyl of $R^m$ and $R^n$ is optionally substituted with one or more groups independently selected from hydroxy, carboxy, and $NR'R''$;

each $R^p$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$) alkyl;

each $R^q$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^s$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^t$ and $R^u$ is independently selected from H, ($C_1$-$C_6$) alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$) alkyl; or $R^t$ and $R^u$ together with the nitrogen to which they are attached form a aziridino, azetidino, morpholino, piperazino, pyrrolidino or piperidino;

each $R^x$ is independently $-NR'''R''$, $-N^+(R^s)_3Z^-$, $-C(=NR^j)-NR'''R''$, or $-NR^q-C(=NR^j)-NR'''R''$;

each $R^y$ is independently $-NR'''R''$, $-N^+(R^s)_3Z^-$, $-C(=NR^j)-NR'''R''$, or $-NR^q-C(=NR^j)-NR'''R''$;

each $R^z$ is independently $-C(=NR^j)-NR'''R''$, or $-NR^q-C(=NR^j)-NR'''R''$;

each $R^{hb}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{hc}$ and $R^{hd}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-$C_6$) alkyl; or $R^{hc}$ and $R^{hd}$ together with the nitrogen to which they are attached form a aziridino, azetidino, morpholino, piperazino, pyrrolidino or piperidino; wherein any ($C_1$-$C_6$) alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl or heteroaryl($C_1$-$C_6$)alkyl of $R^{hc}$ and $R^{hd}$ is optionally substituted with one or more groups independently selected from hydroxy, carboxy, and $NR^{hm}R^{hn}$;

each $R^{he}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{hm}$ and $R^{hn}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-$C_6$) alkyl; or $R^{hm}$ and $R^{hn}$ together with the nitrogen to which they are attached form a aziridino, azetidino, morpholino, piperazino, pyrrolidino or piperidino;

each $R^{kb}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{ke}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

the bond represented by ---- is present; and each $Z^-$ is independently an acceptable counterion;

b) wherein:

X is W—$R^{51}$;

Y is C($R^{52}$);

W is N; $R^{51}$ is absent; or

W is $N^+D^-$; $R^{51}$ is ($C_1$-$C_6$)alkyl, aryl, or aryl($C_1$-$C_6$)alkyl; or W is C; $R^{51}$ is hydrogen, $-N^+(R^{5a})_3D^-$, $-C(=NR^{5b})-NR^{5c}R^{5d}$, $-NR^{5c}-C(=NR^{5b})-NR^cR^d$, $-NR^{5g}R^{5h}$, $-NR^{5ce}-C(=NR^{5cb})R^{5ce}$, $-NR^{5ce}-C(=O)-NR^{5cc}R^{5cd}$, or ($C_1$-$C_6$)alkyl that is substituted with one or more $R^{5f}$;

$R^{52}$ is a ring selected from phenyl, pyridyl, and [$D^-N^+$—($C_1$-$C_6$)alkylpyridyl], which ring is optionally substituted with one or more groups selected from methylenedioxy, Z—$R^{5x}$, $R^{5f}$, $R^{5da}$, and ($C_1$-$C_6$)alkyl that is substituted with one or more $R^{5f}$; and which ring is also optionally substituted with a group $R^{6'}$ at a position ortho to the position where $R^{52}$ connects with the remainder of formula I;

$R^6$ and $R^7$ taken together can be methylenedioxy or each $R^6$ and $R^7$ is independently selected from H, Z—$R^{5x}$, $R^{5f}$, and ($C_1$-$C_6$)alkyl that is substituted with one or more $R^{5f}$;

$R^8$ is hydrogen, ($C_1$-$C_6$)alkyl, aryl, or aryl($C_1$-$C_6$)alkyl wherein each ($C_1$-$C_6$)alkyl of $R^8$ is optionally substituted with one or more groups independently selected from halo, hydroxy, cyano, nitro, ($C_1$-$C_6$)alkoxy, ($C_3$-$C_6$)cycloalkyl, oxo, carboxy, aryloxy, sulfo, and $-NR^{5g}R^{5h}$, and wherein each aryl of $R^8$ is optionally substituted with one or more groups independently selected from ($C_1$-$C_6$)alkyl, halo, hydroxy, cyano, nitro, ($C_1$-$C_6$)alkoxy, ($C_3$-$C_6$)cycloalkyl, carboxy, aryloxy, nitro, $R^{5s}$, and $-NR^{5g}R^{5h}$;

each Z is independently selected from $-O-$, $-S-$, and $-N(R^{5y})-$;

at least one of $R^3$, $R^4$, $R^5$, and $R^{6'}$ is selected from hydroxy, carboxy, cyano, $CF_3SO_3-$, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, aryl($C_1$-$C_6$)alkyl, aryl, heteroaryl, heteroaryl($C_1$-$C_6$)alkyl, aryl($C_1$-$C_6$)alkanoyl, and heteroaryl($C_1$-$C_6$)alkanoyl; and the remainder of $R^3$, $R^4$, $R^5$, and $R^{6'}$ are independently selected from H, hydroxy, carboxy, cyano, $CF_3SO_3-$, ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, aryl($C_1$-$C_6$)alkyl, aryl, heteroaryl, heteroaryl($C_1$-$C_6$)alkyl, aryl($C_1$-$C_6$)alkanoyl, and heteroaryl($C_1$-$C_6$)alkanoyl; wherein each ($C_1$-$C_6$)alkyl, ($C_2$-$C_6$)alkenyl, ($C_2$-$C_6$)alkynyl, ($C_1$-$C_6$)alkoxy, ($C_3$-$C_6$)cycloalkyl, and ($C_1$-$C_6$)alkanoyl of $R^3$, $R^4$, $R^5$, and $R^{6'}$ is optionally substituted with one or more groups independently selected from halo, hydroxy, cyano, nitro, ($C_1$-$C_6$)alkoxy, ($C_3$-$C_6$)cycloalkyl, oxo, carboxy, aryloxy, sulfo, $-S(O)_2NR^{5g}R^{5h}$, $-N(R^{5j})S(O)_2R^{5k}$, $-N^+(R^{5a})_3D^-$, $-C(=NR^{5b})-NR^{5c}R^{5d}$, or $-NR^{5e}-C(=NR^{5b})-NR^{5c}R^{5d}$ and $-NR^{5g}R^{5h}$; and wherein each aryl and heteroaryl of $R^3$, $R^4$, $R^5$, and $R^{6'}$ is optionally substituted with one or more groups independently selected from ($C_1$-$C_6$)alkyl, halo, hydroxy, cyano, nitro, ($C_1$-$C_6$)alkoxy, ($C_3$-$C_6$) cycloalkyl, carboxy, aryloxy, nitro, sulfo, $-S(O)_2NR^{5g}R^{5h}$, $-N(R^{5j})S(O)_2R^{5k}$, $R^{5s}$, $-N^+(R^{5a})_3D^-$, $-C(=NR^{5b})-NR^{5c}R^{5d}$, or $-NR^{5e}-C(=NR^{5b})-NR^{5c}R^{5d}$, $-NR^{5g}R^{5h}$, and ($C_1$-$C_6$)alkyl substituted with one or more groups independently selected from $-N^+(R^{5a})_3D^-$, $-C(=NR^{5b})-NR^{5c}R^{5d}$, or $-NR^{5e}-C(=NR^{5b})-NR^{5c}R^{5d}$, and $-NR^{5g}R^{5h}$;

each $R^{5a}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{5b}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{5c}$ and $R^{5d}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-$C_6$) alkyl; or $R^{5c}$ and $R^{5d}$ together with the nitrogen to which they are attached form a aziridino, azetidino, morpholino, piperazino, pyrrolidino or piperidino; wherein any ($C_1$-$C_6$) alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl or heteroaryl($C_1$-$C_6$)alkyl of $R^{5c}$ and $R^{5d}$ is optionally substituted with one or more groups independently selected from hydroxy, carboxy, and $NR^{5m}R^{5n}$;

each $R^{5e}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{5f}$ is independently selected from —$N^+(R^{5a})_3D^-$, —C(=$NR^{5b}$)—$NR^{5c}R^{5d}$, —$NR^{5e}$—C(=$NR^{5b}$)—$NR^{5c}R^{5d}$, —$NR^{5ce}$—C(=$NR^{5cb}$)$R^{5ce}$, —$NR^{5ce}$—C(=O)—$NR^{5cc}R^{5cd}$, and —$NR^gR^h$;

each $R^{5g}$ and $R^{5h}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$) alkyl; or $R^{5g}$ and $R^{5h}$ together with the nitrogen to which they are attached form a aziridino, azetidino, morpholino, piperazino, pyrrolidino or piperidino; wherein any ($C_1$-$C_6$) alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl or heteroaryl($C_1$-$C_6$)alkyl of $R^{5g}$ and $R^{5h}$ is optionally substituted with one or more groups independently selected from hydroxy, carboxy, and $NR^{5m}R^{5n}$;

each $R^{5j}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{5k}$ is independently selected from ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{5m}$ and $R^{5n}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$) alkyl; or $R^{5m}$ and $R^{5n}$ together with the nitrogen to which they are attached form a aziridino, azetidino, morpholino, piperazino, pyrrolidino or piperidino;

each $R^{5s}$ is independently trifluoromethyl, trifluoromethoxy, aryl, or heteroaryl, wherein each aryl and heteroaryl is optionally substituted with one or more ($C_1$-$C_6$) alkyl, halo, hydroxy, cyano, nitro, ($C_1$-$C_6$)alkoxy, ($C_3$-$C_6$)cycloalkyl, carboxy, aryloxy, nitro, sulfo, —$S(O)_2NR^{5g}R^{5h}$—$N(R^{5j})S(O)_2R^{5k}$, trifluoromethyl, trifluoromethoxy, —$N^+(R^{5a})_3D^-$, —C(=$NR^{5b}$)—$NR^cR^d$, —$NR^{5e}$—C(=$NR^{5b}$)—$NR^{5c}R^{5d}$ and —$NR^{5g}R^{5h}$;

each $R^{5u}$ and $R^{5v}$ is independently selected from H and ($C_1$-$C_6$)alkyl;

each $R^{5x}$ is independently selected from ($C_1$-$C_6$)alkyl, ($C_1$-$C_6$)alkanoyl, and —C(=O)$NR^{5u}R^{5v}$;

each $R^{5y}$ is independently selected from H and ($C_1$-$C_6$) alkyl;

each $D^-$ is independently a counter anion;

each $R^{5cb}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{5cc}$ and $R^{5cd}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-$C_6$) alkyl; or $R^{5cc}$ and $R^{5cd}$ together with the nitrogen to which they are attached form a aziridino, azetidino, morpholino, piperazino, pyrrolidino or piperidino; wherein any ($C_1$-$C_6$) alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl or heteroaryl($C_1$-$C_6$)alkyl of $R^{5cc}$ and $R^{5cd}$ is optionally substituted with one or more groups independently selected from hydroxy, carboxy, and $NR^{5cm}R^{5cn}$;

each $R^{5ce}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{5cm}$ and $R^{5cn}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl($C_1$-$C_6$) alkyl; or $R^{5cm}$ and $R^{5cn}$ together with the nitrogen to which they are attached form a aziridino, azetidino, morpholino, piperazino, pyrrolidino or piperidino;

each $R^{5da}$ is carboxy or ($C_1$-$C_6$)alkoxycarbonyl;

the bond represented by ---- is present;

c) wherein:

X is $^+N(R^{81})(R^{82})B^-$;

Y is C($R^{83}$);

$R^3$ is:

A is N or C—$R^{4'}$;

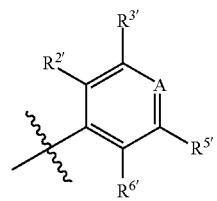

any adjacent $R^6$, $R^7$, $R^8$, $R^{4'}$ and $R^{5'}$ taken together can optionally be methylenedioxy and each remaining $R^6$, $R^7$, $R^8$, $R^{4'}$ and $R^{5'}$ is independently selected from H, fluoro, $R^{8bb}$, and Z—$R^{8x}$;

each Z is independently selected from —O—, —S—, and —N($R^{8y}$)—;

at least one of $R^4$, $R^5$, $R^{2'}$, $R^{3'}$, and $R^{6'}$ is selected from hydroxy, carboxy, cyano, $CF_3SO_3$—, ($C_1$-$C_6$)alkyl, ($C_2$-$C_6$) alkenyl, ($C_2$-$C_6$)alkynyl, ($C_1$-$C_6$)alkoxy, cycloalkyl, aryl($C_1$-$C_6$)alkyl, aryl, heteroaryl, heteroaryl($C_1$-$C_6$)alkyl, arylalkanoyl, and heteroarylalkanoyl; and the remainder of $R^4$, $R^5$, $R^{2'}$, $R^{3'}$, and $R^{6'}$ are independently selected from hydrogen, halo, hydroxy, carboxy, cyano, $CF_3SO_3$—, ($C_1$-$C_6$)alkyl, ($C_2$-$C_6$)alkenyl, ($C_2$-$C_6$)alkynyl, ($C_1$-$C_6$)alkoxy, cycloalkyl, aryl($C_1$-$C_6$)alkyl, aryl, heteroaryl, heteroaryl($C_1$-$C_6$)alkyl, aryl($C_1$-$C_6$)alkanoyl, and heteroaryl($C_1$-$C_6$)alkanoyl; or $R^{6'}$ and $R^{81}$ taken together are —(CR$^{13}_2$)$_2$— or —CR$^{14}$=CR$^{14}$—; wherein each ($C_1$-$C_6$)alkyl, ($C_2$-$C_6$)alkenyl, ($C_2$-$C_6$)alkynyl, ($C_1$-$C_6$)alkoxy, cycloalkyl, and ($C_1$-$C_6$) alkanoyl of $R^4$, $R^5$, $R^{2'}$, $R^{3'}$, and $R^{6'}$ is optionally substituted with one or more groups independently selected from halo, hydroxy, cyano, nitro, ($C_1$-$C_6$)alkoxy, cycloalkyl, oxo, carboxy, aryloxy, sulfo, —$S(O)_2NR^{8g}R^{8h}$, —$N(R^{8j})S(O)_2R^{8k}$, and —$NR^{8g}R^{8h}$; and wherein each aryl, and heteroaryl of $R^4$, $R^5$, $R^{2'}$, $R^{3'}$, and $R^{6'}$ is optionally substituted with one or more groups independently selected from ($C_1$-$C_6$)alkyl, halo, hydroxy, cyano, nitro, ($C_1$-$C_6$)alkoxy, cycloalkyl, carboxy, aryloxy, nitro, sulfo, $R^{8aa}$, —$S(O)_2NR^{8g}R^{8h}$, —$N(R^{8j})S(O)_2R^{8k}$, and —$NR^{8g}R^{8h}$;

the bond represented by ---- is present and $R^{82}$ is absent except as defined below when $R^{81}$ and $R^{8a}$ taken together with the atoms to which they are attached form a 5- or 6-membered heterocyclic ring or a 5- or 6-membered heteroaryl ring;

$R^{81}$ is absent and $B^-$ is absent; or $R^{81}$ is H or ($C_1$-$C_6$)alkyl and $B^-$ is counterion;

or $R^{81}$ and $R^{8a}$ taken together with the atoms to which they are attached form a 5- or 6-membered heterocyclic ring or a 5- or 6-membered heteroaryl ring, wherein a) when the bond represented by ---- is present in the 5- or 6-membered heterocyclic ring or the 5- or 6-membered heteroaryl ring, $R^{82}$ is absent and $B^-$ is a counterion, b) when the bond represented by ---- is absent in the 5- or 6-membered heterocyclic ring or the 5- or 6-membered heteroaryl ring, $R^{82}$ is ($C_1$-$C_6$)alkyl and B⁻ is a counterion, or c) when the bond represented by ---- is absent in the 5- or 6-membered heterocyclic ring or the 5- or 6-membered heteroaryl ring, $R^{82}$ is absent and B⁻ is absent;

$R^{83}$ is H, $(C_1-C_6)$alkyl, $(C_1-C_6)$alkoxy, $(C_1-C_6)$alkylthio, aryloxy, arylthio, —$NR^{8a}R^{8b}$, $R^{8cc}$, or cyano; or $R^{6'}$ and $R^{83}$ taken together are —$(CR^{13}{}_2)_2$— or —$CR^{14}$=$CR^{14}$—;

each $R^{13}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{13}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^{8e}R^{8f}$, and wherein any aryloxy, or arylthio of $R^{13}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^{8e}R^{8f}$;

each $R^{14}$ is independently H, $(C_1-C_6)$alkyl, $(C_1-C_6)$alkoxy, $(C_1-C_6)$alkylthio, aryloxy or arylthio wherein any $(C_1-C_6)$alkyl, $(C_1-C_6)$alkoxy, and $(C_1-C_6)$alkylthio of $R^{14}$ is optionally substituted with one or more groups selected from halo, cyano, oxo (=O), $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^{8e}R^{8f}$, and wherein any aryloxy, or arylthio of $R^{14}$ is optionally substituted with one or more groups selected from halo, cyano, $(C_1-C_6)$alkyl, $(C_3-C_6)$cycloalkyl, carboxy, $NO_2$, hydroxy, $(C_1-C_6)$alkoxy, $(C_1-C_6)$alkoxycarbonyl, $(C_1-C_6)$alkanoyloxy, aryl, heteroaryl, aryloxy, heteroaryloxy, and —$NR^{8e}R^{8f}$;

$R^{8a}$ is hydrogen, $(C_1-C_6)$alkyl, aryl, aryl$(C_1-C_6)$alkyl, heteroaryl, or heteroaryl$(C_1-C_6)$alkyl; wherein each $(C_1-C_6)$alkyl of $R^{8a}$ is optionally substituted with one or more groups selected from halo, hydroxy, cyano, nitro, $(C_1-C_6)$alkoxy, cycloalkyl, oxo, carboxy, —$NR^{8g}R^{8h}$, and aryloxy, and wherein each aryl and heteroaryl of $R^{8a}$ is optionally substituted with one or more groups selected from $(C_1-C_6)$alkyl, halo, hydroxy, cyano, nitro, $(C_1-C_6)$alkoxy, cycloalkyl, carboxy, —$NR^{8g}R^{8h}$, and aryloxy;

$R^{8b}$ is hydrogen, $(C_1-C_6)$alkyl, aryl, aryl$(C_1-C_6)$alkyl, heteroaryl, heteroaryl$(C_1-C_6)$alkyl, —C(=O)—$R^{8m}$, —C(=O)—$OR^{8n}$, —C(=O)—$SR^{8p}$, —C(=O)—$NR^{8q}R^{8r}$, —C(=S)—$R^{8m}$, —C(=S)—$OR^{8n}$, —C(=S)—$SR^{8p}$, —C(=S)—$NR^{8q}R^{8r}$, or —C(=$NR^{8c}$)—$R^{8d}$; wherein each $(C_1-C_6)$alkyl of $R^{8b}$ is optionally substituted with one or more groups independently selected from halo, hydroxy, cyano, nitro, $(C_1-C_6)$alkoxy, cycloalkyl, oxo, carboxy, and aryloxy; and wherein each aryl, and heteroaryl of $R^{8b}$ is optionally substituted with one or more groups independently selected from $(C_1-C_6)$alkyl, halo, hydroxy, cyano, nitro, $(C_1-C_6)$alkoxy, cycloalkyl, carboxy, and aryloxy; or $R^{8a}$ and $R^{8b}$ taken together with the nitrogen to which they are attached form aziridino, azetidino, morpholino, piperazino, pyrrolidino, pyrrole, indole, or piperidino, which aziridino, azetidino, morpholino, piperazino, pyrrolidino pyrrole, indole, or piperidino can optionally be substituted with one or more $(C_1-C_6)$alkyl;

$R^{8c}$ is hydrogen, $(C_1-C_6)$alkyl, aryl, or heteroaryl;

$R^{8d}$ is hydrogen, $(C_1-C_6)$alkyl, $(C_1-C_6)$alkoxy, $(C_1-C_6)$alkylthio, $(C_1-C_6)$alkanoyl, or —$NR^{8e}R^{8f}$;

$R^{8e}$ and $R^{8f}$ are each independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; or $R^{8e}$ and $R^{8f}$ together with the nitrogen to which they are attached form a aziridino, azetidino, morpholino, piperazino, pyrrolidino or piperidino;

each $R^{8g}$ and $R^{8h}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; or $R^g$ and $R^h$ together with the nitrogen to which they are attached form a aziridino, azetidino, morpholino, piperazino, pyrrolidino or piperidino;

each $R^{8j}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl;

each $R^{8k}$ is independently selected from $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl;

each $R^{8m}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl;

each $R^{8n}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl, wherein each aryl, and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —$S(O)_2NR^{8g}R^{8h}$, —$N(R^{8j})S(O)_2R^{8k}$, and —$NR^{8g}R^{8h}$;

each $R^{8p}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl, wherein each aryl, and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —$S(O)_2NR^{8g}R^{8h}$, —$N(R^{8j})S(O)_2R^{8k}$, and —$NR^{8g}R^{8h}$;

each $R^{8q}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; and each $R^{8r}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; or $R^{8q}$ and $R^{8r}$ together with the nitrogen to which they are attached form a aziridino, azetidino, morpholino, piperazino, pyrrolidino or piperidino;

each $R^{8u}$ and $R^{8v}$ is independently selected from H and $(C_1-C_6)$alkyl;

each $R^{8x}$ is independently selected from $(C_1-C_6)$alkyl, $(C_1-C_6)$alkanoyl, and —C(=O)$NR^uR^v$;

each $R^{8y}$ is independently selected from H and $(C_1-C_6)$alkyl;

each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —$S(O)_2NR^{8g}R^{8h}$, —$N(R^j)S(O)_2R^{8k}$, and —$NR^{8g}R^{8h}$;

each $R^{8bb}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —$S(O)_2NR^{8g}R^{8h}$—$N(R^{8j})S(O)_2R^{8k}$, and —$NR^{8g}R^{8h}$;

$R^{8cc}$ is $(C_1-C_6)$alkyl which is substituted with one or more —$N^+(R^{8ha})_3B^-$, —C(=$NR^{8hb}$)—$NR^{8hc}R^{8hd}$, —$NR^{8he}$—C(=$NR^{8hb}$)—$NR^{8hc}R^{8hd}$, —$NR^{8ke}$—C(=$NR^{8kb}$)$R^{8ke}$, or —$NR^{8ke}$—C(=O)—$NR^{8kc}R^{8kd}$;

each $R^{8ha}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{8hb}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{8hc}$ and $R^{8hd}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; or $R^{8hc}$ and $R^{8hd}$ together with the nitrogen to which they are attached form a aziridino, azetidino, morpholino, piperazino, pyrrolidino or piperidino; wherein any $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{hc}$ and $R^{hd}$ is optionally substituted with one or more groups independently selected from hydroxy, carboxy, and $NR^{hm}R^{hn}$;

each $R^{8he}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{8hm}$ and $R^{8hn}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^{8hm}$ and $R^{8hn}$ together with the nitrogen to which they are attached form a aziridino, azetidino, morpholino, piperazino, pyrrolidino or piperidino;

each $R^{8kb}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{8kc}$ and $R^{8kd}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; or $R^{8kc}$ and $R^{8kd}$ together with the nitrogen to which they are attached form a aziridino, azetidino, morpholino, piperazino, pyrrolidino or piperidino; wherein any $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{8kc}$ and $R^{8kd}$ is optionally substituted with one or more groups independently selected from hydroxy, carboxy, and $NR^{8km}R^{8kn}$;

each $R^{8ke}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; and each $R^{8km}$ and $R^{8kn}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^{8km}$ and $R^{8kn}$ together with the nitrogen to which they are attached form a aziridino, azetidino, morpholino, piperazino, pyrrolidino or piperidino;

each $B^-$ is a counterion; and or a salt or prodrug thereof.

A specific compound of the invention is a compound of formula (Ia) or (Ib):

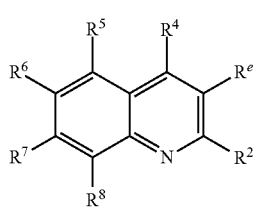
(Ia)

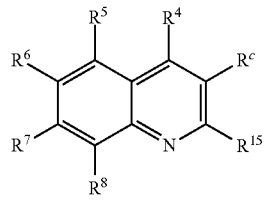
(Ib)

or a salt or prodrug thereof.

A specific compound of the invention is a compound of formula (Ic):

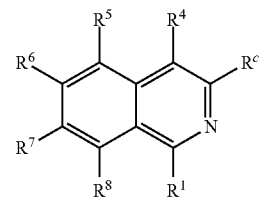
(Ic)

or a salt or prodrug thereof.

A specific compound of the invention is a compound of formula (Id) or (Ie):

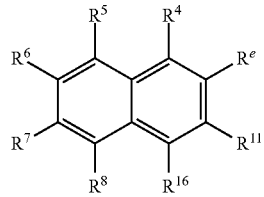
(Id)

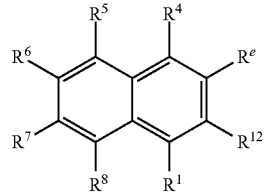
(Ie)

or a salt or prodrug thereof.

A specific compound of the invention is a compound of formula (If) or (Ig):

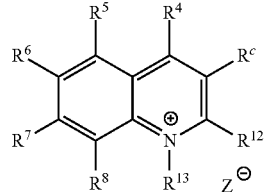
(If)

-continued

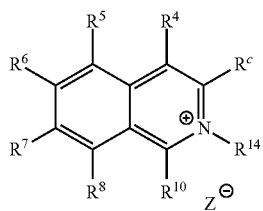

(Ig)

or a salt or prodrug thereof.

A specific compound of the invention is a compound of formula (Ih):

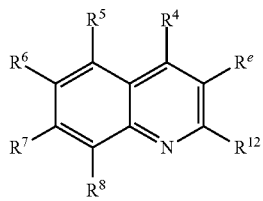

(Ih)

or a salt or prodrug thereof.

A specific compound of the invention is a compound of formula (Ij):

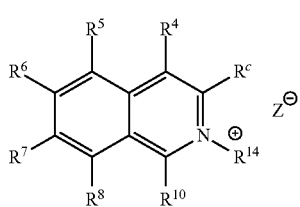

(Ij)

or a salt or prodrug thereof.

A specific compound of the invention is a compound of formula (Ik):

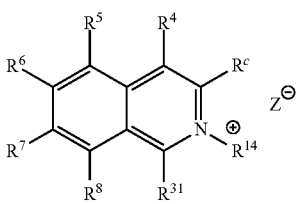

(Ik)

or a salt or prodrug thereof.

A specific compound of the invention is a compound of formula (Im):

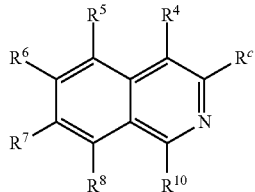

(Im)

or a salt or prodrug thereof.

A specific compound of the invention is a compound of formula (In):

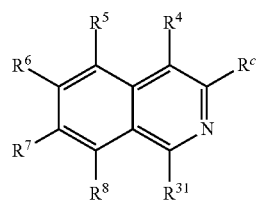

(In)

or a salt or prodrug thereof.

A specific compound of the invention is a compound of formula:

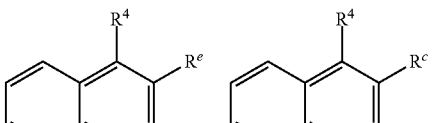

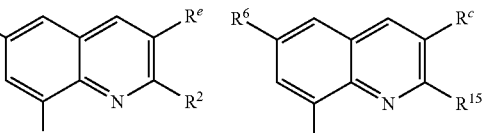

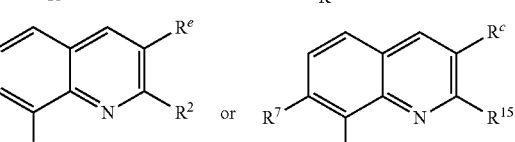

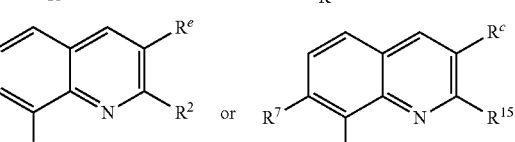

or a salt or prodrug thereof.

A specific compound of the invention is a compound of formula:

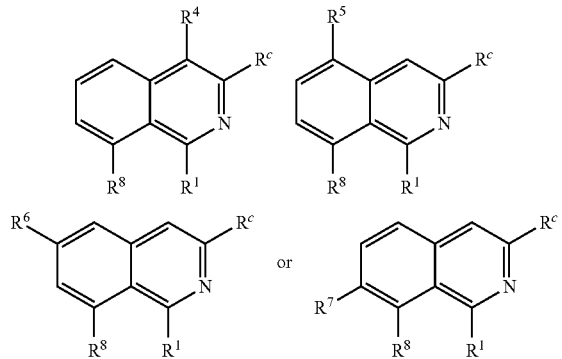

or a salt or prodrug thereof.

A specific compound of the invention is a compound of formula:

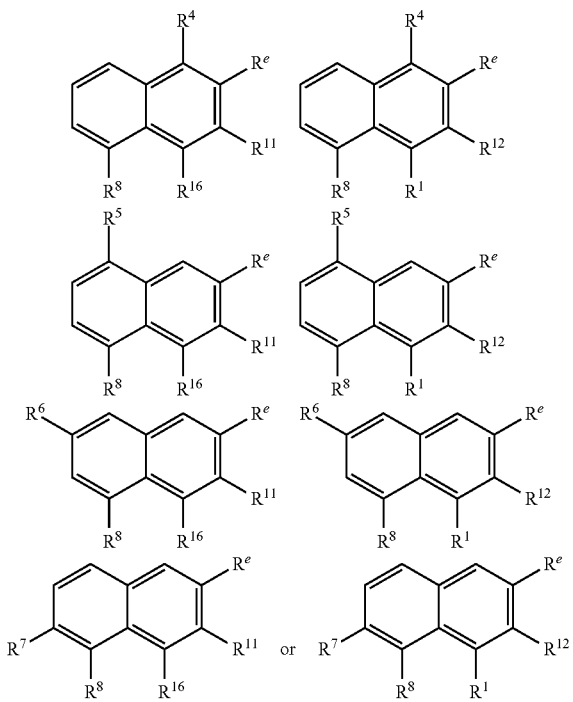

or a salt or prodrug thereof.

A specific compound of the invention is a compound of formula:

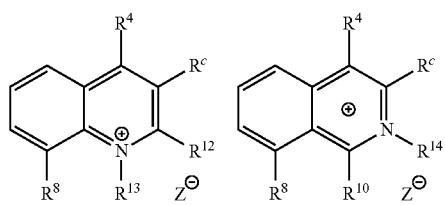

-continued

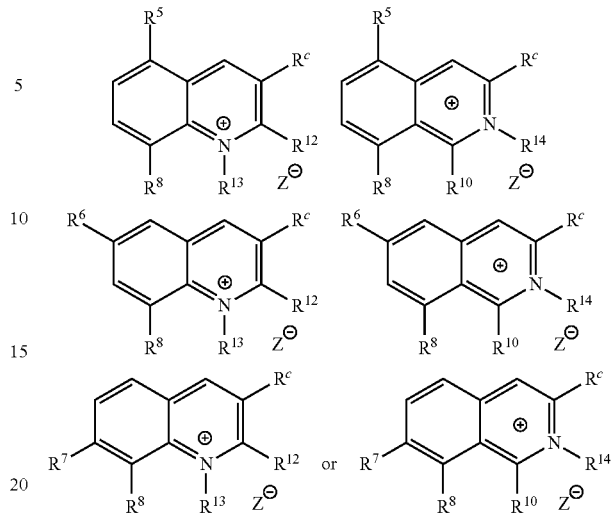

or a salt or prodrug thereof.

A specific value for $R^4$ is phenyl, biphenyl, cyclopropyl, tert-butylphenyl, or furyl.

A specific value for $R^5$ is phenyl, biphenyl, cyclopropyl, tert-butylphenyl, or furyl.

A specific value for $R^6$ is phenyl, biphenyl, cyclopropyl, tert-butylphenyl, or furyl.

A specific value for $R^7$ is phenyl, biphenyl, cyclopropyl, tert-butylphenyl, or furyl.

A specific value for $R^x$ is —$NR'''R''$.

A specific value for $R^x$ is —$N^+(R^s)_3 Z^-$.

A specific value for $R^x$ is —$C(=NR^j)$—$NR'''R''$.

A specific value for $R^x$ is —$NR^q$—$C(=NR^j)$—$NR'''R''$.

A specific value for $R^y$ is —$NR'''R''$.

A specific value for $R^y$ is —$N^+(R^s)_3 Z^-$.

A specific value for $R^y$ is —$C(=NR^j)$—$NR'''R''$.

A specific value for $R^y$ is —$NR^q$—$C(=NR^j)$—$NR'''R''$.

A specific value for $R^z$ is —$C(=NR^j)$—$NR'''R''$.

A specific value for $R^z$ is —$NR^q$—$C(=NR^j)$—$NR'''R''$

A specific compound of the invention is a compound which is:

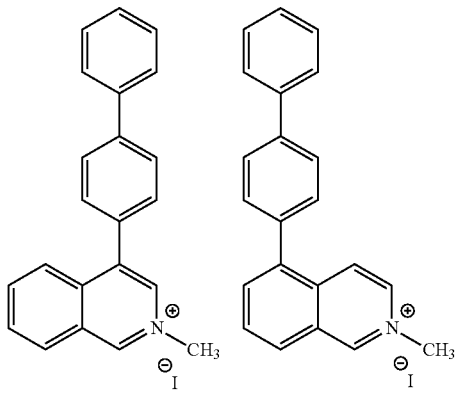

-continued
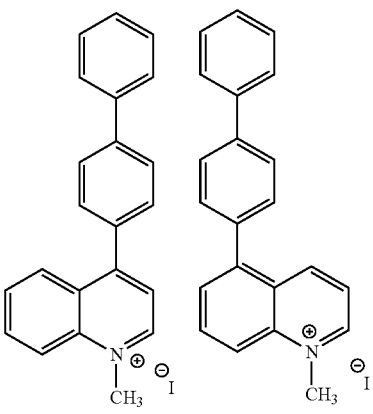
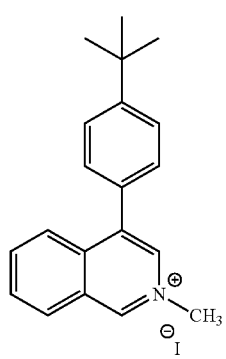
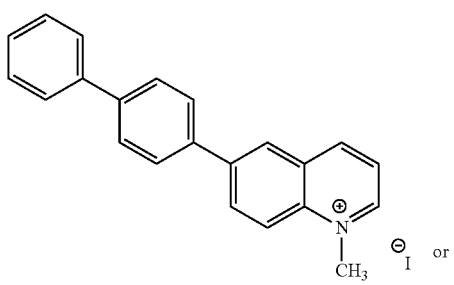
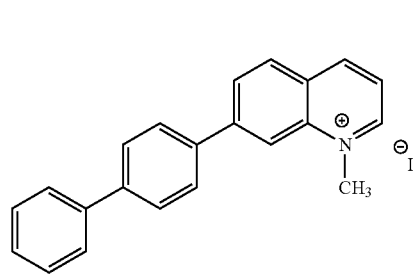 or
or a salt or prodrug thereof.
A specific compound of the invention is a compound which is:
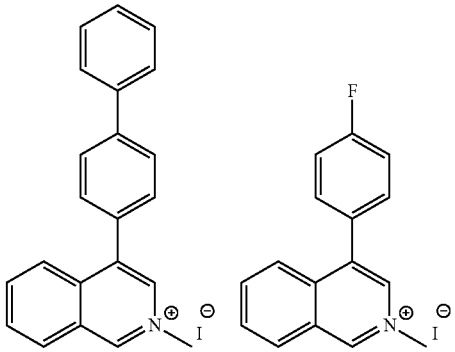
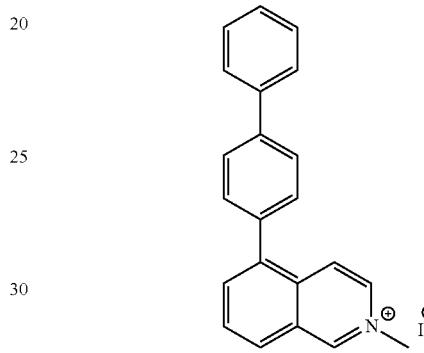
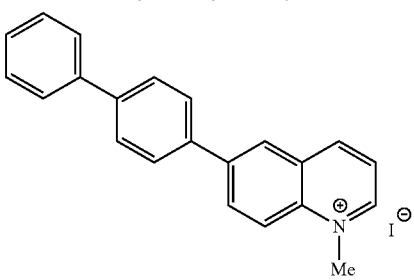
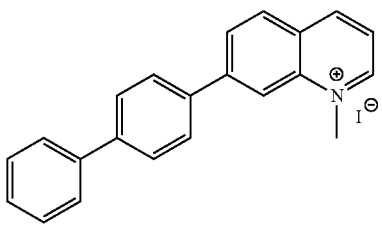
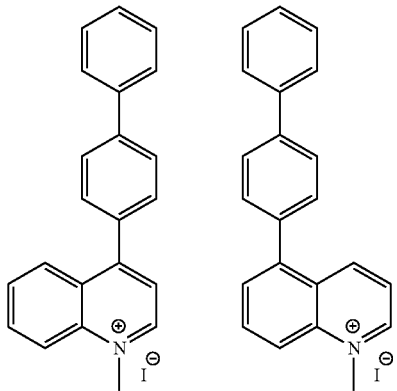

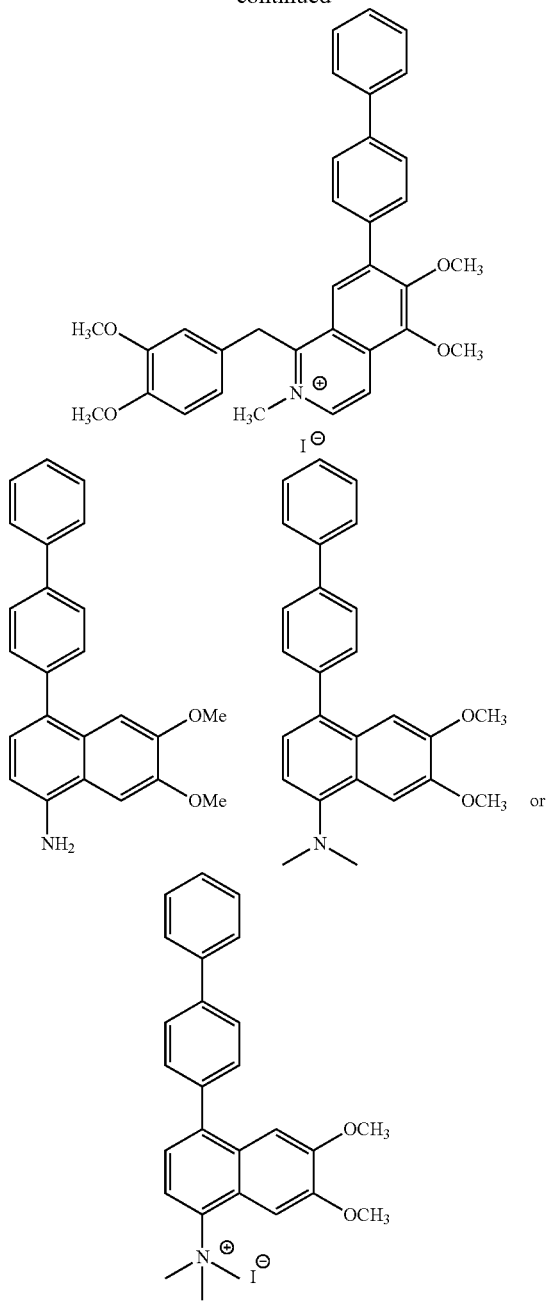

or a salt or prodrug thereof.

A specific value for $Z^-$ is: $Cl^-$, $Br^-$, $I^-$, $CH_3SO_3^-$, $CF_3SO_3^-$, $p\text{-}CH_3C_6H_4SO_3^-$, citrate, tartrate, malate, fumarate, formate, or acetate.

A specific compound of the invention is a compound of formula (I): wherein:

$R^1$ is $R^y$ or $(C_1\text{-}C_6)$alkyl that is substituted with one or more $R^y$;

$R^2$ is $R^z$ or $(C_1\text{-}C_6)$alkyl that is substituted with one or more $R^x$;

at least one of $R^4$ $R^5$ $R^6$ and $R^7$ is aryl or heteroaryl wherein each aryl or heteroaryl is optionally substituted with one or more (e.g. 1, 2, 3, or 4) $R^d$; and the remainder of $R^4, R^5, R^6$ and $R^7$ are each independently H, halo, cyano, nitro, hydroxy, carboxy, trifluoromethyl, trifluoromethoxy, $(C_1\text{-}C_6)$alkyl, $(C_3\text{-}C_6)$cycloalkyl, $(C_1\text{-}C_6)$alkoxy, $(C_1\text{-}C_6)$alkoxycarbonyl, $(C_1\text{-}C_6)$alkanoyloxy, aryl, heteroaryl, aryloxy, heteroaryloxy, $(C_1\text{-}C_6)$alkylthio, $-S(O)R^p$, $-S(O)_2R^p$, $-S(O)_3R^p$, $-S(O)_2NR^gR^h$, and $-NR^gR^h$; wherein any alkyl and any alkyl or alkanoyl portion of any aryl$(C_1\text{-}C_6)$alkyl, heteroaryl$(C_1\text{-}C_6)$alkyl, aryl$(C_1\text{-}C_6)$alkanoyl or heteroaryl$(C_1\text{-}C_6)$alkanoyl is optionally substituted with one or more (e.g. 1, 2, 3, or 4) $R^a$; and wherein any aryl, heteroaryl, or any aryl or heteroaryl portion of any aryl$(C_1\text{-}C_6)$alkyl, heteroaryl$(C_1\text{-}C_6)$alkyl, aryl$(C_1\text{-}C_6)$alkanoyl or heteroaryl$(C_1\text{-}C_6)$alkanoyl of $R^4, R^5, R^6$ and $R^7$ is optionally substituted with one or more (e.g. 1, 2, 3, or 4) $R^b$;

$R^8$ is H, halo, cyano, nitro, hydroxy, carboxy, trifluoromethyl, trifluoromethoxy, $(C_1\text{-}C_6)$alkyl, $(C_3\text{-}C_6)$cycloalkyl, $(C_1\text{-}C_6)$alkoxy, $(C_1\text{-}C_6)$alkoxycarbonyl, $(C_1\text{-}C_6)$alkanoyloxy, aryl, heteroaryl, aryloxy, heteroaryloxy, $(C_1\text{-}C_6)$alkylthio, $-S(O)R^p$, $-S(O)_2R^p$, $-S(O)_3R^p$, $-S(O)_2NR^gR^h$, and $-NR^gR^h$; wherein any alkyl of $R^8$ is optionally substituted with one or more (e.g. 1, 2, 3, or 4) $R^a$; and wherein any aryl, or heteroaryl, of $R^8$ is optionally substituted with one or more (e.g. 1, 2, 3, or 4) $R^b$;

X is N; Y is $C(R^2)$; and $R^3$ is $R^e$; or
X is N; Y is $C(R^{15})$; and $R^3$ is $R^c$; or
X is $C(R^1)$; Y is N; and $R^3$ is $R^c$ or
X is $C(R^{16})$; Y is $C(R^{11})$; and $R^3$ is $R^e$; or
X is $C(R^1)$; Y is $C(R^{12})$; and $R^3$ is $R^e$; or
X is $N^+\text{—}R^{13}(Z^-)$; Y is $C(R^{12})$; and $R^3$ is $R^c$; or
X is $C(R^{10})$; Y is $N^+\text{—}R^{14}(Z^-)$; and $R^3$ is $R^c$;

each $R^{10}$ is H, halo, cyano, nitro, hydroxy, carboxy, trifluoromethyl, trifluoromethoxy, $(C_1\text{-}C_6)$alkyl, $(C_3\text{-}C_6)$cycloalkyl, $(C_1\text{-}C_6)$alkoxy, $(C_1\text{-}C_6)$alkoxycarbonyl, $(C_1\text{-}C_6)$alkanoyloxy, aryl, heteroaryl, aryloxy, heteroaryloxy, and $-NR^gR^h$; wherein any alkyl of $R^{10}$ is optionally substituted with one or more (e.g. 1, 2, 3, or 4) $R^a$; and wherein any aryl, heteroaryl, or any aryl or heteroaryl portion of any aryl$(C_1\text{-}C_6)$alkyl, heteroaryl$(C_1\text{-}C_6)$alkyl, aryloxy, or heteroaryloxy of $R^{10}$ is optionally substituted with one or more (e.g. 1, 2, 3, or 4) $R^b$;

each $R^{11}$ is H, halo, cyano, nitro, hydroxy, carboxy, trifluoromethyl, trifluoromethoxy, $(C_1\text{-}C_6)$alkyl, $(C_3\text{-}C_6)$cycloalkyl, $(C_1\text{-}C_6)$alkoxy, $(C_1\text{-}C_6)$alkoxycarbonyl, $(C_1\text{-}C_6)$alkanoyloxy, aryl, heteroaryl, aryloxy, heteroaryloxy, and $-NR^gR^h$; wherein any alkyl and any alkyl or alkanoyl portion of any aryl$(C_1\text{-}C_6)$alkyl, heteroaryl$(C_1\text{-}C_6)$alkyl, aryl$(C_1\text{-}C_6)$alkanoyl or heteroaryl$(C_1\text{-}C_6)$alkanoyl of $R^{11}$ is optionally substituted with one or more (e.g. 1, 2, 3, or 4) $R^a$; and wherein any aryl, heteroaryl, or any aryl or heteroaryl portion of any aryl$(C_1\text{-}C_6)$alkyl, heteroaryl$(C_1\text{-}C_6)$alkyl, aryl$(C_1\text{-}C_6)$alkanoyl or heteroaryl$(C_1\text{-}C_6)$alkanoyl of $R^{11}$ is optionally substituted with one or more (e.g. 1, 2, 3, or 4) $R^b$;

each $R^{12}$ is H, halo, cyano, nitro, hydroxy, carboxy, trifluoromethyl, trifluoromethoxy, $(C_1\text{-}C_6)$alkyl, $(C_3\text{-}C_6)$cycloalkyl, $(C_1\text{-}C_6)$alkoxy, $(C_1\text{-}C_6)$alkoxycarbonyl, $(C_1\text{-}C_6)$alkanoyloxy, aryloxy, heteroaryloxy, and $-NR^gR^h$; wherein any alkyl and any alkyl or alkanoyl portion of any aryl$(C_1\text{-}C_6)$alkyl, heteroaryl$(C_1\text{-}C_6)$alkyl, aryl$(C_1\text{-}C_6)$alkanoyl or heteroaryl$(C_1\text{-}C_6)$alkanoyl of $R^{12}$ is optionally substituted with one or more (e.g. 1, 2, 3, or 4) $R^a$; and wherein any aryl, heteroaryl, or any aryl or heteroaryl portion of any aryl$(C_1\text{-}C_6)$alkyl, heteroaryl$(C_1\text{-}C_6)$alkyl, aryl$(C_1\text{-}C_6)$alkanoyl or heteroaryl$(C_1\text{-}C_6)$alkanoyl of $R^{12}$ is optionally substituted with one or more (e.g. 1, 2, 3, or 4) $R^b$;

each $R^{13}$ is $(C_1\text{-}C_6)$alkyl, aryl, or aryl$(C_1\text{-}C_6)$alkyl;
each $R^{14}$ is $(C_1\text{-}C_6)$alkyl, aryl, or aryl$(C_1\text{-}C_6)$alkyl;
$R^{15}$ is $R^x$ or $(C_1\text{-}C_6)$alkyl that is substituted with one or more $R^x$;

$R^{16}$ is $R^z$ or $(C_1-C_6)$alkyl that is substituted with one or more $R^y$;

each $R^a$ is independently selected from halo, cyano, nitro, hydroxy, carboxy, oxo, $(C_1-C_6)$alkyl, $(C_3-C_6)$cycloalkyl, $(C_1-C_6)$alkoxy, $(C_1-C_6)$alkoxycarbonyl, $(C_1-C_6)$alkanoyloxy, aryl, heteroaryl, aryloxy, heteroaryloxy, $(C_1-C_6)$alkylthio, —S(O)$R^p$, —S(O)$_2R^p$, —S(O)$_3R^p$, —S(O)$_2NR^gR^h$, and —NR$^g$R$^h$; wherein each aryl, heteroaryl, aryloxy, and heteroaryloxy is optionally substituted with one or more (e.g. 1, 2, 3, or 4) groups independently selected from halo, cyano, nitro, hydroxy, carboxy, trifluoromethyl, trifluoromethoxy, $(C_1-C_6)$alkyl, $(C_3-C_6)$cycloalkyl, $(C_1-C_6)$alkoxy, $(C_1-C_6)$alkoxycarbonyl, $(C_1-C_6)$alkanoyloxy, $(C_1-C_6)$alkylthio, —S(O)$R^p$, —S(O)$_2R^p$, —S(O)$_3R^p$, —S(O)$_2NR^gR^h$, and —NR$^g$R$^h$;

each $R^b$ is independently selected from halo, cyano, nitro, hydroxy, carboxy, trifluoromethyl, trifluoromethoxy, $(C_1-C_6)$alkyl, $(C_3-C_6)$cycloalkyl, $(C_1-C_6)$alkoxy, $(C_1-C_6)$alkoxycarbonyl, $(C_1-C_6)$alkanoyloxy, aryl, heteroaryl, aryloxy, heteroaryloxy, $(C_1-C_6)$alkylthio, —S(O)$R^p$, —S(O)$_2R^p$, —S(O)$_3R^p$, —S(O)$_2NR^gR^h$, and —NR$^g$R$^h$; wherein each aryl, heteroaryl, aryloxy, and heteroaryloxy is optionally substituted with one or more (e.g. 1, 2, 3, or 4) groups independently selected from halo, cyano, nitro, hydroxy, carboxy, trifluoromethyl, trifluoromethoxy, $(C_1-C_6)$alkyl, $(C_3-C_6)$cycloalkyl, $(C_1-C_6)$alkoxy, $(C_1-C_6)$alkoxycarbonyl, $(C_1-C_6)$alkanoyloxy, $(C_1-C_6)$alkylthio, —S(O)$R^p$, —S(O)$_2R^p$, —S(O)$_3R^p$, —S(O)$_2NR^gR^h$, and —NR$^g$R$^h$;

each $R^c$ is H, halo, cyano, nitro, hydroxy, carboxy, trifluoromethyl, trifluoromethoxy, $(C_1-C_6)$alkyl, $(C_3-C_6)$cycloalkyl, $(C_1-C_6)$alkoxy, $(C_1-C_6)$alkoxycarbonyl, $(C_1-C_6)$alkanoyloxy, aryl other than phenyl, heteroaryl other than pyrid-4-yl, aryloxy, heteroaryloxy, and —NR$^g$R$^h$; wherein any alkyl and any alkyl or alkanoyl portion of any aryl($C_1-C_6$)alkyl, heteroaryl($C_1-C_6$)alkyl, aryl($C_1-C_6$)alkanoyl or heteroaryl($C_1-C_6$)alkanoyl of $R^c$ is optionally substituted with one or more (e.g. 1, 2, 3, or 4) $R^a$; and wherein any aryl, heteroaryl, or any aryl or heteroaryl portion of any aryl($C_1-C_6$)alkyl, heteroaryl($C_1-C_6$)alkyl, aryl($C_1-C_6$)alkanoyl or heteroaryl($C_1-C_6$)alkanoyl of $R^c$ is optionally substituted with one or more (e.g. 1, 2, 3, or 4) $R^b$;

each $R^d$ is independently selected from halo, cyano, nitro, hydroxy, carboxy, trifluoromethyl, trifluoromethoxy, $(C_1-C_6)$alkyl, $(C_3-C_6)$cycloalkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^g$R$^h$; wherein each aryl, heteroaryl, aryloxy, and heteroaryloxy is optionally substituted with one or more (e.g. 1, 2, 3, or 4) groups independently selected from halo, cyano, nitro, hydroxy, carboxy, trifluoromethyl, trifluoromethoxy, $(C_1-C_6)$alkyl, $(C_3-C_6)$cycloalkyl, $(C_1-C_6)$alkoxy, $(C_1-C_6)$alkoxycarbonyl, $(C_1-C_6)$alkanoyloxy, and —NR$^g$R$^h$;

each $R^e$ is H, halo, cyano, nitro, hydroxy, carboxy, trifluoromethyl, trifluoromethoxy, $(C_1-C_6)$alkyl, $(C_3-C_6)$cycloalkyl, $(C_1-C_6)$alkoxy, $(C_1-C_6)$alkoxycarbonyl, $(C_1-C_6)$alkanoyloxy, aryl, heteroaryl, aryloxy, heteroaryloxy, and —NR$^g$R$^h$; wherein any alkyl and any alkyl or alkanoyl portion of any aryl($C_1-C_6$)alkyl, heteroaryl($C_1-C_6$)alkyl, aryl ($C_1-C_6$)alkanoyl or heteroaryl($C_1-C_6$)alkanoyl of $R^e$ is optionally substituted with one or more (e.g. 1, 2, 3, or 4) $R^a$; and wherein any aryl, heteroaryl, or any aryl or heteroaryl portion of any aryl($C_1-C_6$)alkyl, heteroaryl($C_1-C_6$)alkyl, aryl ($C_1-C_6$)alkanoyl or heteroaryl($C_1-C_6$)alkanoyl of $R^e$ is optionally substituted with one or more (e.g. 1, 2, 3, or 4) $R^b$;

each $R^g$ and $R^h$ is independently selected from H, $(C_1-C_6)$alkyl, $(C_3-C_6)$cycloalkyl, $(C_3-C_6)$cycloalkyl($C_1-C_6$)alkyl, aryl, heteroaryl, aryl($C_1-C_6$) alkyl and heteroaryl($C_1-C_6$) alkyl; or $R^g$ and $R^h$ together with the nitrogen to which they are attached form a aziridino, azetidino, morpholino, piperazino, pyrrolidino or piperidino; wherein any $(C_1-C_6)$alkyl, $(C_3-C_6)$cycloalkyl, $(C_3-C_6)$cycloalkyl($C_1-C_6$)alkyl, aryl, heteroaryl, aryl($C_1-C_6$) alkyl or heteroaryl($C_1-C_6$)alkyl of $R^g$ and $R^h$ is optionally substituted with one or more groups independently selected from hydroxy, carboxy, and NR$^t$R$^u$;

each $R^j$ is independently selected from H, $(C_1-C_6)$alkyl, $(C_3-C_6)$cycloalkyl, $(C_3-C_6)$cycloalkyl($C_1-C_6$)alkyl, aryl, heteroaryl, aryl($C_1-C_6$) alkyl and heteroaryl($C_1-C_6$)alkyl;

each $R^m$ and $R^n$ is independently selected from H, $(C_1-C_6)$ alkyl, $(C_3-C_6)$cycloalkyl, $(C_3-C_6)$cycloalkyl($C_1-C_6$)alkyl, aryl, heteroaryl, aryl($C_1-C_6$) alkyl and heteroaryl($C_1-C_6$) alkyl; or $R^m$ and $R^n$ together with the nitrogen to which they are attached form a aziridino, azetidino, morpholino, piperazino, pyrrolidino or piperidino; wherein any $(C_1-C_6)$alkyl, $(C_3-C_6)$cycloalkyl, $(C_3-C_6)$cycloalkyl($C_1-C_6$)alkyl, aryl, heteroaryl, aryl($C_1-C_6$) alkyl or heteroaryl($C_1-C_6$) alkyl of $R^m$ and $R^n$ is optionally substituted with one or more groups independently selected from hydroxy, carboxy, and NR$^t$R$^u$;

each $R^p$ is independently selected from H, $(C_1-C_6)$alkyl, $(C_3-C_6)$cycloalkyl, $(C_3-C_6)$cycloalkyl($C_1-C_6$)alkyl, aryl, heteroaryl, aryl($C_1-C_6$) alkyl and heteroaryl($C_1-C_6$) alkyl;

each $R^q$ is independently selected from H, $(C_1-C_6)$alkyl, $(C_3-C_6)$cycloalkyl, $(C_3-C_6)$cycloalkyl($C_1-C_6$)alkyl, aryl, heteroaryl, aryl($C_1-C_6$) alkyl and heteroaryl($C_1-C_6$)alkyl;

each $R^s$ is independently selected from H, $(C_1-C_6)$alkyl, $(C_3-C_6)$cycloalkyl, $(C_3-C_6)$cycloalkyl($C_1-C_6$)alkyl, aryl, heteroaryl, aryl($C_1-C_6$) alkyl and heteroaryl($C_1-C_6$)alkyl;

each $R^t$ and $R^u$ is independently selected from H, $(C_1-C_6)$ alkyl, $(C_3-C_6)$cycloalkyl, $(C_3-C_6)$cycloalkyl($C_1-C_6$)alkyl, aryl, heteroaryl, aryl($C_1-C_6$) alkyl and heteroaryl($C_1-C_6$) alkyl; or $R^t$ and $R^u$ together with the nitrogen to which they are attached form a aziridino, azetidino, morpholino, piperazino, pyrrolidino or piperidino;

each $R^x$ is independently —NR$^m$R$^n$, —N$^+$(R$^s$)$_3$Z$^-$, —C(=NR$^j$)—NR$^m$R$^n$, or —NR$^q$—C(=NR$^j$)—NR$^m$R$^n$;

each $R^y$ is independently —NR$^m$R$^n$, —N$^+$(R$^s$)$_3$Z$^-$, —C(=NR$^j$)—NR$^m$R$^n$, or —NR$^q$—C(=NR$^j$)—NR$^m$R$^n$;

each $R^z$ is independently —C(=NR$^j$)—NR$^m$R$^n$, or —NR$^q$—C(=NR$^j$)—NR$^m$R$^n$;

the bond represented by ---- is present; and each Z$^-$ is independently an acceptable counterion;

or a salt or prodrug thereof.

A specific compound of the invention is a compound of formula (I):

wherein:

X is W—R$^{51}$;

Y is C(R$^{52}$);

W is N; R$^{51}$ is absent; or

W is N$^+$A$^-$; R$^{51}$ is $(C_1-C_6)$alkyl, aryl, or aryl($C_1-C_6$)alkyl; and A$^-$ is counter anion; or W is C; R$^{51}$ is hydrogen, —N$^+$(R$^{5a}$)$_3$D$^-$, —C(=NR$^{5b}$)—NR$^{5c}$R$^{5d}$, —NR$^e$—C(=NR$^{5b}$)—NR$^{5c}$R$^{5d}$, —NR$^{5g}$R$^{5h}$, —NR$^{5ce}$—C(=NR$^{5cb}$)R$^{5ce}$, —NR$^{5ce}$C(=O)—NR$^{5cc}$R$^{5cd}$, or $(C_1-C_6)$alkyl that is substituted with one or more R$^{5f}$; and A$^-$ is absent;

$R^{52}$ is a ring selected from:

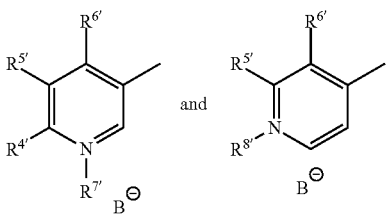

wherein:

any adjacent $R^6$, $R^7$, $R^{4'}$ and $R^{5'}$ taken together can optionally be methylenedioxy and each remaining $R^6$, $R^7$, $R^{4'}$ and $R^{5'}$ is independently selected from H, Z—$R^x$, $R^f$, and $(C_1-C_6)$ alkyl that is substituted with one or more $R^f$;

the bond represented by ---- is present;

$R^{7'}$ is absent and $B^-$ is absent; or $R^{7'}$ is $(C_1-C_6)$alkyl and $B^-$ is a counterion; and $R^{8'}$ is absent and $B^-$ is absent; or $R^{8'}$ is $(C_1-C_6)$alkyl and $B^-$ is a counterion.

A specific compound of the invention is a compound of formula Va:

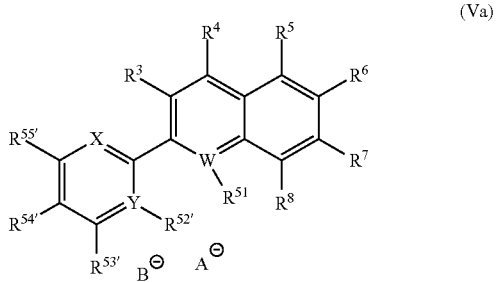

wherein:

X is N or C($R^{56'}$);

W is N; $R^{51}$ is absent; and $A^-$ is absent; or

W is N; $R^{51}$ is $(C_1-C_6)$alkyl, aryl, or aryl$(C_1-C_6)$alkyl; and $A^-$ is counter anion; or W is C; $R^{51}$ is hydrogen, —N$^+$($R^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$, —NR$^{5g}$R$^{5h}$, —NR$^{5ce}$—C(=NR$^{5cb}$)R$^{5ce}$, —NR$^{5ce}$—C(=O)—NR$^{5cc}$R$^{5cd}$, or $(C_1-C_6)$alkyl that is substituted with one or more $R^{5f}$; and $A^-$ is absent;

Y is N; $R^{52'}$ is absent; and $B^-$ is absent; or

Y is N; $R^{52'}$ is $(C_1-C_6)$alkyl, aryl, or aryl$(C_1-C_6)$alkyl; and $B^-$ is counter anion; or Y is C; $R^{52'}$ is hydrogen, —N$^+$($R^{5a}$)$_3$D$^-$, —C(=NR$^{5b}$)—NR$^{5c}$R$^{5d}$, —NR$^e$—C(=NR$^{5b}$)—NR$^{5c}$R$^{5d}$, —NR$^{5ce}$—C(=NR$^{5cb}$)R$^{5ce}$, —NR$^{5ce}$—C(=O)—NR$^{5cc}$R$^{5cd}$, —NR$^{5g}$R$^{5h}$, or $(C_1-C_6)$alkyl that is substituted with one or more $R^{5f}$; and $B^-$ is absent;

any adjacent $R^6$, $R^7$, $R^{53'}$, $R^{54'}$ and $R^{55'}$ taken together can optionally be methylenedioxy and each remaining $R^6$, $R^7$, $R^{53'}$, $R^{54'}$ and $R^{55'}$ is independently selected from H, Z—$R^{5x}$, $R^{5f}$, and $(C_1-C_6)$alkyl that is substituted with one or more $R^{5f}$; or $R^{54'}$ can be $R^{5da}$;

$R^8$ is hydrogen, $(C_1-C_6)$alkyl, aryl, or aryl$(C_1-C_6)$alkyl wherein each $(C_1-C_6)$alkyl of $R^8$ is optionally substituted with one or more groups independently selected from halo, hydroxy, cyano, nitro, $(C_1-C_6)$alkoxy, $(C_3-C_6)$cycloalkyl, oxo, carboxy, aryloxy, sulfo, and —NR$^{5g}$R$^{5h}$, and wherein each aryl of $R^8$ is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, $R^{5s}$, and —NR$^{5g}$R$^{5h}$;

each Z is independently selected from —O—, —S—, and —N($R^{5y}$)—;

at least one of $R^3$, $R^4$, $R^5$, and $R^{56'}$ is selected from hydroxy, carboxy, cyano, CF$_3$SO$_3$—, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl$(C_1-C_6)$alkyl, aryl, heteroaryl, heteroaryl$(C_1-C_6)$alkyl, aryl$(C_1-C_6)$alkanoyl, and heteroaryl$(C_1-C_6)$alkanoyl; and the remainder of $R^3$, $R^4$, $R^5$, and $R^{56'}$ are independently selected from H, hydroxy, carboxy, cyano, CF$_3$SO$_3$—, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl$(C_1-C_6)$alkyl, aryl, heteroaryl, heteroaryl$(C_1-C_6)$alkyl, aryl$(C_1-C_6)$alkanoyl, and heteroaryl$(C_1-C_6)$alkanoyl; wherein each $(C_1-C_6)$alkyl, $(C_2-C_6)$alkenyl, $(C_2-C_6)$alkynyl, $(C_1-C_6)$alkoxy, $(C_3-C_6)$cycloalkyl, and $(C_1-C_6)$alkanoyl of $R^3$, $R^4$, $R^5$, and $R^{56'}$ is optionally substituted with one or more groups independently selected from halo, hydroxy, cyano, nitro, $(C_1-C_6)$alkoxy, $(C_3-C_6)$cycloalkyl, oxo, carboxy, aryloxy, sulfo, —S(O)$_2$NR$^{5g}$R$^{5h}$, —N($R^{5j}$)S(O)$_2$R$^{5k}$, —N$^+$($R^{5a}$)$_3$D$^-$, —C(=NR$^{5b}$)—NR$^{5c}$R$^{5d}$, or —NR$^{5e}$—C(=NR$^{5b}$)—NR$^{5c}$R$^{5d}$ and —NR$^{5g}$R$^{5h}$; and wherein each aryl and heteroaryl of $R^3$, $R^4$, $R^5$, and $R^{56'}$ is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, —S(O)$_2$NR$^{5g}$R$^{5h}$, —N($R^{5j}$)S(O)$_2$R$^{5k}$, Rv$^s$, —N$^+$($R^{5a}$)$_3$D$^-$, —C(=NR$^{5b}$)—NR$^{5c}$R$^{5d}$, or —NR$^{5e}$—C(=NR$^{5b}$)—NR$^{5c}$R$^{5d}$, —NR$^{5g\nu}$R$^h$, and $(C_1-C_6)$alkyl substituted with one or more groups independently selected from —N$^+$($R^{5a}$)$_3$D$^-$, —C(=NR$^{5b}$)—NR$^{5c}$R$^{5d}$, or —NR$^{5e}$—C(=NR$^{5b}$)—NR$^{5c}$R$^{5d}$, and —NR$^{5g}$R$^{5h}$;

each $R^{5a}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5b}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5c}$ and $R^{5d}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$ alkyl; or $R^{5c}$ and $R^{5d}$ together with the nitrogen to which they are attached form a aziridino, azetidino, morpholino, piperazino, pyrrolidino or piperidino; wherein any $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^c$ and $R^{5d}$ is optionally substituted with one or more groups independently selected from hydroxy, carboxy, and NRv$^m$R$^{5n}$;

each $R^{5e}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5f}$ is independently selected from —N$^+$($R^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$, —NR$^{5ce}$—C(=NR$^{5cb}$)R$^{5ce}$, —NR$^{5ce}$—C(=O)—NR$^{5cc}$R$^{5cd}$, and —NR$^{5g}$R$^{5h}$;

each $R^{5g}$ and $R^{5h}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{5g}$ and $R^{5h}$ together with the nitrogen to which they are attached form a aziridino, azetidino, morpholino, piperazino, pyrrolidino or piperidino; wherein any $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{5g}$ and $R^{5h}$ is optionally substituted with one or more groups independently selected from hydroxy, carboxy, and $NR^{5m}R^{5n}$;

each $R^{5j}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5k}$ is independently selected from $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5m}$ and $R^{5n}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{5m}$ and $R^{5n}$ together with the nitrogen to which they are attached form a aziridino, azetidino, morpholino, piperazino, pyrrolidino or piperidino;

each $R^{5s}$ is independently trifluoromethyl, trifluoromethoxy, aryl, or heteroaryl, wherein each aryl and heteroaryl is optionally substituted with one or more $(C_1-C_6)$alkyl, halo, hydroxy, cyano, nitro, $(C_1-C_6)$alkoxy, $(C_3-C_6)$cycloalkyl, carboxy, aryloxy, nitro, sulfo, —S(O)$_2$NR$^g$R$^h$, —N(R$^j$)S(O)$_2$R$^k$, trifluoromethyl, trifluoromethoxy, —N$^+$(R$^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$ and —NR$^{5g}$R$^{5h}$;

each $R^{5u}$ and $R^{5v}$ is independently selected from H and $(C_1-C_6)$alkyl;

each $R^{5x}$ is independently selected from $(C_1-C_6)$alkyl, $(C_1-C_6)$alkanoyl, and —C(=O)NR$^{5u}$R$^{5v}$;

each $R^{5y}$ is independently selected from H and $(C_1-C_6)$alkyl;

each D$^-$ is independently a counter anion;

each $R^{5cb}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5cc}$ and $R^{5cd}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{5cc}$ and $R^{5cd}$ together with the nitrogen to which they are attached form a aziridino, azetidino, morpholino, piperazino, pyrrolidino or piperidino; wherein any $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{5cc}$ and $R^{5cd}$ is optionally substituted with one or more groups independently selected from hydroxy, carboxy, and $NR^{5cm}R^{5cn}$;

each $R^{5ce}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl; and each $R^{5cm}$ and $R^{5cn}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or R$^{cm}$ and R$^{cn}$ together with the nitrogen to which they are attached form a aziridino, azetidino, morpholino, piperazino, pyrrolidino or piperidino; and each $R^{5da}$ is carboxy or $(C_1-C_6)$alkoxycarbonyl;

or a salt or prodrug thereof.

A specific compound of the invention is a compound of formula (I) wherein:

X is N or C(R$^{56'}$);

W is N; $R^{51}$ is absent; and A$^-$ is absent; or

W is N; $R^{51}$ is $(C_1-C_6)$alkyl, aryl, or aryl$(C_1-C_6)$alkyl; and A$^-$ is counter anion; or W is C; $R^{51}$ is hydrogen, —N$^+$(R$^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$, —NR$^{5g}$R$^{5h}$, or $(C_1-C_6)$alkyl that is substituted with one or more R$^{5f}$; and A$^-$ is absent;

Y is N; $R^{52'}$ is absent; and B$^-$ is absent; or

Y is N; $R^{52'}$ is $(C_1-C_6)$alkyl, aryl, or aryl$(C_1-C_6)$alkyl; and B$^-$ is counter anion; or Y is C; $R^{52'}$ is hydrogen, —N$^+$(R$^{5a}$)$_3$D$^-$, —C(=NR$^{5b}$)—NR$^{5c}$R$^{5d}$, —NR$^{5e}$—C(=N$^5$R$^b$)—NR$^{5c}$R$^{5d}$, —NR$^{5g}$R$^{5h}$, or $(C_1-C_6)$alkyl that is substituted with one or more R$^{5f}$; and B$^-$ is absent;

any adjacent $R^6$, $R^7$, $R^{53'}$, $R^{54'}$ and $R^{55'}$ taken together can optionally be methylenedioxy and each remaining $R^6$, $R^7$, $R^{53'}$, $R^{54'}$ and $R^{55'}$ is independently selected from H, Z—R$^{5x}$, R$^{5f}$, and $(C_1-C_6)$alkyl that is substituted with one or more R$^{5f}$;

$R^8$ is hydrogen, $(C_1-C_6)$alkyl, aryl, or aryl$(C_1-C_6)$alkyl wherein each $(C_1-C_6)$alkyl of $R^8$ is optionally substituted with one or more groups independently selected from halo, hydroxy, cyano, nitro, $(C_1-C_6)$alkoxy, $(C_3-C_6)$cycloalkyl, oxo, carboxy, aryloxy, sulfo, and —NR$^{5g}$R$^{5h}$, and wherein each aryl of $R^8$ is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, R$^{5s}$, and —NR$^{5g}$R$^{5h}$;

each Z is independently selected from —O—, —S—, and —N(R$^{5y}$)—;

at least one of $R^3$, $R^4$, $R^5$, and $R^{56'}$ is selected from hydroxy, carboxy, cyano, CF$_3$SO$_3$—, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl$(C_1-C_6)$alkyl, aryl, heteroaryl, heteroaryl$(C_1-C_6)$alkyl, aryl$(C_1-C_6)$alkanoyl, and heteroaryl$(C_1-C_6)$alkanoyl; and the remainder of $R^3$, $R^4$, $R^5$, and $R^{6'}$ are independently selected from H, hydroxy, carboxy, cyano, CF$_3$SO$_3$—, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl$(C_1-C_6)$alkyl, aryl, heteroaryl, heteroaryl$(C_1-C_6)$alkyl, aryl$(C_1-C_6)$alkanoyl, and heteroaryl$(C_1-C_6)$alkanoyl; wherein each $(C_1-C_6)$alkyl, $(C_2-C_6)$alkenyl, $(C_2-C_6)$alkynyl, $(C_1-C_6)$alkoxy, $(C_3-C_6)$cycloalkyl, and $(C_1-C_6)$alkanoyl of $R^3$, $R^4$, $R^5$, and $R^{56'}$ is optionally substituted with one or more groups independently selected from halo, hydroxy, cyano, nitro, $(C_1-C_6)$alkoxy, $(C_3-C_6)$cycloalkyl, oxo, carboxy, aryloxy, sulfo, —S(O)$_2$NR$^{5g}$R$^{5h}$, —N(R$^{5j}$)S(O)$_2$R$^{5k}$, —N$^+$(R$^{5a}$)$_3$D$^-$, —C(=NR$^{5b}$)—NR$^{5c}$R$^{5d}$, or —NR$^{5e}$—C(=NR$^{5b}$)—NR$^{5c}$R$^{5d}$ and —NR$^g$R$^h$; and wherein each aryl and heteroaryl of $R^3$, $R^4$, $R^5$, and $R^{56'}$ is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, —S(O)$_2$NR$^{5g}$R$^{5h}$, —N(R$^{5j}$)S(O)$_2$R$^{5k}$, R$^{5s}$, —N$^+$(R$^{5a}$)$_3$D$^-$, —C(=NR$^{5b}$)—NR$^{5c}$R$^{5d}$, or NR$^{5e}$—C(=NR$^{5b}$)—NR$^{5c}$R$^{5d}$, —NR$^{5g}$R$^{5h}$, and $(C_1-C_6)$alkyl substituted with one or more groups independently selected from —N$^+$(R$^{5a}$)$_3$D$^-$, —C(=NR$^{5b}$)—NR$^{5c}$R$^{5d}$, or —NR$^{5e}$—C(=NR$^{5b}$)—NR$^{5c}$R$^{5d}$, and —NR$^{5g}$R$^{5h}$;

each $R^{5a}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5b}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5c}$ and $R^{5d}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{5c}$ and $R^{5d}$ together with the nitrogen to which they are attached form a aziridino, azetidino, morpholino, piperazino, pyrrolidino or piperidino; wherein any $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of R$^c$ and R$^d$ is optionally substituted with one or more groups independently selected from hydroxy, carboxy, and $NR^{5m}R^{5n}$;

each $R^{5e}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5f}$ is independently selected from —$N^+(R^{5a})_3D^-$, —$C(=NR^{5b})$—$NR^{5c}R^{5d}$, —$NR^{5e}$—$C(=NR^{5b})$—$NR^{5c}R^{5d}$, and —$NR^{5g}R^{5h}$;

each $R^{5g}$ and $^5R^h$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{5g}$ and $R^{5h}$ together with the nitrogen to which they are attached form a aziridino, azetidino, morpholino, piperazino, pyrrolidino or piperidino; wherein any $(C_1-C_6)$ alkyl, $(C_3-C_6)$cycloalkyl, $(C_3-C_6)$cycloalkyl$(C_1-C_6)$alkyl, aryl, heteroaryl, aryl$(C_1-C_6)$ alkyl or heteroaryl$(C_1-C_6)$alkyl of $R^{5g}$ and $R^{5h}$ is optionally substituted with one or more groups independently selected from hydroxy, carboxy, and $NR^{5m}R^{5n}$;

each $R^{5j}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5k}$ is independently selected from $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5m}$ and $R^{5n}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{5m}$ and $R^{5n}$ together with the nitrogen to which they are attached form a aziridino, azetidino, morpholino, piperazino, pyrrolidino or piperidino;

each $R^{5s}$ is independently trifluoromethyl, trifluoromethoxy, aryl, or heteroaryl, wherein each aryl and heteroaryl is optionally substituted with one or more $(C_1-C_6)$ alkyl, halo, hydroxy, cyano, nitro, $(C_1-C_6)$alkoxy, $(C_3-C_6)$ cycloalkyl, carboxy, aryloxy, nitro, sulfo, —$S(O)_2NR^{5g}R^{5h}$, —$N(R^{5j})S(O)_2R^{5k}$, trifluoromethyl, trifluoromethoxy, —$N^+(R^{5a})_3D^-$, —$C(=NR^{5b})$—$NR^{5c}R^{5d}$, —$NR^{5e}$—$C(=NR^{5b})$—$NR^{5c}R^{5d}$ and —$NR^{5g}R^{5h}$;

each $R^{5u}$ and $R^{5v}$ is independently selected from H and $(C_1-C_6)$alkyl;

each $R^{5x}$ is independently selected from $(C_1-C_6)$alkyl, $(C_1-C_6)$alkanoyl, and —$C(=O)NR^{5u}R^{5v}$;

each $R^{5y}$ is independently selected from H and $(C_1-C_6)$ alkyl; and each $D^-$ is independently a counter anion;

or a salt or prodrug thereof.

A specific compound of the invention is a compound of formula (I):

wherein:

X is N or $C(R^{56'})$;

W is N; $R^{51}$ is absent; and $A^-$ is absent; or

W is N; $R^{51}$ is $(C_1-C_6)$alkyl, aryl, or aryl$(C_1-C_6)$alkyl; and $A^-$ is counter anion; or W is C; $R^{51}$ is hydrogen or —$NR^{5aa}R^{5bb}$ and $A^-$ is absent; or W is C; $R^{51}$ is —$N^+(R^{5cc})_3$; and $A^-$ is counter anion;

Y is N; $R^{52'}$ is absent; and $B^-$ is absent; or

Y is N; $R^{52'}$ is $(C_1-C_6)$alkyl, aryl, or aryl$(C_1-C_6)$alkyl; and $B^-$ is counter anion; or Y is C; $R^{52'}$ is hydrogen or —$NR^{5dd}R^{5ee}$; and $B^-$ is absent; or Y is C; $R^{52'}$ is —$N^+(R^{5ff})_3$; and $B^-$ is counter anion;

any adjacent $R^6$, $R^7$, $R^{53'}$, $R^{54'}$ and $R^{55'}$ taken together can optionally be methylenedioxy and each remaining $R^6$, $R^7$, $R^{53'}$, $R^{54'}$ and $R^{55'}$ is independently selected from H and Z—$R^{5x}$;

$R^8$ is hydrogen, $(C_1-C_6)$alkyl, aryl, or aryl$(C_1-C_6)$alkyl wherein each $(C_1-C_6)$alkyl of $R^8$ is optionally substituted with one or more groups independently selected from halo, hydroxy, cyano, nitro, $(C_1-C_6)$alkoxy, $(C_3-C_6)$cycloalkyl, oxo, carboxy, aryloxy, sulfo, and —$NR^{5g}R^{5h}$, and wherein each aryl of $R^8$ is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, $R^{5s}$, and —$NR^{5g}R^{5h}$;

each Z is independently selected from —O—, —S—, and —$N(R^{5y})$—;

at least one of $R^3$, $R^4$, $R^5$, and $R^{56'}$ is selected from hydroxy, carboxy, cyano, $CF_3SO_3$—, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl$(C_1-C_6)$alkyl, aryl, heteroaryl, heteroaryl$(C_1-C_6)$alkyl, arylalkanoyl, and heteroarylalkanoyl; and the remainder of $R^3$, $R^4$, $R^5$, and $R^{56'}$ are independently selected from H, hydroxy, carboxy, cyano, $CF_3SO_3$—, $(C_1-C_6)$alkyl, $(C_2-C_6)$alkenyl, $(C_2-C_6)$alkynyl, $(C_1-C_6)$alkoxy, $(C_3-C_6)$cycloalkyl, aryl$(C_1-C_6)$alkyl, aryl, heteroaryl, heteroaryl$(C_1-C_6)$alkyl, aryl$(C_1-C_6)$alkanoyl, and heteroaryl$(C_1-C_6)$alkanoyl; wherein each $(C_1-C_6)$alkyl, $(C_2-C_6)$alkenyl, $(C_2-C_6)$alkynyl, $(C_1-C_6)$alkoxy, $(C_3-C_6)$cycloalkyl, and $(C_1-C_6)$alkanoyl of $R^3$, $R^4$, $R^5$, and $R^{56'}$ is optionally substituted with one or more groups independently selected from halo, hydroxy, cyano, nitro, $(C_1-C_6)$alkoxy, $(C_3-C_6)$cycloalkyl, oxo, carboxy, aryloxy, sulfo, —$S(O)_2NR^{5g}R^{5h}$, —$N(R^{5j})S(O)_2R^{5k}$, and —$NR^{5g}R^{5h}$; and wherein each aryl and heteroaryl of $R^3$, $R^4$, $R^5$, and $R^{56'}$ is optionally substituted with one or more groups independently selected from $(C_1-C_6)$alkyl, halo, hydroxy, cyano, nitro, $(C_1-C_6)$alkoxy, $(C_3-C_6)$cycloalkyl, carboxy, aryloxy, nitro, sulfo, —$S(O)_2NR^{5g}R^{5h}$, —$N(R^{5j})S(O)_2R^{5k}$, $R^{5s}$, and —$NR^{5g}R^{5h}$;

each $R^{5g}$ and $R^{5h}$ is independently selected from H, $(C_1-C_6)$alkyl, $(C_3-C_6)$cycloalkyl, $(C_3-C_6)$cycloalkyl$(C_1-C_6)$ alkyl, aryl, heteroaryl, aryl$(C_1-C_6)$ alkyl and heteroaryl$(C_1-C_6)$ alkyl; or $R^{5g}$ and $R^{5h}$ together with the nitrogen to which they are attached form a aziridino, azetidino, morpholino, piperazino, pyrrolidino or piperidino;

each $R^{5j}$ is independently selected from H, $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5k}$ is independently selected from $(C_1-C_6)$alkyl, $(C_3-C_6)$cycloalkyl, $(C_3-C_6)$cycloalkyl$(C_1-C_6)$alkyl, aryl, heteroaryl, aryl$(C_1-C_6)$ alkyl and heteroaryl$(C_1-C_6)$alkyl;

each $R^{5s}$ is independently trifluoromethyl, trifluoromethoxy, or aryl optionally substituted with one or more $(C_1-C_6)$alkyl, halo, hydroxy, cyano, nitro, $(C_1-C_6)$alkoxy, $(C_3-C_6)$cycloalkyl, carboxy, aryloxy, nitro, sulfo, —$S(O)_2NR^{5g}R^{5h}$, —$N(R^{5j})S(O)_2R^{5k}$, trifluoromethyl, trifluoromethoxy, and —$NR^{5g}R^{5h}$;

each $R^{5u}$ and $R^{5v}$ is independently selected from H and $(C_1-C_6)$alkyl;

each $R^{5x}$ is independently selected from $(C_1-C_6)$alkyl, $(C_1-C_6)$alkanoyl, and —$C(=O)NR^{5u}R^{5v}$;

each $R^{5y}$ is independently selected from H and $(C_1-C_6)$ alkyl;

each $R^{5aa}$ and $R^{5bb}$ is independently selected from H and $(C_1-C_6)$alkyl; or $R^{5aa}$ and $R^{5bb}$ together with the nitrogen to which they are attached form a aziridino, azetidino, morpholino, piperazino, pyrrolidino or piperidino;

each $R^{5cc}$ is independently selected from H and $(C_1-C_6)$ alkyl each $R^{5dd}$ and $R^{ee}$ is independently selected from H and $(C_1-C_6)$alkyl; or $R^{5dd}$ and $R^{5ee}$ together with the nitrogen to which they are attached form a aziridino, azetidino, morpholino, piperazino, pyrrolidino or piperidino; and each $R^{5ff}$ is independently selected from H and $(C_1-C_6)$ alkyl or a salt or prodrug thereof.

A specific compound of the invention is a compound of formula (Vb):

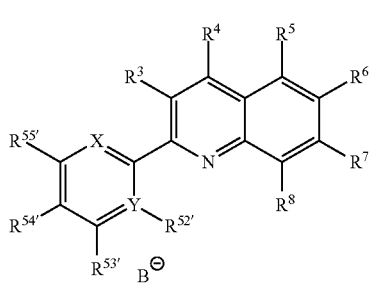

wherein Y is N; $R^{52'}$ is $(C_1-C_6)$alkyl, aryl, or aryl$(C_1-C_6)$alkyl; and $B^-$ is counter anion; or Y is C; $R^{52'}$ is —$N(R^{5ff})_3$; and $B^-$ is counter anion;

or a salt or prodrug thereof.

A specific compound of the invention is a compound of formula (Vc):

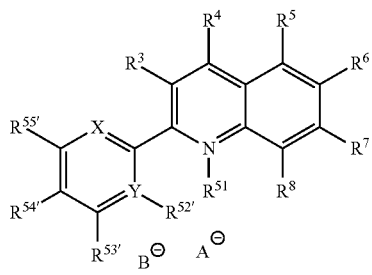

wherein $R^{51'}$ is $(C_1-C_6)$alkyl, aryl, or aryl$(C_1-C_6)$alkyl; and $A^-$ is counter anion;

Y is N; and $R^{52'}$ is absent; or

Y is C; and $R^{2'}$ is hydrogen or —$NR^{5dd}R^{5ee}$;

or a salt or prodrug thereof.

A specific compound of the invention is a compound of formula (Vd):

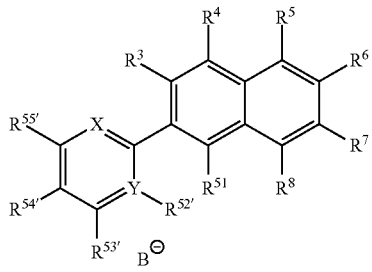

wherein $R^{51}$ is hydrogen or —$NR^{5aa}R^{5bb}$;

Y is N; $R^{52'}$ is $(C_1-C_6)$alkyl, aryl, or aryl$(C_1-C_6)$alkyl; and $B^-$ is counter anion; or Y is C; $R^{52'}$ is —$N(R^{5ff})_3$; and $B^-$ is counter anion;

or a salt or prodrug thereof.

A specific compound of the invention is a compound of formula (Ve):

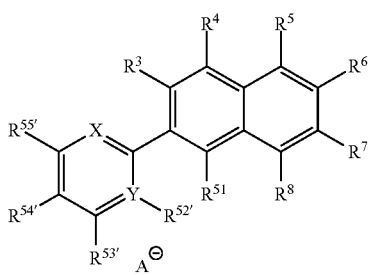

wherein $R^{51}$ is —$N(R^{5cc})_3$ and $A^-$ is counter anion

Y is N; and $R^{52'}$ is absent; or

Y is C; and $R^{52'}$ is hydrogen or —$NR^{5dd}R^{5ee}$;

or a salt or prodrug thereof.

A specific compound of the invention is a compound of formula (Vf):

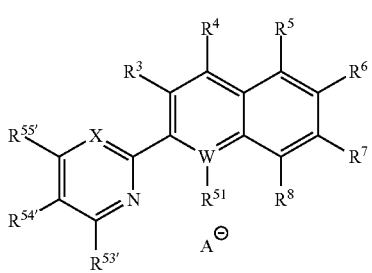

wherein W is N; $R^{51}$ is $(C_1-C_6)$alkyl, aryl, or aryl$(C_1-C_6)$alkyl; and $A^-$ is counter anion; or W is C; $R^{51}$ is —$N(R^{5cc})_3$; and $A^-$ is counter anion;

or a salt or prodrug thereof.

A specific compound of the invention is a compound of formula (Vg):

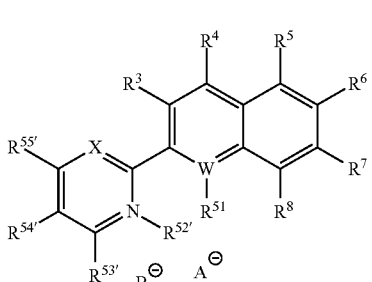

wherein W is N; and $R^{51}$ is absent; or

W is C; and $R^{51}$ is hydrogen or —$NR^{5aa}R^{5bb}$; and $R^{52'}$ is $(C_1-C_6)$alkyl, aryl, or aryl$(C_1-C_6)$alkyl; and $B^-$ is counter anion;

or a salt or prodrug thereof.

A specific compound of the invention is a compound of formula (Vh):

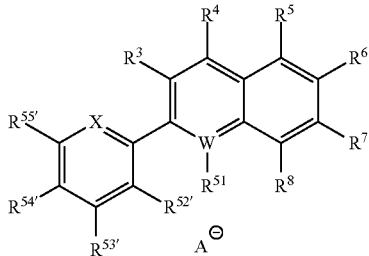

wherein W is N; $R^{51}$ is $(C_1\text{-}C_6)$alkyl, aryl, or aryl$(C_1\text{-}C_6)$alkyl; and $A^-$ is counter anion; or
W is C; $R^{51}$ is —N$(R^{5cc})_3$; and $A^-$ is counter anion; and $R^{2'}$ is hydrogen or —NR$^{5dd}$R$^{5ee}$;
or a salt or prodrug thereof.

A specific compound of the invention is a compound of formula (Vj):

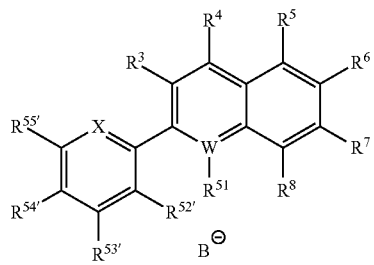

wherein W is N; and $R^{51}$ is absent; or
W is C; and $R^{51}$ is hydrogen or —NR$^{5aa}$R$^{5bb}$;
$R^{52'}$ is —N$(R^{5ff})_3$; and $B^-$ is counter anion;
or a salt or prodrug thereof.

A specific compound of the invention is a compound of formula (Vj) wherein at least one of $R^{53'}$, $R^{54'}$, and $R^{55'}$ is —N$^+$(R$^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$, —NR$^{5g}$R$^{5h}$, or $(C_1\text{-}C_6)$alkyl that is substituted with one or more groups independently selected from —C(=NR$^{5b}$)—NR$^{5c}$R$^{5d}$, —NR$^{5e}$—C(=NR$^{5b}$)—NR$^{5c}$R$^{5d}$, and —NR$^{5g}$R$^{5h}$.

A specific compound of the invention is a compound of formula (Vk):

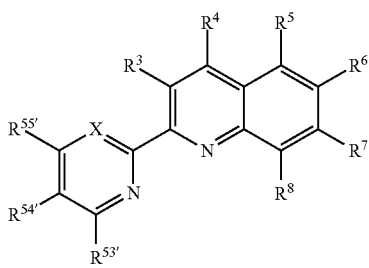

or a salt or prodrug thereof.

A specific compound of the invention is a compound of formula (Vk) wherein at least one of $R^{53'}$, $R^{54'}$, and $R^{55'}$ is —N$^+$(R$^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$, —NR$^{5g}$R$^{5h}$, or $(C_1\text{-}C_6)$alkyl that is substituted with one or more groups independently selected from —C(=NR$^{5b}$)—NR$^{5c}$R$^{5d}$, —NR$^{5e}$—C(=NR$^{5b}$)—NR$^{5c}$R$^{5d}$, and —NR$^{5g}$R$^{5h}$.

A specific compound of the invention is a compound of formula (Vm):

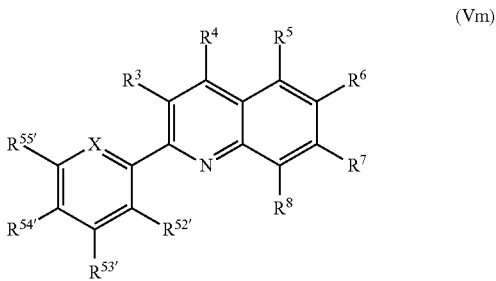

or a salt or prodrug thereof.

A specific compound of the invention is a compound of formula (Vm) wherein $R^{52'}$ is hydrogen, —N$^+$(R$^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$, —NR$^{5g}$R$^{5h}$, or $(C_1\text{-}C_6)$alkyl that is substituted with one or more groups independently selected from —C(=NR$^{5b}$)—NR$^{5c}$R$^{5d}$, —NR$^{5e}$—C(=NR$^{5b}$)—NR$^{5c}$R$^{5d}$, and —NR$^{5g}$R$^{5h}$.

A specific compound of the invention is a compound of formula (Vm) wherein $R^{52'}$ is —C(=NR$^{5b}$)—NR$^{5c}$R$^{5d}$, —NR$^{5e}$—C(=NR$^{5b}$)—NR$^{5c}$R$^{5d}$, —NR$^{5g}$R$^{5h}$, or $(C_1\text{-}C_6)$alkyl that is substituted with one or more groups independently selected from —C(=NR$^{5b}$)—NR$^{5c}$R$^{5d}$, —NR$^{5e}$—C(=NR$^{5b}$)—NR$^{5c}$R$^{5d}$, and —NR$^{5g}$R$^{5h}$.

A specific compound of the invention is a compound of formula (Vm) wherein at least one of $R^{52'}$, $R^{53'}$, $R^{54'}$, and $R^{55'}$ is —N$^+$(R$^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$, —NR$^{5g}$R$^{5h}$, or $(C_1\text{-}C_6)$alkyl that is substituted with one or more groups independently selected from —C(=NR$^{5b}$)—NR$^{5c}$R$^{5d}$, —NR$^{5e}$—C(=NR$^{5b}$)—NR$^{5c}$R$^{5d}$, and —NR$^{5g}$R$^{5h}$.

A specific compound of the invention is a compound of formula (Vn):

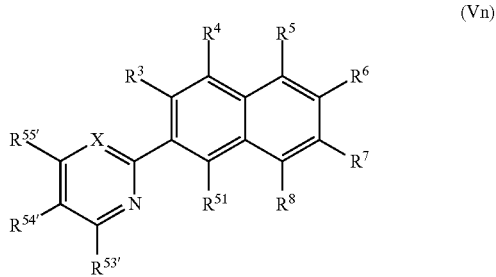

or a salt or prodrug thereof.

A specific compound of the invention is a compound of formula (Vn) wherein at least one of $R^{51}$, $R^{53'}$, $R^{54'}$, and $R^{55'}$ is —N$^+$(R$^{5a}$)$_3$D$^-$, —C(=NR$^{5b}$)—NR$^{5c}$R$^{5d}$, —NR$^{5e}$—C(=NR$^{5b}$)—NR$^{5c}$R$^{5d}$, —NR$^{5g}$R$^{5h}$, or $(C_1\text{-}C_6)$alkyl that is substituted with one or more groups independently selected from —C(=NR$^{5b}$)—NR$^{5c}$R$^{5d}$, —NR$^{5e}$—C(=NR$^{5b}$)—NR$^{5c}$R$^{5d}$, and —NR$^{5g}$R$^{5h}$.

A specific compound of the invention is a compound of formula (Vo):

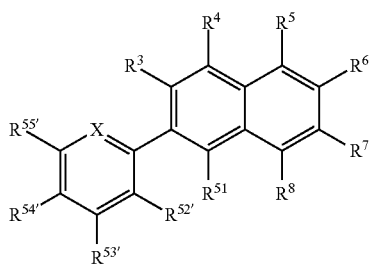

or a salt or prodrug thereof.

A specific compound of the invention is a compound of formula (Vo) wherein at least one of $R^{51'}$, $R^{52'}$, $R^{53'}$, $R^{54'}$, and $R^{55'}$ is $-N^+(R^{5a})_3D^-$, $-C(=NR^{5b})-NR^{5c}R^{5d}$, or $-NR^{5e}-C(=NR^{5b})-NR^{5c}R^{5d}$, $-NR^{5g}R^{5h}$, or $(C_1-C_6)$ alkyl that is substituted with one or more groups independently selected from $-C(=NR^{5b})-NR^{5c}R^{5d}$, $-NR^{5e}-C(=NR^{5b})-NR^{5c}R^{5d}$, and $-NR^{5g}R^{5h}$.

A specific value for $R^3$ is phenyl, benzyl, biphenyl, cyclopropyl, or furyl.

A specific value for $R^4$ is phenyl, biphenyl, cyclopropyl, or furyl.

A specific value for $R^5$ is phenyl, biphenyl, cyclopropyl, or furyl.

A specific value for $R^{56'}$ is phenyl, benzyl, biphenyl, cyclopropyl, or furyl.

A specific value for $R^{51}$ is methyl.

A specific value for W is C and $R^{51}$ is hydrogen.

A specific value for W is C and $R^{51}$ is $-NR^gR^h$.

A specific value for W is C and $R^{51}$ is $-N^+(R^a)_3D^-$.

A specific value for Y is N and $R^{52'}$ is methyl.

A specific value for Y is C and $R^{52'}$ is hydrogen.

A specific value for Y is C and $R^{52'}$ is $-NR^gR^h$.

A specific value for Y is C and $R^{52'}$ is $-N^+(R^a)_3D^-$.

A specific compound of the invention is a compound wherein at least one Z is $-O-$.

A specific compound of the invention is a compound wherein at least one Z is $-S-$.

A specific compound of the invention is a compound wherein at least one Z is $-N(R^{5y})-$.

A specific compound of the invention is a compound wherein each Z is $-O-$.

A specific compound of the invention is a compound wherein each Z is $-S-$.

A specific compound of the invention is a compound wherein Z is $-N(R^{5y})-$.

A specific value for $R^{5x}$ is $(C_1-C_6)$alkyl.

A specific compound of the invention is a compound wherein $R^6$, $R^7$, $R^{53'}$, $R^{54'}$ and $R^{55'}$ are each independently $(C_1-C_3)$alkoxy.

A specific compound of the invention is a compound wherein $R^6$, $R^7$, $R^{53'}$, $R^{54'}$ and $R^{55'}$ are each methoxy.

A specific value for $R^6$ is $(C_1-C_3)$alkoxy.

A specific value for $R^6$ is methoxy.

A specific value for $R^7$ is $(C_1-C_3)$alkoxy.

A specific value for $R^7$ is methoxy.

A specific value for $R^{53'}$ is $(C_1-C_3)$alkoxy.

A specific value for $R^{53'}$ is methoxy.

A specific value for $R^{54'}$ is $(C_1-C_3)$alkoxy.

A specific value for $R^{54'}$ is methoxy.

A specific value for $R^{55'}$ is $(C_1-C_3)$alkoxy.

A specific value for $R^{55'}$ is methoxy.

A specific compound of the invention is a compound wherein $R^6$, $R^7$, $R^{53'}$, and $R^{54'}$ are each methoxy.

A specific compound of the invention is a compound wherein $R^6$, $R^7$, $R^{54'}$, and $R^{55'}$ are each methoxy.

A specific compound of the invention is a compound wherein $R^6$ and $R^7$ taken together are methylenedioxy.

A specific compound of the invention is a compound wherein $R^{53'}$ and $R^{54'}$ taken together are methylenedioxy.

A specific compound of the invention is a compound wherein $R^{54'}$ and $R^{55'}$ taken together are methylenedioxy.

A specific compound of the invention is a compound wherein each $R^{5s}$ is independently trifluoromethyl, trifluoromethoxy, or aryl optionally substituted with one or more $(C_1-C_6)$alkyl, halo, hydroxy, cyano, nitro, $(C_1-C_6)$alkoxy, $(C_3-C_6)$cycloalkyl, carboxy, aryloxy, nitro, sulfo, $-S(O)_2NR^{5g}R^{5h}$, $-N(R^j)S(O)_2R^{5k}$, trifluoromethyl, trifluoromethoxy, and $-NR^{5g}R^{5h}$;

A specific compound of the invention is a compound which is:

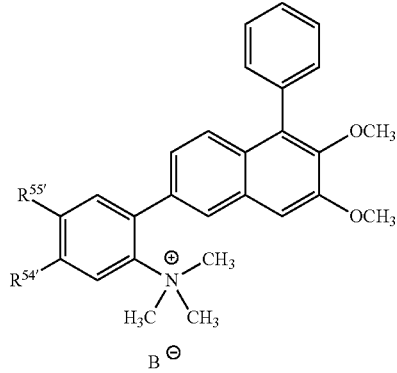

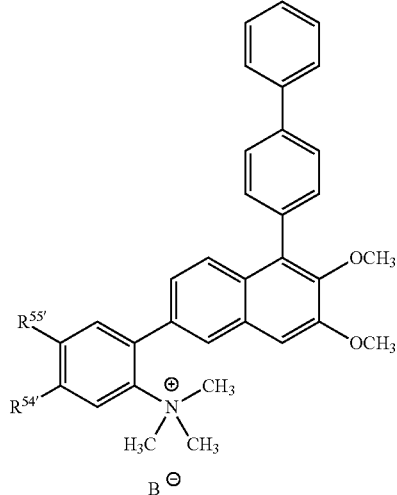

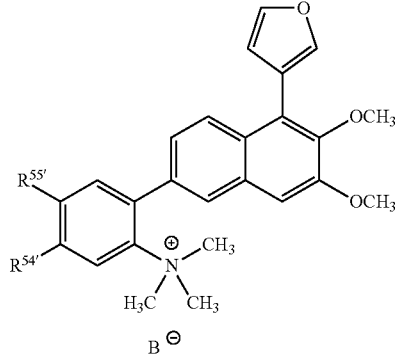

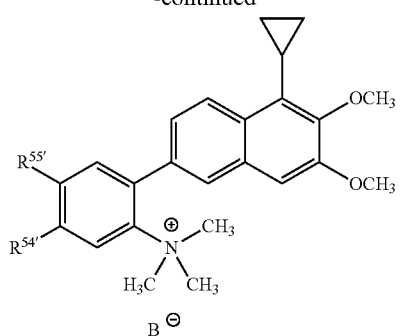
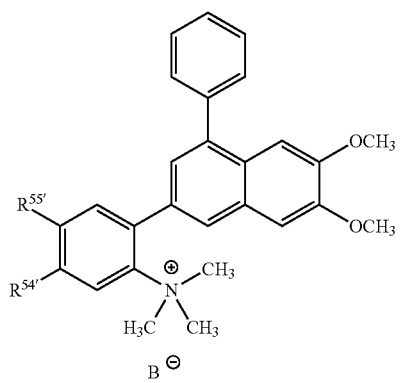
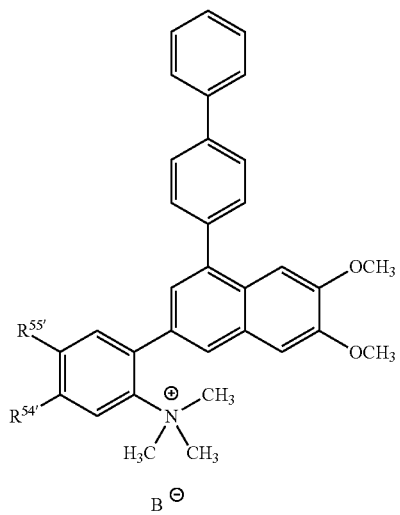
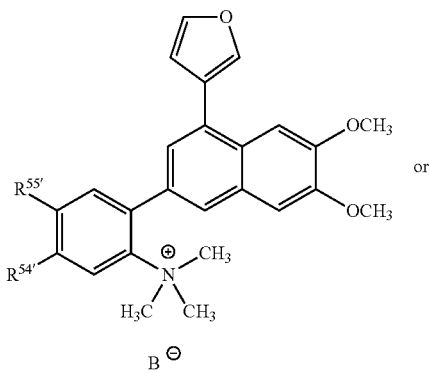
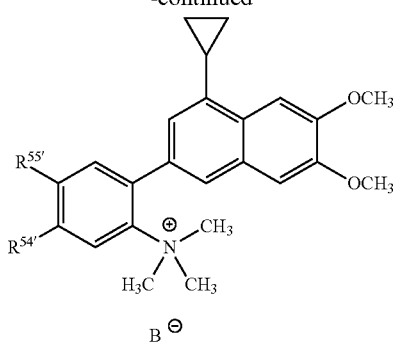
wherein $R^{54'}$ and $R^{5'}$ are each H or methoxy, or taken together are methylenedioxy;
or a salt or prodrug thereof.
A specific compound of the invention is a compound which is:
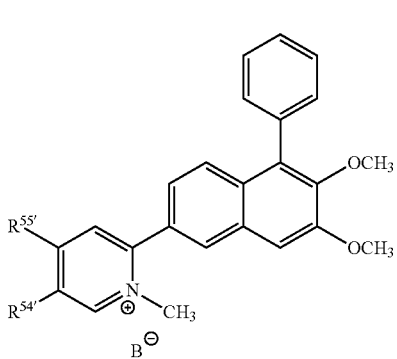
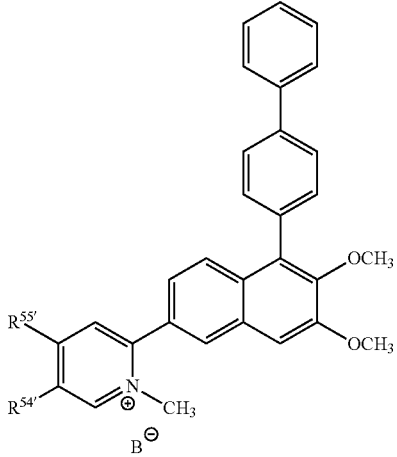
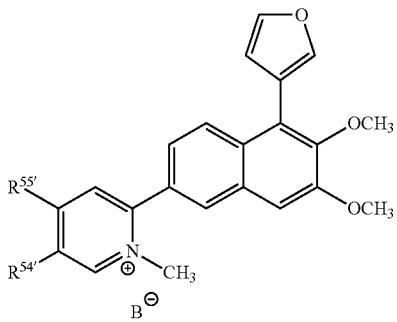

-continued
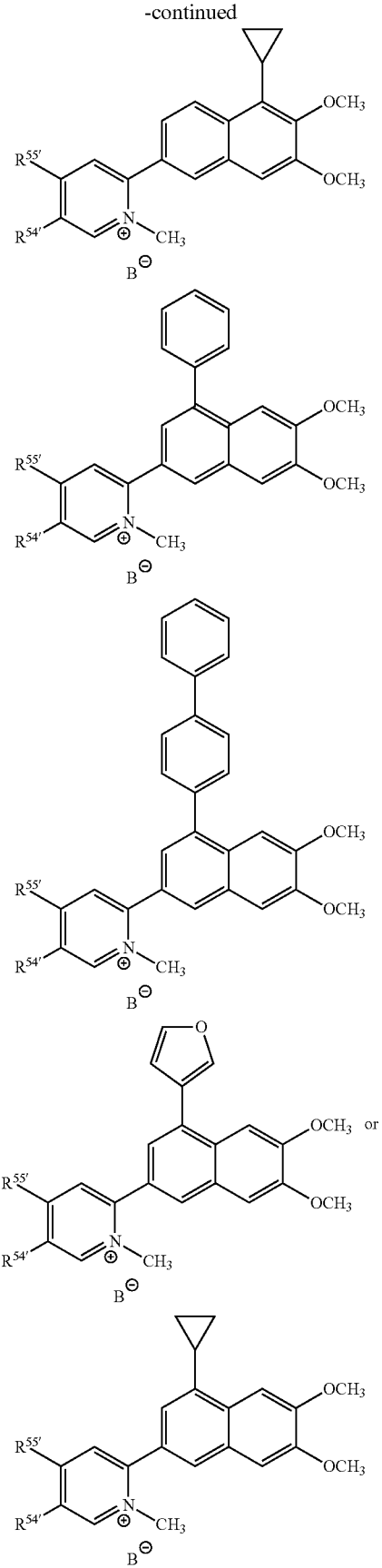
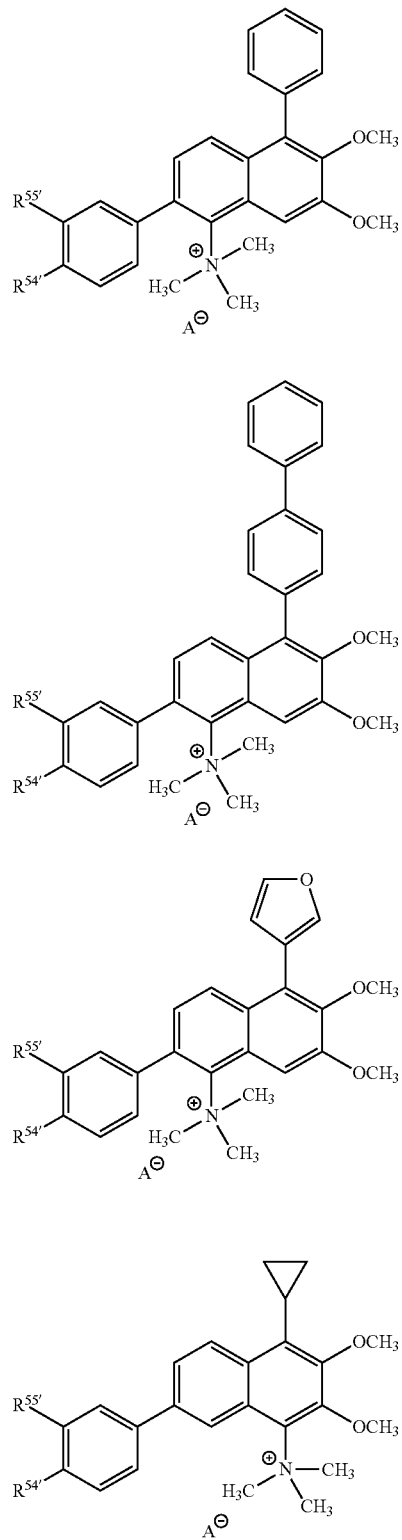
wherein $R^{54'}$ and $R^{55'}$ are each H or methoxy, or taken together are methylenedioxy;
or a salt or prodrug thereof.
A specific compound of the invention is a compound which is:

-continued
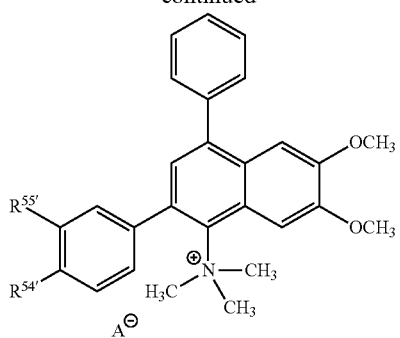
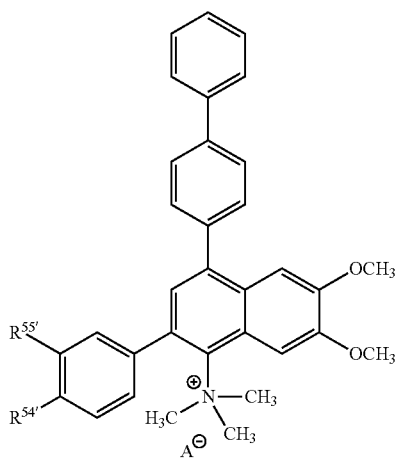
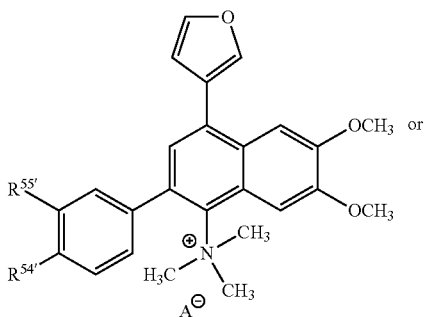 or
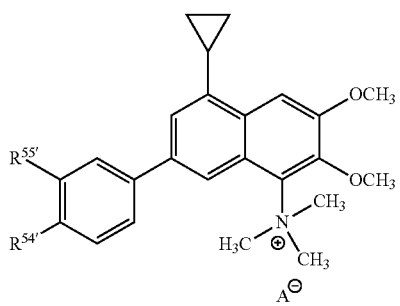
wherein $R^{54'}$ and $R^{55'}$ are each H or methoxy, or taken together are methylenedioxy;
or a salt or prodrug thereof.
A specific compound of the invention is a compound which is:
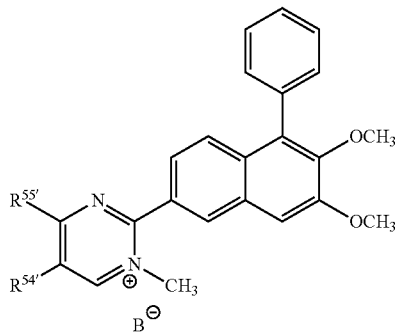
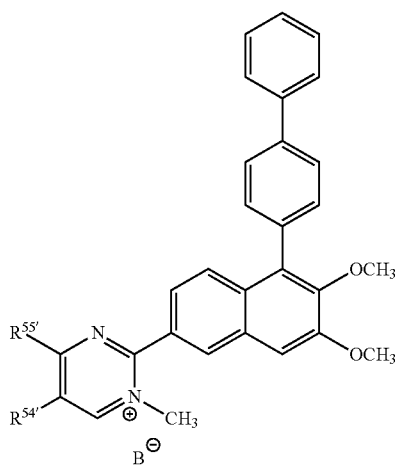
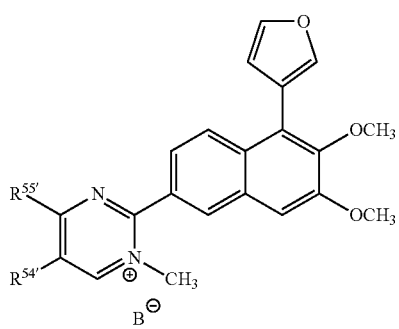
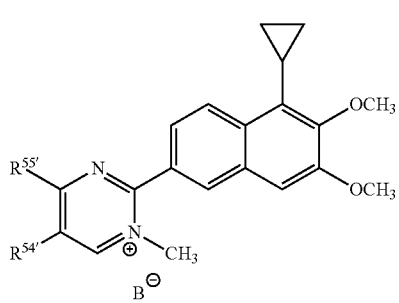

-continued
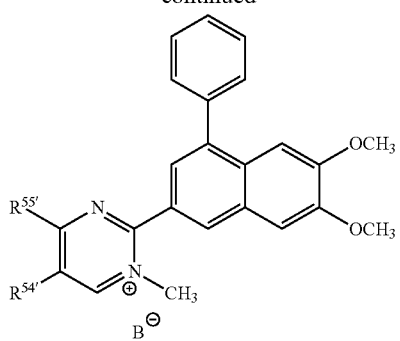
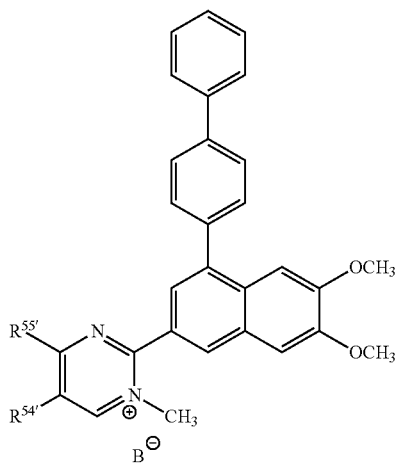
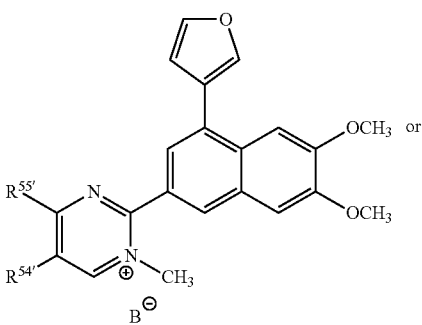 or
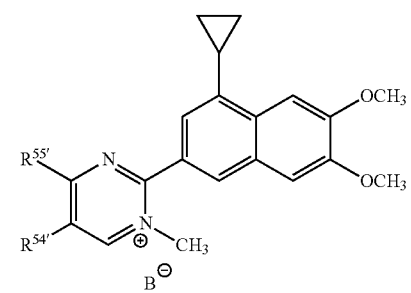
wherein $R^{54'}$ and $R^{55'}$ are each H or methoxy, or taken together are methylenedioxy;
or a salt or prodrug thereof.
A specific compound of the invention is a compound which is:
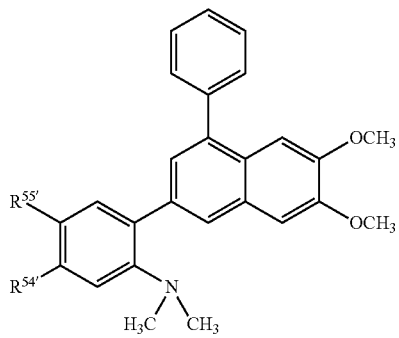
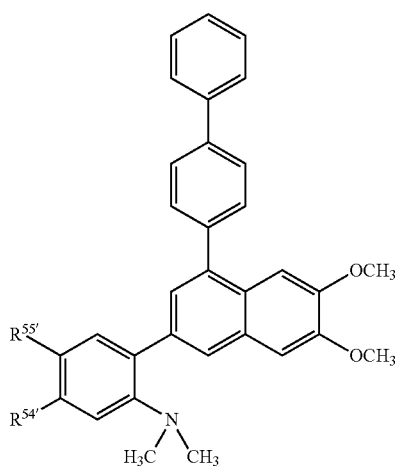
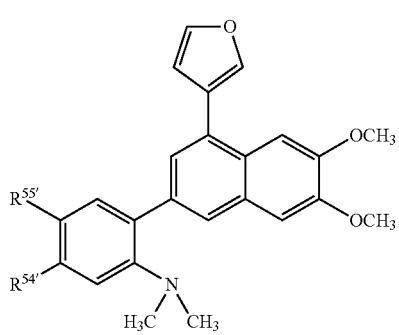
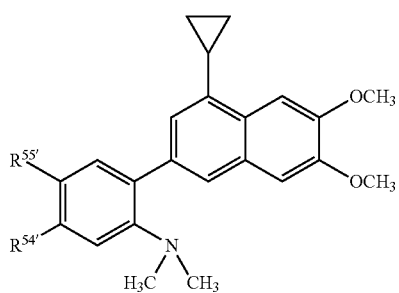

-continued
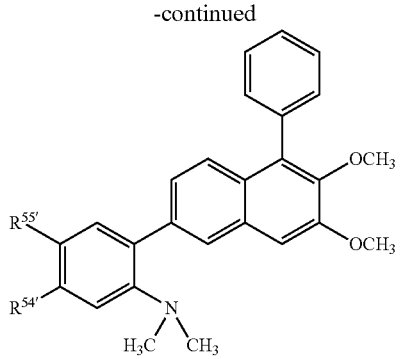
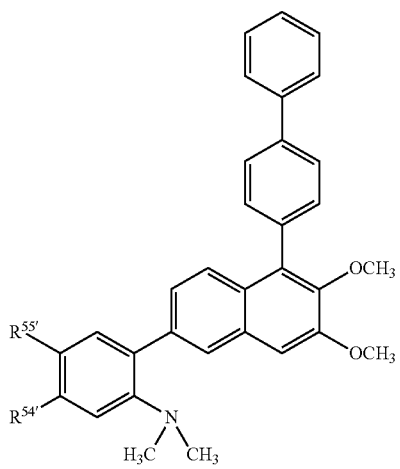
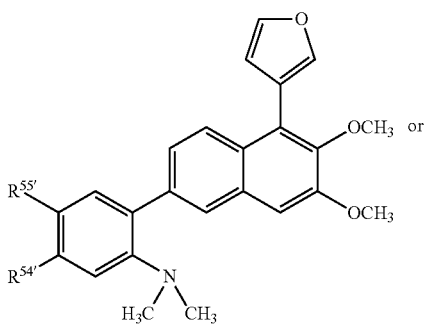 or
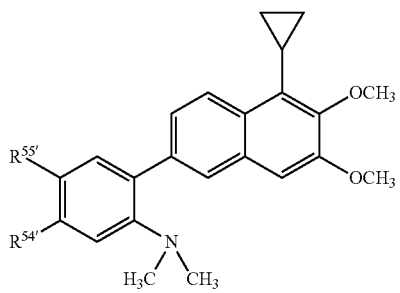
wherein $R^{54'}$ and $R^{55'}$ are each H or methoxy, or taken together are methylenedioxy;
or a salt or prodrug thereof.
A specific compound of the invention is a compound which is:
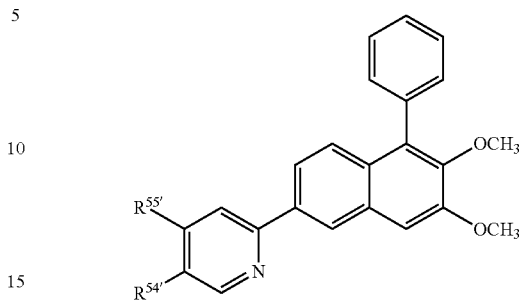
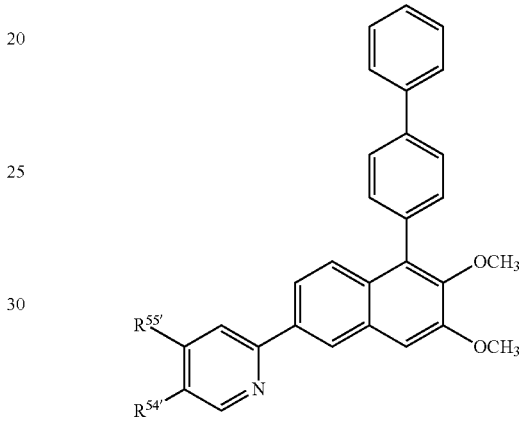
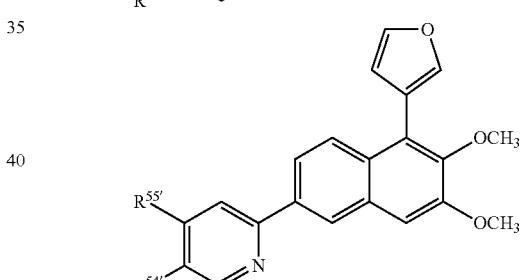
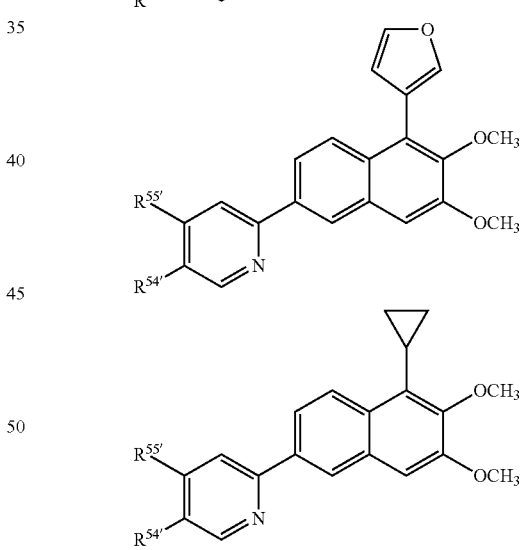
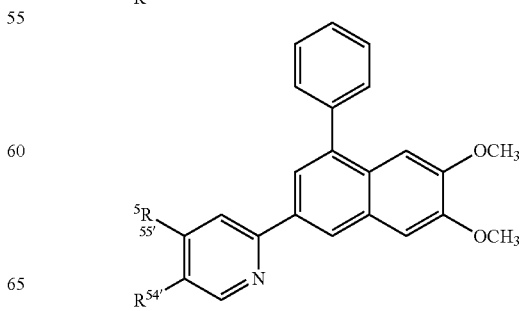

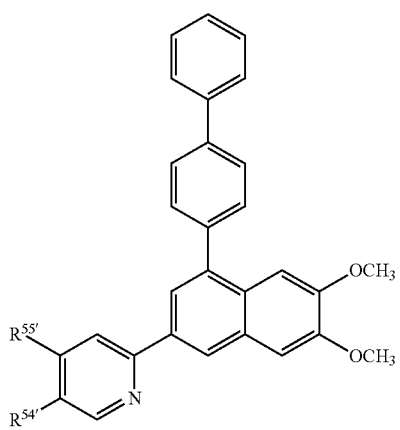
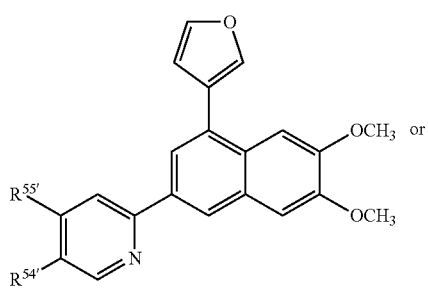 or
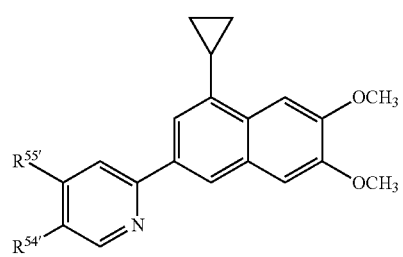
wherein $R^{54'}$ and $R^{55'}$ are each H or methoxy, or taken together are methylenedioxy;
or a salt or prodrug thereof.
A specific compound of the invention is a compound which is:
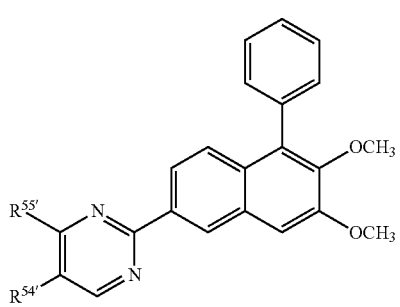
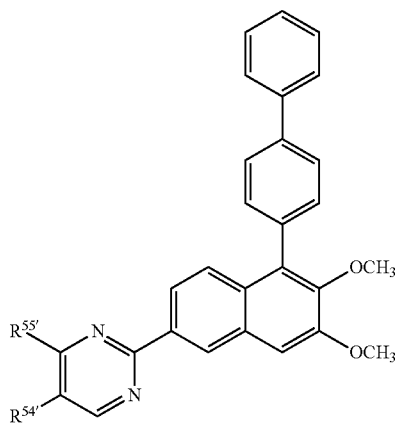
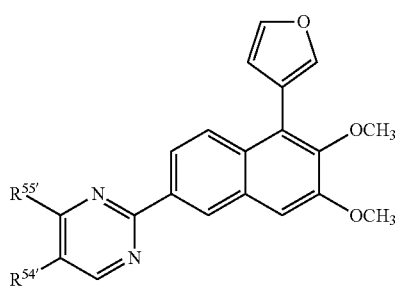
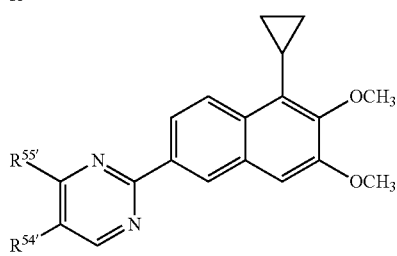
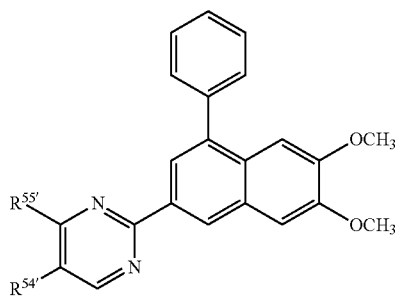
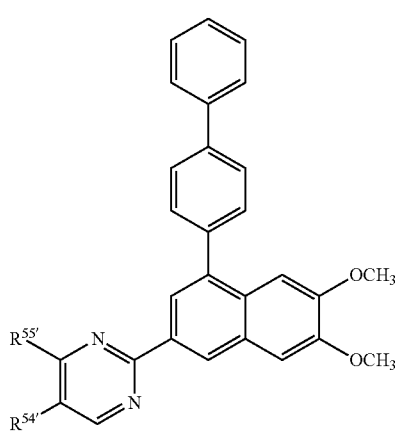

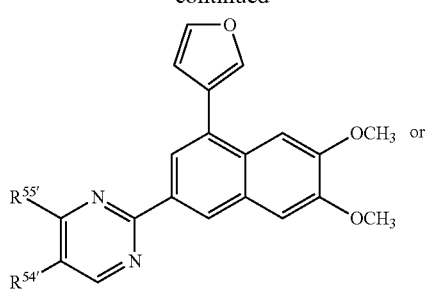
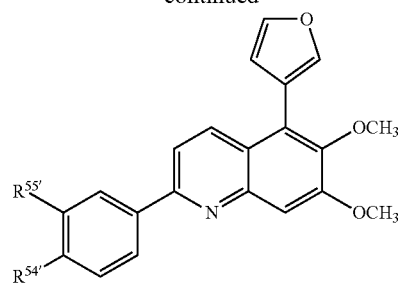
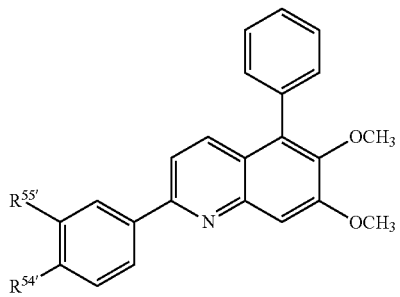
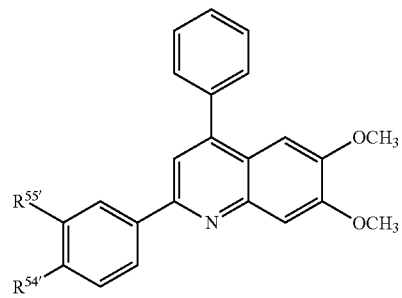
wherein $R^{54'}$ and $R^{55'}$ are each H or methoxy, or taken together are methylenedioxy;
or a salt or prodrug thereof.
A specific compound of the invention is a compound which is:
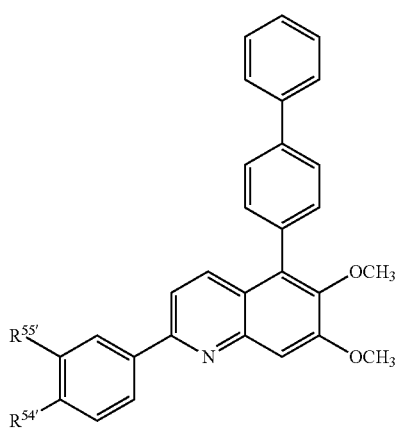
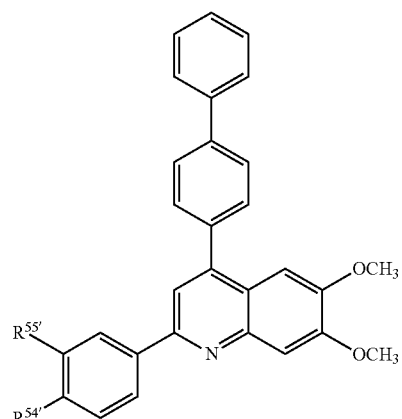
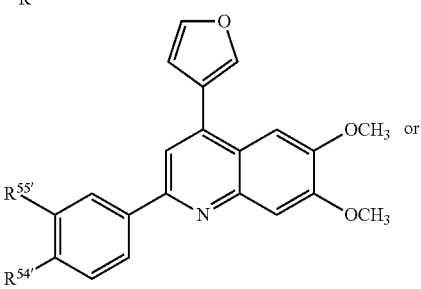

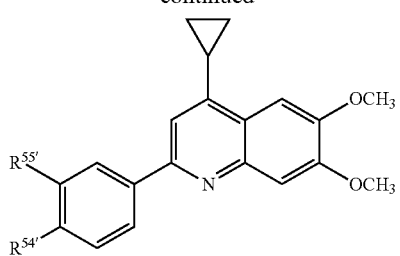
wherein R$^{54'}$ and R$^{55'}$ are each H or methoxy, or taken together are methylenedioxy;
or a salt or prodrug thereof.
A specific compound of the invention is a compound which is:
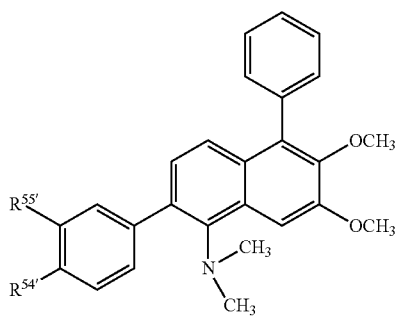
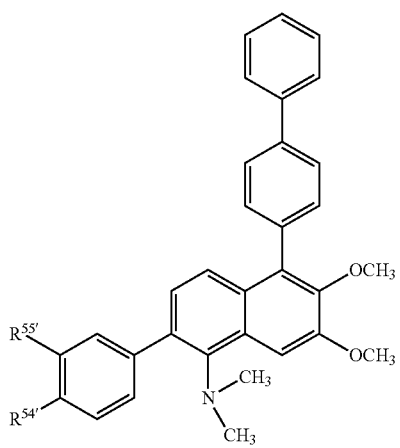
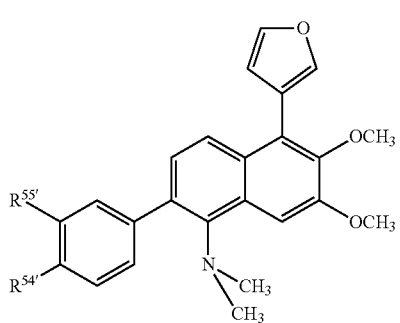
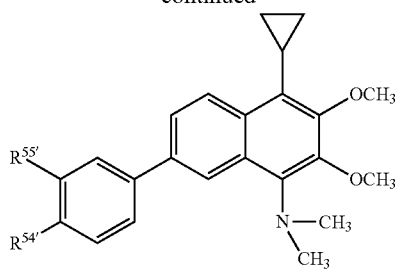
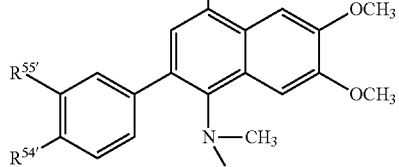
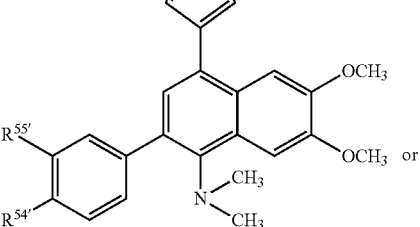
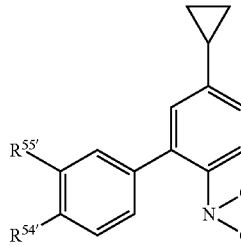 or
wherein R$^{54'}$ and R$^{55'}$ are each H or methoxy, or taken together are methylenedioxy;
or a salt or prodrug thereof.

A specific compound of the invention is a compound which is:
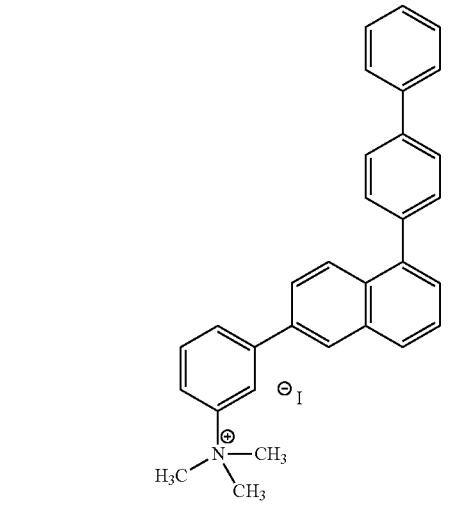
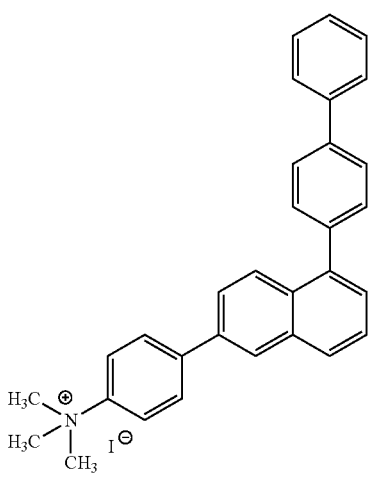
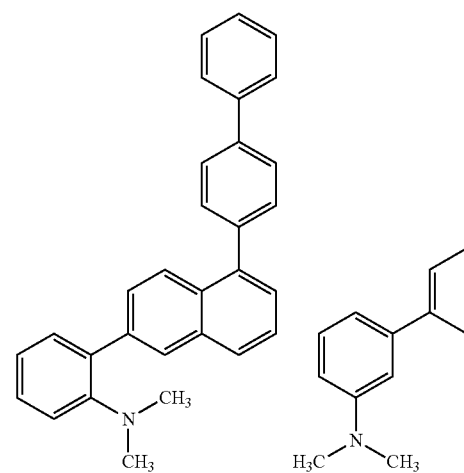
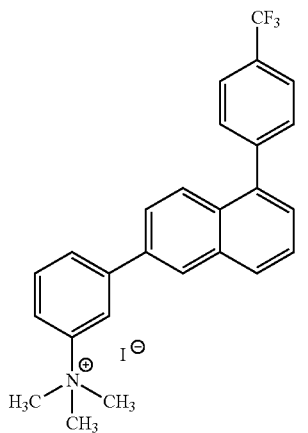
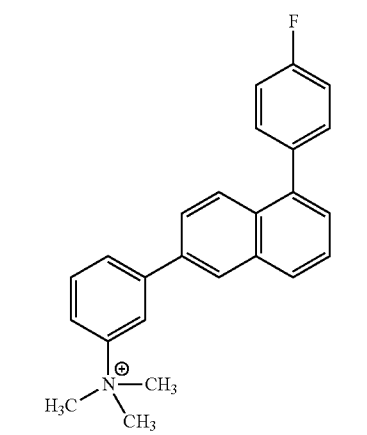
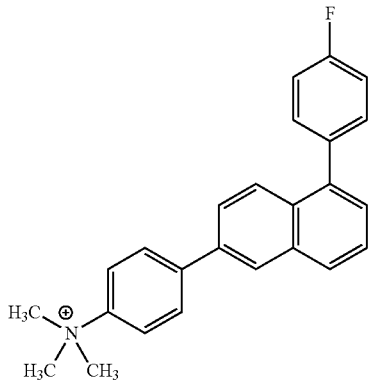
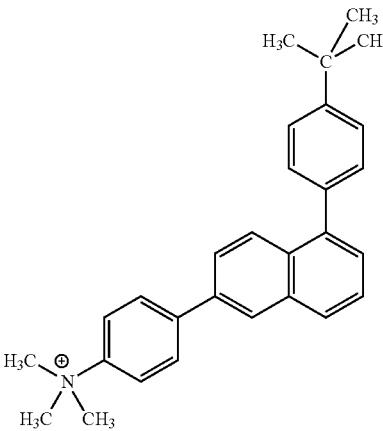

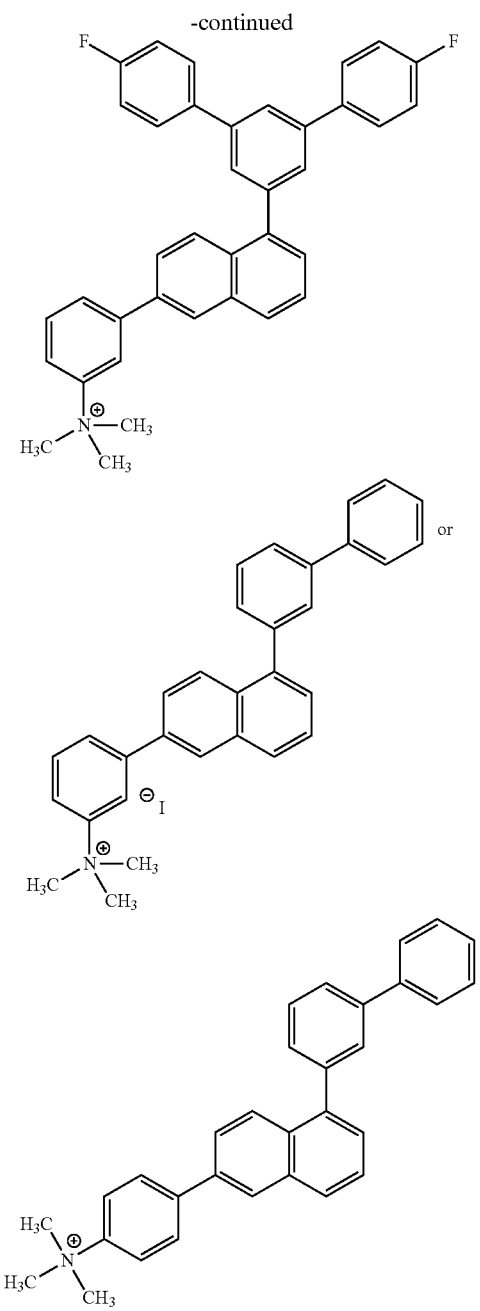

or a salt or prodrug thereof.

A specific compound of the invention is a compound wherein at least one of least one W, X, Y, $R^1$, $R^{52'}$, $R^{53'}$, $R^{54'}$, $R^{55'}$, and $R^{56'}$ comprises at least one nitrogen atom.

A specific compound of the invention is a compound of formula (I) wherein:

X is $^+N(R^{81})(R^{82})B^-$;

Y is $C(R^{83})$;

A is N or $C—R^{4'}$;

any adjacent $R^6$, $R^7$, $R^8$, $R^{4'}$ and $R^{5'}$ taken together can optionally be methylenedioxy and each remaining $R^6$, $R^7$, $R^8$, $R^{4'}$ and $R^{5'}$ is independently selected from H, $R^{bb}$, and $Z—R^x$;

each Z is independently selected from —O—, —S—, and —N(R$^y$)—;

at least one of $R^4$, $R^5$, $R^{2'}$, $R^{3'}$, and $R^{6'}$ is selected from hydroxy, carboxy, cyano, $CF_3SO_3$—, $(C_1$-$C_6)$alkyl, $(C_2$-$C_6)$ alkenyl, $(C_2$-$C_6)$alkynyl, $(C_1$-$C_6)$alkoxy, cycloalkyl, aryl$(C_1$-$C_6)$alkyl, aryl, heteroaryl, heteroaryl$(C_1$-$C_6)$alkyl, arylalkanoyl, and heteroarylalkanoyl; and the remainder of $R^4$, $R^5$, $R^{2'}$, $R^{3'}$, and $R^{6'}$ are independently selected from hydrogen, halo, hydroxy, carboxy, cyano, $CF_3SO_3$—, $(C_1$-$C_6)$alkyl, $(C_2$-$C_6)$alkenyl, $(C_2$-$C_6)$alkynyl, $(C_1$-$C_6)$alkoxy, cycloalkyl, aryl$(C_1$-$C_6)$alkyl, aryl, heteroaryl, heteroaryl$(C_1$-$C_6)$alkyl, aryl$(C_1$-$C_6)$alkanoyl, and heteroaryl$(C_1$-$C_6)$alkanoyl; or $R^{6'}$ and $R^{10}$ taken together are —$(CR^{13}_2)_2$— or —$CR^{14}$=$CR^{14}$—; wherein each $(C_1$-$C_6)$alkyl, $(C_2$-$C_6)$alkenyl, $(C_2$-$C_6)$alkynyl, $(C_1$-$C_6)$alkoxy, cycloalkyl, and $(C_1$-$C_6)$ alkanoyl of $R^4$, $R^5$, $R^{2'}$, $R^{3'}$, and $R^{6'}$ is optionally substituted with one or more groups independently selected from halo, hydroxy, cyano, nitro, $(C_1$-$C_6)$alkoxy, cycloalkyl, oxo, carboxy, aryloxy, sulfo, —$S(O)_2NR^gR^h$, —$N(R^j)S(O)_2R^k$, and —$NR^gR^h$; and wherein each aryl, and heteroaryl of $R^4$, $R^5$, $R^{2'}$, $R^{3'}$, and $R^{6'}$ is optionally substituted with one or more groups independently selected from $(C_1$-$C_6)$alkyl, halo, hydroxy, cyano, nitro, $(C_1$-$C_6)$alkoxy, cycloalkyl, carboxy, aryloxy, nitro, sulfo, $R^{aa}$, —$S(O)_2NR^gR^h$, —$N(R^j)S(O)_2R^k$, and —$NR^gR^h$;

the bond represented by ---- is present and $R^{82}$ is absent except as defined below when $R^{81}$ and $R^{8a}$ taken together with the atoms to which they are attached form a 5- or 6-membered heterocyclic ring or a 5- or 6-membered heteroaryl ring;

$R^{81}$ is absent and $B^-$ is absent; or $R^{81}$ is H or $(C_1$-$C_6)$alkyl and $B^-$ is counterion;

or $R^{81}$ and $R^{8a}$ taken together with the atoms to which they are attached form a 5- or 6-membered heterocyclic ring or a 5- or 6-membered heteroaryl ring, wherein a) when the bond represented by ---- is present in the 5- or 6-membered heterocyclic ring or the 5- or 6-membered heteroaryl ring, $R^{82}$ is absent and $B^-$ is a counterion, b) when the bond represented by ---- is absent in the 5- or 6-membered heterocyclic ring or the 5- or 6-membered heteroaryl ring, $R^{82}$ is $(C_1$-$C_6)$alkyl and $B^-$ is a counterion, or c) when the bond represented by ---- is absent in the 5- or 6-membered heterocyclic ring or the 5- or 6-membered heteroaryl ring, $R^{82}$ is absent and $B^-$ is absent;

$R^{83}$ is H, $(C_1$-$C_6)$alkyl, $(C_1$-$C_6)$alkoxy, $(C_1$-$C_6)$alkylthio, aryloxy, arylthio, —$NR^{8a}R^{8b}$ or cyano; or $R^{6'}$ and $R^{83}$ taken together are —$(CR^{13}_2)_2$— or —$CR^{14}$=$CR^{14}$—;

each $R^{13}$ is independently H, $(C_1$-$C_6)$alkyl, $(C_1$-$C_6)$alkoxy, $(C_1$-$C_6)$alkylthio, aryloxy or arylthio wherein any $(C_1$-$C_6)$ alkyl, $(C_1$-$C_6)$alkoxy, and $(C_1$-$C_6)$alkylthio of $R^{13}$ is optionally substituted with one or more groups selected from halo, cyano, oxo (=O), $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^{8e}R^{8f}$, and wherein any aryloxy, or arylthio of $R^{13}$ is optionally substituted with one or more groups selected from halo, cyano, $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^{8e}R^{8f}$;

each $R^{14}$ is independently H, $(C_1$-$C_6)$alkyl, $(C_1$-$C_6)$alkoxy, $(C_1$-$C_6)$alkylthio, aryloxy or arylthio wherein any $(C_1$-$C_6)$ alkyl, $(C_1$-$C_6)$alkoxy, and $(C_1$-$C_6)$alkylthio of $R^{14}$ is optionally substituted with one or more groups selected from halo, cyano, oxo (=O), $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^{8e}R^{8f}$, and wherein any aryloxy, or arylthio of $R^{14}$ is optionally substituted with one or more groups selected from halo, cyano, $(C_1$-$C_6)$alkyl, $(C_3$-$C_6)$cycloalkyl, carboxy, $NO_2$, hydroxy, $(C_1$-$C_6)$alkoxy, $(C_1$-$C_6)$alkoxycarbonyl, $(C_1$-$C_6)$alkanoyloxy, aryl, heteroaryl, aryloxy, heteroaryloxy, and —$NR^{8e}R^{8f}$;

$R^{8a}$ is hydrogen, $(C_1-C_6)$alkyl, aryl, aryl$(C_1-C_6)$alkyl, heteroaryl, or heteroaryl$(C_1-C_6)$alkyl; wherein each $(C_1-C_6)$alkyl of $R^{8a}$ is optionally substituted with one or more groups selected from halo, hydroxy, cyano, nitro, $(C_1-C_6)$alkoxy, cycloalkyl, oxo, carboxy, —$NR^{8g}R^{8h}$, and aryloxy; and wherein each aryl and heteroaryl of $R^{8a}$ is optionally substituted with one or more groups selected from $(C_1-C_6)$alkyl, halo, hydroxy, cyano, nitro, $(C_1-C_6)$alkoxy, cycloalkyl, carboxy, —$NR^{8g}R^{8h}$, and aryloxy;

$R^{8b}$ is hydrogen, $(C_1-C_6)$alkyl, aryl, aryl$(C_1-C_6)$alkyl, heteroaryl, heteroaryl$(C_1-C_6)$alkyl, —C(=O)—$R^{8m}$, —C(=O)—$OR^{8n}$, —C(=O)—$SR^{8p}$, —C(=O)—$NR^{8q}R^{8r}$, —C(=S)—$R^{8m}$, —C(=S)—$OR^{8n}$, —C(=S)—$SR^{8p}$, —C(=S)—$NR^{8q}R^{8r}$, or —C(=$NR^{8c}$)—$R^{8d}$; wherein each $(C_1-C_6)$alkyl of $R^{8b}$ is optionally substituted with one or more groups independently selected from halo, hydroxy, cyano, nitro, $(C_1-C_6)$alkoxy, cycloalkyl, oxo, carboxy, and aryloxy; and wherein each aryl, and heteroaryl of $R^b$ is optionally substituted with one or more groups independently selected from $(C_1-C_6)$alkyl, halo, hydroxy, cyano, nitro, $(C_1-C_6)$alkoxy, cycloalkyl, carboxy, and aryloxy; or $R^{8a}$ and $R^{8b}$ taken together with the nitrogen to which they are attached form aziridino, azetidino, morpholino, piperazino, pyrrolidino, pyrrole, indole, or piperidino, which aziridino, azetidino, morpholino, piperazino, pyrrolidino pyrrole, indole, or piperidino can optionally be substituted with one or more $(C_1-C_6)$alkyl;

$R^{8c}$ is hydrogen, $(C_1-C_6)$alkyl, aryl, or heteroaryl;

$R^{8d}$ is hydrogen, $(C_1-C_6)$alkyl, $(C_1-C_6)$alkoxy, $(C_1-C_6)$alkylthio, $(C_1-C_6)$alkanoyl, or —$NR^eR^f$;

$R^{8e}$ and $R^{8f}$ are each independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; or $R^{8e}$ and $R^{8f}$ together with the nitrogen to which they are attached form a aziridino, azetidino, morpholino, piperazino, pyrrolidino or piperidino;

each $R^{8g}$ and $R^{8h}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; or $R^{8g}$ and $R^{8h}$ together with the nitrogen to which they are attached form a aziridino, azetidino, morpholino, piperazino, pyrrolidino or piperidino;

each $R^{8j}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl;

each $R^{8k}$ is independently selected from $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl;

each $^8R^m$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl;

each $R^{8n}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl, wherein each aryl, and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —$S(O)_2NR^{8g}R^{8h}$, —$N(R^{8j})S(O)_2R^{8k}$, and —$NR^{8g}R^{8h}$;

each $R^{8p}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl, wherein each aryl, and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —$S(O)_2NR^{8g}R^{8h}$, —$N(R^{8j})S(O)_2R^{8k}$, and —$NR^{8g}R^{8h}$;

each $R^{8q}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; and each $R^{8r}$ is independently selected from H, $(C_1-C_6)$alkyl, cycloalkyl, cycloalkyl$(C_1-C_6)$alkyl, aryl, heteroaryl, aryl$(C_1-C_6)$alkyl and heteroaryl$(C_1-C_6)$alkyl; or $R^{8q}$ and $R^{8r}$ together with the nitrogen to which they are attached form a aziridino, azetidino, morpholino, piperazino, pyrrolidino or piperidino;

each $R^{8u}$ and $R^{8v}$ is independently selected from H and $(C_1-C_6)$alkyl;

each $R^{8x}$ is independently selected from $(C_1-C_6)$alkyl, $(C_1-C_6)$alkanoyl, and —C(=O)$NR^{8u}R^{8v}$;

each $R^{8y}$ is independently selected from H and $(C_1-C_6)$alkyl;

each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —$S(O)_2NR^{8g}R^{8h}$—$N(R^{8j})S(O)_2R^{8k}$, and —$NR^{8g}R^{8h}$; and each $R^{8bb}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —$S(O)_2NR^{8g}R^{8h}$, —$N(R^{8j})S(O)_2R^{8k}$, and —$NR^{8g}R^{8h}$;

or a salt thereof.

A specific value for $R^{83}$ is H, $(C_1-C_6)$alkyl, $(C_1-C_6)$alkoxy, $(C_1-C_6)$alkylthio, aryloxy, arylthio, —$NR^{8a}R^{8b}$ or cyano.

A specific value for $R^{83}$ is H, $(C_1-C_6)$alkyl, $(C_1-C_6)$alkoxy, $(C_1-C_6)$alkylthio, aryloxy, or arylthio.

A specific value for $R^{83}$ is —$NR^{8a}R^{8b}$ or cyano.

A specific value for $R^{6'}$ and $R^{83}$ taken together are —$(CR^{13}_2)_2$— or —$CR^{14}$=$CR^{14}$—.

A specific compound of the invention is a compound wherein the bond represented by ---- is present and $R^{82}$ is absent.

A specific compound of the invention is a compound wherein $R^{81}$ and $R^{8a}$ taken together with the atoms to which they are attached form a 5- or 6-membered heterocyclic ring or a 5- or 6-membered heteroaryl ring.

A specific compound of the invention is a compound wherein $R^{81}$ is absent and $B^-$ is absent.

A specific compound of the invention is a compound wherein $R^{81}$ is H or $(C_1-C_6)$alkyl and $B^-$ is a counterion.

A specific compound of the invention is a compound of formula (VIIIa):

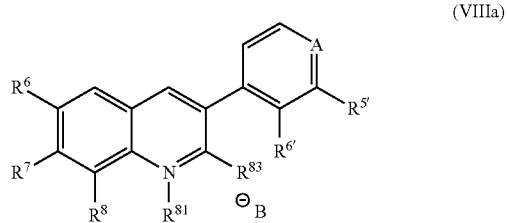

(VIIIa)

wherein $R^{6'}$ is selected from hydroxy, carboxy, cyano, $CF_3SO_3$—, $(C_1-C_6)$alkyl, $(C_2-C_6)$alkenyl, $(C_2-C_6)$alkynyl, $(C_1-C_6)$alkoxy, cycloalkyl, aryl$(C_1-C_6)$alkyl, aryl, heteroaryl, heteroaryl$(C_1-C_6)$alkyl, arylalkanoyl, and heteroarylalkanoyl; wherein each $(C_1-C_6)$alkyl, $(C_2-C_6)$alkenyl, $(C_2-C_6)$alkynyl, $(C_1-C_6)$alkoxy, cycloalkyl, and $(C_1-C_6)$alkanoyl of $R^{6'}$ is optionally substituted with one or more groups independently selected from halo, hydroxy, cyano, nitro, $(C_1-C_6)$ alkoxy, cycloalkyl, oxo, carboxy, aryloxy, sulfo, —S(O)$_2$NR$^{8g}$R$^{8h}$, —N(R$^{8j}$)S(O)$_2$R$^{8k}$, and —NR$^{8g}$R$^{8h}$; and wherein each aryl, and heteroaryl of R$^{6'}$ is optionally substituted with one or more groups independently selected from (C$_1$-C$_6$)alkyl, halo, hydroxy, cyano, nitro, (C$_1$-C$_6$)alkoxy, cycloalkyl, carboxy, aryloxy, nitro, sulfo, R$^{8aa}$, —S(O)$_2$NR$^{8g}$R$^{8h}$, —N(R$^{8j}$)S(O)$_2$R$^{8k}$, and —NR$^{8g}$R$^{8h}$; or a salt thereof.

A specific compound of the invention is a compound of formula (VIIIb):

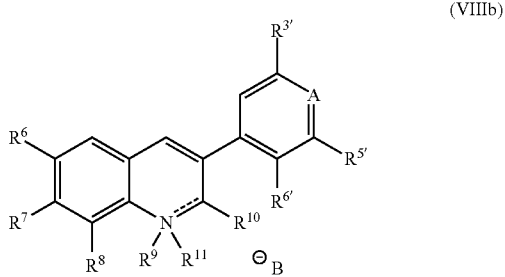

(VIIIb)

wherein R$^{3'}$ is selected from hydroxy, carboxy, cyano, CF$_3$SO$_3$—, (C$_1$-C$_6$)alkyl, (C$_2$-C$_6$)alkenyl, (C$_2$-C$_6$)alkynyl, (C$_1$-C$_6$)alkoxy, cycloalkyl, aryl(C$_1$-C$_6$)alkyl, aryl, heteroaryl, heteroaryl(C$_1$-C$_6$)alkyl, arylalkanoyl, and heteroarylalkanoyl; wherein each (C$_1$-C$_6$)alkyl, (C$_2$-C$_6$)alkenyl, (C$_2$-C$_6$)alkynyl, (C$_1$-C$_6$)alkoxy, cycloalkyl, and (C$_1$-C$_6$)alkanoyl of R$^{3'}$ is optionally substituted with one or more groups independently selected from halo, hydroxy, cyano, nitro, (C$_1$-C$_6$)alkoxy, cycloalkyl, oxo, carboxy, aryloxy, sulfo, —S(O)$_2$NR$^{8g}$R$^{8h}$, —N(R$^{8j}$)S(O)$_2$R$^{8k}$, and —NR$^{8g}$R$^{8h}$; and wherein each aryl, and heteroaryl of R$^{3'}$ is optionally substituted with one or more groups independently selected from (C$_1$-C$_6$)alkyl, halo, hydroxy, cyano, nitro, (C$_1$-C$_6$)alkoxy, cycloalkyl, carboxy, aryloxy, nitro, sulfo, R$^{8aa}$, —S(O)$_2$NR$^{8g}$R$^{8h}$, —N(R$^{8j}$)S(O)$_2$R$^{8k}$, and —NR$^{8g}$R$^{8h}$; or a salt thereof.

A specific compound of the invention is a compound of formula (VIIIc):

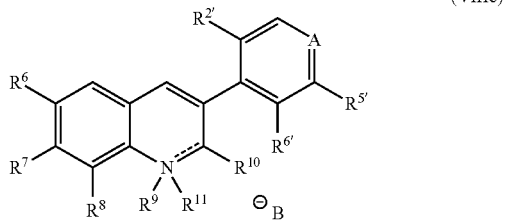

(VIIIc)

wherein R$^{2'}$ is selected from hydroxy, carboxy, cyano, CF$_3$SO$_3$—, (C$_1$-C$_6$)alkyl, (C$_2$-C$_6$)alkenyl, (C$_2$-C$_6$)alkynyl, (C$_1$-C$_6$)alkoxy, cycloalkyl, aryl(C$_1$-C$_6$)alkyl, aryl, heteroaryl, heteroaryl(C$_1$-C$_6$)alkyl, arylalkanoyl, and heteroarylalkanoyl; wherein each (C$_1$-C$_6$)alkyl, (C$_2$-C$_6$)alkenyl, (C$_2$-C$_6$)alkynyl, (C$_1$-C$_6$)alkoxy, cycloalkyl, and (C$_1$-C$_6$)alkanoyl of R$^{2'}$ is optionally substituted with one or more groups independently selected from halo, hydroxy, cyano, nitro, (C$_1$-C$_6$)alkoxy, cycloalkyl, oxo, carboxy, aryloxy, sulfo, —S(O)$_2$NR$^{8g}$R$^{8h}$, —N(R$^{8j}$)S(O)$_2$R$^{8k}$, and —NR$^{8g}$R$^{8h}$; and wherein each aryl, and heteroaryl of R$^{2'}$ is optionally substituted with one or more groups independently selected from (C$_1$-C$_6$)alkyl, halo, hydroxy, cyano, nitro, (C$_1$-C$_6$)alkoxy, cycloalkyl, carboxy, aryloxy, nitro, sulfo, R$^{8aa}$, —S(O)$_2$NR$^{8g}$R$^{8h}$, —N(R$^{8j}$)S(O)$_2$R$^{8k}$, and —NR$^{8g}$R$^{8h}$; or a salt thereof.

A specific compound of the invention is a compound of formula (VIIId):

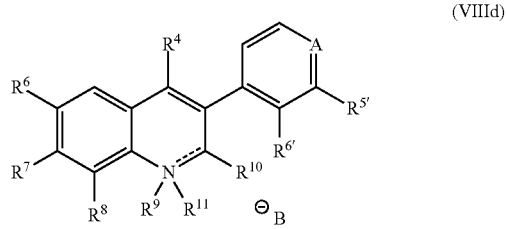

(VIIId)

wherein R$^4$ is selected from hydroxy, carboxy, cyano, CF$_3$SO$_3$—, (C$_1$-C$_6$)alkyl, (C$_2$-C$_6$)alkenyl, (C$_2$-C$_6$)alkynyl, (C$_1$-C$_6$)alkoxy, cycloalkyl, aryl(C$_1$-C$_6$)alkyl, aryl, heteroaryl, heteroaryl(C$_1$-C$_6$)alkyl, arylalkanoyl, and heteroarylalkanoyl; wherein each (C$_1$-C$_6$)alkyl, (C$_2$-C$_6$)alkenyl, (C$_2$-C$_6$)alkynyl, (C$_1$-C$_6$)alkoxy, cycloalkyl, and (C$_1$-C$_6$)alkanoyl of R$^4$ is optionally substituted with one or more groups independently selected from halo, hydroxy, cyano, nitro, (C$_1$-C$_6$)alkoxy, cycloalkyl, oxo, carboxy, aryloxy, sulfo, —S(O)$_2$NR$^{8g}$R$^{8h}$, —N(R$^{8j}$)S(O)$_2$R$^{8k}$, and —NR$^{8g}$R$^{8h}$; and wherein each aryl, and heteroaryl of R$^4$ is optionally substituted with one or more groups independently selected from (C$_1$-C$_6$)alkyl, halo, hydroxy, cyano, nitro, (C$_1$-C$_6$)alkoxy, cycloalkyl, carboxy, aryloxy, nitro, sulfo, R$^{8aa}$, —S(O)$_2$NR$^{8g}$R$^{8h}$, —N(R$^{8j}$)S(O)$_2$R$^{8k}$, and —NR$^{8g}$R$^{8h}$; or a salt thereof.

A specific compound of the invention is a compound of formula (VIIIe):

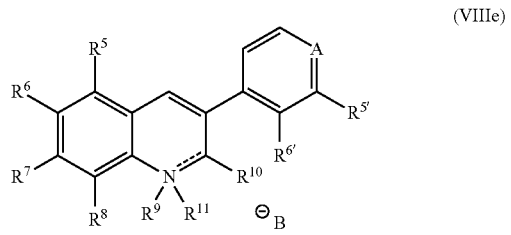

(VIIIe)

wherein R$^5$ is selected from hydroxy, carboxy, cyano, CF$_3$SO$_3$—, (C$_1$-C$_6$)alkyl, (C$_2$-C$_6$)alkenyl, (C$_2$-C$_6$)alkynyl, (C$_1$-C$_6$)alkoxy, cycloalkyl, aryl(C$_1$-C$_6$)alkyl, aryl, heteroaryl, heteroaryl(C$_1$-C$_6$)alkyl, arylalkanoyl, and heteroarylalkanoyl; wherein each (C$_1$-C$_6$)alkyl, (C$_2$-C$_6$)alkenyl, (C$_2$-C$_6$)alkynyl, (C$_1$-C$_6$)alkoxy, cycloalkyl, and (C$_1$-C$_6$)alkanoyl of R$^5$ is optionally substituted with one or more groups independently selected from halo, hydroxy, cyano, nitro, (C$_1$-C$_6$)alkoxy, cycloalkyl, oxo, carboxy, aryloxy, sulfo, —S(O)$_2$NR$^{8g}$R$^{8h}$, —N(R$^{8j}$)S(O)$_2$R$^{8k}$, and —NR$^{8g}$R$^{8h}$; and wherein each aryl, and heteroaryl of R$^5$ is optionally substituted with one or more groups independently selected from (C$_1$-C$_6$)alkyl, halo, hydroxy, cyano, nitro, (C$_1$-C$_6$)alkoxy, cycloalkyl, carboxy, aryloxy, nitro, sulfo, R$^{8aa}$, —S(O)$_2$NR$^{8g}$R$^{8h}$, —N(R$^{8j}$)S(O)$_2$R$^{8k}$, and —NR$^{8g}$R$^{8h}$; or a salt thereof.

A specific compound of the invention is a compound wherein at least one Z is —N(R$^{8y}$)—.

A specific compound of the invention is a compound wherein each Z is —N($R^{8y}$)—.

A specific compound of the invention is a compound wherein $R^{8x}$ is ($C_1$-$C_6$)alkyl.

A specific compound of the invention is a compound wherein $R^6$, $R^7$, $R^8$, $R^{4'}$ and $R^{5'}$ are each independently ($C_1$-$C_3$)alkoxy.

A specific compound of the invention is a compound wherein $R^6$, $R^7$, $R^8$, $R^{4'}$ and $R^{5'}$ are each methoxy.

A specific compound of the invention is a compound wherein $R^8$ is ($C_1$-$C_3$)alkoxy.

A specific compound of the invention is a compound wherein $R^8$ is methoxy.

A specific compound of the invention is a compound wherein $R^{4'}$ is ($C_1$-$C_3$)alkoxy.

A specific compound of the invention is a compound wherein $R^{4'}$ is methoxy.

A specific compound of the invention is a compound wherein $R^{5'}$ is ($C_1$-$C_3$)alkoxy.

A specific compound of the invention is a compound wherein $R^{5'}$ is methoxy.

A specific compound of the invention is a compound wherein $R^7$, $R^8$, $R^{4'}$ and $R^{5'}$ are each methoxy.

A specific compound of the invention is a compound wherein $R^7$ and $R^8$ taken together are methylenedioxy.

A specific compound of the invention is a compound wherein $R^{4'}$ and $R^{5'}$ taken together are methylenedioxy.

A specific compound of the invention is a compound wherein $R^6$ and $R^7$ taken together are methylenedioxy and $R^{4'}$ and $R^{5'}$ taken together are methylenedioxy.

A specific value for $R^{83}$ is cyano.

A specific value for $R^{83}$ is —$NR^aR^b$.

A specific value for $R^{8a}$ is hydrogen or methyl.

A specific value for $R^{8b}$ is hydrogen, ($C_1$-$C_6$)alkyl, aryl, aryl($C_1$-$C_6$)alkyl, heteroaryl, or heteroaryl($C_1$-$C_6$)alkyl.

A specific value for $R^{8b}$ is hydrogen, methyl, phenyl, or benzyl.

A specific value for $R^{8b}$ is —C(=$NR^{8c}$)—$R^{8d}$.

A specific value for $R^{8a}$ and $R^{8b}$ taken together with the nitrogen to which they are attached form aziridino, azetidino, morpholino, piperazino, pyrrolidino or piperidino, which aziridino, azetidino, morpholino, piperazino, pyrrolidino or piperidino can optionally be substituted with one or more ($C_1$-$C_6$)alkyl.

A specific value for $R^{8c}$ is hydrogen.

A specific value for $R^{8d}$ is methyl or amino.

A specific value for $R^{83}$ is H.

A specific compound of the invention is a compound which is:

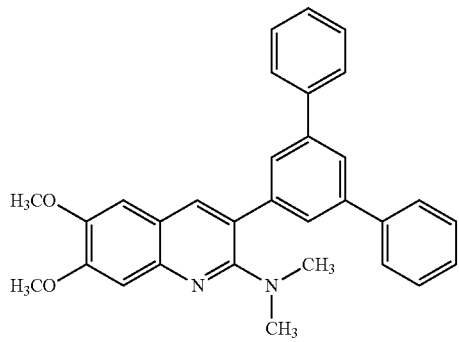

-continued

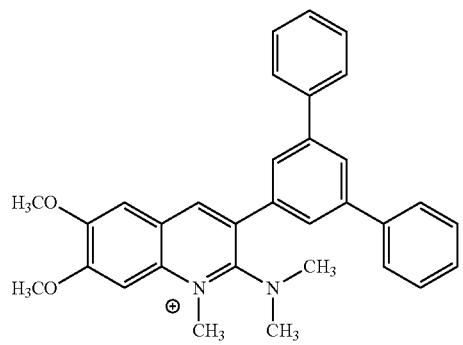

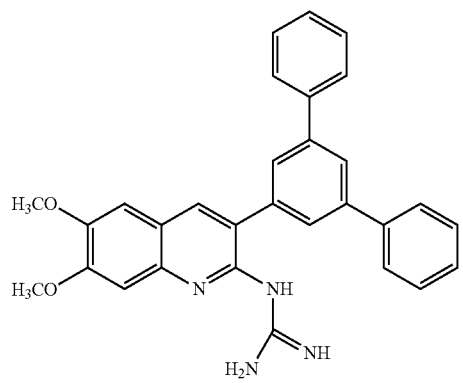

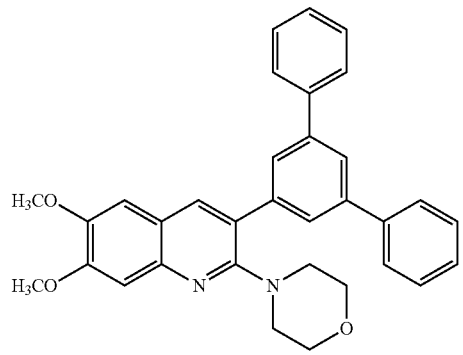

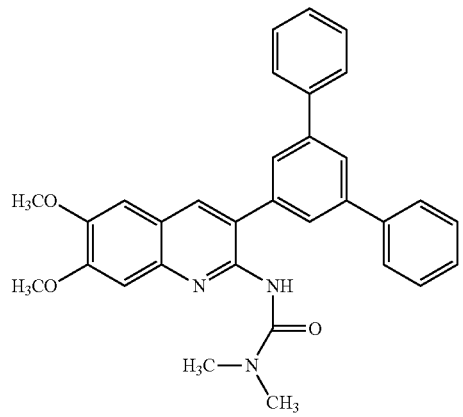

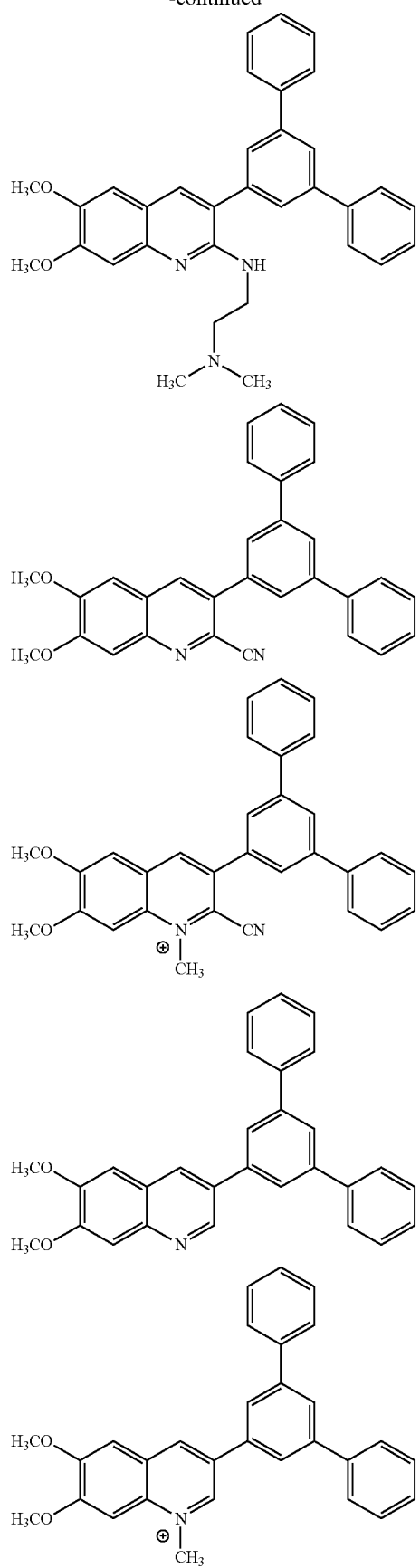
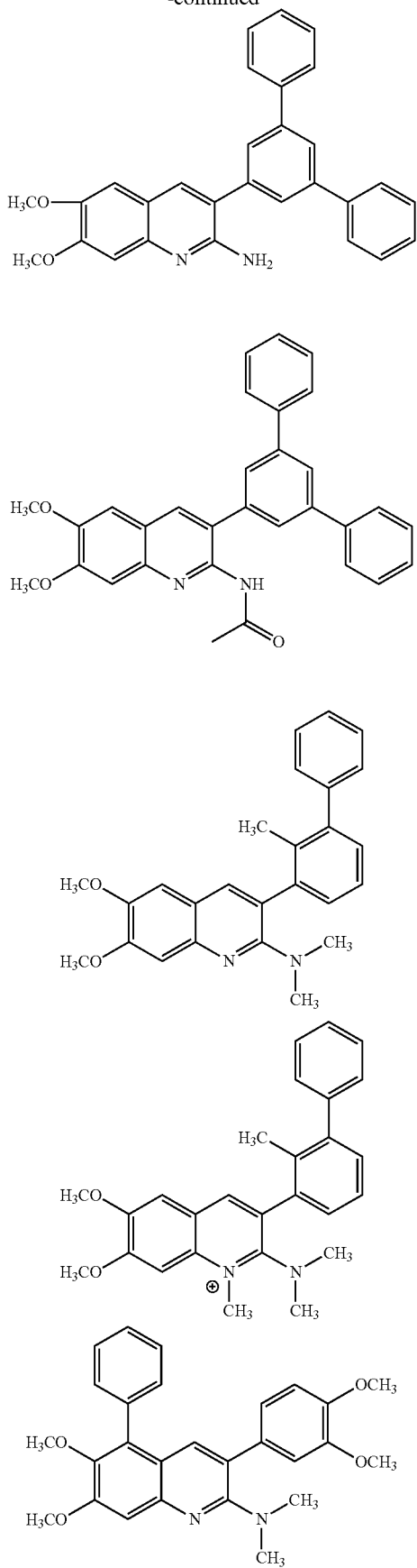

73
-continued
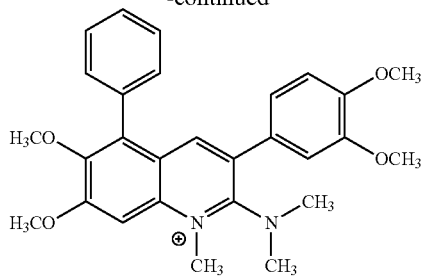
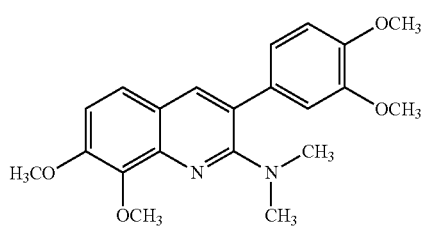

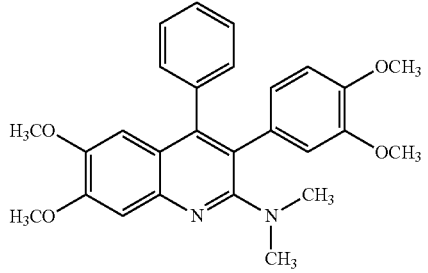
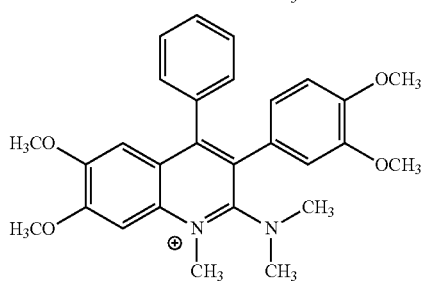
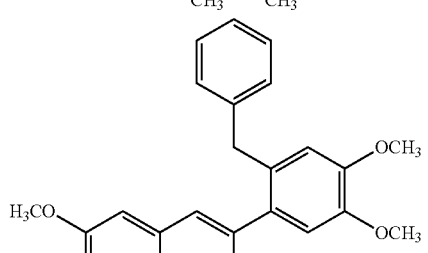
74
-continued
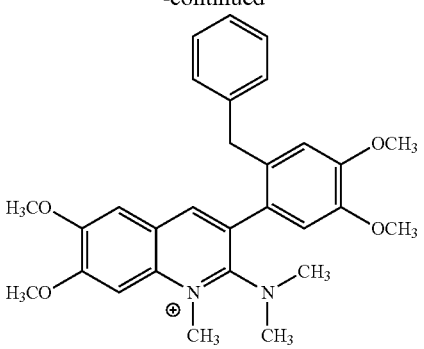
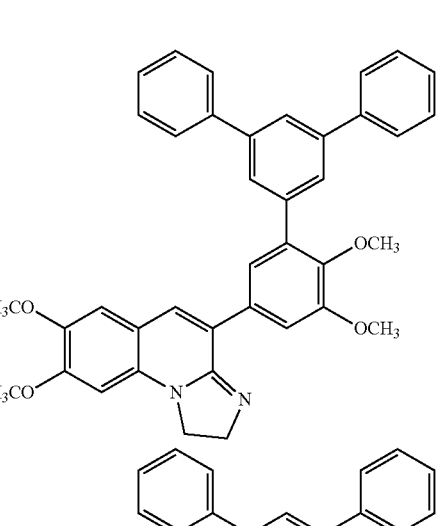
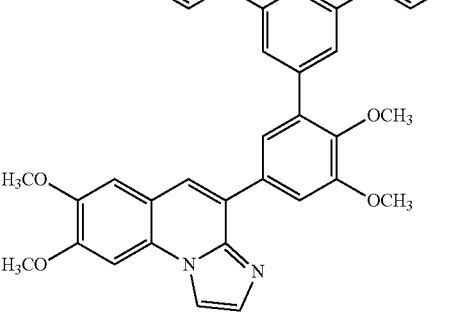
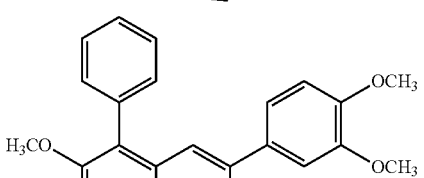
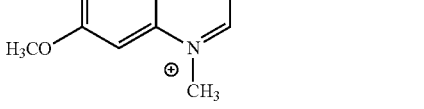

75
-continued
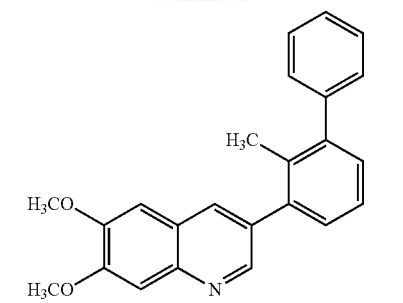
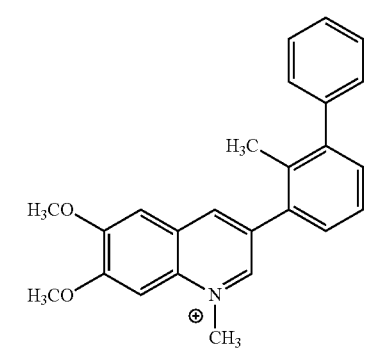
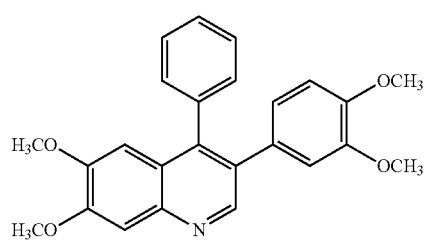
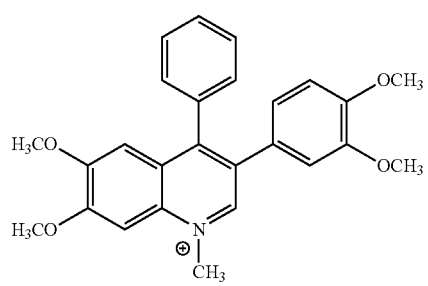
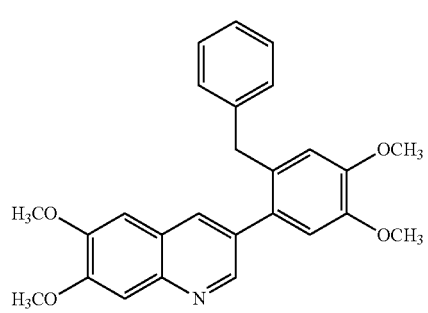
76
-continued
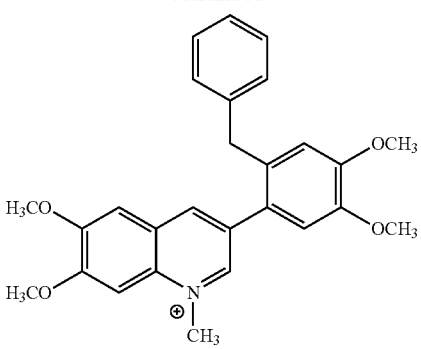
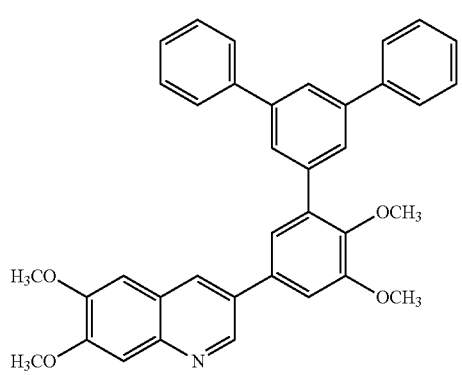
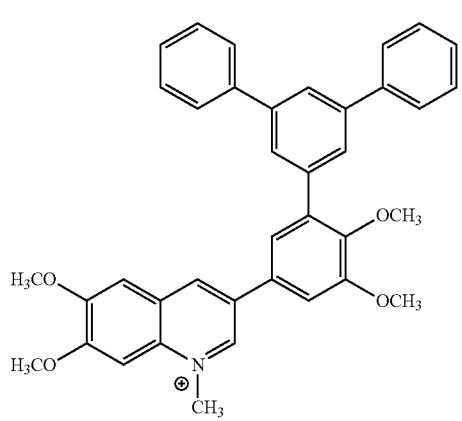
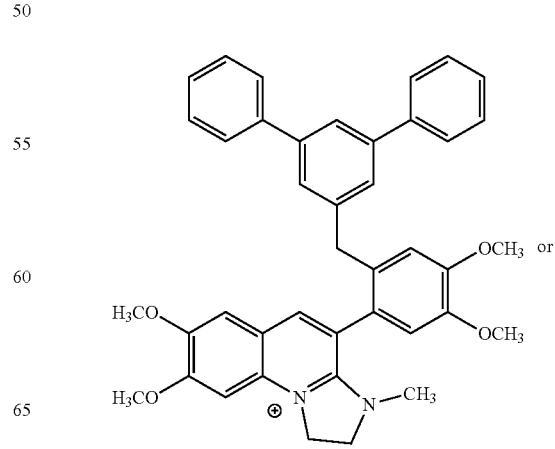 or -continued
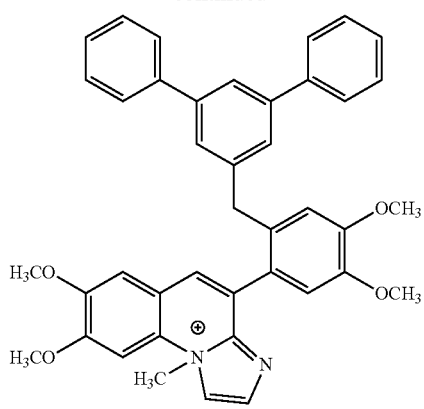
or a salt thereof.
A specific compound of the invention is a compound which is:
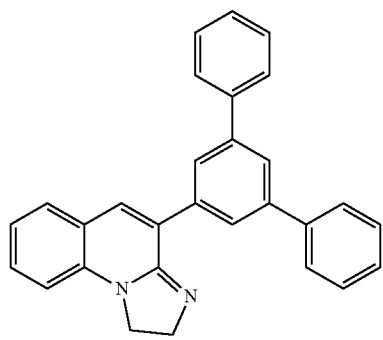
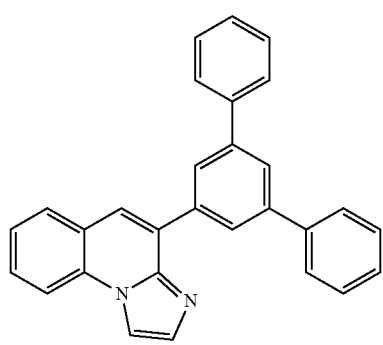
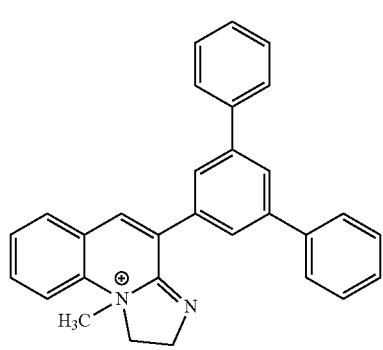
-continued
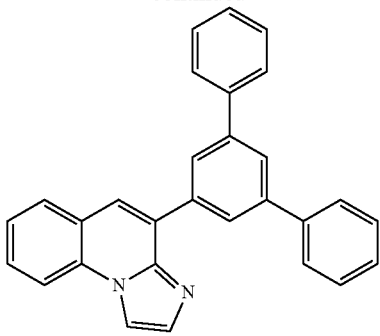
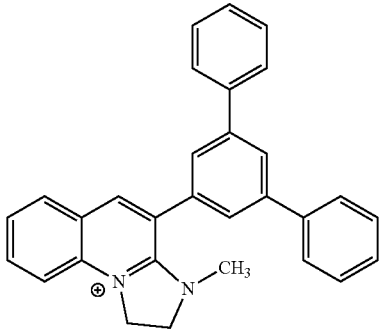
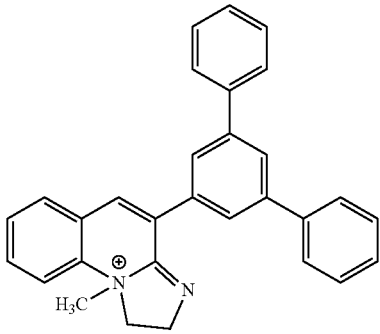
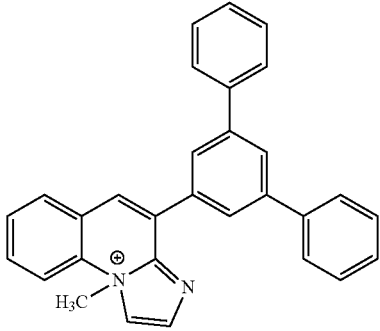 or
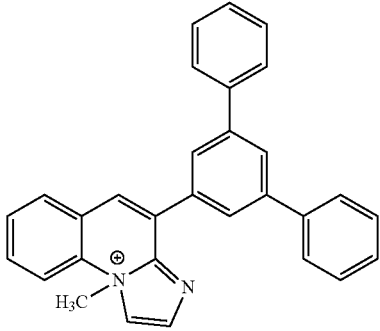
or a salt thereof.

A specific compound of the invention is a compound of formula (VIIIa) wherein $R^{6'}$ is selected from aryl and heteroaryl, which aryl, and heteroaryl of $R^{6'}$ is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{8aa}$, —S(O)$_2$NR$^{8g}$R$^{8h}$, —N(R$^{8j}$)S(O)$_2$$^8$R$^k$, and —NR$^{8g}$R$^{8h}$; and each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{8g}$R$^{8h}$, —N(R$^{8j}$)S(O)$_2$R$^{8k}$, and —NR$^{8g}$R$^{8h}$.

A specific compound of the invention is a compound of formula (VIIIb) wherein $R^{3'}$ is selected from aryl and heteroaryl, which aryl, and heteroaryl of $R^{3'}$ is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{8aa}$, —S(O)$_2$NR$^{8g}$R$^{8h}$, —N(R$^{8j}$)S(O)$_2$R$^{8k}$, and —NR$^{8g}$R$^{8h}$; and each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{8g}$R$^{8h}$, —N(R$^{8j}$)S(O)$_2$R$^{8k}$, and —NR$^{8g}$R$^{8h}$.

A specific compound of the invention is a compound of formula (VIIIc) wherein $R^{2'}$ is selected from aryl and heteroaryl, which aryl, and heteroaryl of $R^{2'}$ is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{8aa}$, —S(O)$_2$NR$^{8g}$R$^{8h}$, —N(R$^{8j}$)S(O)$_2$R$^{8k}$, and —NR$^{8g}$R$^{8h}$; and each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{8g}$R$^{8h}$, —N(R$^{8j}$)S(O)$_2$R$^{8k}$, and —NR$^{8g}$R$^{8h}$.

A specific compound of the invention is a compound of formula (VIIId) wherein $R^4$ is selected from aryl and heteroaryl, which aryl, and heteroaryl of $R^4$ is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{8aa}$, —S(O)$_2$NR$^{8g}$R$^{8h}$, —N(R$^{8j}$)S(O)$_2$R$^{8k}$, and —NR$^{8g}$R$^{8h}$; and each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{8g}$R$^{8h}$, —N(R$^{8j}$)S(O)$_2$R$^{8k}$, and —NR$^{8g}$R$^{8h}$.

A specific compound of the invention is a compound of formula (VIIIe) wherein $R^5$ is selected from aryl and heteroaryl, which aryl, and heteroaryl of $R^5$ is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{8aa}$, —S(O)$_2$NR$^{8g}$R$^{8h}$, —N(R$^{8j}$)S(O)$_2$R$^{8k}$, and —NR$^{8g}$R$^{8h}$; and each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{8g}$R$^{8h}$, —N(R$^{8j}$)S(O)$_2$R$^{8k}$, and —NR$^{8g}$R$^{8h}$.

A specific compound of the invention is a compound of formula (VIIIa) wherein $R^{6'}$ is selected from phenyl, pyridyl and furanyl and is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{8aa}$, —S(O)$_2$NR$^{8g}$R$^{8h}$, —N(R$^{8j}$)S(O)$_2$R$^{8k}$, and —NR$^{8g}$R$^{8h}$; and each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{8g}$R$^{8h}$, —N(R$^{8j}$)S(O)$_2$R$^{8k}$, and —NR$^{8g}$R$^{8h}$.

A specific compound of the invention is a compound of formula (Ib) wherein $R^{3'}$ is selected from phenyl, pyridyl and furanyl and is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{8aa}$, —S(O)$_2$NR$^{8g}$R$^{8h}$, —N(R$^{8j}$)S(O)$_2$R$^{8k}$, and —NR$^{8g}$R$^{8h}$; and each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{8g}$R$^{8h}$, —N(R$^{8j}$)S(O)$_2$R$^{8k}$, and —NR$^{8g}$R$^{8h}$.

A specific compound of the invention is a compound of formula (VIIIc) wherein $R^{2'}$ is selected from aryl and heteroaryl, which aryl, and heteroaryl of $R^{2'}$ is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{8aa}$, —S(O)$_2$NR$^{8g}$R$^{8h}$, —N(R$^{8j}$)S(O)$_2$R$^{8k}$, and NR$^{8g}$R$^{8h}$; and each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{8g}$R$^{8h}$, —N(R$^{8j}$)S(O)$_2$R$^{8k}$, and —NR$^g$R$^h$.

A specific compound of the invention is a compound of formula (VIIId) wherein $R^4$ is selected from phenyl, pyridyl and furanyl and is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{8aa}$, —S(O)$_2$NR$^{8g}$R$^{8h}$, —N(R$^{8j}$)S(O)$_2$R$^{8k}$, and —NR$^{8g}$R$^{8h}$; and each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{8g}$R$^{8h}$—N(R$^{8j}$)S(O)$_2$R$^{8k}$, and —NR$^{8g}$R$^{8h}$.

A specific compound of the invention is a compound of formula (VIIIe) wherein $R^5$ is selected from phenyl, pyridyl and furanyl and is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, $R^{8aa}$, —S(O)$_2$NR$^{8g}$R$^{8h}$, —N(R$^{8j}$)S(O)$_2$R$^{8k}$, and —NR$^{8g}$R$^{8h}$; and each $R^{8aa}$ is independently selected from aryl and heteroaryl, which aryl and heteroaryl is optionally substituted with one or more groups independently selected from $(C_1-C_6)$alkyl, halo, hydroxy, cyano, nitro, $(C_1-C_6)$alkoxy, cycloalkyl, carboxy, aryloxy, nitro, sulfo, —S(O)$_2$NR$^{8g}$R$^{8h}$, —N(R$^{8j}$)S(O)$_2$R$^{8k}$, and —NR$^{8g}$R$^{8h}$.

A specific compound of the invention is a compound of formula (VIIIa) wherein $R^{6'}$ is selected from phenyl, pyridyl and furanyl and is optionally substituted with one or more groups independently selected from phenyl, pyridyl, —NR$^{8g}$R$^{8h}$, $(C_1-C_6)$alkoxy, dimethylaminophenyl, and halo.

A specific compound of the invention is a compound of formula (VIIIb) wherein R$^{3'}$ is selected from phenyl, pyridyl and furanyl and is optionally substituted with one or more groups independently selected from phenyl, pyridyl, —NR$^{8g}$R$^{8h}$, (C$_1$-C$_6$)alkoxy, dimethylaminophenyl, and halo.

A specific compound of the invention is a compound of formula (VIIIc) wherein R$^{2'}$ is selected from phenyl, pyridyl and furanyl and is optionally substituted with one or more groups independently selected from phenyl, pyridyl, —NR$^{8g}$R$^{8h}$, (C$_1$-C$_6$)alkoxy, dimethylaminophenyl, and halo.

A specific compound of the invention is a compound of formula (VIIId) wherein R$^4$ is selected from phenyl, pyridyl and furanyl and is optionally substituted with one or more groups independently selected from phenyl, pyridyl, —NR$^{8g}$R$^{8h}$, (C$_1$-C$_6$)alkoxy, dimethylaminophenyl, and halo.

A specific compound of the invention is a compound of formula (VIIIe) wherein R$^5$ is selected from phenyl, pyridyl and furanyl and is optionally substituted with one or more groups independently selected from phenyl, pyridyl, —NR$^{8g}$R$^{8h}$, (C$_1$-C$_6$)alkoxy, dimethylaminophenyl, and halo.

A specific compound of the invention is a compound wherein at least one of R$^4$, R$^5$, R$^{2'}$, R$^{3'}$, and R$^{6'}$ is selected from 3-biphenyl, 3-(4'-fluoro)biphenyl, 4-biphenyl, 4-(4'-fluoro) biphenyl, 3,5-bis(4-fluorophenyl)phenyl, 4-fluorophenyl, phenyl, 3-pyridyl, 4-pyridyl, 3-dimethylaminophenyl, 3-furanyl, 3-methoxyphenyl, 4-pyrid-3-ylphenyl, 4-pyrid-4-ylphenyl, 4-(3-dimethylaminophenyl)phenyl, 4-(3-furanyl) phenyl, 2-phenylpyrid-4-yl, 2-(3-methoxyphenyl)pyrid-3-yl, 2-phenylfur-4-yl, and 2-pyrid-4-yl)pyrid-5-yl.

A specific compound of the invention is a compound wherein at least one of R$^4$, R$^5$, R$^6$, R$^7$, R$^8$, and R$^{31}$ is selected from 3-biphenyl, 3-(4'-fluoro)biphenyl, 4-biphenyl, 4-(4'-fluoro)biphenyl, 3,5-bis(4-fluorophenyl)phenyl, 4-fluorophenyl, phenyl, 3-pyridyl, 4-pyridyl, 3-dimethylaminophenyl, 3-furanyl, 3-methoxyphenyl, 4-pyrid-3-ylphenyl, 4-pyrid-4-ylphenyl, 4-(3-dimethylaminophenyl)phenyl, 4-(3-furanyl)phenyl, 2-phenylpyrid-4-yl, 2-(3-methoxyphenyl)pyrid-3-yl, 2-phenylfur-4-yl, and 2-pyrid-4-yl)pyrid-5-yl.

A specific compound of the invention is a compound wherein at least one of R$^4$, R$^5$, R$^6$, and R$^7$ is selected from 3-biphenyl, 3-(4'-fluoro)biphenyl, 4-biphenyl, 4-(4'-fluoro) biphenyl, 3,5-bis(4-fluorophenyl)phenyl, 4-fluorophenyl, phenyl, 3-pyridyl, 4-pyridyl, 3-dimethylaminophenyl, 3-furanyl, 3-methoxyphenyl, 4-pyrid-3-ylphenyl, 4-pyrid-4-ylphenyl, 4-(3-dimethylaminophenyl)phenyl, 4-(3-furanyl) phenyl, 2-phenylpyrid-4-yl, 2-(3-methoxyphenyl)pyrid-3-yl, 2-phenylfur-4-yl, and 2-pyrid-4-yl)pyrid-5-yl.

A specific compound of the invention is a compound wherein at least one of R$^3$, R$^4$, R$^5$, and R$^{6'}$ is selected from 3-biphenyl, 3-(4'-fluoro)biphenyl, 4-biphenyl, 4-(4'-fluoro) biphenyl, 3,5-bis(4-fluorophenyl)phenyl, 4-fluorophenyl, phenyl, 3-pyridyl, 4-pyridyl, 3-dimethylaminophenyl, 3-furanyl, 3-methoxyphenyl, 4-pyrid-3-ylphenyl, 4-pyrid-4-ylphenyl, 4-(3-dimethylaminophenyl)phenyl, 4-(3-furanyl) phenyl, 2-phenylpyrid-4-yl, 2-(3-methoxyphenyl)pyrid-3-yl, 2-phenylfur-4-yl, and 2-pyrid-4-yl)pyrid-5-yl.

A specific value for A is N.

A specific value for A is C—R$^{4'}$.

A specific compound of the invention is a compound which is:

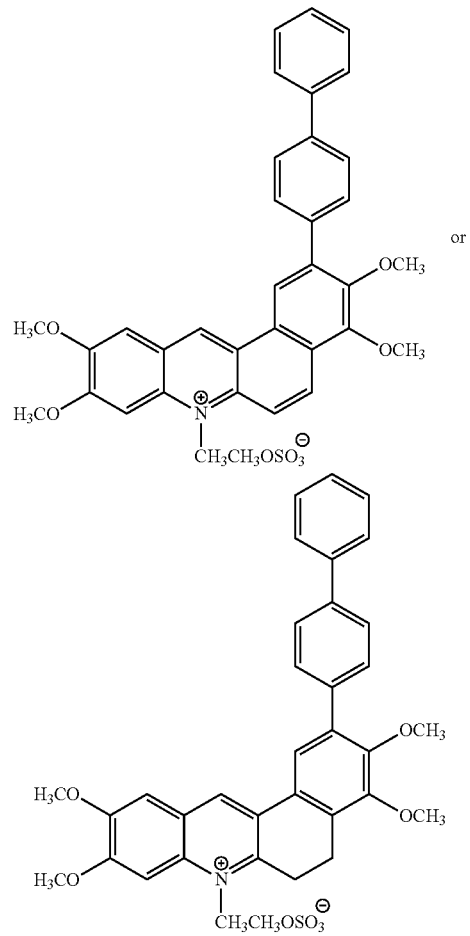

or a salt thereof.

A specific value for B$^-$ is Cl$^-$, Br$^-$, I$^-$, CF$_3$SO$_3^-$, malate, fumarate, formate, tosylate, methanesulfonate, acetate, citrate, malonate, tartrate, succinate, benzoate, ascorbate, α-ketoglutarate, or α-glycerophosphate.

A specific value for D$^-$ is Cl$^-$, Br$^-$, I$^-$, CF$_3$SO$_3^-$, malate, fumarate, formate, tosylate, methanesulfonate, acetate, citrate, malonate, tartrate, succinate, benzoate, ascorbate, α-ketoglutarate, or α-glycerophosphate.

A specific value for Z$^-$ is Cl$^-$, Br$^-$, I$^-$, CF$_3$SO$_3^-$, malate, fumarate, formate, tosylate, methanesulfonate, acetate, citrate, malonate, tartrate, succinate, benzoate, ascorbate, α-ketoglutarate, or α-glycerophosphate.

A specific value for B$^-$ is: Cl$^-$, Br$^-$, I$^-$, CH$_3$SO$_3^-$, CF$_3$SO$_3^-$, p-CH$_3$C$_6$H$_4$-SO$_3^-$, citrate, tartrate, malate, fumarate, formate, or acetate.

A specific value for D$^-$ is: Cl$^-$, Br$^-$, I$^-$, CH$_3$SO$_3^-$, CF$_3$SO$_3^-$, p-CH$_3$C$_6$H$_4$SO$_3^-$, citrate, tartrate, malate, fumarate, formate, or acetate.

A specific value for Z$^-$ is: Cl$^-$, Br$^-$, I$^-$, CH$_3$SO$_3^-$, CF$_3$SO$_3^-$, p-CH$_3$C$_6$H$_4$SO$_3^-$, citrate, tartrate, malate, fumarate, formate, or acetate.

A specific compound of the invention is a compound wherein:
X is N; Y is C(R$^2$); and R$^3$ is R$^e$; or
X is N; Y is C(R$^{15}$); and R$^3$ is R$^c$; or X is N⁺—R¹³ (Z⁻); Y is C(R¹²); and R³ is Rᶜ; or X is N; Y is C(R¹²); and R³ is Rᵉ; or X is W—R⁵¹; Y is C(R⁵²); W is N; and R⁵¹' is absent; or X is W—R⁵¹; Y is C(R⁵²); W is N⁺D⁻; and R⁵¹ is (C₁-C₆)alkyl, aryl, or aryl(C₁-C₆)alkyl; or X is ⁺N(R⁸¹)(R⁸²) B⁻; and Y is C(R⁸³).

A specific compound of the invention is a compound wherein:

X is C(R¹); Y is N; and R³ is Rᶜ or

X is C(R¹⁰) or C(R³¹); Y is N⁺—R¹⁴ (Z⁻); and R³ is Rᶜ; or

X is C(R¹⁰) or C(R³¹); Y is N; and R³ is Rᶜ.

A specific compound of the invention is a compound wherein:

X is C(R¹⁶); Y is C(R¹¹); and R³ is Rᵉ; or

X is C(R¹); Y is C(R¹²); and R³ is Rᵉ; or

X is C(R³⁰); Y is C(R³¹); and R³ is Rᵉ; or

X is W—R⁵¹; Y is C(R⁵²); W is C; and R⁵¹ is hydrogen, —N⁺(R⁵ᵃ)₃D⁻, —C(=NR⁵ᵇ)—NR⁵ᶜR⁵ᵈ, —NRᵉ—C(=NR⁵ᵇ)—NR⁵ᶜR⁵ᵈ, —NR⁵ᵍR⁵ʰ, —NR⁵ᶜᵉ—C(=NR⁵ᶜᵇ)R⁵ᶜᵉ, —NR⁵ᶜᵉ—C(=O)—NR⁵ᶜᶜR⁵ᶜᵈ, or (C₁-C₆)alkyl that is substituted with one or more R⁵ᶠ.

A specific compound of the invention is a compound wherein:

X is N; Y is C(R²); and R³ is Rᵉ; or

X is N; Y is C(R¹⁵); and R³ is Rᶜ; or

X is N⁺—R¹³ (Z⁻); Y is C(R¹²); and R³ is Rᶜ; or

X is N; Y is C(R¹²); and R³ is Rᵉ.

A specific compound of the invention is a compound wherein:

X is C(R¹); Y is N; and R³ is Rᶜ or

X is C(R¹⁰) or C(R³¹); Y is N⁺—R¹⁴ (Z⁻); and R³ is Rᶜ; or

X is C(R¹⁰) or C(R³¹); Y is N; and R³ is Rᶜ.

A specific compound of the invention is a compound wherein:

X is C(R¹⁶); Y is C(R¹¹); and R³ is Rᵉ; or

X is C(R¹); Y is C(R¹²); and R³ is Rᵉ; or

X is C(R³⁰); Y is C(R³¹); and R³ is Rᵉ.

A specific compound of the invention is a compound of any one of the Examples hereinbelow or a salt or prodrug thereof.

Generally, compounds of the invention including compounds of formula I as well as synthetic intermediates that can be used for preparing compounds of formula I, can be prepared as illustrated in the following Schemes. It is understood that variable groups (e.g. R¹-R¹⁵, A, W, X, Y, etc.) shown in the Schemes below can represent the final groups present in a corresponding compound of formula I or that these groups can represent groups that can be converted to the final groups present in a corresponding compound of formula I at a convenient point in a synthetic sequence. For example, in the Schemes below, the variable groups can contain one or more protecting groups that can be removed at a convenient point in a synthetic sequence to provide the corresponding final groups in the compound of formula I.

When R⁴ is an aryl or heteroaryl substituent it can conveniently be introduced into a compound of formula I as illustrated in Scheme 1.

Scheme 1

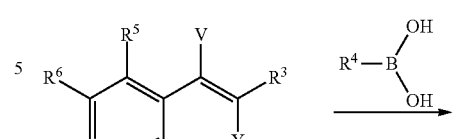

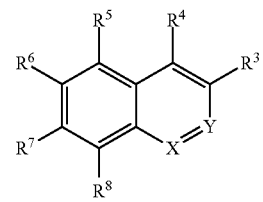

V = Br, OTf

When R⁵ is an aryl or heteroaryl substituent it can conveniently be introduced into a compound of formula I as illustrated in Scheme 2.

Scheme 2

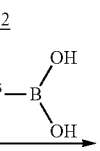

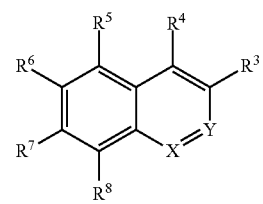

V = Br, OTf

When R⁶ is an aryl or heteroaryl substituent it can conveniently be introduced into a compound of formula I as illustrated in Scheme 3.

Scheme 3

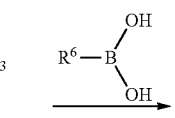

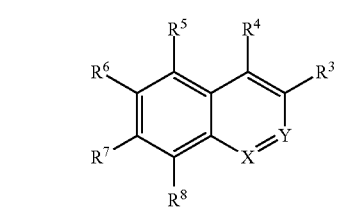

V = Br, OTf

When $R^7$ is an aryl or heteroaryl substituent it can conveniently be introduced into a compound of formula I as illustrated in Scheme 4.

Scheme 4

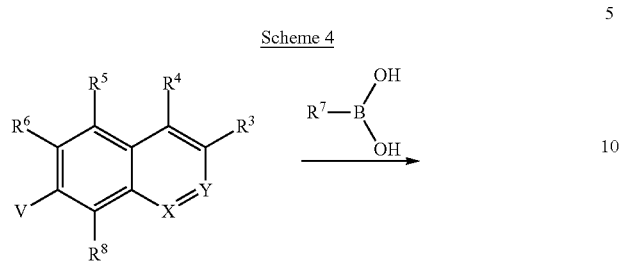

V = Br, OTf

A compound of formula I wherein X is N—$R^{13}$ can conveniently be prepared from a corresponding compound wherein X is N as illustrated in Scheme 5.

Scheme 5

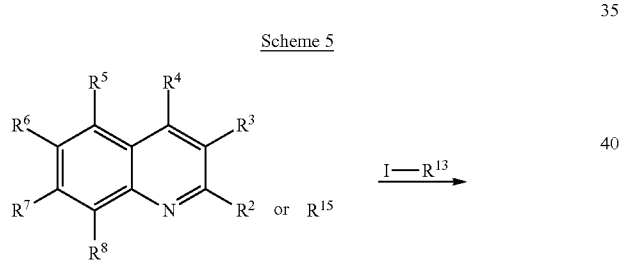

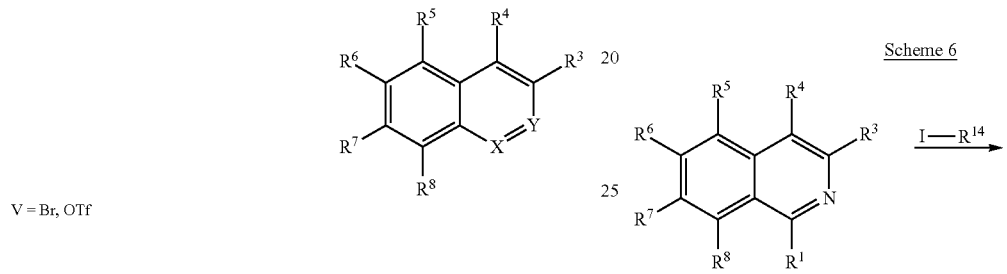

A compound of formula I wherein Y is N—$R^{14}$ can conveniently be prepared from a corresponding compound wherein Y is N as illustrated in Scheme 6.

Scheme 6

Scheme 7 illustrates a general method for preparing 5-substituted 2-(substituted phenyl)naphthalenes, 2-(pyridin-2-yl)naphthalenes, and 2-(pyrimidin-2-yl)naphthalenes.

Scheme 7

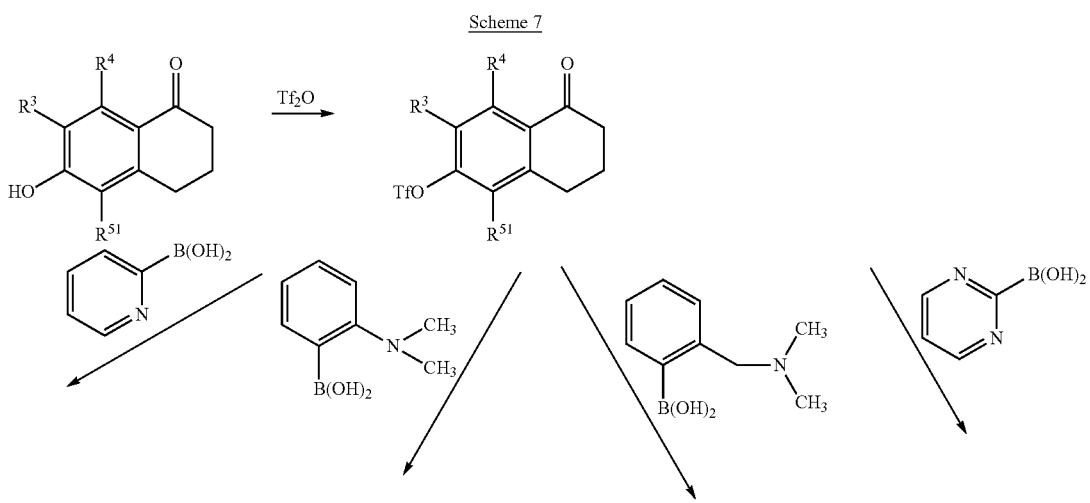

87
-continued
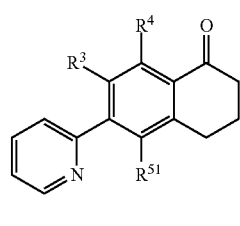 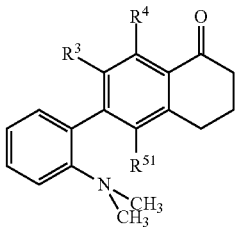 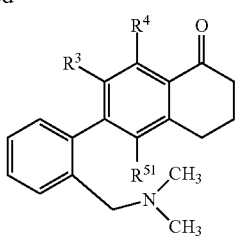 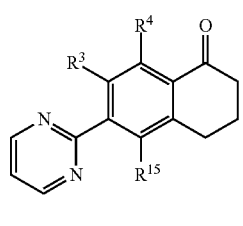
↓ Dehydrogenate ↓ ↓ Dehydrogenate ↓
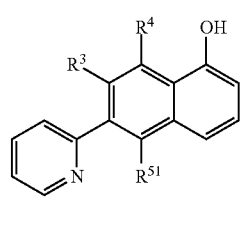 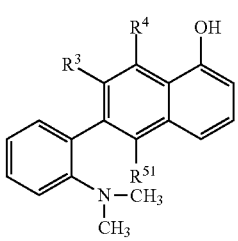 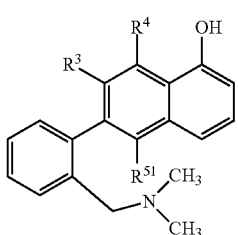 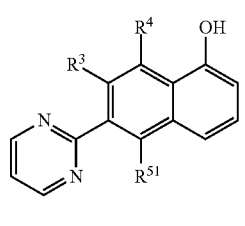
↓ Tf₂O ↓ Tf₂O ↓ Tf₂O ↓ Tf₂O
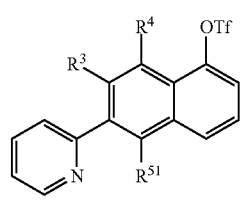 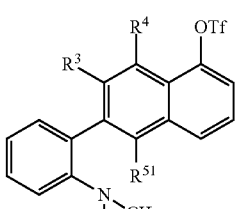 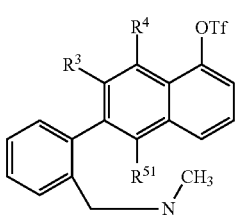 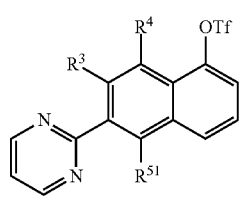
↓ ↓ ↓ ↓
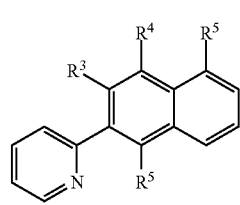 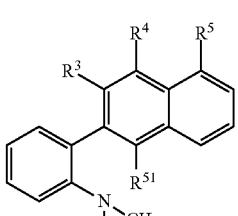 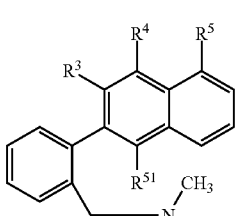 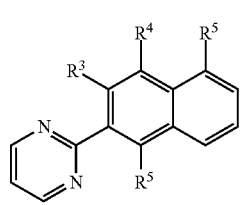
↓ CH₃I ↓ CH₃I ↓ CH₃I ↓ CH₃I -continued
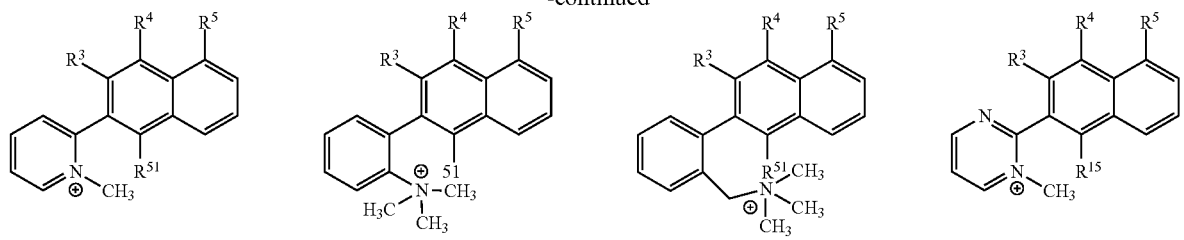
Scheme 8 illustrates a method for preparing various 5-substituted 2-(phenyl)naphthalenes and 2-(heteroaryl)naphthalenes.
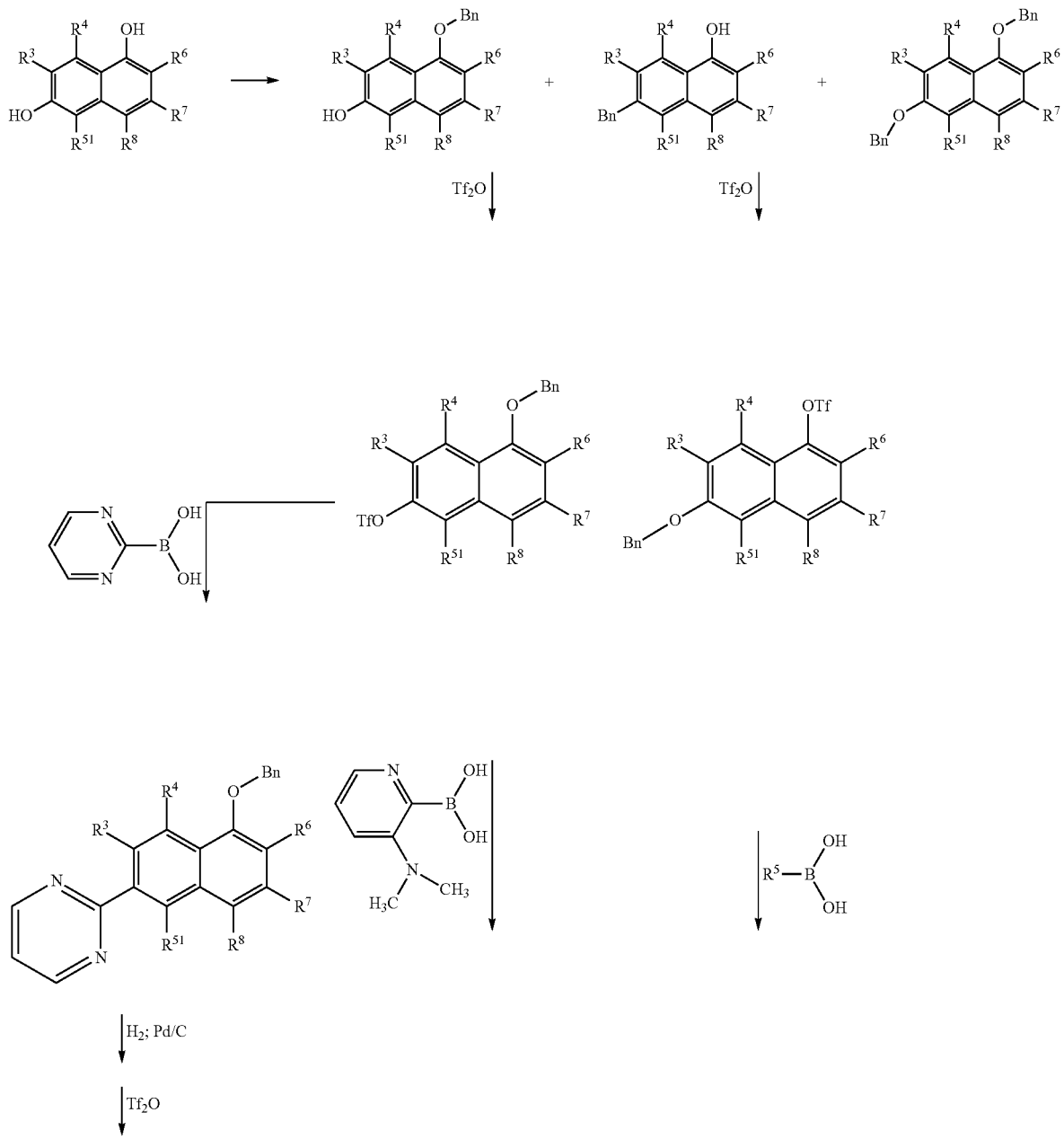

91  -continued   92
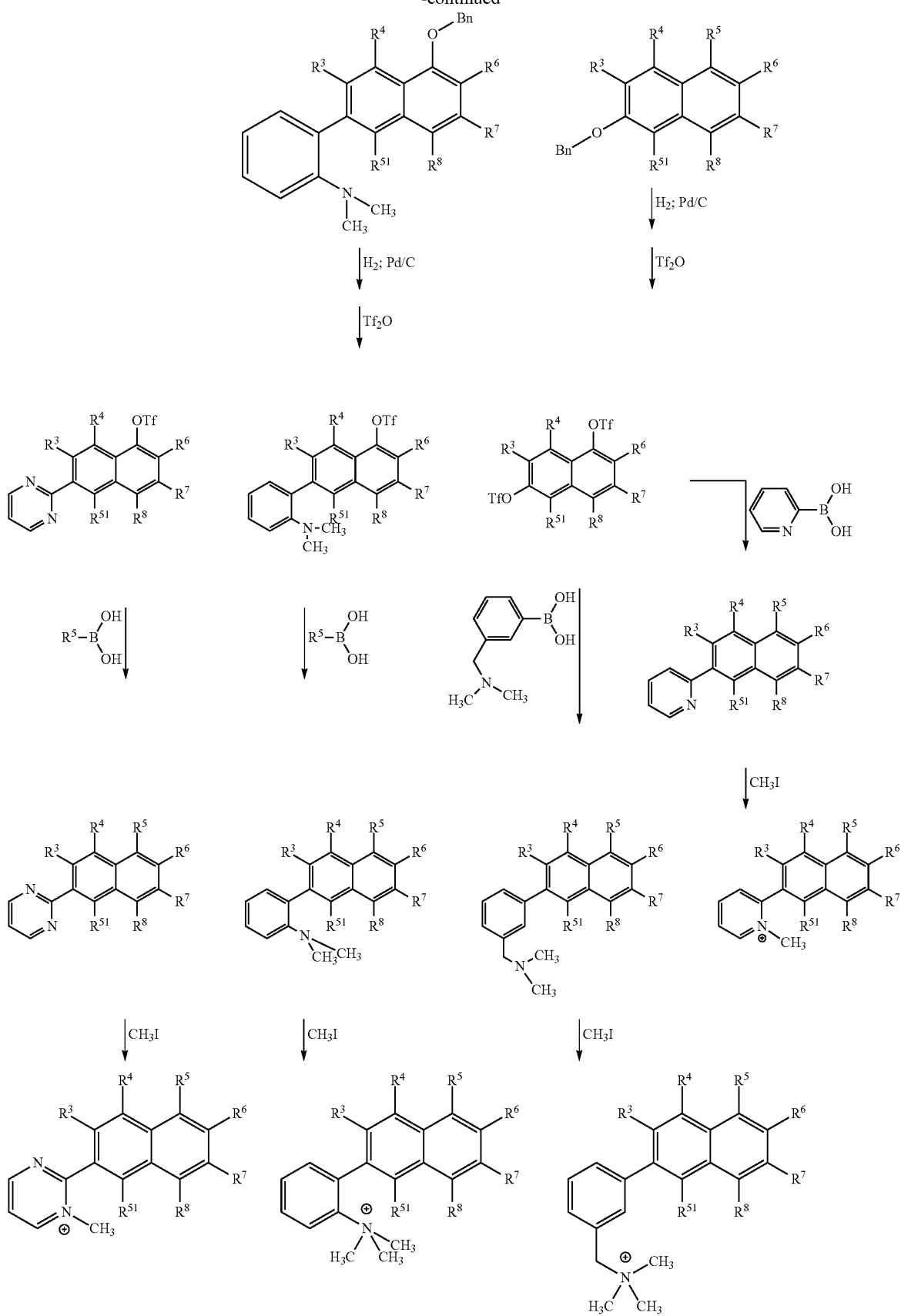

Scheme 9 illustrates a method for preparing 5-substituted 2-(phenyl)naphthalenes and 2-(heteroaryl)naphthalenes.
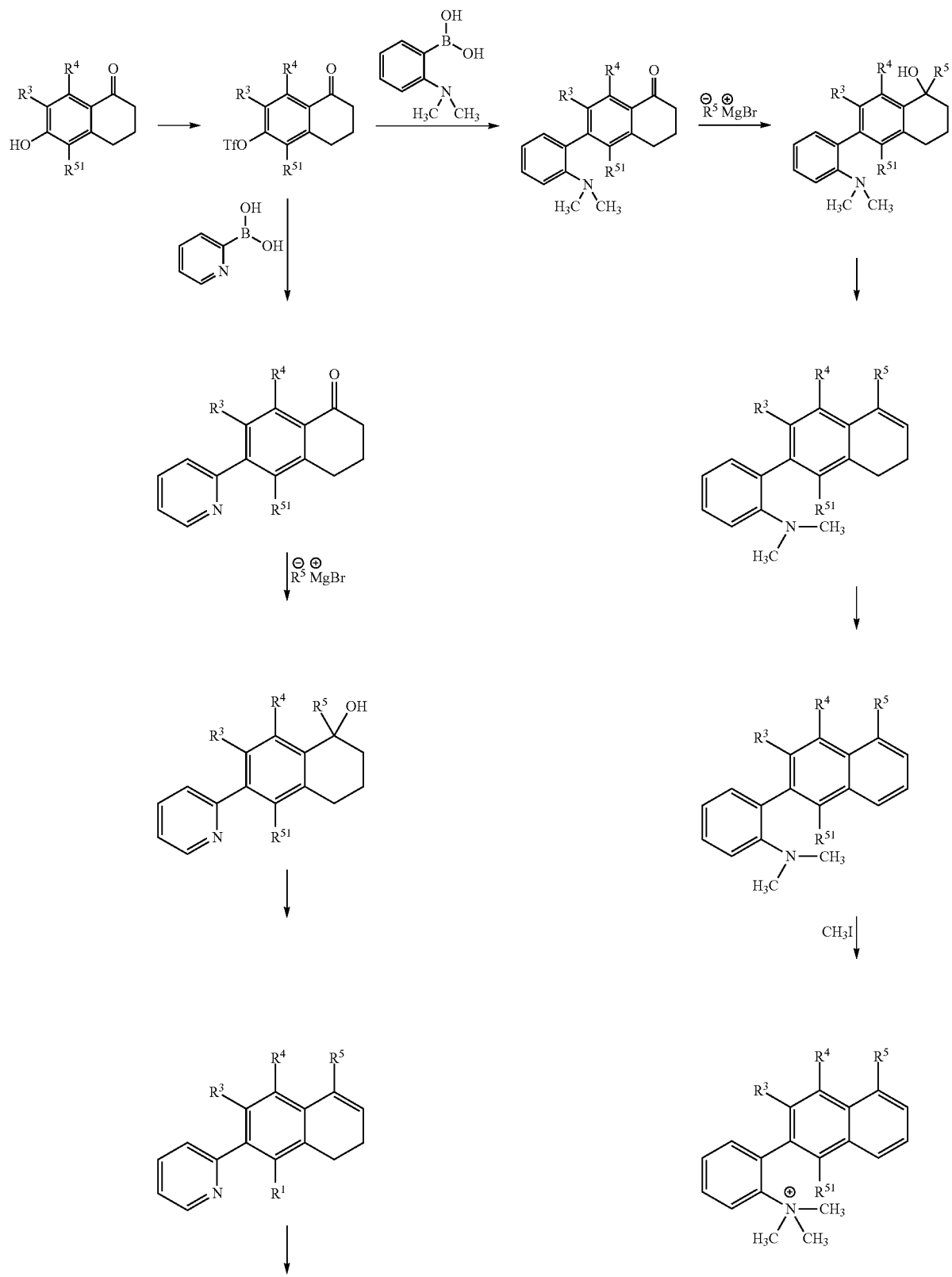

-continued
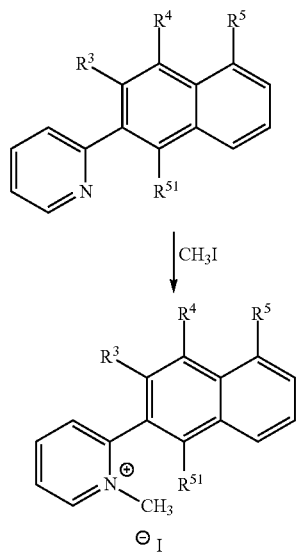
Scheme 10 illustrates a method for the preparation of various 4-substituted 2-phenylnaphthalenes and 2-(heteroaryl)naphthalenes.
Scheme 10
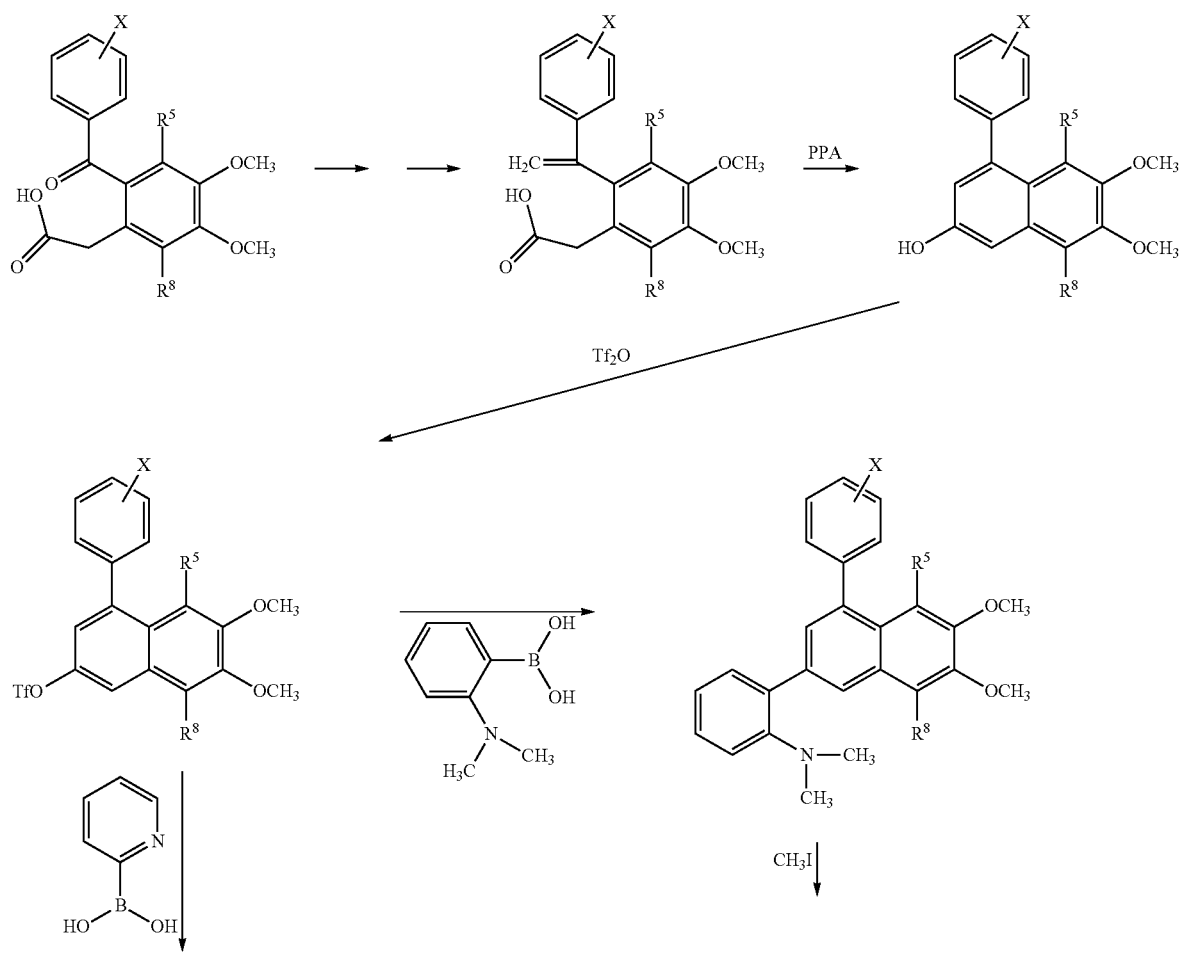

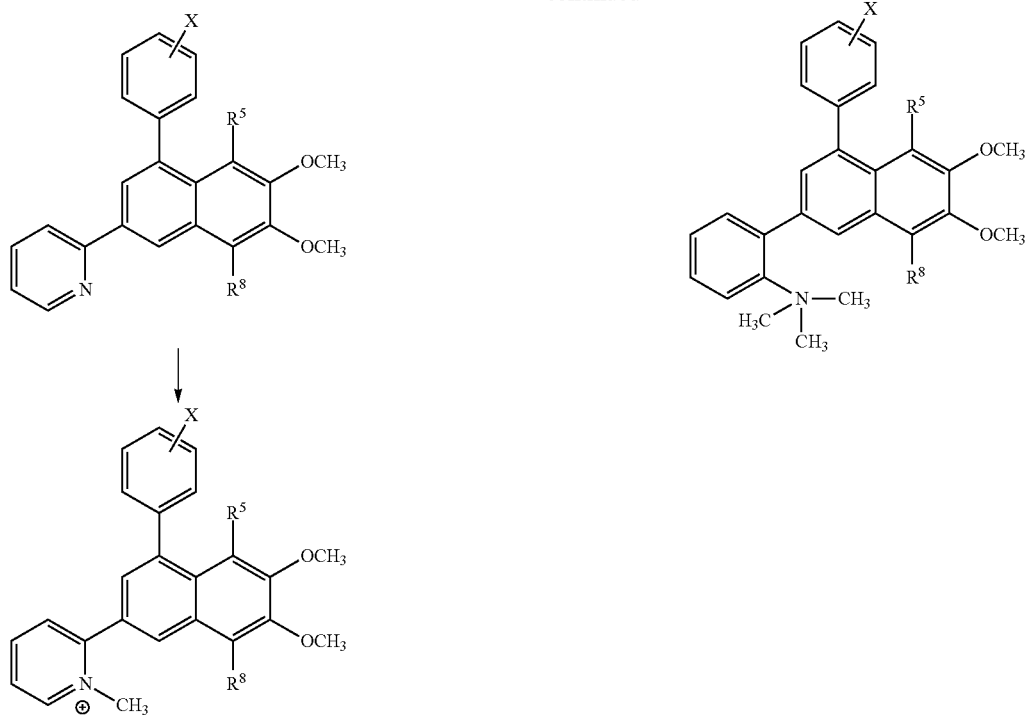
Scheme 11 illustrates a method for the preparation of various 4-substituted 2-(phenyl)naphthalenes or 4-substituted 2-(heteroaryl)naphthalenes.
Scheme 11
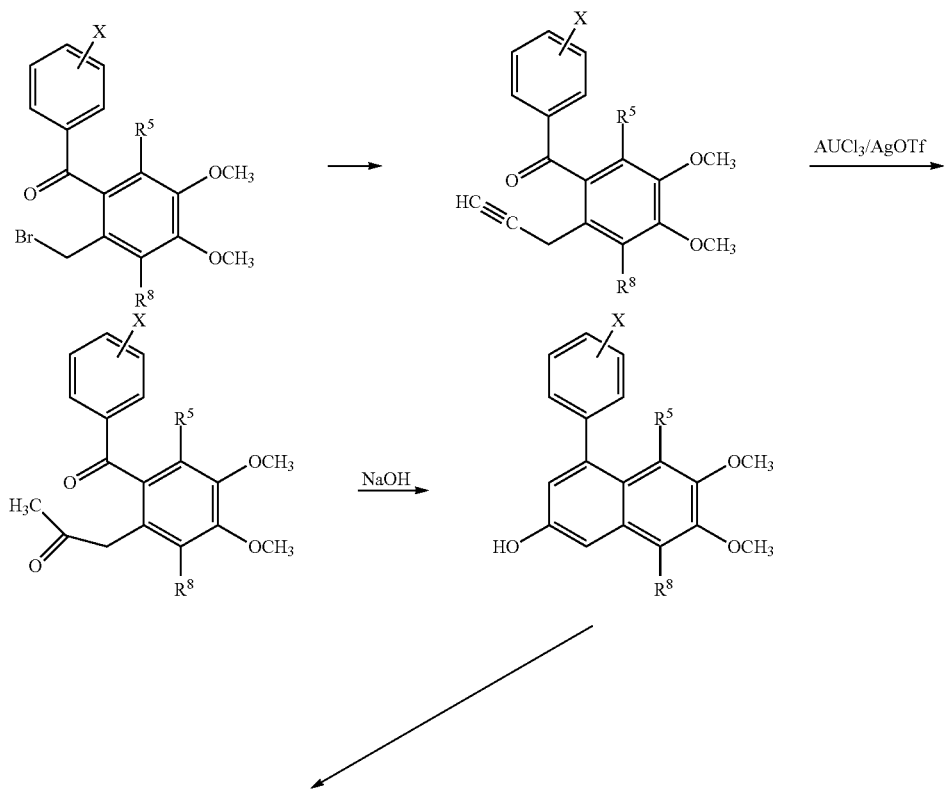

99
-continued
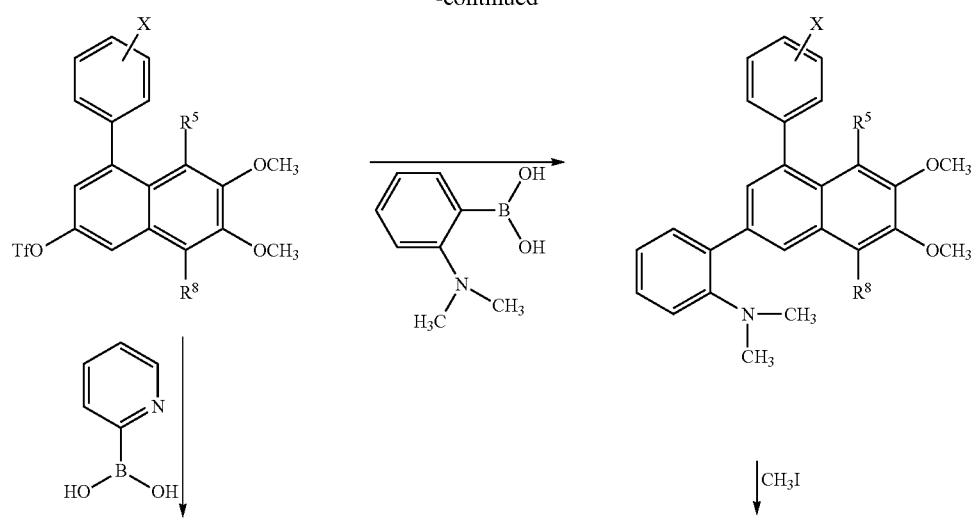
100
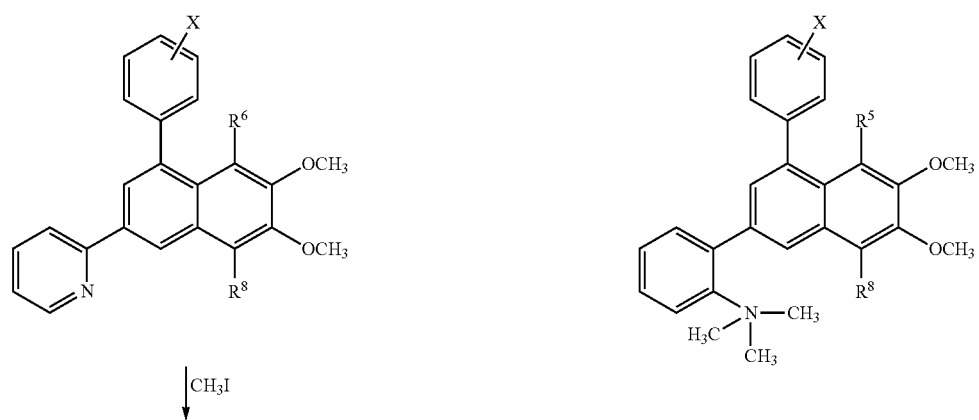
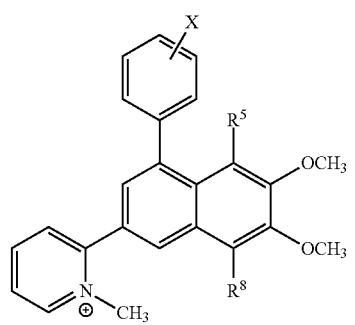

Scheme 12 illustrates a method for preparing 5-substituted 2-[2-(dimethylamino)phenyl]-naphthalenes using the carbanion of tetralone and aryl halides.
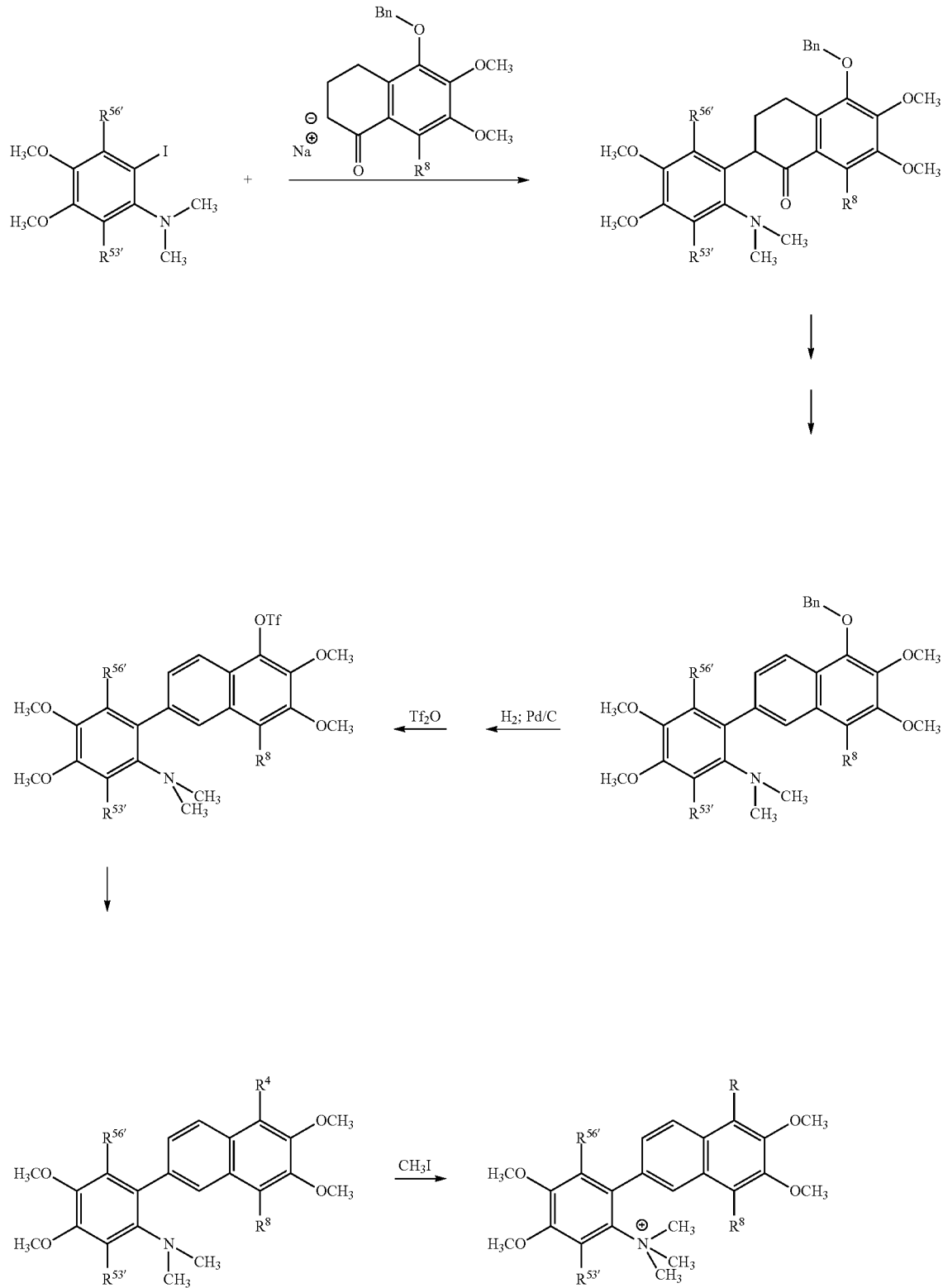

Scheme 13 illustrates the use of 2-naphthyl boronates to form 2-[2-amino)phenyl]- and 2-pyrimidinyl-naphthalene compounds.
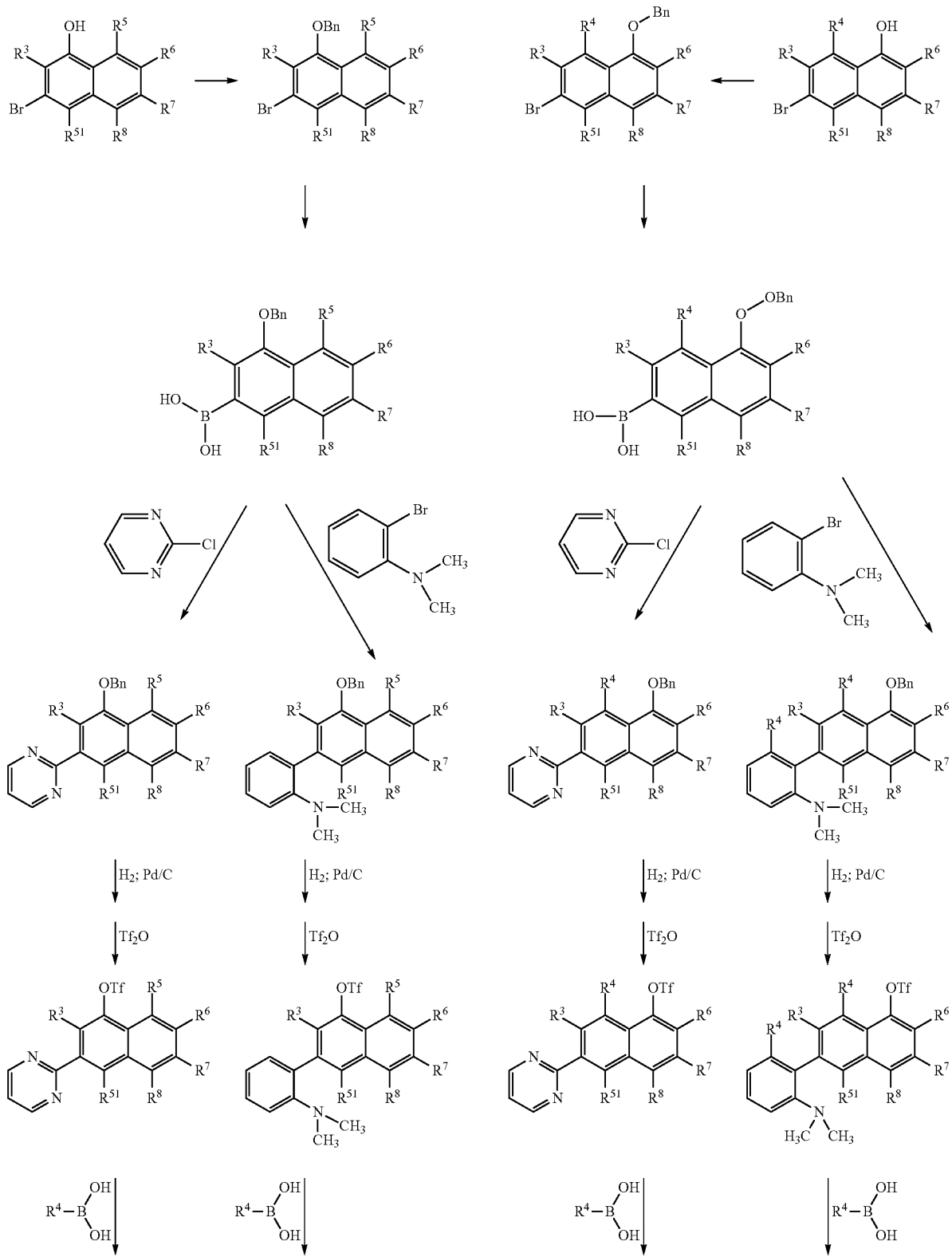
Scheme 13

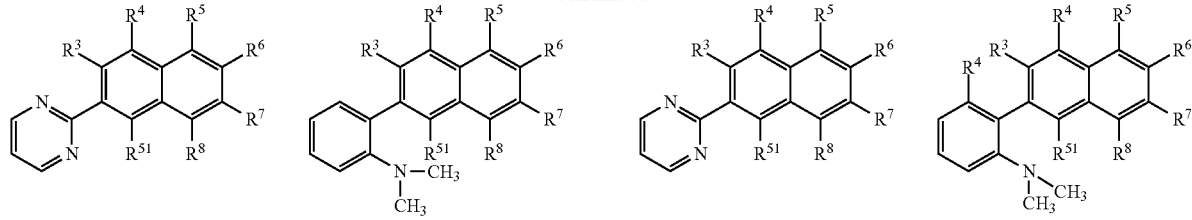
   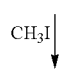
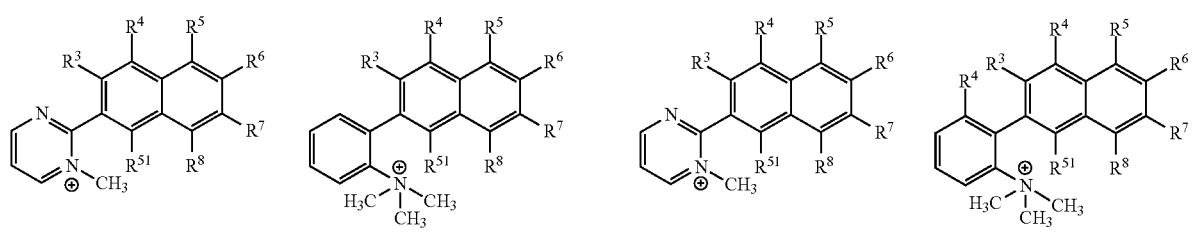
Scheme 14 illustrates the use of 2-naphthyl boronates to form 2-[2-amino)phenyl]- and 2-pyrimidinyl-naphthalene compounds.
Scheme 14
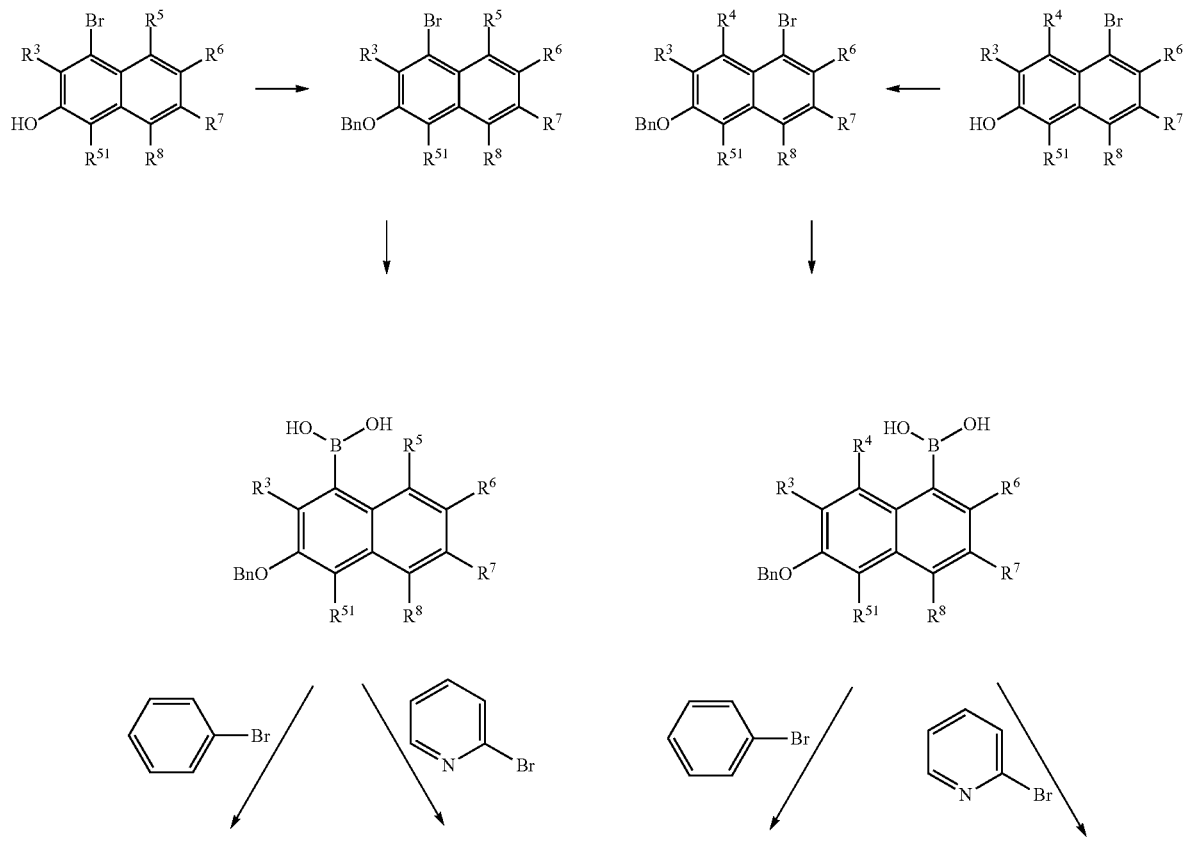

107 108
-continued
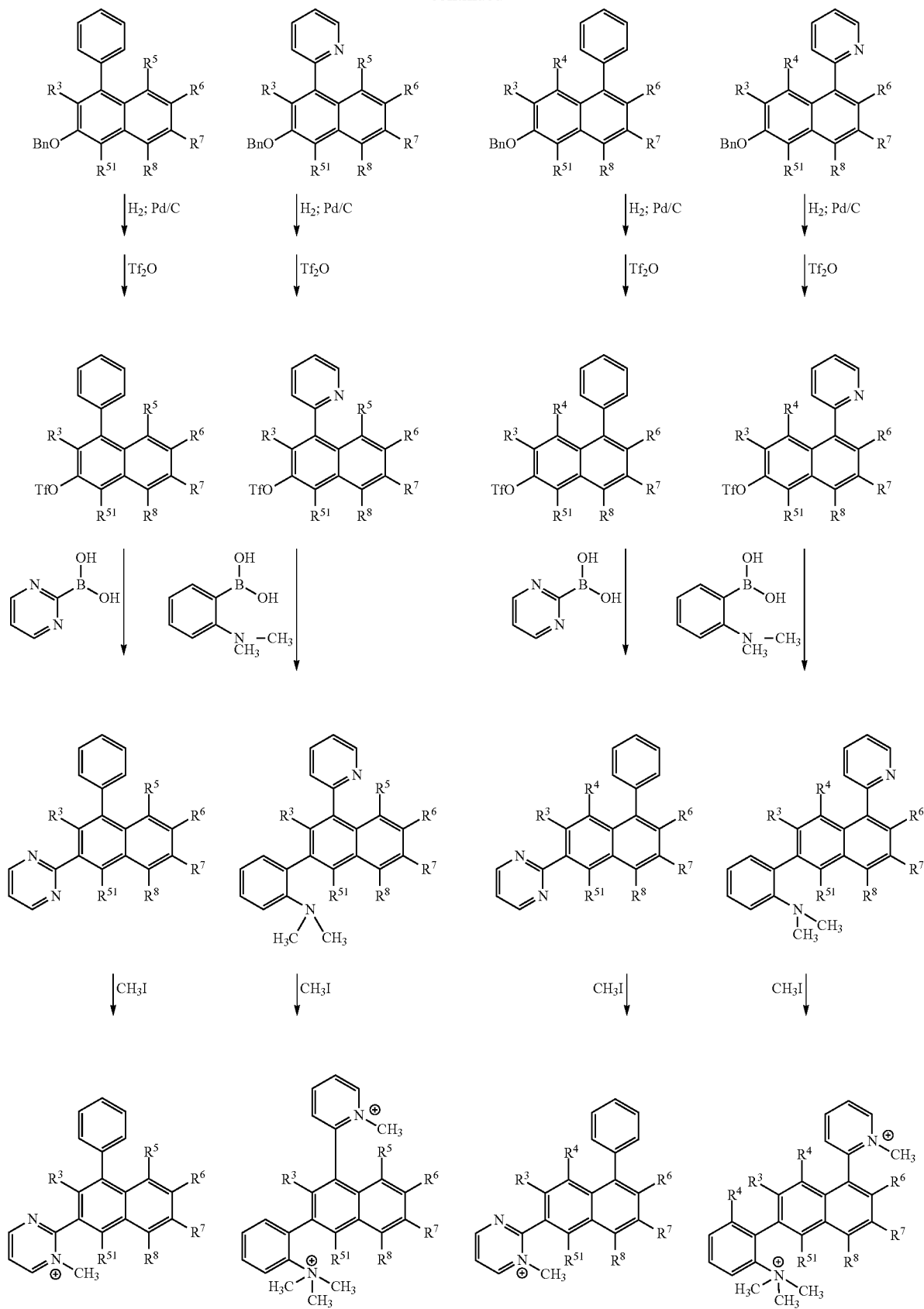

Scheme 15 illustrates a method for preparing various 4-substituted 2-phenyl-aminonaphthalenes using substituted-1-amino-4-bromo-2-hydroxynaphthalenes as intermediates.
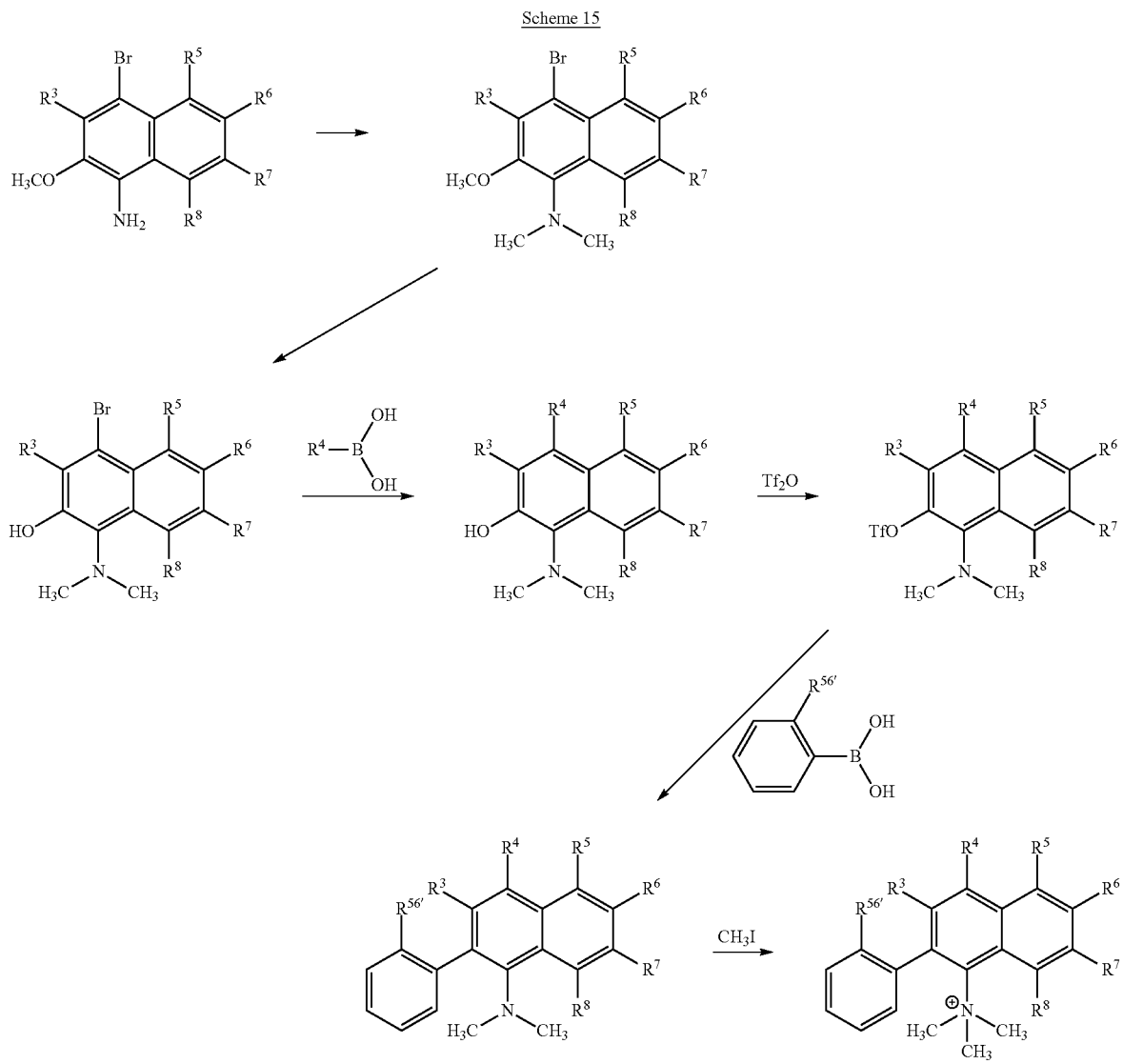
Scheme 16 illustrates a method for preparing various 5-substituted 2-phenyl-aminonaphthalenes using substituted-1-nitro-5-bromonaphthalenes as intermediates.
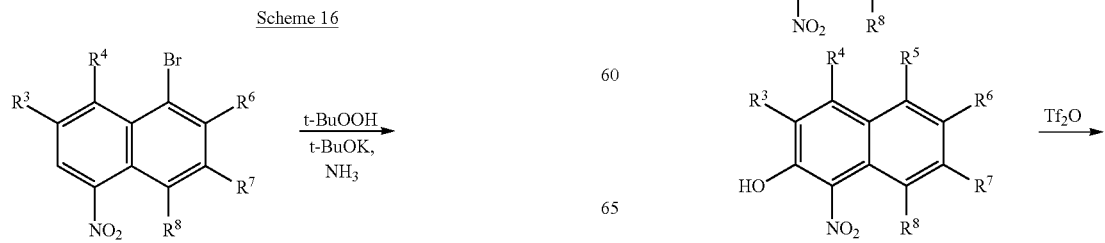

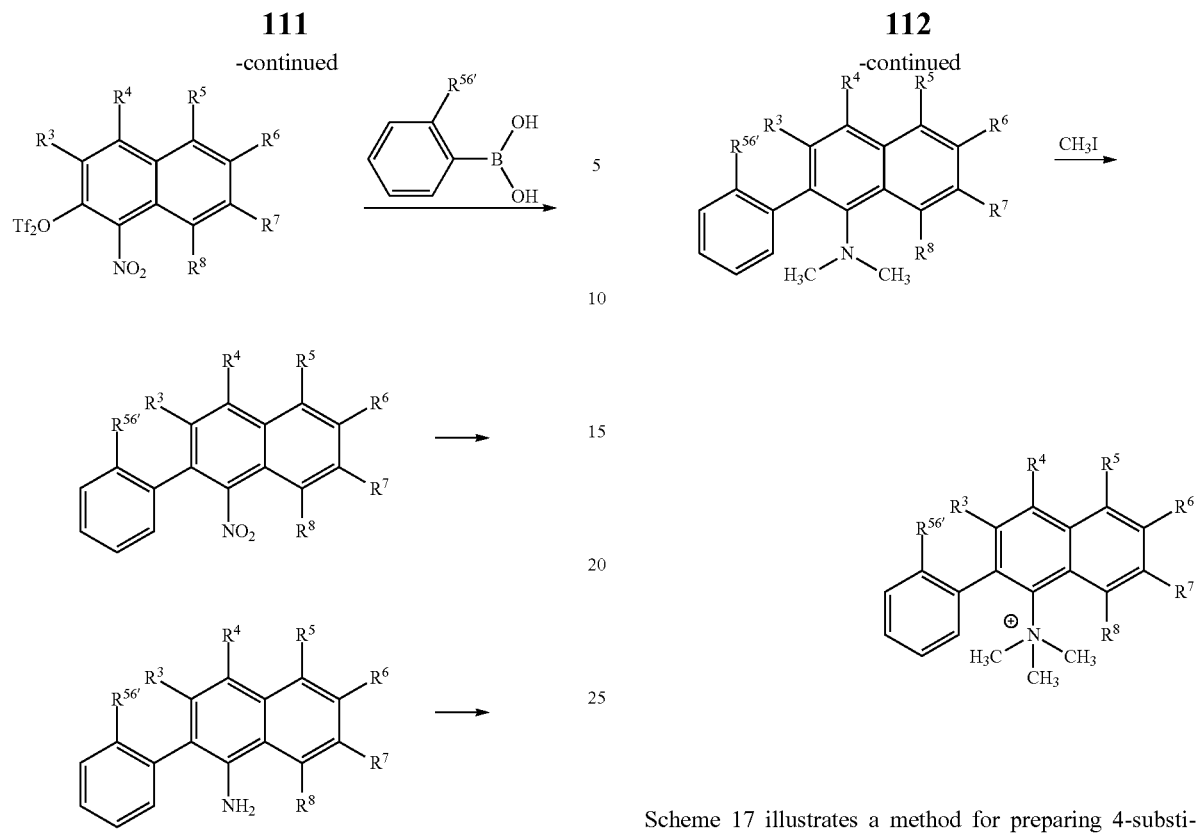
Scheme 17 illustrates a method for preparing 4-substituted-2-phenylquinolines using 2,4-dibromonaphthalenes.
Scheme 17
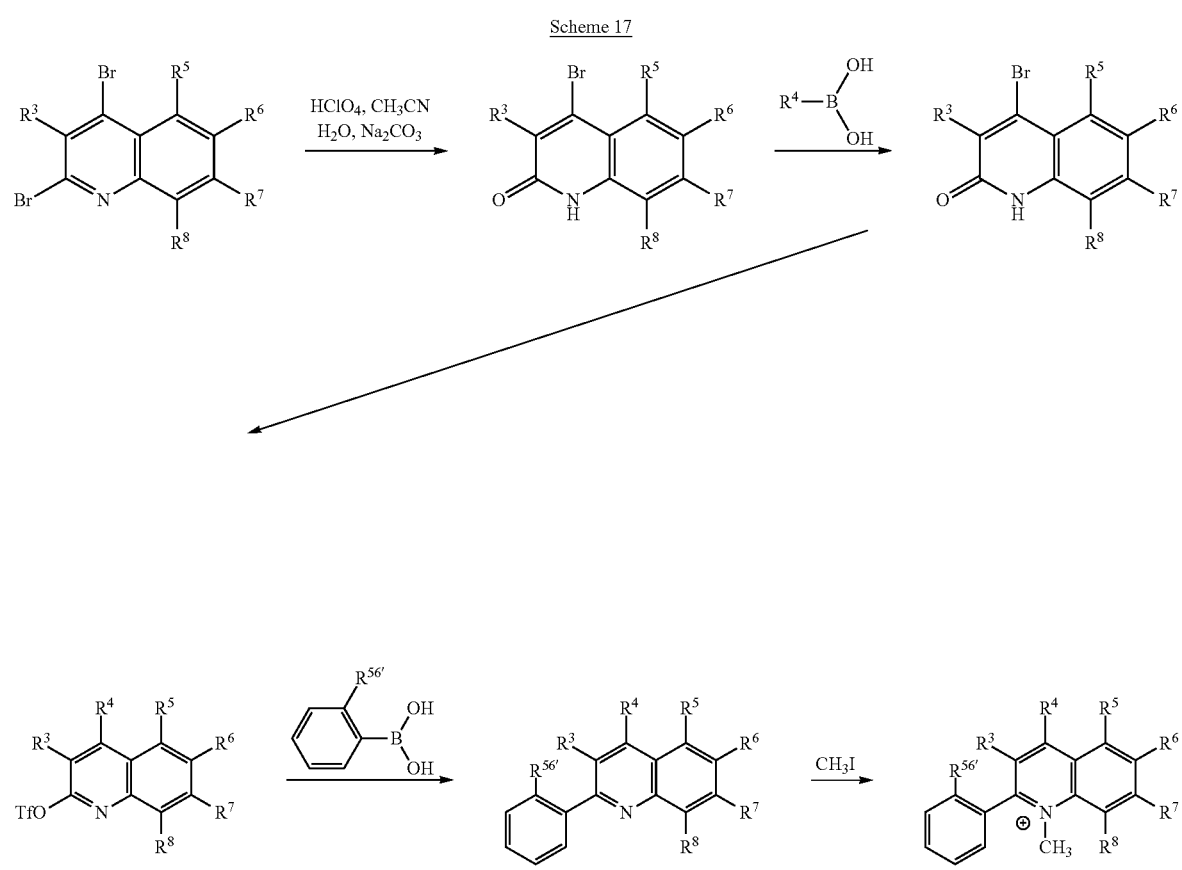

Scheme 18 illustrates a method for preparing 4-aryl-2-phenylquinolines using 4-aryl-2-quinolones, which can be synthesized by a variety of established methods.
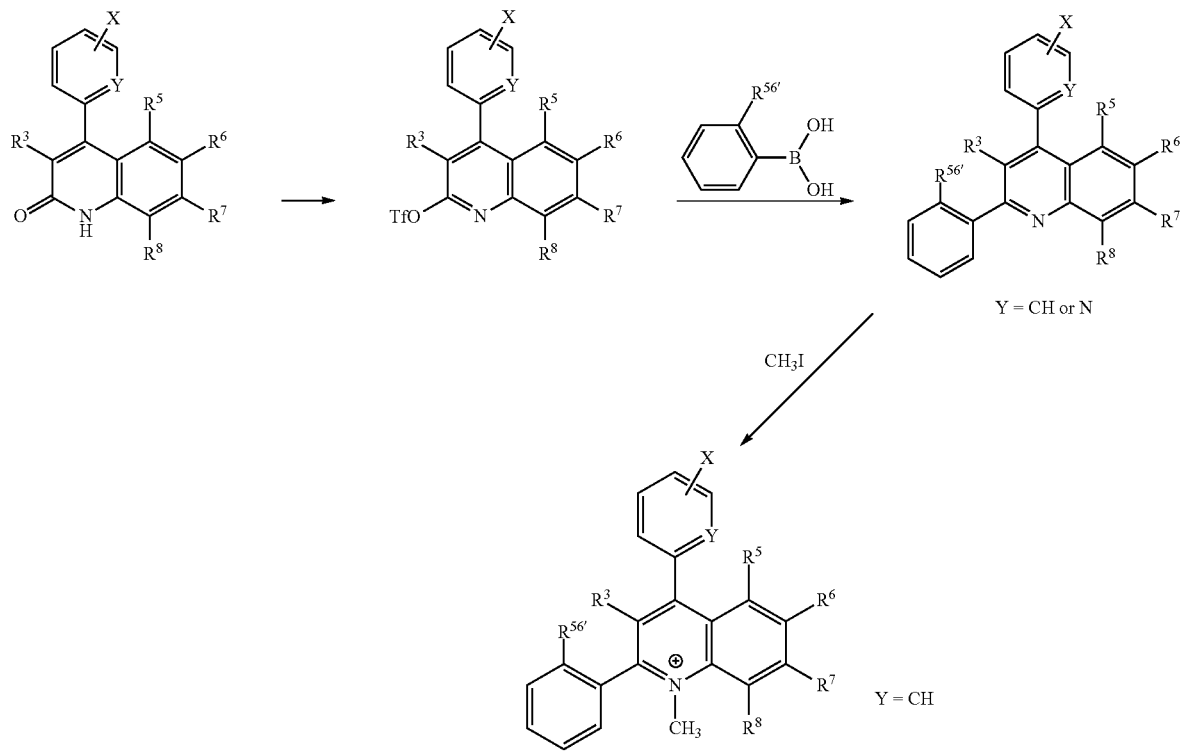
Scheme 19 illustrates a method for preparing 5-substituted-2-phenylquinolines with varied 6'-substituents from 5-bromo-2-quinolinones.
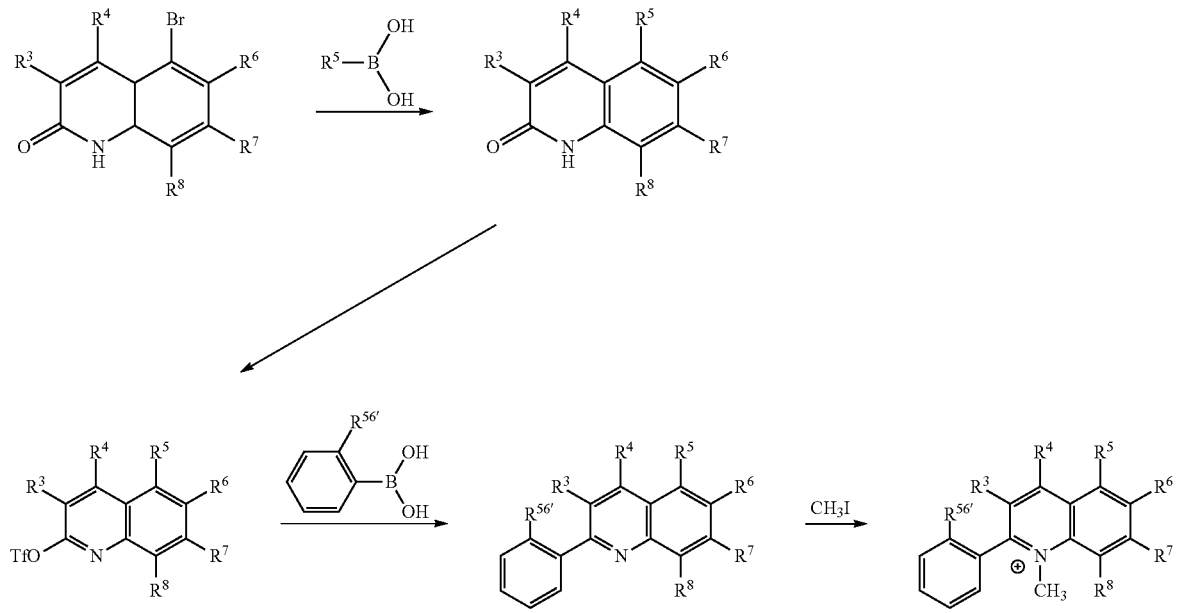

Scheme 20 illustrates a method for preparing 5-substituted phenyl and 5-substituted pyridyl 2-phenylquinolines with varied 6'-substituents from 5-phenyl- and 5-(2-pyridyl)-2-quinolinones.

Scheme 20

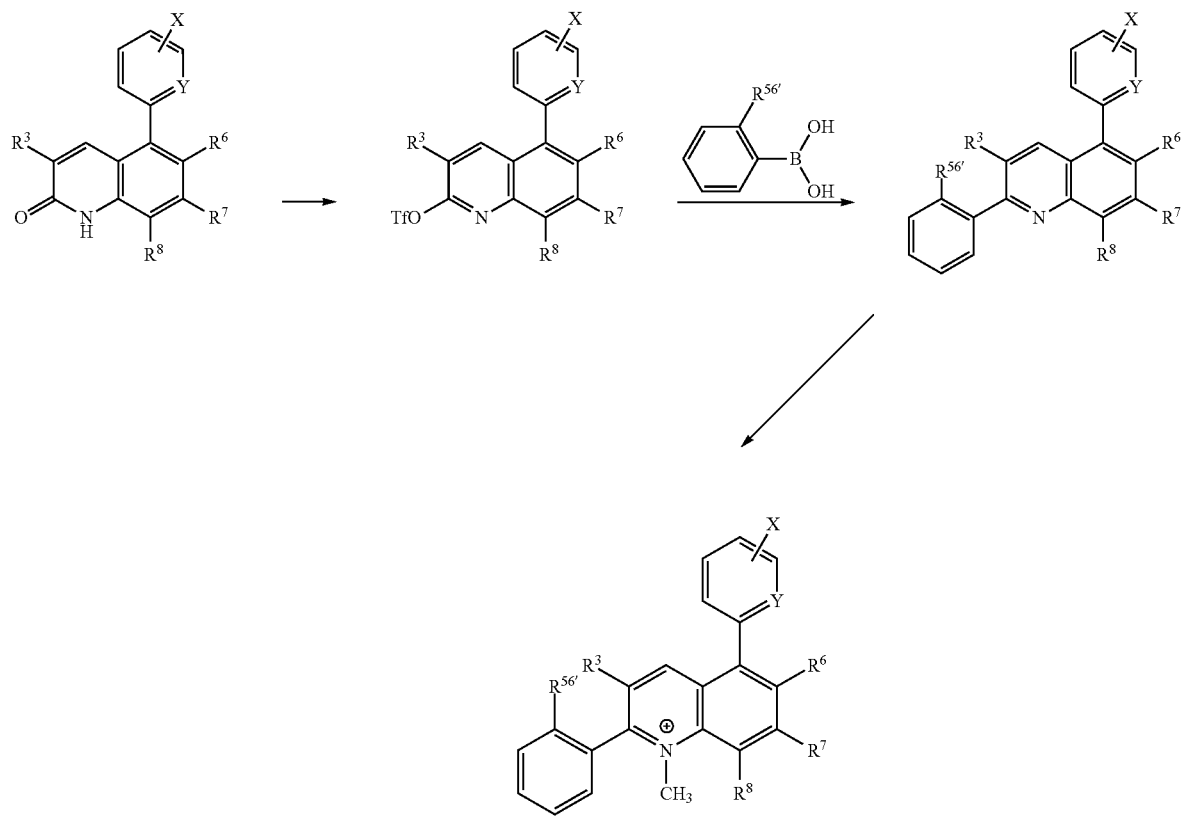

40

Scheme 21 illustrates a method for varying substituents at the $R^{56'}$-position by incorporation of a $R^{56'}$-protected phenol within an organoboronate that can be used to prepare various compounds as exemplified for 2-(2'-aminophenyl)naphthalene analogs.

Scheme 21

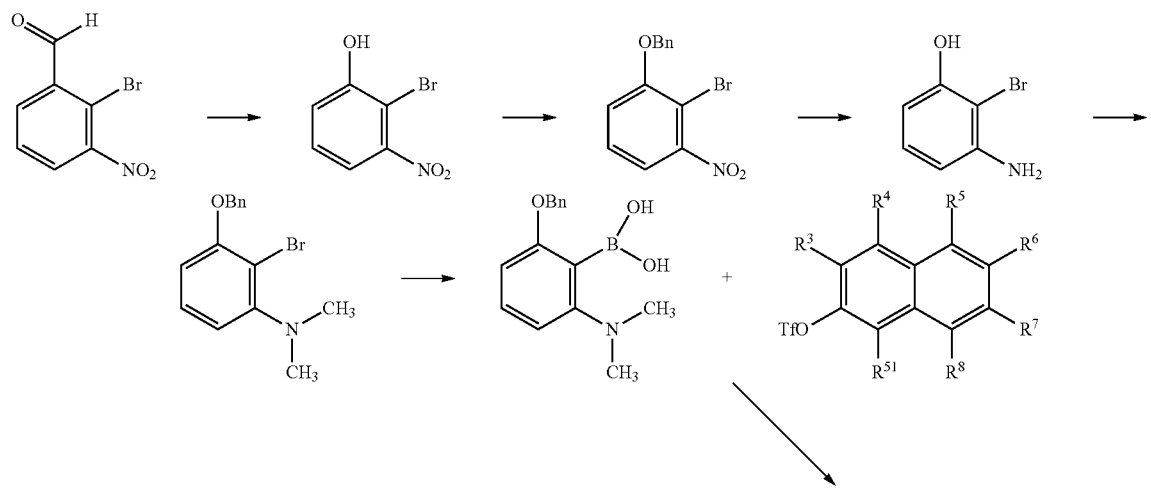

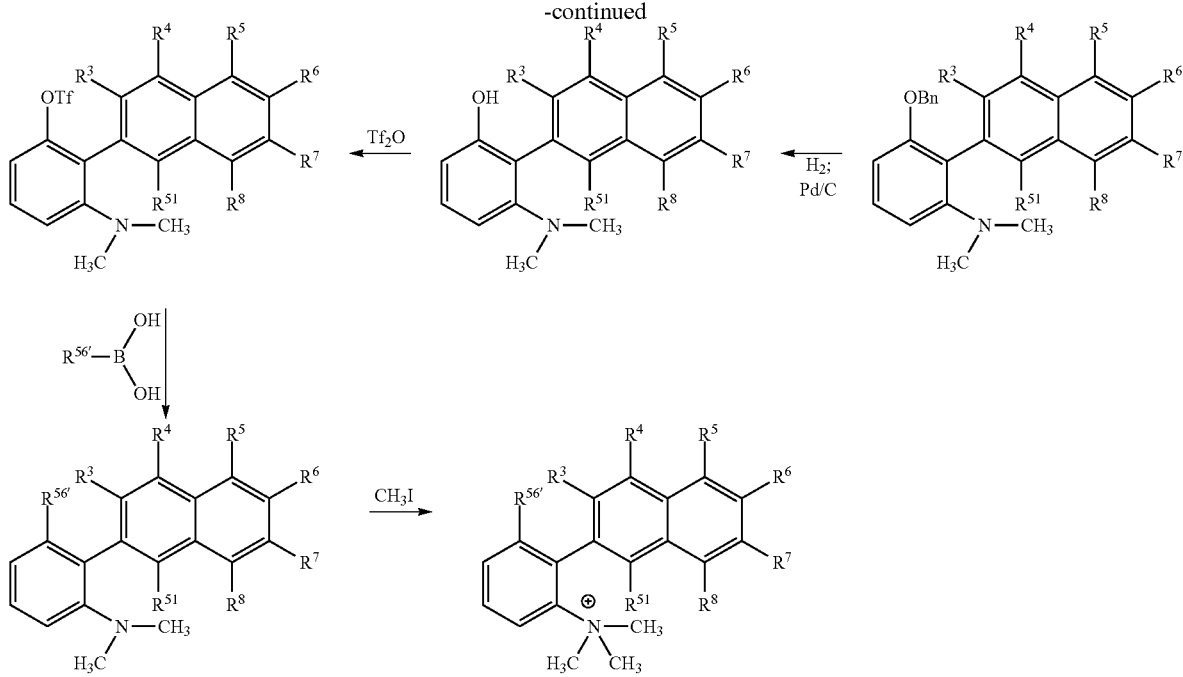
Scheme 22 illustrates a method for varying substituents at the $R^{56'}$-position by incorporation of a $R^{56'}$-phenyl within an organoboronate that can be used to prepare various compounds as exemplified for 2-(3'-phenylpyridin-2'-yl)naphthalene analogs.
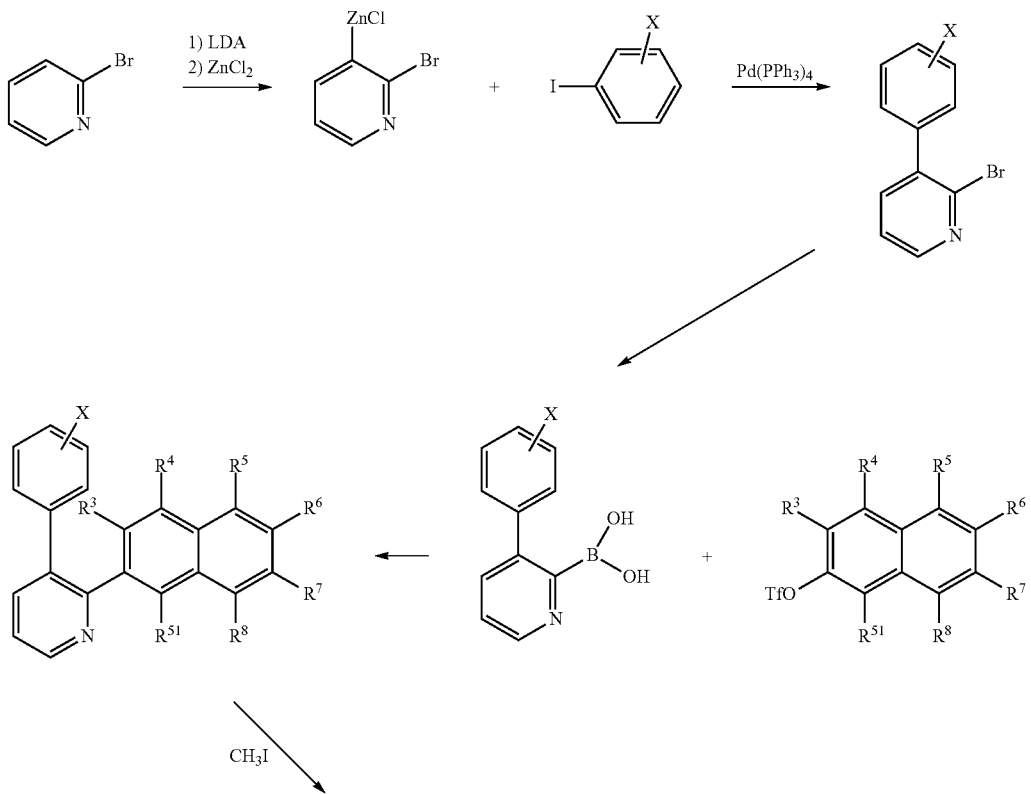

-continued
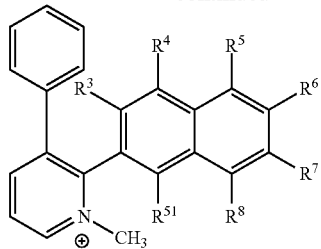
Scheme 23 illustrates a general method for the preparation of 3-phenylquinoline and 1-alkyl-3-phenylquinolinium compounds with varied 3'-substituents.
Scheme 23
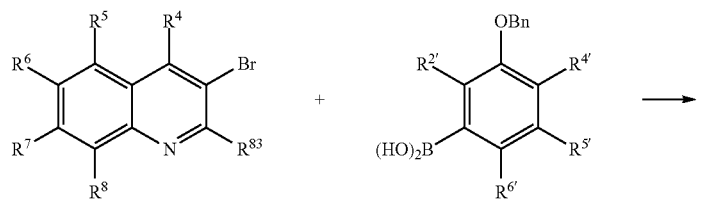
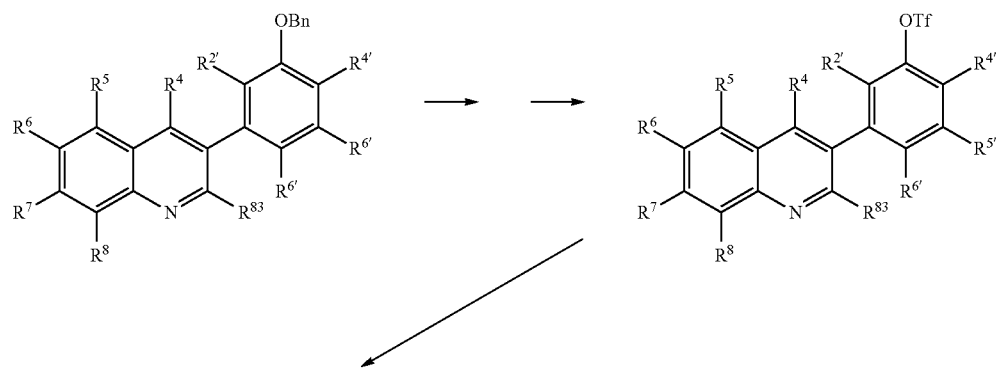
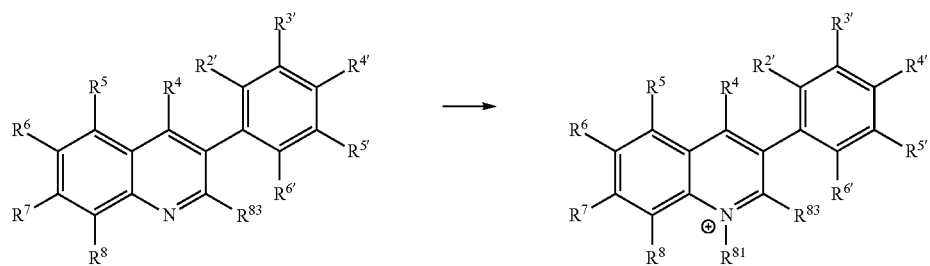

Scheme 24 illustrates a method for the preparation of substituted 3'phenyl-4',5'-dimethoxyphenyl-6,7-dimethoxy-3- phenylquinoline compounds and their methylquinolinium iodide derivatives.
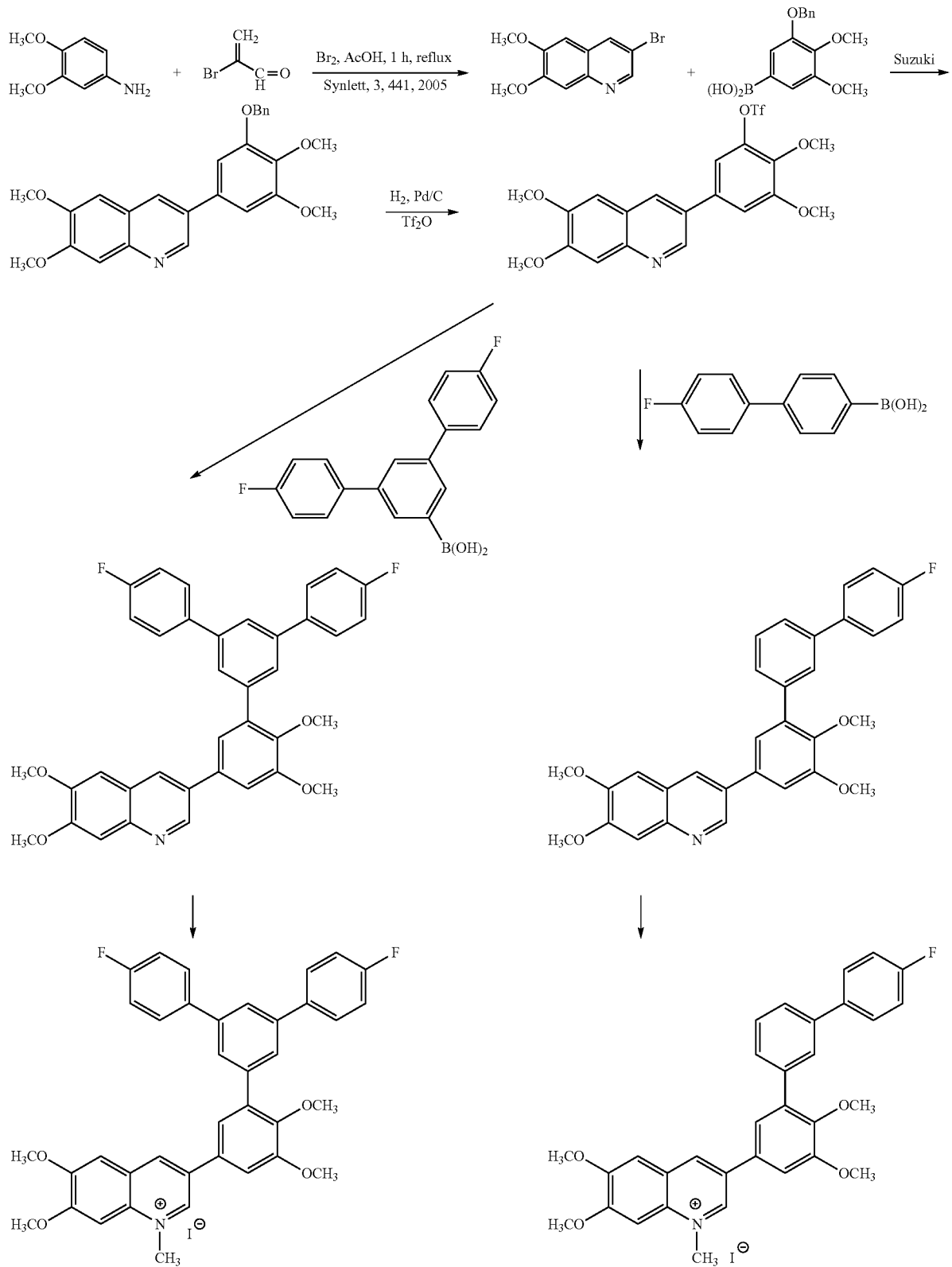

Scheme 25 illustrates a general method for the preparation of substituted 3'phenyl-4',5'-dimethoxyphenyl-6,8-dimethoxy-3-phenylquinoline compounds and their methylquinolinium iodide derivatives.

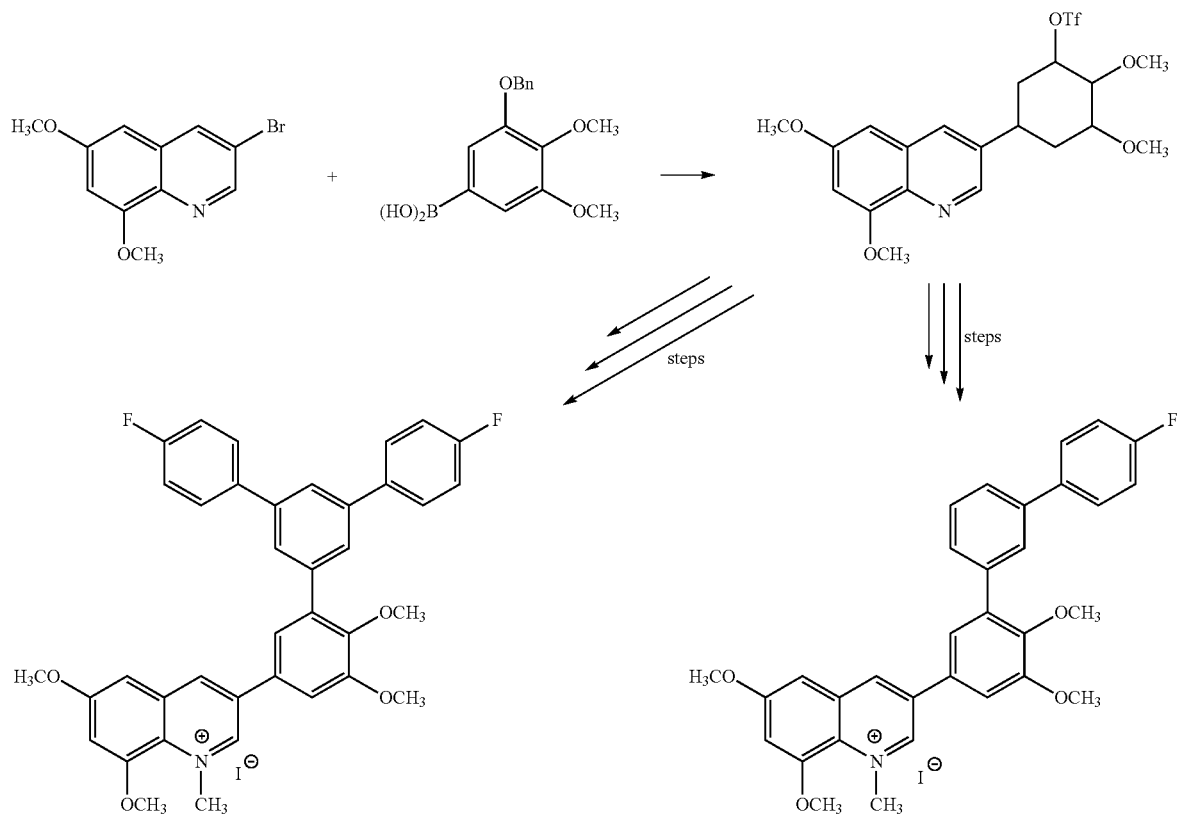

Scheme 26 illustrates a general method for the preparation of substituted 3'-phenyl-4',5'-dimethoxyphenyl-6,7-dimethoxy-3,4-diphenylquinoline compounds and their methylquinolinium iodide derivatives.

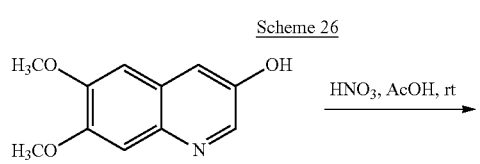

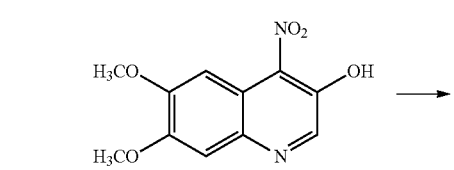

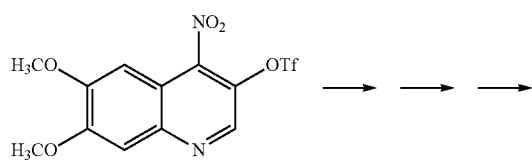

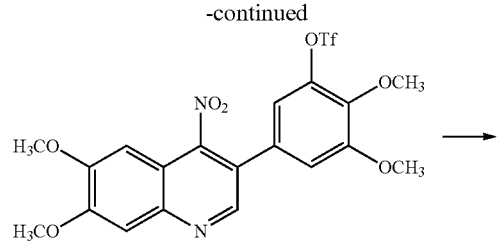

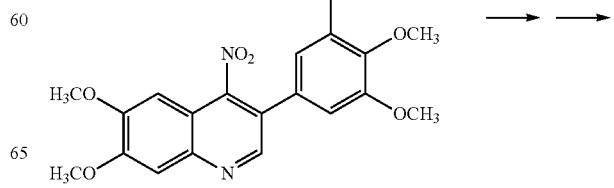

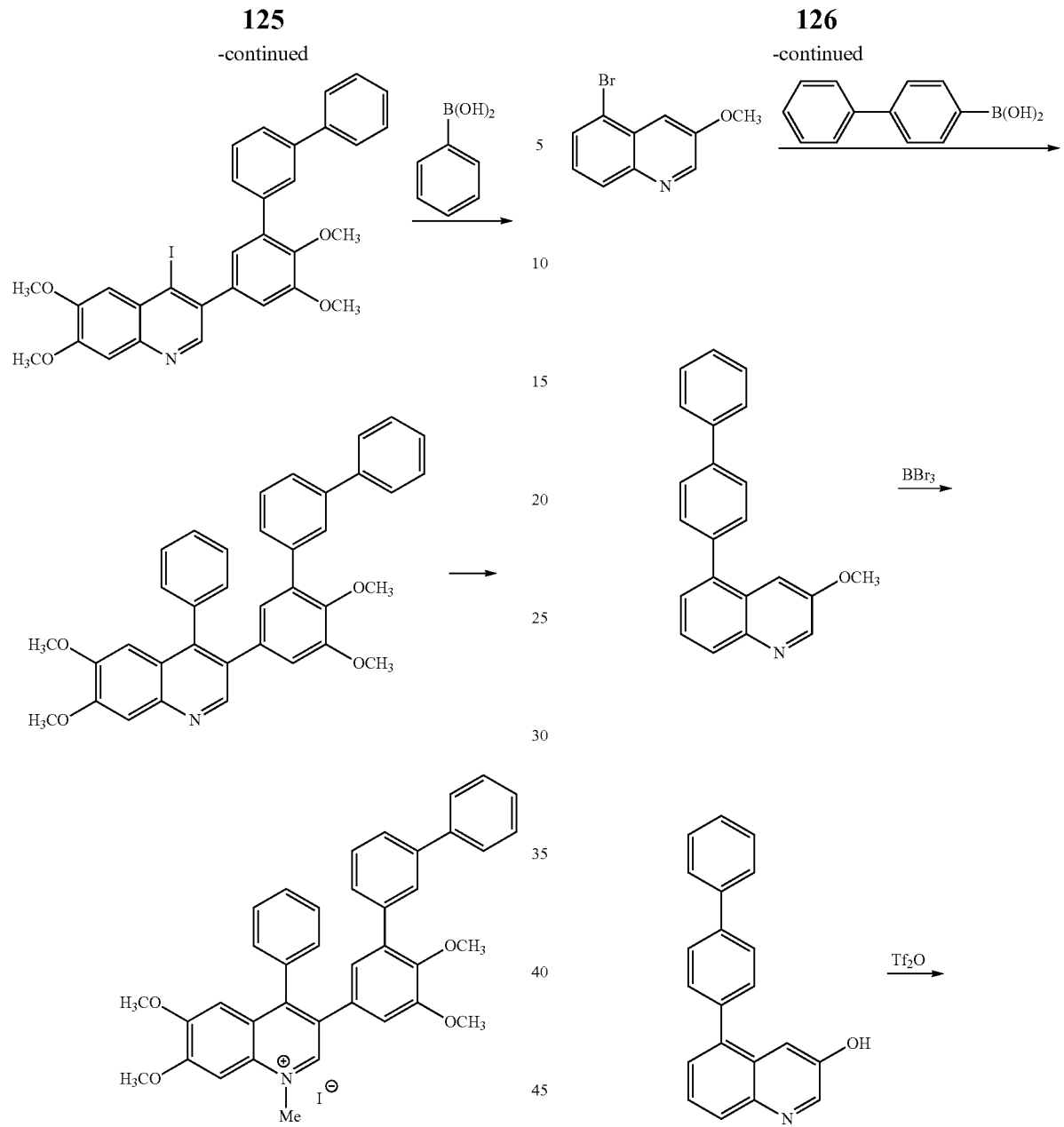
Scheme 27 illustrates a general method for the preparation of substituted 3'-phenyl-4',5'-dimethoxyphenyl-6,7-dimethoxy-3,5-diphenylquinoline compounds and their methylquinolinium iodide derivatives.
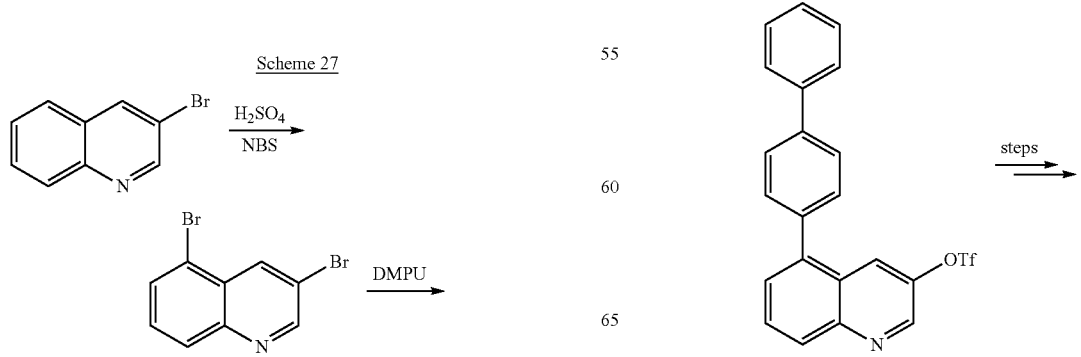

127
-continued
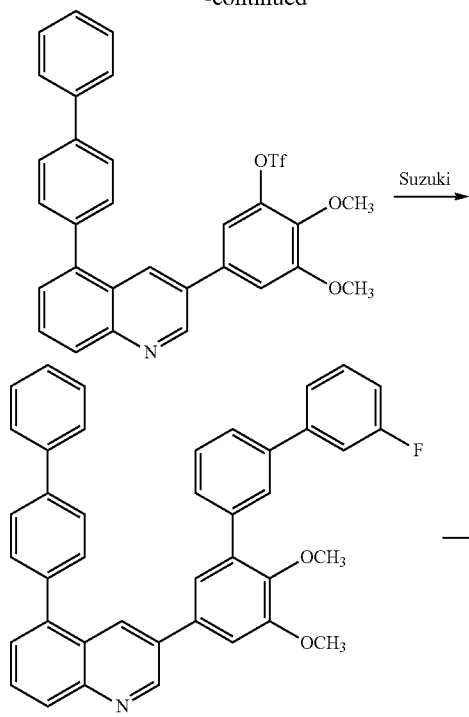
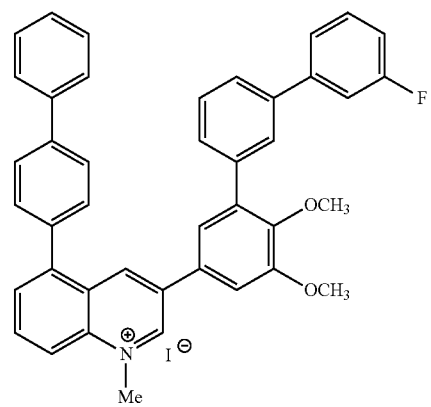
128
-continued
Scheme 28 illustrates a general method for the preparation of substituted 2-substituted 3,4,9,10-tetramethoxybenzo[a]acridines and their 7-methylbenzo[a]acridinium derivatives.
Scheme 28
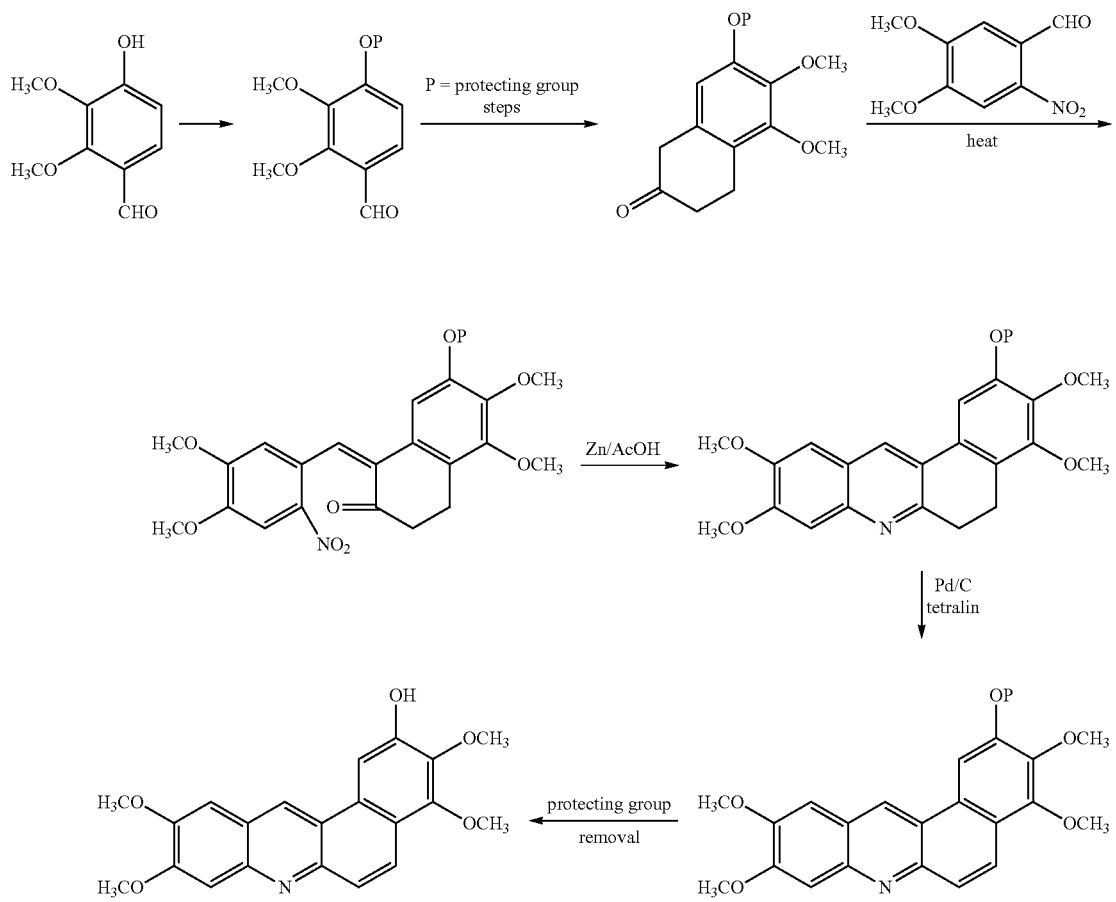

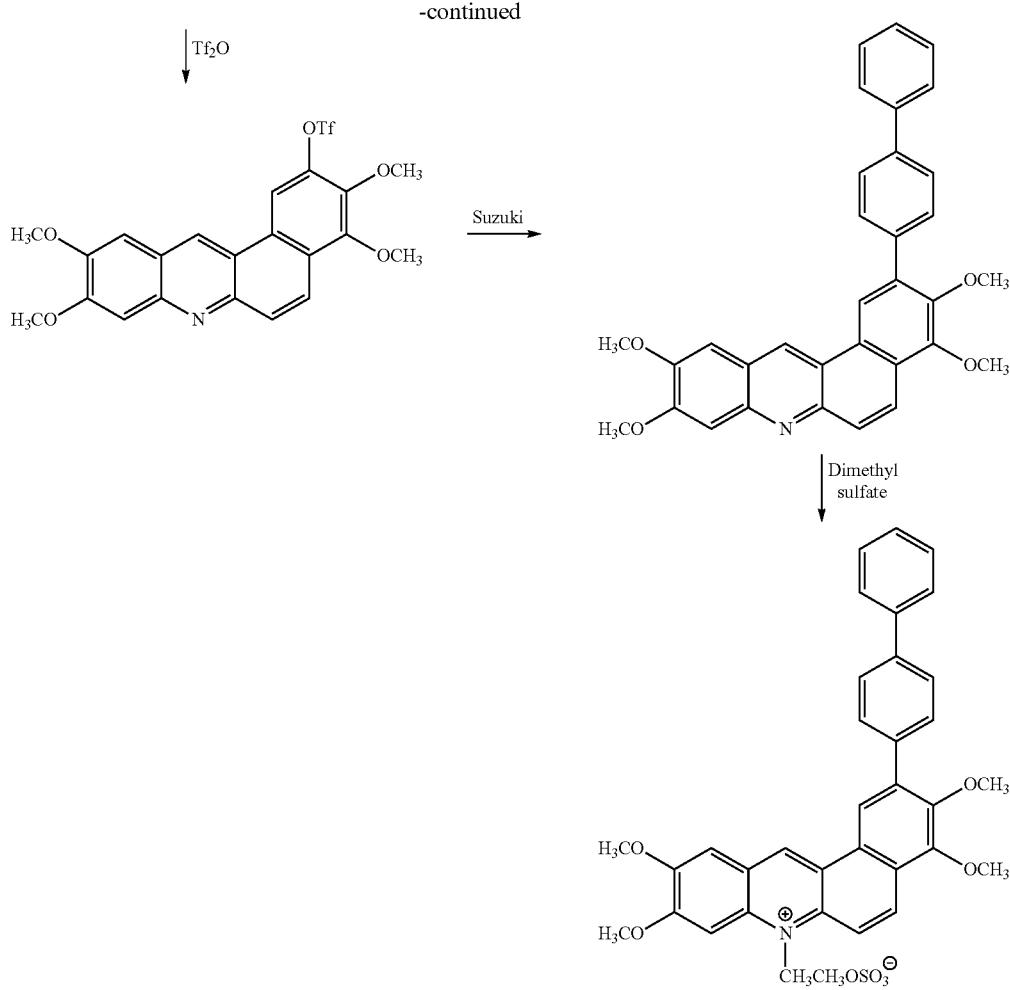

By binding to FtsZ, the compounds of the present invention inhibit the ability of the protein to hydrolyze GTP. This inhibition of FtsZ GTPase activity, in turn, inhibits the ability of the protein to polymerize into Z-rings, as Z-ring formation requires GTP hydrolysis as an energy source for driving the reaction. Since the Z-ring serves as the scaffold for recruitment of all other proteins that comprise the divisome complex, inhibition of Z-ring formation by the compounds of the present invention also results in a corresponding inhibition of divisome protein recruitment.

The compounds of the invention are useful to treat bacterial infections including infections by Gram-negative bacterial strains, Gram-positive bacterial strains and multiple drug-resistant bacterial strains Gram-negative bacterial strains include *Escherchia coli, Caulobacter crescentus, Pseudomonas aeruginosa, Agrobacterium tumefaciens, Branhamella catarrhalis, Citrobacter diversus, Enterobacter aerogenes, Enterobacter cloacae, Enterobacter sakazakii, Enterobacter asburiae, Pantoea agglomerans, Klebsiella pneumoniae, Klebsiella oxytoca, Klebsiella rhinoscleromatis, Proteus mirabilis, Salmonella typhimurium, Salmonella enteriditis, Serratia marcescens, Shigella sonnei, Neisseria gonorrhoeae, Acinetobacter baumannii, Acinetobacter calcoaceticus, Acinetobacter lwoffi, Fusobacterium nucleatum, Veillonella parvula, Bacteroides forsythus, Actinobacillus actinomycetemcomitans, Aggregatibacter actinomycetemcomitans, Porphyromonas gingivalis, Helicobacter pylori, Francisella tularensis, Yersinia pestis, Borrelia burgdorferi, Neisseria meningitidis* and *Haemophilus influenza.*

Gram-positive bacterial strains include *Staphylococcus aureus, Staphylococcus epidermidis, Staphylococcus saprophyticus, Streptococcus pyogenes, Streptococcus faecalis, Enterococcus faecalis, Enterococcus faecium, Bacillus subtilis, Bacillus anthracis, Bacillus cereus, Micrococcus luteus, Mycobacterium tuberculosis, Clostridium difficile, Propionibacterium acnes, Streptococcus mutans, Actinomyces viscosus, Actinomyces naeslundii, Streptococcus sanguis, Streptococcus pneumoniae, Streptococcus viridans* and *Streptococcus salivarius.*

Multiple drug-resistant bacterial strains include methicillin-resistant *Staphylococcus aureus*, vancomycin-resistant Enterococci, multiple drug-resistant *Mycobacterium tuberculosis*, and multidrug-resistant *Clostridium difficile.*

In one embodiment compounds of the present invention may be administered as a composition used to treat and/or prevent a bacterial infection wherein the bacterial cell uses polymerized FtsZ protein, or a homolog thereof, to facilitate cytokinesis. To this end, compounds of the present invention may be administered to treat Staph Infections, Tuberculosis, Urinary Tract Infections, Meningitis, Enteric Infections, Wound Infections, Acne, Encephalitis, Skin Ulcers, Bed Sores, Gastric and Duodenal Ulcers, Eczema, Periodontal disease, Gingivitis, Halitosis, Anthrax, Tularemia, Endocarditis, Prostatitis, Osteomyelitis, Lyme Disease, Pneumonia, or the like.

The compositions can, if desired, also contain other active therapeutic agents, such as a narcotic, a non-steroid anti-inflammatory drug (NSAID), an analgesic, an anesthetic, a sedative, a local anesthetic, a neuromuscular blocker, an anti-cancer, other antimicrobial (for example, an aminoglycoside, an antifungal, an antiparasitic, an antiviral, a carbapenem, a cephalosporin, a fluororquinolone, a macrolide, a penicillin, a sulfonamide, a tetracycline, another antimicrobial), an anti-psoriatic, a corticosteriod, an anabolic steroid, a diabetes-related agent, a mineral, a nutritional, a thyroid agent, a vitamin, a calcium-related hormone, an antidiarrheal, an anti-tussive, an anti-emetic, an anti-ulcer, a laxative, an anticoagulant, an erythropieitin (for example, epoetin alpha), a filgrastim (for example, G-CSF, Neupogen), a sargramostim (GM-CSF, Leukine), an immunization, an immunoglobulin, an immunosuppressive (for example, basiliximab, cyclosporine, daclizumab), a growth hormone, a hormone replacement drug, an estrogen receptor modulator, a mydriatic, a cycloplegic, an alkylating agent, an anti-metabolite, a mitotic inhibitor, a radiopharmaceutical, an anti-depressant, an anti-manic agent, an anti-psychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog thereof, dornase alpha (Pulmozyme), a cytokine, or any combination thereof.

The term "prodrug" as used herein refers to any compound that when administered to a biological system (e.g. a mammal such as a human) generates the drug substance, i.e. active ingredient, as a result of spontaneous chemical reaction(s), enzyme catalyzed chemical reaction(s), photolysis, and/or metabolic chemical reaction(s) or by some other process. A prodrug is thus a modified (e.g. covalently modified) analog or latent form of a therapeutically-active compound. A prodrug may also be an active metabolite or therapeutically-active compound itself.

By way of example a prodrug may generate the active inhibitory compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191; Tranoyl-Opalinski, I., Fernandes, A., Thomas, M., Gesson, J.-P., and Papot, S., Anti-Cancer Agents in Med. Chem., 8 (2008) 618-637). Enzymes which are capable of an enzymatic activation mechanism with the prodrug compounds of the invention include, but are not limited to nitroreductase, proteases (e.g. serine proteases such as prostate specific antigen (PSA), amidases, esterases, microbial enzymes, phospholipases, cholinesterases, and phosphases).

Processes for preparing compounds of formula I are provided as further embodiments of the invention and are illustrated by the following procedures in which the meanings of the generic radicals are as given above unless otherwise qualified.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts. Salts may be obtained using standard procedures well known in the art, for example by reacting a sufficiently basic compound such as an amine with a suitable acid affording the corresponding anion. Alkali metal (for example, sodium, potassium or lithium) or alkaline earth metal (for example calcium) salts of carboxylic acids can also be made.

Pharmaceutically suitable counterions include pharmaceutically suitable cations and pharmaceutically suitable anions that are well known in the art. Examples of pharmaceutically suitable anions include, but are not limited to those described above (e.g. physiologically acceptable anions) including $Cl^-$, $Br^-$, $I^-$, $CH_3SO_3^-$, $CF_3SO_3^-$, $p\text{-}CH_3C_6H_4SO_3^-$, citrate, tartrate, malate, fumarate, formate, or acetate.

It will be appreciated by those skilled in the art that a compound of the invention comprising a counterion can be converted to a compound of the invention comprising a different counterion. Such a conversion can be accomplished using a variety of well known techniques and materials including but not limited to ion exchange resins, ion exchange chromatography and selective crystallization.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent, excipient or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 90% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations, particles, and devices.

The active compound may also be administered intravenously or intramuscularly by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, nanoparticles, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.1 to about 500 mg/kg, e.g., from about 0.5 to about 400 mg/kg of body weight per day, such as 1 to about 250 mg per kilogram body weight of the recipient per day.

The compound is conveniently formulated in unit dosage form; for example, containing 0.5 to 500 mg, 1 to 400 mg, or 0.5 to 100 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The ability of a compound of the invention to alter the polymerization dynamics of FtsZ can be determined using a method like Test A described below.

Test A. Determining the Impact of the Compounds of the Invention on FtsZ Polymerization Dynamics.

Compound-induced alteration in FtsZ polymerization dynamics can be tested using a light scattering-based competition binding assay using purified FtsZ. Upon addition of GTP, FtsZ self-associates to form polymeric structures that scatter light at 340 nm to a greater extent than the monomeric protein. The impact of the compounds of the invention on the polymerization dynamics of FtsZ can be detected by an increase of decrease in the extent of GTP-induced light scattering relative to that observed in the absence of compound. Quantitation of the overall extent of light scattering as a function of compound concentration to yield a compound concentration at which FtsZ polymerization is inhibited by 50% ($IC_{50}$) provides an indication of the potency of that compound at altering FtsZ polymerization dynamics.

The ability of a compound of the invention to inhibit FtsZ GTPase activity can be determined using a method like Test B described below.

Test B. Determining the FtsZ GTPase Inhibitory Activities of Compounds of the Invention.

Compound-induced inhibition of the FtsZ GTPase activity can be tested using a colorimetric assay in which the inorganic phosphate ($P_i$) released upon FtsZ-catalyzed hydrolysis of GTP reacts with malachite green and molybdate under acidic conditions to form a ternary complex that absorbs light at 650 nm, thus enabling quantitation of $P_i$ levels by recording the absorbance at 650 nm ($A_{650}$). Differing concentrations of test compound are combined with GTP and the reactions (run in triplicate) are initiated by addition of FtsZ. After incubation for 60 minutes at room temperature, the reactions are stopped by addition of an acidic malachite green-molybdate solution containing malachite green oxalate, sodium molybdate, Triton X-100, and 0.7 N HCl. For the purposes of generating a standard curve, each experiment includes reactions containing known concentrations of monobasic potassium phosphate ($KH_2PO_4$) in place of FtsZ. Ten minutes following addition of the acidic malachite green-molybdate solution, the $A_{650}$ value for each reaction is recorded. A standard curve of $A_{650}$ versus $P_i$ concentration is constructed using the average $A_{650}$ value obtained for each known $KH_2PO_4$ concentration. This standard curve is then fit by linear regression analysis to yield the quantitative relationship between $A_{650}$ and $P_i$ concentration. The resulting relationship as well as the average $A_{650}$ value for each test reaction is used to calculate the concentrations of $P_i$ released by the GTPase activity of FtsZ. The released $P_i$ concentration in the absence of test compound is set as the mark for 100% GTPase activity, and is used to calculate the percent GTPase activities in reactions containing test compounds. The percent GTPase activity is then plotted as a function of log (compound concentration), with the resulting curves being fit using an appropriate sigmoidal relationship to obtain the compound concentrations at which GTPase activity is inhibited by 50% ($IC_{50}$ values). These $IC_{50}$ values provide quantitative measures of the potencies with which the test compounds of the invention inhibit FtsZ GTPase activity.

TABLE 1

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 2 | 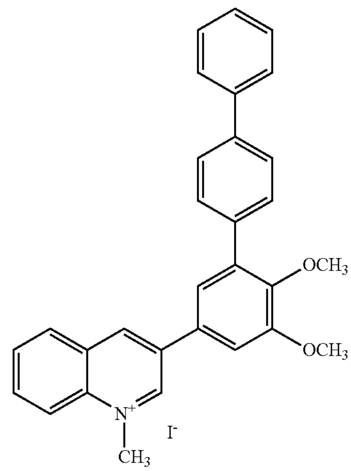 [SMILES: COc1cc(-c2cc3ccccc3[n+](C)c2)cc(-c2ccc(-c3ccccc3)cc2)c1OC ; [I-]] | ≤8.0 | — |
| Example 4 | 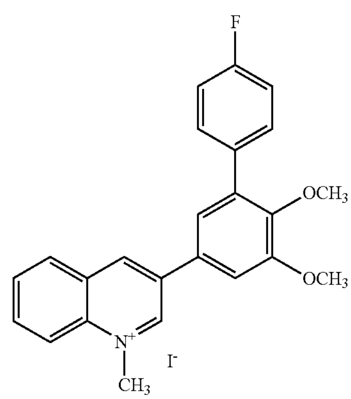 [SMILES: COc1cc(-c2cc3ccccc3[n+](C)c2)cc(-c2ccc(F)cc2)c1OC ; [I-]] | 16.0 | — |
| Example 6 | 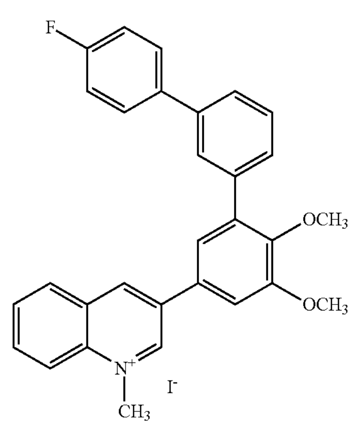 [SMILES: COc1cc(-c2cc3ccccc3[n+](C)c2)cc(-c2cccc(-c3ccc(F)cc3)c2)c1OC ; [I-]] | ≤8.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
|---------|-----------|---------------------|---------------------|
| Example 8 | 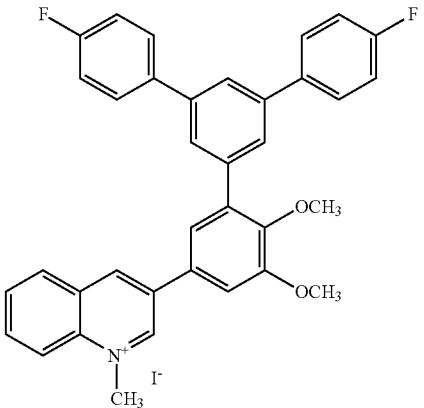 [SMILES: COc1cc(-c2cc3ccccc3[n+](C)c2)cc(-c2cc(-c3ccc(F)cc3)cc(-c3ccc(F)cc3)c2)c1OC ; [I-]] | ≤8.0 | — |
| Example 11 | 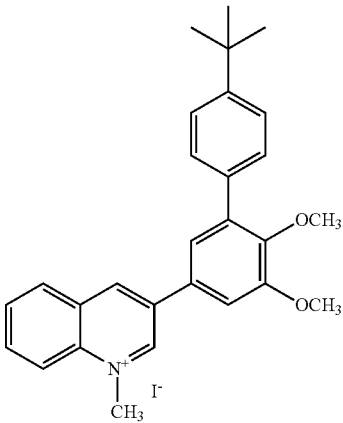 [SMILES: COc1cc(-c2cc3ccccc3[n+](C)c2)cc(-c2ccc(C(C)(C)C)cc2)c1OC ; [I-]] | ≤8.0 | ≤8.0 |
| Example 13 | 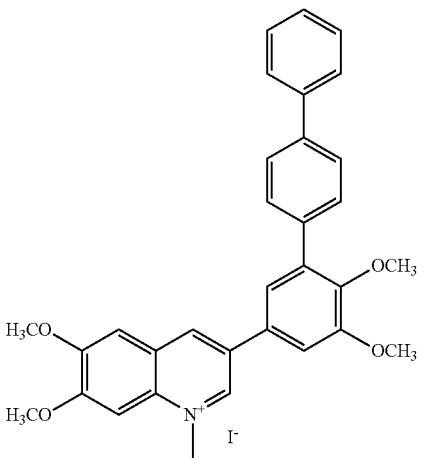 [SMILES: COc1cc2cc(-c3cc(OC)c(OC)c(-c4ccc(-c5ccccc5)cc4)c3)c[n+](C)c2cc1OC ; [I-]] | ≤8.0 | — |

TABLE 1-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 14 | 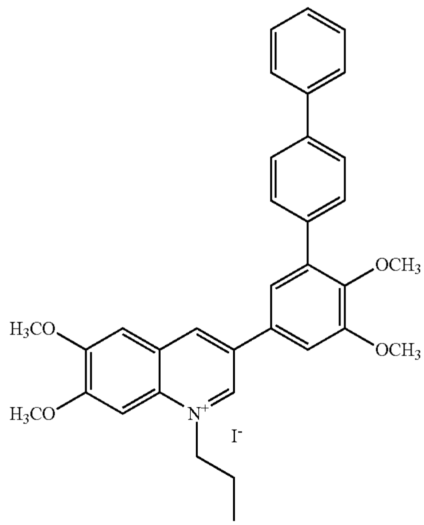 [SMILES: CCC[n+]1cc(-c2cc(OC)c(OC)c(-c3ccc(-c4ccccc4)cc3)c2)cc2cc(OC)c(OC)cc21 ; [I-]] | ≤8.0 | — |
| Example 16 | 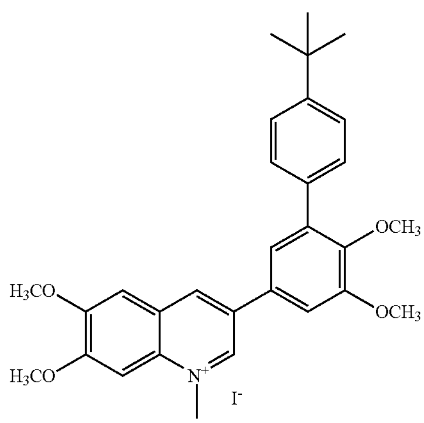 [SMILES: COc1cc2cc(-c3cc(OC)c(OC)c(-c4ccc(C(C)(C)C)cc4)c3)c[n+](C)c2cc1OC ; [I-]] | ≤8.0 | — |
| Example 19 | 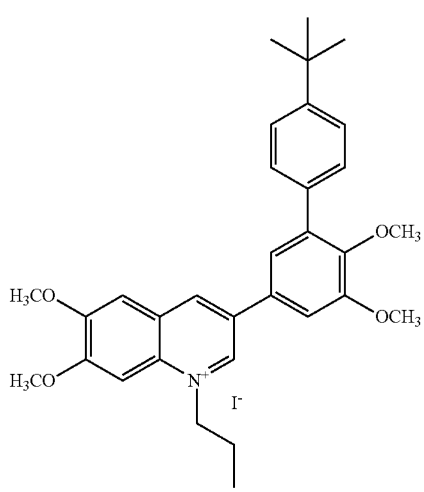 [SMILES: CCC[n+]1cc(-c2cc(OC)c(OC)c(-c3ccc(C(C)(C)C)cc3)c2)cc2cc(OC)c(OC)cc21 ; [I-]] | ≤8.0 | ≤8.0 |

TABLE 1-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 21 | 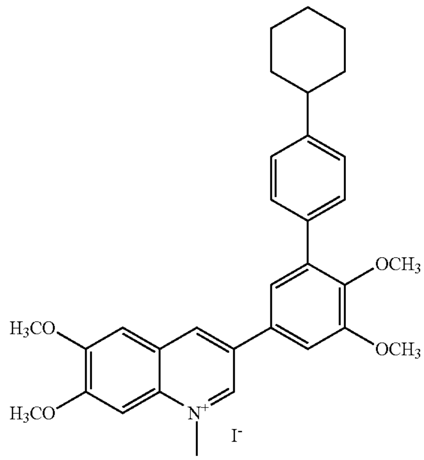 [SMILES: COc1cc2cc(-c3cc(OC)c(OC)c(-c4ccc(C5CCCCC5)cc4)c3)c[n+](C)c2cc1OC ; [I-]] | ≤8.0 | — |
| Example 22 | 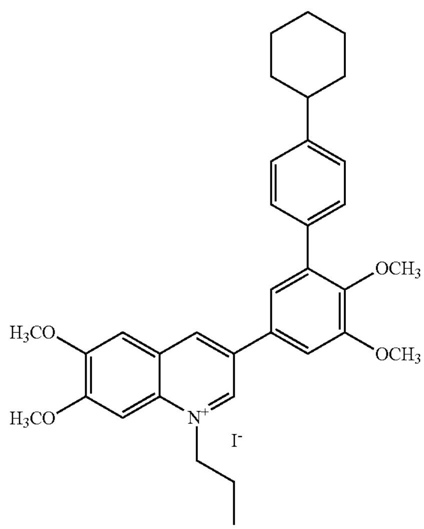 [SMILES: CCC[n+]1cc(-c2cc(OC)c(OC)c(-c3ccc(C4CCCCC4)cc3)c2)cc2cc(OC)c(OC)cc21 ; [I-]] | ≤8.0 | — |
| Example 25 | 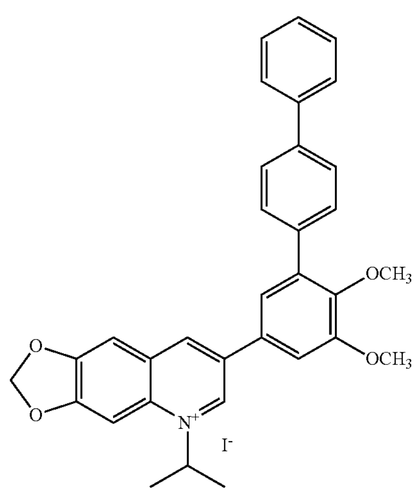 [SMILES: COc1cc(-c2cc3cc4c(cc3[n+](C(C)C)c2)OCO4)cc(-c2ccc(-c3ccccc3)cc2)c1OC ; [I-]] | ≤8.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
|---|---|---|---|
| Example 26a | 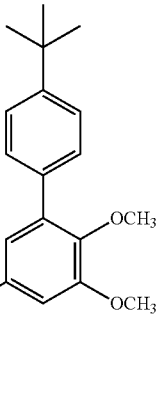 | ≤8.0 | — |
| Example 28 | 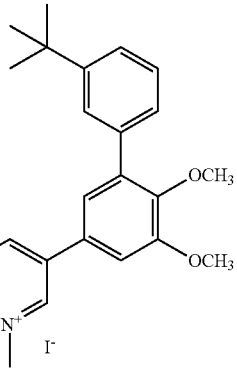 | ≤8.0 | — |
| Example 30 | 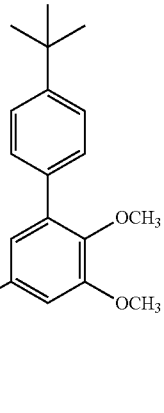 | ≤8.0 | — |

TABLE 1-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 31 | [structure: 2-(aminomethyl)-3-[3,5-dimethoxy-4'-tert-butylbiphenyl]quinoline, NH$_3^+$ TFA$^-$ salt] | ≤8.0 | — |
| Example 33 | [structure: 3-(3,4-difluoro-4'-phenylbiphenyl)-1-methylquinolinium iodide] | ≤8.0 | — |
| Example 35 | [structure: 1-methyl-3-(3,5-diphenylphenyl)quinolinium iodide] | ≤8.0 | ≤8.0 |

TABLE 1-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 36 | 4-(4-tert-butylphenyl)-naphthalen-1-yl ethylamine | ≤8.0 | ≤8.0 |
| Example 37 | 4-(4-tert-butylphenyl)-naphthalen-1-yl ethylguanidine | ≤8.0 | ≤8.0 |
| Example 38 | 4-(4-tert-butylphenyl)-naphthalen-1-yl ethylamine (isomer) | ≤8.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
|---|---|---|---|
| Example 39 | 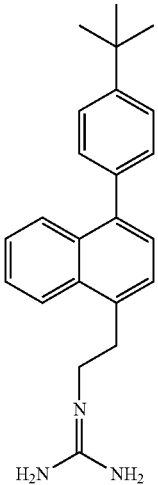 [SMILES: CC(C)(C)c1ccc(-c2ccc(CCN=C(N)N)c3ccccc23)cc1] | ≤8.0 | — |
| Example 40 | 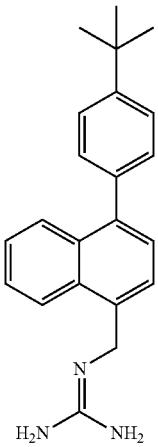 [SMILES: CC(C)(C)c1ccc(-c2ccc(CN=C(N)N)c3ccccc23)cc1] | ≤8.0 | — |
| Example 41 | 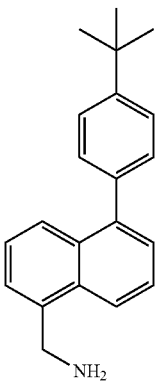 [SMILES: CC(C)(C)c1ccc(-c2cccc3c(CN)cccc23)cc1] | ≤8.0 | ≤8.0 |

TABLE 1-continued
Minimal Inhibitory Concentrations against MSSA for representative compounds of the Invention
| Example | Structure | MIC vs MSSA (ug/ml) | MIC vs MRSA (ug/ml) |
|---|---|---|---|
| Example 42 | 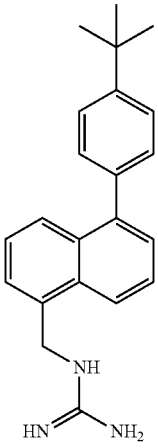 [SMILES: CC(C)(C)c1ccc(-c2cccc3c(CNC(=N)N)cccc23)cc1] | ≤8.0 | ≤8.0 |
| Example 43 | 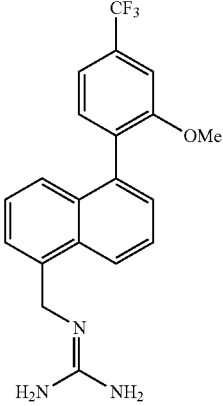 [SMILES: COc1cc(C(F)(F)F)ccc1-c1cccc2c(CN=C(N)N)cccc12] | ≤8.0 | — |
| Example 44 | 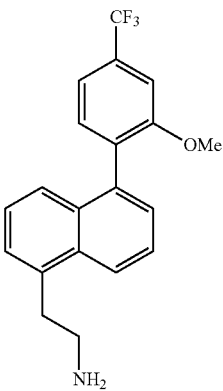 [SMILES: COc1cc(C(F)(F)F)ccc1-c1cccc2c(CCN)cccc12] | ≤8.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
|---|---|---|---|
| Example 45 | 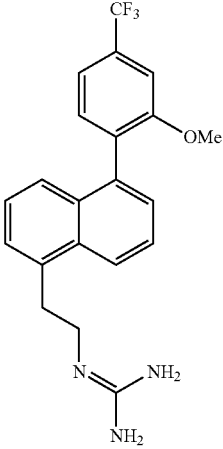 [SMILES: COc1cc(C(F)(F)F)ccc1-c1cccc2c(CCN=C(N)N)cccc12] | ≤8.0 | — |
| Example 46 | 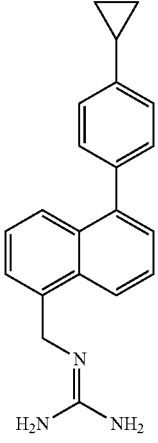 [SMILES: NC(N)=NCc1cccc2c(-c3ccc(C4CC4)cc3)cccc12] | ≤8.0 | — |
| Example 47 | 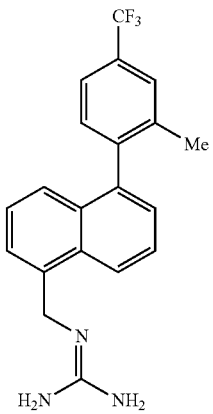 [SMILES: Cc1cc(C(F)(F)F)ccc1-c1cccc2c(CN=C(N)N)cccc12] | ≤8.0 | — |

TABLE 1-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 50 | [4-biphenyl-substituted 6,7-dimethoxynaphthalene with trimethylammonium iodide] | ≤8.0 | — |
| Example 51 | [5-(4-bromophenyl)naphthalen-1-yl]methyl guanidine | ≤8.0 | — |
| Example 52 | [5-(4-chlorophenyl)naphthalen-1-yl]methyl guanidine | ≤8.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
|---|---|---|---|
| Example 53 | 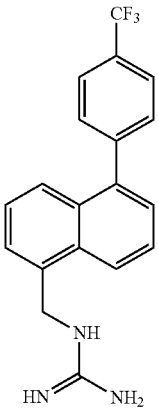 [SMILES: N=C(N)NCc1cccc2c(-c3ccc(C(F)(F)F)cc3)cccc12] | ≤8.0 | — |
| Example 55 | 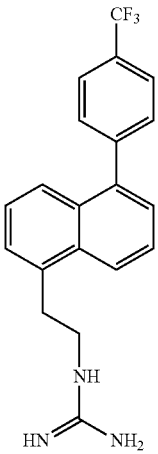 | ≤8.0 | — |
| Example 56 | 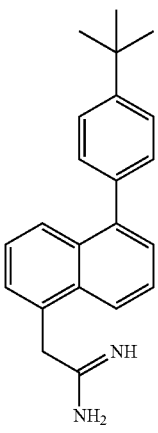 [SMILES: CC(C)(C)c1ccc(-c2cccc3c(CC(=N)N)cccc23)cc1] | ≤8.0 | ≤8.0 |

TABLE 1-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 58 | 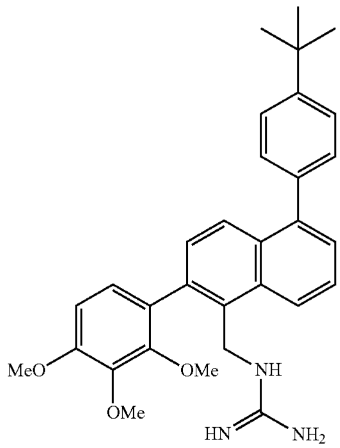 [SMILES: COc1ccc(-c2ccc3c(-c4ccc(C(C)(C)C)cc4)cccc3c2CNC(=N)N)c(OC)c1OC] | ≤8.0 | — |
| Example 59 | 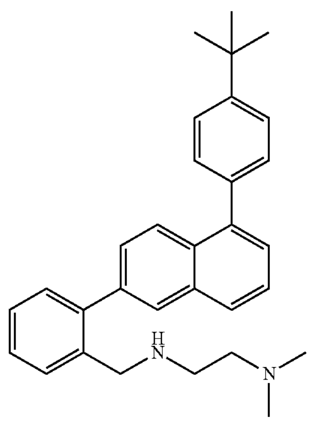 [SMILES: CN(C)CCNCc1ccccc1-c1ccc2c(-c3ccc(C(C)(C)C)cc3)cccc2c1] | ≤8.0 | ≤8.0 |
| Example 60 | 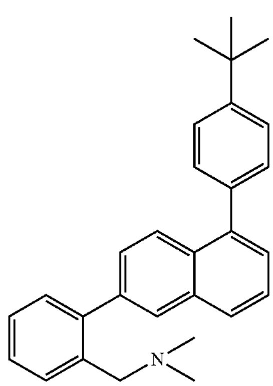 [SMILES: CN(C)Cc1ccccc1-c1ccc2c(-c3ccc(C(C)(C)C)cc3)cccc2c1] | 32.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
| --- | --- | --- | --- |
| Example 61 | 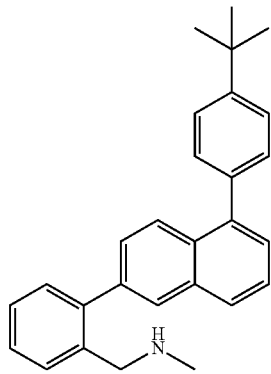 | ≤8.0 | ≤8.0 |
| Example 62 | 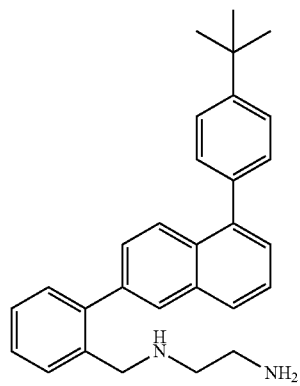 [SMILES: CC(C)(C)c1ccc(-c2cccc3cc(-c4ccccc4CNCCN)ccc23)cc1] | ≤8.0 | ≤8.0 |
| Example 63 | 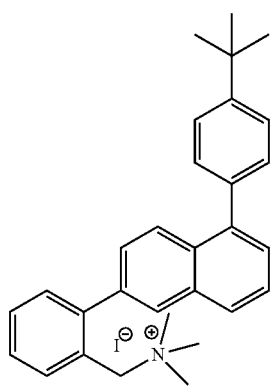 [SMILES: CC(C)(C)c1ccc(-c2cccc3cc(-c4ccccc4C[N+](C)(C)C)ccc23)cc1 ; [I-]] | ≤8.0 | ≤8.0 |

TABLE 1-continued
Minimal Inhibitory Concentrations against MSSA for representative compounds of the Invention
| Example | Structure | MIC vs MSSA (ug/ml) | MIC vs MRSA (ug/ml) |
|---|---|---|---|
| Example 65 | 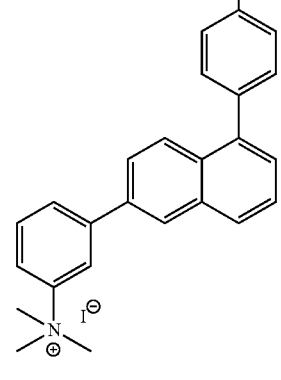 | ≤8.0 | — |
| Example 67 | 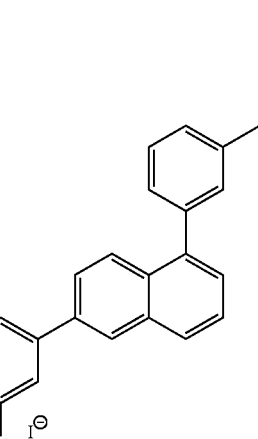 | ≤8.0 | — |
| Example 69 | 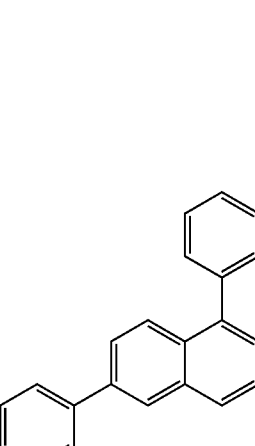 | ≤8.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
|---|---|---|---|
| Example 70 | 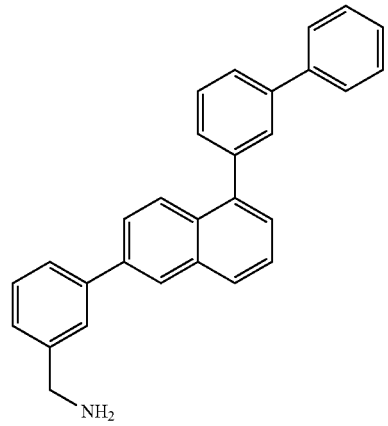 [SMILES: NCc1cccc(-c2ccc3c(-c4cccc(-c5ccccc5)c4)cccc3c2)c1] | ≤8.0 | ≤8.0 |
| Example 71 | 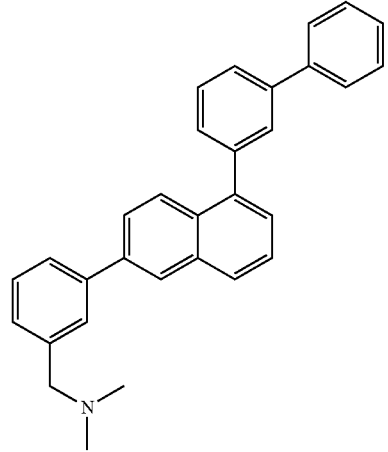 [SMILES: CN(C)Cc1cccc(-c2ccc3c(-c4cccc(-c5ccccc5)c4)cccc3c2)c1] | ≤8.0 | — |
| Example 72 | 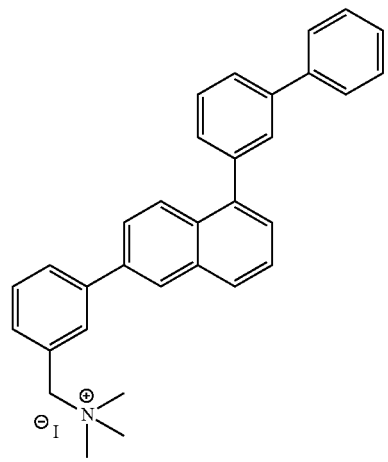 [SMILES: C[N+](C)(C)Cc1cccc(-c2ccc3c(-c4cccc(-c5ccccc5)c4)cccc3c2)c1 ; [I-]] | ≤8.0 | — |

TABLE 1-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 74 | (structure) | ≤8.0 | — |
| Example 76 | (structure) | ≤8.0 | — |
| Example 78 | (structure) | ≤8.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
|---|---|---|---|
| Example 80 | 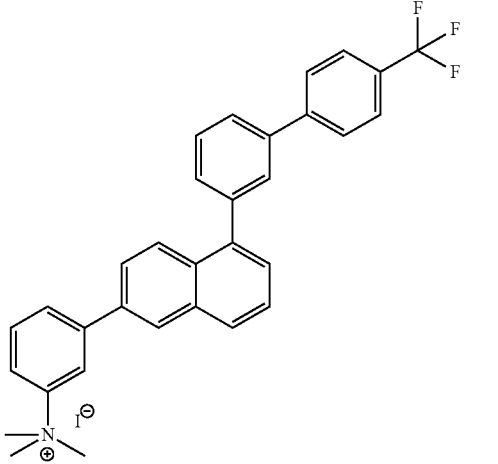 [SMILES: C[N+](C)(C)c1cccc(-c2ccc3c(-c4cccc(-c5ccc(C(F)(F)F)cc5)c4)cccc3c2)c1 ; [I-]] | ≤8.0 | — |
| Example 82 | 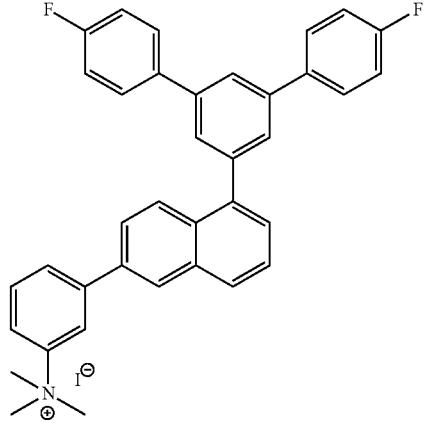 [SMILES: C[N+](C)(C)c1cccc(-c2ccc3c(-c4cc(-c5ccc(F)cc5)cc(-c5ccc(F)cc5)c4)cccc3c2)c1 ; [I-]] | ≤8.0 | — |
| Example 84 | 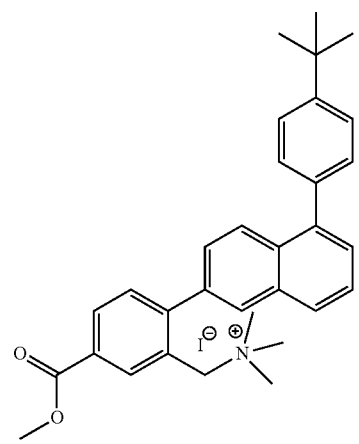 [SMILES: COC(=O)c1ccc(-c2ccc3c(-c4ccc(C(C)(C)C)cc4)cccc3c2)c(C[N+](C)(C)C)c1 ; [I-]] | ≤8.0 | — |

TABLE 1-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 85 | 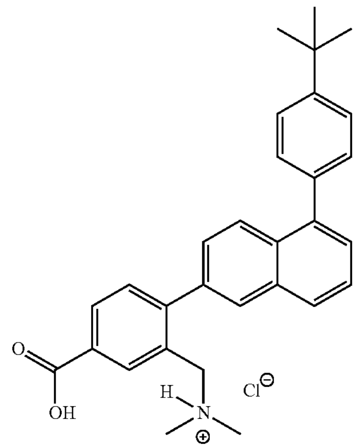 [SMILES: C[NH+](C)Cc1cc(C(=O)O)ccc1-c1ccc2c(-c3ccc(C(C)(C)C)cc3)cccc2c1 ; [Cl-]] | ≤8.0 | — |
| Example 86 | 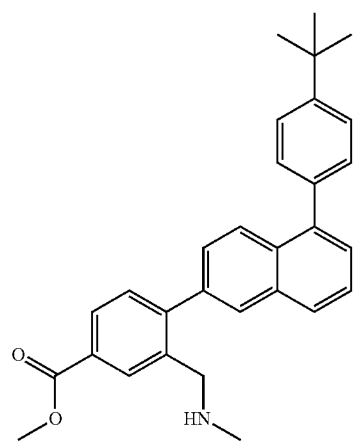 [SMILES: CNCc1cc(C(=O)OC)ccc1-c1ccc2c(-c3ccc(C(C)(C)C)cc3)cccc2c1] | ≤8.0 | — |
| Example 87 | 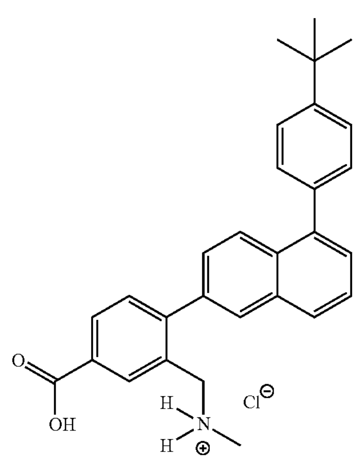 [SMILES: C[NH2+]Cc1cc(C(=O)O)ccc1-c1ccc2c(-c3ccc(C(C)(C)C)cc3)cccc2c1 ; [Cl-]] | ≤8.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
|---|---|---|---|
| Example 88 | 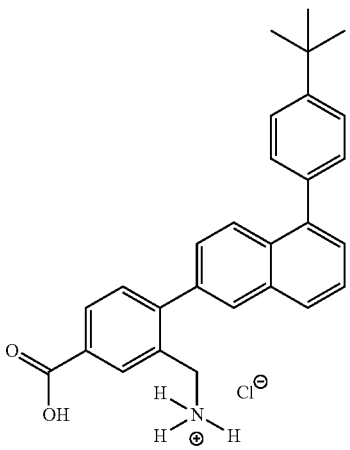 | >64.0 | — |
| Example 89 | 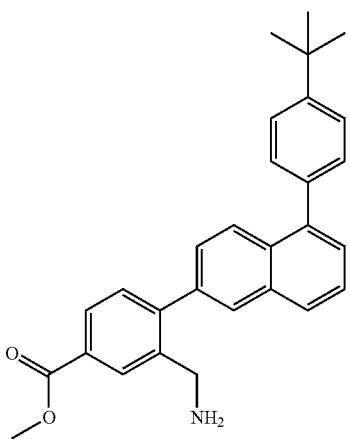 | ≤8.0 | — |
| Example 93 | 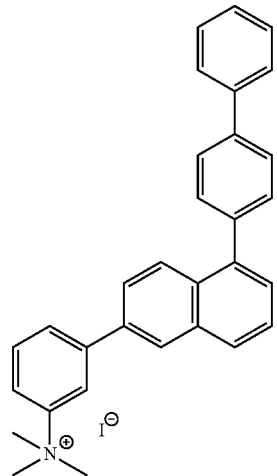 [SMILES: C[N+](C)(C)c1cccc(-c2ccc3c(-c4ccc(-c5ccccc5)cc4)cccc3c2)c1 ; [I-]] | ≤8.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
|---------|-----------|---------------------|---------------------|
| Example 95 | 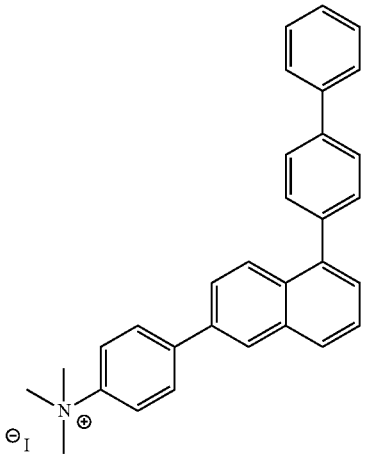 [SMILES: [I-] ; C[N+](C)(C)c1ccc(-c2ccc3c(-c4ccc(-c5ccccc5)cc4)cccc3c2)cc1] | ≤8.0 | — |
| Example 97 | 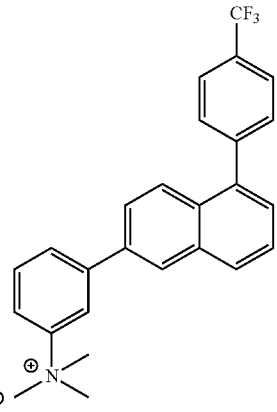 | ≤8.0 | — |
| Example 100 | 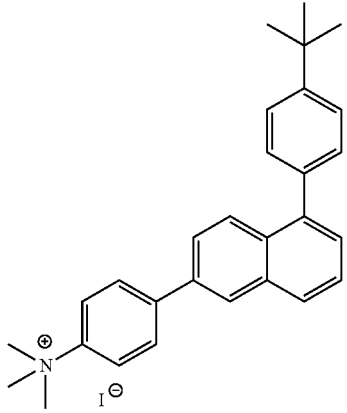 [SMILES: CC(C)(C)c1ccc(-c2cccc3cc(-c4ccc([N+](C)(C)C)cc4)ccc23)cc1 ; [I-]] | ≤8.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
| --- | --- | --- | --- |
| Example 101 | 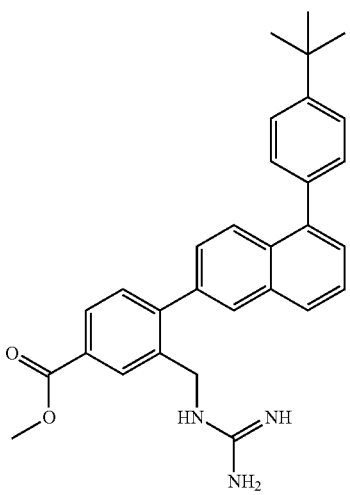 [SMILES: COC(=O)c1ccc(-c2ccc3c(-c4ccc(C(C)(C)C)cc4)cccc3c2)c(CNC(=N)N)c1] | ≤8.0 | — |
| Example 102 | 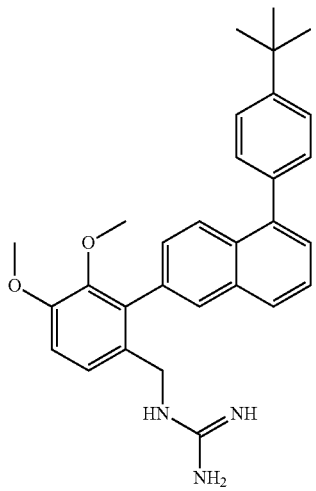 [SMILES: COc1ccc(CNC(=N)N)c(-c2ccc3c(-c4ccc(C(C)(C)C)cc4)cccc3c2)c1OC] | ≤8.0 | — |
| Example 103 | 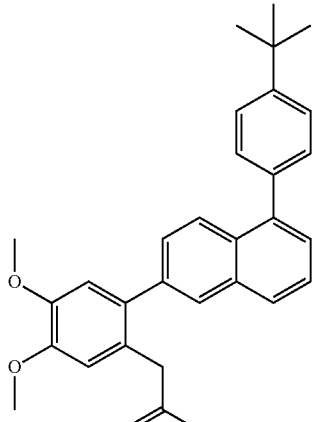 | ≤8.0 | — |

TABLE 1-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 104 | 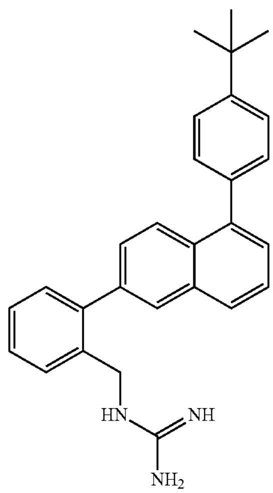 [SMILES: CC(C)(C)c1ccc(-c2cccc3cc(-c4ccccc4CNC(=N)N)ccc23)cc1] | ≤8.0 | — |
| Example 105 | 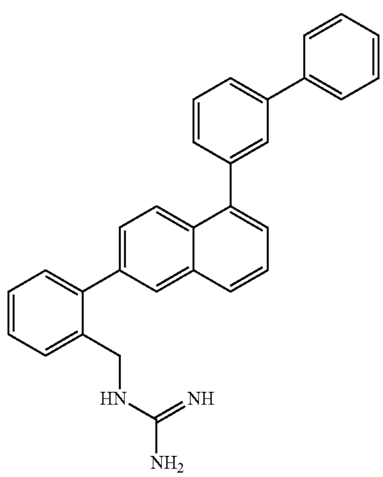 [SMILES: N=C(N)NCc1ccccc1-c1ccc2c(-c3cccc(-c4ccccc4)c3)cccc2c1] | ≤8.0 | — |
| Example 106 | 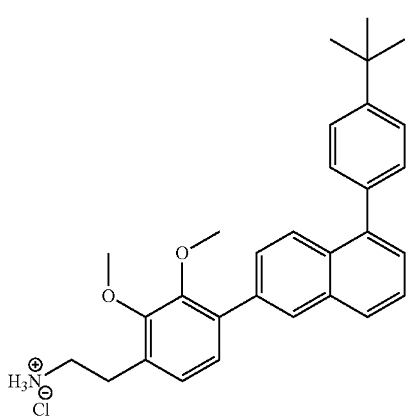 [SMILES: COc1c(CC[NH3+])ccc(-c2ccc3c(-c4ccc(C(C)(C)C)cc4)cccc3c2)c1OC ; [Cl-]] | ≤8.0 | — |

TABLE 1-continued
Minimal Inhibitory Concentrations against MSSA for representative compounds of the Invention
| Example | Structure | MIC vs MSSA (ug/ml) | MIC vs MRSA (ug/ml) |
|---|---|---|---|
| Example 107 | 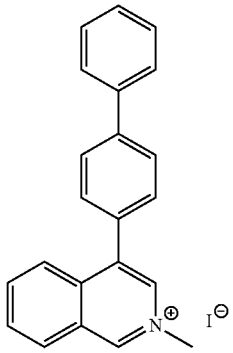 [SMILES: C[n+]1cc(-c2ccc(-c3ccccc3)cc2)c2ccccc2c1 ; [I-]] | ≤8.0 | — |
| Example 112 | 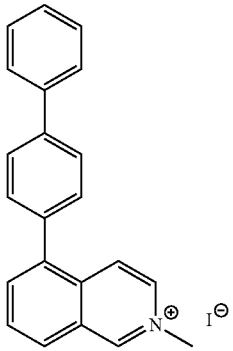 [SMILES: C[n+]1ccc2c(-c3ccc(-c4ccccc4)cc3)cccc2c1 ; [I-]] | ≤8.0 | 32 |
| Example 114 | 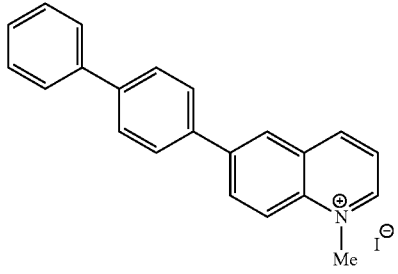 [SMILES: C[n+]1cccc2cc(-c3ccc(-c4ccccc4)cc3)ccc21 ; [I-]] | ≤8.0 | ≤8.0 |
| Example 116 | 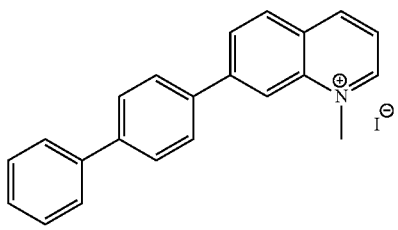 [SMILES: C[n+]1cccc2ccc(-c3ccc(-c4ccccc4)cc3)cc21 ; [I-]] | ≤8.0 | 16 |

TABLE 1-continued

Minimal Inhibitory Concentrations against MSSA for representative compounds of the Invention

| Example | Structure | MIC vs MSSA (ug/ml) | MIC vs MRSA (ug/ml) |
|---|---|---|---|
| Example 118 | 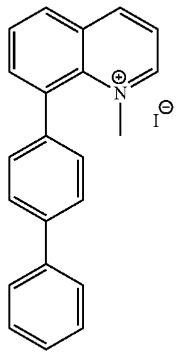 [SMILES: C[n+]1cccc2cccc(-c3ccc(-c4ccccc4)cc3)c21 ; [I-]] | 16.0 | — |
| Example 120 | 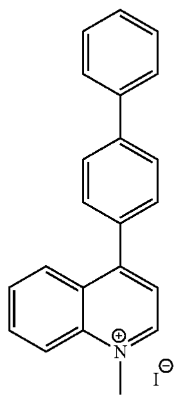 [SMILES: C[n+]1ccc(-c2ccc(-c3ccccc3)cc2)c2ccccc21 ; [I-]] | ≤8.0 | >32 |
| Example 122 | 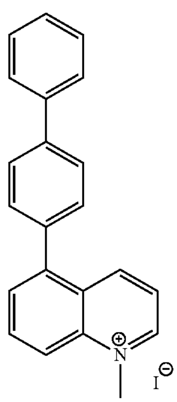 [SMILES: C[n+]1cccc2c(-c3ccc(-c4ccccc4)cc3)cccc21 ; [I-]] | ≤8.0 | — |
| Comparative Example A | 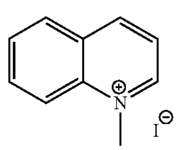 | >64.0 | — |
| Comparative Example B | 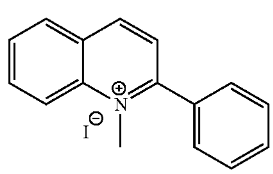 [SMILES: C[n+]1c(-c2ccccc2)ccc2ccccc21 ; [I-]] | >64.0 | — |

The antibacterial activity of a compound of the invention can be determined using a method like Test C described below.

Test C. Planktonic (Free-Living) Antibacterial Assay.

Planktonic antibacterial activity can be determined using a broth microdilution assay in which log-phase bacteria are grown at 37° C. in appropriate medium containing two-fold serial dilutions of a compound to yield a final concentration ranging from 256 to 0.1 µg/ml. For determination of minimal inhibitory concentration (MIC) values, bacterial growth is monitored after 24 to 48 hours by measuring optical density at 600 nm. MIC values reflect the minimal compound concentrations at which bacterial growth is completely inhibited. The minimal inhibitory concentration against methicillin-sensitive *Staphylococcus aureus* (MSSA) for each of the following representative compounds of the invention was determined to be less than 32 µg/ml.

TABLE 2

Inhibition of *S. aureus* FtsZ Polymerization and GTPase Activity by Representative Compounds of the Invention

| Compound | [1]IC$_{50}$ (µg/mL) |
| --- | --- |
| Example 19 | <50 |
| Example 41 | <50 |
| Example 42 | <50 |
| Example 63 | <50 |
| Example 104 | <50 |
| Example 112 | <50 |
| Example 114 | <50 |
| Example 120 | <50 |

[1]IC$_{50}$ reflects the compound concentration at which FtsZ polymerization and/or GTPase activity is inhibited by 50%.

Representative compounds of the invention were also tested against methicillin-resistant *Staphylococcus aureus*, vancomycin-resistant *Enterococcus faecalis* and *Enterococcus faecium* (VRE), vancomycin-sensitive *Enterococcus faecalis* and *Enterococcus faecium* (VSE). *Streptococcus pyogenes, Streptococcus agalactiae, Clostridium difficile, Propionibacterium acnes, Bacillus subtilis*, and *Escherichia coli*, and they were found to have significant antibacterial activity.

The invention will now be illustrated by the following non-limiting examples.

EXAMPLES

The following general methods A-C can be used to prepare compounds of the invention.

General Methods of Preparation

A. Suzuki Reaction

A mixture of either the aryl triflate or aryl bromide (commercially available), appropriate boronic acid (2 equiv.), Cs$_2$CO$_3$, Pd (PPh$_3$)$_2$Cl$_2$ (5 mol %) in dioxane was microwaved for 15 minutes. The crude reaction mixture was diluted with ethyl acetate and was filtered through a plug of Celite and silica gel. The filtrate was concentrated under vacuo and was subjected to flash column chromatography to afford the desired product.

B. Quaternization

The starting material (approx. 100 mg-150 mg) was dissolved in methyl iodide (1.5 ml-2 ml) in a sealed tube and was heated at 80° C. for 15-30 minutes. The resulting solid was then diluted with acetone, filtered and washed with diethyl ether twice to afford the quaternary salts as pure solids.

C. Triflation Reaction

The required hydroxyl compound was dissolved in dichloromethane to which added 2.0 equivalent of triethylamine and 1.5 equivalent of Tf$_2$O at −78° C. After the reaction is completed, the reaction mixture was diluted with more methylene chloride which was then washed with saturated sodium bicarbonate and brine. The crude mixture was then purified by flash column chromatography to afford the product.

Example 1

Preparation of Compound

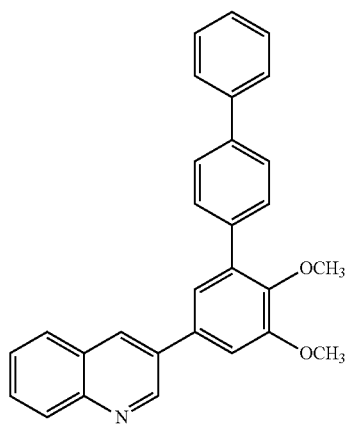 [SMILES: COc1cc(-c2cnc3ccccc3c2)cc(-c2ccc(-c3ccccc3)cc2)c1OC]

To a nitrogen-flushed mixture of 2,3-dimethoxy-5-(quinolin-3-yl)phenyl trifluoroethanesulfonate (0.10 g, 0.24 mmol), bi-phenylboronic acid (72 mg, 0.36 mmol) and potassium carbonate (83 mg, 0.60 mmol) in a mixture of acetonitrile (8 mL) and water (2 mL) at room temperature under nitrogen were added palladium acetate (3 mg, 0.013 mmol) and Xphos (13 mg, 0.027 mmol), the resultant mixture was heated at 90° C. for 2 h. It was dried over MgSO$_4$, filtered and concentrated to a crude product. Purification by flash chromatography (SiO$_2$, EtOAc/hexane 0-50%) gave the desired product as a pale oil (46 mg, 54%). $^1$H NMR (CDCl$_3$, 400 MHz) δ: 3.65 (s, 3H), 3.97 (s, 3H), 6.91 (s, 1H), 7.28 (m, 2H), 7.40 (m, 2H), 7.52 (t, J=8.0 Hz, 1H), 7.59-7.68 (m, 7H), 7.82 (d, J=8.0 Hz, 1H), 8.08 (d, J=8.0 Hz, 1H), 8.25 (s, 1H), 9.14 (s, 1H).

The requisite intermediate for the preparation of this compound was prepared as follows.

a. Preparation of Compound

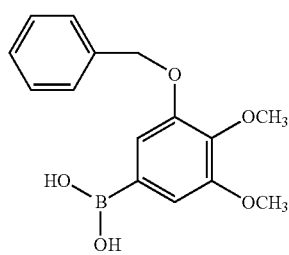 [SMILES: COc1cc(B(O)O)cc(OCc2ccccc2)c1OC]

To a nitrogen-flushed mixture of triisopropylborate (4.6 mL, 20 mmol), (3-(benzyloxy)-4,5-dimethoxy)bromobenzene (5.20 g, 16.1 mmol) in a mixture of THF (40 mL) and toluene (160 mL) at −78° C. under nitrogen was added dropwise n-BuLi (1.0 M/THF, 13 mL) over 25 min. The resultant mixture was stirred at −78° C. for 1 h, slowly warmed up to −50° C. and quenched with 2N HCl (20 mL). The reaction mixture was stirred at room temperature for 1 h. The organic layer was sepatated and diluted with EtOAc (100 mL), washed with brine twice and dried over $Na_2SO_4$, filtered and concentrated. The crude oil slowly solidified and treated with CH3CN to give a soft solid as the desired product. The mother liquid was purified with flash column ($SiO_2$, $MeOH/CH_2Cl_2$, 0-5%) to give the desired product. The total yield of combined product was 3.52 g (75%). $^1H$ NMR ($CDCl_3$, 400 MHz) δ: 3.97 (s, 6H), 5.25 (s, 2H), 7.31.

b. Preparation of Compound

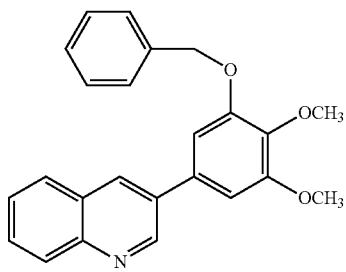 [SMILES: COc1cc(-c2cnc3ccccc3c2)cc(OCc2ccccc2)c1OC]

To a nitrogen-flushed mixture of 3-bromoquinoline (0.50 mL, 3.7 mmol), (3-(benzyloxy)-4,5-dimethoxyphenyl)boronic acid (1.26 g, 4.37 mmol) and potassium carbonate (2.0 g, 14.5 mmol) in a mixture of dioxane (25 mL) and water (5 mL) at room temperature under nitrogen was added tetrakis (triphenylphosphine)palladium (0.20 g, 0.17 mmol), the resultant mixture was heated at 100° C. for 4 h. It was dried over $MgSO_4$, filtered and concentrated and purified with flash column ($SiO_2$, EtOAc/hexane 10-30%) to give the desired product as a pale oil (1.33 g, 96%). $^1H$ NMR ($CDCl_3$, 400 MHz) δ: 3.96 (s, 3H), 3.97 (s, 3H), 5.25 (s, 2H), 6.90 (dd, J=12.0 Hz, 4.0 Hz, 2H), 7.33 (m, 1H), 7.38-7.41 (m, 2H), 7.49 m, 2H), 7.58 (m, 1H), 7.87 (d, J=8.0 Hz, 1H), 8.13 (d, J=8.0 Hz, 1H), 8.19 (s, 1H), 9.07 (m, 1H).

c. Preparation of Compound

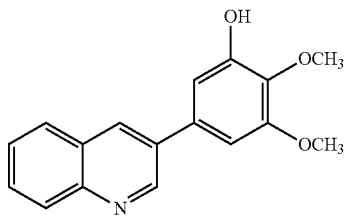 [SMILES: COc1cc(-c2cnc3ccccc3c2)cc(O)c1OC]

A mixture of 3-(3-(benzyloxy)-45-dimethoxyphenyl) quinoline (1.30 g, 3.5 mmol) and 10% palladium on carbon (0.39 g, 30% w/w) was stirred at room temperature under 1 atm of hydrogen for 2 days. The catalyst was filtered off and the filtrate concentrated to an oil. Purification by flash chromatography ($SiO_2$, EtOAc/hexane 10-70%) gave the desired product as a white solid (0.97 g, 99%). $^1H$ NMR ($CDCl_3$, 400 MHz) δ: 3.98 (s, 6H), 6.03 (s, 1H), 6.79 (s, 1H), 6.96 (s, 1H), 7.58 (t, J=8.0 Hz, 1H), 7.70-7.74 (m, 1H), 7.87 (d, J=8.0 Hz, 1H), 8.13 (d, J=8.0 Hz, 1H), 8.25 (s, 1H), 9.14 (s, 1H).

d. Preparation of Compound

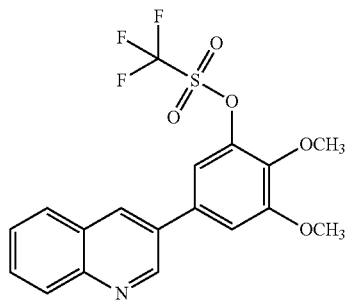 [SMILES: COc1cc(-c2cnc3ccccc3c2)cc(OS(=O)(=O)C(F)(F)F)c1OC]

To a solution of 2,3-dimethoxy-5-(quinolin-3-yl)phenol (0.48 g, 1.7 mmol) and triethylamine (0.47 mL, 3.8 mmol) in $CH_2Cl_2$ (20 mL) at −78° C. under nitrogen was added triflate anhydride (0.36 mL, 2.1 mmol) slowly, the resultant mixture was stirred at −78° C. and warmed up to 0° C. The reaction was diluted with methylenechloride to 50 mL and washed with aq. $NaHCO_3$ solution. The organic solution was dried over $MgSO_4$ and concentrated to an oil. Purification by flash chromatography ($SiO_2$, EtOAc/hexane 10-50%) gave the desired product as an oil (0.26 g, 37%). $^1H$ NMR ($CDCl_3$, 400 MHz) δ: 3.95 (s, 3H), 3.98 (s, 3H), 7.08-7.15 (m, 1H), 7.20 (s, 1H), 7.59 (t, J=8.0 Hz, 1H) 7.73 (t, J=8.0 Hz, 1H), 7.86 (d, J=8.0 Hz, 1H), 8.17 (d, J=8.0 Hz, 1H), 8.24 (s, 1H), 9.05 (s, 1H).

Example 2

Preparation of Compound

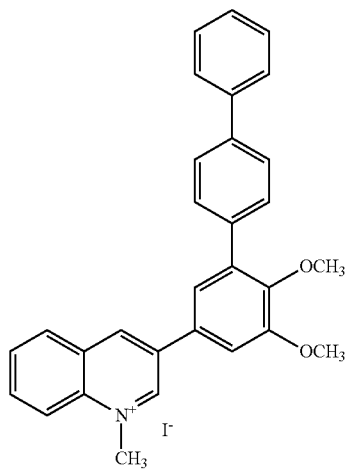 [SMILES: COc1cc(-c2cc3ccccc3[n+](C)c2)cc(-c2ccc(-c3ccccc3)cc2)c1OC ; [I-]]

A mixture of 3-(4'-fluoro-5,6-dimethoxy-[1,1'-biphenyl]-3-yl)quinoline (45 mg, 0.13 mmol) in iodomethane (1 mL) was heated at 60° C. under nitrogen for 15 h. The reaction mixture was concentrated to dryness. The residue was treated with $Et_2O$. A yellow solid was collected to give the desired product (51 mg, 80%). $^1H$ NMR (DMSO, 400 MHz) δ: 3.77 (s, 3H), 4.12 (s, 3H), 4.78 (s, 3H), 7.46 (m, 1H), 7.57 (t, J=8.0

Hz, 2H), 7.73-7.88 (m, 8H), 8.15 (t, J=8.0 Hz, 1H), 8.33 (t, J=8.0 Hz, 1H), 8.55 (dd, J=12.0 Hz, 8.0 Hz, 2H), 9.77 (s, 1H), 10.1 (s, 1H).

Example 3

Preparation of Compound

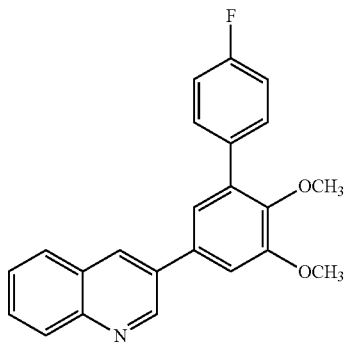 [SMILES: COc1cc(-c2cnc3ccccc3c2)cc(-c2ccc(F)cc2)c1OC]

To a nitrogen-flushed mixture of 2,3-dimethoxy-5-(quinolin-3-yl)phenyl trifluoromethanesulfonate (0.12 g, 0.29 mmol), 4-fluorophenylboronic acid (61 mg, 0.44 mmol) and potassium carbonate (0.1 g, 0.72 mmol) in a mixture of acetonitrile (12 mL) and water (2 mL) at room temperature under nitrogen were added palladium acetate (3 mg, 0.013 mmol) and Xphos (13 mg, 0.027 mmol), the resultant mixture was heated at 90° C. for 2 h. It was dried over $MgSO_4$, filtered and concentrated to a crude product. Purification by flash chromatography ($SiO_2$, EtOAc/hexane 0-50%) gave the desired product as a pale oil (76 mg, 88%). $^1$H NMR ($CDCl_3$, 400 MHz) δ: 3.59 (s, 3H), 3.96 (s, 3H), 7.07 (t, J=8.0 Hz, 2H), 7.16 (m, 2H), 7.50-7.54 (m, 3H), 7.81 (m, 1H), 8.07 (d, J=8.0 Hz, 1H), 8.22 (s, 1H), 9.11 (s, 1H).

Example 4

Preparation of Compound

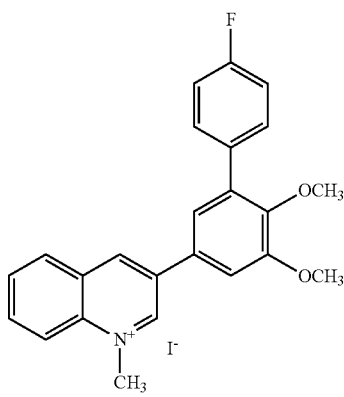 [SMILES: COc1cc(-c2cc3ccccc3[n+](C)c2)cc(-c2ccc(F)cc2)c1OC ; [I-]]

The compound of Example 3 (70 mg, 0.24 mmol) in iodomethane (1.5 mL) was heated at 60° C. under nitrogen for overnight. The reaction mixture was concentrated to dryness. The residue was treated with $Et_2O$. A yellow solid was collected to give the desired product (79 mg, 77%). $^1$H NMR (DMSO, 400 MHz) δ: 3.72 (s, 3H), 4.10 (s, 3H), 4.77 (s, 3H), 7.41 (t, J=8.0 Hz, 2H), 7.68-7.78 (m, 3H), 7.79 (s, 1H), 8.15 (t, J=8.0 Hz, 1H), 8.34 (t, J=8.0 Hz, 1H), 8.52 (d, J=8.0 Hz, 1H), 8.58 (d, J=8.0 Hz, 1H), 9.75 (s, 1H), 10.05 (s, 1H).

Example 5

Preparation of Compound

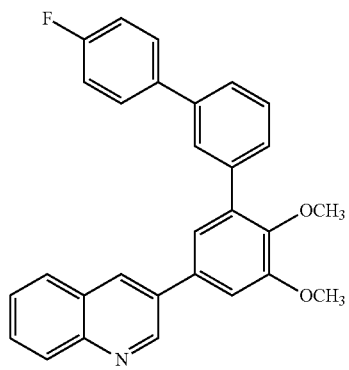 [SMILES: COc1cc(-c2cnc3ccccc3c2)cc(-c2cccc(-c3ccc(F)cc3)c2)c1OC]

To a nitrogen-flushed mixture of Intermediate d in Example 1,2,3-dimethoxy-5-(quinolin-3-yl)phenyl trifluoromethanesulfonate, (0.12 g, 0.29 mmol), 3(4-fluorophenyl) phenylboronic acid (0.10 g, 0.46 mmol) and potassium carbonate (0.1 g, 0.72 mmol) in a mixture of acetonitrile (8.5 mL) and water (1.5 mL) at room temperature under nitrogen were added palladium acetate (5 mg, 0.022 mmol) and Xphos (20 mg, 0.042 mmol), the resultant mixture was heated at 90° C. for 2 h. It was dried over $MgSO_4$, filtered and concentrated to a crude product. Purification by flash chromatography ($SiO_2$, EtOAc/hexane 10-50%) gave the desired product as a pale oil (16 mg, 13%). $^1$H NMR ($CDCl_3$, 400 MHz) δ: 3.59 (s, 3H), 3.96 (s, 3H), 7.07 (t, J=8.0 Hz, 2H), 7.17 (m, 2H), 7.50-7.54 (m, 3H), 7.65 (t, J=8.0 Hz, 1H), 7.81 (d, J=8.0 Hz, 1H), 8.07 (d, J=8.0 Hz, 1H), 8.22 (d, J=4.0 Hz, 1H), 9.1 (s, 1H).

Example 6

Preparation of Compound

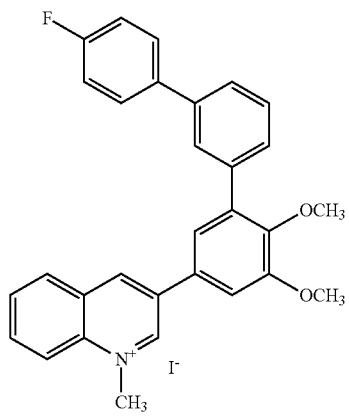 [SMILES: COc1cc(-c2cc3ccccc3[n+](C)c2)cc(-c2cccc(-c3ccc(F)cc3)c2)c1OC ; [I-]]

The compound of Example 5 (15 mg, 0.03 mmol) in iodomethane (0.35 mL) was heated at 60° C. under nitrogen for overnight. The reaction mixture was concentrated to dryness. The residue was treated with Et$_2$O. A yellow solid was collected to give the desired product (20 mg, 100%). $^1$H NMR (CDCl$_3$, 400 MHz) δ: 3.71 (s, 3H), 4.06 (s, 3H), 4.71 (s, 3H), 7.32 (t, J=8.0 Hz, 2H), 7.59 (d, J=4.0 Hz, 2H), 7.70-7.81 (m, 5H), 8.08 (t, J=8.0 Hz, 1H), 8.26 (t, J=8.0 Hz, 1H), 8.48 (dd, J=24.0 Hz, 8.0 Hz, 2H), 9.7 (s, 1H), 10.0 (s, 1H).

Example 7

Preparation of Compound

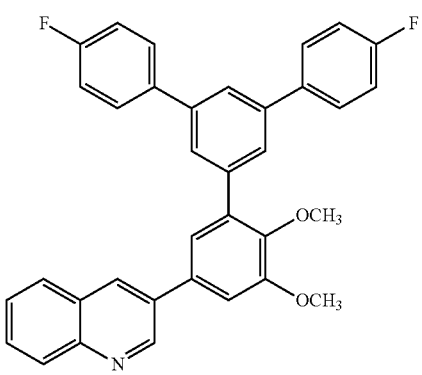 [SMILES: COc1cc(-c2cnc3ccccc3c2)cc(-c2cc(-c3ccc(F)cc3)cc(-c3ccc(F)cc3)c2)c1OC]

To a nitrogen-flushed mixture of Intermediate d in Example 1 (0.12 g, 0.29 mmol), bis-3,5-(4-fluorophenyl)phenylboronic acid (0.13 g, 0.42 mmol) and potassium carbonate (0.1 g, 0.72 mmol) in a mixture of acetonitrile (8.5 mL) and water (1.5 mL) at room temperature under nitrogen were added palladium acetate (5 mg, 0.022 mmol) and Xphos (20 mg, 0.042 mmol), the resultant mixture was heated at 90° C. for 2 h. It was dried over MgSO$_4$, filtered and concentrated to a crude product. Purification by flash chromatography (SiO$_2$, EtOAc/hexane 10-50%) gave the desired product as a pale oil (108 mg, 70%). $^1$H NMR (CDCl$_3$, 400 MHz) δ: 3.79 (s, 3H), 4.08 (s, 3H), 7.18 (t, J=8.0 Hz, 4H), 7.29 (m, 3H), 7.4 (s, 1H), 7.66-7.70 (m, 4H), 7.75-7.80 (m, 4H), 7.94 (d, J=8.0 Hz, 1H), 8.26 (d, J=8.0 Hz, 1H), 8.43 (s, 1H), 9.25 (s, 1H).

Example 8

Preparation of Compound

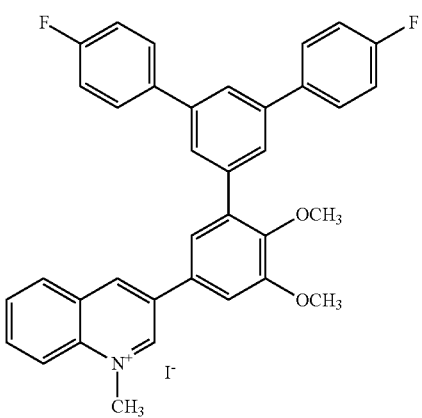 [SMILES: COc1cc(-c2cc3ccccc3[n+](C)c2)cc(-c2cc(-c3ccc(F)cc3)cc(-c3ccc(F)cc3)c2)c1OC ; [I-]]

A mixture of the compound of Example 7 (0.1 g, 0.19 mmol) in iodomethane (1 mL) was heated at 60° C. under nitrogen for overnight. The reaction mixture was concentrated to dryness. The residue was treated with Et$_2$O. A yellow solid was collected to give the desired product (108 mg, 86%). $^1$H NMR (DMSO, 400 MHz) δ: 3.76 (s, 3H), 4.07 (s, 3H), 4.71 (s, 3H), 7.34 (t, J=8.0 Hz, 4H), 7.79 (d, J=8.0 Hz, 4H), 7.88-7.92 (m, 4H), 8.08 (t, J=8.0 Hz, 1H), 8.48 (dd, J=24.0 Hz, 8.0 Hz, 2H), 9.71 (s, 1H), 10.01 (s, 1H).

Example 9

Preparation of Compound

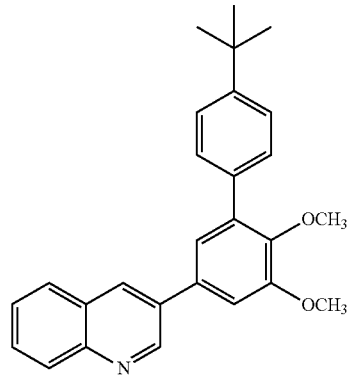 [SMILES: COc1cc(-c2cnc3ccccc3c2)cc(-c2ccc(C(C)(C)C)cc2)c1OC]

To a nitrogen-flushed mixture of Intermediate d in Example 1 (60 mg, 0.15 mmol), 4-t-butylphenylboronic acid (46 mg, 0.26 mmol) and potassium carbonate (75 mg, 0.54 mmol) in a mixture of acetonitrile (6 mL) and water (1.5 mL) at room temperature under nitrogen were added palladium acetate (7.5 mg, 0.03 mmol) and Xphos (30 mg, 0.06 mmol), the resultant mixture was heated at 90° C. for 2 h. It was dried over MgSO$_4$, filtered and concentrated to a crude product. Purification by flash chromatography (SiO$_2$, EtOAc/hexane 10-50%) gave the desired product as a pale oil (35 mg, 60%). $^1$H NMR (CDCl$_3$, 400 MHz) δ: 3.69 (s, 3H), 4.02 (s, 3H), 6.9 (s, 4H), 7.3 (m, 1H), 7.45 (m, 1H), 7.57 (d, J=8.0 Hz, 1H), 7.7 (m, 1H), 7.87 (d, J=8.0 Hz, 1H), 8.14 (d, J=8.0 Hz, 1H), 8.29 (s, 1H), 9.20 (s, 1H).

Example 10

Preparation of Compound

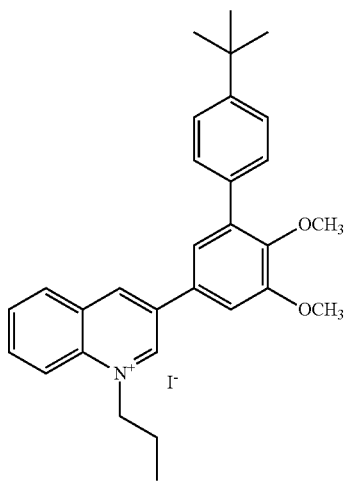 [SMILES: CCC[n+]1cc(-c2cc(OC)c(OC)c(-c3ccc(C(C)(C)C)cc3)c2)cc2ccccc21 ; [I-]]

A mixture of the compound of Example 9 (20 mg, 0.03 mmol) in 1-iodopropane (1 mL) was heated at 60° C. under nitrogen for overnight. The reaction mixture was concentrated to dryness. The residue was treated with Et₂O. A yellow solid was collected to give the desired product (13 mg, 47%). ¹H NMR (DMSO, 400 MHz) δ: 1.03 (t, J=8.0 Hz, 3H), 1.35 (s, 9H), 2.06 (qt, 2H), 3.68 (s, 3H), 4.04 (s, 3H), 5.09 (t, J=8.0 Hz, 2H), 7.48 (m, 3H), 7.61 (s, 1H), 7.70 (s, 1H), 8.07 (t, J=8.0 Hz, 1H), 8.25 (t, J=8.0 Hz, 1H), 8.46 (d, J=8.0 Hz, 1H), 8.64 (d, J=8.0 Hz, 1H), 9.70 (s, 1H), 10.00 (s, 1H).

Example 11

Preparation of Compound

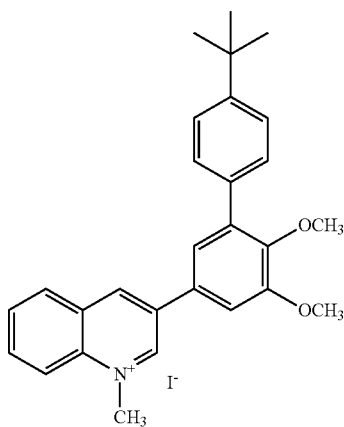 [SMILES: COc1cc(-c2cc3ccccc3[n+](C)c2)cc(-c2ccc(C(C)(C)C)cc2)c1OC ; [I-]]

A mixture of the compound of Example 9 (10 mg, 0.03 mmol) in iodomethane (0.8 mL) was heated at 60° C. under nitrogen for overnight. The reaction mixture was concentrated to dryness. The residue was treated with Et₂O. A yellow solid was collected to give the desired product (8.0 mg, 59%). ¹H NMR (DMSO, 400 MHz) δ: 1.35 (s, 9H), 3.68 (s, 3H), 4.04 (s, 3H), 4.71 (s, 3H), 7.51 (s, 4H), 7.61 (s, 1H), 7.70 (s, 1H), 8.08 (t, J=8.0 Hz, 1H), 8.26 (t, J=8.0 Hz, 1H), 8.48 (dd, J=16.0 Hz, 2H), 9.68 (s, 1H), 9.99 (s, 1H).

Example 12

Preparation of Compound

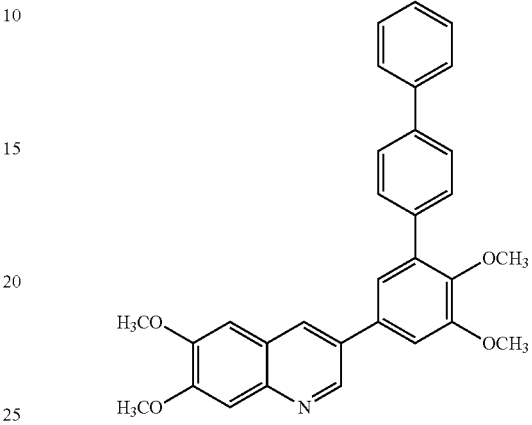

To a nitrogen-flushed mixture of 5-(6,7-dimethoxyquinolin-3-yl)-2,3-dimethoxyphenyl trifluoromethanesulfonate (50 mg, 0.11 mmol), 4-biphenylboronic acid (30 mg, 0.15 mmol) and potassium carbonate (35 mg, 0.26 mmol) in a mixture of dioxane (6 mL) and water (1 mL) at room temperature under nitrogen were added palladium acetate (5 mg, 0.02 mmol) and Xphos (21 mg, 0.04 mmol), the resultant mixture was heated at 95° C. for 3 h. It was dried over MgSO₄, filtered and concentrated to a crude product. Purification by flash chromatography (SiO₂, EtOAc/hexane 10-50%) gave the desired product SL-1-148 as a pale oil (28 mg, 55%). ¹H NMR (CDCl₃, 400 MHz) δ: 3.66 (s, 3H), 3.97 (s, 3H), 4.00 (s, 3H), 4.08 (s, 3H), 7.13 (d, J=16.0 Hz, 2H), 7.23 (m, 1H), 7.32 (m, 1H), 7.40 (m, 2H), 7.62 (m, 6H), 7.88 (s, 1H), 8.48 (s, 1H), 8.92 (s, 1H).

a. Preparation of Compound

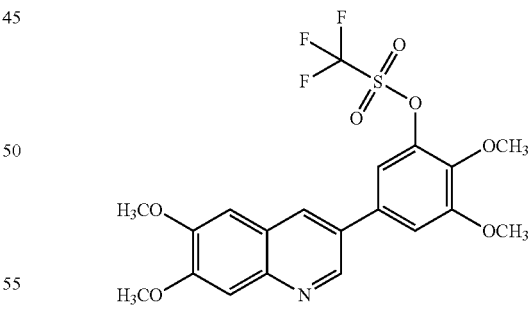

To a solution of 5-(6,7-dimethoxyquinolin-3-yl)-2,3-dimethoxyphenol (0.36 g, 1.1 mmol) and triethylamine (0.30 mL, 2.2 mmol) in CH₂Cl₂ (20 mL) at −78° C. under nitrogen was added triflate anhydride (0.26 mL, 1.54 mmol) slowly, the resultant mixture was stirred at −78° C. and warmed up to 0° C. The reaction was diluted with methylenechloride to 50 mL and washed with aq. NaHCO₃ solution. The organic solution was dried over MgSO₄ and concentrated to an oil. Purification by flash chromatography (SiO₂, EtOAc/hexane 10-60%) gave the desired product, as an oil (0.28 g, 56%). ¹H NMR (CDCl₃, 400 MHz) δ: 4.00 (s, 3H), 4.04 (s, 3H), 4.08 (s, 3H), 4.14 (s, 3H), 5.33 (s, 1H), 7.15 (s, 1H), 7.21 (s, 1H), 7.5 (s, 1H), 7.7 (s, 1H), 8.25 (s, 1H), 8.92 (s, 1H).

b. Preparation of Compound

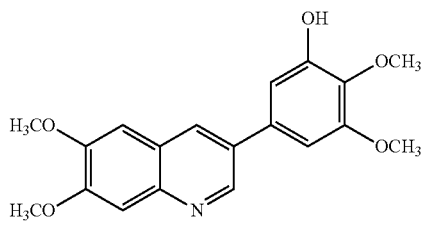 [SMILES: COc1cc2cc(-c3cc(O)c(OC)c(OC)c3)cnc2cc1OC]

A mixture of 3-(3-(benzyloxy)-,5-dimethoxyphenyl)-67-dimethoxyquinoline (0.58 g, 1.3 mmol), 0.5 mL of HOAc and 10% palladium on carbon (0.12 g, 30% w/w) was stirred at room temperature under 1 atm of hydrogen overnight, then at 60° C. for 4 h. The catalyst was filtered off and the filtrate was concentrated to an oil. Purification by flash chromatography (SiO₂, EtOAc/hexane 10-70%) gave the desired product as a white solid (0.36 g, 78%). ¹H NMR (CDCl₃, 400 MHz) δ: 3.97 (s, 3H), 3.99 (s, 3H), 4.04 (s, 3H), 4.06 (s, 3H), 6.00 (s, 1H), 6.75 (s, 1H), 6.95 (s, 1H), 7.11 (s, 1H), 7.46 (s, 1H), 8.11 (s, 1H), 8.94 (s, 1H).

c. Preparation of Compound

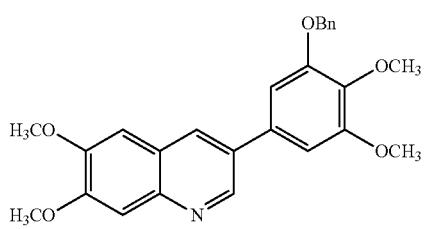 [SMILES: COc1cc2cc(-c3cc(OC)c(OC)c(OCc4ccccc4)c3)cnc2cc1OC]

To a nitrogen-flushed mixture of Intermediate a of Example 1 (0.64 g, 2.2 mmol), 3-bromo-6,7-dimethoxyquinoline (0.50 g, 1.9 mmol) and potassium carbonate (0.77 g, 5.6 mmol) in a mixture of dioxane (20 mL) and water (2 mL) at room temperature under nitrogen was added tetrakis(triphenylphosphine)palladium (0.11 g, 0.01 mmol), the resultant mixture was heated at 100° C. for 5 h. It was dried over MgSO₄, filtered and concentrated and purified with flash column (SiO₂, EtOAc/hexane 10-50%) to give the desired product as a pale oil (0.57 g, 99%). ¹H NMR (CDCl₃, 400 MHz) δ: 3.97 (s, 3H), 3.99 (s, 3H), 4.05 (s, 3H), 4.06 (s, 3H), 5.22 (s, 1H), 6.95 (dd, J=6.0 Hz, 3.0 Hz, 1H), 7.16 (s, 1H), 7.2-7.8 (m, 6H), 8.18 (s, 1H), 8.94 (s, 1H).

d. Preparation of Compound

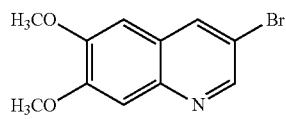

A mixture of 3,4-dimethoxylanline (1.0 g, 6.5 mmol), 2-bromomalonaldehyde (1.10 g, 7.28 mmol) and concentrated hydrochloric acid (3.0 mL, 18 mmol) in EtOH (12 mL) was heated at reflux under nitrogen for 12 h. All EtOH and HCl were removed under reduced pressure. The residue was basified with 4 N NaOH to pH 9, extracted with EtOAc (3×30 mL). The EtOAc solution was dried over MgSO₄, filtered and concentrated and purified with flash column (SiO₂, EtOAc/hexane 0-50%) to give the desired product as a pale oil (0.50 g, 29%). ¹H NMR (CDCl₃, 400 MHz) δ: 4.01 (s, 3H), 4.03 (s, 3H), 6.95 (s, 1H), 7.38 (s, 1H), 8.13 (s, 1H), 8.71 (s, 1H).

Example 13

Preparation of Compound

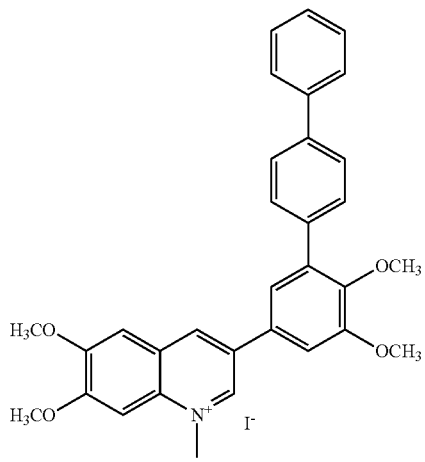 [SMILES: COc1cc2cc(-c3cc(OC)c(OC)c(-c4ccc(-c5ccccc5)cc4)c3)c[n+](C)c2cc1OC ; [I-]]

The compound of Example 12 (14 mg, 0.03 mmol) in iodomethane (0.5 mL) was heated at 60° C. under nitrogen for overnight. The reaction mixture was concentrated to dryness. The residue was treated with Et₂O. A yellow solid was collected to give the desired product (14 mg, 75%). ¹H NMR (DMSO, 400 MHz) δ: 3.69 (s, 3H), 4.04 (s, 6H), 4.17 (s, 3H), 4.64 (s, 3H), 7.40 (t, J=8.0 Hz, 1H), 7.51 (m, 2H), 7.59 (s, 1H), 7.67-7.81 (m, 9H), 9.45 (s, 1H), 9.68 (s, 1H).

Example 14

Preparation of Compound

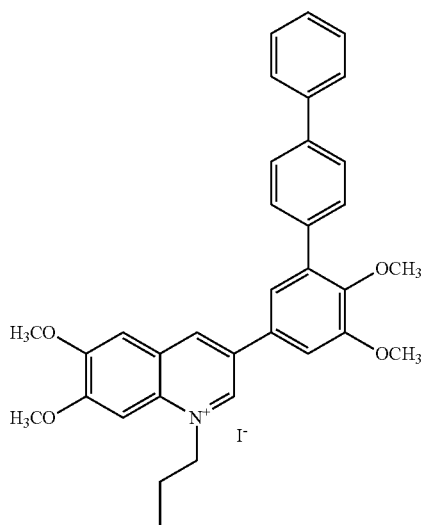 [SMILES: CCC[n+]1cc(-c2cc(OC)c(OC)c(-c3ccc(-c4ccccc4)cc3)c2)cc2cc(OC)c(OC)cc21 ; [I-]]

The compound of Example 12 (14 mg, 0.03 mmol) in 1-iodopropane (0.5 mL) was heated at 80° C. under nitrogen for 8 h. The reaction mixture was treated with Et₂O. A yellow solid was collected to give the desired product (12 mg, 64%). ¹H NMR (DMSO, 400 MHz) δ: 1.01 (t, J=8.0 Hz, 3H), 2.07 (m, 2H), 3.70 (s, 3H), 4.05 (s, 6H), 4.17 (s, 1H), 5.07 (t, J=8.0 Hz, 2H), 7.40 (m, 1H), 7.51 (m, 2H), 7.60 (s, 1H), 7.65-7.80 (m, 6H), 7.81 (d, J=8.0 Hz, 3H), 9.46 (s, 1H), 9.67 (s, 1H).

Example 15

Preparation of Compound

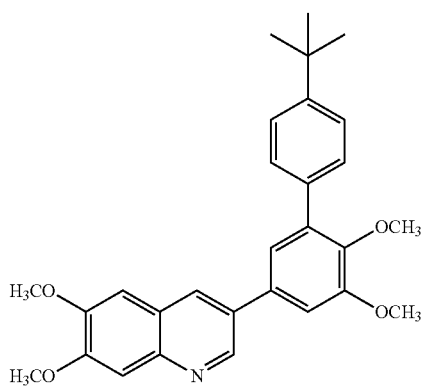 [SMILES: COc1cc2cc(-c3cc(OC)c(OC)c(-c4ccc(C(C)(C)C)cc4)c3)cnc2cc1OC]

To a nitrogen-flushed mixture the Intermediate a of Example 12 (50 mg, 0.11 mmol), 4-t-butylphenylboronic acid (30 mg, 0.15 mmol) and potassium carbonate (35 mg, 0.26 mmol) in a mixture of dioxane (6 mL) and water (1 mL) at room temperature under nitrogen were added palladium acetate (5 mg, 0.02 mmol) and Xphos (25 mg, 0.05 mmol), the resultant mixture was heated at 95° C. for 3 h. It was dried over MgSO₄, filtered and concentrated to a crude product. Purification by flash chromatography (SiO₂, EtOAc/hexane 10-50%) gave the desired product SL-1-148 as a pale oil (29 mg, 60%). ¹H NMR (CDCl₃, 400 MHz) δ: 1.31 (s, 9H), 3.63 (s, 3H), 3.96 (s, 3H), 4.00 (s, 3H), 4.09 (s, 3H), 7.08 (s, 1H), 7.40-7.47 (m, 6H), 7.9 (s, 1H), 8.52 (s, 1H), 8.91 (s, 1H).

Example 16

Preparation of Compound

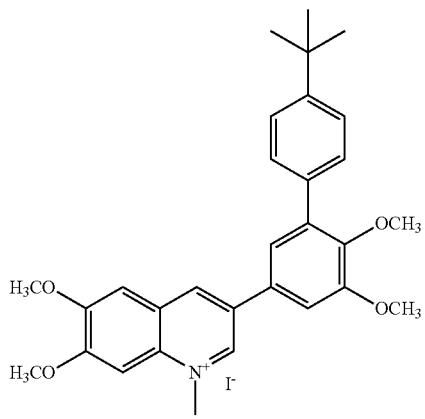 [SMILES: COc1cc2cc(-c3cc(OC)c(OC)c(-c4ccc(C(C)(C)C)cc4)c3)c[n+](C)c2cc1OC ; [I-]]

The compound of Example 15 (14 mg, 0.03 mmol) in iodomethane (0.5 mL) was heated at 60° C. under nitrogen for 6 h. The reaction mixture was treated with Et₂O. A yellow solid was collected to give the desired product (6.5 mg, 38%). ¹H NMR (DMSO, 400 MHz) δ: 1.35 (s, 9H), 3.67 (s, 3H), 4.03 (s, 3H), 4.17 (s, 3H), 4.63 (s, 3H), 7.53 (m, 5H), 7.64 (m, 2H), 7.80 (s, 1H), 9.43 (s, 1H), 9.66 (s, 1H).

Example 17

Preparation of Compound

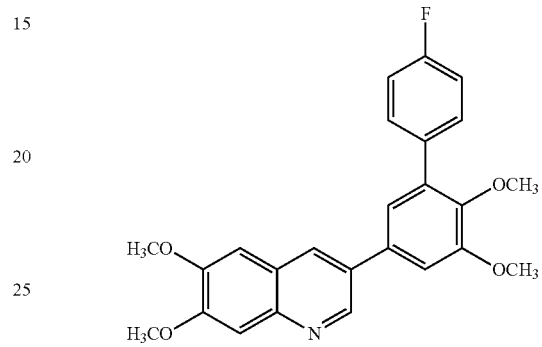

To a nitrogen-flushed mixture of Intermediate a of Example 12 (50 mg, 0.11 mmol), 4-fluorophenylboronic acid (30 mg, 0.21 mmol) and potassium carbonate (36 mg, 0.26 mmol) in a mixture of dioxane (8 mL) and water (1.5 mL) at room temperature under nitrogen were added palladium acetate (5 mg, 0.02 mmol) and Xphos (20 mg, 0.04 mmol), the resultant mixture was heated at 95° C. for 3 h. It was dried over MgSO₄, filtered and concentrated to a crude product. Purification by flash chromatography (SiO₂, EtOAc/hexane 10-50%) gave the desired product as a pale oil (15 mg, 34%). ¹H NMR (CDCl₃, 400 MHz) δ: 3.68 (s, 3H), 4.05 (s, 3H), 4.07 (s, 3H), 4.10 (s, 3H), 7.14-7.29 (m, 5H), 7.57-7.64 (m, 3H), 8.25 (s, 1H), 9.00 (s, 1H).

Example 18

Preparation of Compound

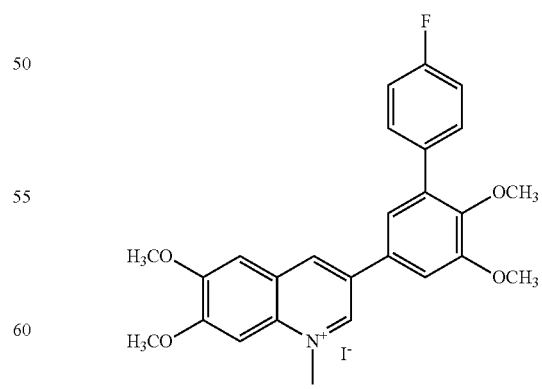

A mixture of the compound of Example 17 (6.0 mg, 0.01 mmol) in iodomethane (0.5 mL) was heated at 60° C. under nitrogen for 2 h. The reaction mixture was treated with Et₂O. A yellow solid was collected to give the desired product (4.2 mg, 52%). $^1$H NMR (CDCl$_3$, 400 MHz) δ: 3.60 (S, 3H), 4.04 (S, 6H), 4.19 (S, 3H), 4.73 (S, 3H), 7.06-7.57 (m, 8H), 8.83 (S, 1H), 9.42 (S, 1H).

Example 19

Preparation of Compound

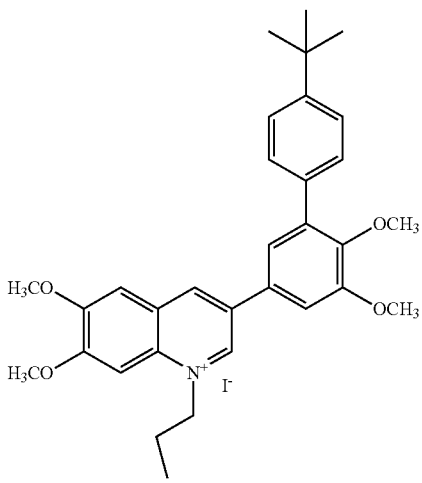 [SMILES: CCC[n+]1cc(-c2cc(OC)c(OC)c(-c3ccc(C(C)(C)C)cc3)c2)cc2cc(OC)c(OC)cc21 ; [I-]]

A mixture of the compound of Example 17 (14 mg, 0.03 mmol) in 1-iodopropane (0.5 mL) was heated at 80° C. under nitrogen for 8 h. The reaction mixture was treated with Et$_2$O. A yellow solid was collected to give the desired product (12 mg, 66%). $^1$H NMR (DMSO, 400 MHz) δ: 1.00 (t, J=8.0 Hz, 3H), 1.35 (s, 9H), 2.06 (qt, 2H), 3.67 (s, 3H), 4.03 (s, 6H), 4.17 (s, 3H), 5.65 (t, J=8.0 Hz, 2H), 7.53 (m, 5H), 7.62 (s, 1H), 7.68 (s, 1H), 7.81 (s, 1H), 9.44 (s, 1H), 9.65 (s, 1H).

Example 20

Preparation of Compound

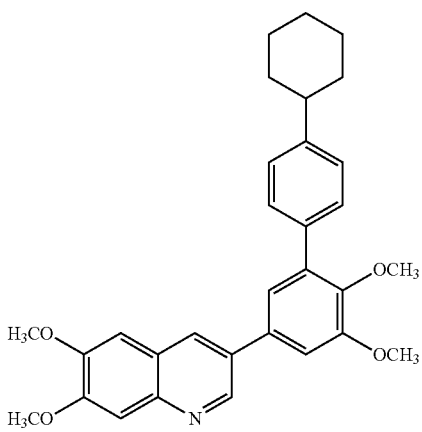 [SMILES: COc1cc2cc(-c3cc(OC)c(OC)c(-c4ccc(C5CCCCC5)cc4)c3)cnc2cc1OC]

To a nitrogen-flushed mixture of the Intermediate a of Example 12 (50 mg, 0.11 mmol), 4-cyclohexylphenylboronic acid (45 mg, 0.22 mmol) and potassium carbonate (50 mg, 0.26 mmol) in a mixture of dioxane (10 mL) and water (2 mL) at room temperature under nitrogen were added palladium acetate (7.0 mg, 0.03 mmol) and Xphos (30 mg, 0.06 mmol), the resultant mixture was heated at 95° C. for 3 h. It was dried over MgSO$_4$, filtered and concentrated to a crude product. Purification by flash chromatography (SiO$_2$, EtOAc/hexane 10-50%) gave the desired product as a pale oil (26 mg, 51%). $^1$H NMR (CDCl$_3$, 400 MHz) δ: 1.40-1.90 (m, 10H), 2.60 (m, 1H), 3.70 (s, 3H), 4.04 (s, 3H), 4.06 (s, 3H), 4.09 (s, 3H), 7.13 (s, 1H), 7.21 (s, 1H), 7.30 (d, J=3.0 Hz, 2H), 7.33 (s, 1H), 7.52-7.58 (m, 3H), 8.21 (s, 1H), 9.0 (s, 1H).

Example 21

Preparation of Compound

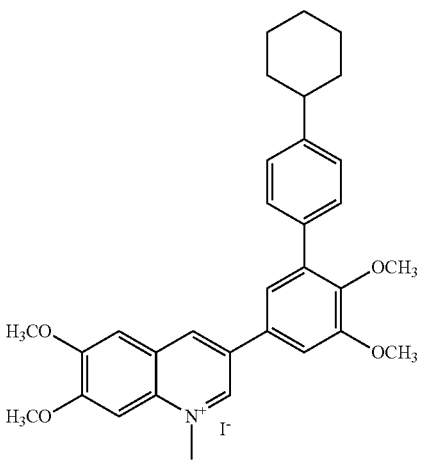

A mixture of the compound of Example 20 (12 mg, 0.03 mmol) in iodomethane (0.5 mL) was heated at 60° C. under nitrogen for 4 h. The reaction mixture was treated with Et$_2$O. A yellow solid was collected to give the desired product (12 mg, 77%). $^1$H NMR (CDCl$_3$, 400 MHz) δ: 1.47-1.98 (m, 10H), 2.59 (m, 1H), 3.70 (s, 3H), 4.11 (s, 3H), 4.13 (s, 3H), 4.86 (s, 3H), 7.31 (m, 5H), 7.60 (d, J=8.0 Hz, 2H), 7.65 (s, 1H), 9.06 (s, 1H), 10.11 (s, 1H).

Example 22

Preparation of Compound

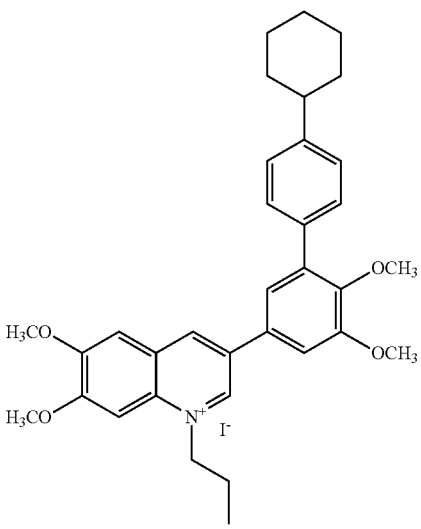 [SMILES: CCC[n+]1cc(-c2cc(OC)c(OC)c(-c3ccc(C4CCCCC4)cc3)c2)cc2cc(OC)c(OC)cc21 ; [I-]]

A mixture of the compound of Example 20 (12 mg, 0.03 mmol) in isopropyliodide (0.5 mL) was heated at 80° C. under nitrogen for 6 h. The reaction mixture was treated with Et$_2$O. A yellow solid was collected to give the desired product (10 mg, 61%). $^1$H NMR (CDCl$_3$, 400 MHz) δ: 1.14-1.98 (m, 13H), 2.12 (m, 2H), 2.59 (m, 1H), 3.70 (s, 3H), 4.11 (s, 6H), 4.25 (s, 3H), 5.32 (m, 2H), 7.29-7.34 (m, 4H), 7.61 (d, J=8.0 Hz, 2H), 7.69 (s, 2H), 9.07 (s, 1H), 9.97 (s, 1H).

Example 23

Preparation of Compound

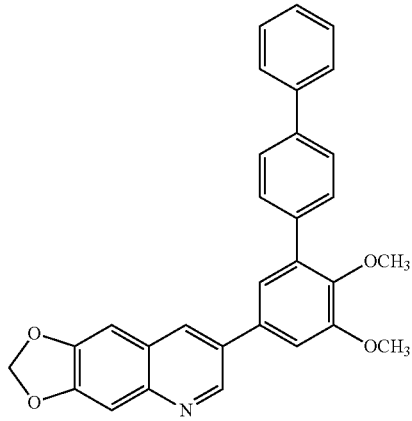 [SMILES: COc1cc(-c2cnc3cc4c(cc3c2)OCO4)cc(-c2ccc(-c3ccccc3)cc2)c1OC]

To a nitrogen-flushed mixture of Intermediate d of Example 26 (50 mg, 0.11 mmol), 4-biphenylboronic acid (35 mg, 0.18 mmol) and potassium carbonate (45 mg, 0.33 mmol) in a mixture of acetonitrile (9 mL) and water (1.5 mL) at room temperature under nitrogen were added palladium acetate (5 mg, 0.02 mmol) and Xphos (20 mg, 0.04 mmol), the resultant mixture was heated at 90° C. for 3 h. It was dried over MgSO$_4$, filtered and concentrated to a crude product. Purification by flash chromatography (SiO$_2$, EtOAc/hexane 10-50%) gave the desired product SL-1-148 as a pale oil (20 mg, 40%). $^1$H NMR (CDCl$_3$, 300 MHz) δ: 3.73 (S, 3H), 4.06 (S, 3H), 6.16 (S, 2H), 7.14 (S, 1H), 7.23 (S, 1H), 7.32 (d, J=3.0 Hz, 1H), 7.39-7.42 (m, 1H), 7.46-7.52 (m, 3H), 7.69-7.72 (m, 6H), 8.16 (S, 1H), 9.00 (S, 1H).

Example 24

Preparation of Compound

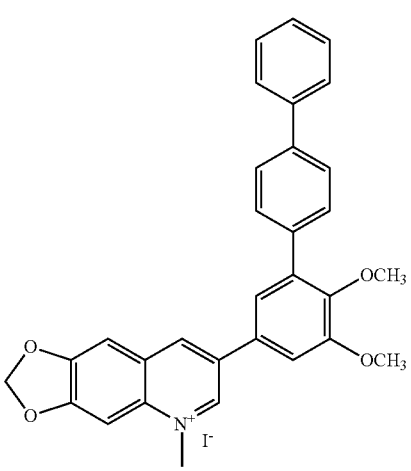 [SMILES: COc1cc(-c2cc3cc4c(cc3[n+](C)c2)OCO4)cc(-c2ccc(-c3ccccc3)cc2)c1OC ; [I-]]

A mixture of the compound of Example 23 (11 mg, 0.03 mmol) in iodomethane (0.5 mL) was heated at 60° C. under nitrogen for 2 h. The reaction mixture was treated with Et$_2$O. A yellow solid was collected to give the desired product (19 mg, 90%). $^1$H NMR (DMSO, 400 MHz) δ: 3.69 (s, 3H), 4.03 (s, 3H), 4.56 (s, 3H), 6.50 (s, 2H), 7.40-7.82 (m, 12H), 8.06 (s, 1H), 9.38 (s, 1H), 9.66 (s, 1H).

Example 25

Preparation of Compound

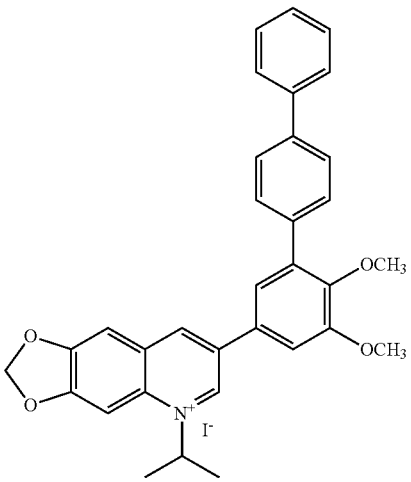 [SMILES: COc1cc(-c2cc3cc4c(cc3[n+](C(C)C)c2)OCO4)cc(-c2ccc(-c3ccccc3)cc2)c1OC ; [I-]]

A mixture of the compound of Example 23 (8.0 mg, 0.02 mmol) in isopropyliodide (0.5 mL) was heated at 80° C. under nitrogen for 6 h. The reaction mixture was treated with Et$_2$O. A yellow solid was collected to give the desired product (7 mg, 64%). $^1$H NMR (CDCl$_3$, 400 MHz) δ: 1.82 (d, J=8.0 Hz, 6H), 3.63 (S, 3H), 3.96 (S, 3H), 4.35 (m, 1H), 6.06 (S, 2H), 6.91 (S, 1H), 7.04 (S, 1H), 7.13-7.62 (m, 11H), 8.05 (S, 1H), 8.90 (S, 1H).

Example 26

Preparation of Compound

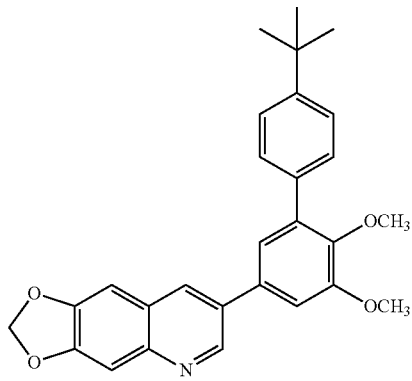 [SMILES: COc1cc(-c2cnc3cc4c(cc3c2)OCO4)cc(-c2ccc(C(C)(C)C)cc2)c1OC]

To a nitrogen-flushed mixture of 5-([1,3]dioxolo[4,5-g]quinolin-7-yl)-2,3-dimethoxyphenyl trifluoromethanesulfonate, Intermediate d of Example 26, (50 mg, 0.11 mmol), 4-t-butylboronic acid (30 mg, 0.16 mmol) and potassium carbonate (45 mg, 0.33 mmol) in a mixture of acetonitrile (9 mL) and water (1.5 mL) at room temperature under nitrogen were added palladium acetate (5 mg, 0.02 mmol) and Xphos (20 mg, 0.04 mmol), the resultant mixture was heated at 90° C. for 3 h. It was dried over MgSO$_4$, filtered and concentrated to a crude product. Purification by flash chromatography (SiO$_2$, EtOAc/hexane 10-50%) gave the desired product SL-1-148 as a pale oil (48 mg, 99%). $^1$H NMR (CDCl$_3$, 400 MHz) δ: 1.34 (s, 9H), 3.70 (s, 3H), 4.04 (s, 3H), 6.15 (s, 2H), 7.01 (s, 1H), 7.12 (s, 1H), 7.19 (d, J=3.0 Hz, 1H), 7.28 (d, J=3.0 Hz, 1H), 7.45-7.59 (m, 4H), 8.14 (s, 1H), 8.98 (s, 1H).

The requisite intermediate for the preparation of this compound was prepared as follows.

a. Preparation of Compound

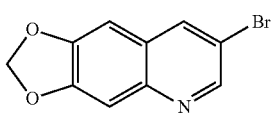 [SMILES: Brc1cnc2cc3c(cc2c1)OCO3]

Using the same procedure used for Intermediate d in Example 12, the 3-bromo-6,7-methylenedioxyquinoline was prepared. A mixture of 3,4-methylenedioxyaniline (5.0 g, 36 mmol), 2-bromomalonaldehyde (8.0 g, 7.28 mmol) and concentrated hydrochloric acid (18 mL, 216 mmol) in EtOH (35 mL) was heated at reflux under nitrogen for 12 h. All EtOH and HCl were removed under reduced pressure. The residue was basified with 4 N NaOH to pH 9, extracted with EtOAc (3×30 mL). The EtOAc solution was dried over MgSO$_4$, filtered and concentrated and purified with flash column (SiO$_2$, EtOAc/hexane 0-50%) to give the desired product as a pale oil (0.45 g, 5%).

b. Preparation of Compound

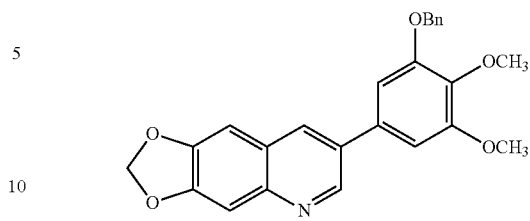

To a nitrogen-flushed mixture of 3-bromo-6,7-methylenedioxyquinoline (0.64 g, 1.3 mmol), Intermediate a of Example 26 (0.45 g, 1.8 mmol) and potassium carbonate (0.74 g, 5.4 mmol) in a mixture of dioxane (20 mL) and water (2 mL) at room temperature under nitrogen was added tetrakis(triphenylphosphine)palladium (0.10 g, 0.09 mmol), the resultant mixture was heated at 100° C. for 5 h. It was dried over MgSO$_4$, filtered and concentrated and purified with flash column (SiO$_2$, EtOAc/hexane 10-50%) to give the desired product as a pale oil (0.38 g, 51%). $^1$H NMR (CDCl$_3$, 400 MHz) δ: 3.90 (s, 3H), 3.92 (s, 3H), 5.19 (s, 2H), 6.09 (s, 2H), 6.81 (d, J=8.0 Hz, 2H), 7.06 (s, 1H), 7.29 (d, J=8.0 Hz, 1H), 7.35 (t, J=8.0 Hz, 2H) 7.42 (m, 3H), 7.9 (s, 1H), 8.80 (s, 1H).

c. Preparation of Compound

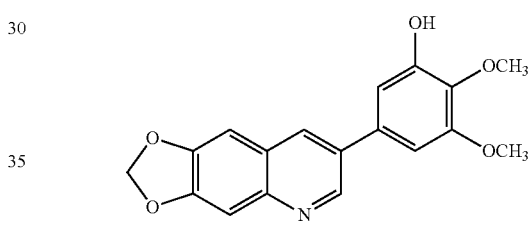

A mixture of 7-(3-(benzyloxy)-4,5-dimethoxyphenyl)-[1,3-dioxolo[4,5-g]quinoline (0.35 g, 0.84 mmol) and 10% palladium on carbon (0.07 g, 20% w/w) was stirred at room temperature under 1 atm of hydrogen at 60° C. for 8 h. The catalyst was filtered off and the filtrate was concentrated to give the desired product (0.27 g, 100%). $^1$H NMR (CDCl$_3$, 400 MHz) δ: 3.72 (s, 3H), 3.88 (s, 3H), 6.21 (s, 2H), 6.86 (d, J=12.0 Hz, 2H), 7.35 (d, J=12.0 Hz, 2H), 8.33 (s, 1H), 8.91 (s, 1H), 9.32 (s, 1H).

d. Preparation of Compound

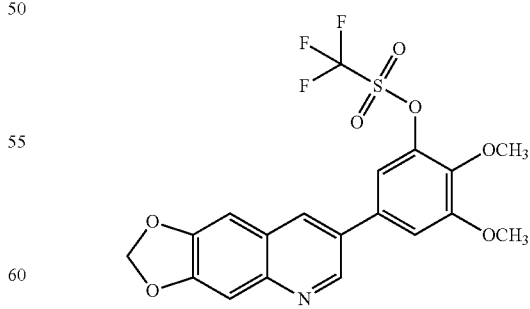

To a solution of 5-([13]dioxolo[45-g]quinolin-7-yl)-2,3-dimethoxyphenol (0.27 g, 0.83 mmol) and triethylamine (0.25 mL, 1.8 mmol) in CH$_2$Cl$_2$ (25 mL) at −(30-40)° C. under nitrogen was added triflate anhydride (0.22 mL, 1.3 mmol) slowly, the resultant mixture was stirred at −78° C. and warmed up to 0° C. The reaction was diluted with methylenechloride to 50 mL and washed with aq. NaHCO₃ solution. The organic solution was dried over MgSO₄ and concentrated to an oil. Purification by flash chromatography (SiO₂, EtOAc/hexane 10-60%) gave the desired product as an oil (0.23 g, 60%). ¹H NMR (CDCl₃, 400 MHz) δ: 4.02 (s, 3H), 4.03 (s, 3H), 6.17 (s, 2H), 7.12 (m, 2H), 7.18 (d, J=3.0 Hz, 1H), 7.44 (s, 1H), 8.07 (s, 1H), 8.89 (s, 1H).

Example 26a

Preparation of Compound

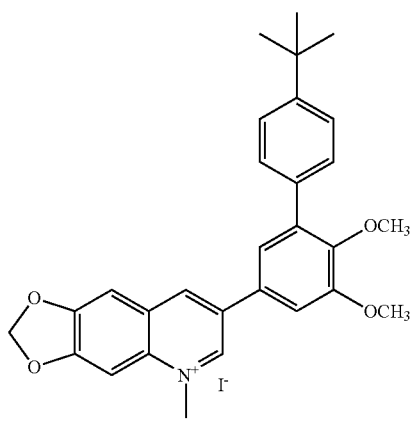 [SMILES: COc1cc(-c2cc3cc4c(cc3[n+](C)c2)OCO4)cc(-c2ccc(C(C)(C)C)cc2)c1OC ; [I-]]

A mixture of the compound of Example 26 (11 mg, 0.03 mmol) in iodomethane (0.5 mL) was heated at 60° C. under nitrogen for overnight. The reaction mixture was concentrated to dryness. The residue was treated with Et₂O. A yellow solid was collected to give the desired product (13 mg, 89%). ¹H NMR (CDCl₃, 300 MHz) δ: 1.38 (S, 9H), 3.72 (S, 3H), 4.21 (S, 3H), 4.80 (S, 3H), 6.38 (S, 2H), 7.27 (m, 3H), 7.42 (S, 1H), 7.51 (d, J=9.0 Hz, 1H), 7.63 (m, 2H), 7.77 (S, 1H), 9.00 (S, 1H), 10.09 (S, 1H).

Example 27

Preparation of Compound

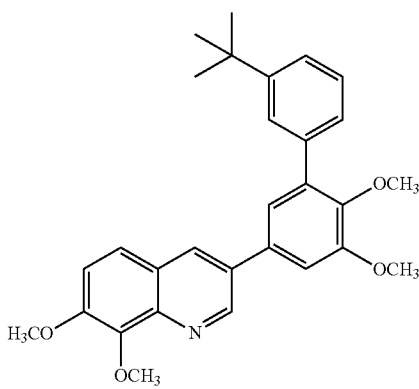 [SMILES: COc1cc(-c2cnc3c(OC)c(OC)ccc3c2)cc(-c2cccc(C(C)(C)C)c2)c1OC]

To a nitrogen-flushed mixture of Intermediate d of Example 29 (30 mg, 0.06 mmol), 3-t-butylphenylboronic acid (20 mg, 0.11 mmol) and potassium carbonate (26 mg, 0.19 mmol) in a mixture of acetonitrile (6 mL) and water (1 mL) at room temperature under nitrogen were added palladium acetate (5 mg, 0.02 mmol) and Xphos (20 mg, 0.04 mmol), the resultant mixture was heated at 90° C. for 4 h. It was dried over MgSO₄, filtered and concentrated to a crude product. Purification by flash chromatography (SiO₂, EtOAc/hexane 10-50%) gave the desired product SL-1-148 as a pale oil (19 mg, 66%). ¹H NMR (CDCl₃, 400 MHz) δ: 1.40 (s, 9H), 3.69 (s, 3H), 4.05 (s, 3H), 4.08 (s, 3H), 4.19 (s, 3H), 7.24 (d, J=3.0 Hz, 1H), 7.31 (d, J=3.0 Hz, 1H), 7.41-7.44 (m, 4H), 7.65 (d, J=9.0 Hz, 1H), 7.71 (m, 1H), 8.26 (s, 1H), 9.24 (s, 1H).

Example 28

Preparation of Compound

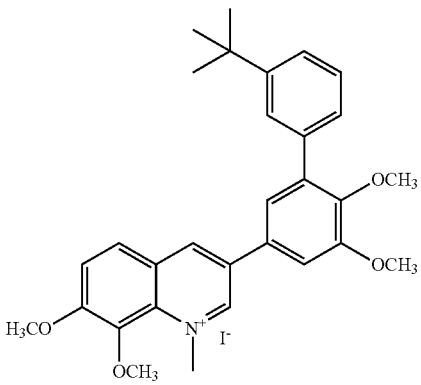 [SMILES: COc1cc(-c2cc3ccc(OC)c(OC)c3[n+](C)c2)cc(-c2cccc(C(C)(C)C)c2)c1OC ; [I-]]

A mixture of the compound of Example 27 (18 mg, 0.04 mmol) in iodomethane (0.3 mL) was heated at 80° C. under nitrogen for 1 h. The reaction mixture was treated with Et₂O. A yellow solid was collected to give the desired product (11 mg, 47%). ¹H NMR (CDCl₃, 400 MHz) δ: 1.37 (S, 9H), 3.47 (S, 3H), 3.87 (S, 3H), 3.95 (S, 3H), 4.02 (S, 3H), 4.92 (S, 3H), 6.99 (S, 1H), 7.17-7.21 (m, 3H), 7.44-7.47 (m, 2H), 7.77 (d, J=4.0 Hz, 1H), 7.84 (d, J=8.0 Hz, 1H), 8.72 (S, 1H), 9.81 (S, 1H).

Example 29

Preparation of Compound

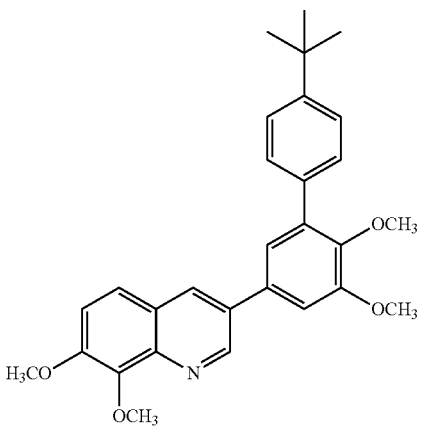 [SMILES: COc1cc(-c2cnc3c(OC)c(OC)ccc3c2)cc(-c2ccc(C(C)(C)C)cc2)c1OC]

To a nitrogen-flushed mixture of 5-(7,8-dimethoxyquinolin-3-yl)-2,3-dimethoxyphenyl trifluoromethane sulfonate (75 mg, 0.16 mmol), 4-t-butylphenylboronic acid (45 mg, 0.25 mmol) and potassium carbonate (60 mg, 0.43 mmol) in a mixture of acetonitrile (9 mL) and water (2 mL) at room temperature under nitrogen were added palladium acetate (7 mg, 0.03 mmol) and Xphos (30 mg, 0.06 mmol), the resultant mixture was heated at 90° C. for 3 h. It was dried over MgSO$_4$, filtered and concentrated to a crude product. Purification by flash chromatography (SiO$_2$, EtOAc/hexane 10-50%) gave the desired product SL-1-148 as a pale oil (45 mg, 61%). $^1$H NMR (CDCl$_3$, 400 MHz) δ: 1.40 (s, 9H), 3.70 (s, 3H), 4.04 (s, 3H), 4.07 (s, 3H), 4.19 (s, 3H), 7.23 (d, J=3.0 Hz, 1H), 7.31 (d, J=3.0 Hz, 1H), 7.42 (d, J=9.0 Hz, 1H), 7.50 (m, 2H), 7.57-7.65 (m, 3H), 8.25 (d, J=3.0 Hz, 1H), 9.23 (d, J=3.0 Hz, 1H).

The requisite intermediate for the preparation of this compound was prepared as follows.

a. Preparation of Compound

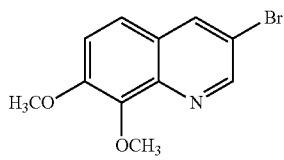 [SMILES: COc1ccc2cc(Br)cnc2c1OC]

A mixture of 2,3-dimethoxylaniline (2.0 g, 13 mmol), 2-bromomalonaldehyde (2.5 g, 17 mmol) and concentrated hydrochloric acid (8 mL, 96 mmol) in EtOH (35 mL) was heated at reflux under nitrogen for 16 h. All EtOH and HCl were removed under reduced pressure. The residue was basified with 4 N NaOH to pH 9, extracted with EtOAc (3×30 mL). The EtOAc solution was dried over MgSO$_4$, filtered and concentrated and purified with flash column (SiO$_2$, EtOAc/hexane 0-50%) to give the desired product as a pale oil (0.31 g, 38%). $^1$H NMR (CDCl$_3$, 400 MHz) δ: 4.06 (s, 3H), 4.14 (s, 3H), 7.40 (d, J=6.0 Hz, 1H), 7.53 (d, J=6.0 Hz, 1H), 8.26 (s, 1H), 8.91 (s, 1H).

b. Preparation of Compound

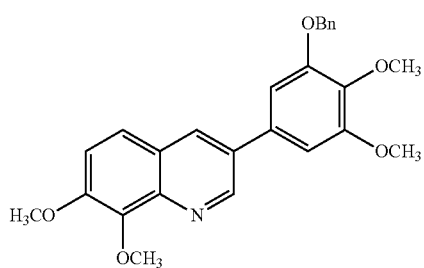 [SMILES: COc1cc(-c2cnc3c(OC)c(OC)ccc3c2)cc(OCc2ccccc2)c1OC]

To a nitrogen-flushed mixture of the Intermediate a of Example 1 (0.40 g, 1.4 mmol), 3-bromo-7,8-dimethoxyquinoline (0.30 g, 1.1 mmol) and potassium carbonate (0.45 g, 3.3 mmol) in a mixture of dioxane (10 mL) and water (2 mL) at room temperature under nitrogen was added tetrakis(triphenylphosphine)palladium (65 mg, 0.06 mmol), the resultant mixture was heated at 100° C. for 5 h. It was dried over MgSO$_4$, filtered and concentrated and purified with flash column (SiO$_2$, EtOAc/hexane 10-60%) to give the desired product as a pale oil (0.25 g, 52%). $^1$H NMR (CDCl$_3$, 400 MHz) δ: 3.97 (s, 3H), 3.99 (s, 3H), 4.08 (s, 3H), 4.19 (s, 3H), 5.26 (s, 2H), 6.91 (d, J=16.0 Hz, 2H), 7.35 (d, J=4.0 Hz, 1H), 7.42 (m, 3H), 7.50 (d, J=8.0 Hz, 1H), 8.16 (s, 1H), 9.11 (s, 1H).

c. Preparation of Compound

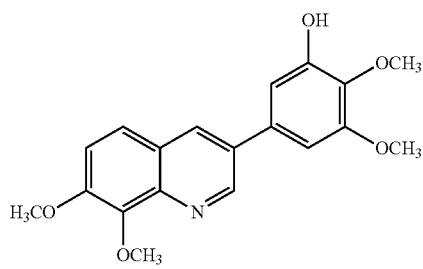 [SMILES: COc1cc(-c2cnc3c(OC)c(OC)ccc3c2)cc(O)c1OC]

A mixture of 3-(3-benzyloxy)-4,5-dimethoxyphenylquinoline (0.25 g, 0.58 mmol) and 10% palladium on carbon (40 mg, 16% w/w) was stirred under 1 atm of hydrogen at 60° C. for 6 h. The catalyst was filtered off and the filtrate was concentrated to to an oil. Purification by flash chromatography (SiO$_2$, EtOAc/hexane 10-60%) gave the desired product (0.20 g, 100%). $^1$H NMR (CD$_3$OD, 300 MHz) δ: 3.88 (S, 3H), 4.00 (S, 3H), 4.20 (S, 6H), 7.00-7.02 (m, 2H), 7.93 (d, J=9.0 Hz, 1H), 8.15 (d, J=9.0 Hz, 1H), 9.23 (dd, J=9.0 Hz, 3.0 Hz, 2H).

d. Preparation of Compound

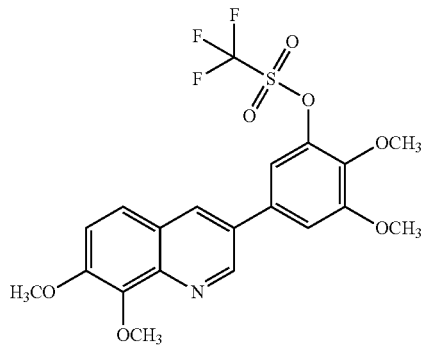 [SMILES: COc1cc(-c2cnc3c(OC)c(OC)ccc3c2)cc(OS(=O)(=O)C(F)(F)F)c1OC]

To a solution of 5-(7,8-dimethoxyquinolin-3-yl)-2,3-dimethoxyphenol (0.21 g, 0.61 mmol) and triethylamine (0.17 mL, 1.2 mmol) in CH$_2$Cl$_2$ (25 mL) at −30° C. under nitrogen was added triflate anhydride (0.26 mL, 1.5 mmol) slowly, the resultant mixture was stirred at −30° C. and warmed up to 0° C. The reaction was diluted with methylenechloride to 50 mL and washed with aq. NaHCO$_3$ solution. The organic solution was dried over MgSO$_4$ and concentrated to an oil. Purification by flash chromatography (SiO$_2$, EtOAc/hexane 10-60%) gave the desired product as an oil (0.15 g, 51%). $^1$H NMR (CDCl$_3$, 300 MHz) δ: 4.03 (S, 3H), 4.04 (S, 3H), 4.09 (S, 3H), 4.18 (S, 3H), 7.14 (d, J=3.0 Hz, 1H), 7.21

(d, J=3.0 Hz, 1H), 7.45 (d, J=9.0 Hz, 1H), 7.68 (d, J=9.0 Hz, 1H), 8.19 (d, J=3.0 Hz, 1H), 9.13 (S, 1H).

Example 30

Preparation of Compound

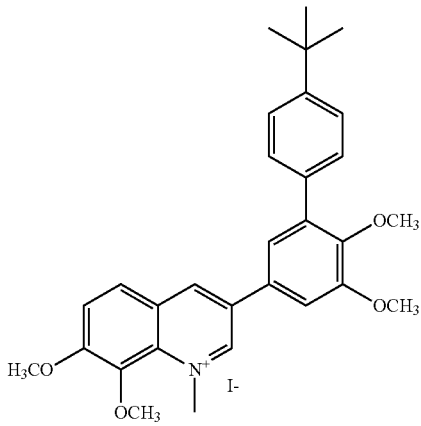 [SMILES: COc1cc(-c2cc3ccc(OC)c(OC)c3[n+](C)c2)cc(-c2ccc(C(C)(C)C)cc2)c1OC ; [I-]]

A mixture of the Compound of Example 29 (12 mg, 0.03 mmol) in iodomethane (0.5 mL) was heated at 80° C. under nitrogen for 2 h. The reaction mixture was treated with Et$_2$O. A yellow solid was collected to give the desired product (7.4 mg, 47%). $^1$H NMR (CDCl$_3$, 400 MHz) δ: 1.30 (s, 9H), 3.62 (s, 3H), 3.98 (s, 3H), 4.07 (s, 3H), 4.11 (s, 3H), 5.01 (s, 3H), 7.16 (s, 1H), 7.40 (d, J=8.0 Hz, 2H), 7.49 (d, J=8.0 Hz, 2H), 7.56 (d, J=8.0 Hz, 1H), 7.81 (d, J=4.0 Hz, 1H), 8.04 (d, J=8.0 Hz, 1H), 8.95 (s, 1H), 9.88 (s, 1H).

Example 31

Preparation of Compound

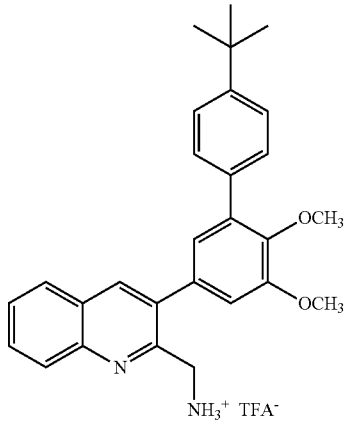

A mixture of t-butyl((3-(4'-(tert-butyl)-5,6-dimethoxy-[1,1'-biphenyl]-3-yl)quinolin-2-yl)methyl)carbamate (8.8 mg, 0.02 mmol) in a mixture of TFA/CH$_2$Cl$_2$ (0.1/0.1 mL) was set at room temperature overnight. All TFA/CH$_2$Cl$_2$ were removed under reduced pressure to give the desired product as a pale oil (9 mg, 100%). $^1$H NMR (CDCl$_3$, 400 MHz) δ: 3.69 (s, 3H), 3.90 (s, 3H0, 4.48 (s, 2H), 7.06 (d, J=3.0 Hz, 1H), 7.15 (d, J=3.0 Hz, 1H), 7.48-7.56 (m, 3H), 7.69 (t, J=6.0 Hz, 2H), 7.85 (t, J=6.0 Hz, 2H), 8.04 (d, J=6.0 Hz, 1H), 8.19 (d, J=6.0 Hz, 1H), 8.35 (s, 1H).

The requisite intermediate for the preparation of this compound was prepared as follows.

a. Preparation of Compound

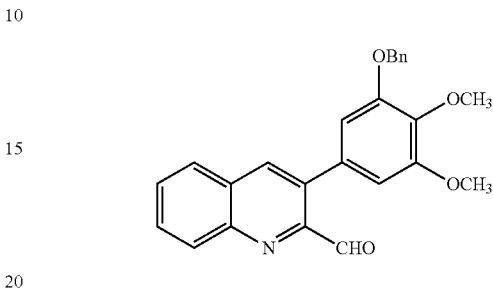

To a nitrogen-flushed mixture of intermediate a of Example 1 (0.38 g, 1.3 mmol), 3-bromo-2-formylquinoline (0.26 g, 1.1 mmol) (*Eur. J. Org. Chem.* 1781, 2009) and potassium carbonate (0.45 g, 3.3 mmol) in a mixture of dioxane (10 mL) and water (2 mL) at room temperature under nitrogen was added tetrakis(triphenylphosphine)palladium (60 mg, 0.05 mmol), the resultant mixture was heated at 100° C. for 3.5 h. It was dried over MgSO$_4$, filtered and concentrated and purified with flash column (SiO$_2$, EtOAc/hexane 10-60%) to give the desired product as a pale oil (0.44 g, 100%). $^1$H NMR (CDCl$_3$, 400 MHz) δ: 3.92 (s, 3H), 3.99 (s, 3H), 5.2 (s, 2H), 6.68 (d, J=6.0 Hz, 2H), 7.34-7.49 (m, 5H), 7.70-7.76 (m, 1H), 7.83-7.93 (m, 2H), 8.20 (s, 1H), 8.36 (d, J=9.0 Hz, 1H), 10.24 (s, 1H).

b. Preparation of Compound

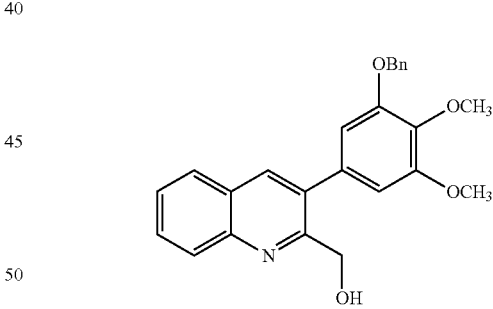

A mixture of 3-(3-(benzyloxy)-4,5-dimethoxyphenyl) quinoline-2-carboxaldehyde (0.15 g, 0.37 mmol) and 10% palladium on carbon (15 mg, 10% w/w) in MeOH (20 mL) was stirred under 1 atm of hydrogen at r.t for 6 h. The catalyst was filtered off and the filtrate was concentrated to to an oil. Purification by flash chromatography (SiO$_2$, EtOAc/hexane 10-60%) gave the desired product (34 mg, 23%). $^1$H NMR (CDCl$_3$, 400 MHz) δ: 3.88 (s, 3H), 3.98 (s, 3H), 4.82 (s, 2H), 5.14 (bs, 1H), 6.06 (bs, 1H), 6.46 (d, J=3.0 Hz, 1H), 6.61 (d, J=3.0 Hz, 1H), 7.56 (dt, J=6.0 Hz, 3.0 Hz, 1H), 7.71-7.70 (m, 1H), 7.84 (d, J=9.0 Hz, 1H), 8.01 (s, 1H), 8.12 (d, J=9.0 Hz, 1H).

c. Preparation of Compound

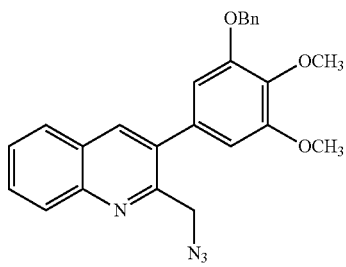 [SMILES: COc1cc(-c2cc3ccccc3nc2CN=[N+]=[N-])cc(OCc2ccccc2)c1OC]

To a mixture of (3-(3-(benzyloxy)-4,5-dimethoxyphenyl)quinolin-2-yl)methanol (64 mg, 0.16 mmol) in THF (5 mL) at 0° C. under nitrogen were added DPPA (0.07 mL, 0.32 mmol) and then DBU (0.05 mL, 0.33 mmol) dropwise, the resultant mixture was stirred at 0° C. and warwed up to r.t overnight. The reaction mixture was diluted with EtOAc to 30 mL, washed with aq NaHCO$_3$ solution and brine. It was dried over MgSO$_4$, filtered and concentrated and purified with flash column (SiO$_2$, EtOAc/hexane 10-60%) to give the desired product as a pale oil (42 mg, 62%). $^1$H NMR (CDCl$_3$, 400 MHz) δ: 3.93 (s, 3H), 3.99 (s, 3H), 4.52 (s, 3H), 5.22 (s, 2H), 6.69 (s, 2H), 6.68 (s, 2H), 7.35-7.48 (m, 3H), 7.65 (t, J=6.0 Hz, 1H), 7.8 (m, 1H), 7.87 (d, J=9.0 Hz, 1H), 8.14 (s, 1H), 8.25 (d, J=6.0 Hz, 1H).

d. Preparation of Compound

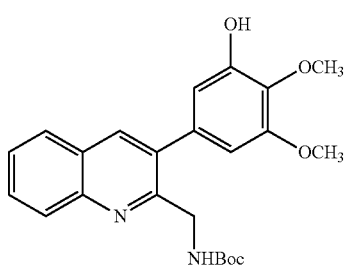 [SMILES: COc1cc(-c2cc3ccccc3nc2CNC(=O)OC(C)(C)C)cc(O)c1OC]

A mixture of 2-(azidomethyl)-3-(3-(benzyloxy)-4,5-dimethoxyphenyl)quinoline (83 mg, 0.19 mmol), Boc anhydride (80 mg, 0.37 mmol) and 10% palladium on carbon (16 mg, 20% w/w) in MeOH (20 mL) was stirred under 1 atm of hydrogen at r.t overnight. The catalyst was filtered off and the filtrate was concentrated to to an oil. Purification by flash chromatography (SiO$_2$, EtOAc/hexane 10-60%) gave the desired product (15 mg, 19%). $^1$H NMR (CDCl$_3$, 400 MHz) δ: 1.52 (s, 9H), 3.90 (s, 3H), 3.99 (s, 3H), 4.57 (d, J=3.0 Hz, 2H), 5.96 (bs, 1H), 6.46 (d, J=3.0 Hz, 1H), 6.55 (bs, 1H), 6.62 (d, J=3.0 Hz, 1H), 7.55-7.60 (m, 1H), 7.72-7.78 (m, 1H), 7.84 (d, J=9.0 Hz, 1H), 8.00 (s, 1H), 8.15 (d, J=9.0 Hz, 1H).

e. Preparation of Compound

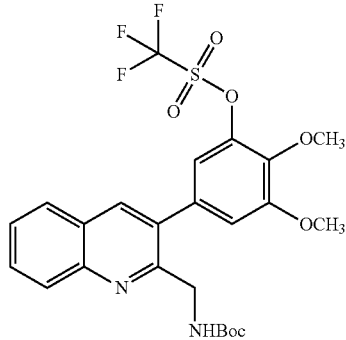 [SMILES: COc1cc(-c2cc3ccccc3nc2CNC(=O)OC(C)(C)C)cc(OS(=O)(=O)C(F)(F)F)c1OC]

To a solution of t-butyl((3-(3-hydroxy-4,5-dimethoxyphenyl)quinolin-2-yl)methylcarbamate (13 mg, 0.03 mmol) and triethylamine (0.009 mL, 0.06 mmol) in CH$_2$Cl$_2$ (2 mL) at −78° C. under nitrogen was added triflate anhydride (0.008 mL, 0.05 mmol) slowly, the resultant mixture was stirred at −78° C. for 20 min and warmed up to −10° C. The reaction was diluted with methylenechloride to 50 mL and washed with aq. NaHCO$_3$ solution. The organic solution was dried over MgSO$_4$ and concentrated to an oil. Purification by flash chromatography (SiO$_2$, EtOAc/hexane 10-60%) gave the desired product as an oil (15 mg, 88%). $^1$H NMR (CDCl$_3$, 400 MHz) δ: 1.52 (s, 9H), 3.96 (s, 3H), 4.06 (s, 3H), 4.53 (d, J=3.0 Hz, 2H), 6.47 (bs), 6.89 (s, 1H), 6.96 (s, 1H), 7.61 (t, J=6.0 Hz, 1H), 7.66-7.82 (m, 1H), 7.86 (d, J=6.0 Hz, 1H), 8.03 (s, 1H), 8.16 (d, J=9.0 Hz, 1H).

f. Preparation of Compound

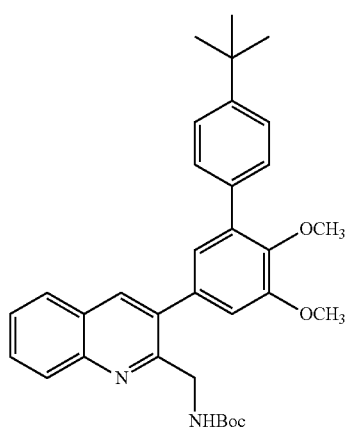 [SMILES: COc1cc(-c2cc3ccccc3nc2CNC(=O)OC(C)(C)C)cc(-c2ccc(C(C)(C)C)cc2)c1OC]

A mixture of 5-(2-(((t-butoxycarbonyl)amino)methyl)quinolin-3-yl)-2,3-dimethoxyphenyl trifluoromethanesulfonate (15 mg, 0.028 mmol), t-butylphenylboronic acid (7 mg), Pd (OAc)$_2$ (2 mg), XPhos (4 mg), K$_2$CO$_3$ (10 mg) in ACN: H$_2$O (3.0 ml:0.3 ml) was heated at 90° C. for 5 h. The reaction mixture was dried and chromatographed to yield 8.8 mg (59%) product. $^1$H NMR (CDCl$_3$, 400 MHz) δ: 1.34 (s, 9H), 1.52 (s, 9H), 3.72 (s, 3H), 3.96 (s, 3H), 4.62 (d, J=3.0 Hz, 2H), 6.58 (bs, 1H), 6.9 (d, J=18.0 Hz, 2H), 7.47 (m, 2H), 7.56-7.61 (m, 3H), 7.76 (t, J=6.0 Hz, 1H).

Example 32

Preparation of Compound

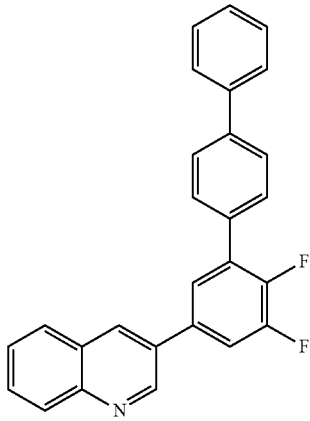 [SMILES: Fc1cc(-c2cnc3ccccc3c2)cc(-c2ccc(-c3ccccc3)cc2)c1F]

A mixture of 4-biphenylboronic acid (0.2 g), 2,3-difluorophenyltriflate (0.1 g), Cs$_2$CO$_3$ (0.4 g), Pd (PPh$_3$)$_2$Cl$_2$ (5 mol %) in dioxane (3.0 mL) was micro waved for 15 minutes. The crude reaction mixture was diluted with ethyl acetate and was filtered through a plug of Celite and silica gel. The filtrate was concentrated under vacuo and was subjected to flash column chromatography to afford the desired product (0.115 g). $^1$H NMR (CDCl$_3$, 400 MHz) δ: 7.34 (m, 1H), 7.39-7.50 (m, 3H), 7.51-7.5 (m, 2H), 7.58 (m, 2H), 7.64 (m, 5H), 7.83 (d, J=8.0 Hz, 1H), 8.09 (d, J=8.0 Hz, 1H), 8.25 (d, J=4.0 Hz, 1H), 9.10 (s, 1H).

The requisite intermediate for the preparation of this compound was prepared as follows.

a. Preparation of Compound

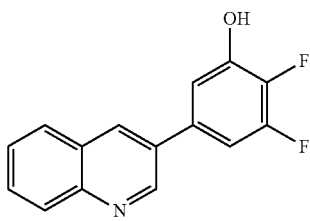 [SMILES: Oc1cc(-c2cnc3ccccc3c2)cc(F)c1F]

A mixture of quinoline 3-boronic acid (0.34 g, 2.0 mmol), 5-bromo-2,3-difluorophenol (0.5 g, 2.5 mmol), Cs$_2$CO$_3$ (0.8 g), Pd (PPh$_3$)$_2$Cl$_2$ (5 mol %) in dioxane (3.0 mL) was micro waved for 15 minutes. The crude reaction mixture was diluted with ethyl acetate and was filtered through a plug of Celite and silica gel. The filtrate was concentrated under vacuo and was subjected to flash column chromatography to afford the desired product (0.35 g). $^1$H NMR (CDCl$_3$, 400 MHz) δ: 7.09-7.13 (m, 1H), 7.24-7.26 (m, 1H), 7.65 (m, 1H), 7.80 (m, 1H), 7.93 (d, J=8.0 Hz, 1H), 8.22 (d, J=8.0 Hz, 1H), 8.32 (s, 1H), 9.22 (s, 1H).

b. Preparation of Compound

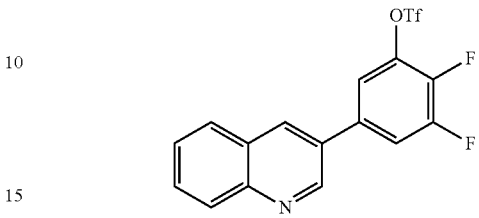

The hydroxyl compound (120 mg) was dissolved in dichloromethane (3.0 mL) to which added 2.0 equivalent of triethyl amine and 1.5 equivalent of Tf$_2$O at −78° C. After the reaction is completed, the reaction mixture was diluted with more methylene chloride which was then washed with saturated sodium bicarbonate and brine. The crude mixture was then purified by flash column chromatography to afford the product (110 mg). $^1$H NMR (CDCl$_3$, 400 MHz) δ: 7.32 (m, 1H), 7.42-7.52 (m, 2H), 7.63-7.68 (m, 1H), 7.78 (d, J=8.0 Hz, 1H), 8.03 (d, J=8.0 Hz, 1H), 8.13 (s, 1H), 8.94 (d, J=4.0 Hz, 1H).

Example 33

Preparation of Compound

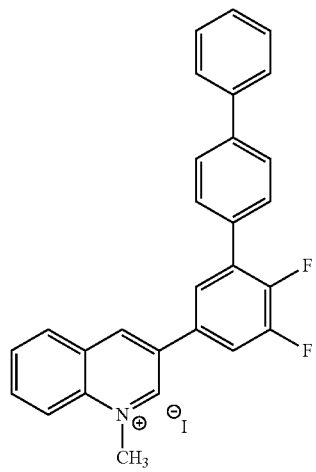 [SMILES: C[n+]1cc(-c2cc(F)c(F)c(-c3ccc(-c4ccccc4)cc3)c2)cc2ccccc21 ; [I-]]

The starting material (50 mg) was dissolved in methyl iodide (2.0 ml) in a sealed tube and was heated at 80° C. for 30 minutes. The resulting solid was then diluted with acetone, filtered and washed with diethyl ether twice to afford the quaternary salts as pure solid (40 mg). $^1$H NMR (CDCl$_3$, 400

MHz) δ: 7.36 (m, 2H), 7.61 (m, 2H), 7.76 (m, 2H), 7.90 (m, 3H), 8.0-8.3 (m, 6H), 9.04 (s, 1H), 10.1 (s, 1H).

Example 34

Preparation of Compound

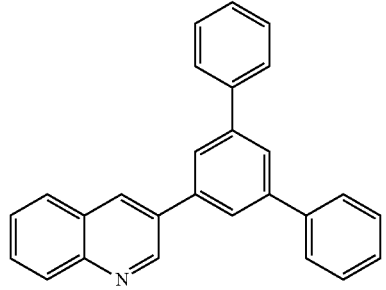 [SMILES: c1ccc(-c2cc(-c3ccccc3)cc(-c3cnc4ccccc4c3)c2)cc1]

To a nitrogen-flushed mixture of 3-bromoquinoline (1 equiv), terphenylboronic acid (1.5 equiv), and Potassium carbonate in a mixture of acetonitrile and water at room temperature were added palladium acetate (5 mol %) and Xphos (10 mol %). The resultant mixture was heated at 90° C. for 3 h. It was dried over MgSO4, filtered and concentrated to a crude product. Purification on silica using 10% EtOAc in hexane afforded the pure product. $^1$H NMR (CDCl$_3$, 400 MHz) δ: 7.43-7.47 (m, 2H), 7.54 (m, 4H), 7.65 (m, 1H), 7.77 (m, 5H), 7.90-7.95 (m, 4H), 8.22 (d, J=12.0 Hz, 1H), 8.44 (s, 1H), 9.33 (s, 1H).

Example 35

Preparation of Compound

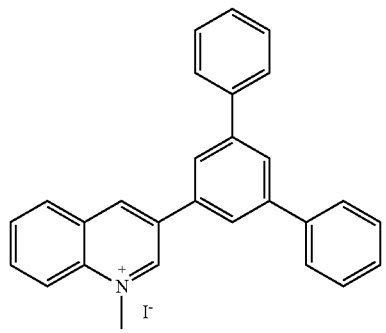

The compound of Example 34 (150 mg) was dissolved in methyl iodide (2 ml) in a sealed tube and was heated at 80° C. for 15 minutes. The resulting solid was then diluted with acetone, filtered and washed with diethyl ether twice to afford the quaternary salts as pure solid (110 mg). $^1$H NMR (CDCl$_3$, 400 MHz) δ: 7.31 (m, 2H), 7.41 (m, 4H), 7.75 (m, 4H), 7.81 (s, 1H), 7.85 (t, J=8.0 Hz, 1H), 8.03 (s, 2H), 8.08 (t, J=8.0 Hz, 1H), 8.2 (d, J=8.0 Hz, 1H), 8.34 (d, J=8.0 Hz, 1H), 9.20 (s, 1H), 10.12 (s, 1H).

Example 36

Preparation of Compound

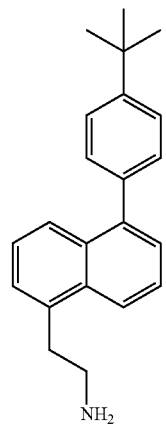 [SMILES: CC(C)(C)c1ccc(-c2cccc3c(CCN)cccc23)cc1]

A solution of 2-(5-(4-t-butyl)phenyl)naphthalen-1-yl)acetonitrile (85 mg, 0.28 mmol) in THF (5 mL) was added dropwise to a solution of LiAlH$_4$ (1.0 M/THF, 0.9 mL) in THF (5 mL) at 0° C. under nitrogen, the resultant mixture was heated at reflux for 7 h. It was cooled to 0° C. and carefully treated with aq NaOH and extracted with EtOAc (3×20 mL) and dried over MgSO$_4$, filtered and concentrated. Purification with flash column (SiO$_2$, 1.5% NH$_4$OH-MeOH/CH$_2$Cl$_2$ 0-20%) gave the desired product as a pale oil (15 mg, 17%). $^1$H NMR (CDCl$_3$, 400 MHz) δ: 1.34 (s, 3H), 1.92 (bs, 2H), 3.08 (t, J=6.0 Hz, 1H), 3.21 (t, J=6.0 Hz, 1H), 7.29 (m, 2H), 3.34 (m, 3H), 7.41-7.5 (m, 3H), 7.77 (d, J=6.0 Hz, 1H), 8.99 (d, J=6.0 Hz, 1H).

The requisite intermediate for the preparation of this compound was prepared as follows.

a. Preparation of Compound

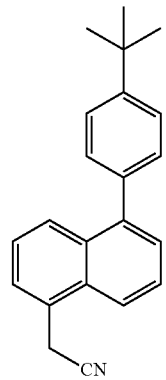 [SMILES: CC(C)(C)c1ccc(-c2cccc3c(CC#N)cccc23)cc1]

To a solution of (5-(4-(t-butyl)phenyl)naphthalen-1-yl) methanol (1.0 g, 3.4 mmol) and triethylamine (0.80 mL, 5.8 mmol) in CH$_2$Cl$_2$ (25 mL) at 0° C. under nitrogen was added methanesulfonyl chloride (0.33 mL, 4.3 mmol) slowly, the resultant mixture was stirred at 0° C. for 30 min. The reaction was quenched with aq. NaHCO$_3$ solution and extracted with EtOAc (3×30 mL). The organic solution was dried over MgSO$_4$ and concentrated to an oil.

A mixture of the oil residue prepared above and KCN (0.31 g, 4.8 mmol) in DMSO (10 mL) was stirred at room temperature overnight. Water was added, the reaction mixture was extracted with EtOAc (3×80 mL). The EtOAc solution was washed with water and brine, dried over over MgSO$_4$, filtered and concentrated. Purification with flash column (SiO$_2$, EtOAc/hexane 10-50%) gave the desired product as a pale oil (0.51 g, 50%). $^1$H NMR (CDCl$_3$, 400 MHz) δ: 1.46 (s, 9H), 4.24 (s, 2H).

b. Preparation of Compound

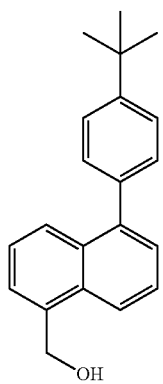

A mixture of 5-(4-(t-butyl)phenyl)-1-naphthaldehyde (0.75 g, 2.6 mmol) and NaBH$_4$ (70 mg, 1.85 mmol) in 95% EtOH (20 mL) was stirred at room temperature for 1 h. It was filtered and the filtrate was concentrated and redissolved in EtOAc (80 mL). The EtOAc solution was washed with aq. NaHCO$_3$ and brine, dried over over MgSO$_4$, filtered and concentrated. Purification with flash column (SiO$_2$, EtOAc/hexane 10-30%) gave the desired product as a white solid (0.74 g, 99%). $^1$H NMR (CDCl$_3$, 300 MHz) δ: 1.41 (S, 9H), 5.20 (d, J=3.0 Hz, 2H), 7.36-7.62 (m, 8H), 7.94 (d, J=9.0 Hz, 1H), 8.16 (d, J=9.0 Hz, 1H).

c. Preparation of Compound

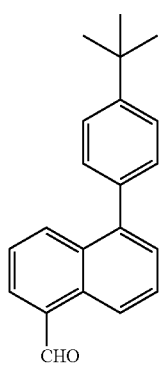 [SMILES: CC(C)(C)c1ccc(-c2cccc3c(C=O)cccc23)cc1]

To a nitrogen-flushed mixture of 5-bromo-1-naphthaldehyde (0.50 g, 2.1 mmol) (*J. Med. Chem.*, 36, 2810, 1993), 4-t-butylphenylboronic acid (0.47 g, 2.6 mmol) and potassium carbonate (0.88 g, 6.4 mmol) in a mixture of dioxane (15 mL) and water (3 mL) at room temperature under nitrogen was added tetrakis(triphenylphosphine)-palladium (73 mg, 0.06 mmol), the resultant mixture was heated at 100° C. for 5 h. It was dried over MgSO$_4$, filtered and concentrated and purified with flash column (SiO$_2$, EtOAc/hexane 10-50%) to give the desired product as a pale solid (0.49 g, 88%). $^1$H NMR (CDCl$_3$, 300 MHz) δ: 1.42 (S, 9H), 7.39-7.42 (m, 2H), 7.51-7.60 (m, 4H), 7.70-7.76 (m, 1H), 8.00 (d, J=9.0 Hz, 1H), 8.24 (d, J=9.0 Hz, 1H), 9.29 (d, J=6.0 Hz, 1H), 10.45 (S, 1H).

Example 37

Preparation of Compound

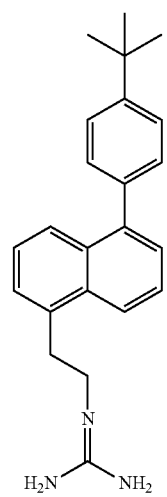 [SMILES: CC(C)(C)c1ccc(-c2cccc3c(CCN=C(N)N)cccc23)cc1]

The Intermediate a for Example 37 (40 mg, 0.09 mmol) in a mixture of TFA/CH$_2$Cl$_2$ (0.8/0.8 mL) was set at room temperature overnight. All TFA/CH$_2$Cl$_2$ were removed under reduced pressure, the residue was purified with flash column (SiO$_2$, 3% NH4OH-MeOH/CH$_2$Cl$_2$ 0-15%) gave the desired product as a white solid (29 mg, 96%). $^1$H NMR (CD$_3$OD, 300 MHz) δ: 1.43 (S, 9H), 3.46 (t, J=6.0 Hz, 2H), 3.66 (t, J=6.0 Hz, 2H), 7.36-7.45 (m, 5H), 7.55-7.65 (m, 3H), 7.81 (d, J=9.0 Hz, 1H), 8.13 (d, J=9.0 Hz, 1H).

The requisite intermediate for the preparation of this compound was prepared as follows.

a. Preparation of Compound

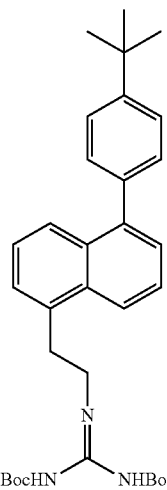

The compound of Example 36 (35 mg, 0.12 mmol) and triethylamine (0.04 mL, 0.29 mmol) in CH$_2$Cl$_2$ (6 mL) was added di-Boc guanidine triflate (55 mg, 0.14 mmol). The reaction mixture was stirred at room temperature overnight. The reaction mixture was concentrated to an oily residue. Purification with flash column (SiO$_2$, EtOAc/hexane 10-20%) gave the desired product as a white solid (51 mg, 81%). $^1$H NMR (CDCl$_3$, 300 MHz) δ: 1.41 (S, 9H), 1.43 (S, 9H), 1.56 (S, 9H), 3.43 (t, J=6.0 Hz, 2H), 3.8 (m, 2H), 7.33-7.46 (m, 4H), 7.50-7.62 (m, 3H), 7.87 (dd, J=6.0 Hz, 3.0 Hz, 1H), 8.30 (d, J=9.0 Hz, 1H), 8.50 (t, J=3.0 Hz, 1H).

Example 38

Preparation of Compound

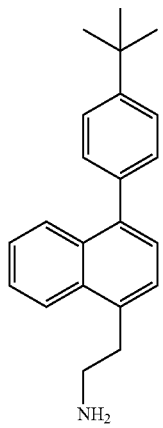 [SMILES: CC(C)(C)c1ccc(-c2ccc(CCN)c3ccccc23)cc1]

A solution of Intermediate c of Example 38 (0.30 g, 0.90 mmol) in THF (5 mL) was added dropwise to a solution of LiAlH$_4$ (1.0 M/THF, 2.7 mL) in THF (5 mL) at 0° C. under nitrogen, the resultant mixture was stirred at room temperature overnight. It was cooled to 0° C. and carefully treated with aq NaOH and extracted with EtOAc (3×20 mL) and dried over MgSO$_4$, filtered and concentrated. Purification with flash column (SiO$_2$, 3% NH$_4$OH-MeOH/CH$_2$Cl$_2$ 0-20%) gave the desired product as a white solid (75 mg, 27%). $^1$H NMR (CD$_3$OD, 300 MHz) δ: 1.40 (S, 9H), 3.08 (t, J=6.0 Hz, 2H), 3.33 (m, 2H), 7.29-7.43 (m, 5H), 7.49-7.57 (m, 3H), 7.89 (d, J=6.0 Hz, 1H), 8.17 (d, J=6.0 Hz, 1H).

The requisite intermediate for the preparation of this compound was prepared as follows.

a. Preparation of Compound

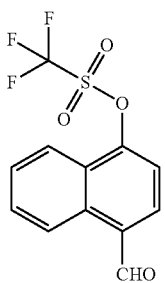 [SMILES: O=Cc1ccc(OS(=O)(=O)C(F)(F)F)c2ccccc12]

To a solution of 4-hydroxynaphalenaldehyde (0.50 g, 2.8 mmol) and triethylamine (0.78 mL, 5.6 mmol) in CH$_2$Cl$_2$ (10 mL) at −62° C. under nitrogen was added triflate anhydride (0.70 mL, 4.2 mmol) slowly, the resultant mixture was stirred at −60° C. for 30 min. The reaction was quenched with aq. NaHCO$_3$ solution and extracted with methylenechloride (3×30 mL). The organic solution was dried over MgSO$_4$ and concentrated to an oil. Purification by flash chromatography (SiO$_2$, EtOAc/hexane 10-60%) gave the desired product as a pale solid (0.56 g, 66%). $^1$H NMR (CDCl$_3$, 300 MHz) δ: 7.65 (d, J=9.0 Hz, 1H), 7.74-7.85 (m, 2H), 8.05 (d, J=6.0 Hz, 1H), 8.18 (d, J=9.0 Hz, 1H), 9.32 (d, J=9.0 Hz, 1H), 10.42 (S, 1H).

b. Preparation of Compound

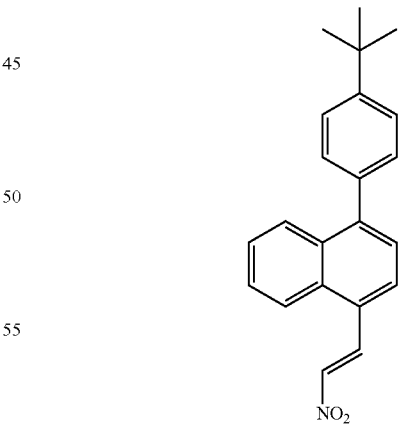

To a nitrogen-flushed mixture of 4-formylnaphthalen-1-yl trifluoromethanesulfonate (0.56 g, 1.8 mmol), 4-t-butylphenylboronic acid (0.60 g, 3.3 mmol) and potassium carbonate (0.85 g, 6.2 mmol) in a mixture of acetonitrile (10 mL) and water (2 mL) at room temperature under nitrogen were added palladium acetate (30 mg, 0.13 mmol) and Xphos (120 mg, 0.25 mmol), the resultant mixture was heated at 90° C. for 6 h. It was dried over MgSO$_4$, filtered and concentrated to a crude product. Purification by flash chromatography (SiO$_2$, EtOAc/hexane 10-50%) gave the desired product as a pale solid (0.52 g, 99%). $^1$H NMR (CDCl$_3$, 300 MHz) δ: 1.43 (S, 9H), 7.41-7.49 (m, 6H), 7.54 (m, 1H), 7.74 (d, J=9.0 Hz, 1H), 8.01 (d, J=9.0 Hz, 1H), 8.16 (d, J=9.0 Hz, 1H), 10.46 (S, 1H).

c. Preparation of Compound

A mixture of 4-(4-t-butylphenyl)-1-naphthaldehyde (0.26 g, 0.9 mmol) and ammonium acetate (80 mg, 1.0 mmol) in nitromethane (3 mL) was heated at reflux for 2 h. The reaction mixture was concentrated to an oil residue. Purification with flash column (SiO$_2$, EtOAc/hexane 5-30%) gave the desired product as a pale oil (0.30 g, 100%). $^1$H NMR (CDCl$_3$, 300 MHz) δ: 1.43 (S, 9H), 7.39-7.56 (m, 6H), 7.66-7.73 (m, 2H), 7.81 (dd, J=9.0 Hz, 3.0 Hz, 1H), 8.05 (d, J=6.0 Hz, 1H), 8.21 (d, J=6.0 Hz, 1H), 8.91 (dd, J=9.0 Hz, 3.0 Hz, 1H).

Example 39

Preparation of Compound

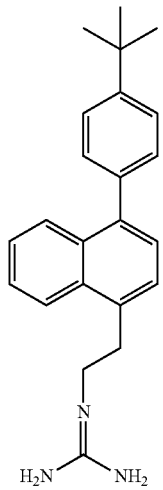 [SMILES: CC(C)(C)c1ccc(-c2ccc(CCN=C(N)N)c3ccccc23)cc1]

A mixture of Intermediate a of Example 39 (36 mg, 0.07 mmol) in a mixture of TFA/CH$_2$Cl$_2$ (0.8/0.8 mL) was set at room temperature overnight. All TFA/CH$_2$Cl$_2$ were removed under reduced pressure, the residue was purified with flash column (SiO$_2$, 3% NH$_4$OH-MeOH/CH$_2$Cl$_2$ 0-20%) gave the desired product to give the desired product as a white solid (21 mg, 91%). $^1$H NMR (CD$_3$OD, 300 MHz) δ: 1.43 (S, 9H), 3.44 (t, J=6.0 Hz, 2H), 3.66 (t, J=6.0 Hz, 2H), 7.38 (m, 3H), 7.47 (m, 2H), 7.57 (m, 3H), 7.92 (d, J=6.0 Hz, 1H), 8.16 (d, J=6.0 Hz, 1H).

The requisite intermediate for the preparation of this compound was prepared as follows.

a. Preparation of Compound

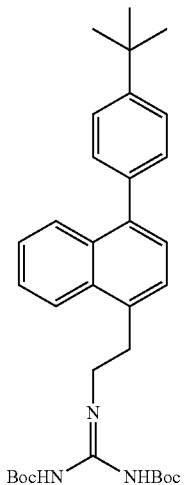

The compound of Example 38 2-(4-(4-(t-butyl)phenyl) naphthalen-1-yl)ethanamine, (25 mg, 0.08 mmol) and triethylamine (0.03 mL, 0.22 mmol) in CH$_2$Cl$_2$ (4 mL) was added di-Boc guanidine triflate (40 mg, 0.10 mmol). The reaction mixture was stirred at room temperature overnight. The reaction mixture was concentrated to an oil residue. Purification with flash column (SiO$_2$, EtOAc/hexane 5-10%) gave the desired product as a white solid (38 mg, 84%). $^1$H NMR (CDCl$_3$, 300 MHz) δ: 1.42 (S, 9H), 1.49 (S, 9H), 1.55 (S, 9H), 3.42 (t, J=6.0 Hz, 2H), 3.82 (m, 2H), 7.34-7.56 (m, 7H), 8.18 (d, J=6.0 Hz, 1H), 8.35 (d, J=9.0 Hz, 1H), 8.50 (m, 1H).

Example 40

Preparation of Compound

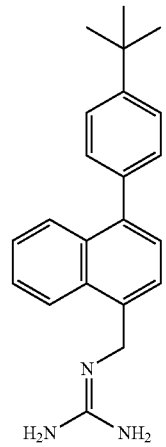 [SMILES: CC(C)(C)c1ccc(-c2ccc(CN=C(N)N)c3ccccc23)cc1]

A mixture of Intermediate b of Example 40 (70 mg, 0.13 mmol) in a mixture of TFA/CH$_2$Cl$_2$ (0.5/0.5 mL) was set at room temperature overnight. All TFA/CH$_2$Cl$_2$ were removed under reduced pressure, the residue was purified with flash column (SiO$_2$, 3% NH$_4$OH-MeOH/CH$_2$Cl$_2$ 0-20%) gave the desired product to give the desired product as a white solid (35 mg, 80%). $^1$H NMR (CDCl$_3$, 300 MHz) δ: 1.41 (S, 9H), 7.39 (m, 2H), 7.47 (d, J=9.0 Hz, 1H), 7.52 (d, J=9.0 Hz, 1H), 7.60 (m, 4H), 7.90 (d, 1H), 7.98 (d, J=9.0 Hz, 1H).

The requisite intermediate for the preparation of this compound was prepared as follows.

a. Preparation of Compound

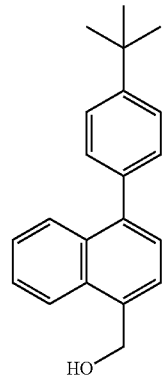 [SMILES: CC(C)(C)c1ccc(-c2ccc(CO)c3ccccc23)cc1]

A mixture of 4-(4-tert-butylphenyl)-1-naphthaldehyde (0.26 g, 0.90 mmol) and NaBH$_4$ (70 mg, 1.85 mmol) in 95% EtOH (10 mL) was stirred at room temperature for 2 h. It was filtered and the filtrate was concentrated and redissolved in CH$_2$Cl$_2$ (40 mL). The CH$_2$Cl$_2$ solution was washed with aq. NaHCO$_3$ and brine, dried over over MgSO$_4$, filtered and concentrated. Purification with flash column (SiO$_2$, EtOAc/hexane 10-30%) gave the desired product as a white solid (0.16 g, 63%). $^1$H NMR (CDCl$_3$, 300 MHz) δ: 1.42 (S, 9H), 1.76 (t, 1H), 5.21 (d, J=6.0 Hz, 2H), 7.40-7.59 (m, 8H), 8.0 (d, J=6.0 Hz, 1H), 8.20 (d, J=6.0 Hz, 1H).

b. Preparation of Compound

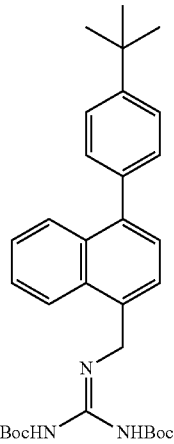

To a mixture of 4-(4.(t-butyl)phenyl)naphthalen-1-yl)methanol (40 mg, 0.14 mmol), di-Boc guanidine (70 mg, 0.27 mmol) and Ph$_3$P (60 mg, 0.23 mmol) in toluene (3 mL) at 0° C. under nitrogen was added DIAD (0.04 mL, 0.20 mmol). The reaction mixture was stirred at room temperature overnight. The reaction mixture was concentrated to an oil residue. Purification with flash column (SiO$_2$, EtOAc/hexane 0-30%) gave the desired product as a yellow solid (70 mg, 97%). $^1$H NMR (CDCl$_3$, 300 MHz) δ: 1.44 (S, 9H), 1.45 (S, 9H), 1.48 (S, 9H), 5.78 (S, 2H), 7.23 (d, J=6.0 Hz, 1H), 7.30-7.52 (m, 7H), 8.06 (m, 2H), 9.51 (bs, 2H).

Example 41

Preparation of Compound

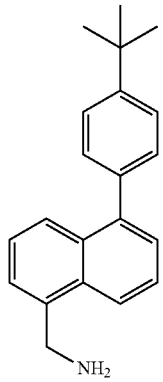 [SMILES: CC(C)(C)c1ccc(-c2cccc3c(CN)cccc23)cc1]

To a solution of crude 1-(azidomethyl)-5-(4-t-butyl)phenyl)naphthalene (50 mg) in 5.0 ml of THF and 0.5 ml of water was added 300 mg of the polymer supported PPh$_3$. The reaction mixture was stirred at room temperature overnight after which the solids were filtered off and purified by column chromatography to furnish the desired amine. $^1$H NMR (CDCl$_3$, 400 MHz) δ: 1.34 (s, 9H), 1.58 (bs, 2H), 4.31 (s, 2H), 7.29-7.44 (m, 7H), 7.51 (m, 1H), 7.80 (d, J=8.0 Hz, 1H), 8.03 (d, J=8.0 Hz, 1H).

The requisite intermediate for the preparation of this compound was prepared as follows.

a. Preparation of Compound

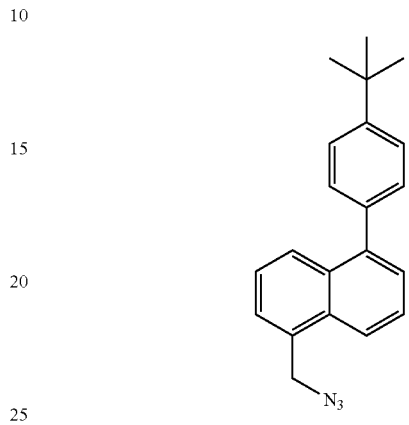

To a mixture of the alcohol (66 mg, 0.23 mmol) in 1:4 (CCl$_4$:DMF) was added sodium azide (18 mg, 0.27 mmol) and PPh$_3$ (125 mg, 0.48 mmol). The reaction mixture was heated at 90° C. overnight. Removal of the solvent and chromatography yielded azido compound partially mixed with PPh$_3$. The crude mixture was not purified and was used directly to form Example 41.

Example 42

Preparation of Compound

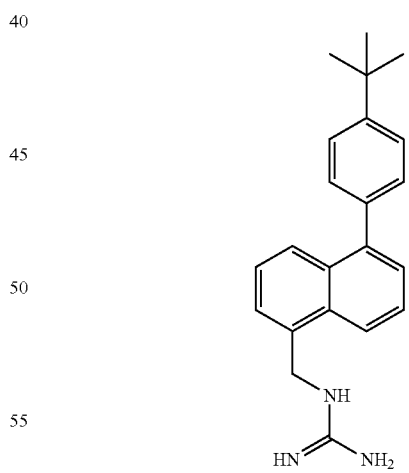

A mixture of diBoc protected napthalene, Intermediate a of Example 42 (20 mg, 0.07 mmol) in a mixture of TFA/CH$_2$Cl$_2$ (0.5/0.5 mL) was set at room temperature overnight. All TFA/CH$_2$Cl$_2$ were removed under reduced pressure, the residue was purified with flash column (SiO$_2$, 3% NH$_4$OH-MeOH/CH$_2$Cl$_2$ 0-20%) gave the desired product to give the desired product as a white solid (17 mg). $^1$H NMR (CD$_3$OD, 400 MHz) δ: 1.41 (s, 9H), 4.89 (s, 2H), 7.36-7.56 (m, 5H), 7.6-8.0 (m, 5H).

The requisite intermediate for the preparation of this compound was prepared as follows.

a. Preparation of Compound

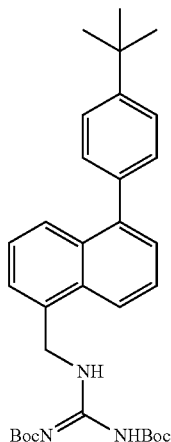

To a mixture of alcohol (106 mg, 0.364 mmol), di-Bocguanidine (132 mg, 0.52 mmol) and Ph₃P (100 mg) in toluene (3 mL) at 0° C. under nitrogen was added DIAD (0.1 mL). The reaction mixture was stirred at room temperature overnight. The reaction mixture was concentrated to an oil residue. Purification with flash column (SiO₂, EtOAc/hexane 0-30%) gave the desired product (104 mg). ¹H NMR (CDCl₃, 400 MHz) δ: 1.20 (s, 9H), 1.43 (s, 9H), 1.46 (s, 9H), 5.77 (s, 2H), 7.18 (d, J=4.0 Hz, 1H), 7.36-7.39 (m, 2H), 7.43-7.47 (m, 2H), 7.51-7.59 (m, 3H), 7.87 (d, J=8.0 Hz, 1H), 8.06 (d, J=8.0 Hz, 1H), 9.5 (bs, 1H), 9.55 (bs, 1H).

Example 43

Preparation of Compound

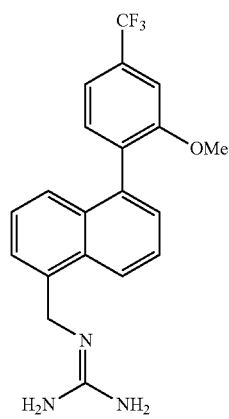 [SMILES: COc1cc(C(F)(F)F)ccc1-c1cccc2c(CN=C(N)N)cccc12]

To a cooled solution of di-Boc protected guanidine compound, Intermediate c in Example 43 (55 mg) in 1.5 mL CH₂CL₂ was added 1.5 mL trifluoroacetic acid. Reaction was taken off ice bath and stirred at room temperature for 2 hours then solvents were evaporated. Chromatography achieved using ISCO max gradient 10% MeOH/methylene chloride yielding product as a white solid (31 mg, 86% yield). ¹H NMR (400 MHz) (MeOD₄) δ 7.96 (d, J=8 Hz, 1H), 7.59-7.55 (m, 1H), 7.43-7.36 (m, 2H), 7.34-7.28 (m, 5H), 4.84-4.82 (m, 2H), 3.62 (s, 3H). ¹³C NMR (100 MHz) (MeOD₄) δ 159.08, 158.84, 138.10, 134.98, 133.69, 133.24, 132.89, 132.44, 128.62, 128.00, 127.26, 126.98, 126.52, 124.08, 118.46, 118.42, 108.89, 56.25, 44.76.

The requisite intermediate for the preparation of this compound was prepared as follows.

a. Preparation of Compound

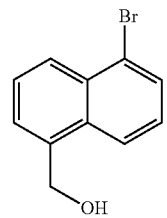 [SMILES: OCc1cccc2c(Br)cccc12]

To a solution of 5-bromo-1-naphthaldehyde (500 mg) in 20 mL ethanol was slowly added NaBH₄ (243 mg, 3 eq.), and reaction was stirred for 30 minutes at room temperature. Acetone (2 ml) was then added and solution was filtered through filter paper. Filtrate was concentrated then re-dissolved in methylene chloride and washed with H₂O. The organic layer was dried over sodium sulfate and concentrated to yield pure product as a white solid (473 mg, 94% yield). ¹H NMR (400 MHz) (CDCl₃) δ 8.19-8.17 (m, 1H), 8.04 (d, J=8 Hz, 1H), 7.75-7.73 (m, 1H), 7.51-7.46 (m, 2H), 7.33-7.29 (m, 1H), 5.08 (d, J=8 Hz, 2H). ¹³C NMR (100 MHz) (CDCl₃) δ136.71, 132.59, 132.38, 130.10, 127.76, 126.80, 126.58, 126.17, 123.62, 63.63.

b. Preparation of Compound

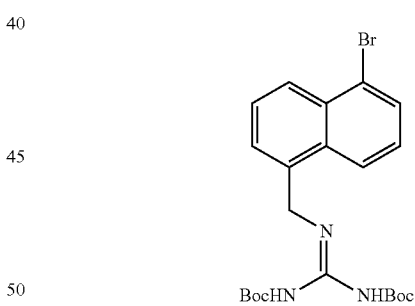

(5-Bromonaphthalen-1-yl)methanol (275 mg), PPh₃ (456 mg, 1.5 eq.), and 1,3-bis(t-butoxycarbonyl)guanidine (601 mg, 2 eq.) in 5 mL toluene at 0° C. was added diisopropylazodicarboxylate (0.34 mL, 1.5 eq.) drop wise over 15 minutes. Reaction was stirred for 3 hours at room temperature then 2 drops H₂O were added, and the solution was concentrated. Chromatography achieved using ISCO max gradient 20% EtOAc/hexane yielding product as a white solid (493 mg, 90% yield). ¹H NMR (400 MHz) (CDCl₃) δ 9.47 (bs, 2H), 8.11 (d, J=8 Hz, 1H), 7.91 (d, J=8 Hz, 1H), 7.73 (d, J=8 Hz, 1H), 7.46 (t, J=16 Hz, 1H), 7.28 (t, J=16 Hz, 1H), 7.16 (d, J=8 Hz, 1H), 5.62 (s, 2H), 1.36 (s, 9H), 1.07 (s, 9H). ¹³C NMR (100 MHz) (CDCl₃) δ160.83, 154.95, 135.04, 131.95, 129.89, 126.71, 126.26, 126.16, 123.71, 122.87, 122.73, 84.19, 79.03, 45.10, 28.23, 27.61.

c. Preparation of Compound

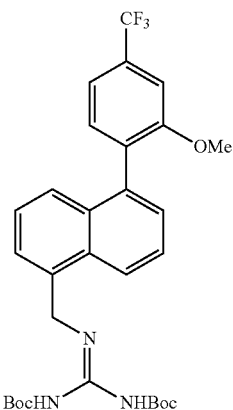 [SMILES: COc1cc(C(F)(F)F)ccc1-c1cccc2c(CN=C(NC(=O)OC(C)(C)C)NC(=O)OC(C)(C)C)cccc12]

Intermediate b of Example 43, the Di-boc guanidine compound (100 mg), 2-methoxy-4-trifluoromethylphenylboronic acid (55 mg, 1.2 eq.), Pd(OAc)$_2$ (5 mg, 0.1 eq.), Xphos (20 mg, 0.2 eq.), and K$_2$CO$_3$ (87 mg, 3 eq.) were combined in a flask with 3 mL dioxane and 1 mL H$_2$O and degassed. Reaction mixture was then refluxed at 100° C. for 2 hours. Solution was cooled to room temperature then diluted with EtOAc and washed with saturated NaHCO$_3$. The organic layer was dried over sodium sulfate and concentrated. Chromatography achieved using ISCO max gradient 15% EtOAc/hexane yielding product as a clear oil (55 mg, 46% yield). $^1$H NMR (400 MHz) (CDCl$_3$) δ 9.55 (bs, 1H), 9.48 (bs, 1H), 8.08 (d, J=12 Hz, 1H), 7.61-7.57 (m, 1H), 7.42-7.33 (m, 5H), 7.27 (s, 1H), 7.19 (d, J=4 Hz, 1H), 5.86-5.70 (m, 2H), 3.75 (s, 3H), 1.47 (s, 9H), 1.21 (s, 9H). $^{13}$C NMR (100 MHz) (CDCl$_3$) δ163.81, 160.94, 157.44, 155.13, 136.18, 134.66, 132.17, 131.88, 126.96, 125.30, 124.98, 123.00, 121.92, 84.04, 78.96, 55.76, 45.37, 28.25, 27.61.

Example 44

Preparation of Compound

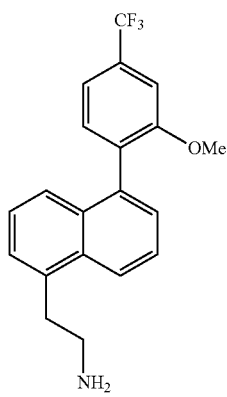 [SMILES: COc1cc(C(F)(F)F)ccc1-c1cccc2c(CCN)cccc12]

A flask was charged with LAH (15.6 mg, 2 eq.) in 3 mL anhydrous ether. To the suspension was added 2-(5-(2-methoxy-4-(trifluoromethyl)phenyl)naphthalen-1-yl)acetonitrile (70 mg) in 2 mL anhydrous ether drop wise. Reaction was stirred at room temperature for 30 minutes then placed on an ice bath. H$_2$O (10 drops) was carefully dropped in to react with the remaining LAH then 1M NaOH was added to get solution to pH>9. Solution was then diluted with additional ether and extracted from aqueous. The organic layer was dried over sodium sulfate and concentrated. Chromatography achieved using ISCO max gradient 10% MeOH/methylene chloride yielding product as clear oil (31 mg, 44% yield). $^1$H NMR (400 MHz) (CDCl$_3$) δ 8.15 (d, J=8 Hz, 1H), 7.62-7.58 (m, 1H), 7.43-7.32 (m, 6H), 7.28 (s, 1H), 3.77 (s, 3H), 3.33-3.29 (m, 2H), 3.19 (t, J=12 Hz, 2H). $^{13}$C NMR (100 MHz) (CDCl$_3$) δ157.47, 136.32, 135.94, 133.69, 132.31, 132.23, 132.04, 126.98, 126.78, 125.49, 125.24, 124.98, 123.94, 117.39, 117.36, 107.73, 55.78, 42.89, 37.45.

The requisite intermediate for the preparation of this compound was prepared as follows.

a. Preparation of Compound

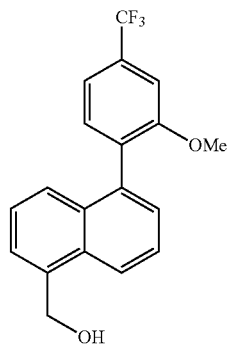 [SMILES: COc1cc(C(F)(F)F)ccc1-c1cccc2c(CO)cccc12]

(5-Bromonaphthalen-1-yl)methanol (150 mg), 2-methoxy-4-trifluoromethylphenylboronic acid (167 mg, 1.2 eq.), Pd(OAc)$_2$ (14 mg, 0.1 eq.), Xphos (60 mg, 0.2 eq.), and K$_2$CO$_3$ (262 mg, 3 eq.) were combined in a flask with 5 mL dioxane and 1.6 mL H$_2$O and degassed. Reaction mixture was then refluxed at 100° C. for 2 hours. Solution was cooled to room temperature then diluted with EtOAc and washed with saturated NaHCO$_3$. The organic layer was dried over sodium sulfate and concentrated. Chromatography achieved using ISCO max gradient 35% EtOAc/hexane yielding product as a clear oil (55 mg, 86% yield). $^1$H NMR (400 MHz) (CDCl$_3$) δ 8.24-8.22 (m, 1H), 7.64 (dd, J=8 Hz, J=8 Hz, 1H), 7.55 (d, J=8 Hz, 1H), 7.51 (d, J=8 Hz, 1H), 7.45-7.37 (m, 4H), 7.29 (s, 1H), 5.22 (s, 2H), 3.76 (s, 3H). $^{13}$C NMR (100 MHz) (CDCl$_3$) δ157.45, 136.48, 136.27, 133.49, 132.21, 132.16, 131.47, 131.29, 131.15, 127.29, 126.61, 125.77, 125.48, 125.41, 123.88, 122.79, 117.44, 117.40, 107.72, 63.94, 55.76.

b. Preparation of Compound

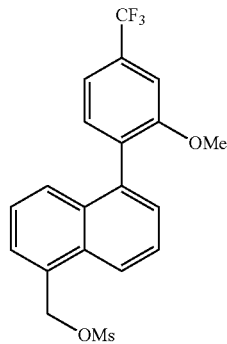 [SMILES: COc1cc(C(F)(F)F)ccc1-c1cccc2c(COS(C)(=O)=O)cccc12]

To a solution of (5-(2-methoxy-4-(trifluoromethyl)phenyl) naphthalene-1-yl)methanol (180 mg) and Et₃N (0.15 mL, 2 eq.) in 5 mL methylene chloride was added MsCl (0.06 mL, 1.5 eq.), and the reaction mixture was stirred overnight at room temperature. Reaction was then diluted with methylene chloride and washed with saturated NaHCO₃. The organic layer was dried over sodium sulfate and concentrated. No further purification required, crude product was taken to next step.

c. Preparation of Compound

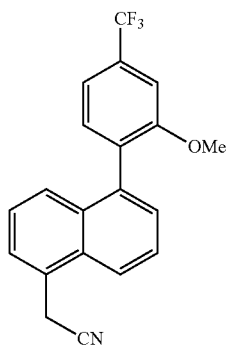

(5-(2-Methoxy-4-(trifluoromethyl)phenyl)naphthalene-1-yl)methyl methanesulfonate (150 mg) was combined with KCN (48 mg, 2 eq.) in 3 mL anhydrous DMF and stirred at room temperature overnight. Reaction mixture was then diluted with EtOAc and washed with 10% LiCl solution. The organic layer was dried over sodium sulfate and concentrated. Chromatography achieved using ISCO max gradient 30% EtOAc/hexane yielding product as clear oil (125 mg, quanitative). ¹H NMR (400 MHz) (CDCl₃) δ 7.97 (d, J=12 Hz, 1H), 7.72-7.68 (m, 1H), 7.63 (d, J=8 Hz, 1H), 7.56 (d, J=8 Hz, 1H), 7.47 (d, J=4 Hz, 1H), 7.44-7.40 (m, 3H), 7.30 (s, 1H), 4.21 (s, 2H), 3.77 (s, 3H). ¹³C NMR (100 MHz) (CDCl₃) δ157.41, 136.80, 133.01, 132.18, 132.16, 130.87, 127.20, 126.56, 126.50, 126.06, 125.53, 122.57, 117.66, 117.50, 117.46, 107.80, 107.77, 55.76, 22.01.

Example 45

Preparation of Compound

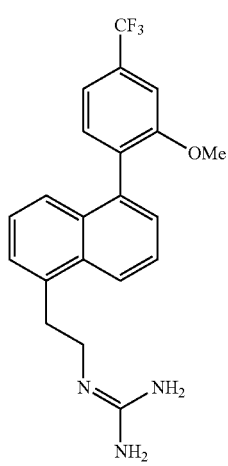 [SMILES: COc1cc(C(F)(F)F)ccc1-c1cccc2c(CCN=C(N)N)cccc12]

To a cooled solution of Intermediate a of Example 45, the di-Boc protected guanidine compound (35 mg) in 1 mL methylene chloride was added 1 mL trifluoroacetic acid. Reaction was taken off ice bath and stirred at room temperature for 2 hours then solvents were evaporated. Chromatography achieved using ISCO max gradient 10% MeOH/methylene chloride yielding product as a clear oil (19 mg, 83% yield). ¹H NMR (400 MHz) (MeOD₄) δ 8.16 (d, J=12 Hz, 1H), 7.66-7.62 (m, 1H), 7.44-7.34 (m, 7H), 3.74 (s, 3H), 3.65 (t, J=16 Hz, 2H), 3.46-3.42 (m, 2H). ¹³C NMR (100 MHz) (MeOD₄) δ159.10, 158.71, 138.00, 135.51, 135.25, 133.71, 133.29, 133.18, 128.27, 128.09, 127.01, 126.76, 126.64, 126.58, 124.49, 118.39, 118.35, 108.83, 56.23, 43.18, 33.14.

The requisite intermediate for the preparation of this compound was prepared as follows.

a. Preparation of Compound

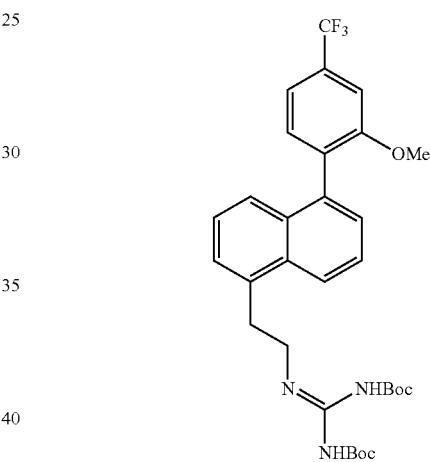

2-(5-(2-Methoxy-4-(trifluoromethyl)phenyl)naphthalen-1-yl)ethanamine (25 mg), 1,3-di-Boc-2-(trifluoromethylsulfonyl)-guanidine (34 mg, 1.2 eq.), and Et₃N (0.01 mL, 1.2 eq.) in 2.5 mL methylene chloride were stirred at room temperature overnight. Reaction mixture was then diluted with methylene chloride and washed with NaHCO₃. The organic layer was dried over sodium sulfate and concentrated. Chromatography achieved using ISCO max gradient 30% EtOAc/hexane yielding product as a clear oil (37 mg, 88% yield). ¹H NMR (400 MHz) (CDCl₃) δ 11.50 (bs, 1H), 8.50 (t, J=12 Hz, 1H), 8.38 (d, J=8 Hz, 1H), 7.62 (dd, J=8 Hz, J=8 Hz, 1H), 7.43-7.36 (m, 5H), 7.35-7.31 (m, 1H), 7.27 (s, 1H), 3.85-3.79 (m, 2H), 3.76 (s, 3H), 3.50-3.37 (m, 2H), 1.57 (s, 9H), 1.51 (s, 9H). ¹³C NMR (100 MHz) (CDCl₃) δ163.67, 157.50, 156.14, 153.21, 136.15, 134.95, 133.77, 132.24, 132.05, 127.08, 126.75, 125.49, 125.46, 125.30, 124.34, 117.33, 83.03, 79.10, 55.77, 41.78, 32.96, 28.38, 28.06.

Example 46

Preparation of Compound

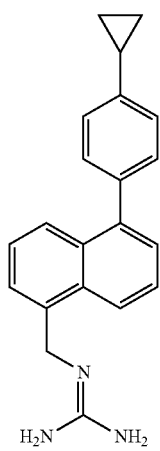 [SMILES: NC(N)=NCc1cccc2c(-c3ccc(C4CC4)cc3)cccc12]

To a cooled solution of Intermediate b of Example 46, di-Boc protected guanidine compound (35 mg) in 1 mL methylene chloride was added 1 mL trifluoroacetic acid. Reaction was taken off ice bath and stirred at room temperature for 2 hours then solvents were evaporated. Chromatography achieved using ISCO max gradient 10% MeOH/methylene chloride yielding product as a tan solid (18 mg, 20% yield over 2 steps). $^1$H NMR (400 MHz) (MeOD$_4$) δ 8.02-8.00 (m, 1H), 7.90-7.88 (m, 1H), 7.67-7.63 (m, 1H), 7.54-7.50 (m, 1H), 7.47-7.42 (m, 1H), 7.33-7.31 (m, 2H), 7.24-7.22 (m, 2H), 4.93 (s, 2H), 2.06-1.99 (m, 1H), 1.06-1.02 (m, 2H), 0.79-0.76 (m, 2H). $^{13}$C NMR (100 MHz) (MeOD$_4$) δ158.85, 144.86, 142.73, 139.06, 133.62, 132.84, 130.95, 129.42, 128.20, 128.13, 127.31, 126.69, 126.63, 126.38, 123.27, 44.69, 15.98, 9.74.

The requisite intermediate for the preparation of this compound was prepared as follows.

a. Preparation of Compound

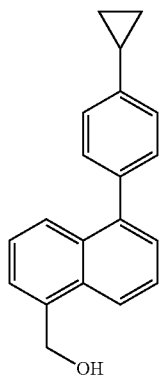 [SMILES: OCc1cccc2c(-c3ccc(C4CC4)cc3)cccc12]

(5-(4-Bromophenyl)naphthalen-1-yl)methanol (130 mg), cyclopropylboronic acid (71 mg, 2 eq.), Pd(OAc)$_2$ (5 mg, 0.05 eq.), tricyclohexylphosphine (12 mg, 0.1 eq.), and K$_2$PO$_4$ (308 mg, 3.5 eq.) were combined in a flask with 3 mL toluene and 1 mL H$_2$O and degassed. Reaction mixture was then refluxed at 100° C. for 3 hours. Solution was cooled to room temperature then diluted with EtOAc and washed with saturated NaHCO$_3$. The organic layer was dried over sodium sulfate and concentrated. Chromatography achieved using ISCO max gradient 35% EtOAc/hexane yielding product as a brown oil (86 mg, 75% yield). $^1$H NMR (400 MHz) (CDCl$_3$) δ 8.17-8.15 (m, 1H), 7.96-7.94 (m, 1H), 7.61 (dd, J=8 Hz, J=8 Hz, 1H), 7.56-7.53 (m, 2H), 7.49-7.47 (m, 1H), 7.43-7.40 (m, 2H), 7.25-7.23 (m, 2H), 5.19 (s, 2H), 2.08-2.01 (m, 1H), 1.11-1.06 (m, 2H), 0.87-0.83 (m, 2H). $^{13}$C NMR (100 MHz) (CDCl$_3$) δ143.16, 141.02, 138.03, 136.48, 132.17, 131.62, 130.13, 130.05, 138.27, 126.80, 125.84, 125.55, 125.36, 125.27, 123.00, 63.90, 15.28, 9.41.

b. Preparation of Compound

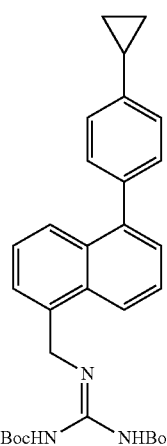

(5-(4-Cyclopropylphenyl)naphthalen-1-yl)methanol (80 mg), PPh$_3$ (115 mg, 1.5 eq.), and 1,3-bis(t-butoxycarbonyl)guanidine (151 mg, 2 eq.) in 3 mL toluene at 0° C. was added diisopropylazodicarboxylate (0.09 mL, 1.5 eq.) drop wise over 15 minutes. Reaction was stirred for 3 hours at room temperature then 2 drops H$_2$O were added, and the solution was concentrated. Solid was then re-dissolved in methylene chloride and passed through silica column and resulting crude product was taken to next step.

Example 47

Preparation of Compound

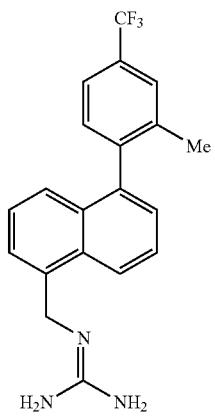 [SMILES: Cc1cc(C(F)(F)F)ccc1-c1cccc2c(CN=C(N)N)cccc12]

To a cooled solution of di-Boc protected guanidine compound (80 mg) in 1 mL methylene chloride was added 1 mL trifluoroacetic acid. Reaction was taken off ice bath and stirred at room temperature for 2 hours then the solvents were evaporated. Chromatography achieved using ISCO max gradient 10% MeOH/methylene chloride yielding product as a clear oil (50 mg, quantitative). $^1$H NMR (400 MHz) (MeOD$_4$) δ 8.11 (d, J=8 Hz, 1H), 7.74-7.69 (m, 2H), 7.64 (d, J=8 Hz, 1H), 7.57-7.55 (m, 1H), 7.47-7.37 (m, 4H), 4.96 (m, 2H), 2.06 (s, 3H). $^{13}$C NMR (100 MHz) (MeOD$_4$) δ158.91, 145.64, 140.57, 139.28, 133.32, 132.63, 131.96, 127.97, 127.64, 127.40, 127.38, 127.05, 126.88, 124.18, 123.65, 123.61, 44.55, 20.05.

The requisite intermediate for the preparation of this compound was prepared as follows.

a. Preparation of Compound

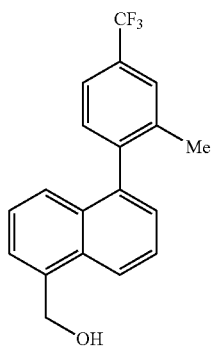 [SMILES: Cc1cc(C(F)(F)F)ccc1-c1cccc2c(CO)cccc12]

(5-Bromonaphthalen-1-yl)methanol (165 mg), 2-methyl-4-trifluoromethylphenylboronic acid (170 mg, 1.2 eq.), Pd(PPh$_3$)$_4$ (80 mg, 0.1 eq.), and K$_2$CO$_3$ (288 mg, 3 eq.) were combined in a flask with 5 mL dioxane and 2.5 mL H$_2$O and degassed. Reaction mixture was then refluxed at 100° C. overnight. Solution was cooled to room temperature then diluted with EtOAc and washed with saturated NaHCO$_3$. The organic layer was dried over sodium sulfate and concentrated. Chromatography achieved using ISCO max gradient 30% EtOAc/hexane yielding product as a yellow oil (208 mg, 95% yield). $^1$H NMR (400 MHz) (CDCl$_3$) δ 8.24 (d, J=8 Hz, 1H), 7.65-7.64 (m, 1H), 7.63-7.56 (m, 2H), 7.40-7.36 (m, 5H), 5.23 (s, 2H), 2.10 (s, 3H). $^{13}$C NMR (100 MHz) (CDCl$_3$) δ144.16, 139.06, 137.81, 136.68, 131.92, 131.42, 130.74, 126.63, 126.51, 126.20, 125.82, 125.56, 123.73, 122.52, 122.48, 63.84, 20.06.

b. Preparation of Compound

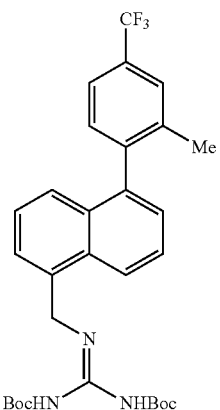

(5-(2-Methyl-4-(trifluoromethyl)phenyl)naphthalen-1-yl) methanol (67 mg), PPh$_3$ (83 mg, 1.5 eq.), and 1,3-bis(t-butoxycarbonyl)guanidine (110 mg, 2 eq.) in 3 mL toluene at 0° C. was added diisopropylazodicarboxylate (0.06 mL, 1.5 eq.) drop wise over 15 minutes. Reaction was stirred for 3 hours at room temperature then 2 drops H$_2$O were added, and the solution was concentrated. Chromatography achieved using ISCO max gradient 30% EtOAc/hexane yielding product as a clear oil (93 mg, 79% yield). $^1$H NMR (400 MHz) (CDCl$_3$) δ 9.55 (bs, 2H), 8.10 (d, J=8 Hz, 1H), 7.62-7.57 (m, 3H), 7.41-7.22 (m, 5H), 5.84-5.74 (m, 2H), 2.06 (s, 3H), 1.48 (s, 9H), 1.17 (s, 9H). $^{13}$C NMR (100 MHz) (CDCl$_3$) δ163.80, 160.97, 155.04, 138.98, 137.77, 135.08, 131.60, 130.85, 130.69, 126.61, 126.20, 125.71, 125.37, 124.60, 122.88, 122.45, 122.23, 84.03, 78.99, 45.23, 28.26, 27.57, 19.93.

Example 48

Preparation of Compound

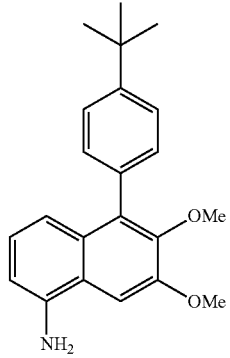 [SMILES: COc1cc2c(N)cccc2c(-c2ccc(C(C)(C)C)cc2)c1OC]

1-(4-(t-butyl)phenyl)-2,3-dimethoxy-5-nitronaphthalene (1.159 g) was combined with 3 mL hydrazine monohydrate and 200 mg Pd/C in 35 mL ethanol and refluxed at 85° C. for 1.5 hours. Pd/C was then filtered out and filtrate concentrated yielding product as a pinkish-white solid (1.03 g, 97% yield). $^1$H NMR (400 MHz) (CDCl$_3$) δ 7.41-7.39 (m, 2H), 7.22-7.20 (m, 2H), 7.07 (s, 1H), 7.00-6.96 (m, 1H), 6.86 (d, J=8 Hz, 1H), 6.67-6.65 (m, 1H), 3.94 (s, 3H), 3.54 (s, 3H), 1.33 (s, 9H). $^{13}$C NMR (100 MHz) (CDCl$_3$) δ 151.69, 149.88, 146.68, 133.25, 132.90, 130.11, 130.01, 124.91, 124.19, 121.34, 117.88, 110.12, 100.37, 61.01, 55.77, 34.64, 31.56.

The requisite intermediate for the preparation of this compound was prepared as follows.
a. Preparation of Compound

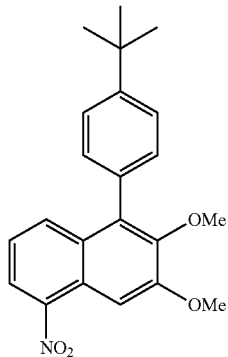

1-Bromo-2,3-dimethoxy-5-nitronaphthalene (1 g), 4-t-butylphenylboronic acid (685 mg, 1.2 eq.), Pd(PPh$_3$)$_4$ (370 mg, 0.1 eq.), and Na$_2$CO$_3$ (680 mg, 2 eq.) were combined in a flask with 20 mL dioxane and 5 mL H$_2$O and degassed. Reaction mixture was then refluxed at 100° C. overnight. Solution was cooled to room temperature then diluted with EtOAc and washed with saturated NaHCO$_3$. The organic layer was dried over sodium sulfate and concentrated. Chromatography achieved using ISCO max gradient 20% EtOAc/hexane yielding product as a yellow solid (1.159 g, 99% yield). $^1$H NMR (400 MHz) (CDCl$_3$) δ 8.18 (dd, J=8 Hz, J=4 Hz, 1H), 8.08 (s, 1H), 7.79-7.77 (m, 1H), 7.54 (dt, J=8 Hz, J=4 Hz, 2H), 7.30 (t, J=4 Hz, 1H), 7.28-7.27 (m, 2H), 3.99 (s, 3H), 3.58 (s, 3H), 1.34 (s, 9H). $^{13}$C NMR (100 MHz) (CDCl$_3$) δ 155.05, 150.69, 147.53, 145.44, 132.89, 132.72, 131.97, 130.66, 130.06, 125.26, 123.59, 123.54 121.87, 102.16, 61.08, 55.91, 34.71, 31.43.

Example 49

Preparation of Compound

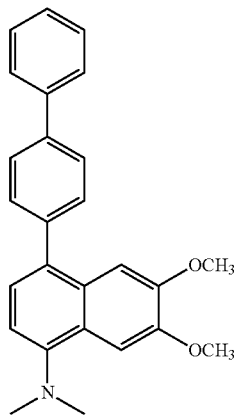 [SMILES: COc1cc2c(-c3ccc(-c4ccccc4)cc3)ccc(N(C)C)c2cc1OC]

To a solution of the compound of Example 48 (120 mg) in 25.0 ml of methanol containing 0.17 ml para-formaldehyde was added solution of NaCNBH$_3$ (45 mg) and ZnCl$_2$ (50 mg in 2.5 mL of MeOH). After the reaction is stirred for 12 hour, the solution was washed with dilute HCl and saturated sodium bicarbonate to give the crude product which was then purified by flash column chromatography giving 67% desired product. $^1$H NMR (CDCl$_3$, 400 MHz) δ: 2.94 (s, 6H), 3.86 (s, 3H), 4.09 (s, 3H), 7.10 (d, J=8.0 Hz, 1H), 7.29 (d, J=8.0 Hz, 1H), 7.30 (s, 1H), 7.40 (t, J=8.0 Hz, 1H), 7.50 (t, J=8.0 Hz, 2H), 7.60 (d, J=8.0 Hz, 2H), 7.67 (s, 1H), 7.73 (m, 4H).

Example 50

Preparation of Compound

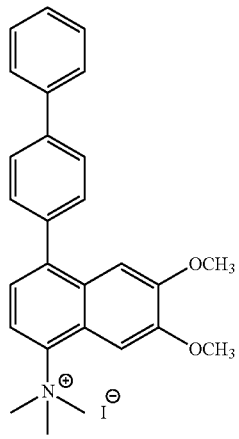 [SMILES: COc1cc2c(-c3ccc(-c4ccccc4)cc3)ccc([N+](C)(C)C)c2cc1OC ; [I-]]

Prepared from the compound of Example 49 by General Method B (72% yield); $^1$H NMR (CDCl$_3$, 400 MHz) δ: 3.86 (s, 3H), 4.20 (s, 3H), 4.39 (s, 9H), 7.42 (m, 4H), 7.51-7.55 (m, 4H), 7.72 (d, J=8.0 Hz, 2H), 7.80 (d, J=8.0 Hz, 3H).

Example 51

Preparation of Compound

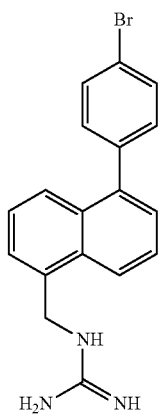 [SMILES: N=C(N)NCc1cccc2c(-c3ccc(Br)cc3)cccc12]

A mixture of diBoc protected 1-((5-(4-bromophenyl)naphthalen-1-yl)methyl)guanidine (34 mg, 0.06 mmol) in a mixture of TFA/CH$_2$Cl$_2$ (0.8/0.8 mL) was set at room temperature overnight. All TFA/CH$_2$Cl$_2$ were removed under reduced pressure, the residue was purified with flash column (SiO$_2$, 3% NH$_4$OH-MeOH/CH$_2$Cl$_2$ 0-20%) gave the desired product to give the desired product as a white solid (18 mg, 75%). $^1$H NMR (DMSO, 300 MHz) δ: 4.90 (s, 2H), 7.12 (bs, 4H), 7.52 (m, 2H), 7.67-7.75 (m, 2H), 8.06 (m, 2H).

The requisite intermediate for the preparation of this compound was prepared as follows.

a. Preparation of Compound

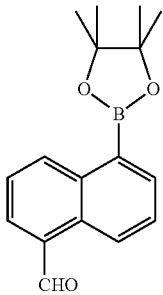 [SMILES: CC1(C)OB(c2cccc3c(C=O)cccc23)OC1(C)C]

To a stirred mixture of 5-bromo-1-napthaldehyde (0.50 g, 2.12 mmol), diborane (0.81 g), KOAc (0.80 g) in DMF (10 mL) was added Pd(OAc)₂ (20 mg). The reaction mixture was degassed for 5 min and heated at 80° C. for 6 h. The reaction mixture was diluted with EtOAc, washed with brine and was dried over MgSO₄ filtered and concentrated and purified with flash column (SiO₂, EtOAc/hexane 0-15%) to give the desired product as oil. ¹H NMR (CDCl₃, 300 MHz) δ: 1.46 (s, 12H), 7.69-7.73 (m, 2H), 8.01 (d, J=8.0 Hz, 1H), 8.21 (d, J=8.0 Hz, 1H), 9.12 (d, J=8.0 Hz, 1H), 9.42 (d, J=8.0 Hz, 1H), 10.4 (s, 1H).

b. Preparation of Compound

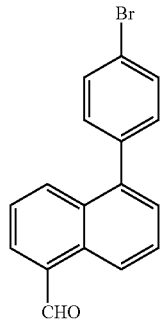 [SMILES: O=Cc1cccc2c(-c3ccc(Br)cc3)cccc12]

To a nitrogen-flushed mixture of pinacole boronate ester (0.209 g, 0.7 mmol), 4-bromo iodobenzene (0.23) and potassium carbonate (0.20 g, 6.4 mmol) in a mixture of dioxane (8 mL) and water (1.5 mL) at room temperature under nitrogen was added tetrakis(triphenylphosphine)-palladium (40 mg, 5 mol %), the resultant mixture was heated at 100° C. for 5 h. It was dried over MgSO₄, filtered and concentrated and purified with flash column (SiO₂, EtOAc/hexane 10-50%) to give the desired product as a semi yellow solid (0.142 g, 65%). ¹H NMR (CDCl₃, 300 MHz) δ: 7.36-7.39 (m, 2H), 7.55 (d, J=9.0 Hz, 1H), 7.60-7.69 (m, 3H), 7.76 (m, 2H), 8.05 (d, J=9.0 Hz, 1H), 8.15 (d, J=9.0 Hz, 1H), 10.5 (s, 1H).

c. Preparation of Compound

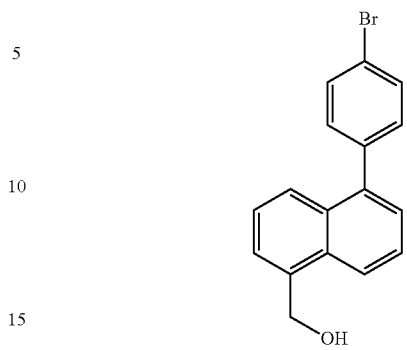

A mixture of aldehyde (0.14 g, 0.45 mmol) and NaBH₄ (12 mg) in 95% EtOH (8 mL) was stirred at room temperature for 2 h. It was filtered and the filtrate was concentrated and redissolved in CH₂Cl₂ (40 mL). The CH₂Cl₂ solution was washed with aq. NaHCO₃ and brine, dried over over MgSO₄, filtered and concentrated. Purification with flash column (SiO₂, EtOAc/hexane 10-30%) gave the desired product (0.14 g, 100%). ¹H NMR (CDCl₃, 300 MHz) δ: 5.14 (s, 2H), 7.26-7.36 (m, 4H), 7.47-7.56 (m, 4H), 7.74 (d, J=9.0 Hz, 1H), 8.11 (d, J=9.0 Hz, 1H).

d. Preparation of Compound

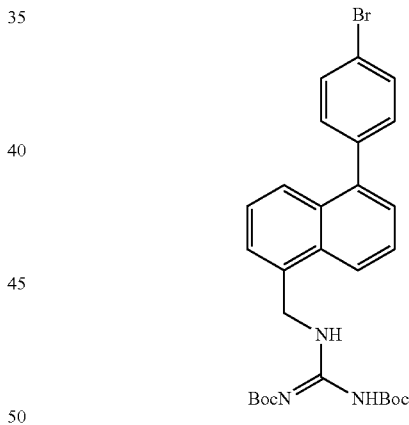

To a mixture of (5-(4-bromophenyl)naphthalen-1-yl)methanol (40 mg, 0.128 mmol), di-Boc guanidine (66 mg, 0.26 mmol) and Ph₃P (60 mg, 0.23 mmol) in toluene (3 mL) at 0° C. under nitrogen was added DIAD (0.04 mL, 0.20 mmol). The reaction mixture was stirred at room temperature overnight. The reaction mixture was concentrated to an oil residue. Purification with flash column (SiO₂, EtOAc/hexane 0-30%) gave the desired product (34 mg, 47%). ¹H NMR (CDCl₃, 300 MHz) δ: 1.22 (s, 9H), 1.47 (s, 9H), 5.78 (s, 2H), 7.21 (d, J=6.0 Hz, 1H), 7.37-7.66 (m, 7H), 7.75 (d, J=9.0 Hz, 1H), 8.06 (d, J=9.0 Hz, 1H), 9.50 (bs, 1H), 9.60 (bs, 1H).

Example 52

Preparation of Compound

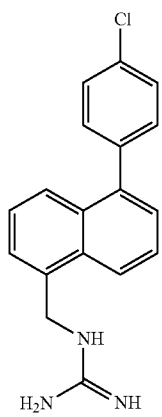 [SMILES: N=C(N)NCc1cccc2c(-c3ccc(Cl)cc3)cccc12]

A mixture of diBoc protected napthalene (46 mg, 0.09 mmol) in a mixture of TFA/CH$_2$Cl$_2$ (0.8/0.8 mL) was set at room temperature overnight. All TFA/CH$_2$Cl$_2$ were removed under reduced pressure, the residue was purified with flash column (SiO$_2$, 3% NH$_4$OH-MeOH/CH$_2$Cl$_2$ 0-20%) gave the desired product to give the desired product as a white solid (27 mg, 78%). $^1$H NMR (DMSO, 300 MHz) δ: 4.89 (d, J=3.0 Hz, 2H), 7.46-7.53 (m, 4H), 7.59-7.75 (m, 4H), 8.08 (m, 2H).

The requisite intermediate for the preparation of this compound was prepared as follows.

a. Preparation of Compound

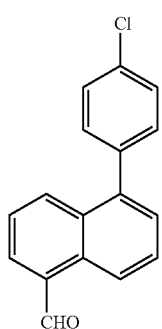 [SMILES: O=Cc1cccc2c(-c3ccc(Cl)cc3)cccc12]

To a nitrogen-flushed mixture of pinacole boronate ester (0.20 g, 0.7 mmol), 4-chloro bromobenzene (0.16 g) and potassium carbonate (0.20 g, 6.4 mmol) in a mixture of dioxane (6 mL) and water (1.5 mL) at room temperature under nitrogen was added tetrakis(triphenylphosphine)-palladium (40 mg, 5 mol %), the resultant mixture was heated at 100° C. for 5 h. It was dried over MgSO$_4$, filtered and concentrated and purified with flash column (SiO$_2$, EtOAc/hexane 0-15%) to give the desired product as a pale solid (0.16 g, 84%). $^1$H NMR (CDCl$_3$, 300 MHz) δ: 7.14-7.44 (m, 2H), 7.50-7.56 (m, 4H), 7.63 (m, 1H), 7.77 (m, 1H), 8.06 (d, J=9.0 Hz, 1H), 8.15 (d, J=9.0 Hz, 1H).

b. Preparation of Compound

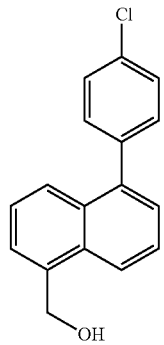 [SMILES: OCc1cccc2c(-c3ccc(Cl)cc3)cccc12]

A mixture of 5-(4-chlorophenyl)-1-naphthaldehyde (0.16 g, 0.60 mmol) and NaBH$_4$ (16 mg) in 95% EtOH (10 mL) was stirred at room temperature for 1 h. It was filtered and the filtrate was concentrated and redissolved in CH$_2$Cl$_2$ (40 mL). The CH$_2$Cl$_2$ solution was washed with aq. NaHCO$_3$ and brine, dried over over MgSO$_4$, filtered and concentrated. Purification with flash column (SiO$_2$, EtOAc/hexane 10-30%) gave the desired product (0.16 g, 100%). $^1$H NMR (CDCl$_3$, 300 MHz) δ: 5.23 (s, 2H), 7.42-7.52 (m, 6H), 7.58-7.66 (m, 2H), 7.84 (d, J=9.0 Hz, 1H), 8.21 (d, J=9.0 Hz, 1H).

c. Preparation of Compound

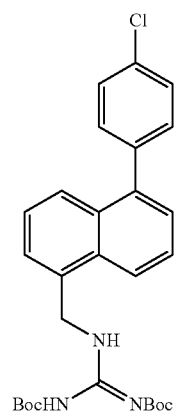

To a mixture of (5-(4-chlorophenyl)naphthalen-1-yl) methanol (50 mg, 0.186 mmol), di-Boc guanidine (96 mg) and Ph$_3$P (73 mg) in toluene (3 mL) at 0° C. under nitrogen was added DIAD (0.06 mL). The reaction mixture was stirred at room temperature overnight. The reaction mixture was concentrated to an oil residue. Purification with flash column (SiO$_2$, EtOAc/hexane 0-30%) gave the desired product (46 mg, 48%). $^1$H NMR (CDCl$_3$, 400 MHz) δ:1.21 (s, 9H), 1.47 (s, 9H), 5.80 (s, 2H), 7.21 (d, J=6.0 Hz, 1H), 7.37-7.61 (m, 7H), 7.75 (d, J=9.0 Hz, 1H), 8.06 (d, J=9.0 Hz, 1H).

Example 53

Preparation of Compound

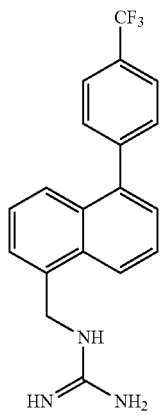 [SMILES: N=C(N)NCc1cccc2c(-c3ccc(C(F)(F)F)cc3)cccc12]

A mixture of diBoc protected napthalene, Intermediate c Example 53, (56 mg, 0.1 mmol) in a mixture of TFA/CH$_2$Cl$_2$ (0.8/0.8 mL) was set at room temperature overnight. All TFA/CH$_2$Cl$_2$ were removed under reduced pressure, the residue was purified with flash column (SiO$_2$, 3% NH$_4$OH-MeOH/CH$_2$Cl$_2$ 0-20%) gave the desired product to give the desired product as a white solid (20 mg, 51%). $^1$H NMR (CDCl$_3$, 300 MHz) δ: 4.97 (s, 2H), 7.50-7.56 (m, 3H), 7.65-7.23 (m, 3H), 7.84 (m, 3H), 8.11 (d, J=6.0 Hz, 1H).

The requisite intermediate for the preparation of this compound was prepared as follows.

a. Preparation of Compound

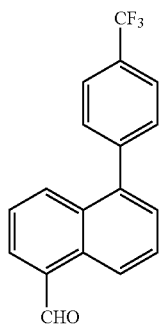 [SMILES: O=Cc1cccc2c(-c3ccc(C(F)(F)F)cc3)cccc12]

To a nitrogen-flushed mixture of 5-bromo-1-napthaldehyde (0.50 g, 2.1 mmol), 4-CF$_3$ phenylboronic acid (0.62 g) and potassium carbonate (0.88 g, 6.4 mmol) in a mixture of dioxane (10 mL) and water (2 mL) at room temperature under nitrogen was added tetrakis(triphenylphosphine)-palladium (73 mg, 0.06 mmol), the resultant mixture was heated at 100° C. for 5 h. It was dried over MgSO$_4$, filtered and concentrated and purified with flash column (SiO$_2$, EtOAc/hexane 10-30%) to give the desired product as a pale solid (0.56 g, 88%). $^1$H NMR (CDCl$_3$, 400 MHz) δ: 7.52 (d, J=8.0 Hz, 1H), 7.58-7.62 (m, 3H), 7.73-7.78 (m, 3H), 8.01-8.08 (m, 2H), 9.35 (d, J=8.0 Hz, 1H), 10.45 (s, 1H).

b. Preparation of Compound

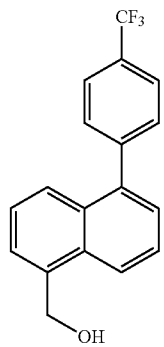 [SMILES: OCc1cccc2c(-c3ccc(C(F)(F)F)cc3)cccc12]

A mixture of 5-(4-(trifluoromethyl)phenyl)-1-naphthaldehyde (0.35 g, 1.16 mmol) and NaBH$_4$ (31 mg) in 95% EtOH (15 mL) was stirred at room temperature for 1 h. It was filtered and the filtrate was concentrated and redissolved in CH$_2$Cl$_2$ (40 mL). The CH$_2$Cl$_2$ solution was washed with aq. NaHCO$_3$ and brine, dried over over MgSO$_4$, filtered and concentrated. Purification with flash column (SiO$_2$, EtOAc/hexane 10-30%) gave the desired product as a white solid (0.35 g). $^1$H NMR (CDCl$_3$, 300 MHz) δ: 5.15 (s, 2H), 7.4 (m, 2H), 7.56 (m, 4H), 7.7 (m, 3H), 8.16 (d, J=6.0 Hz, 1H).

c. Preparation of Compound

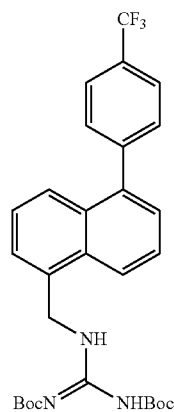

To a mixture of (5-(4-(trifluoromethyl)phenyl)naphthalen-1-yl)methanol (40 mg, 0.13 mmol), di-Bocguanidine (70 mg) and Ph$_3$P (55 mg) in toluene (3 mL) at 0° C. under nitrogen was added DIAD (0.04 mL). The reaction mixture was stirred at room temperature overnight. The reaction mixture was concentrated to an oil residue. Purification with flash column (SiO$_2$, EtOAc/hexane 0-30%) gave the desired product as a white solid (56 mg, 80%). $^1$H NMR (CDCl$_3$, 400 MHz) δ: 1.12 (s, 9H), 1.37 (s, 9H), 5.68 (s, 2H), 7.12 (d, J=4.0 Hz, 1H), 7.28-7.35 (m, 2H), 7.48-7.53 (m, 3H), 7.61 (d, J=8.0 Hz, 1H), 7.67 (d, J=8.0 Hz, 2H), 8.00 (d, J=8.0 Hz, 1H), 9.44 (bs, 2H).

Example 54

Preparation of Compound 5

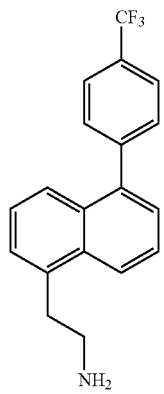

To a stirred solution of (E)-1-(2-nitrovinyl)-5-(4-(trifluoromethyl)phenyl)naphthalene (0.21 g, 0.62 mmol) in THF (10 mL) at room temperature was added LAH slowly. The reaction mixture was stirred at room temperature overnight. After normal LAH work-up and the evaporation of the solvent gave the desired product as pale solid. $^1$H NMR (CDCl$_3$, 300 MHz) δ: 3.23 (m, 2H), 3.36 (m, 2H), 7.37-7.44 (m, 3H), 7.57-7.63 (m, 3H), 7.71-7.80 (m, 3H), 8.16 (d, J=9.0 Hz, 1H).

The requisite intermediate for the preparation of this compound was prepared as follows.

a. Preparation of Compound

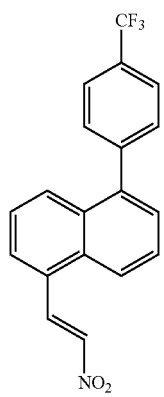 [SMILES: O=[N+]([O-])/C=C/c1cccc2c(-c3ccc(C(F)(F)F)cc3)cccc12]

A mixture of 5-(4-(trifluoromethyl)phenyl)-1-napthaldehyde (0.20 g), NH$_4$OAc (60 mg) in nitromethane (3.0 mL) was heated to reflux for 6 h. Excess nitromethane was removed and the crude mixture was purified by column chromatography using 5-10% EtOAc/hexane to afford a yellow product (0.21 g, 91%). $^1$H NMR (CDCl$_3$, 300 MHz) δ: 7.41 (m, 2H), 7.52 (d, J=8.0 Hz, 2H), 7.58-7.65 (m, 2H), 7.70 (m, 3H), 7.88 (d, J=8.0 Hz, 1H), 8.13 (d, J=8.0 Hz, 1H), 8.82 (d, J=16.0 Hz, 1H).

Example 55

Preparation of Compound

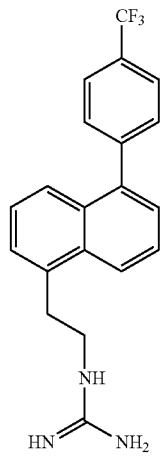 [SMILES: N=C(N)NCCc1cccc2c(-c3ccc(C(F)(F)F)cc3)cccc12]

A mixture of diBoc protected napthalene, Intermediate a of Example 55 (20 mg, 0.036 mmol) in a mixture of TFA/CH$_2$Cl$_2$ (0.5/0.5 mL) was set at room temperature overnight. All TFA/CH$_2$Cl$_2$ were removed under reduced pressure, the residue was purified with flash column (SiO$_2$, 3% NH$_4$OH-MeOH/CH$_2$Cl$_2$ 0-20%) gave the desired product to give the desired product as a white solid (10.5 mg). $^1$H NMR (CDCl$_3$, 300 MHz) δ: 3.46 (t, J=6.0 Hz, 2H), 3.66 (t, J=6.0 Hz, 2H), 7.43-7.51 (m, 3H), 7.64-7.73 (m, 4H), 7.84 (d, J=6.0 Hz, 2H), 8.21 (d, J=6.0 Hz, 1H).

The requisite intermediate for the preparation of this compound was prepared as follows.

a. Preparation of Compound

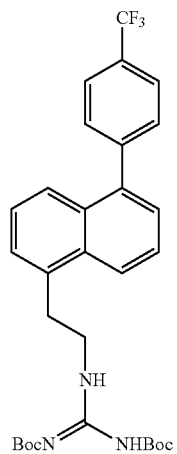

To a stirred solution of 2-(5-(4-(trifluoromethyl)phenyl)napthalen-1-yl)ethanamine (25 mg, 0.08 mmol), triethylamine (0.03 mL) in methylene chloride (6 mL) was added diBoc guanidine triflate (40 mg) under nitrogen. The reaction mixture was stirred overnight at room temp. The reaction mixture was concentrated to an oil residue. Purification with flash column (SiO$_2$, EtOAc/hexane 10-30%) gave the desired product (20 mg, 44%). $^1$H NMR (CDCl$_3$, 300 MHz) δ: 1.50 (s, 9H), 1.56 (s, 9H), 3.44 (t, J=6.0 Hz, 2H), 3.81 (m, 2H), 7.35-7.44 (m, 3H), 7.60-7.78 (m, 6H), 8.4-8.5 (m, 3H).

Example 56

Preparation of Compound

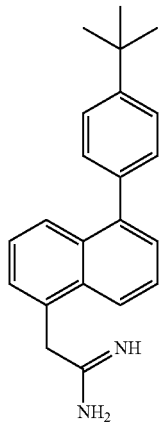 [SMILES: CC(C)(C)c1ccc(-c2cccc3c(CC(=N)N)cccc23)cc1]

A mixture of 2-(5-(4-(t-butyl)phenyl)napthalen-1-yl)acetonitrile (0.12 g, 0.4 mmol), in Et$_2$O (2 mL) was treated with 4N HCl/dioxane (2 mL), and was stirred at 0° C. for 4 h. The mixture was then put into the refrigerator overnight. The solid thus formed was filtered and then treated with NH$_4$OH/EtOH (6 mL) and heated to reflux for 6 h. The reaction mixture was concentrated to dryness and was subjected to column chromatography using 3% NH$_4$OH/MeOH/methylene chloride (0-20%) to give the desired product (37 mg, 29%). $^1$H NMR (CD$_3$OD, 300 MHz) δ: 1.44 (s, 9H), 4.41 (s, 2H), 7.40 (m, 1H), 7.45-7.52 (m, 3H), 7.57-7.59 (m, 3H), 7.68 (m, 1H), 7.96 (m, 2H).

The requisite intermediate for the preparation of this compound was prepared as follows.

a. Preparation of Compound

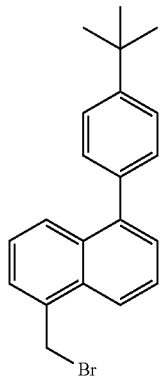

To a solution of (5-(4-(t-butyl)phenyl)napthalen-1-yl)methanol (0.60 g, 2.0 mmol) in dry methylene chloride (12 ml) at 0° C. under nitrogen was added drop wise PBr$_3$ (0.40 mL). The reaction mixture was stirred at 0° C. for 1 h. The reaction was quenched by the addition of sodium bicarbonate and extracted with methylene chloride. The solvent was then removed to give product as pale oil (0.67 g, 86%). $^1$H NMR (CDCl$_3$, 300 MHz) δ: 1.45 (s, 9H), 5.06 (s, 2H), 7.36-7.46 (m, 3H), 7.50-7.60 (m, 3H), 7.69 (m, 2H), 8.00 (d, J=9.0 Hz, 1H), 8.21 (d, J=9.0 Hz, 1H).

b. Preparation of Compound

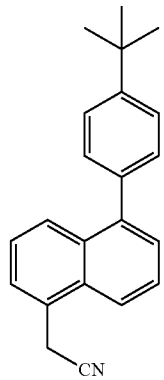 [SMILES: CC(C)(C)c1ccc(-c2cccc3c(CC#N)cccc23)cc1]

A mixture of 1-(bromomethyl)-5-(4-(tert-butyl)phenyl)naphthalene (0.20 g, 0.57 mmol), and KCN (55 mg) in DMSO (6 mL) was stirred at room temperature overnight. The reaction mixture was diluted with water and was extracted with diethyl ether. The crude product was then purified by column chromatography using EtOAc/hexane (20%) to afford the product as solid (0.12 g, 74%). $^1$H NMR (CDCl$_3$, 300 MHz) δ: 1.41 (s, 9H), 4.19 (s, 2H), 7.39-7.44 (m, 3H), 7.50-7.53 (m, 3H), 7.61 (d, J=6.0 Hz, 1H), 7.66 (d, J=6.0 Hz, 1H), 7.88 (d, J=6.0 Hz, 1H), 7.97 (d, J=9.0 Hz, 1H).

Example 57

Preparation of Compound

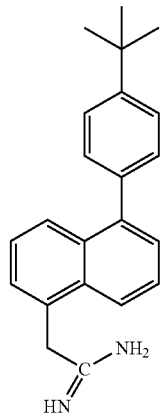 [SMILES: CC(C)(C)c1ccc(-c2cccc3c(CC(=N)N)cccc23)cc1]

A mixture of 2-(5-(4-(CF$_3$)phenyl)napthalen-1-yl)acetonitrile (0.10 g, 0.32 mmol), in Et$_2$O (2.0 mL) was treated with 4N HCl/dioxane (2.0 mL), and was stirred at 0° C. for 4 h. The mixture was then put into the refrigerator overnight. The solid thus formed was filtered and then treated with NH$_4$OH/EtOH (5 mL) and heated to reflux for 8 h. The reaction mixture was concentrated to dryness and was subjected to column chromatography using 3% NH$_4$OH/MeOH/methylene chloride (0-20%) to give the desired product (22 mg, 20%). $^1$H NMR (CDCl$_3$, 300 MHz) δ: 4.44 (s, 2H), 7.50-7.62 (m, 4H), 7.67-7.76 (m, 3H), 7.86 (d, J=9.0 Hz, 2H), 8.06 (d, J=6.0 Hz, 1H).

The requisite intermediate for the preparation of this compound was prepared as follows.

a. Preparation of Compound 5

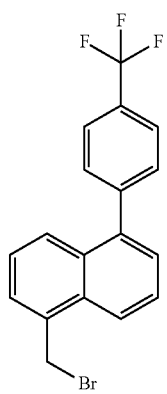 [SMILES: FC(F)(F)c1ccc(-c2cccc3c(CBr)cccc23)cc1]

To a solution of (5-(4-(CF$_3$)phenyl)napthalen-1-yl)methanol (0.30 g, 0.99 mmol) in dry methylene chloride (10 ml) at 0° C. under nitrogen was added drop-wise PBr$_3$ (0.14 mL). The reaction mixture was stirred at 0° C. for 1 h. The reaction was quenched by the addition of sodium bicarbonate and extracted with methylene chloride. The solvent was then removed to give product as pale gum and used for the next step as crude.

b. Preparation of Compound

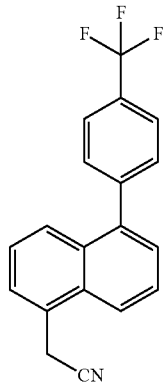 [SMILES: N#CCc1cccc2c(-c3ccc(C(F)(F)F)cc3)cccc12]

A mixture of 1-(bromomethyl)-5-(4-(CF$_3$)phenyl)naphthalene (0.30 g), and KCN (100 mg) in DMSO (8.0 mL) was stirred at room temperature overnight. The reaction mixture was diluted with water and was extracted with diethyl ether. The crude product was then purified by column chromatography using EtOAc/hexane (20%) to afford the product as solid (0.26 g, 84%). $^1$H NMR (CDCl$_3$, 300 MHz) δ: 4.18 (s, 2H), 7.46-7.55 (m, 2H), 7.62-7.75 (m, 4H), 7.80-7.88 (m, 3H), 7.99 (m, 1H).

Example 58

Preparation of Compound

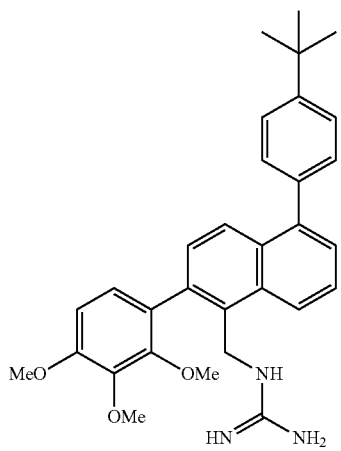 [SMILES: COc1ccc(-c2ccc3c(-c4ccc(C(C)(C)C)cc4)cccc3c2CNC(=N)N)c(OC)c1OC]

A mixture of diBoc protected starting material, Intermediate f of Example 58 (18 mg) in a mixture of TFA/CH$_2$Cl$_2$ (0.8/0.8 mL) was set at room temperature overnight. All TFA/CH$_2$Cl$_2$ were removed under reduced pressure, the residue was purified with flash column (SiO$_2$, 3% NH$_4$OH-MeOH/CH$_2$Cl$_2$ 0-20%) gave the desired product to give the desired product as a white solid (10 mg). $^1$H NMR (CDCl$_3$, 400 MHz) δ: 1.34 (S, 9H), 3.48 (S, 3H), 3.82 (S, 3H), 4.62 (bs, 2H), 6.71 (M, 1H), 6.80 (M, 1H), 7.35 (M, 3H), 7.44 (M, 2H), 7.52 (M, 2H), 7.90 (M, 2H).

The requisite intermediate for the preparation of this compound was prepared as follows.

a. Preparation of Compound

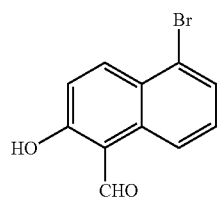 [SMILES: O=Cc1c(O)ccc2c(Br)cccc12]

A solution of titanium tetrachloride (2.1 mL, 2.1 mmol) and dichloromethyl ether (0.1 mL) was stirred at 0° C. for 15 minutes. A solution of 2-hydroxy-5-bromonapthalene (223 mg, 1.0 mmol) in 3.0 mL of methylene chloride was added drop wise, the solution was allowed to warm to room temperature and stirred for 12 h. 10 mL of 1N HCl was added, and the mixture was extracted with methylene chloride. The organic layer was washed with water, dried and evaporated to give crude product. Silica gel chromatography produced 120 mg of the desired product. $^1$H NMR (CDCl$_3$, 400 MHz) δ: 7.25 (d, J=8.0 Hz, 1H), 7.46 (t, J=8.0 Hz, 1H), 7.74 (d, J=8.0 Hz, 1H), 8.33 (d, J=8.0 Hz, 1H), 8.47 (d, J=8.0 Hz, 1H), 10.8 (S, 1H), 13.2 (S, 1H).

b. Preparation of Compound

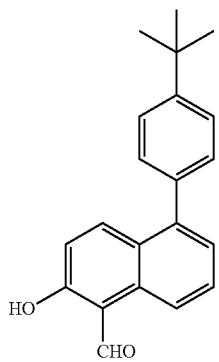 [SMILES: CC(C)(C)c1ccc(-c2cccc3c(C=O)c(O)ccc23)cc1]

A mixture of 2-hydroxy-5-bromo-1-naphthaldehyde (120 mg), 4-t-butylphenylboronic acid (2 equiv.), $Cs_2CO_3$ (2 equiv.), Pd $(PPh_3)_2Cl_2$ (5 mol %) in dioxane (3 mL) was subject to a microwave reactor for 15 minutes. The crude reaction mixture was diluted with ethyl acetate and was filtered through a plug of Celite and silica gel. The filtrate was concentrated under vacuo and was subjected to flash column chromatography to afford the desired product (120 mg). $^1$H NMR ($CDCl_3$, 400 MHz) δ: 7.1 (d, J=8.0 Hz, 1H), 7.29-7.43 (M, 3H), 7.56 (M, 2H), 7.67 (M, 1H), 8.16 (d, J=8.0 Hz, 1H), 8.39 (d, J=8.0 Hz, 1H), 10.9 (S, 1H), 13.2 (S, 1H).

c. Preparation of Compound

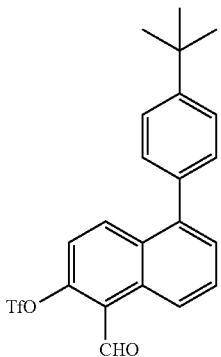 [SMILES: CC(C)(C)c1ccc(-c2cccc3c(C=O)c(OS(=O)(=O)C(F)(F)F)ccc23)cc1]

5-(4-t-Butylphenyl)-2-hydroxy-1-naphthaldehyde (113 mg) was dissolved in dichloromethane to which added 2.0 equivalent of triethylamine and 1.5 equivalent of $Tf_2O$ at −78° C. After the reaction was complete, the reaction mixture was diluted with more methylene chloride which was then washed with saturated sodium bicarbonate and brine. The crude mixture was then purified by flash column chromatography to afford the product (70 mg). $^1$H NMR ($CDCl_3$, 400 MHz) δ: 1.34 (s, 9H), 7.29-7.34 (m, 3H), 7.45 (m, 2H), 7.52 (d, J=4.0 Hz, 1H), 7.72 (m, 1H), 8.25 (d, J=12.0 Hz, 1H), 9.11 (d, J=12.0 Hz, 1H), 10.76 (s, 1H).

d. Preparation of Compound

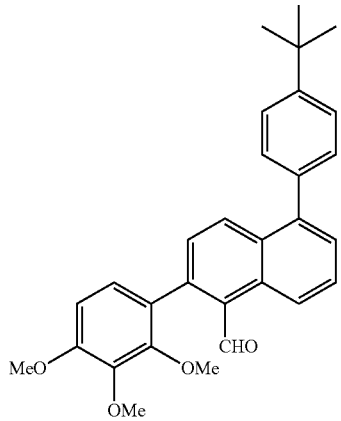 [SMILES: COc1ccc(-c2ccc3c(-c4ccc(C(C)(C)C)cc4)cccc3c2C=O)c(OC)c1OC]

A mixture of 5-(4-t-butylphenyl)-1-formylnaphthalen-2-yl trifluoromethanesulfonate (60 mg), 2,3,4-trimethoxyphenylboronic acid (60 mg), $Cs_2CO_3$ (300 mg), Pd $(PPh_3)_2Cl_2$ (5 mol %) in dioxane (3 mL) was subject to a micro wave reaction for 15 minutes. The crude reaction mixture was diluted with ethyl acetate and was filtered through a plug of Celite and silica gel. The filtrate was concentrated under vacuo and was subjected to flash column chromatography to afford the desired product (40 mg). $^1$H NMR ($CDCl_3$, 400 MHz) δ: 3.65 (S, 3H), 3.97 (S, 6H), 6.81 (d, J=8.0 Hz, 1H), 7.00 (d, J=8.0 Hz, 1H), 7.42-7.47 (M, 3H), 7.54-7.57 (M, 3H), 7.72-7.76 (M, 1H), 8.22 (d, J=8.0 Hz, 1H), 9.35 (d, J=8.0 Hz, 1H), 10.24 (S, 1H).

e. Preparation of Compound

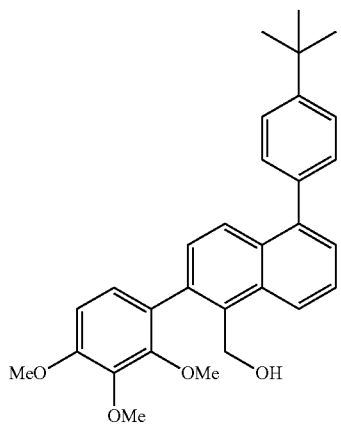 [SMILES: COc1ccc(-c2ccc3c(-c4ccc(C(C)(C)C)cc4)cccc3c2CO)c(OC)c1OC]

A mixture of 5-(4-t-butylphenyl)-2-(2,3,4-trimethoxyphenyl)-1-naphthaldehyde (40 mg) and $NaBH_4$ (20 mg) in 95% EtOH (3 mL) was stirred at room temperature for 1 h. After 1 h, acetone was added and the filtered solution was concentrated to give pure desired product as a white solid (35 mg). $^1$H NMR ($CDCl_3$, 400 MHz) δ: 1.45 (S, 9H), 3.52 (S, 3H), 3.96 (S, 3H), 4.01 (S, 3H), 4.71-4.74 (M, 1H), 5.09 (M, 1H), 6.84 (d, J=8.0 Hz, 1H), 7.00 (d, J=8.0 Hz, 1H), 7.33 (d, J=8.0 Hz, 1H), 7.47-7.56 (M, 4H), 7.69 (t, J=8.0 Hz, 1H), 8.00 (d, J=8.00 Hz, 1H), 8.43 (d, J=8.0 Hz, 1H).

f. Preparation of Compound

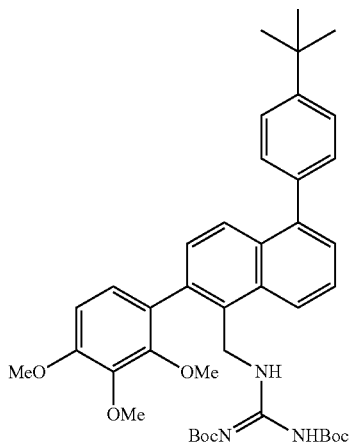

To a mixture of (5-(4-tert-butylphenyl)-2-(2,3,4-trimethoxyphenyl)naphthalen-1-yl)methanol (35 mg), di-Bocguanidine (42 mg) and Ph₃P (32 mg, 0.13 mmol) in toluene (3 mL) at 0° C. under nitrogen was added DIAD (0.02 mL, 0.10 mmol). The reaction mixture was stirred at room temperature overnight. The reaction mixture was concentrated to an oil residue. Purification with flash column (SiO$_2$, EtOAc/hexane 0-30%) gave the desired product (30 mg). $^1$H NMR (CDCl$_3$, 400 MHz) δ: 1.34 (s, 18H), 1.48 (s, 9H), 3.64 (s, 3H), 3.81 (s, 3H), 3.82 (s, 3H), 5.40 (d, J=12.0 Hz, 1H), 5.90 (d, J–16.0 Hz, 1H), 6.54 (d, J=8.0 Hz, 1H), 6.82 (d, J=8.0 Hz, 1H), 7.11 (d, J=8.0 Hz, 1H), 7.37-7.48 (m, 6H), 7.80 (d, J=8.0 Hz, 1H), 8.10 (d, J–8.0 Hz, 1H), 8.48 (bs, 1H), 8.99 (bs, 1H).

Example 59

Preparation of Compound

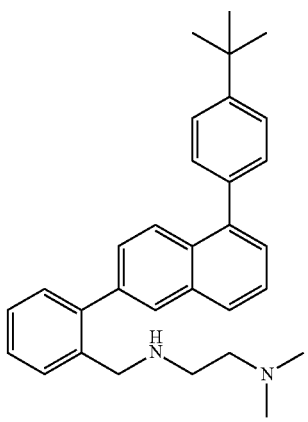 [SMILES: CN(C)CCNCc1ccccc1-c1ccc2c(-c3ccc(C(C)(C)C)cc3)cccc2c1]

A 2-dram vial was added 2-(1-(4-t-butylphenyl)naphthalen-6-yl)phenyl)methanesulfonate (18 mg, 0.04 mmol), CH$_3$CN (1 mL), N,N-dimethylethane-1,2-diamine (36 mg, 0.4 mmol). The sealed vial was heated to 80° C. for 12 h. After cooled to room temperature, the reaction mixture was diluted with EtOAc (30 mL), washed with saturated NaHCO$_3$ (10 mL), brine (10 mL), dried over Na$_2$SO$_4$, concentrated in rotavapor and purified on silica gel. Elution with CH$_2$Cl$_2$ to (10/89/1: MeOH/CHCl$_3$/ammonium hydroxide) afforded the desired compound (8.0 mg, 45%) as colorless oil. $^1$H NMR (CDCl$_3$, 400 MHz) δ 7.92 (d, 1H, J=8.64 Hz), 7.82 (d, 1H, J=1.20 Hz), 7.78 (d, 1H, J=8.08 Hz), 7.36-7.50 (m, 8H), 7.25-7.32 (m, 3H), 3.72 (s, 2H), 2.48 (t, 2H, J=6.12 Hz), 2.22 (t, 2H, J=6.12 Hz), 2.00 (s, 6H), 1.35 (s, 9H).

The requisite intermediate for the preparation of this compound was prepared as follows.

a. Preparation of Compound

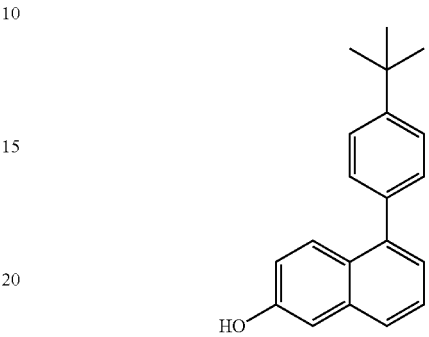

A 50-mL round bottom flask equipped with a magnetic stirrer, a condenser and a nitrogen in/outlet adapter was charged with 5-bromonaphthalen-2-ol (500 mg, 2.24 mmol), 4-t-butylphenylboronic acid (600 mg, 3.36 mmol), water/dioxane (4 mL/16 ml), K$_2$CO$_3$ (68 mg, 4.46 mmol). The resulting solution was degassed for 5 min, then Pd(PPh$_3$)$_4$ (130 mg, 0.112 mmol) was added. The reaction mixture was warmed to 90° C. and stirred for 3 h. After cooled to room temperature, the reaction mixture was diluted with EtOAc (60 mL) and washed with saturated NaHCO$_3$ (20 mL), brine (20 mL), dried over NaSO$_4$. The organic layer was concentrated in rotavapor and purified on silica gel. Elution with 10% EtOAc/hexanes afforded the desired compound (570 mg, 92%) as an off white solid. $^1$H NMR (CDCl$_3$, 400 MHz) δ 7.87 (d, 1H, J=9.16 Hz), 7.68 (d, 1H, J=7.68 Hz), 7.40-7.51 (m, 5H), 7.20-7.28 (m, 2H), 7.04 (dd, 1H, J=2.60, 9.16 Hz), 5.03 (s, 1H), 1.41 (s, 9H).

b. Preparation of Compound

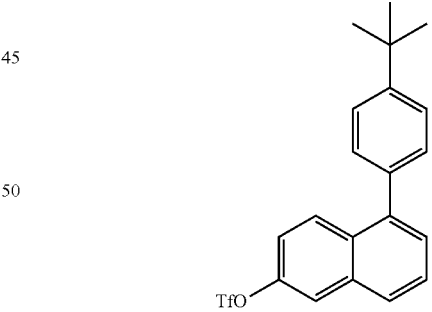

A 50-mL round bottom flask equipped with a magnetic stirrer under nitrogen was charged with 5-(4-t-butylphenyl)naphthalen-2-ol (570 mg, 2.06 mmol), CH$_2$Cl$_2$ (10 mL), and triethylamine (0.78 ml, 5.58 mmol). After cooling to –70° C., triflic anhydride (0.52 ml, 3.07 mmol) was added via a syringe over 5 min, then stirred at –70° C. for 30 min. The reaction mixture was diluted with CH$_2$Cl$_2$ (60 mL) and washed with saturated NaHCO$_3$ (20 ml), brine (20 mL), dried over Na$_2$SO$_4$, concentrated in rotavapor and purified on silica gel. Elution with 5% EtOAc/hexanes afforded the desired compound (802 mg, 95%) as a white solid. $^1$H NMR (CDCl$_3$, 400 MHz) δ 8.07 (d, 1H, J=9.32 Hz), 7.88 (d, 1H, J=8.20 Hz), 7.40-7.51 (m, 5H), 7.82 (d, 1H, J=2.52 Hz 7.64 (t, 1H, J=7.84 Hz), 7.52-7.56 (m, 3H), 7.41-7.43 (m, 2H), 7.32 (dd, 1H, J=2.56, 9.32 Hz), 1.44 (s, 9H).

c. Preparation of Compound

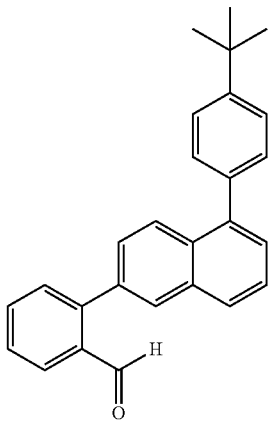 [SMILES: CC(C)(C)c1ccc(-c2cccc3cc(-c4ccccc4C=O)ccc23)cc1]

A 50-mL round bottom flask equipped with a magnetic stirrer, a condenser and a nitrogen in/outlet adapter was charged with 1-(4-t-butylphenyl)naphthalen-6-yl trifluoromethanesulfonate (280 mg, 0.69 mmol), 2-formalphenylboronic acid (123 mg, 0.82 mmol), water/acetonitrile (2 mL/6 ml), K$_2$CO$_3$ (193 mg, 1.4 mmol), 2-dicyclohexylphosphino-2',4',6'-triisopropylbiphenyl (33 mg, 0.07 mmol). The resulting solution was degassed for 5 min, then Pd(OAc)$_2$ (8.0 mg, 0.03 mmol) was added and the solution was carefully degassed. The reaction mixture was warmed to 100° C. and stirred for 2 h. After cooled to room temperature, the reaction mixture was diluted with EtOAc (50 mL) and washed with saturated NaHCO$_3$ (15 mL), brine (15 mL), dried over Na$_2$SO$_4$. The organic layer was concentrated in rotavapor and purified on silica gel. Elution with 5% EtOAc/hexanes afforded the desired compound (182 mg, 73%) as colorless oil. $^1$H NMR (CDCl$_3$, 400 MHz) δ 9.98 (s, 1H), 7.98-8.01 (m, 2H), 7.80-7.81 (m, 2H), 7.38-7.48 (m, 10H), 4.69 (s, 2H), 1.35 (s, 9H).

d. Preparation of Compound

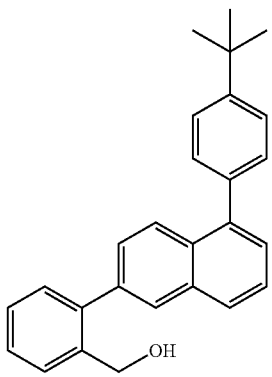 [SMILES: CC(C)(C)c1ccc(-c2cccc3cc(-c4ccccc4CO)ccc23)cc1]

A 25-mL round bottom flask equipped with a magnetic stirrer was charged with 2-(1-(4-t-butylphenyl)naphthalen-6-yl)benzaldehyde (180 mg, 0.49 mmol), ethanol (95%, 5 mL), NaBH$_4$ (38 mg, 1.0 mmol) was added in one portion. The reaction mixture was stirred at room temperature for 1 h. Acetone (1 mL) was added to the reaction mixture. After 20 min, the reaction mixture was concentrated and the residue was partitioned between EtOAc (50 mL) and 1 N HCl (15 mL). The organic layer was washed with saturated NaHCO$_3$ (15 mL), brine (15 mL), dried over Na$_2$SO$_4$, concentrated in rotavapor and purified on silica gel. Elution with 10% EtOAc/hexanes afforded the desired compound (158 mg, 88%) as a white solid. $^1$H NMR (CDCl$_3$, 400 MHz) δ 8.01 (d, 1H, J=8.68 Hz), 7.89 (s, 1H), 7.86 (d, 1H, J=8.20 Hz), 7.52-7.60 (m, 4H), 7.38-7.48 (m, 7H), 4.69 (s, 2H), 1.42 (s, 9H).

e. Preparation of Compound

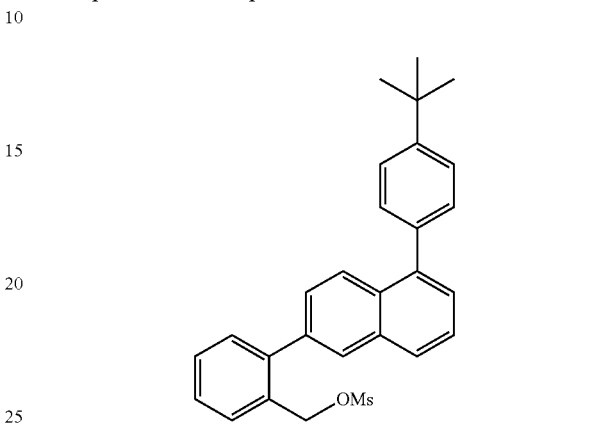

A 25-mL round bottom flask equipped with a magnetic stirrer under nitrogen was charged with 2-(1-(4-tert-butylphenyl)naphthalen-6-yl)phenylmethanol (140 mg, 0.38 mmol), CH$_2$Cl$_2$ (5 mL), and triethylamine (0.11 ml, 0.76 mmol). Methanesulfonyl chloride (44 μL, 0.57 mmol) was added via a syringe. The resulting reaction mixture was stirred at room temperature overnight. The reaction mixture was diluted with CH$_2$Cl$_2$ (30 mL) and washed with saturated NaHCO$_3$ (10 ml), brine (10 mL), dried over Na$_2$SO$_4$, and concentrated in rotavapor and purified on silica gel. Elution with 10% EtOAc/hexanes afforded the desired compound (170 mg, quantitative) as a white solid. $^1$H NMR (CDCl$_3$, 400 MHz) δ 8.03 (d, 1H, J=8.72 Hz), 7.95 (d, 1H, J=1.52 Hz), 7.37-7.60 (m, 11H), 4.58 (s, 2H), 2.20 (s, 3H), 1.42 (s, 9H).

Example 60

Preparation of Compound

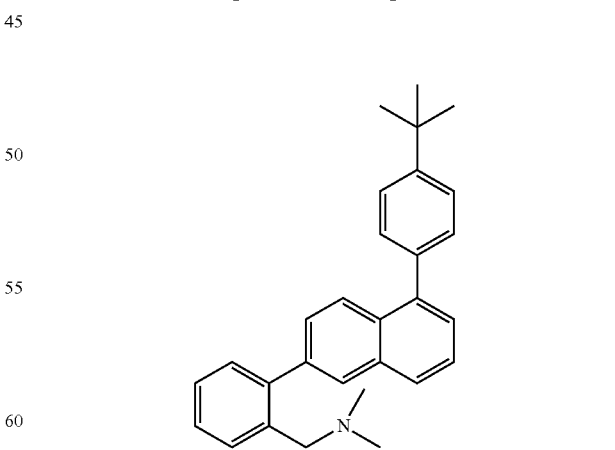

A 2-dram vial was added 2-(1-(4-tert-butylphenyl)naphthalen-6-yl)phenyl)methanesulfonate (18 mg, 0.04 mmol), dimethylamine (2 M in THF, 2 mL)). The sealed vial was heated to 60° C. for 12 h. After cooled to room temperature, the reaction mixture was diluted with EtOAc (30 mL), washed with saturated NaHCO$_3$ (10 mL), brine (10 mL), dried over Na$_2$SO$_4$, concentrated in rotavapor and purified on silica gel. Elution with CH$_2$Cl$_2$ to (10/89/1: MeOH/CHCl$_3$/ammonium hydroxide) afforded the desired compound (10.0 mg, 63%) as colorless oil. $^1$H NMR (CDCl$_3$, 400 MHz) δ 8.01 (d, 1H, J=8.64 Hz), 7.94 (s, 1H), 7.89 (d, 1H, J=8.12 Hz), 7.40-7.62 (m, 8H), 7.33-7.44 (m, 3H), 3.44 (s, 2H), 2.19 (s, 6H), 1.45 (s, 9H).

Example 61

Preparation of Compound

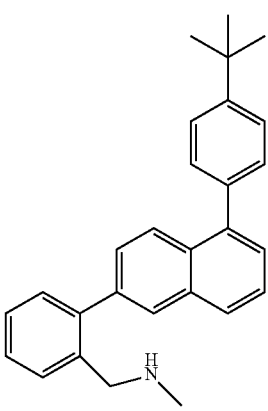 [SMILES: CNCc1ccccc1-c1ccc2c(-c3ccc(C(C)(C)C)cc3)cccc2c1]

A 2-dram vial was added 2-(1-(4-t-butylphenyl)naphthalen-6-yl)phenyl)methanesulfonate (18 mg, 0.04 mmol), methanamine (2 M in THF, 2 mL)). The sealed vial was heated to 60° C. for 12 h. After cooled to room temperature, the reaction mixture was diluted with EtOAc (30 mL), washed with saturated NaHCO$_3$ (10 mL), brine (10 mL), dried over Na$_2$SO$_4$, concentrated in rotavapor and purified on silica gel. Elution with CH$_2$Cl$_2$ to (10/89/1: MeOH/CHCl$_3$/ammonium hydroxide) afforded the desired compound (7.6 mg, 50%) as colorless oil. $^1$H NMR (CDCl$_3$, 400 MHz) δ 7.93 (d, 1H, J=8.64 Hz), 7.78-7.83 (m, 2H), 7.36-7.51 (m, 8H), 7.26-7.33 (m, 3H), 3.69 (s, 2H), 2.24 (s, 3H), 1.35 (s, 9H).

Example 62

Preparation of Compound

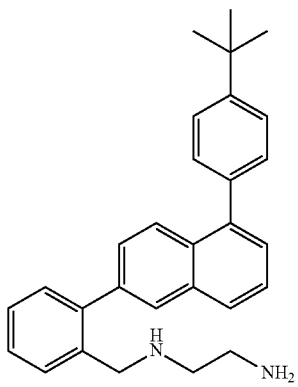

A 2-dram vial was added 2-(1-(4-t-butylphenyl)naphthalen-6-yl)phenyl)methanesulfonate (14 mg, 0.03 mmol), CH$_3$CN (1 mL), ethane-1,2-diamine (20 mg, 0.3 mL). The sealed vial was heated to 60° C. for 12 h. After cooled to room temperature, the reaction mixture was diluted with EtOAc (30 mL), washed with saturated NaHCO$_3$ (10 mL), brine (10 mL), dried over Na$_2$SO$_4$, concentrated in rotavapor and purified on silica gel. Elution with CH$_2$Cl$_2$ to (10/89/1: MeOH/CHCl$_3$/saturated NH$_3$ in water) afforded the desired compound (13 mg, quantitative) as colorless oil. $^1$H NMR (CDCl$_3$, 400 MHz) δ 8.03 (d, 1H, J=8.64 Hz), 7.93 (d, 1H, J=1.20 Hz), 7.88 (d, 1H, J=8.08 Hz), 7.48-7.60 (m, 8H), 7.35-7.43 (m, 3H), 3.82 (s, 2H), 2.70 (t, 2H, J=5.60 Hz), 2.58 (t, 2H, J=5.48 Hz), 1.45 (s, 9H).

Example 63

Preparation of Compound

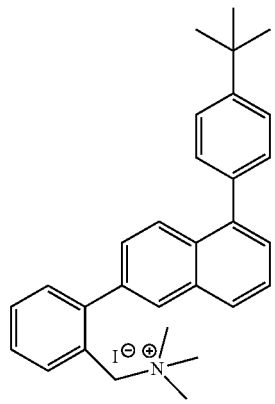 [SMILES: CC(C)(C)c1ccc(-c2cccc3cc(-c4ccccc4C[N+](C)(C)C)ccc23)cc1 ; [I-]]

A solution of (2-(1-(4-t-butylphenyl)naphthalen-6-yl)phenyl)-N,N-dimethylmethanamine (82.0 mg, 0.21 mmol) in iodomethane (1.5 mL) in a sealed 2-dram vial was stirred at 50° C. overnight. After cooled to room temperature, Et$_2$O was added to the reaction mixture. The solid was collected by filtration. After triturated with Et$_2$O and dried, there was obtained the desired compound (70 mg, 63%) as a white solid. $^1$H NMR (CDCl$_3$, 400 MHz) δ 8.11 (d, 1H, J=8.68 Hz), 8.07 (d, 1H, J=7.64 Hz), 7.88 (d, 1H, J=7.96 Hz), 7.81 (d, 1H, J=1.52 Hz), 7.45-7.65 (m, 9H), 7.32 (dd, 1H, J=1.84, 8.60 Hz), 5.0 (s, 2H), 3.07 (s, 9H), 1.43 (s, 9H).

Example 64

Preparation of Compound

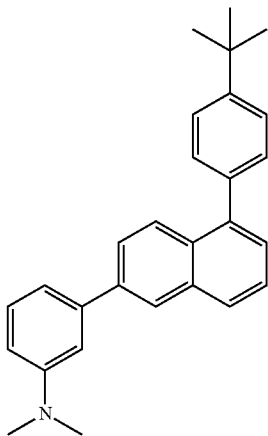 [SMILES: CN(C)c1cccc(-c2ccc3c(-c4ccc(C(C)(C)C)cc4)cccc3c2)c1]

A 25-mL round bottom flask equipped with a magnetic stirrer, a condenser and a nitrogen in/outlet adapter was charged with 1-(4-t-butylphenyl)naphthalen-6-yl trifluoromethanesulfonate (55 mg, 0.135 mmol), 3-(dimethylamino)phenylboronic acid (27 mg, 0.16 mmol), water/acetonitrile (1 mL/3 ml), K$_2$CO$_3$ (40 mg, 0.27 mmol), 2-dicyclohexylphosphino-2',4',6'-triisopropylbiphenyl (7 mg, 0.014 mmol). The resulting solution was degassed for 5 min, then Pd(OAc)$_2$ (2.0 mg, 0.007 mmol) was added and the solution was carefully degassed. The reaction mixture was warmed to 100° C. and stirred for 2 h. After cooled to room temperature, the reaction mixture was diluted with EtOAc (50 mL) and washed with saturated NaHCO$_3$ (15 mL), brine (15 mL), dried over Na$_2$SO$_4$. The organic layer was concentrated in rotavapor and purified on silica gel. Elution with 5% EtOAc/hexanes afforded the desired compound (30 mg, 59%) as a white solid. $^1$H NMR (CDCl$_3$, 400 MHz) δ 8.02 (d, 1H, J=1.60 Hz), 7.94 (d, 1H, J=8.68 Hz), 7.82 (d, 1H, J=8.20 Hz), 7.62 (dd, 1H, J=1.64, 8.76 Hz), 7.26-7.48 (m, 7H), 6.98-7.01 (m, 2H), 6.71 (dd, 1H, J=2.48, 8.28 Hz), 2.96 (s, 6H), 1.35 (s, 9H).

Example 65

Preparation of Compound

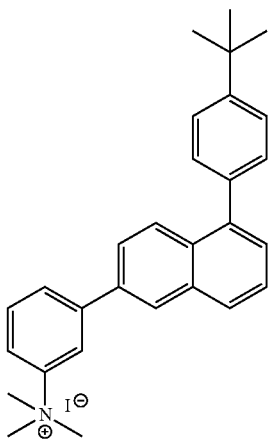 [SMILES: CC(C)(C)c1ccc(-c2cccc3cc(-c4cccc([N+](C)(C)C)c4)ccc23)cc1 ; [I-]]

A solution of the 3-(1-(4-t-butylphenyl)naphthalen-6-yl)-N,N-dimethylbenzenamine (30 mg, 0.08 mmol) in iodomethane (1.0 mL) in a sealed 2-dram vial was stirred at 80° C. overnight. After cooled to room temperature, Et$_2$O was added to the suspension. The solid was collected by filtration to afford the desired compound (35 mg, 85%) as an off white solid. $^1$H NMR (CDCl$_3$, 400 MHz) δ 8.30 (d, 1H, J=1.72 Hz), 8.10-8.14 (m, 2H), 8.05 (d, 1H, J=8.28 Hz), 7.88-7.95 (m, 2H), 7.68-7.78 (m, 2H), 7.48-7.64 (m, 6H), 4.14 (s, 9H), 1.45 (s, 9H).

Example 66

Preparation of Compound

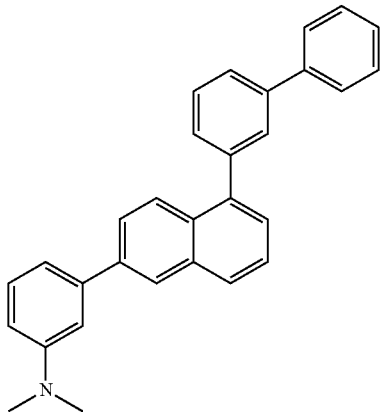 [SMILES: CN(C)c1cccc(-c2ccc3c(-c4cccc(-c5ccccc5)c4)cccc3c2)c1]

A 25-mL round bottom flask equipped with a magnetic stirrer, a condenser and a nitrogen in/outlet adapter was charged with the triflate (25 mg, 0.06 mmol), 3-(dimethylamino)phenylboronic acid (14 mg, 0.07 mmol), water/acetonitrile (1 mL/3 ml), K$_2$CO$_3$ (17 mg, 0.12 mmol), 2-dicyclohexylphosphino-2',4',6'-triisopropylbiphenyl (5 mg, 0.01 mmol). The resulting solution was degassed for 5 min, then Pd(OAc)$_2$ (2.0 mg, 0.009 mmol) was added and the solution was carefully degassed. The reaction mixture was warmed to 100° C. and stirred for 1.5 h. After cooled to room temperature, the reaction mixture was diluted with EtOAc (30 mL) and washed with saturated NaHCO$_3$ (10 mL), brine (10 mL), dried over Na$_2$SO$_4$. The organic layer was concentrated with a rotavapor and purified on silica gel. Elution with 5% EtOAc/hexanes afforded the desired compound (16 mg, 67%) as a white solid. $^1$H NMR (CDCl$_3$, 400 MHz) δ 8.03 (d, 2H, J=1.52 Hz), 7.94 (d, 1H, J=8.80 Hz), 7.86 (d, 1H, J=8.20 Hz), 7.58-7.70 (m, 5H), 7.25-7.52 (m, 8H), 7.67-7.01 (m, 2H), 6.69-6.72 (m, 1H), 2.95 (s, 6H).

The requisite intermediate for the preparation of this compound was prepared as follows.
a. Preparation of Compound

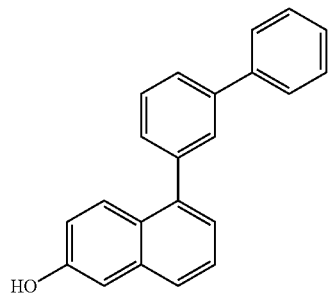 [SMILES: Oc1ccc2c(-c3cccc(-c4ccccc4)c3)cccc2c1]

A 100-mL round bottom flask equipped with a magnetic stirrer, a condenser and a nitrogen in/outlet adapter was charged with 5-bromonaphthalen-2-ol (300 mg, 1.35 mmol), 3-biphenylboronic acid (523 mg, 2.69 mmol), water/dioxane (4 mL/16 ml), K$_2$CO$_3$ (383 mg, 2.78 mmol). The resulting solution was degassed for 5 min, then Pd(PPh$_3$)$_4$ (77 mg, 0.07 mmol) was added. The reaction mixture was heated to 100° C. for 12 h. After cooled to room temperature, the reaction mixture was diluted with EtOAc (60 mL) and washed with saturated NaHCO$_3$ (20 mL), brine (20 mL), dried over Na$_2$SO$_4$. The organic layer was concentrated in rotavapor and purified on silica gel. Elution with 10% EtOAc/hexanes afforded the desired compound (323 mg, 81%) as a white solid. $^1$H NMR (CDCl$_3$, 400 MHz) δ 7.90 (d, 1H, J=9.12 Hz), 7.67-7.75 (m, 5H), 7.59 (t, 1H, J=7.56 Hz), 7.46-7.53 (m, 4H), 7.34-7.41 (m, 2H), 7.25 (d, 1H, J=2.56 Hz), 7.09 (dd, 1H, J=2.56, 9.12 Hz), 5.20 (s, 1H).
b. Preparation of Compound

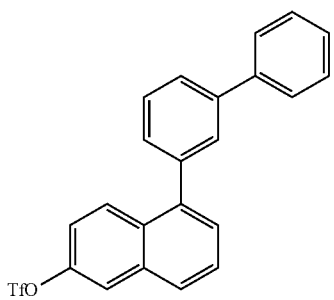 [SMILES: O=S(=O)(Oc1ccc2c(-c3cccc(-c4ccccc4)c3)cccc2c1)C(F)(F)F]

A 50-mL round bottom flask equipped with a magnetic stirrer under nitrogen was charged with the 5-(biphenyl-3-yl) naphthalen-2-ol (323 mg, 1.09 mmol), CH$_2$Cl$_2$ (10 mL), and triethylamine (0.31 ml, 2.20 mmol). After cooling to −70° C., triflic anhydride (0.21 ml, 1.20 mmol) was added via a syringe. The resulting reaction mixture was stirred at −70° C. for 30 min, then room temperature for 30 min. The reaction mixture was diluted with CH$_2$Cl$_2$ (50 mL) and washed with saturated NaHCO$_3$ (20 ml), brine (20 mL), dried over Na$_2$SO$_4$, and concentrated in rotavapor and purified on silica gel. Elution with 5% EtOAc/hexanes afforded the desired compound (434 mg, 93%) as a white solid. $^1$H NMR (CDCl$_3$, 400 MHz) δ 7.98 (d, 1H, J=9.32 Hz), 7.83 (d, 1H, J=8.16 Hz), 7.75 (d, 1H, J=2.56 Hz), 7.48-7.65 (m, 7H), 7.36-7.42 (m, 3H), 7.27-7.33 (m, 1H), 7.25 (dd, 1H, J=9.32, 2.65 Hz).

Example 67

Preparation of Compound

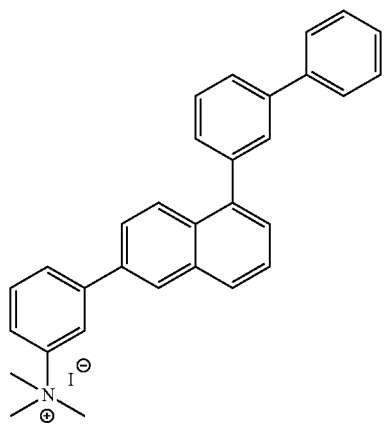 [SMILES: C[N+](C)(C)c1cccc(-c2ccc3c(-c4cccc(-c5ccccc5)c4)cccc3c2)c1 ; [I-]]

A solution of the compound of Example 66 (15 mg, 0.04 mmol) in iodomethane (1.0 mL) was stirred in a sealed 2-dram vial at 80° C. overnight. After cooled to room temperature, the reaction mixture was added Et$_2$O. The solid was collected by filtration to afford the desired compound (18 mg, 90%) as a light yellow solid. $^1$H NMR (CDCl$_3$, 400 MHz) δ 8.38 (s, 1H), 8.17 (s, 1H), 8.10-8.13 (m, 2H), 7.89-7.95 (m, 2H), 7.36-7.76 (m, 13H), 4.14 (s, 9H).

Example 68

Preparation of Compound

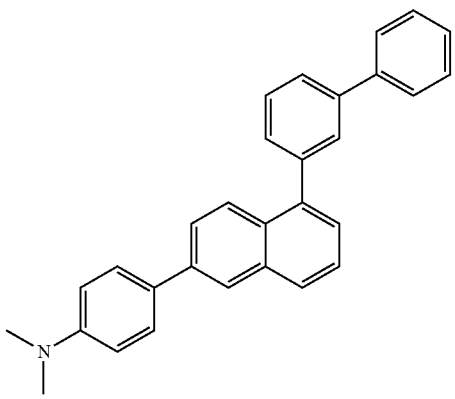 [SMILES: CN(C)c1ccc(-c2ccc3c(-c4cccc(-c5ccccc5)c4)cccc3c2)cc1]

A 25-mL round bottom flask equipped with a magnetic stirrer, a condenser and a nitrogen in/outlet adapter was charged with the triflate (25 mg, 0.06 mmol), 4-(dimethylamino)phenylboronic acid (14 mg, 0.07 mmol), water/acetonitrile (1 mL/3 ml), K$_2$CO$_3$ (17 mg, 0.12 mmol), 2-dicyclohexylphosphino-2',4',6'-triisopropylbiphenyl (5 mg, 0.01 mmol). The resulting solution was degassed for 5 min, then Pd(OAc)$_2$ (2.0 mg, 0.009 mmol) was added and the solution was carefully degassed. The reaction mixture was warmed to 100° C. and stirred for 1.5 h. After cooled to room temperature, the reaction mixture was diluted with EtOAc (30 mL) and washed with saturated NaHCO$_3$ (10 mL), brine (10 mL), dried over Na$_2$SO$_4$. The organic layer was concentrated on a rotavapor and purified on silica gel. Elution with 5% EtOAc/hexanes afforded the desired compound (20 mg, 83%) as a white solid. $^1$H NMR (CDCl$_3$, 400 MHz) δ 7.98 (s, 1H), 7.90 (d, 1H, J=8.79 Hz), 7.82 (d, 1H, J=8.02 Hz), 7.18-7.79 (m, 14H), 6.77-6.80 (m, 2H), 2.94 (s, 6H).

Example 69

Preparation of Compound

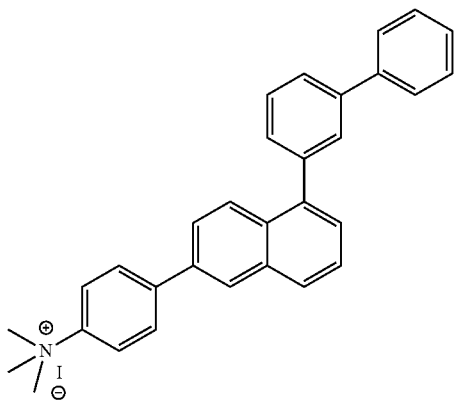 [SMILES: C[N+](C)(C)c1ccc(-c2ccc3c(-c4cccc(-c5ccccc5)c4)cccc3c2)cc1 ; [I-]]

A solution of the compound of Example 68 (20 mg, 0.05 mmol) in iodomethane (1.0 mL) was stirred in a sealed 2-dram vial at 80° C. overnight. After cooled to room temperature, Et$_2$O was added to the suspension. The solid was collected by filtration to afford the desired compound (16 mg, 59%) as a light yellow solid. $^1$H NMR (CDCl$_3$, 400 MHz) δ 8.15 (d, 1H, J=1.76 Hz), 8.11 (d, 1H, J=8.88 Hz), 8.04-8.06 (m, 2H), 7.97-8.00 (m, 2H), 7.36-7.78 (m, 13H), 4.11 (s, 9H).

Example 70

Preparation of Compound

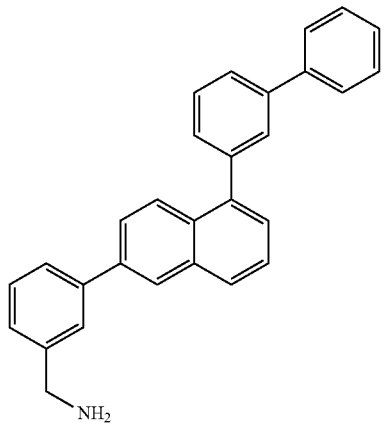 [SMILES: NCc1cccc(-c2ccc3c(-c4cccc(-c5ccccc5)c4)cccc3c2)c1]

A 100-mL round bottom flask equipped with a magnetic stirrer, a condenser and a nitrogen in/outlet adapter was charged with the starting material cyano (82 mg, 0.21 mmol), THF/toluene (10 mL/10 mL). After cooled to 0° C., LiAlH$_4$ (30 mg, 0.79 mmol) was added to the reaction mixture. The reaction mixture was heated to 100° C. and stirred for 3 h. After cooled to 0° C., the reaction mixture was diluted with EtOAc (50 mL) and quenched with 15% NaOH (0.24 mL), water (1 mL). The organic layer was decanted, dried over Na$_2$SO$_4$, concentrated in rotavapor and purified on silica gel. Elution with 5% MeOH/CH$_2$Cl$_2$ afforded the desired compound (25 mg, 30%) as a white solid. $^1$H NMR (CDCl$_3$, 400 MHz) δ 8.13 (d, 1H, J=1.68 Hz), 8.04 (d, 1H, J=8.80 Hz), 7.94 (d, 1H, J=7.88 Hz), 7.33-7.78 (m, 16H), 3.99 (s, 2H).

The requisite intermediate for the preparation of this compound was prepared as follows.

a. Preparation of Compound

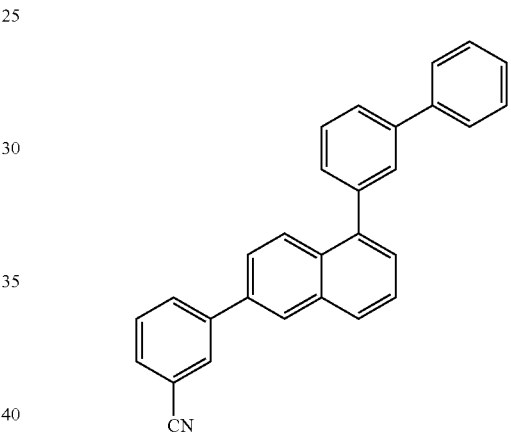

A 25-mL round bottom flask equipped with a magnetic stirrer, a condenser and a nitrogen in/outlet adapter was charged with the triflate (100 mg, 0.23 mmol), 3-cyanophenylboronic acid (45 mg, 0.30 mmol), water/acetonitrile (2 mL/6 ml), K$_2$CO$_3$ (17 mg, 0.12 mmol), 2-dicyclohexylphosphino-2',4',6'-triisopropylbiphenyl (11 mg, 0.023 mmol). The resulting solution was degassed for 5 min, then Pd(OAc)$_2$ (2.0 mg, 0.009 mmol) was added and the solution was carefully degassed. The reaction mixture was heated to 80° C. and stirred for 4 h. After cooled to room temperature, the reaction mixture was diluted with EtOAc (30 mL) and washed with saturated NaHCO$_3$ (10 mL), brine (10 mL), dried over Na$_2$SO$_4$. The organic layer was concentrated with a rotavapor and purified on silica gel. Elution with 5% EtOAc/hexanes afforded the desired compound (82 mg, 92%) as a white solid. $^1$H NMR (CDCl$_3$, 400 MHz) δ 8.13 (d, 1H, J=1.72 Hz), 8.10 (d, 1H, J=8.84 Hz), 8.04 (s, 1H), 7.98 (d, 2H, J=8.12 Hz), 7.78 (s, 1H), 7.46-7.74 (m, 12H), 7.40 (m, 1H).

Example 71

Preparation of Compound

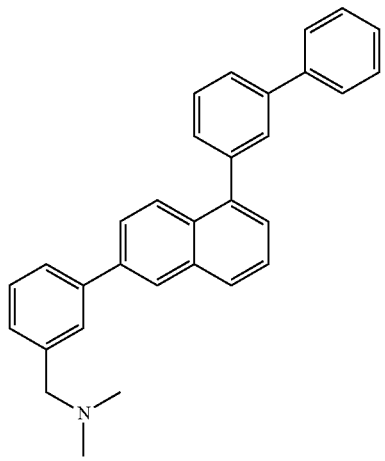 [SMILES: CN(C)Cc1cccc(-c2ccc3c(-c4cccc(-c5ccccc5)c4)cccc3c2)c1]

A 25-mL round bottom flask equipped with a magnetic stirrer under N₂ was charged with the starting material amine (20 mg, 0.05 mmol), MeOH (2 mL), formaldehyde (37% in water, 44 µl, 0.5 mmol), and zinc chloride (4 mg, 0.025 mmol) at room temperature. Sodium cyanoborohydride (4 mg, 0.05) was added. After being stirred at room temperature for 12 h, the reaction mixture was treated with 0.1 N NaOH (1 mL). After most of methanol was evaporated under reduced pressure, the aqueous solution was extracted with ethyl acetate (20 mL×2). The combined extracts were washed with water and brine, dried over $Na_2SO_4$, concentrated with a rotavapor and purified on silica gel. Elution with 5% MeOH/CHCl₃ afforded the desired compound (20 mg, 91%) as a white foam solid. ¹H NMR (CDCl₃, 400 MHz) δ 8.17 (d, 1H, J=1.36 Hz), 8.06 (d, 1H, J=8.80 Hz), 7.96 (d, 1H, J=8.12 Hz), 7.34-7.80 (m, 16H), 3.56 (s, 2H), 2.33 (s, 6H).

Example 72

Preparation of Compound

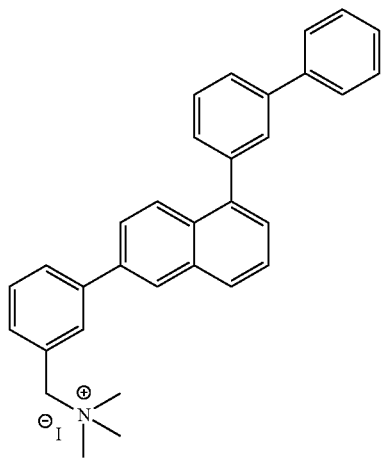 [SMILES: C[N+](C)(C)Cc1cccc(-c2ccc3c(-c4cccc(-c5ccccc5)c4)cccc3c2)c1 ; [I-]]

A solution of the compound of Example 71 dimethylamine (15 mg, 0.04 mmol) in iodomethane (1.0 mL) was stirred in a sealed 2-dram vial at 60° C. overnight. After cooled to room temperature, the reaction mixture was added Et₂O. The solid was collected by filtration to afford the desired compound (10 mg, 50%) as a light yellow solid. ¹H NMR (CDCl₃, 400 MHz) δ 8.15 (d, 1H, J=1.36 Hz), 8.04 (d, 1H, J=8.92 Hz), 8.00 (s, 1H), 7.96 (d, 1H, J=7.96 Hz), 7.85 (d, 1H, J=7.96 Hz), 7.64-7.74 (m, 6H), 7.50-7.60 (m, 3H), 7.43-7.52 (m, 4H), 7.33-7.38 (m, 1H), 5.14 (s, 2H), 3.44 (s, 9H).

Example 73

Preparation of Compound

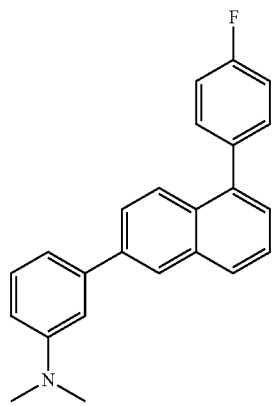 [SMILES: CN(C)c1cccc(-c2ccc3c(-c4ccc(F)cc4)cccc3c2)c1]

A 25-mL round bottom flask equipped with a magnetic stirrer, a condenser and a nitrogen in/outlet adapter was charged with 1-(4-fluorophenyl)naphthalene-6-yl trifluoromethanesulfonate (40 mg, 0.11 mmol), 3-(dimethylamino)phenylboronic acid (30 mg, 0.18 mmol), water/acetonitrile (1 mL/3 ml), K₂CO₃ (30 mg, 0.27 mmol), 2-dicyclohexylphosphino-2',4',6'-triisopropylbiphenyl (6 mg, 0.011 mmol). The resulting solution was degassed for 5 min, then Pd(OAc)₂ (2.0 mg, 0.006 mmol) was added and the solution was carefully degassed. The reaction mixture was warmed to 100° C. and stirred for 1 h. After cooled to room temperature, the reaction mixture was diluted with EtOAc (30 mL) and washed with saturated NaHCO₃ (10 mL), brine (10 mL), dried over Na₂SO₄. The organic layer was concentrated on a rotavapor and purified on silica gel. Elution with 5% EtOAc/hexanes afforded the desired compound (30 mg, 82%) as a white solid. ¹H NMR (CDCl₃, 400 MHz) δ 8.03 (d, 1H, J=1.56 Hz), 7.80-7.86 (m, 2H), 7.64 (dd, 1H, J=1.88, 8.84 Hz), 7.39-7.48 (m, 3H), 7.27-7.32 (m, 2H), 7.10-7.18 (m, 2H), 6.97-7.01 (m, 2H), 6.71 (dd, 1H, J=2.56, 8.28 Hz), 2.30 (s, 6H).

The requisite intermediate for the preparation of this compound was prepared as follows.

a. Preparation of Compound

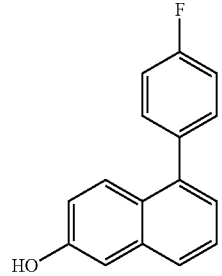 [SMILES: Oc1ccc2c(-c3ccc(F)cc3)cccc2c1]

A 100-mL round bottom flask equipped with a magnetic stirrer, a condenser and a nitrogen in/outlet adapter was charged with 5-bromonaphthalen-2-ol (100 mg, 0.45 mmol), 4-fluorophenylboronic acid (125 mg, 0.89 mmol), water/dioxane (2 mL/6 ml), $K_2CO_3$ (124 mg, 0.90 mmol). The resulting solution was degassed for 5 min, then $Pd(PPh_3)_4$ (26 mg, 0.02 mmol) was added. The reaction mixture was warmed to 100° C. and stirred for 3 h. After cooled to room temperature, the reaction mixture was diluted with EtOAc (30 mL) and washed with saturated $NaHCO_3$ (15 mL), brine (15 mL), dried over $NaSO_4$. The organic layer was concentrated in rotavapor and purified on silica gel. Elution with 10% EtOAc/hexanes afforded the desired compound (98 mg, 92%) as a white solid. $^1$H NMR ($CDCl_3$, 400 MHz) δ 7.73 (d, 1H, J=9.16 Hz), 7.68 (d, 1H, J=8.24 Hz), 7.38-7.48 (m, 3H), 7.12-7.26 (m, 5H), 7.04 (dd, 1H, J=2.6, 9.12 Hz), 5.11 (s, 3H).

b. Preparation of Compound

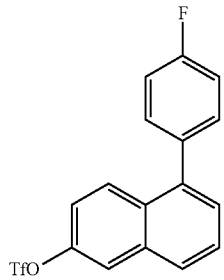 [SMILES: O=S(=O)(Oc1ccc2c(-c3ccc(F)cc3)cccc2c1)C(F)(F)F]

A 50-mL round bottom flask equipped with a magnetic stirrer under nitrogen was charged with 5-(4-fluorophenyl)naphthalene-2-ol (98 mg, 0.41 mmol), $CH_2Cl_2$ (10 mL), and triethylamine (0.15 ml, 1.1 mmol). After cooling to −70° C., triflic anhydride (0.1 ml, 0.59 mmol) was added via a syringe. The resulting reaction mixture was stirred at −70→−30° C. for 30 min. The reaction mixture was diluted with $CH_2Cl_2$ (30 mL) and washed with saturated $NaHCO_3$ (10 ml), brine (10 mL), dried over $Na_2SO_4$, concentrated in rotavapor and purified on silica gel. Elution with 5% EtOAc/hexanes afforded the desired compound (133 mg, 88%) as colorless oil. $^1$H NMR ($CDCl_3$, 400 MHz) δ 7.85 (d, 1H, J=9.32 Hz), 7.81 (d, 1H, J=8.28 Hz), 7.74 (d, 1H, J=2.44 Hz), 7.55 (t, 1H, J=7.20 Hz), 7.42 (dd, 1H, J=0.96, 6.12 Hz), 7.30-7.38 (m, 2H), 7.25 (dd, 1H, J=2.48, 9.32 Hz), 7.13 (m, 2H).

Example 74

Preparation of Compound

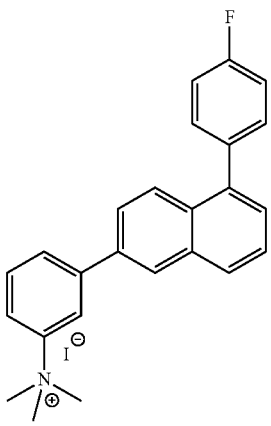 [SMILES: C[N+](C)(C)c1cccc(-c2ccc3c(-c4ccc(F)cc4)cccc3c2)c1 ; [I-]]

A solution of the 3-(1-(4-fluorophenyl)naphthalen-6-yl)-N,N-dimethylbenzenamine (30 mg, 0.09 mmol) in iodomethane (1.0 mL) was stirred in a sealed 2-dram vial at 70° C. overnight. After cooled to room temperature, $Et_2O$ was added to the suspension. The solid was collected by filtration to afford the desired compound (35 mg, 83%) as off white solid. $^1$H NMR (DMSO, 400 MHz) δ 8.55 (s, 1H), 8.42 (s, 1H), 8.01-8.16 (m, 4H), 7.95 (d, 1H, J=8.88 Hz), 7.85 (t, 1H, J=8.12 Hz), 7.73 (t, 1H, J=7.96 Hz), 7.60-7.65 (m, 2H), 7.56 (d, 1H, J=7.00 Hz), 7.46 (t, 2H, J=8.76 Hz), 3.77 (s, 9H).

Example 75

Preparation of Compound

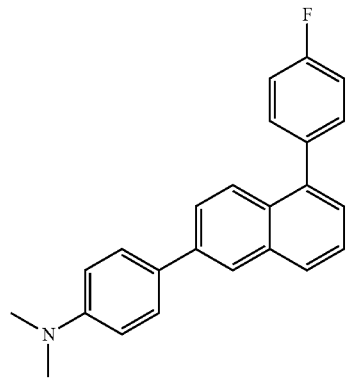 [SMILES: CN(C)c1ccc(-c2ccc3c(-c4ccc(F)cc4)cccc3c2)cc1]

A 25-mL round bottom flask equipped with a magnetic stirrer, a condenser and a nitrogen in/outlet adapter was charged with 1-(4-fluorophenyl)naphthalene-6-yl trifluoromethanesulfonate (43 mg, 0.12 mmol), 4-(dimethylamino)phenylboronic acid (30 mg, 0.18 mmol), water/acetonitrile (1 mL/3 ml), $K_2CO_3$ (30 mg, 0.27 mmol), 2-dicyclohexylphosphino-2',4'6'-triisopropylbiphenyl (6 mg, 0.011 mmol). The resulting solution was degassed for 5 min, then $Pd(OAc)_2$ (2.0 mg, 0.006 mmol) was added and the solution was carefully degassed. The reaction mixture was warmed to 100° C. and stirred for 1 h. After cooled to room temperature, the reaction mixture was diluted with EtOAc (30 mL) and washed with saturated NaHCO$_3$ (10 mL), brine (10 mL), dried over Na$_2$SO$_4$. The organic layer was concentrated in rotavapor and purified on silica gel. Elution with 5% EtOAc/hexanes afforded the desired compound (35 mg, 88%) as a white solid. $^1$H NMR (CDCl$_3$, 400 MHz) δ 7.97 (d, 1H, J=1.48 Hz), 7.80 (t, 2H, J=8.20 Hz), 7.62 (dd, 1H, J=1.64, 8.84 Hz), 7.57 (d, 2H, J=8.64), 7.38-7.45 (m, 3H), 7.27 (d, 1H, J=7.0 Hz), 7.09-7.14 (m, 2H), 6.78 (d, 2H, J=8.7 Hz), 2.95 (s, 6H).

Example 76

Preparation of Compound

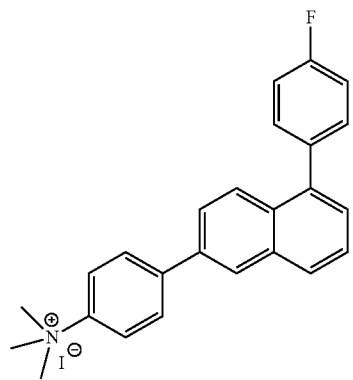 [SMILES: C[N+](C)(C)c1ccc(-c2ccc3c(-c4ccc(F)cc4)cccc3c2)cc1 ; [I-]]

A solution of 4-(1-(4-fluorophenyl)naphthalen-6-yl)-N,N-dimethylbenzenamine (35 mg, 0.10 mmol) in iodomethane (1.0 mL) was stirred in a sealed 2-dram vial at 70° C. overnight. After cooled to room temperature, Et$_2$O was added to the suspension. The solid was collected by filtration to afford the desired compound (40 mg, 80%) as a light yellow solid. $^1$H NMR (DMSO, 400 MHz) δ 8.51 (s, 1H), 8.14-8.20 (m, 5H), 7.92-8.00 (m, 2H), 7.72 (t, 1H, J=7.20 Hz), 7.58-7.65 (m, 2H), 7.55 (d, 1H, J=7.04 Hz), 7.46 (t, 2H, J=8.84 Hz), 3.73 (s, 9H).

Example 77

Preparation of Compound

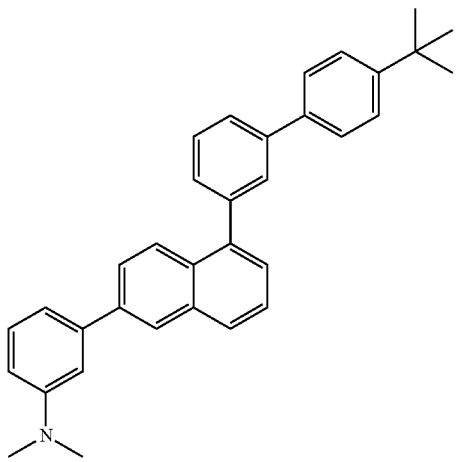 [SMILES: CN(C)c1cccc(-c2ccc3c(-c4cccc(-c5ccc(C(C)(C)C)cc5)c4)cccc3c2)c1]

A 25-mL round bottom flask equipped with a magnetic stirrer, a condenser and a nitrogen in/outlet adapter was charged with 3-(2-(3-(dimethylamino)phenyl)naphthalen-5-yl)phenyl trifluoromethanesulfonate (32 mg, 0.07 mmol), 4-tert-butylphenylboronic acid (15 mg, 0.08 mmol), water/acetonitrile (1 mL/3 ml), K$_2$CO$_3$ (20 mg, 0.14 mmol), 2-dicyclohexylphosphino-2',4',6'-triisopropylbiphenyl (10 mg, 0.02 mmol). The resulting solution was degassed for 5 min, then Pd(OAc)$_2$ (2.0 mg, 0.009 mmol) was added and the solution was carefully degassed. The reaction mixture was warmed to 80° C. and stirred for 12 h. After cooled to room temperature, the reaction mixture was diluted with EtOAc (50 mL) and washed with saturated NaHCO$_3$ (15 mL), brine (15 mL), dried over Na$_2$SO$_4$, concentrated with a rotavapor and purified on silica gel. Elution with 5% EtOAc/hexanes afforded the desired compound (15 mg, 48%) as a white solid. $^1$H NMR (CDCl$_3$, 400 MHz) δ 8.03 (d, 1H, J=1.60 Hz 1H), 7.95 (d, 1H, J=8.80 Hz), 7.85 (d, 1H, J=8.08 Hz), 7.38-7.69 (m, 11H), 7.28 (t, 1H, J=7.88 Hz), 6.97-7.01 (m, 2H), 6.70 (dd, 1H, J=2.50, 8.24 Hz), 2.96 (s, 6H), 1.29 (s, 9H).

The requisite intermediate for the preparation of this compound was prepared as follows.

a. Preparation of Compound

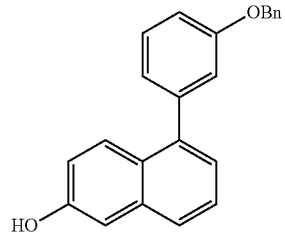 [SMILES: Oc1ccc2c(-c3cccc(OCc4ccccc4)c3)cccc2c1]

A 100-mL round bottom flask equipped with a magnetic stirrer, a condenser and a nitrogen in/outlet adapter was charged with 5-bromonaphthalen-2-ol (500 mg, 2.24 mmol), 3-(benzyloxy)phenylboronic acid (1.02 g, 4.48 mmol), water/dioxane (4 mL/12 ml), K$_2$CO$_3$ (618 mg, 4.48 mmol). The resulting solution was degassed for 5 min, then Pd(PPh$_3$)$_4$ (129 mg, 0.11 mmol) was added. The reaction mixture was warmed to 100° C. and stirred for 12 h. After cooled to room temperature, the reaction mixture was diluted with EtOAc (60 mL) and washed with saturated NaHCO$_3$ (20 mL), brine (20 mL), dried over Na$_2$SO$_4$, concentrated in rotavapor and purified on silica gel. Elution with 10% EtOAc/hexanes afforded the desired compound (371 mg, 51%) as a white solid. $^1$H NMR (CDCl$_3$, 400 MHz) δ 7.71 (d, 1H, J=9.12 Hz), 7.61 (d, 1H, J=8.20 Hz), 7.12-7.40 (m, 9H), 7.69-7.02 (m, 4H), 5.04 (s, 2H), 4.96 (s, 1H).

b. Preparation of Compound

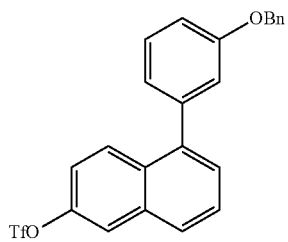 [SMILES: O=S(=O)(Oc1ccc2c(-c3cccc(OCc4ccccc4)c3)cccc2c1)C(F)(F)F]

A 50-mL round bottom flask equipped with a magnetic stirrer under nitrogen was charged with 5-(3-(benzyloxy)phenyl)naphthalene-2-ol (371 mg, 1.14 mmol), CH$_2$Cl$_2$ (10 mL), and triethylamine (0.32 ml, 2.28 mmol). After cooling to −70° C., triflic anhydride (0.21 ml, 1.25 mmol) was added via a syringe. The resulting reaction mixture was stirred at −70→−30° C. for 30 min. The reaction mixture was diluted with CH$_2$Cl$_2$ (30 mL) and washed with saturated NaHCO$_3$ (10 ml), brine (10 mL), dried over Na$_2$SO$_4$, concentrated with a rotavapor and purified on silica gel. Elution with 5% EtOAc/hexanes afforded the desired compound (480 mg, 92%) as colorless oil. $^1$H NMR (CDCl$_3$, 400 MHz) δ 7.86 (d, 1H, J=9.28 Hz), 7.80 (d, 1H, J=7.96 Hz), 7.72 (d, 1H, J=2.52 Hz), 7.54 (t, 1H, J=8.04 Hz), 7.18-7.43 (m, 9H), 7.97-7.00 (m, 2H), 5.06 (s, 2H).

c. Preparation of Compound

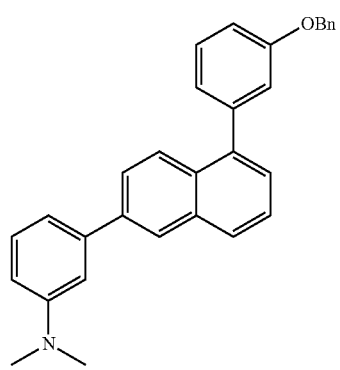 [SMILES: CN(C)c1cccc(-c2ccc3c(-c4cccc(OCc5ccccc5)c4)cccc3c2)c1]

A 25-mL round bottom flask equipped with a magnetic stirrer, a condenser and a nitrogen in/outlet adapter was charged with 1-(3-(benzyloxy)phenyl)naphthalen-6-yl trifluoromethanesulfonate (195 mg, 0.12 mmol), 4-(dimethylamino)phenylboronic acid (84 mg, 0.51 mmol), water/acetonitrile (1 mL/4 ml), K$_2$CO$_3$ (200 mg, 1.44 mmol), 2-dicyclohexylphosphino-2',4',6'-triisopropylbiphenyl (20 mg, 0.04 mmol). The resulting solution was degassed for 5 min, then Pd(OAc)$_2$ (5.0 mg, 0.02 mmol) was added and the solution was carefully degassed. The reaction mixture was heated to 100° C. and stirred for 1 h. After cooled to room temperature, the reaction mixture was diluted with EtOAc (50 mL) and washed with saturated NaHCO$_3$ (15 mL), brine (15 mL), dried over Na$_2$SO$_4$, concentrated on a rotavapor and purified on silica gel. Elution with 5% EtOAc/hexanes afforded the desired compound (168 mg, 92%) as a white solid. $^1$H NMR (CDCl$_3$, 400 MHz) δ 8.02 (s, 1H), 7.87 (d, 1H, J=8.92 Hz), 7.84 (d, 1H, J=8.52 Hz), 7.61 (d, 1H, J=8.76 Hz), 7.24-7.48 (m, 9H), 6.99-7.08 (m, 5H), 6.71 (1H, d, J=8.16 Hz), 5.06 (s, 2H), 2.97 (s, 6H).

d. Preparation of Compound

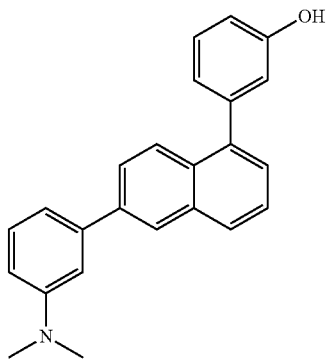 [SMILES: CN(C)c1cccc(-c2ccc3c(-c4cccc(O)c4)cccc3c2)c1]

A 100-mL round bottom flask equipped with a magnetic stirrer was charged with 3-(1-(3-(benzyloxy)phenyl)naphthalen-6-yl)-N,N-dimethylbenzenamine (168 mg, 0.26 mmol), MeOH (15 mL), and Pd/C (10%, 20 mg). The reaction flask was sealed with septum and purge with N$_2$ three times; H$_2$ three times. The reaction mixture was stirred at room temperature under H$_2$ balloon for 12 h. TLC showed the starting material was consumed. The reaction mixture was passed through a pad of Celite and washed with MeOH. The filtrate was concentrated to afford the crude desired compound as a grey solid. The crude product was used in next step without further purification.

e. Preparation of Compound

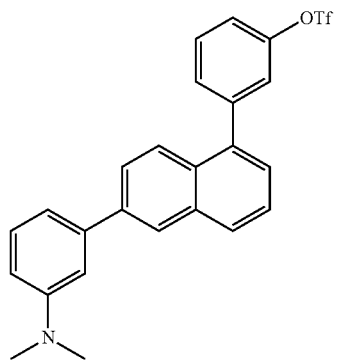 [SMILES: CN(C)c1cccc(-c2ccc3c(-c4cccc(OS(=O)(=O)C(F)(F)F)c4)cccc3c2)c1]

A 50-mL round bottom flask equipped with a magnetic stirrer under nitrogen was charged with 3-(2-(3-(dimethylamino)phenyl)naphthalen-5-yl)phenol (140 mg, 0.41 mmol), CH$_2$Cl$_2$ (5 mL), and triethylamine (0.11 ml, 0.82 mmol). After cooling to −70° C., triflic anhydride (76 μl, 0.45 mmol) was added via a syringe. The resulting reaction mixture was stirred at −70° C. for 30 min. The reaction mixture was diluted with CH$_2$Cl$_2$ (30 mL) and washed with saturated NaHCO$_3$ (10 ml), brine (10 mL), dried over Na$_2$SO$_4$, concentrated and purified on silica gel. Elution with 5% EtOAc/hexanes afforded the desired compound (140 mg, 72%) as colorless oil. $^1$H NMR (CDCl$_3$, 400 MHz) δ 8.04 (d, 1H, J=1.64 Hz), 7.89 (d, 1H, J=8.20 Hz), 7.79 (d, 1H, J=8.76 Hz), 7.68 (dd, 1H, J=1.84, 8.80 Hz), 7.46-7.55 (m, 3H), 7.26-7.38 (m, 4H), 7.67-7.00 (m, 2H), 6.72 (dd, 1H, d, J=2.56, 8.28 Hz), 2.97 (s, 6H).

Example 78

Preparation of Compound

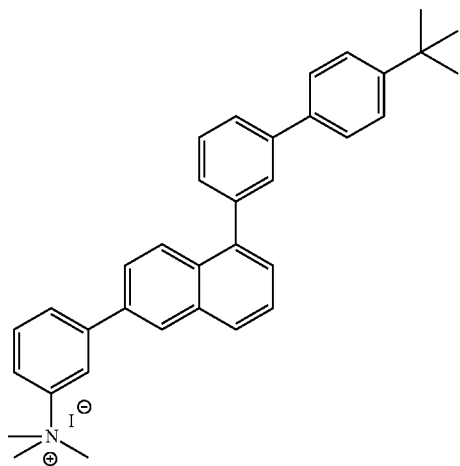 [SMILES: CC(C)(C)c1ccc(-c2cccc(-c3cccc4cc(-c5cccc([N+](C)(C)C)c5)ccc34)c2)cc1 ; [I-]]

A solution of the compound of Example 77 (12 mg, 0.03 mmol) in iodomethane (1.0 mL) was stirred in a sealed 2-dram vial at 80° C. overnight. After cooled to room temperature, Et$_2$O was added to the suspension. The solid was collected by filtration to afford the desired compound (8.8 mg, 55%) as a light yellow solid. $^1$H NMR (CDCl$_3$, 400 MHz) δ 8.28 (s, 1H), 8.00-8.06 (m, 3H), 7.80-7.83 (m, 2H), 7.38-7.67 (m, 12H), 4.05 (s, 9H), 1.29 (s, 9H).

Example 79

Preparation of Compound

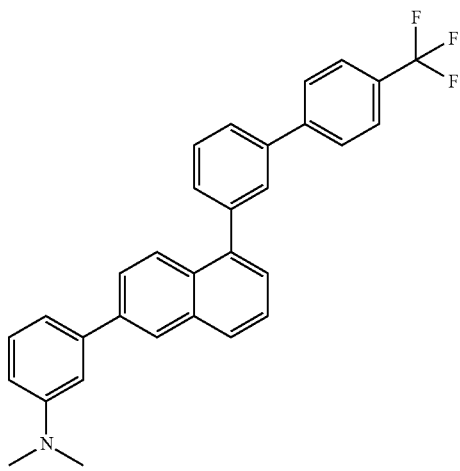 [SMILES: CN(C)c1cccc(-c2ccc3c(-c4cccc(-c5ccc(C(F)(F)F)cc5)c4)cccc3c2)c1]

A 25-mL round bottom flask equipped with a magnetic stirrer, a condenser and a nitrogen in/outlet adapter was charged with 3-(2-(3-(dimethylamino)phenyl)naphthalen-5-yl)phenyl trifluoromethanesulfonate (32 mg, 0.07 mmol), 4-(trifluoromethyl)phenylboronic acid (26 mg, 0.14 mmol), water/acetonitrile (1 mL/3 ml), K$_2$CO$_3$ (20 mg, 0.14 mmol), 2-dicyclohexylphosphino-2',4',6'-triisopropylbiphenyl (10 mg, 0.03 mmol). The resulting solution was degassed for 5 min, then Pd(OAc)$_2$ (2 mg, 0.008 mmol) was added and the solution was carefully degassed. The reaction mixture was warmed to 80° C. and stirred for 4 h. After cooled to room temperature, the reaction mixture was diluted with EtOAc (30 mL) and washed with saturated NaHCO$_3$ (10 mL), brine (10 mL), dried over Na$_2$SO$_4$, concentrated in rotavapor and purified on silica gel. Elution with 5% EtOAc/hexanes afforded the desired compound (22 mg, 69%) as a white solid. $^1$H NMR (CDCl$_3$, 400 MHz) δ 8.04 (s, 1H), 7.87-7.92 (m, 2H), 7.60-7.77 (m, 7H), 7.47-7.56 (m, 3H), 7.40 (d, 1H, J=6.96 Hz), 7.28 (t, 1H, J=7.92 Hz), 6.98-7.01 (m, 2H), 6.72 (dd, 1H, J=2.48, 8.12 Hz), 2.96 (s, 6H).

Example 80

Preparation of Compound

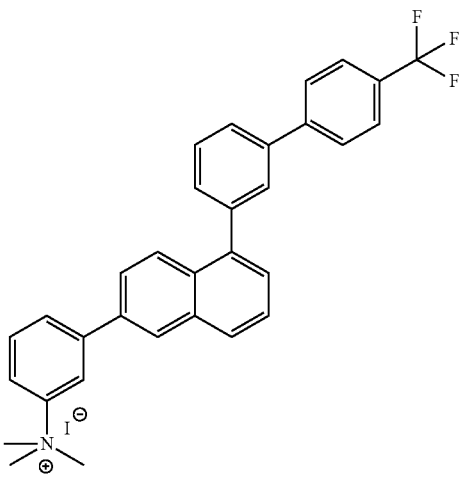 [SMILES: C[N+](C)(C)c1cccc(-c2ccc3c(-c4cccc(-c5ccc(C(F)(F)F)cc5)c4)cccc3c2)c1 ; [I-]]

A solution of the compound of Example 79 (22 mg, 0.05 mmol) in iodomethane (1.0 mL) was stirred in a sealed 2-dram vial at 80° C. overnight. After cooled to room temperature, Et$_2$O was added to the suspension. The solid was collected by filtration to afford the desired compound (20 mg, 69%) as a white solid. $^1$H NMR (CDCl$_3$, 400 MHz) δ 8.47 (d, 1H, J=1.88 Hz), 8.28-8.29 (m, 1H), 8.22 (d, 1H, J=8.16 Hz), 8.18 (d, 1H, J=8.84 Hz), 7.96-8.02 (m, 2H), 7.78-7.89 (m, 8H), 7.70-7.75 (m, 2H), 7.63-7.67 (m, 2H), 4.24 (s, 9H).

Example 81

Preparation of Compound

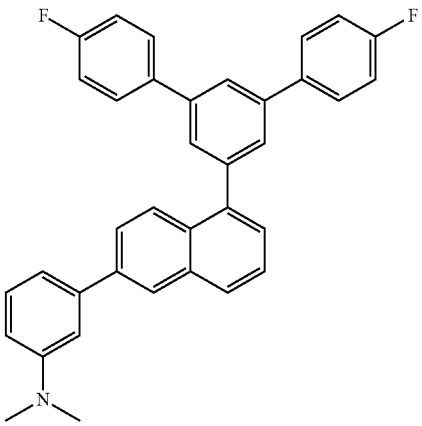 [SMILES: CN(C)c1cccc(-c2ccc3c(-c4cc(-c5ccc(F)cc5)cc(-c5ccc(F)cc5)c4)cccc3c2)c1]

A 25-mL round bottom flask equipped with a magnetic stirrer, a condenser and a nitrogen in/outlet adapter was charged with the starting material the triflate (16 mg, 0.03 mmol), 3-(dimethylamino)phenylboronic acid (7 mg, 0.45 mmol), water/acetonitrile (1 mL/3 ml), K$_2$CO$_3$ (20 mg, 0.14 mmol), 2-dicyclohexylphosphino-2',4',6'-triisopropylbiphenyl (6 mg, 0.012 mmol). The resulting solution was degassed for 5 min, then Pd(OAc)$_2$ (2.0 mg, 0.009 mmol) was added and the solution was carefully degassed. The reaction mixture was warmed to 100° C. and stirred for 1 h. After cooled to room temperature, the reaction mixture was diluted with EtOAc (30 mL) and washed with saturated NaHCO$_3$ (10 mL), brine (10 mL), dried over Na$_2$SO$_4$. The organic layer was concentrated in rotavapor and purified on silica gel. Elution with 5% EtOAc/hexanes afforded a mixture (10 mg, ~90% pure) of the desired compound and some impurity. The mixture was used in next step without further purification.

The requisite intermediate for the preparation of this compound was prepared as follows.

a. Preparation of Compound

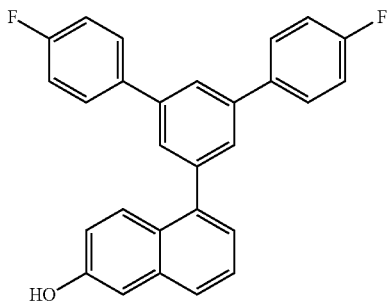 [SMILES: O=S(=O)(Oc1ccc2c(-c3cc(-c4ccc(F)cc4)cc(-c4ccc(F)cc4)c3)cccc2c1)C(F)(F)F]

A 50-mL round bottom flask equipped with a magnetic stirrer, a condenser and a nitrogen in/outlet adapter was charged with 5-bromonaphthalen-2-ol (40 mg, 0.18 mmol), 3,5-di(4-fluorophenyl)phenylboronic acid (67 mg, 0.22 mmol), water/dioxane (1 mL/3 ml), K$_2$CO$_3$ (50 mg, 0.36 mmol). The resulting solution was degassed for 5 min, then Pd(PPh$_3$)$_4$ (10 mg, 0.009 mmol) was added. The reaction mixture was heated to 90° C. and stirred for 12 h. After cooled to room temperature, the reaction mixture was diluted with EtOAc (60 mL) and washed with saturated NaHCO$_3$ (20 mL), brine (20 mL), dried over Na$_2$SO$_4$, concentrated in rotavapor and purified on silica gel. Elution with 10% EtOAc/hexanes afforded a mixture of the desired compound and some impurity (80 mg) as a white solid. The crude product was used in next step without further purification.

b. Preparation of Compound

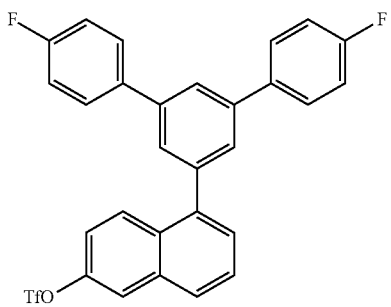

A 25-mL round bottom flask equipped with a magnetic stirrer under nitrogen was charged with the starting material phenol (80 mg, ~0.20 mmol), CH$_2$Cl$_2$ (5 mL), and triethylamine (56 μl, 0.40 mmol). After cooling to −70° C., triflic anhydride (40 μl, 0.24 mmol) was added via a syringe. The resulting reaction mixture was stirred at −70° C. for 30 min, then room temperature for 1 h. The reaction mixture was diluted with CH$_2$Cl$_2$ (30 mL) and washed with saturated NaHCO$_3$ (10 ml), brine (10 mL), dried over Na$_2$SO$_4$, concentrated, and purified on silica gel. Elution with 5% EtOAc/hexanes afforded the desired compound (16 mg) as a white solid. $^1$H NMR (CDCl$_3$, 400 MHz) δ 8.00 (d, 1H, J=9.32 Hz), 7.86 (d, 1H, J=8.08 Hz), 7.72 (s, 1H), 7.52-7.61 (m, 8H), 7.27 (dd, 1H, J=2.48, 9.32 Hz), 7.07-7.11 (m, 4H).

Example 82

Preparation of Compound

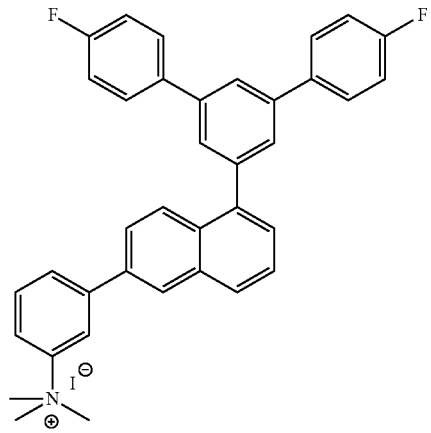 [SMILES: C[N+](C)(C)c1cccc(-c2ccc3c(-c4cc(-c5ccc(F)cc5)cc(-c5ccc(F)cc5)c4)cccc3c2)c1 ; [I-]]

A solution of the compound of Example 80 (10 mg, ~0.02 mmol) in iodomethane (1.0 mL) was stirred in a sealed 2-dram vial at 80° C. overnight. After cooled to room temperature, Et$_2$O was added to the suspension. The solid was collected by filtration to afford the desired compound (6 mg) as a light yellow solid. $^1$H NMR (CDCl$_3$, 400 MHz) δ 8.30 (s, 1H), 8.04-8.11 (m, 3H), 7.78-7.84 (m, 2H), 7.49-7.72 (m, 11H), 7.07-7.11 (m, 4H), 4.06 (s, 9H).

Example 83

Preparation of Compound

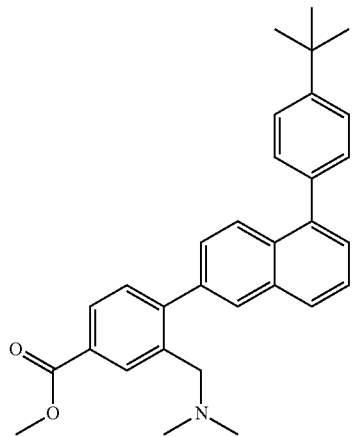 [SMILES: COC(=O)c1ccc(-c2ccc3c(-c4ccc(C(C)(C)C)cc4)cccc3c2)c(CN(C)C)c1]

A 2-dram vial was added methyl 4-(1-(4-t-butylphenyl) naphthalen-6-yl)-3-(bromomethyl)benzoate (50 mg, 0.1 mmol), acetonitrile (3 mL), methanamine (2 M in THF, 0.3 mL). The sealed vial was stirred at room temperature for 15 min. The reaction mixture was diluted with EtOAc (30 mL), washed with saturated NaHCO$_3$ (10 mL), brine (10 mL), dried over Na$_2$SO$_4$, concentrated on a rotavapor and purified on silica gel. Elution with CH$_2$Cl$_2$ to (10/89/1: MeOH/CHCl/ ammonium hydroxide) afforded the desired compound (40 mg, 86%) as a white solid. $^1$H NMR (CDCl$_3$, 400 MHz) δ 8.27 (d, 1H, J=1.08 Hz), 8.01-8.05 (m, 2H), 7.97 (s, 1H), 7.90 (d, 1H, J=8.04 Hz), 7.44-7.61 (m, 8H), 3.97 (s, 3H), 3.44 (s, 2H), 2.20 (s, 6H), 1.45 (s, 9H).

The requisite intermediate for the preparation of this compound was prepared as follows.

a. Preparation of Compound

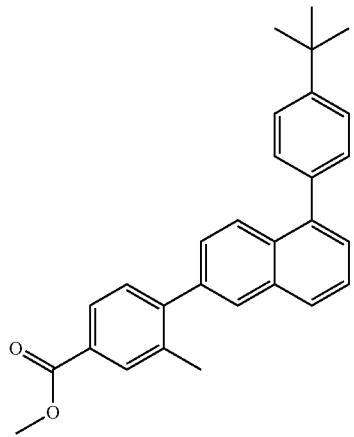 [SMILES: COC(=O)c1ccc(-c2ccc3c(-c4ccc(C(C)(C)C)cc4)cccc3c2)c(C)c1]

A 50-mL round bottom flask equipped with a magnetic stirrer, a condenser and a nitrogen in/outlet adapter was charged with 1-(4-t-butylphenyl)naphthalen-6-yl trifluoromethanesulfonate (500 mg, 1.22 mmol), methyl 3-methyl-4-(4,4,5,5-tetramethyl-1,3,2-dioxaborolan-2-yl)benzoate (30 mg, 1.45 mmol), water/acetonitrile (3 mL/9 ml), K$_2$CO$_3$ (337 mg, 2.44 mmol), 2-dicyclohexylphosphino-2',4',6'-triisopropylbiphenyl (30 mg, 0.061 mmol). The resulting solution was degassed for 5 min, then Pd(OAc)$_2$ (11.2 mg, 0.05 mmol) was added and the solution was carefully degassed. The reaction mixture was heated to 100° C. and stirred for 2 h. After cooled to room temperature, the reaction mixture was diluted with EtOAc (60 mL) and washed with saturated NaHCO$_3$ (20 mL), brine (20 mL), dried over Na$_2$SO$_4$. The organic layer was concentrated in rotavapor and purified on silica gel. Elution with 5% EtOAc/hexanes afforded the desired compound (466 mg, 93%) as a white solid. $^1$H NMR (CDCl$_3$, 400 MHz) δ 8.02 (d, 1H, j=8.68 Hz), 7.99 (s, 1H), 7.94 (dd, 1H, J=1.32, 7.88 Hz), 7.87 (d, 1H, J=8.12 Hz), 7.83 (d, 1H, J=1.68 Hz), 7.39-7.58 (m, 8H), 3.95 (s, 3H), 2.36 (s, 3H), 1.42 (s, 9H).

b. Preparation of Compound

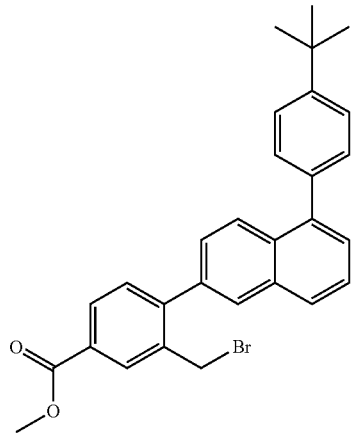 [SMILES: COC(=O)c1ccc(-c2ccc3c(-c4ccc(C(C)(C)C)cc4)cccc3c2)c(CBr)c1]

A 100-mL round bottom flask equipped with a magnetic stirrer, a condenser and a nitrogen in/outlet adapter was charged with methyl 4-(1-(4-t-butylphenyl)naphthalen-6-yl)-3-methylbenzoate (466 mg, 1.14 mmol), CCl$_4$ (10 mL), AIBN (19 mg, 0.11 mmol), and NBS (213 mg, 1.20 mmol). The reaction mixture was degassed for 5 min then heated to 80° C. for 1 h. After additional NBS (50 mg) was added. The reaction mixture was stirred for another 1 h. After cooled to room temperature, the reaction mixture was added hexanes (60 mL). The solid was removed by filtration and the filtrate was concentrated on a rotavapor and purified on silica gel. Elution with 2% EtOAc/hexanes afforded the desired compound (395 mg, 71%) as a white solid. $^1$H NMR (CDCl$_3$, 400 MHz) δ 8.26 (d, 1H, J=1.64 Hz), 7.80-8.08 (m, 3H), 7.90 (d, 1H, J=8.16 Hz), 7.43-7.61 (m, 8H), 4.52 (s, 2H), 3.97 (s, 3H), 1.42 (s, 9H).

Example 84

Preparation of Compound

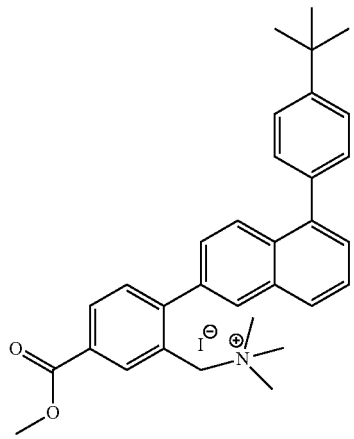 [SMILES: COC(=O)c1ccc(-c2ccc3c(-c4ccc(C(C)(C)C)cc4)cccc3c2)c(C[N+](C)(C)C)c1 ; [I-]]

A solution of methyl 4-(1-(4-tert-butylphenyl)naphthalen-6-yl)-3-(dimethylaminomethyl)benzoate (10 mg, 0.21 mmol) in iodomethane (1.0 mL) in a sealed 2-dram vial was stirred at 50° C. overnight. After cooled to room temperature, Et$_2$O was added to the reaction mixture. The solid was collected by filtration. After triturated with Et$_2$O and dried, there was obtained the desired compound (8 mg, 62%) as a white solid. $^1$H NMR (MeOD, 400 MHz) δ 8.30 (d, 1H, J=1.64 Hz), 8.19 (dd, 1H, J=1.72, 8.04 Hz), 8.99 (d, 1H, J=8.76 Hz), 7.94 (d, 1H, J=1.64 Hz), 7.88 (d, 1H, J=8.28 Hz), 7.33-7.62 (m, 8H), 4.77 (s, 2H), 3.89 (s, 3H), 2.74 (s, 9H), 1.32 (s, 9H).

Example 85

Preparation of Compound

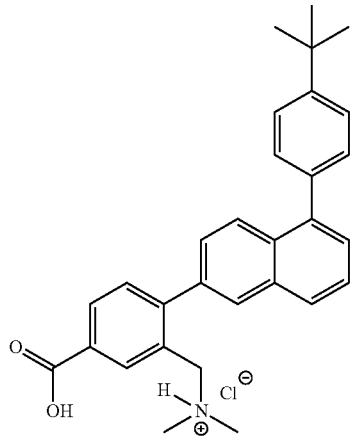 [SMILES: C[NH+](C)Cc1cc(C(=O)O)ccc1-c1ccc2c(-c3ccc(C(C)(C)C)cc3)cccc2c1 ; [Cl-]]

A 10-ml flask was added methyl 4-(1-(4-t-butylphenyl)naphthalen-6-yl)-3-((dimethylamino)methyl)benzoate (28 mg, 0.06 mmol), THF/H$_2$O (1 mL/0.5 mL), LiOH (26 mg, 0.6 mmol). After stirred at 60° C. for 12 h, the reaction mixture was cooled to room temperature and adjusted to pH=2 by adding 1 N HCl. The solid was collected and washed with Et$_2$O to afford the desired compound (12 mg, 41%) as a white solid. $^1$H NMR (MeOD, 400 MHz) δ 8.30 (d, 1H, J=1.32 Hz), 8.12 (dd, 1H, J=1.60, 8.00 Hz), 7.96 (d, 1H, J=8.68 Hz), 7.80-7.89 (m, 1H), 7.33-7.56 (m, 8H), 4.41 (s, 2H), 2.53 (s, 6H), 1.32 (s, 9H).

Example 86

Preparation of Compound

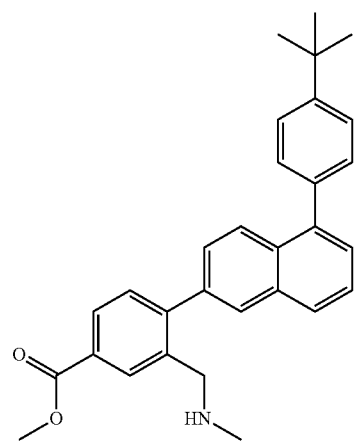 [SMILES: CNCc1cc(C(=O)OC)ccc1-c1ccc2c(-c3ccc(C(C)(C)C)cc3)cccc2c1]

A 2-dram vial was added methyl 4-(1-(4-t-butylphenyl)naphthalen-6-yl)-3-(bromomethyl)benzoate (50 mg, 0.1 mmol), acetonitrile (3 mL), methanamine (2 M in THF, 0.5 mL)). The sealed vial was stirred at room temperature for 30 min. The reaction mixture was diluted with EtOAc (30 mL), washed with saturated NaHCO$_3$ (10 mL), brine (10 mL), dried over Na$_2$SO$_4$, concentrated with a rotavapor and purified on silica gel. Elution with CH$_2$Cl$_2$ to (10/89/1: MeOH/CHCl$_3$/ammonium hydroxide) afforded the desired compound (30 mg, 67%) as colorless oil. $^1$H NMR (CDCl$_3$, 400 MHz) δ 8.28 (s, 1H), 8.03-8.07 (m, 2H), 7.90-7.94 (m, 2H), 7.44-7.62 (m, 8H), 3.97 (s, 3H), 3.87 (s, 2H), 2.38 (s, 3H), 1.44 (s, 9H).

Example 87

Preparation of Compound

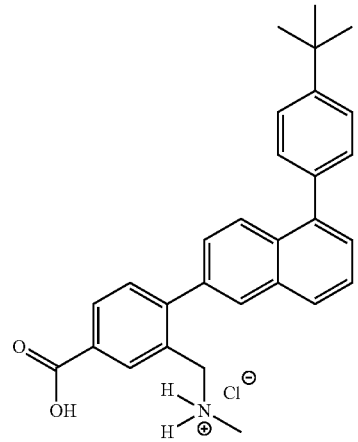 [SMILES: C[NH2+]Cc1cc(C(=O)O)ccc1-c1ccc2c(-c3ccc(C(C)(C)C)cc3)cccc2c1 ; [Cl-]]

A 10-ml flask was added methyl 4-(1-(4-t-butylphenyl)naphthalen-6-yl)-3-((methylamino)methyl)benzoate (25 mg, 0.06 mmol), THF/H₂O (1 mL/0.5 mL), LiOH (26 mg, 0.6 mmol). After stirred at 80° C. for 12 h, the reaction mixture was cooled to room temperature and adjusted to pH=2 by adding 1 N HCl. The solid was collected and washed with Et₂O to afford the desired compound (8 mg, 31%) as a white solid. ¹H NMR (MeOD, 400 MHz) δ 8.20 (s, 1H), 8.06 (dd, 1H, J=1.56, 8.00 Hz), 7.94 (d, 1H, J=8.72 Hz), 7.85-7.87 (m, 2H), 7.32-7.54 (m, 8H), 4.22 (s, 2H), 2.46 (s, 3H), 1.32 (s, 9H).

Example 88

Preparation of Compound

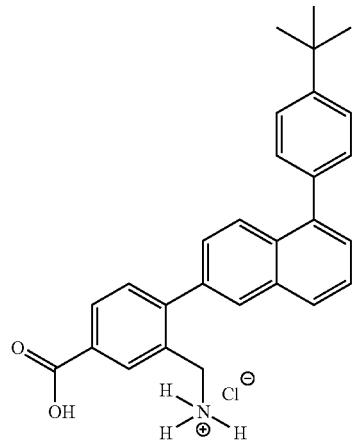 [SMILES: CC(C)(C)c1ccc(-c2cccc3cc(-c4ccc(C(=O)O)cc4C[NH3+])ccc23)cc1 ; [Cl-]]

A 10-ml flask was added methyl 4-(1-(4-t-butylphenyl)naphthalen-6-yl)-3-(aminomethyl)benzoate (14 mg, 0.03 mmol), THF/H₂O (1 mL/0.5 mL), LiOH (25 mg, 0.5 mmol). After stirred at 80° C. for 12 h, the reaction mixture was cooled to room temperature and adjusted to pH=2 by adding 1 N HCl. The solid was collected and washed with Et₂O to afford the desired compound (6 mg, 40%) as a white solid. ¹H NMR (MeOD, 400 MHz) δ 7.98 (d, 1H, J=1.48 Hz), 7.80-7.86 (m, 4H), 7.44-7.49 (m, 3H), 7.32-7.36 (m, 4H), 7.22 (d, 1H, J=7.84 Hz), 3.71 (s, 2H), 1.32 (s, 9H).

Example 89

Preparation of Compound

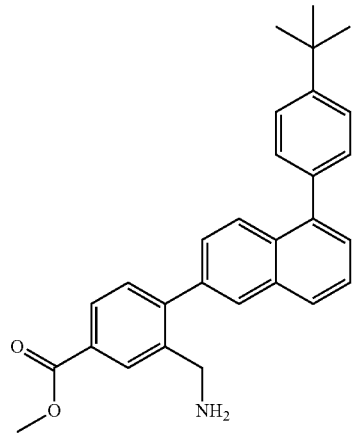 [SMILES: COC(=O)c1ccc(-c2ccc3c(-c4ccc(C(C)(C)C)cc4)cccc3c2)c(CN)c1]

A 10-ml flask was added methyl 4-(1-(4-tert-butylphenyl)naphthalen-6-yl)-3-(azidomethyl)benzoate (45 mg, 0.1 mmol), THF/water (3 mL/0.3 mL), and triphenylphosphine polymer bound (~3.0 mmol/g, 100 mg). The reaction mixture was stirred at room temperature for 12 h. The solid was removed by filtration and the filtrate was dried over Na₂SO₄, concentrated in rotavapor and purified on silica gel. Elution with 50% EtOAc/hexanes afforded the desired compound (16 mg, 37%) as colorless oil. ¹H NMR (MeOD, 400 MHz) δ 8.15 (s, 1H), 7.80-7.91 (m, 4H), 7.46-7.51 (m, 3H), 7.33-7.38 (m, 5H), 3.85 (s, 3H), 3.77 (s, 2H), 1.32 (s, 9H). The requisite intermediate for the preparation of this compound was prepared as follows.

a. Preparation of Compound

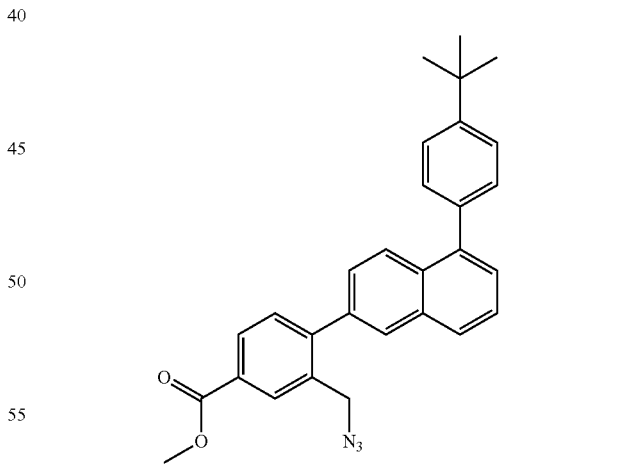

A 10-ml flask was added methyl 4-(1-(4-t-butylphenyl)naphthalen-6-yl)-3-(bromomethyl)benzoate (50 mg, 0.1 mmol), DMF (1 mL), sodium azide (13 mg, 0.2 mmol). After stirred at room temperature for 12 h, the reaction mixture was diluted with EtOAc (30 mL), washed with 10% LiCl (10×2 mL), dried over Na₂SO₄, concentrated with a rotavapor and purified on silica gel. Elution with 10% EtOAc/hexanes afforded the desired compound (45 mg, 97%) as a white solid. ¹H NMR (CDCl₃, 400 MHz) δ 8.11 (d, 1H, J=1.52 Hz), 8.02

(dd, 1H, J=1.72, 7.96 Hz), 7.98 (d, 1H, J=8.72 Hz), 7.80-7.82 (m, 2H), 7.38-7.53 (m, 7H), 7.33 (dd, 1H, J=1.80, 8.72 Hz), 4.32 (s, 2H), 3.90 (s, 3H), 1.35 (s, 9H).

Example 90

Preparation of Compound

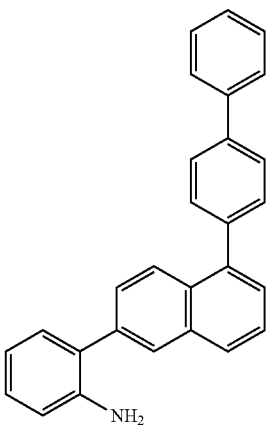 [SMILES: Nc1ccccc1-c1ccc2c(-c3ccc(-c4ccccc4)cc3)cccc2c1]

1-([1,1'-Biphenyl]-4-yl)-6-(2-nitrophenyl)naphthalene (64 mg, 0.159 mM) was dissolved with 1 mL of hydrazine in 20 mL of ethanol. 15 mg Pd/C was added and mixture was allowed to stir at 85° C. for 2.5 hours. Crude mixture was then diluted with 40 mL of EtOAc and filtered through a layer Celite and silica. Filtrate was then subjected to drying with Na$_2$SO$_4$ followed by in vacuo concentration. Crude was subjected to flash chromatography in which 20% EtOAc/hexanes eluted product (58 mg, 99%) $^1$H NMR (400 MHz, CDCl$_3$) d=3.72 (s, 2H), 6.69 (1, J=7.96 1H), 6.78 (t, J=7.48 1H), 7.10 (t, J=8.08, 1H), 7.13 (d, J=7.13 Hz, 1H), 7.28 (t, J=7.56, 1H), 7.37 (t, J=5.76 Hz, 3H), 7.45-7.50 (m, 4H), 7.57-763 (m, 4H), 7.78 (d, J=8.04 Hz, 1H), 7.88 (s, 1H), 7.96 (d, J=8.72, 1H).

The requisite intermediate for the preparation of this compound was prepared as follows.

a. Preparation of Compound

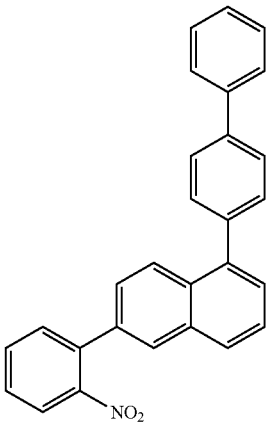 [SMILES: O=[N+]([O-])c1ccccc1-c1ccc2c(-c3ccc(-c4ccccc4)cc3)cccc2c1]

5-([1,1'-Biphenyl]-4-yl)naphthalen-2-yl trifluoromethanesulfonate (308 mg, 0.719 mM) was combined with (2-nitrophenyl)boronic acid (240 mg, 1.4 mM), K$_2$CO$_3$ (248 mg, 1.8 mM), and XPhos (34 mg, 0.072 mM). All this was dissolved in a solution consisting of 9 mL of acetonitrile and 3 mL H$_2$O. The mixture was then brought to 100° C. Pd(OAc)$_2$ (10 mg, 0.046 mM) was then added and mixture was allowed to stir overnight. After cooling to room temperature, crude reaction mixture was diluted with 50 mL of EtOAc and then filtered through a plug of Celite and silica. Contents were then dried using Na$_2$SO$_4$ followed by vacuum concentration. Final product (103 mg, 36% yield) was afforded as a yellow solid using flash chromatography (10% EtOAc/hexanes). $^1$H NMR (400 MHz, CDCl$_3$) d=7.25-7.30 (m, 1H) 7.36-7.43 (m, 5H), 7.43-7.55 (m, 5H), 7.57-7.66 (m, 4H), 7.75-7.82 (m, 3H), 7.93 (d, J=8.76 Hz, 1H)

b. Preparation of Compound

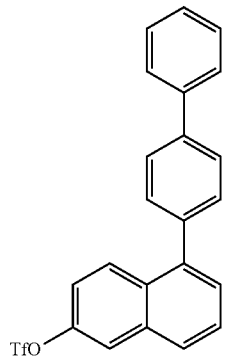 [SMILES: O=S(=O)(Oc1ccc2c(-c3ccc(-c4ccccc4)cc3)cccc2c1)C(F)(F)F]

5-([1,1'-Biphenyl]-4-yl)naphthalen-2-ol (249 mg, 0.84 mM) was dissolved with triethylamine (0.23 mL, 1.68 mM) in 12 mL of anhydrous dichloromethane. Mixture was then cooled down to −78° C. After cooling, triflic anhydride (0.212 mL, 1.26 mM) was added drop wise to the mixture. After stirring for one hour, mixture was diluted with 50 mL of dichloromethane and washed with saturated NaHCO$_3$ followed by a washing with brine. The organic layer was dried using Na$_2$SO$_4$ and then concentrated in vacuo. Crude product was then subjected to flash chromatography in which purified product eluted with 5% EtOAc/hexanes. 309 mg of product (89% yield) was afforded as a white solid. $^1$H NMR (400 MHz, CDCl$_3$) d=7.30 (dd, J=9.32 Hz, J=2.56 Hz, 1H) 7.39 (t, J=7.2 Hz, 1H), 7.48 (t, J=7.48 Hz, 2H), 7.52-7.55 (m, 3H), 7.63 (t, J=7.28 Hz, 1H), 7.68 (d, J=7.28 Hz, 2H), 7.74 (d, J=8.08 Hz, 2H), 7.81 (dd, J=2.52 Hz, 1H), 7.88 (d, J=8.16 Hz, 1H), 8.06 (d, J=9.32 Hz, 1H).

c. Preparation of Compound

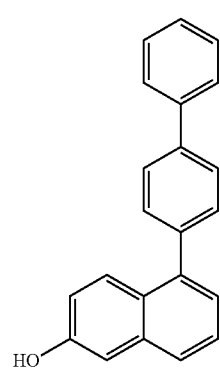 [SMILES: Oc1ccc2c(-c3ccc(-c4ccccc4)cc3)cccc2c1]

5-Bromo-2-naphthol (201 mg, 0.91 mM) was combined with [1,1'-biphenyl]-4-ylboronic acid (360 mg, 1.82 mM), $K_2CO_3$ (314 mg, 2.28 mM), and XPhos (43 mg, 0.091 mM). All this was dissolved in a solution consisting of 6 mL of acetonitrile and 2 mL $H_2O$. The mixture was then brought to 100° C. $Pd(OAc)_2$ (10 mg, 0.046 mM) was then added and mixture was allowed to stir for 4.5 hours. After cooling to room temperature, crude reaction mixture was diluted with 50 mL of EtOAc and then filtered through a plug containing Celite and silica. The filtrate was then dried using $Na_2SO_4$ followed by vacuum concentration. Final product was isolated using flash chromatography (10% EtOAc/hexanes). 249 mg of 5-([1,1'-biphenyl]-4-yl)naphthalen-2-ol as a white solid was afforded (93% yield). $^1$H NMR (400 MHz, $CDCl_3$) d=5.4 (s, 1H), 7.1 (dd, J=2.5 Hz, J=9.12 Hz, 1H), 7.26 (d, J=2.48 Hz, 1H), 7.35 (d, J=7.04, 1H), 7.39-7.45 (m, 1H), 7.53 (t, J=7.28 Hz, 3H), 7.60 (d, J=7.92 Hz, 2H), 7.74 (t, J=8.20 Hz, 5H), 7.92 (d, J=9.12 Hz, 1H)

Example 91

Preparation of Compound

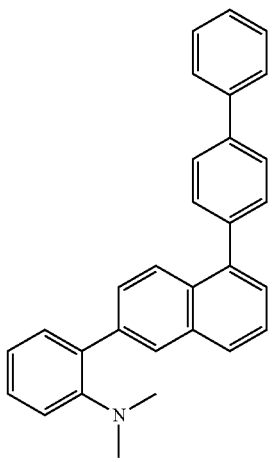 [SMILES: CN(C)c1ccccc1-c1ccc2c(-c3ccc(-c4ccccc4)cc3)cccc2c1]

2-(5-([1,1'-Biphenyl]-4-yl)naphthalen-2-yl)aniline (54 mg, 0.145 mM) was dissolved with $NaBH_3CN$ (29 mg, 0.465 mM) in 5 mL of $CH_3CN$. Several drops of acetic acid were added to lower the pH to 6. After the desired pH was achieved, 1 mL of formaldehyde was added and the mixture was allowed to stir overnight at room temperature. The next day, TLC revealed that the reaction mixture contained a considerable amount of the monomethylated product. An additional 15 mg of $NaBH_3CN$ was then added and after 4 hours of stirring, the monomethylated product had fully converted to the desired dimethylated compound. Product was extracted by diluting the reaction mixture with dichloromethane (50 mL) and washing with $NaHCO_3$ and Brine. The organic layer was then dried with $Na_2SO_4$ followed by in vacuo concentration. Crude was subjected to flash chromatography in which 10% EtOAc/hexanes eluted 23 mg of product (40% yield) as a white solid. $^1$H NMR (400 MHz, $CDCl_3$) d=2.48 (s, 6H), 6.97-7.00 (m, 2H), 7.20-7.31 (m, 3H), 7.37-7.47 (m, 4H), 7.55 (d, J=8 Hz, 2H), 760-7.66 (m, 4H), 7.71 (dd, J=8.8 Hz, J=1.6 Hz, 1H), 7.81 (d, J=8.08 Hz, 1H), 7.91 (d, J=8.84 Hz, 1H), 7.95 (s, 1H)

Example 92

Preparation of Compound

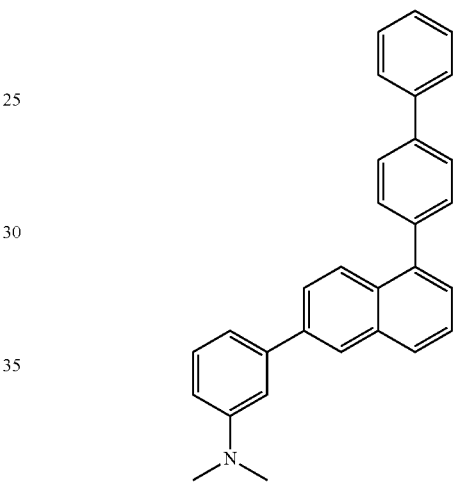

5-([1,1'-Biphenyl]-4-yl)naphthalen-2-yl trifluoromethanesulfonate (24 mg, 0.056 mM) was combined with (3-(dimethylamino)phenyl)boronic acid (18.5 mg, 0.112 mM), $K_2CO_3$ (3 mg, 0.18 mM), and XPhos (3 mg, 0.006 mM). All this was dissolved in a solution consisting of 6 mL of acetonitrile and 2 mL $H_2O$. The mixture was then brought to 100° C. $Pd(OAc)_2$ (10 mg, 0.046 mM) was then added and mixture was allowed to stir for 1.5 hours. After cooling to room temperature, crude reaction mixture was diluted with 50 mL of EtOAc and then filtered through a plug containing Celite and silica gel. Contents were then dried using $Na_2SO_4$ followed by vacuum concentration. Final product (5.4 mg, 24% yield) was afforded as a white solid using flash chromatography (10% EtOAc/hexanes). $^1$H NMR (400 MHz, $CDCl_3$) d=3.03 (s, 6H), 6.78 (dd, J=2.32 Hz, J=8.28 Hz, 1H), 7.04-7.10 (m, 1H), 7.33-7.41 (m, 2H), 7.45-7.52 (m, 3H), 7.56 (t, J=7.20 Hz, 2H), 7.61 (d, J=8.20 Hz, 2H), 7.68-7.75 (m, 5H), 7.93 (d, J=8.16 Hz, 1H), 8.04 (d, J=8.84 Hz, 1H), 8.11 (d, J=1.72 Hz, 1H)

Example 93

Preparation of Compound

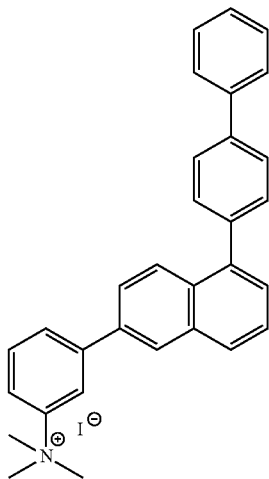 [SMILES: C[N+](C)(C)c1cccc(-c2ccc3c(-c4ccc(-c5ccccc5)cc4)cccc3c2)c1 ; [I-]]

3-(5-([1,1'-biphenyl]-4-yl)naphthalen-2-yl)-N,N-dimethylaniline was dissolved in 4 mL of iodomethane and heated in a sealed tube at 100° C. for 24 hours. Unreacted Iodomethane was evaporated and crude product was washed three times with ether to remove any unreacted starting material. The result was 2.8 mg of product (39% yield) as a beige powder. $^1$H NMR (400 MHz, CDCl$_3$) d=4.09 (s, 9H), 7.39 (t, 7.32 Hz, 1H), 7.49 (t, J=7.4, 2H), 7.53-7.65 (m, 4H), 7.67-7.78 (m, 6H), 7.82-7.83 (m, 1H), 7.93 (d, J=7.52 Hz, 1H), 8.06 (d, J=8.2 Hz, 1H), 8.08 (s, 1H), 8.13 (d, J=8.68 Hz, 1H), 8.27 (s, 1H)

Example 94

Preparation of Compound

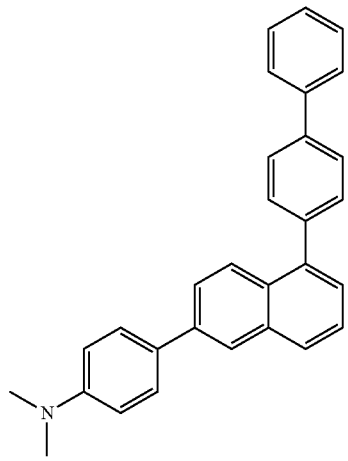 [SMILES: CN(C)c1ccc(-c2ccc3c(-c4ccc(-c5ccccc5)cc4)cccc3c2)cc1]

5-([1,1'-Biphenyl]-4-yl)naphthalen-2-yl trifluoromethanesulfonate (31 mg, 0.072 mM) was combined with (4-(dimethylamino)phenyl)boronic acid (25 mg, 0.145 mM), K$_2$CO$_3$ (25 mg, 0.18 mM), and XPhos (4 mg, 0.007 mM). All this was dissolved in a solution consisting of 5 mL of acetonitrile and 3 mL H$_2$O. The mixture was then brought to 100° C. Pd(OAc)$_2$ (5 mg, 0.22 mM) was then added and mixture was allowed to stir overnight. After cooling to room temperature, crude reaction mixture was diluted with 50 mL of EtOAc and then filtered through a plug containing Celite and silica gel. Contents were then dried using Na$_2$SO$_4$ followed by vacuum concentration. Final product (18 mg, 62% yield) was afforded as a white solid using flash chromatography (10% EtOAc/hexanes). $^1$H NMR (400 MHz, CDCl$_3$) d=2.94 (s, 6H), 6.78 (d, J=Hz, 2H), 7.28-7.36 (m, 2H), 7.39-7.48 (m, 3H), 7.53 (m, 2H), 7.58 (m, 2H), 7.60-7.68 (m, 5H), 7.81 (d, J=8.20 Hz, 1H), 7.92 (d, J=8.84 Hz, 1H), 7.98 (d, J=1.76 Hz, 1H)

Example 95

Preparation of Compound

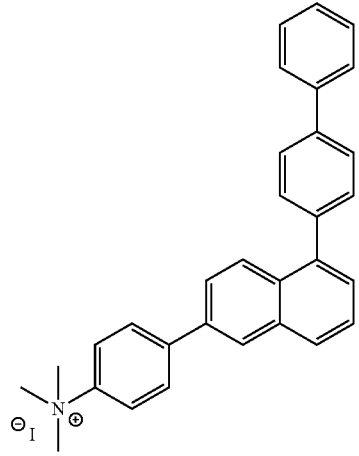 [SMILES: C[N+](C)(C)c1ccc(-c2ccc3c(-c4ccc(-c5ccccc5)cc4)cccc3c2)cc1 ; [I-]]

4-(5-([1,1'-Biphenyl]-4-yl)naphthalen-2-yl)-N,N-dimethylaniline was dissolved in 4 mL of iodomethane and heated in a sealed tube at 100° C. for 24 hours. Unreacted Iodomethane was evaporated and the crude reaction mixture was washed three times with ether to remove any unreacted starting material. The result was 7 mg of product (37% yield) as a beige powder. $^1$H NMR (400 MHz, CDCl$_3$) d=4.03 (s, 9H), 7.32 (t, J=7.4 Hz, 1H), 7.40-7.46 (m, 3H), 7.52 (t, J=6.52

Hz, 3H), 7.55-7.59 (m, 2H), 7.63 (d, J=7.36 Hz, 2H), 7.68 (d, J=8.08 Hz, 2H), 7.89-7.87 (m, 3H), 8.01 (s, 1H), 8.03-8.05 (m, 2H)

Example 96

Preparation of Compound

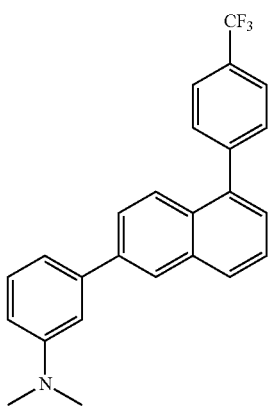 [SMILES: CN(C)c1cccc(-c2ccc3c(-c4ccc(C(F)(F)F)cc4)cccc3c2)c1]

5-(4-(Trifluoromethyl)phenyl)naphthalen-2-yl trifluoromethanesulfonate (98 mg, 0.233 mM) was combined with (3-(dimethylamino)phenyl)boronic acid (77 mg, 0.466 mM), K$_2$CO$_3$ (81 mg, 0.583 mM), and XPhos (11 mg, 0.0233 mM). All this was dissolved in a solution consisting of 5 mL of acetonitrile and 3 mL H$_2$O. The mixture was then brought to 100° C. Pd(OAc)$_2$ (5 mg, 0.222 mM) was then added and mixture was allowed to stir for 24 hours. After cooling to room temperature, crude reaction mixture was diluted with 50 mL of EtOAc and then filtered through a plug containing Celite and silica gel. Contents were then dried using Na$_2$SO$_4$ followed by vacuum concentration. Final product (74 mg, 81% yield) was afforded as a white solid using flash chromatography (10% EtOAc/hexanes). $^1$H NMR (400 MHz, CDCl$_3$) d=2.92 (s, 6H), 6.70 (dd, J=2.32 Hz, J=8.28 Hz, 1H), 6.95 (m, 2H), 7.27 (m, 2H), 7.44 (t, J=7.28 Hz, 1H), 7.54 (d, J=8.06 Hz, 2H), 7.63 (dd, J=1.9 Hz, J=8.84 Hz, 1H), 7.67 (d, J=8.16 Hz, 2H), 7.77 (d, J=8.8 Hz, 1H), 7.85 (d, J=8.2 Hz, 1H), 8.01 (s, 1H)

The requisite intermediate for the preparation of this compound was prepared as follows.

a. Preparation of Compound

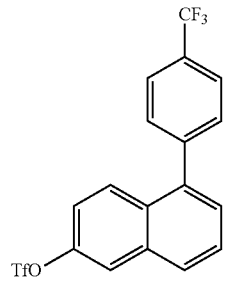 [SMILES: O=S(=O)(Oc1ccc2c(-c3ccc(C(F)(F)F)cc3)cccc2c1)C(F)(F)F]

5-(4-(trifluoromethyl)phenyl)naphthalen-2-ol (115 mg, 0.398 mM) was dissolved with triethylamine (0.11 mL, 0.80 mM) in 8 mL of anhydrous dichloromethane. Mixture was then cooled to −78° C. Triflic anhydride (0.11 mL, 0.63 mM) was then added drop wise to the mixture. After stirring for one hour, mixture was then diluted with 50 mL of dichloromethane and first washed with NaHCO$_3$ then organic layer was washed brine. The organic layer was dried using Na$_2$SO$_4$ and then was concentrated in vacuo. Flash chromatography (5% EtOAc/hexanes) was used to afford pure 5-(4-(trifluoromethyl)phenyl)naphthalen-2-yl trifluoromethanesulfonate (98 mg, 59% yield) as a white solid. $^1$H NMR (400 MHz, CDCl$_3$) d=7.24 (dd, J=2.56 Hz, J=9.28 Hz, 1H), 7.40 (d, J=7 Hz, 1H), 7.49 (d, J=8.32 Hz, 2H), 7.54 (t, J=7.36 Hz, 1H), 7.68 (d, J=8.24 Hz, 2H), 7.74 (d, J=2.56 Hz, 1H), 7.81 (m, 2H)

b. Preparation of Compound

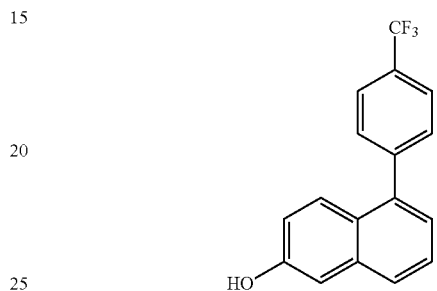

5-Bromo-2-naphthol (125 mg, 0.56 mM) was combined with (4-(trifluoromethyl)phenyl)boronic acid (213 mg, 1.12 mM) and K$_2$CO$_3$ (194 mg, 1.4 mM). All this was dissolved in a solution consisting of 6 mL of dioxane and 2 mL H$_2$O. This mixture was degassed and then Pd(PPh$_3$)$_4$ (42 mg, 0.036 mM) was then added to the mixture. Mixture was allowed to reflux at 100° C. for 24 hours. Crude mixture was then diluted with 50 mL of EtOAc and filtered through a plug containing Celite and silica gel. Filtrate was then dried using Na$_2$SO$_4$ followed by in vacuo concentration. Flash chromatography was used to isolate product (115 mg, 70% yield) which eluded from the column with 10% EtOAc/hexanes as a white solid. $^1$H NMR (400 MHz, CDCl$_3$) d=5.34 (s, 1H), 6.96 (dd, J=2.5 Hz, J=9.12 Hz, 1H), 7.11 (d, J=2.68 Hz, 1H), 7.13 (d, J=7.08 Hz, 1H), 7.36 (t, J=7.32 Hz, 1H), 7.46 (d, J=8.0 Hz, 2H), 7.61 (t, J=8.88 Hz, 4H)

Example 97

Preparation of Compound

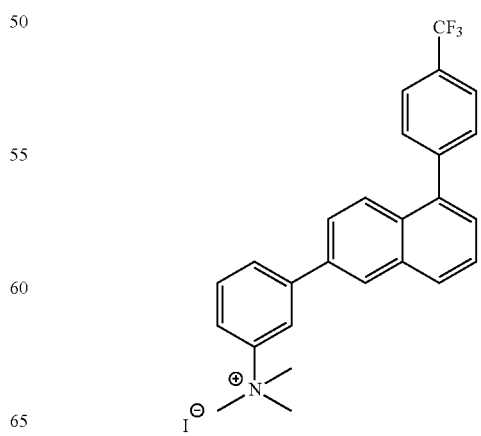

N,N-dimethyl-3-(5-(4-(trifluoromethyl)phenyl)naphthalen-2-yl)aniline was dissolved in 5 mL of iodomethane and heated in a sealed tube at 100° C. for 3.5 hours. Unreacted iodomethane was evaporated and the crude reaction mixture was washed three times with ether to remove any unreacted starting material. The result was 69.5 mg of product (80% yield) as a white powder. $^1$H NMR (400 MHz, CDCl$_3$) d=4.17 (s, 9H), 7.49 (d, J=7.04 Hz, 1H), 7.62 (m, 3H), 7.77 (m, 4H), 7.90-7.97 (m, 3H), 8.18 (d, J=8.24 Hz, 1H), 8.27 (s, 1H), 8.45 (s, 1H).

Example 98

Preparation of Compound

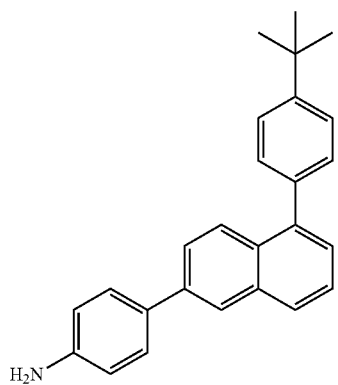

1-(4-(t-Butyl)phenyl)-6-(4-nitrophenyl)naphthalene (75 mg, 0.197 mM) was dissolved with 1 mL of hydrazine in 20 mL of ethanol. 15 mg Pd/C was added and mixture was allowed to stir at 85° C. overnight. The reaction mixture was then diluted with 50 mL of EtOAc and filtered through a plug of Celite and silica gel. Filtrate was then subjected to drying with Na$_2$SO$_4$ followed by in vacuo concentration. Crude was subjected to flash chromatography in which 20% EtOAc/hexanes eluted product as a white solid (quantitative yield). $^1$H NMR (400 MHz, CDCl$_3$) d=1.34 (s, 9H), 3.69 (s, 2H), 6.74 (d, J=8.16 Hz, 2H), 7.32 (d, J=7.04 Hz, 1H), 7.37-749 (m, 7H), 7.58 (d, J=8.84 Hz, 1H), 7.79 (d, J=8.16 Hz, 1H), 7.92 (d, J=8.84 Hz, 1H), 7.94 (s, 1H)

The requisite intermediate for the preparation of this compound was prepared as follows.

a. Preparation of Compound

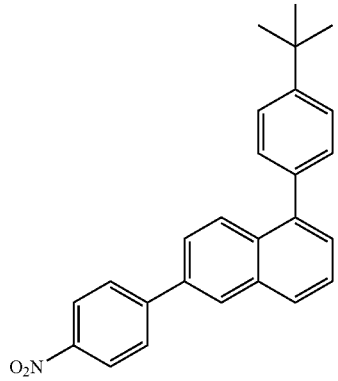 [SMILES: CC(C)(C)c1ccc(-c2cccc3cc(-c4ccc([N+](=O)[O-])cc4)ccc23)cc1]

5-(4-(t-Butyl)phenyl)naphthalen-2-yl trifluoromethanesulfonate (105 mg, 0.26 mM) was combined with (4-nitrophenyl)boronic acid (52 mg, 0.308 mM), K$_2$CO$_3$ (88 mg, 0.643 mM), and XPhos (12 mg, 0.0257 mM). All this was dissolved in a solution consisting of 9 mL of acetonitrile and 3 mL H$_2$O. The mixture was then brought to 100° C. Pd(OAc)$_2$ (8 mg, 0.0356 mM) was then added and mixture was allowed to stir overnight. After cooling to room temperature, crude reaction mixture was diluted with 50 mL of EtOAc and then filtered through a plug containing Celite and silica gel. Contents were then dried using Na$_2$SO$_4$ followed by vacuum concentration. Final product (76 mg, 89% yield) was afforded as a yellow solid using flash chromatography (15% EtOAc/hexanes). $^1$H NMR (400 MHz, CDCl$_3$) d=1.45 (s, 9H), 7.47-7.64 (m, 6H), 7.71 (dd, J=1.96 Hz, J=8.88 Hz 1H), 7.90 (d, J=8.88 Hz, 2H), 7.96 (d, J=8.12, 1H), 8.12 (d, J=8.96 Hz, 1H), 8.18 (s, 1H), 8.38 (d, J=8.84 Hz, 2H)

b. Preparation of Compound

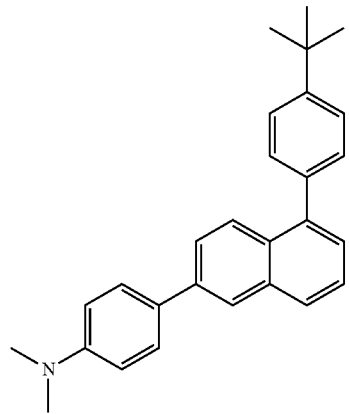 [SMILES: CN(C)c1ccc(-c2ccc3c(-c4ccc(C(C)(C)C)cc4)cccc3c2)cc1]

5-(4-(t-butyl)phenyl)naphthalen-2-yl trifluoromethanesulfonate was prepared as described for Intermediate b of Example 59.

Example 99

Preparation of Compound

NaBH₃CN (30 mg, 0.482 mM) and 1.5 mL of formaldehyde were dissolved in 10 mL of CH₃CN. Several drops of acetic acid was used to lower the pH to 6. After desired pH was achieved, 4-(5-(4-(t-butyl)phenyl)naphthalen-2-yl) aniline (56 mg, 0.150 mM) was added to the solution and the mixture was allowed to stir overnight at room temperature. Product was then extracted by diluting reaction mixture with dichloromethane (50 mL) and washing with NaHCO₃ and brine. The organic layer was then dried with Na₂SO₄ followed by in vacuo concentration. Crude product was subjected to flash chromatography in which 10% EtOAc/hexanes eluted 56 mg of product (98% yield) as a white solid. ¹H NMR (400 MHz, CDCl₃) d=1.34 (s, 9H), 2.93 (s, 6H), 6.76-6.80 (m, 2H), 7.29-7.32 (m, 1H), 7.37-7.45 (m, 5H), 7.55-7.61 (m, 3H), 7.77-7.80 (m, 1H), 7.89-7.97 (m, 2H)

Example 100

Preparation of Compound

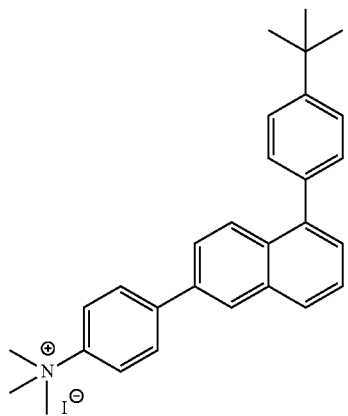 [SMILES: CC(C)(C)c1ccc(-c2cccc3cc(-c4ccc([N+](C)(C)C)cc4)ccc23)cc1 ; [I-]]

4-(5-(4-(t-Butyl)phenyl)naphthalen-2-yl)-N,N-dimethylaniline (26.2 mg, 0.069 mM) was dissolved in 4 mL of iodomethane and heated in a sealed tube at 100° C. overnight. The next day, very little product had precipitated. The iodomethane was then evaporated and crude product was dissolved in 2 mL of iodomethane and heated in a sealed tube for 8 hours. After a reasonable amount of product had precipitated out, the cap of the sealed tube was removed and the iodomethane was allowed to evaporate. The crude reaction mixture was washed three times with ether to remove any unreacted starting material. The result was 12 mg of product (33% yield) as a beige powder. ¹H NMR (400 MHz, CDCl₃) d=1.32 (s, 9H), 3.64 (s, 9H), 7.31-7.36 (m, 3H), 7.42-7.53 (m, 5H), 7.68 (dd, J=8.8 Hz, J=1.92 Hz 1H), 7.79 (d, J=9.2 Hz, 1H), 7.86-7.92 (m, 3H), 8.17 (s, 1H)

Example 101

Preparation of Compound

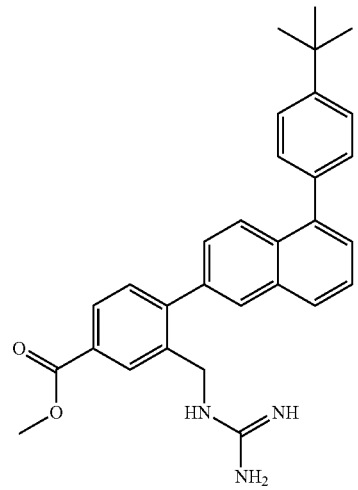 [SMILES: COC(=O)c1ccc(-c2ccc3c(-c4ccc(C(C)(C)C)cc4)cccc3c2)c(CNC(=N)N)c1]

A 50-mL round bottom flask equipped with a magnetic stirrer, a condenser and a nitrogen in/outlet adapter was charged with methyl 3-(bromomethyl)-4-(5-(4-(tert-butyl) phenyl)naphthalen-2-yl)benzoate (30 mg, 0.06 mmol), DMF (1 mL), K₂CO₃ (16 mg, 0.12 mmol), and 1,3-bis(t-butoxycarbonyl)guanidine (20 mg, 0.07 mmol) The reaction mixture was stirred at room temperature for 12 h. The reaction mixture was diluted with EtOAc (60 mL), washed with water (20 mL), 10% LiCl (20 mL), brine (20 mL), dried over Na₂SO₄, concentrated, and purified on silica gel. Elution with 5% EtOAc/hexanes afforded the desired compound (35 mg, 85%) as a white solid. ¹H NMR (CDCl₃, 400 MHz) δ 9.44 (broad s, 1H), 9.26 (broad s, 1H), 8.00-8.05 (m, 2H), 7.90-7.91 (m, 2H), 7.85 (s, 1H), 7.49-7.61 (m, 6H), 7.43 (d, 1H, J=7.92 Hz), 5.28 (s, 2H), 3.97 (s, 3H), 1.50 (s, 9H), 1.45 (s, 9H), 1.26 (s, 9H).

The requisite intermediate for the preparation of this compound was prepared as follows.

a. Preparation of Compound

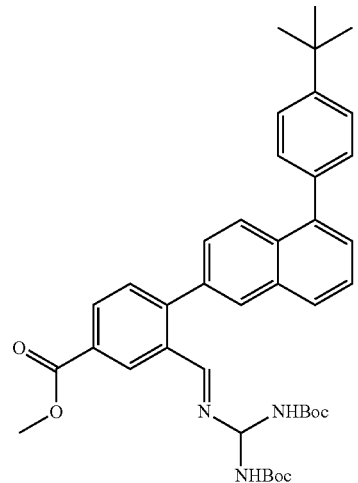 [SMILES: COC(=O)c1ccc(-c2ccc3c(-c4ccc(C(C)(C)C)cc4)cccc3c2)c(/C=N/C(NC(=O)OC(C)(C)C)NC(=O)OC(C)(C)C)c1]

A 10-mL vial was added methyl 4-(5-(4-(t-butyl)phenyl)naphthalen-2-yl)-3-(((2,2,10,10-tetramethyl-4,8-dioxo-3,9-dioxa-5,7-diazaundecan-6-yl)amino)methyl)benzoate (35 mg, 0.05 mmol), CH$_2$Cl$_2$ (1 mL), and TFA (1 mL). The sealed vial was stirred at 50° C. for 1 h. The solvent was removed and the residue was purified on silica gel. Elution with CH$_2$Cl$_2$ to (10/89/1: MeOH/CHCl$_1$/ammonium hydroxide) afforded the desired compound (16 mg, 67%) as a white solid. $^1$H NMR (CDCl$_3$, 400 MHz) δ 8.38 (broad s, 1H), 7.92-7.98 (m, 3H), 7.77 (d, 1H, J=8.08 Hz), 7.71 (s, 1H), 7.41-7.52 (m, 4H), 7.34-7.37 (m, 3H), 7.23 (dd, 1H, J=1.68, 8.80 Hz), 4.29 (d, 2H, J=5.40 Hz), 3.76 (s, 3H), 1.34 (s, 9H).

Example 102

Preparation of Compound

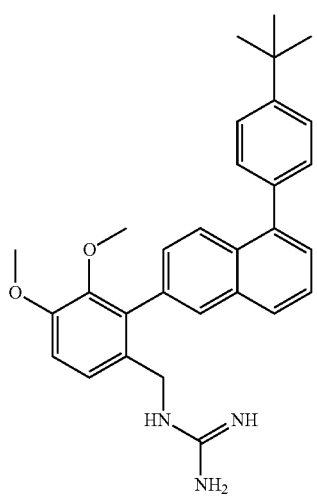 [SMILES: COc1ccc(CNC(=N)N)c(-c2ccc3c(-c4ccc(C(C)(C)C)cc4)cccc3c2)c1OC]

A 10-mL vial was added di-t-butyl(((2-(5-(4-(t-butyl)phenyl)naphthalen-2-yl)-3,4-dimethoxybenzyl)amino)methylene)dicarbamate (35 mg, 0.05 mmol), CH$_2$Cl$_2$ (1 mL), and TFA (1 mL). The sealed vial was stirred at 50° C. for 1 h. The solvent was removed and the residue was purified on silica gel. Elution with CH$_2$Cl$_2$ to (10/89/1: MeOH/CHCl$_3$/ammonium hydroxide) afforded the desired compound (20 mg, 80%) as a white solid. $^1$H NMR (CDCl$_3$, 400 MHz) δ 8.34 (t, 1H, J=5.24 Hz), 7.90-7.92 (m, 2H), 7.77 (d, 1H, J=8.12 Hz), 7.75 (dd, 1H, J=1.52, 8.88 Hz), 7.41-7.45 (m, 3H), 7.33-7.37 (m, 3H), 6.83 (d, 1H, J=1.68 Hz), 6.74 (d, 1H, J=1.76 Hz), 4.16 (d, 2H, J=5.32 Hz), 3.79 (s, 3H), 3.48 (s, 3H), 1.33 (s, 9H).

The requisite intermediate for the preparation of this compound was prepared as follows.

a. Preparation of Compound

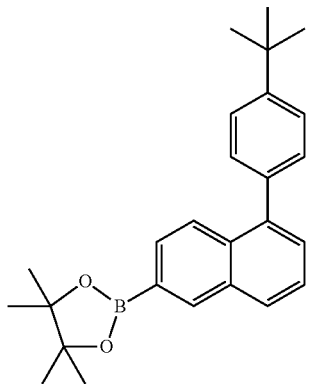 [SMILES: CC(C)(C)c1ccc(-c2cccc3cc(B4OC(C)(C)C(C)(C)O4)ccc23)cc1]

A 100-mL round bottom flask equipped with a magnetic stirrer, a condenser and a nitrogen in/outlet adapter was charged with 5-(4-(t-butyl)phenyl)naphthalen-2-yl trifluoromethanesulfonate (1.0 g, 2.45 mmol), 4,4,4',4',5,5,5',5'-octamethyl-2,2'-bi(1,3,2-dioxaborolane) (746 mg, 2.94 mmol), dioxane (20 ml), KOAc (720 mg, 2.94 mmol). The resulting solution was degassed for 5 min, then Pd(dppf)Cl$_2$ (70 mg, 0.09 mmol) was added and the solution was carefully degassed. The reaction mixture was warmed to 80° C. and stirred for 1.5 h. After cooling to room temperature, the reaction mixture was diluted with EtOAc (100 mL) and washed with saturated NaHCO$_3$ (30 mL), brine (30 mL), dried over Na$_2$SO$_4$. The organic layer was concentrated and purified on silica gel. Elution with 5% EtOAc/hexanes afforded the desired compound (836 mg, 88%) as a white solid. $^1$H NMR (CDCl$_3$, 400 MHz) δ 8.35 (s, 1H), 7.87 (d, 1H, J=8.48 Hz), 7.81 (d, 1H, J=8.00 Hz), 7.70 (dd, 1H, J=1.20, 8.48 Hz), 7.41-7.45 (m, 3H), 7.34-7.39 (m, 3H), 1.34 (s, 9H), 1.32 (s, 12H).

b. Preparation of Compound

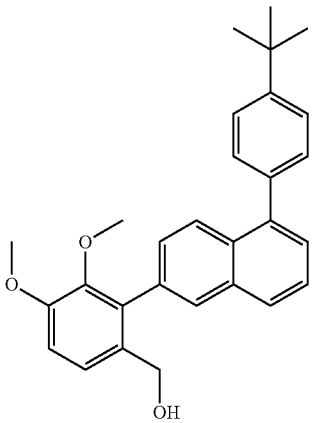 [SMILES: COc1ccc(CO)c(-c2ccc3c(-c4ccc(C(C)(C)C)cc4)cccc3c2)c1OC]

A 25-mL round bottom flask equipped with a magnetic stirrer, a condenser and a nitrogen in/outlet adapter was charged with 2-(5-(4-(t-butyl)phenyl)naphthalen-2-yl)-4,4,5,5-tetramethyl-1,3,2-dioxaborolane (70 mg, 0.18 mmol), (2-bromo-3,4-dimethoxyphenyl)methanol (35 mg, 0.16 mmol), water/dioxane (1 mL/4 ml), K$_2$CO$_3$ (50 mg, 0.36 mmol). The resulting solution was degassed for 5 min, then Pd(PPh$_3$)$_4$ (5 mg, 0.004 mmol) was added. The reaction mixture was warmed to 100° C. and stirred for 2 h. After cooling to room temperature, the reaction mixture was diluted with EtOAc (50 mL) and washed with saturated NaHCO$_3$ (20 mL), brine (20 mL), dried over NaSO$_4$. The organic layer was concentrated and purified on silica gel. Elution with 30% EtOAc/hexanes afforded the desired compound (74 mg, 96%) as a white solid. $^1$H NMR (CDCl$_3$, 400 MHz) δ 7.98 (d, 1H, =1.64 Hz), 7.92 (d, 1H, J=8.81 Hz), 7.81 (d, 1H, =8.20 Hz), 7.60 (dd, 1H, J=1.80, 8.80 Hz), 7.36-7.49 (m, 6H), 6.99 (d, 1H, J=1.92 Hz), 6.94 (d, 1H, J=1.92 Hz), 4.65 (d, 2H, J=5.8 Hz), 3.88 (s, 3H), 3.51 (s, 3H), 1.35 (s, 9H).

c. Preparation of Compound

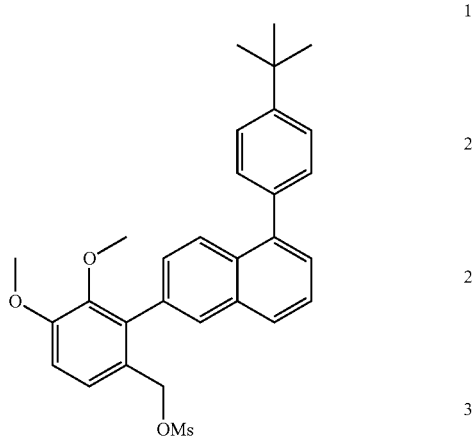

A 25-mL round bottom flask equipped with a magnetic stirrer under nitrogen was charged with (2-(5-(4-(t-butyl)phenyl)naphthalen-2-yl)-3,4-dimethoxyphenyl)methanol (74 mg, 0.18 mmol), CH$_2$Cl$_2$ (5 mL), and triethylamine (50 μl, 0.36 mmol). Methanesulfonyl chloride (20 μL, 0.27 mmol) was added via a syringe. The resulting reaction mixture was stirred at room temperature overnight. The reaction mixture was diluted with CH$_2$Cl$_2$ (30 mL) and washed with saturated NaHCO$_3$ (10 ml), brine (10 mL), dried over Na$_2$SO$_4$, and concentrated to afford the desired compound (80 mg, 90%) as an off white solid. The crude product was used in next step without further identification and purification.

d. Preparation of Compound

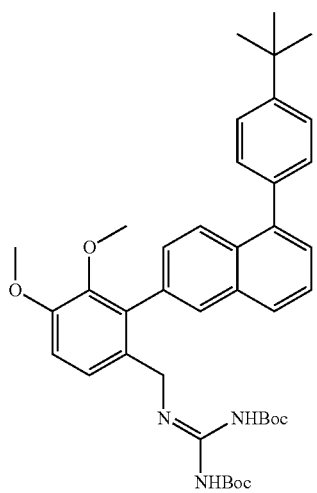 [SMILES: COc1ccc(CN=C(NC(=O)OC(C)(C)C)NC(=O)OC(C)(C)C)c(-c2ccc3c(-c4ccc(C(C)(C)C)cc4)cccc3c2)c1OC]

A 25-mL round bottom flask equipped with a magnetic stirrer, a condenser and a nitrogen in/outlet adapter was charged with 2-(5-(4-(t-butyl)phenyl)naphthalen-2-yl)-3,4-dimethoxybenzyl methanesulfonate (40 mg, 0.08 mmol), DMF (1 mL), K$_2$CO$_3$ (22 mg, 0.16 mmol), and 1,3-bis(t-butoxycarbonyl)guanidine (31 mg, 0.12 mmol) The reaction mixture was stirred at 50° C. for 12 h. The reaction mixture was diluted with EtOAc (40 mL), washed with water (10 mL), 10% LiCl (10 mL), brine (10 mL), dried over Na$_2$SO$_4$, concentrated, and purified on silica gel. Elution with 10% EtOAc/hexanes afforded the desired compound (35 mg, 66%) as a white solid, which was used in next step without further identification.

e. Preparation of Compound

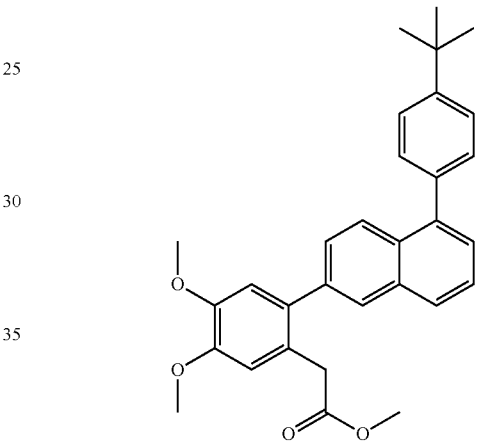

A 25-mL round bottom flask equipped with a magnetic stirrer, a condenser and a nitrogen in/outlet adapter was charged with 2-(5-(4-(tert-butyl)phenyl)naphthalen-2-yl)-4,4,5,5-tetramethyl-1,3,2-dioxaborolane (75 mg, 0.19 mmol), methyl 2-(2-bromo-4,5-dimethoxyphenyl)acetate (36 mg, 0.13 mmol), water/dioxane (1 mL/4 ml), K$_2$CO$_3$ (36 mg, 0.26 mmol). The resulting solution was degassed for 5 min, then Pd(PPh$_3$)$_4$ (7 mg, 0.006 mmol) was added. The reaction mixture was warmed to 100° C. and stirred for 1 h. After cooling to room temperature, the reaction mixture was diluted with EtOAc (50 mL) and washed with saturated NaHCO$_3$ (20 mL), brine (20 mL), dried over NaSO$_4$. The organic layer was concentrated and purified on silica gel. Elution with 10% EtOAc/hexanes afforded the desired compound (48 mg, 89%) as a white solid. $^1$H NMR (CDCl$_3$, 400 MHz) δ 7.92 (d, 1H, J=8.72 Hz), 7.76-7.78 (m, 2H), 7.45-7.50 (m, 3H), 7.37-7.41 (m, 3H), 7.33 (dd, 1H, J=1.76, 8.68 Hz), 6.83 (s, 1H), 6.80 (s, 1H), 3.87 (s, 3H), 3.81 (s, 3H), 3.57 (s, 3H), 3.51 (s, 2H), 1.35 (s, 9H).

Example 103

Preparation of Compound

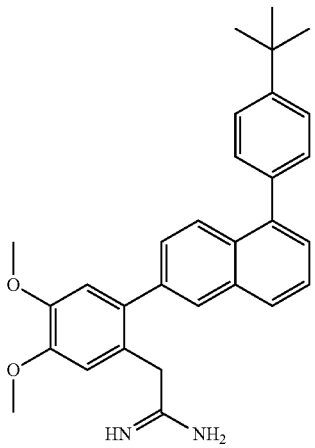 [SMILES: COc1cc(CC(=N)N)c(-c2ccc3c(-c4ccc(C(C)(C)C)cc4)cccc3c2)cc1OC]

A 50-mL round bottom flask equipped with a magnetic stirrer, a condenser and a nitrogen in/outlet adapter was charged with NH$_4$Cl (22 mg, 0.41 mmol), toluene (2 mL), and cooled to 0° C. To this suspension, AlMe$_3$ (2 M in hexanes, 0.20 mL, 0.41 mmol) was added drop wise over min then warmed to room temperature and stirred for 30 min. Methyl 2-(2-(5-(4-(t-butyl)phenyl)naphthalen-2-yl)-4,5-dimethoxyphenyl)acetate (40 mg, 0.08 mmol) was added as one portion and the resulting mixture was heated to 80° C. and stirred for 12 h. After cooling to 0° C., MeOH (3 mL) was added over 5 min, then the reaction mixture was stirred at room temperature for 1 h. The solid was removed by filtration and the filtrate was concentrated and purified with silica gel. Elution with EtOAc afforded the desired compound (25 mg, 66%) as a white solid. $^1$H NMR (CDCl$_3$, 400 MHz) δ 7.93 (d, 1H, J=8.68 Hz), 7.77 (d, 1H, J=8.20 Hz), 7.74 (d, 1H, J=1.76 Hz, 7.44-7.51 (m, 3H), 7.38-7.40 (m, 3H), 7.31 (d, 1H, J=1.88, 8.68 Hz), 6.85 (s, 1H), 6.83 (s, 1H), 5.21 (broad s, 2H), 3.88 (s, 3H), 3.82 (s, 3H), 3.47 (s, 2H), 1.35 (s, 9H).

Example 104

Preparation of Compound

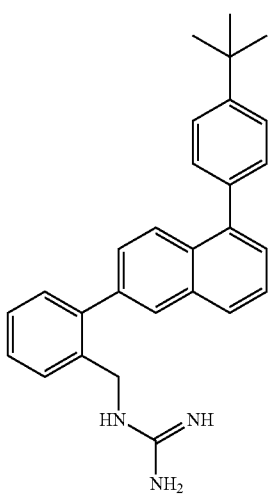 [SMILES: CC(C)(C)c1ccc(-c2cccc3cc(-c4ccccc4CNC(=N)N)ccc23)cc1]

A 20-mL vial was charged with di-t-butyl(((2-(5-(4-(t-butyl)phenyl)naphthalen-2-yl)benzyl)amino)methylene)dicarbamate (330 mg, 0.54 mmol), CH$_2$Cl$_2$ (2 mL), and TFA (2 mL). The sealed vial was stirred at 50° C. for 1 h. The solvent was removed and the residue was purified on silica gel. Elution with CH$_2$Cl$_2$ to (10/89/1: MeOH/CHCl$_3$/ammonium hydroxide) afforded the desired compound (200 mg, 91%) as a white solid. $^1$H NMR (CDCl$_3$, 400 MHz) δ 8.29 (t, 1H, J=5.12 Hz), 8.05 (d, 1H, J=8.64 Hz), 7.86 (d, 1H, J=8.12 Hz), 7.79 (d, 1H, J=1.56 Hz), 7.36-7.61 (m, 12H), 7.32 (dd, 1H, J=1.76, 8.80 Hz), 4.32 (d, 2H, J=5.64 Hz), 1.44 (s, 9H). The requisite intermediate for the preparation of this compound was prepared as follows.

a. Preparation of Compound

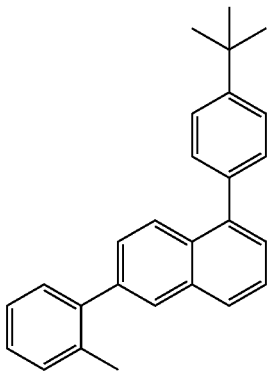 [SMILES: Cc1ccccc1-c1ccc2c(-c3ccc(C(C)(C)C)cc3)cccc2c1]

A 100-mL round bottom flask equipped with a magnetic stirrer, a condenser and a nitrogen in/outlet adapter was charged with 5-(4-(t-butyl)phenyl)naphthalen-2-yl trifluoromethanesulfonate, prepared as described for Intermediate b of Example 59, (300 mg, 0.73 mmol), o-tolylboronic acid (150 mg, 1.10 mmol), water/acetonitrile (4 mL/16 ml), K$_2$CO$_3$ (202 mg, 1.47 mmol), 2-dicyclohexylphosphino-2',4', 6'-triisopropylbiphenyl (35 mg, 0.073 mmol). The resulting solution was degassed for 5 min, then Pd(OAc)$_2$ (8.2 mg, 0.04 mmol) was added and the solution was carefully degassed. The reaction mixture was heated to 100° C. for 1 h. After cooling to room temperature, the reaction mixture was diluted with EtOAc (60 mL) and washed with saturated NaHCO$_3$ (20 mL), brine (20 mL), dried over Na$_2$SO$_4$. The organic layer was concentrated and purified on silica gel. Elution with hexanes afforded the desired compound (240 mg, 93%) as a white solid. $^1$H NMR (CDCl$_3$, 400 MHz) δ 7.92 (d, 1H, J=8.72 Hz), 7.79 (d, 1H, J=8.24 Hz), 7.76 (d, 1H, J=1.72 Hz), 7.34-7.48 (m, 7H), 7.18-7.27 (m, 4H), 2.25 (s, 3H), 1.35 (s, 9H).

b. Preparation of Compound

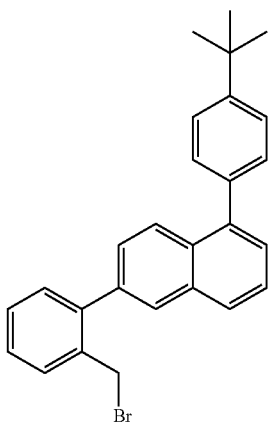 [SMILES: CC(C)(C)c1ccc(-c2cccc3cc(-c4ccccc4CBr)ccc23)cc1]

A 50-mL round bottom flask equipped with a magnetic stirrer, a condenser and a nitrogen in/outlet adapter was charged with 1-(4-(t-butyl)phenyl)-6-(o-tolyl)naphthalene (240 mg, 0.68 mmol), CCl$_4$ (3 mL), AIBN (11 mg, 0.068 mmol), and NBS (134 mg, 0.75 mmol). The reaction mixture was degassed for 5 min then heated to 85° C. for 1 h. After cooling to room temperature, the reaction mixture was added hexanes (20 mL). The solid was removed by filtration and the filtrate was concentrated and purified with silica gel. Elution with hexanes afforded the desired compound (241 mg, 82%) as yellow oil. $^1$H NMR (CDCl$_3$, 400 MHz) δ 7.97 (d, 1H, J=8.68 Hz), 7.91 (d, 1H, J=1.68 Hz), 7.81 (d, 1H, J=8.16 Hz), 7.39-7.51 (m, 8H), 7.27-7.34 (m, 3H), 4.44 (s, 2H), 1.35 (s, 9H).

c. Preparation of Compound

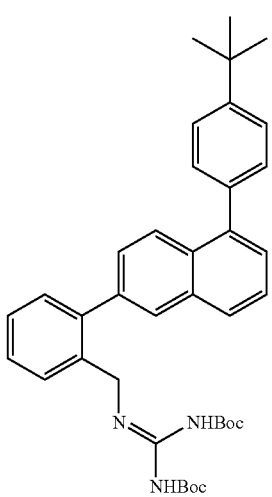 [SMILES: CC(C)(C)OC(=O)NC(=NCc1ccccc1-c1ccc2c(-c3ccc(C(C)(C)C)cc3)cccc2c1)NC(=O)OC(C)(C)C]

A 25-mL round bottom flask equipped with a magnetic stirrer, a condenser and a nitrogen in/outlet adapter was charged with 6-(2-(bromomethyl)phenyl)-1-(4-(t-butyl)phenyl)naphthalene (240 mg, 0.56 mmol), DMF (3 mL), K$_2$CO$_3$ (154 mg, 1.12 mmol), and 1,3-bis(t-butoxycarbonyl)guanidine (290 mg, 1.12 mmol) The reaction mixture was stirred at 50° C. for 12 h. The reaction mixture was diluted with EtOAc (60 mL), washed with water (20 mL), 10% LiCl (20 mL), brine (20 mL), dried over Na$_2$SO$_4$, concentrated, and purified on silica gel. Elution with 5% EtOAc/hexanes afforded the desired compound (330 mg, 97%) as a white solid. $^1$H NMR (CDCl$_3$, 400 MHz) δ 9.37 (broad s, 1H), 9.23 (broad s, 1H), 7.92 (d, 1H, J=8.72 Hz), 7.78-7.81 (m, 2H), 7.37-7.50 (m, 7H), 7.24-7.29 (m, 3H), 7.07 (d, 1H, J=7.84 Hz), 5.19 (broad s, 2H), 1.41 (s, 9H), 1.35 (s, 9H), 1.12 (s, 9H).

Example 105

Preparation of Compound

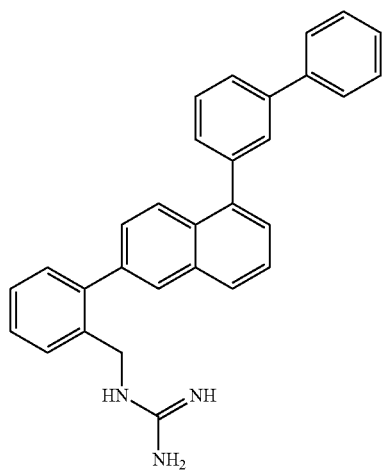 [SMILES: N=C(N)NCc1ccccc1-c1ccc2c(-c3cccc(-c4ccccc4)c3)cccc2c1]

A 10-mL vial was charged with di-t-butyl(((2-(5-([1,1'-biphenyl]-3-yl)naphthalen-2-yl)benzyl)amino)methylene) dicarbamate (40 mg, 0.06 mmol), CH$_2$Cl$_2$ (1 mL), and TFA (1 mL). The sealed vial was stirred at 50° C. for 1 h. The solvent was removed and the residue was purified on silica gel. Elution with CH$_2$Cl$_2$ to (10/89/1: MeOH/CHCl$_3$/ammonium hydroxide) afforded the desired compound (25 mg, 92% in yield) as a white solid. $^1$H NMR (CDCl$_3$, 400 MHz) δ 8.33 (broad s, 1H), 8.00-8.06 (m, 2H), 7.90 (d, 1H, J=6.88 Hz), 7.34-7.74 (m, 16H), 7.21 (broad s, 1H), 4.32 (broad s, 2H).

The requisite intermediate for the preparation of this compound was prepared as follows.

a. Preparation of Compound

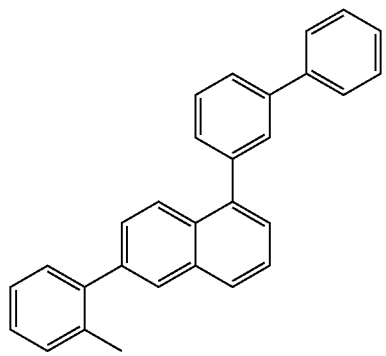 [SMILES: Cc1ccccc1-c1ccc2c(-c3cccc(-c4ccccc4)c3)cccc2c1]

A 100-mL round bottom flask equipped with a magnetic stirrer, a condenser and a nitrogen in/outlet adapter was charged with 5-([1,1'-biphenyl]-3-yl)naphthalen-2-yl trifluoromethanesulfonate (389 mg, 0.91 mmol), o-tolylboronic acid (185 mg, 1.36 mmol), water/acetonitrile (4 mL/16 ml), $K_2CO_3$ (251 mg, 1.82 mmol), 2-dicyclohexylphosphino-2',4', 6'-triisopropylbiphenyl (43 mg, 0.09 mmol). The resulting solution was degassed for 5 min, then Pd(OAc)$_2$ (10 mg, 0.05 mmol) was added and the solution was carefully degassed. The reaction mixture was heated to 100° C. for 1 h. After cooling to room temperature, the reaction mixture was diluted with EtOAc (60 mL) and washed with saturated NaHCO$_3$ (20 mL), brine (20 mL), dried over Na$_2$SO$_4$. The organic layer was concentrated and purified on silica gel. Elution with hexanes afforded the desired compound (220 mg, 65% in yield) as a white solid. $^1$H NMR (CDCl$_3$, 400 MHz) δ 8.14 (d, 1H, J=1.72 Hz), 8.06 (d, 1H, J=8.80 Hz), 7.96 (d, 1H, J=8.20 Hz), 7.80 (t, 1H, J=1.64 Hz), 7.69-7.80 (m, 4H), 7.46-7.64 (m, 8H), 7.37-7.43 (m, 2H), 7.23 (d, 1H, J=7.52 Hz), 2.49 (s, 3H).

b. Preparation of Compound

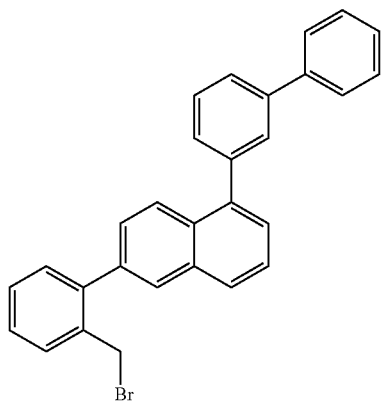 [SMILES: BrCc1ccccc1-c1ccc2c(-c3cccc(-c4ccccc4)c3)cccc2c1]

A 50-mL round bottom flask equipped with a magnetic stirrer, a condenser and a nitrogen in/outlet adapter was charged with 1-([1,1'-biphenyl]-3-yl)-6-(o-tolyl)naphthalene (220 mg, 0.59 mmol), CCl$_4$ (4 mL), AIBN (10 mg, 0.06 mmol), and NBS (116 mg, 0.65 mmol). The reaction mixture was degassed for 5 min then heated to 80° C. for 2 h. After cooling to room temperature, the reaction mixture was added hexanes (20 mL). The solid was removed by filtration and the filtrate was concentrated and purified with silica gel. Elution with hexanes afforded the desired compound (240 mg, 90% in yield) as a solid. $^1$H NMR (CDCl$_3$, 400 MHz) δ 8.00 (d, 1H, J=1.80 Hz), 7.93 (d, 1H, J=8.72 Hz), 7.82 (d, 1H, J=7.80 Hz), 7.23-7.65 (m, 16H), 4.48 (s, 2H).

c. Preparation of Compound

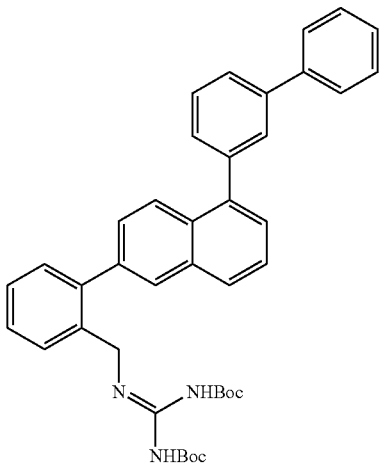 [SMILES: CC(C)(C)OC(=O)NC(=NCc1ccccc1-c1ccc2c(-c3cccc(-c4ccccc4)c3)cccc2c1)NC(=O)OC(C)(C)C]

A 25-mL round bottom flask equipped with a magnetic stirrer, a condenser and a nitrogen in/outlet adapter was charged with 1-([1,1'-biphenyl]-3-yl)-6-(2-(bromomethyl)phenyl)naphthalene (30 mg, 0.07 mmol), DMF (1 mL), K$_2$CO$_3$ (17 mg, 0.13 mmol), and 1,3-bis(tert-butoxycarbonyl)guanidine (26 mg, 0.1 mmol) The reaction mixture was stirred at 50° C. for 12 h. The reaction mixture was diluted with EtOAc (60 mL), washed with water (20 mL), 10% LiCl (20 mL), brine (20 mL), dried over Na$_2$SO$_4$, concentrated, and purified on silica gel. Elution with 5% EtOAc/hexanes afforded the desired compound (40 mg, 95%) as a white solid. $^1$H NMR (CDCl$_3$, 400 MHz) δ 9.51 (broad s, 1H), 9.36 (broad s, 1H), 8.12 (d, 1H, J=1.48 Hz), 8.05 (d, 1H, J=8.80 Hz), 7.95 (d, 1H, J=8.12 Hz), 7.80 (t, 1H, J=1.64 Hz), 7.69-7.80 (m, 5H), 7.37-7.65 (m, 9H), 7.29 (d, 1H, J=7.32 Hz), 5.30 (broad s, 2H), 1.50 (s, 9H), 1.38 (s, 9H).

Example 106

Preparation of Compound

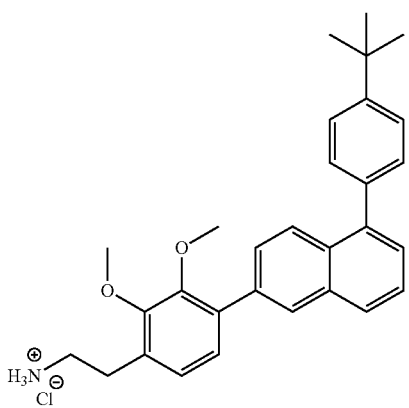 [SMILES: COc1c(CC[NH3+])ccc(-c2ccc3c(-c4ccc(C(C)(C)C)cc4)cccc3c2)c1OC ; [Cl-]]

A 50-mL round bottom flask equipped with a magnetic stirrer, a condenser was charged with N-(4-(5-(4-(t-butyl)phenyl)naphthalen-2-yl)-2,3-dimethoxyphenethyl)acetamide (30 mg, 0.06 mmol) and 50% HCl/MeOH (6 mL/6 mL). The reaction mixture was warmed to 100° C. and stirred for 12 h. After cooling to room temperature, the solid was collected by filtration and washed with $Et_2O$. After drying, there was obtained the desired compound (20 mg, 67% in yield) as a white solid.

a.—Preparation of Compound

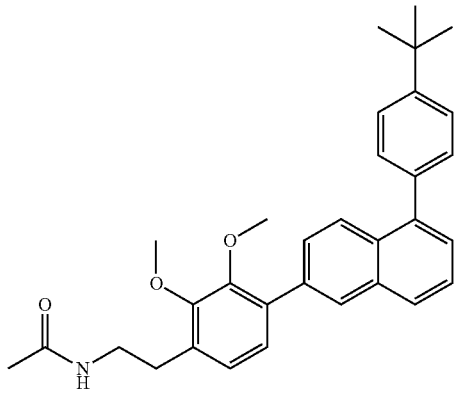 [SMILES: COc1c(CCNC(C)=O)ccc(-c2ccc3c(-c4ccc(C(C)(C)C)cc4)cccc3c2)c1OC]

A 25-mL round bottom flask equipped with a magnetic stirrer, a condenser and a nitrogen in/outlet adapter was charged with 2-(5-(4-(t-butyl)phenyl)naphthalen-2-yl)-4,4,5,5-tetramethyl-1,3,2-dioxaborolane (50 mg, 0.13 mmol), N-(4-bromo-2,3-dimethoxyphenethyl)acetamide (39 mg, 0.13 mmol), water/dioxane (1 mL/4 ml), $K_2CO_3$ (36 mg, 0.26 mmol). The resulting solution was degassed for 5 min, then $Pd(PPh_3)_4$ (7 mg, 0.006 mmol) was added. The reaction mixture was warmed to 100° C. and stirred for 2 h. After cooling to room temperature, the reaction mixture was diluted with EtOAc (50 mL) and washed with saturated $NaHCO_3$ (20 mL), brine (20 mL), dried over $NaSO_4$. The organic layer was concentrated and purified on silica gel. Elution with 90% EtOAc/hexanes afforded the desired compound (47 mg, 76% in yield) as a white solid. $^1$H NMR ($CDCl_3$, 400 MHz) δ 8.06 (d, 1H, J=1.60 Hz), 8.03 (d, 1H, J=8.88 Hz), 7.91 (d, 1H, J=8.16 Hz), 7.64-7.72 (m, 2H), 7.46-7.58 (m, 5H), 7.18 (d, 1H, J=7.88 Hz), 7.03 (d, 1H, J=8.04 Hz), 3.99 (s, 3H), 3.64 (s, 3H), 3.37 (m, 2H), 2.91 (t, 2H, J=6.56 Hz), 1.99 (s, 3H), 1.45 (s, 9H).

Example 107

Preparation of Compound

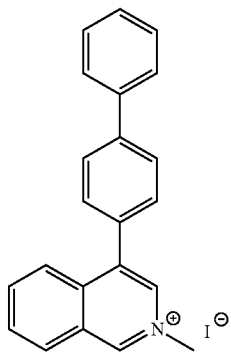 [SMILES: C[n+]1cc(-c2ccc(-c3ccccc3)cc2)c2ccccc2c1 ; [I-]]

Prepared by General Method B (87% Yield); $^1$H NMR (DMSO-d6, 400 MHz) δ: 4.52 (s, 3H), 7.45-7.47 (m, 1H), 7.55 (t, J=8.0 Hz, 2H), 7.75 (d, J=8.0 Hz, 2H), 7.81 (d, J=8.0 Hz, 2H), 7.99 (d, J=8.0 Hz, 2H), 8.20 (d, J=8.0 Hz, 1H), 8.26 (d, J=8.0 Hz, 1H), 8.29 (m, 1H), 8.59 9d, J=8.0 Hz, 1H), 8.85 (s, 1H), 10.04 (s, 1H).

Example 108

Preparation of Compound

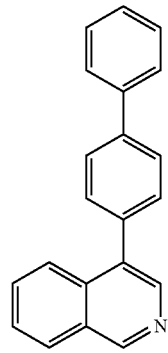 [SMILES: c1ccc(-c2ccc(-c3cncc4ccccc34)cc2)cc1]

Prepared by General Method A (85% Yield); $^1$H NMR ($CDCl_3$, 400 MHz) δ: 7.40 (m, 2H), 7.52 (m, 3H), 7.60 (d, J=8.0 Hz, 2H), 7.69 (d, J=8.0 Hz, 2H), 7.76 (m, 3H), 8.00 (d, J=8.0 Hz, 1H), 8.19 (d, J=8.0 Hz, 1H), 8.97 (d, J=4.0 Hz, 1H).

Example 109

Preparation of Compound

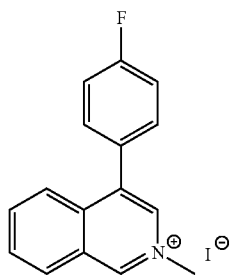 [SMILES: C[n+]1cc(-c2ccc(F)cc2)c2ccccc2c1 ; [I-]]

Prepared by General Method B (91% yield); ¹H NMR (CDCl₃, 400 MHz) δ: 4.85 (s, 3H), 7.26-7.32 (m, 2H), 7.63-7.66 (m, 2H), 7.97-8.11 (m, 3H), 8.37 (s, 1H), 8.75 (d, J=8.0 Hz, 1H), 10.88 (s, 1H).

Example 110

Preparation of Compound

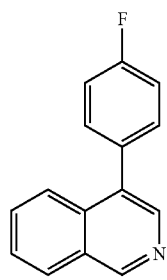 [SMILES: Fc1ccc(-c2cncc3ccccc23)cc1]

Prepared by General Method A (88% yield); ¹H NMR (CDCl₃, 400 MHz) δ: 7.22 (m, 2H), 7.47 (m. 2H), 7.66 (2H), 7.86 (d J=8.0 Hz, 1H), 8.05 (d, J=8.0 Hz, 1H), 8.46 (s, 1H), 9.26 (s, 1H).

Example 111

Preparation of Compound

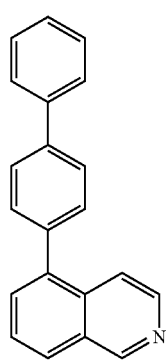 [SMILES: c1ccc(-c2ccc(-c3cccc4cnccc34)cc2)cc1]

Prepared by General Method A (88% yield); ¹H NMR (CDCl₃, 400 MHz) δ: 7.39 (t, J=8.0 Hz, 1H), 7.49 (t, J=8.0 Hz, 2H), 7.56 (d, J=8.0 Hz, 2H), 7.70 (m, 4H), 7.75 (d, J=8.0 Hz, 2H), 8.0 (d, J=8.0 Hz, 1H), 8.51 (d, J=4.0 Hz, 1H), 9.32 (s, 1H).

The requisite intermediate for the preparation of this compound was prepared as follows.

a. Preparation of Compound

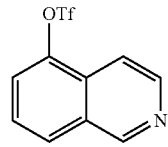 [SMILES: O=S(=O)(Oc1cccc2cnccc12)C(F)(F)F]

Prepared by General Method C (94% yield); ¹H NMR (CDCl₃, 400 MHz) δ: 7.55-7.60 (m, 2H), 7.76 (t, J=8.0 Hz, 1H), 8.18 (d, J=8.0 Hz, 1H), 8.42 (d, J=8.0 Hz, 1H), 9.03 (m, 1H).

Example 112

Preparation of Compound

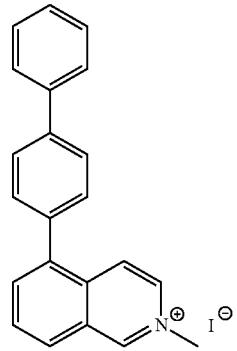 [SMILES: C[n+]1ccc2c(-c3ccc(-c4ccccc4)cc3)cccc2c1 ; [I-]]

Prepared by General Method B (87% yield); ¹H NMR (CDCl₃, 400 MHz) δ: 4.84 (s, 3H), 7.43 (m, 1H), 7.49-7.52 (m, 4H), 7.68 (d, J=4.0 Hz, 2H), 7.78 (d, J=8.0 Hz, 2H), 8.04-8.12 (m, 2H), 8.34 (d, J=4.0 Hz, 1H), 8.53 (bs, 1H), 8.72 (d, J=8.0 Hz, 1H), 10.9 (m, 1H).

Example 113

Preparation of Compound

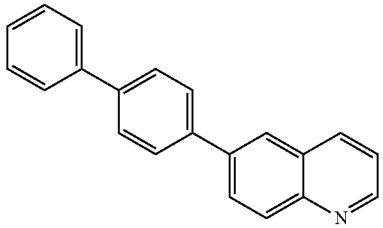 [SMILES: c1ccc(-c2ccc(-c3ccc4ncccc4c3)cc2)cc1]

Prepared by General Method A (84% yield); ¹H NMR (CDCl₃, 400 MHz) δ: 7.41 (m, 1H), 7.48 (m, 3H), 7.70 (d, J=8.0 Hz, 2H), 7.77 (d, J=8.0 Hz, 2H), 7.83 (d, J=8.0 Hz, 2H), 8.06 (m, 2H), 8.25 (t, 8.0 Hz, 2H), 8.97 (m, 1H).

The requisite intermediate for the preparation of this compound was prepared as follows.

a. Preparation of Compound

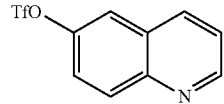 [SMILES: O=S(=O)(Oc1ccc2ncccc2c1)C(F)(F)F]

Prepared by General Method C (94% yield) was used as isolated without further purification.

Example 114

Preparation of Compound

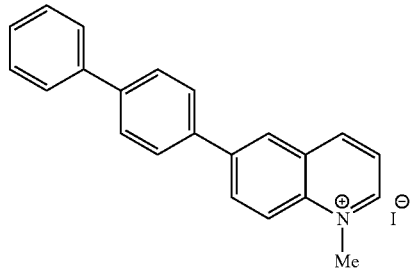 [SMILES: C[n+]1cccc2cc(-c3ccc(-c4ccccc4)cc3)ccc21 ; [I-]]

Prepared by General Method B (78% yield); $^1$H NMR (DMSO-d6, 400 MHz) δ: 4.68 (s, 3H), 7.45 (m, 1H), 7.53 (m, 2H), 7.79 (d, J=8.0 Hz, 2H), 7.92 (d, J=8.0 Hz, 2H), 8.08 (d, J=8.0 Hz, 2H), 8.20 (m, 1H), 8.60 (d, J=12.0 Hz, 1H), 8.72 (d, J=8.0 Hz, 1H), 8.89 (s, 1H), 9.29 (d, J=8.0 Hz, 1H), 9.48 (d, J=8.0 Hz, 1H).

Example 115

Preparation of Compound

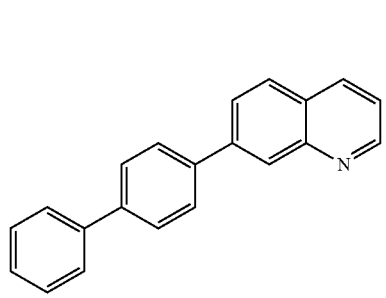 [SMILES: c1ccc(-c2ccc(-c3ccc4cccnc4c3)cc2)cc1]

Prepared by General Method A (77% yield); $^1$H NMR (CDCl$_3$, 400 MHz) δ: 7.53-7.66 (m, 4H), 7.84 (d, J=8.0 Hz, 2H), 7.91 (d, J=8.0 Hz, 2H), 8.01 (d, J=8.0 Hz, 2H), 8.06 (d, J=8.0 Hz, 2H), 8.36 (d, J=8.0 Hz, 1H), 8.57 (s, 1H), 9.13 (m, 1H).

The requisite intermediate for the preparation of this compound was prepared as follows.

a. Preparation of Compound

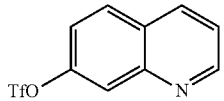

Prepared by General Method C (94% yield); $^1$H NMR (CDCl$_3$, 400 MHz) δ: 6.16 (d, J=8.0 Hz, 1H), 6.34 (m, 1H), 6.82 (d, J=8.0 Hz, 1H), 7.25 (m, 1H), 7.39 (d, J=8.0 Hz, 1H), 7.76 (s, 1H).

Example 116

Preparation of Compound

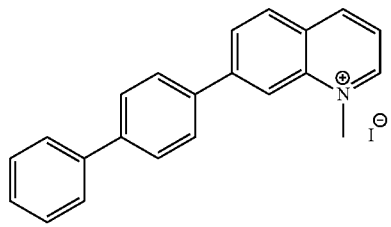 [SMILES: C[n+]1cccc2ccc(-c3ccc(-c4ccccc4)cc3)cc21 ; [I-]]

Prepared by General Method B (83% yield); $^1$H NMR (DMSO-d6, 400 MHz) δ: 4.75 (s, 3H), 7.45 (m, 1H), 7.54 (t, J=8.0 Hz, 2H), 7.81 (d, J=8.0 Hz, 2H), 7.95 (d, J=8.0 Hz, 2H), 8.17 (m, 3H), 8.5 (d, J=8.0 Hz, 1H), 8.58 (d, J=8.0 Hz, 1H), 8.71 (s, 1H), 9.28 (d, J=8.0 Hz, 1H), 9.49 (d, J=8.0 Hz, 1H).

Example 117

Preparation of Compound

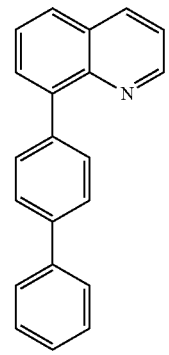 [SMILES: c1ccc(-c2ccc(-c3cccc4cccnc34)cc2)cc1]

Prepared by General Method A (84% yield); $^1$H NMR (CDCl$_3$, 400 MHz) δ: 7.30-7.41 (m, 4H), 7.52 (t, J=8.0 Hz, 1H), 7.57 (d, J=8.0 Hz, 2H), 7.62 (d, J=8.0 Hz, 2H), 7.63-7.74 (m, 3H), 8.11 (d, J=8.0 Hz, 1H), 8.23 (d, J=8.0 Hz, 1H), 8.88 (m, 1H)

The requisite intermediate for the preparation of this compound was prepared as follows.

a. Preparation of Compound

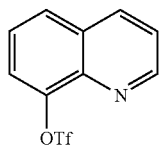

Prepared by General Method C (92% yield); ¹H NMR (CDCl₃, 400 MHz) δ: 7.52 (m, 1H), 7.57 (d, J=8.0 Hz, 1H), 7.61 (d, J=8.0 Hz, 1H), 7.86 (d, J=8.0 Hz, 1H), 8.22 (d, J=8.0 Hz, 1H), 9.04 (m, 1H).

Example 118

Preparation of Compound

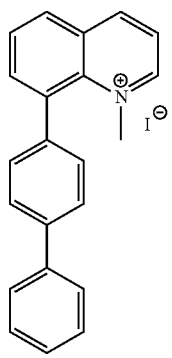 [SMILES: C[n+]1cccc2cccc(-c3ccc(-c4ccccc4)cc3)c21 ; [I-]]

Prepared by General Method B (78% yield); ¹H NMR (DMSO-d6, 400 MHz) δ: 4.03 (s, 3H), 7.44 (t, J=8.0 Hz, 1H), 7.52 (t, J=8.0 Hz, 2H), 7.64 (d, J=8.0 Hz, 2H), 7.81 (d, J=8.0 Hz, 2H), 7.88 (d, J=8.0 Hz, 2H), 8.09 (m, 2H), 8.21-8.24 (m, 1H), 8.54 (d, J=8.0 Hz, 1H), 9.34 (m, 2H).

Example 119

Preparation of Compound

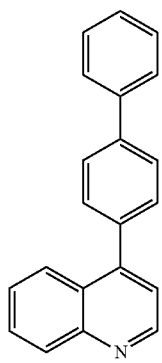 [SMILES: c1ccc(-c2ccc(-c3ccnc4ccccc34)cc2)cc1]

Prepared by General Method A (92% yield); ¹H NMR (CDCl₃, 400 MHz) δ 7.40 (m, 2H), 7.48-7.55 (m, 3H), 7.60 (d, J=8.0 Hz, 2H), 7.69 (d, J=8.0 Hz, 2H), 7.75 (m, 3H), 8.00 (d, J=8.0 Hz, 1H), 8.19 (d, J=8.0 Hz, 1H), 8.96 (d J=4.0 Hz, 1H).

Example 120

Preparation of Compound

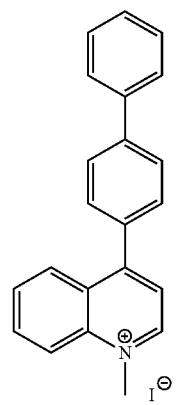 [SMILES: C[n+]1ccc(-c2ccc(-c3ccccc3)cc2)c2ccccc21 ; [I-]]

Prepared by General Method B (91% yield); ¹H NMR (CDCl₃, 400 MHz) δ: 4.99 (s, 3H), 7.37-7.44 (m, 1H), 7.46-7.54 (m, 2H), 7.66-7.70 (m, 4H), 7.84-7.86 (m, 2H), 7.9 (t, J=8.0 Hz, 1H), 8.05 (t, J=8.0 Hz, 1H), 8.25 (t, J=8.0 Hz, 1H), 8.36 (d, J=8.0 Hz, 1H), 8.51 (m, 1H), 10.31 (m, 1H).

Example 121

Preparation of Compound

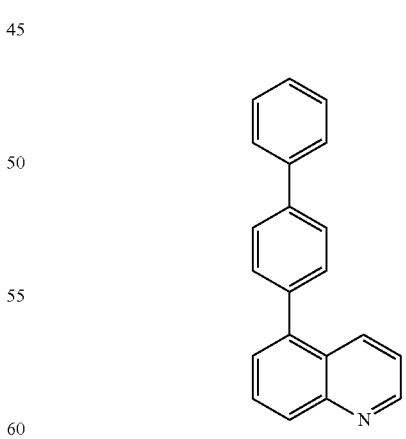

Prepared by General Method A from 5-bromoquinoline and 4-[1,1']biphenylboronic acid. ¹H NMR (CDCl₃, 400 MHz) δ: 7.37 (t J=8.0 Hz, 1H), 7.49 (t, J=8.0 Hz, 2H), 7.56 (d, J=8.0 Hz, 2H), 7.68-7.76 (m, 7H), 8.00 (d, J=8.0 Hz, 1H), 8.51 (d J=8.0 Hz, 1H, 9.32 (s, 1H).

Example 122

Preparation of Compound

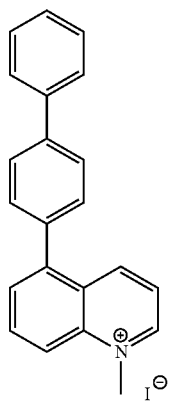 [SMILES: C[n+]1cccc2c(-c3ccc(-c4ccccc4)cc3)cccc21 ; [I-]]

Prepared by General Method B; $^1$H NMR (DMSO-d6, 400 MHz) δ: 4.76 (s, 3H), 7.52 (m, 1H), 7.61 (t, J=8.0 Hz, 2H), 7.73 (d, J=8.0 Hz, 2H), 7.86 (d, J=8.0 Hz, 2H), 8.00 (d, J=8.0 Hz, 2H), 8.13-8.20 (m, 2H), 8.43 (m, 1H), 8.64 (d, J=8.0 Hz, 1H), 9.16 (d, J=8.0 Hz, 1H), 9.60 (d, J=8.0 Hz, 1H).

Comparative Example A

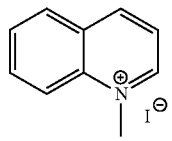

Prepared by General Method B from quinoline (93% yield); $^1$H NMR (DMSO-d6, 400 MHz) δ: 4.65 (s, 3H), 8.08 (t, J=8.0 Hz, 1H), 8.19 (m, 1H), 8.31 (m, 1H), 8.50 (m, 2H), 9.29 (d, J=8.0 Hz, 1H), 9.51 (d, J=8.0 Hz, 1H).

Comparative Example B

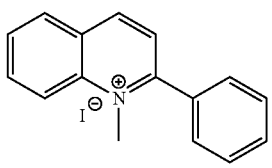 [SMILES: C[n+]1c(-c2ccccc2)ccc2ccccc21 ; [I-]]

Prepared by General Method B from commercially available 2-phenylisoquinoline (87% yield); $^1$H NMR (DMSO-d6, 400 MHz) δ: 4.40 (s, 3H), 7.75 (m, 3H), 7.83 (m, 2H), 8.01 (t, J=8.0 Hz, 1H), 8.18 (d, J=8.0 Hz, 1H), 8.35 (m, 1H), 8.54 (d, J=8.0 Hz, 1H), 8.64 (d, J=8.0 Hz, 1H), 9.30 (d, J=8.0 Hz, 1H).

Example 123

The following can illustrate representative pharmaceutical dosage forms, containing a compound of formula I ('Compound X') or a pharmaceutically acceptable salt thereof, for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

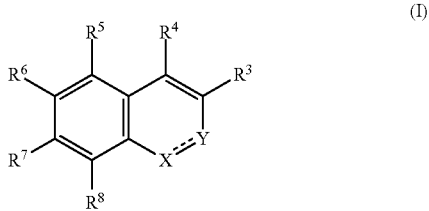

wherein:

X is C—$R^{51}$;

Y is C($R^{52}$);

$R^{51}$ is hydrogen and $R^{52}$ is a ring selected from phenyl, pyridyl, and [D⁻N⁺($C_1$-$C_6$)alkylpyridyl], wherein the phenyl is substituted with one or more groups selected from methylenedioxy, $R^{5f}$, $R^{5da}$, and ($C_1$-$C_6$)alkyl that is substituted with one or more $R^{5f}$, and wherein the pyridyl, and [D⁻N⁺—($C_1$-$C_6$)alkylpyridyl] is optionally substituted with one or more groups selected from methylenedioxy, Z—$R^{5x}$, $R^{5f}$, $R^{5da}$, and ($C_1$-$C_6$)alkyl that is substituted with one or more $R^{5f}$; or $R^{51}$ is —N⁺($R^{5a}$)$_3$D⁻, —NR$^{5g}$R$^{5h}$, or ($C_1$-$C_6$)alkyl that is substituted with one or more $R^{5f}$; and $R^{52}$ is a ring selected from phenyl, pyridyl, and [D⁻N⁺—($C_1$-$C_6$) alkylpyridyl], which ring is optionally substituted with one or more groups selected from methylenedioxy, Z—$R^{5x}$, $R^{5f}$, $R^{5da}$, and ($C_1$-$C_6$)alkyl that is substituted with one or more $R^{5f}$;

$R^6$ and $R^7$ taken together can be methylenedioxy or each $R^6$ and $R^7$ is independently selected from H and Z—$R^{5x}$;

$R^8$ is hydrogen;

each Z is —O—;

at least one of $R^4$ and $R^5$ is selected from ($C_3$-$C_6$)cycloalkyl, aryl, and heteroaryl; and the remainder of $R^3$, $R^4$, and $R^5$ are H; wherein each aryl and heteroaryl of $R^4$ and $R^5$ is optionally substituted with one or more groups independently selected from ($C_1$-$C_6$)alkyl, halo, and $R^{5s}$;

each $R^{5a}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{5b}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{5c}$ and $R^{5d}$ is independently selected from H, ($C_1$-$C_6$)alkyl, ($C_3$-$C_6$)cycloalkyl, ($C_3$-$C_6$)cycloalkyl($C_1$-$C_6$) alkyl, aryl, heteroaryl, aryl($C_1$-$C_6$) alkyl and heteroaryl ($C_1$-$C_6$) alkyl; wherein any ($C_1$-$C_6$)alkyl, ($C_3$-$C_6$) cycloalkyl, ($C_3$-$C_6$)cycloalkyl($C_1$-$C_6$)alkyl, aryl, heteroaryl, aryl($C_1$-$C_6$) alkyl or heteroaryl($C_1$-$C_6$)alkyl of $R^{5c}$ and $R^{5d}$ is optionally substituted with one or more groups independently selected from hydroxy, carboxy, and NR$^{5m}$R$^{5n}$;

each $R^{5e}$ is independently selected from H, ($C_1$-$C_6$)alkyl, ($C_3$-$C_6$)cycloalkyl, ($C_3$-$C_6$)cycloalkyl($C_1$-$C_6$)alkyl, aryl, heteroaryl, aryl($C_1$-$C_6$) alkyl and heteroaryl($C_1$-$C_6$)alkyl;

each $R^{5f}$ is independently selected from —N⁺($R^{5a}$)$_3$D⁻, —C(=NR$^{5b}$)—NR$^{5c}$R$^{5d}$, —NR$^{5e}$—C(=NR$^{5b}$)—NR$^{5c}$R$^{5d}$, and —NR$^{5g}$R$^{5h}$;

each $R^{5g}$ and $R^{5h}$ is independently selected from H, and ($C_1$-$C_6$)alkyl; wherein any ($C_1$-$C_6$)alkyl of $R^{5g}$ and $R^{5h}$ is optionally substituted with one or more groups independently selected from hydroxy, carboxy, and NR$^{5m}$R$^{5n}$;

each $R^{5m}$ and $R^{5n}$ is independently selected from H, and ($C_1$-$C_6$)alkyl;

each $R^{5s}$ is independently trifluoromethyl, trifluoromethoxy, aryl, or heteroaryl, wherein each aryl and heteroaryl is optionally substituted with one or more ($C_1$-$C_6$)alkyl, halo, hydroxy, cyano, nitro, ($C_1$-$C_6$) alkoxy, ($C_3$-$C_6$)cycloalkyl, carboxy, trifluoromethyl, and trifluoromethoxy;

each $R^{5x}$ is independently selected from ($C_1$-$C_6$)alkyl;

each D⁻ is independently a counter anion;

each $R^{5da}$ is carboxy or ($C_1$-$C_6$)alkoxycarbonyl; and the bond represented by ---- is present;

or a salt or prodrug thereof.

2. The compound

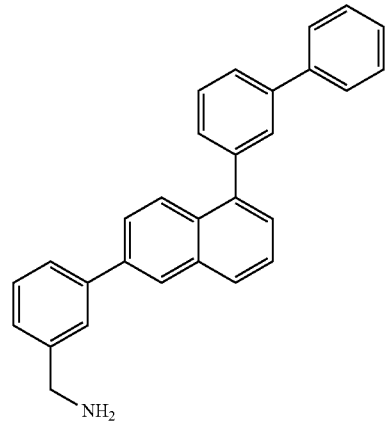 [SMILES: NCc1cccc(-c2ccc3c(-c4cccc(-c5ccccc5)c4)cccc3c2)c1]

or a salt thereof.

3. A compound selected from the group consisting of

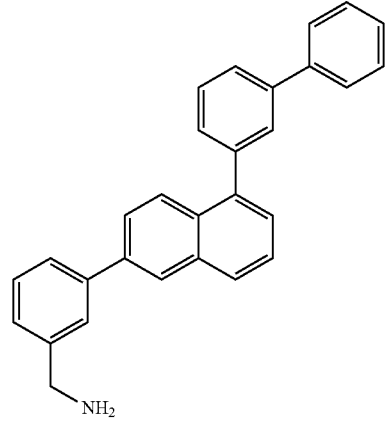 [SMILES: NCc1cccc(-c2ccc3c(-c4cccc(-c5ccccc5)c4)cccc3c2)c1]

315
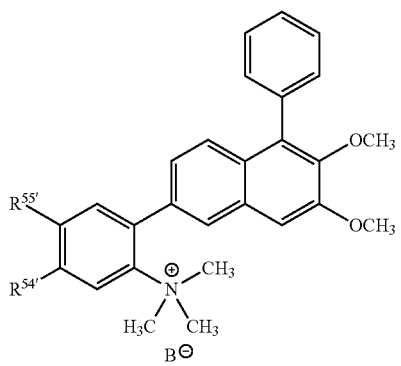
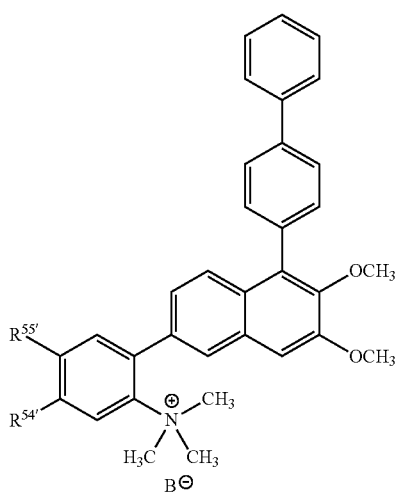
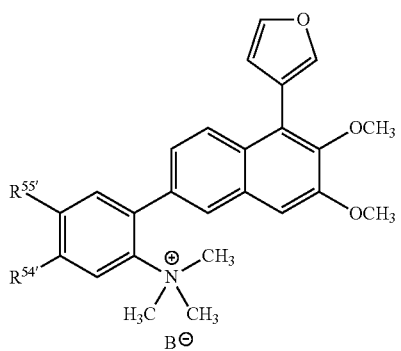
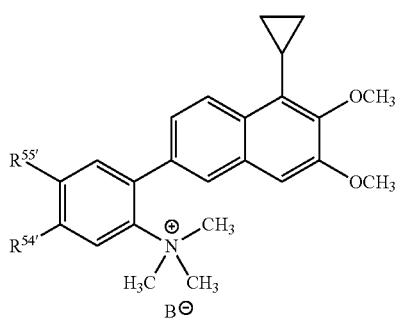
316
-continued
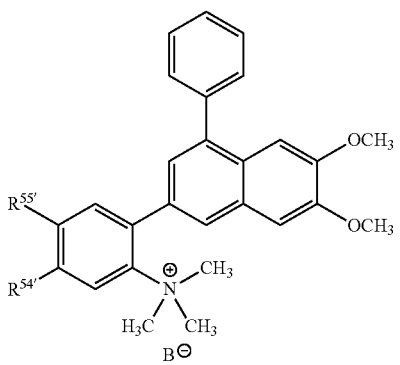
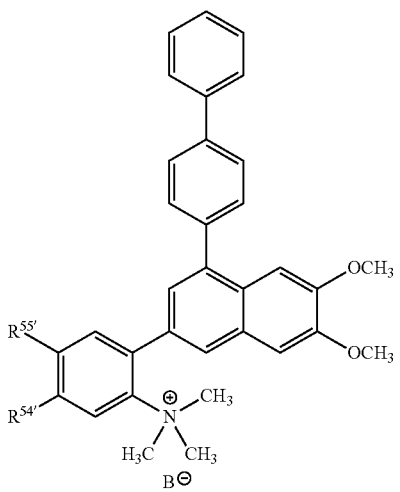
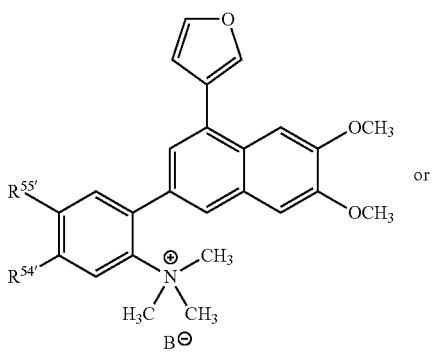
or
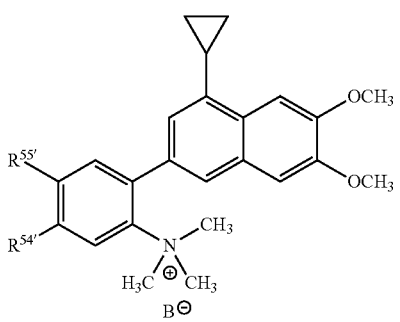
wherein $R^{54'}$ and $R^{5'}$ are each H or methoxy, or taken together are methylenedioxy and B is an acceptable counterion; or a salt or prodrug thereof.

4. A compound selected from the group consisting of
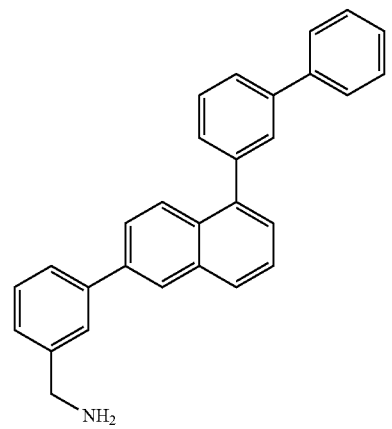 [SMILES: NCc1cccc(-c2ccc3c(-c4cccc(-c5ccccc5)c4)cccc3c2)c1]
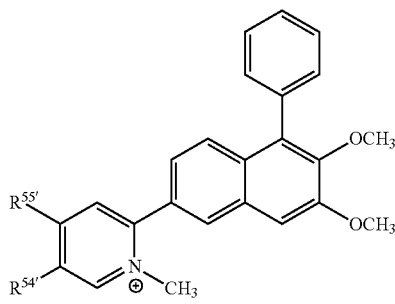
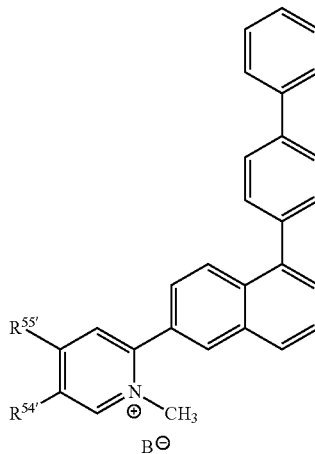
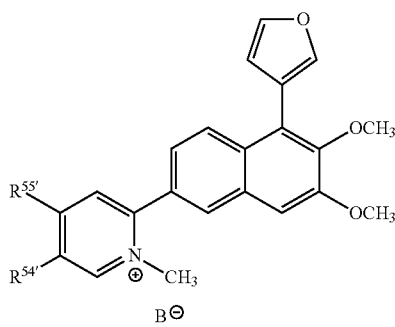
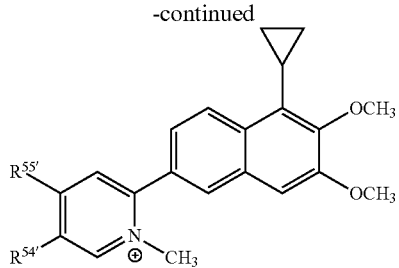
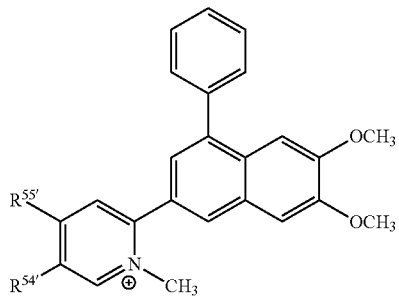
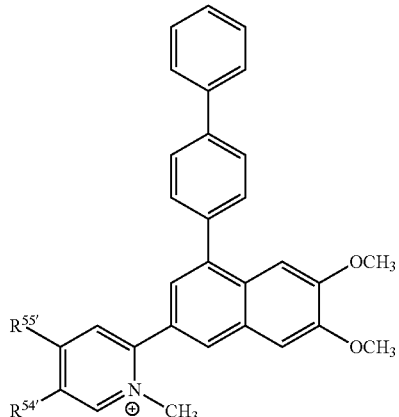
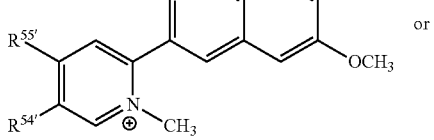 or
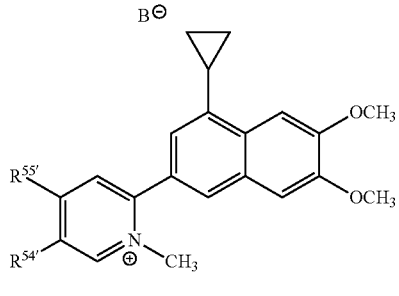

wherein $R^{54'}$ and $R^{55'}$ are each H or methoxy, or taken together are methylenedioxy and B is an acceptable counterion; or a salt or prodrug thereof.
5. A compound selected from the group consisting of
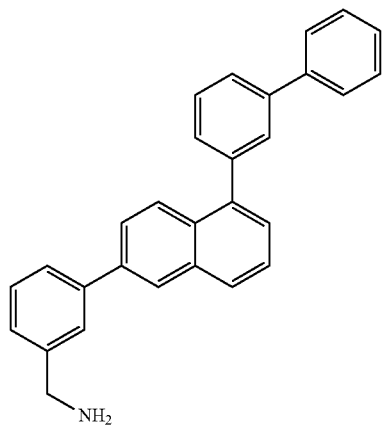 [SMILES: NCc1cccc(-c2ccc3c(-c4cccc(-c5ccccc5)c4)cccc3c2)c1]
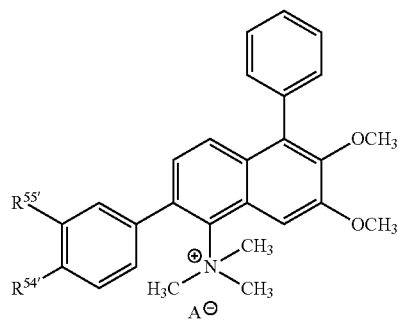
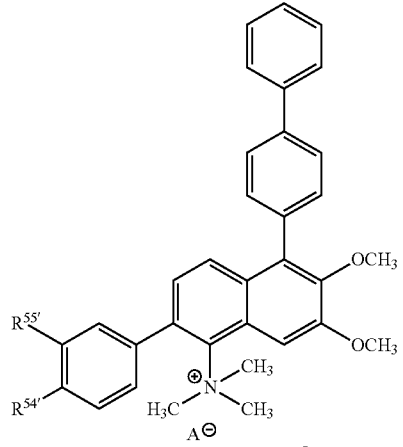
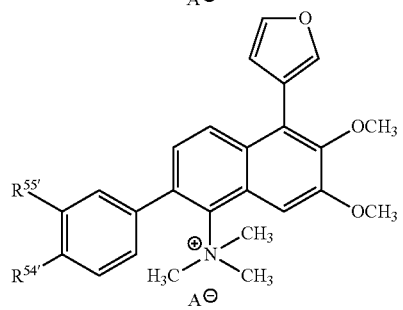
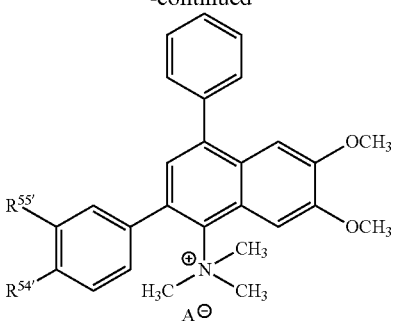
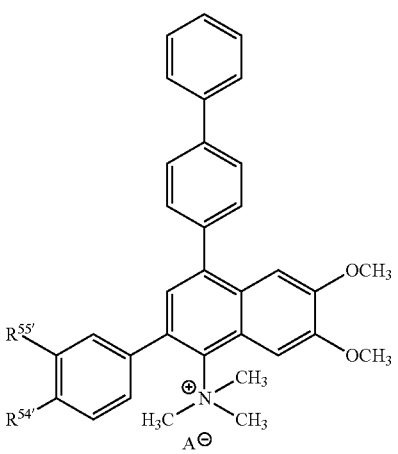
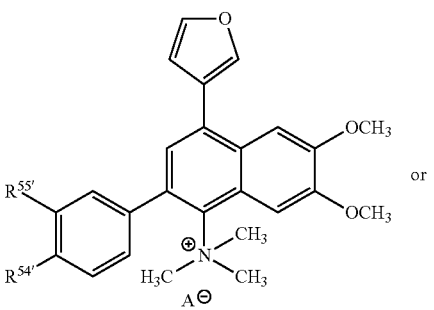
or
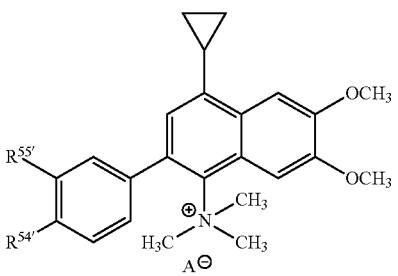
wherein $R^{54'}$ and $R^{55'}$ are each H or methoxy, or taken together are methylenedioxy and A is an acceptable counterion; or a salt or prodrug thereof.

6. A compound selected from the group consisting of
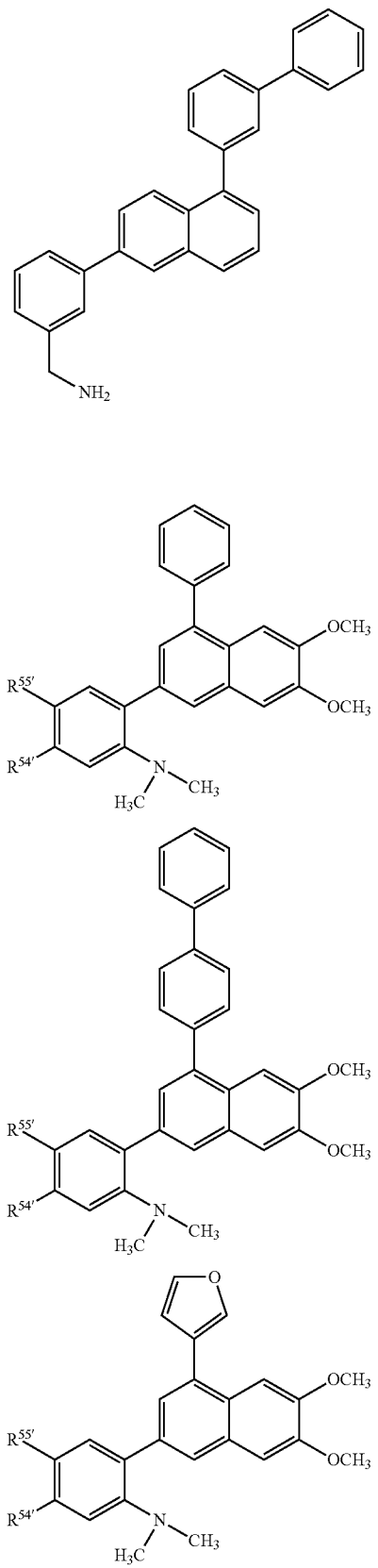
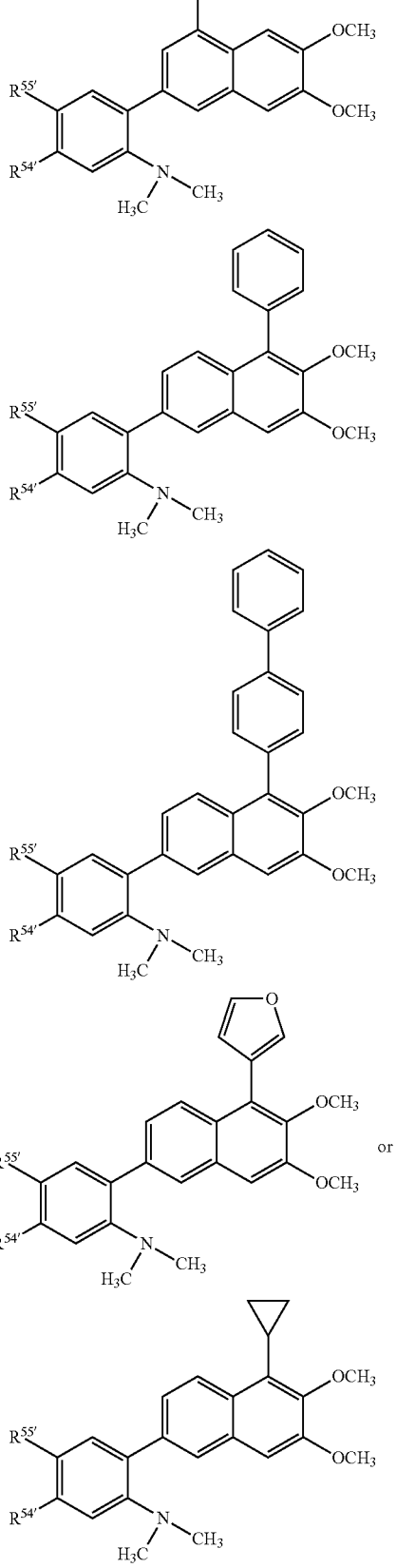
or wherein $R^{54'}$ and $R^{55'}$ are each H or methoxy, or taken together are methylenedioxy;
or a salt or prodrug thereof.
7. A compound selected from the group consisting of
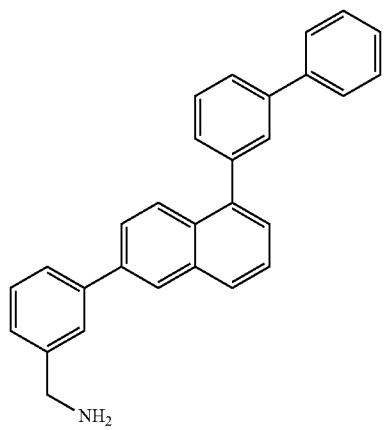 [SMILES: NCc1cccc(-c2ccc3c(-c4cccc(-c5ccccc5)c4)cccc3c2)c1]
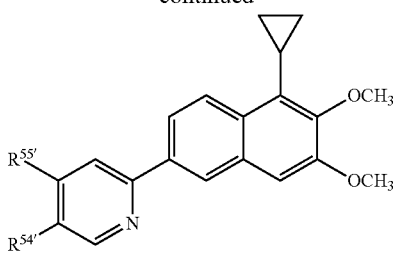
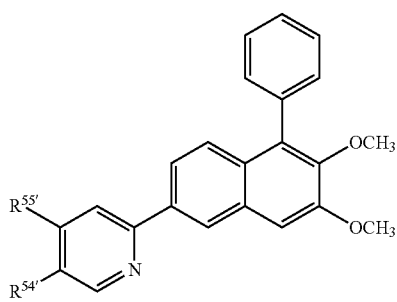
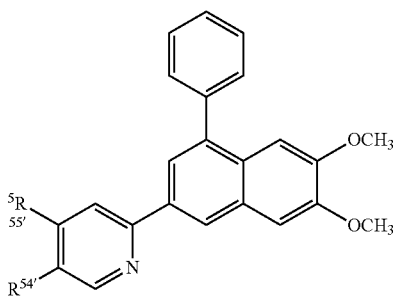
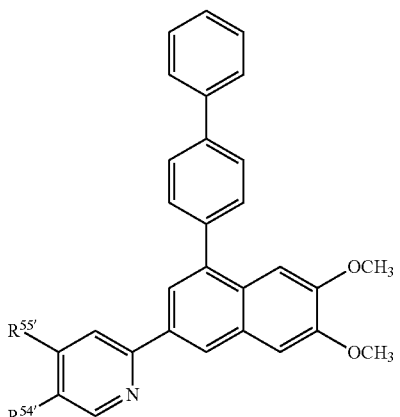
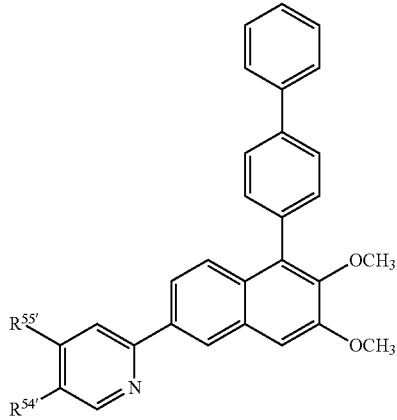
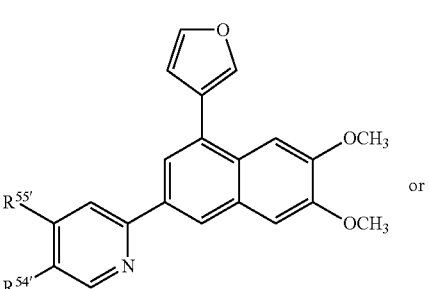
or
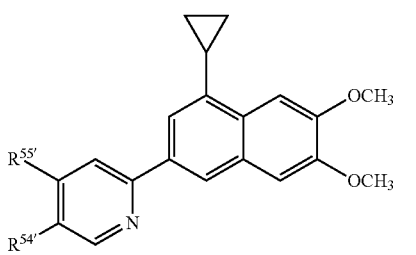
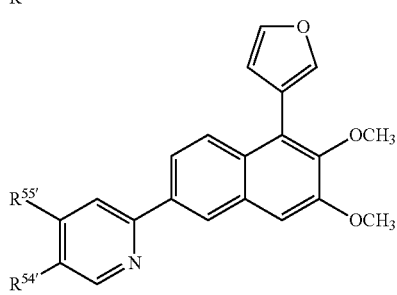
wherein $R^{54'}$ and $R^{55'}$ are each H or methoxy, or taken together are methylenedioxy;
or a salt or prodrug thereof.

8. A compound selected from the group consisting of
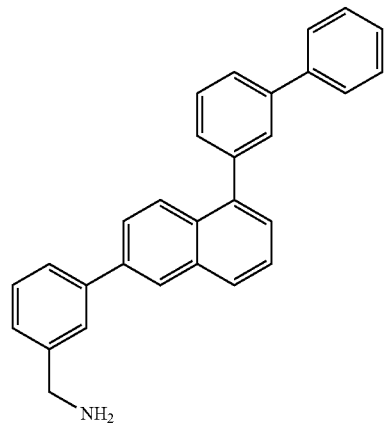 [SMILES: NCc1cccc(-c2ccc3c(-c4cccc(-c5ccccc5)c4)cccc3c2)c1]
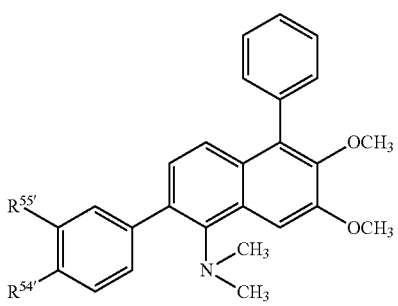
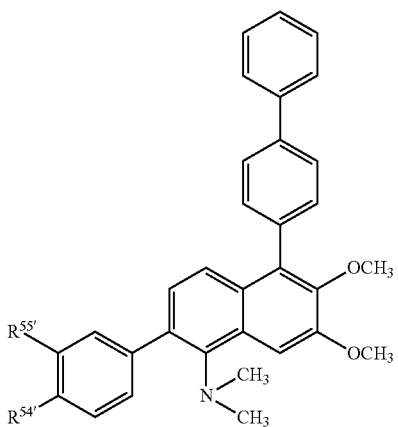
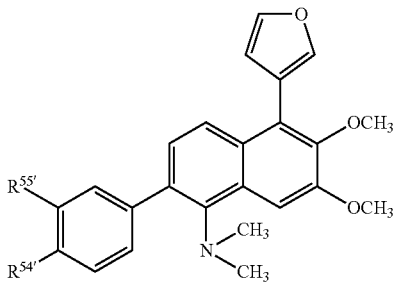
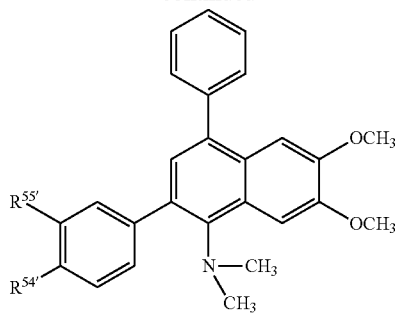
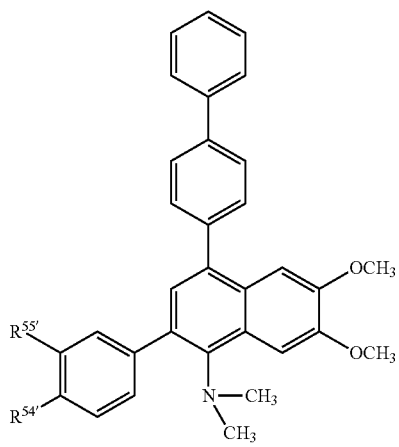
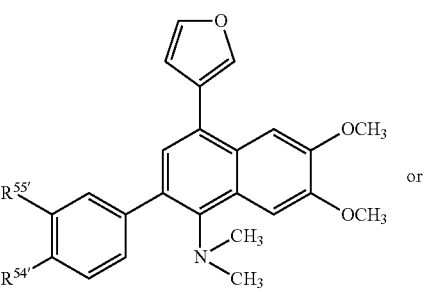
or
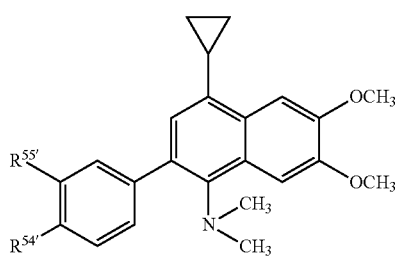
wherein $R^{54'}$ and $R^{55'}$ are each H or methoxy, or taken together are methylenedioxy;
or a salt or prodrug thereof.

9. A compound selected from the group consisting of
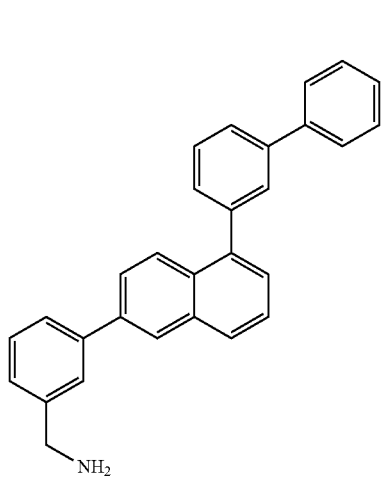 [SMILES: NCc1cccc(-c2ccc3c(-c4cccc(-c5ccccc5)c4)cccc3c2)c1]
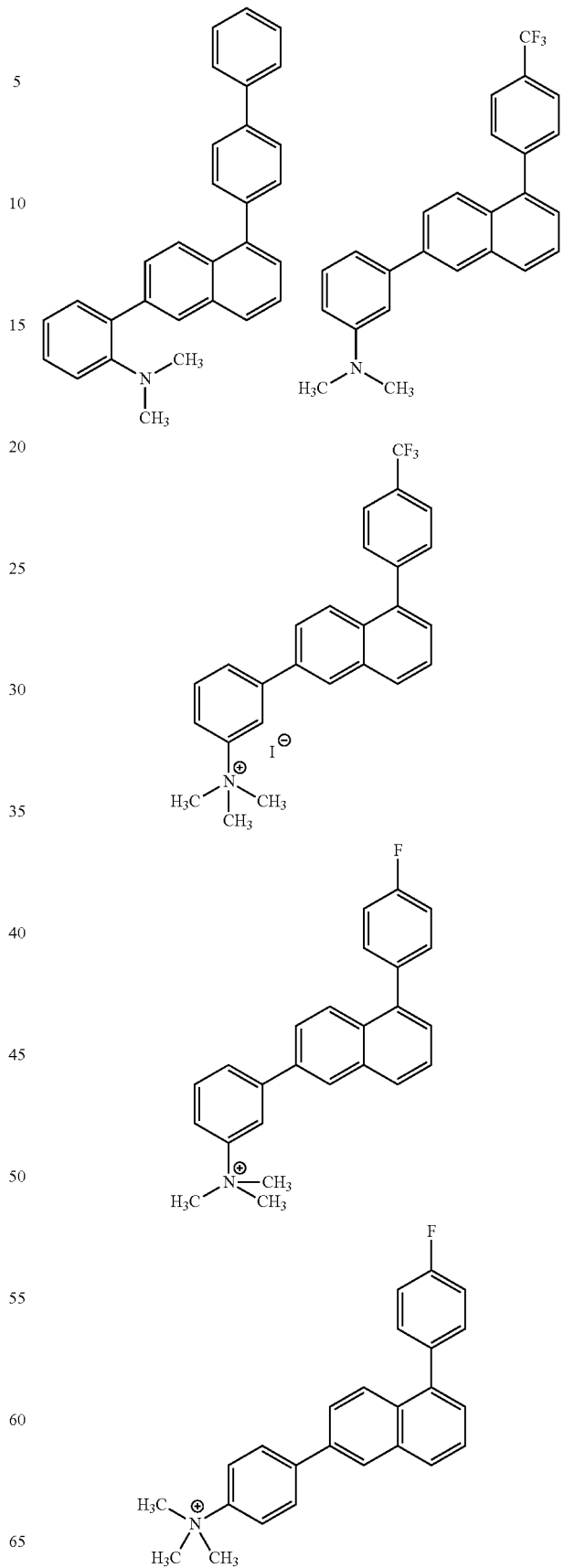

329
-continued
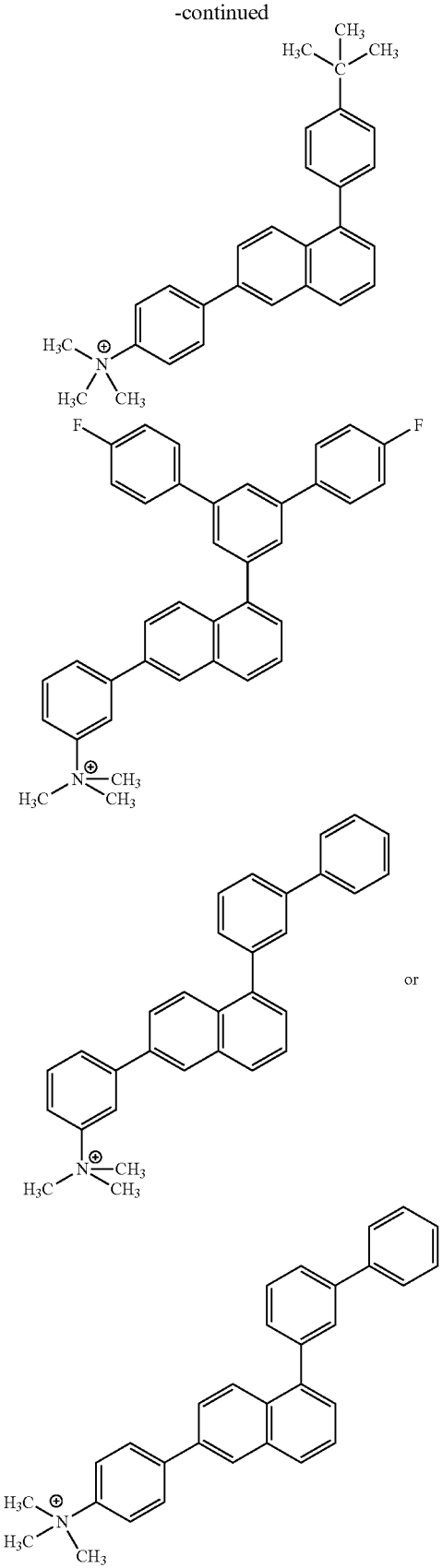
or a salt or prodrug thereof.
330
10. A compound selected from the group consisting of
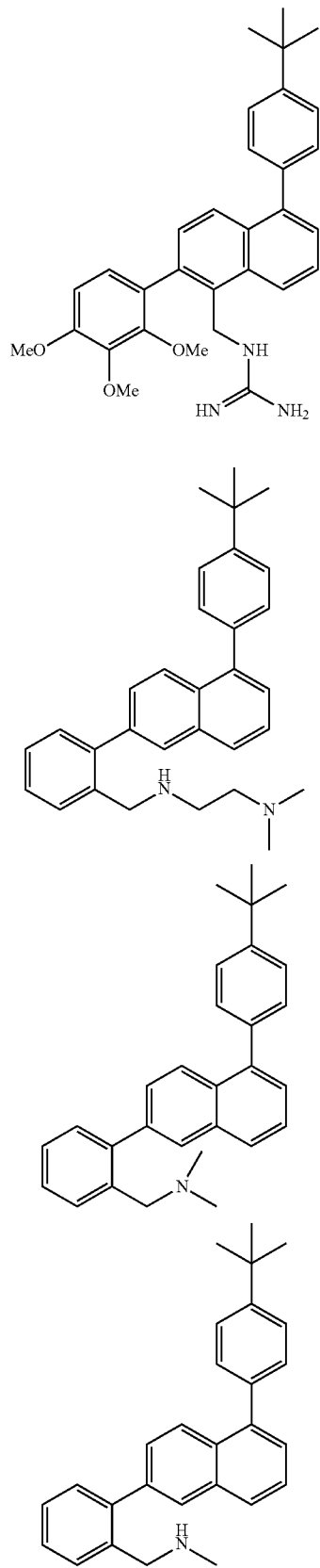
or

331
-continued
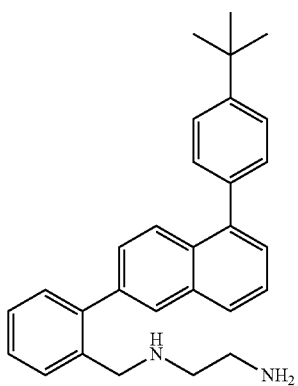
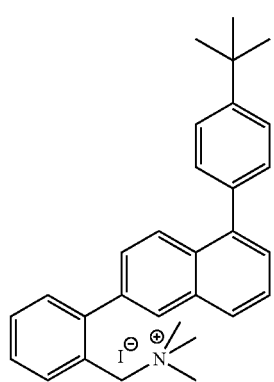
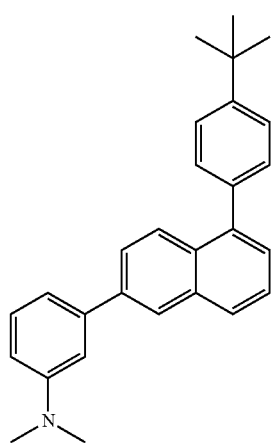
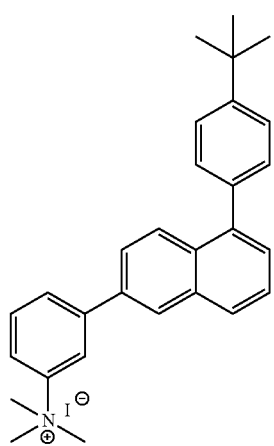
332
-continued
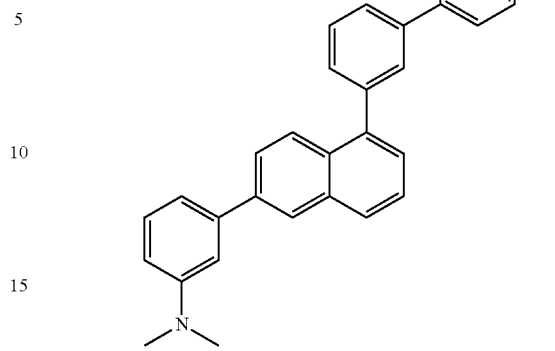
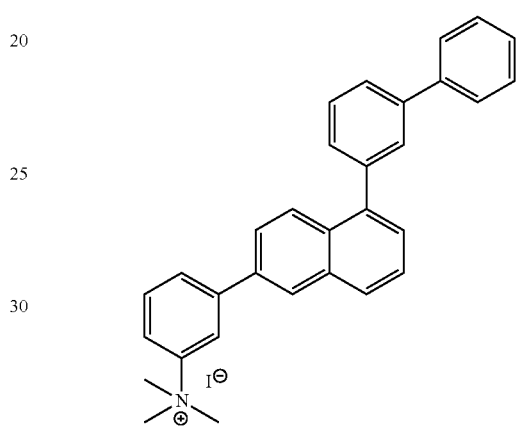
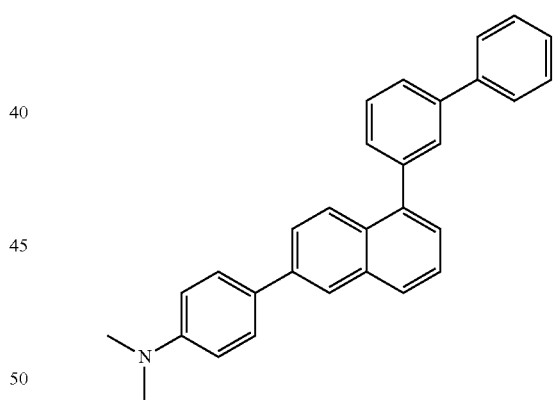
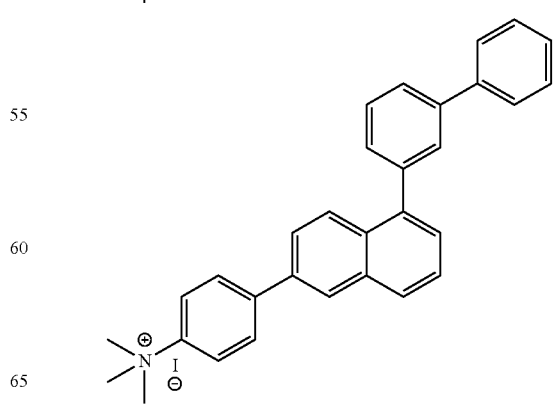

333
-continued
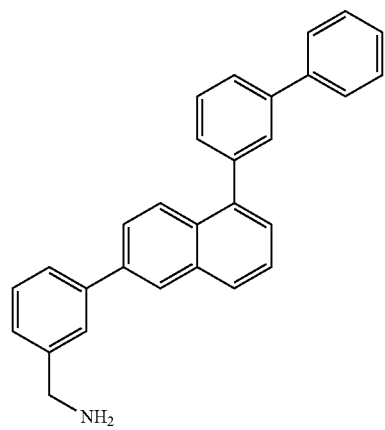 [SMILES: NCc1cccc(-c2ccc3c(-c4cccc(-c5ccccc5)c4)cccc3c2)c1]
334
-continued
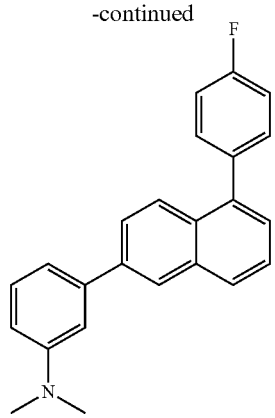
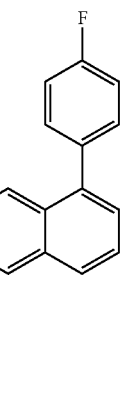
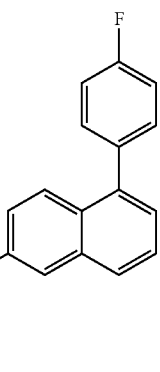
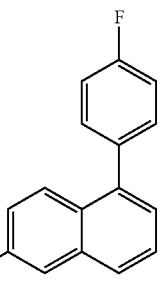

335
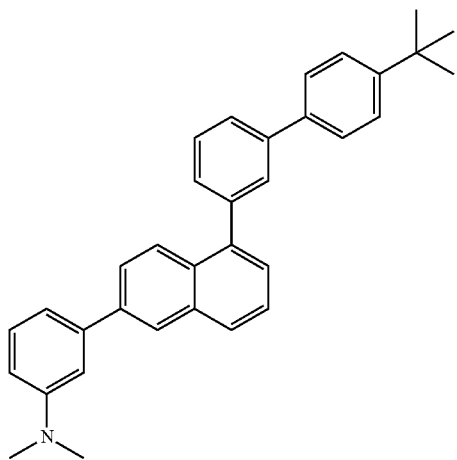
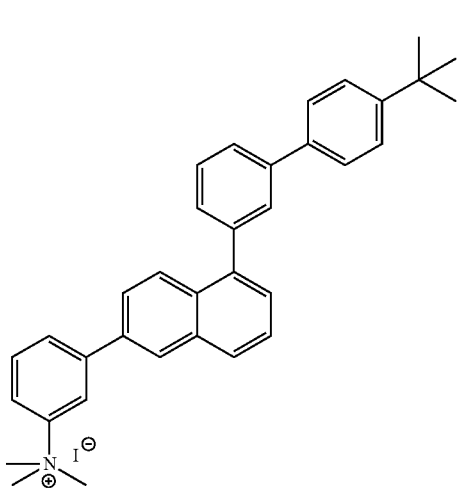
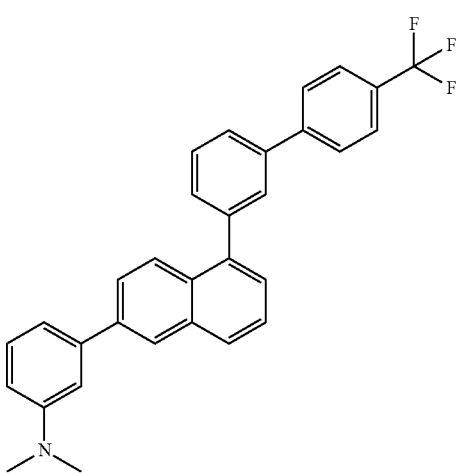
336
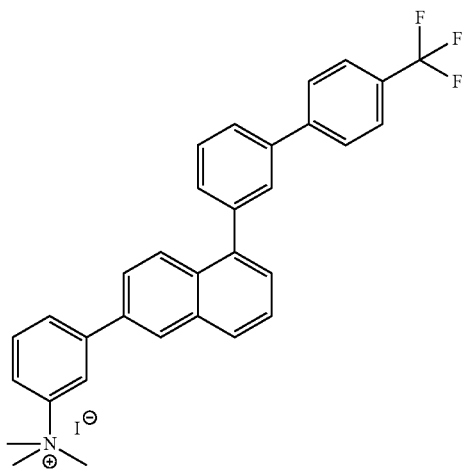
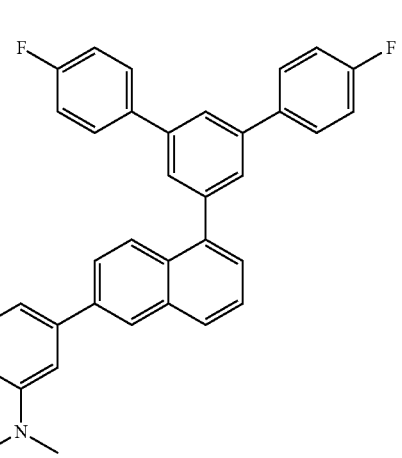
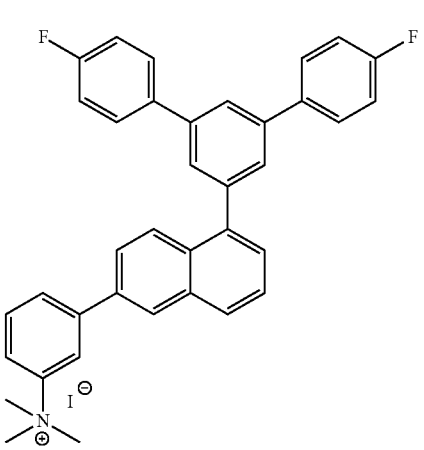

| 337 | 338 |
|---|---|
| -continued | -continued |
| 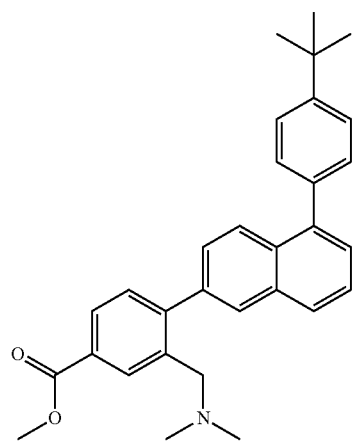 | 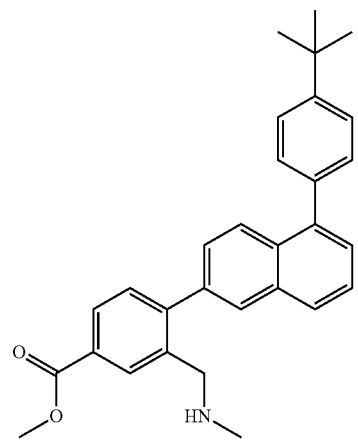 |
| 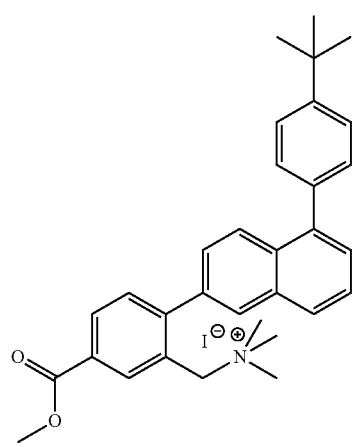 | 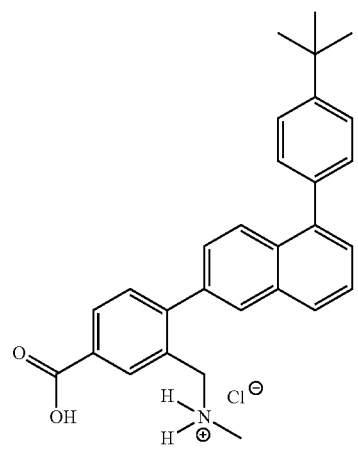 |
| 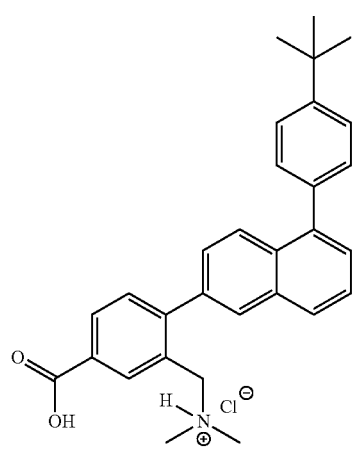 | 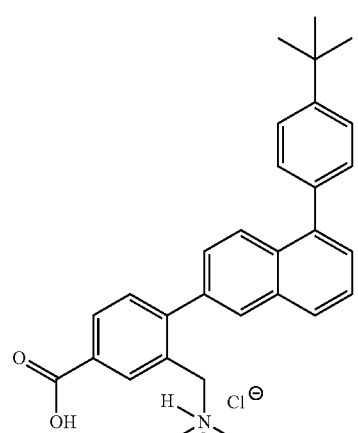 |

339
-continued
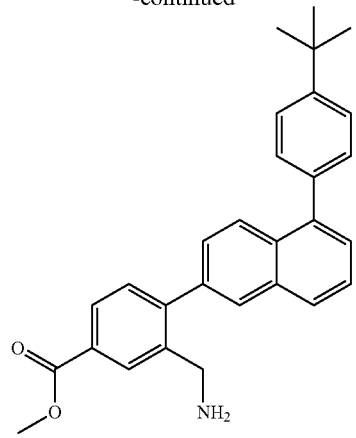
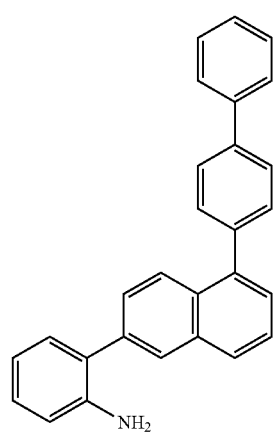
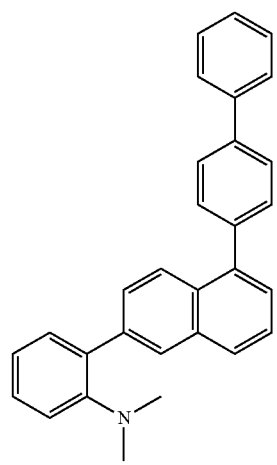
340
-continued
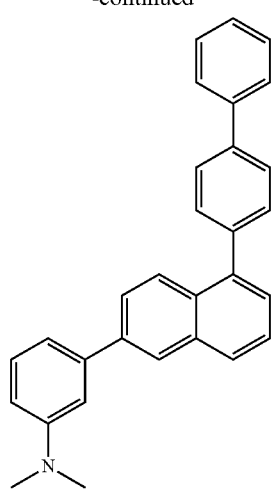
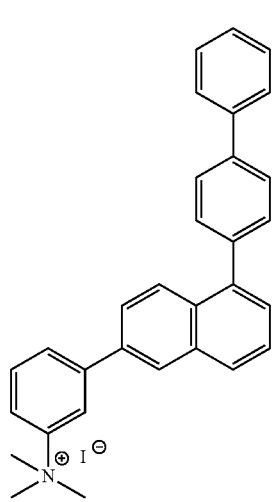
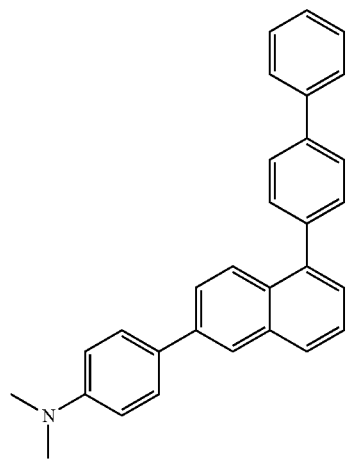

| 341 | 342 |
|---|---|
| -continued | -continued |
| 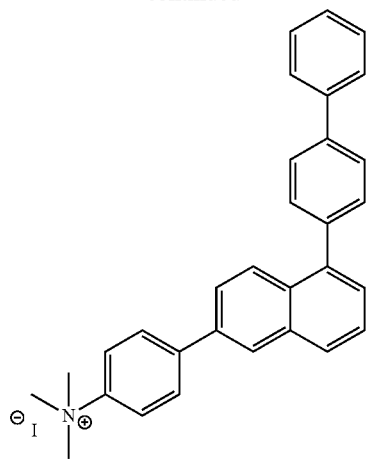 | 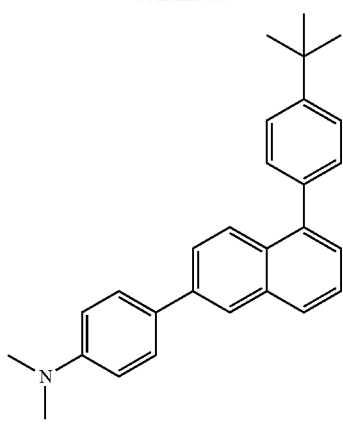 |
| 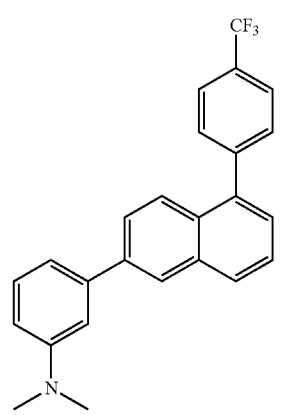 | 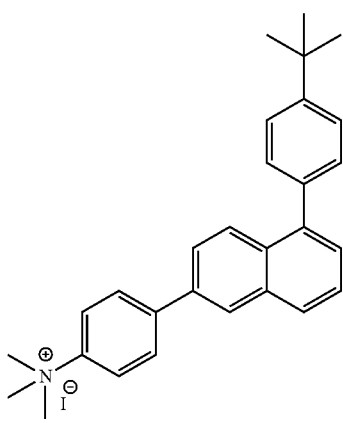 |
| 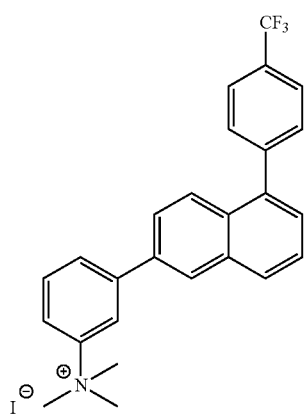 | |
| 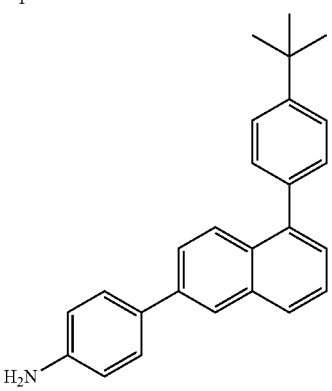 | 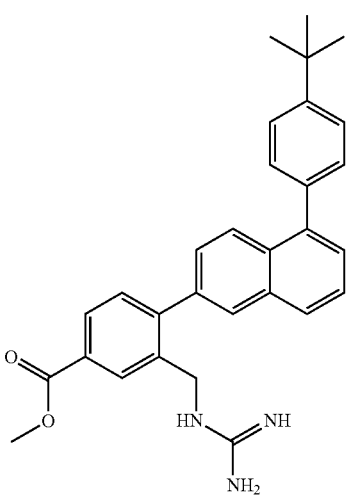 |

343
-continued
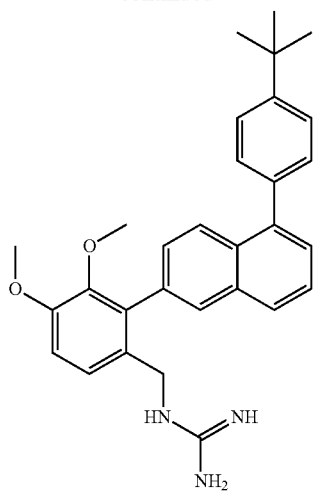
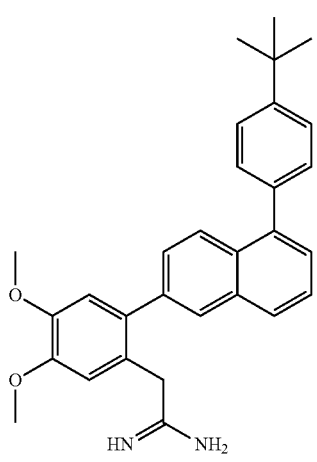
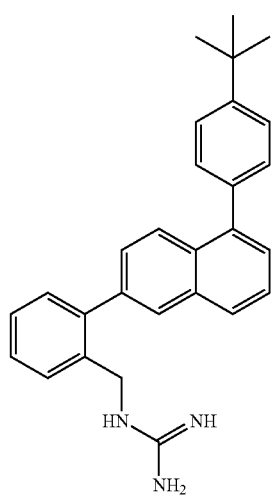
344
-continued
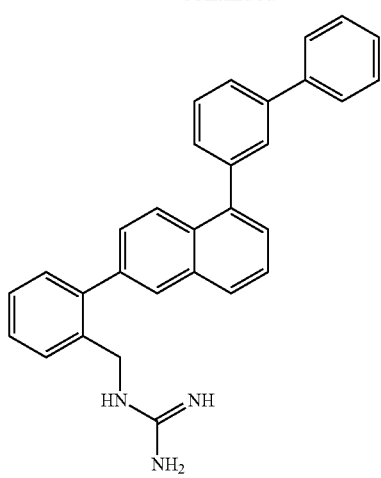
or
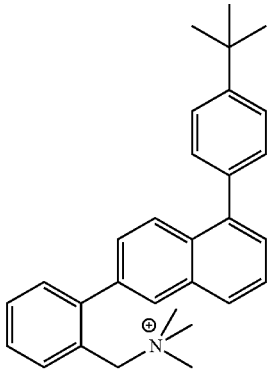
or a salt or prodrug thereof.
11. A compound selected from the group consisting of

345
-continued
346
-continued
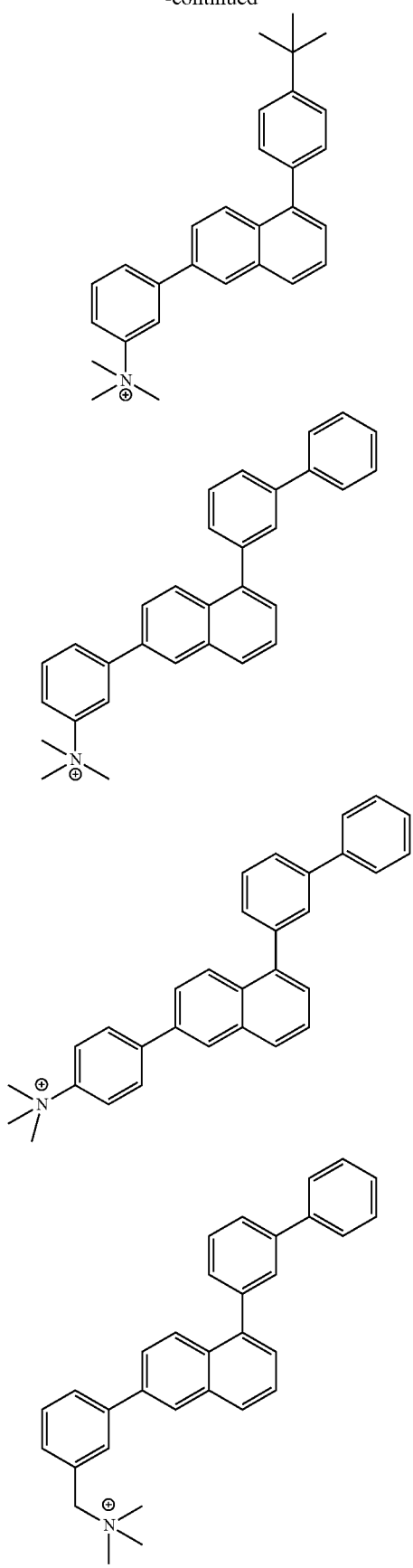
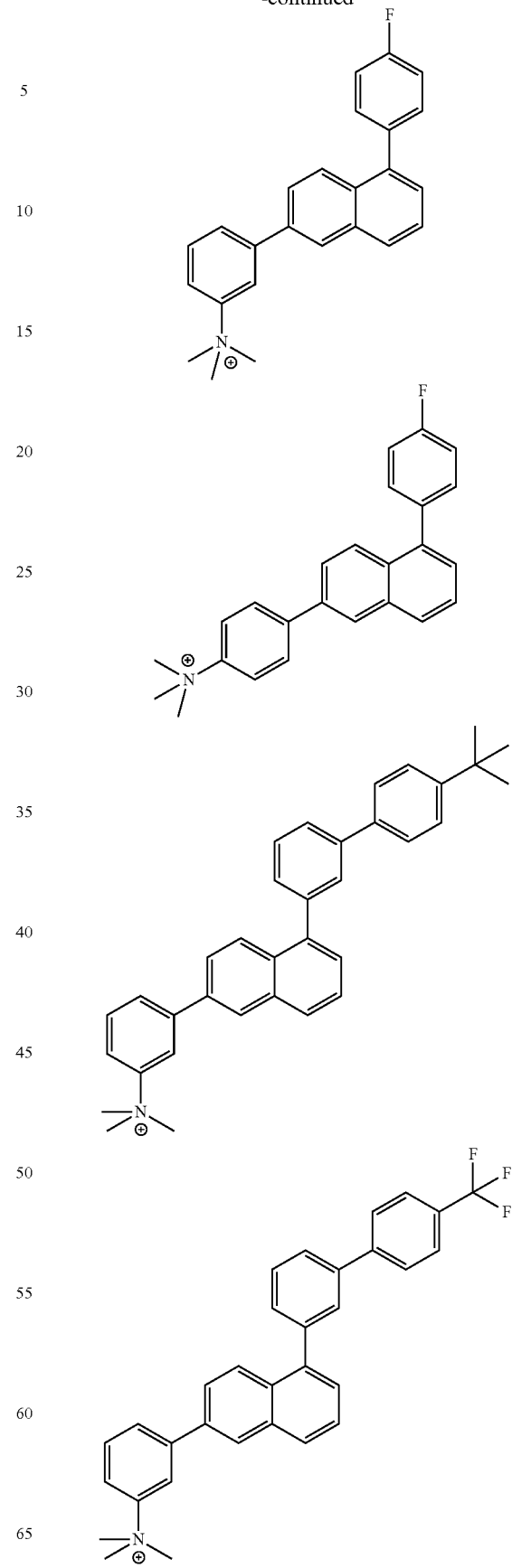

347
-continued
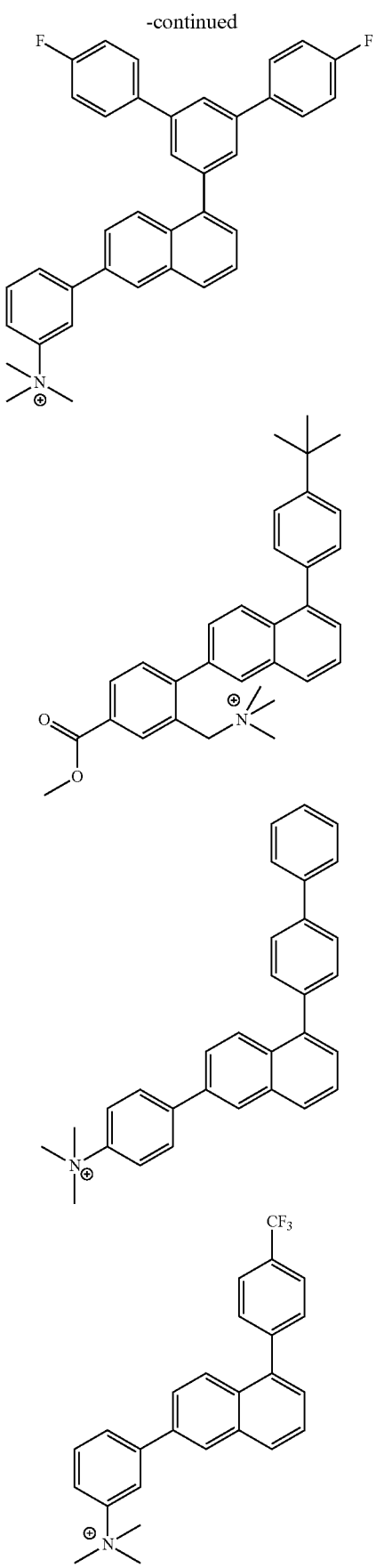
348
-continued
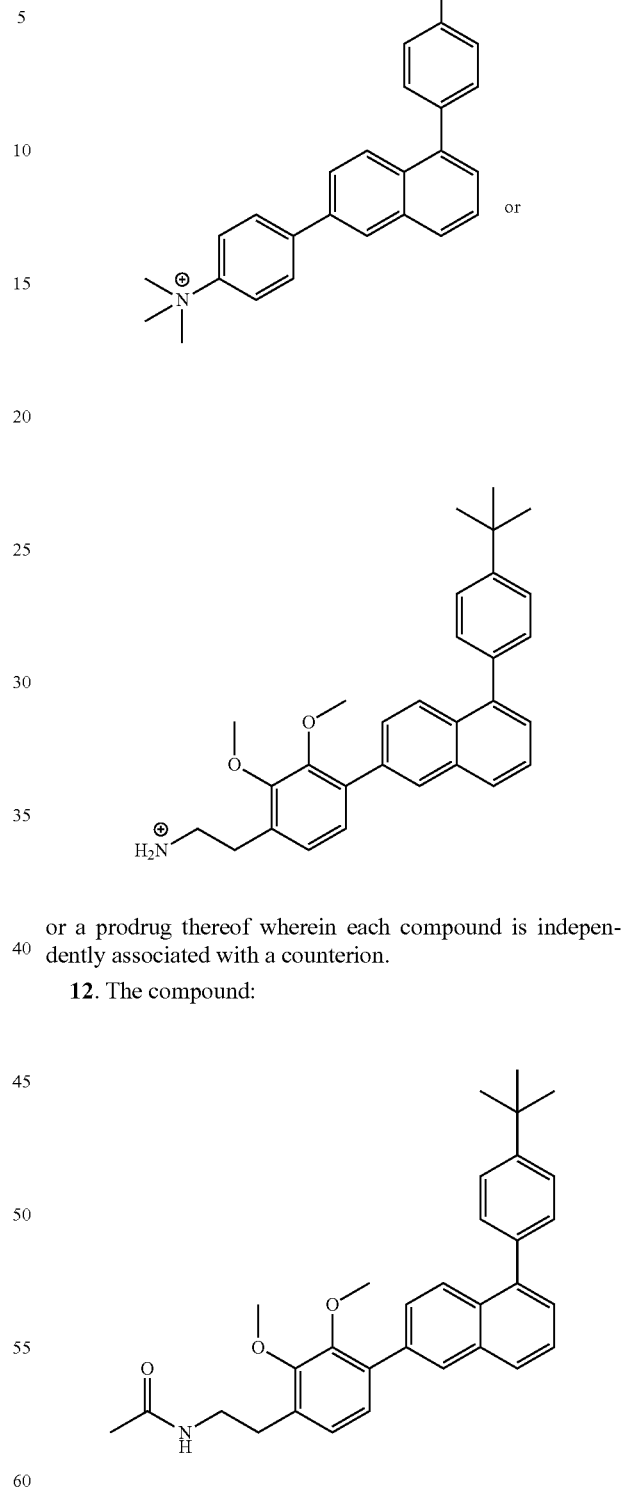
or a prodrug thereof wherein each compound is independently associated with a counterion.
12. The compound:
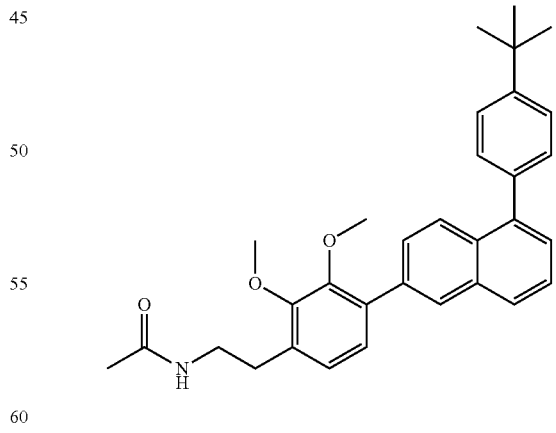
or a salt or prodrug thereof.
13. A composition comprising a compound of formula I as described in claim 1 or a pharmaceutically acceptable salt or prodrug thereof, and a pharmaceutically acceptable vehicle.
* * * * *

UNITED STATES PATENT AND TRADEMARK OFFICE
CERTIFICATE OF CORRECTION

PATENT NO. : 9,102,617 B2
APPLICATION NO. : 13/806033
DATED : August 11, 2015
INVENTOR(S) : Edmond J. Lavoie Page 1 of 1

It is certified that error appears in the above-identified patent and that said Letters Patent is hereby corrected as shown below:

In the Claims:

In Claim 3, Column 316, Line 65:

Replace: "$R^{5'}$" With: -- $R^{55'}$ --

In Claim 7, Column 324, Lines 13-23:

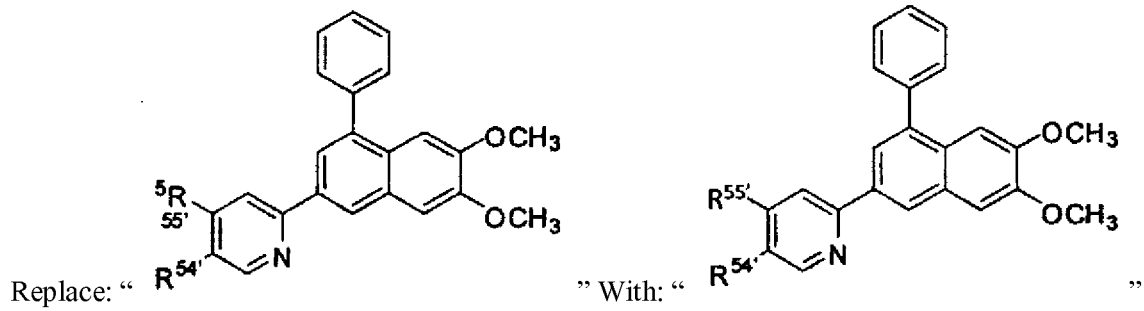

Replace: " " With: " "

In Claim 9, Column 329, Lines 33-49:

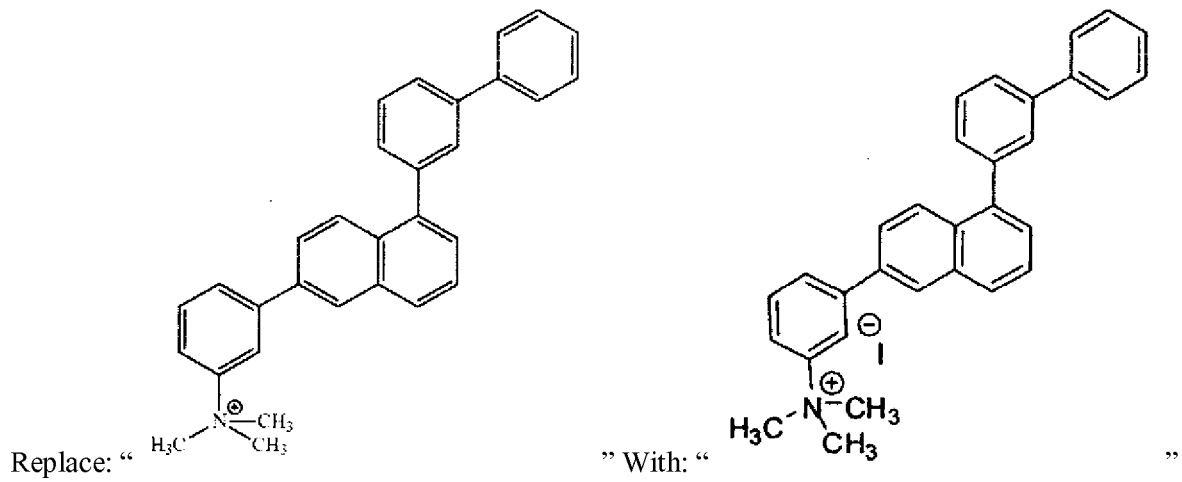

Replace: " " With: " "

Signed and Sealed this
Ninth Day of February, 2016

Michelle K. Lee
*Director of the United States Patent and Trademark Office*